US012338289B2

(12) United States Patent
De Jong et al.

(10) Patent No.: US 12,338,289 B2
(45) Date of Patent: Jun. 24, 2025

(54) ANTIBODY VARIANT COMBINATIONS AND USES THEREOF

(71) Applicant: GENMAB B.V., Utrecht (NL)

(72) Inventors: Rob De Jong, Utrecht (NL); Frank Beurskens, Utrecht (NL); Simone Oostindie, Utrecht (NL); Aran Frank Labrijn, Nigtevecht (NL); Kristin Strumane, Werkhoven (NL); Janine Schuurman, Diemen (NL); Bart-Jan De Kreuk, Utrecht (NL)

(73) Assignee: GENMAB B.V., Utrecht (NL)

( * ) Notice: Subject to any disclaimer, the term of this patent is extended or adjusted under 35 U.S.C. 154(b) by 908 days.

(21) Appl. No.: 17/051,205

(22) PCT Filed: May 3, 2019

(86) PCT No.: PCT/EP2019/061455
§ 371 (c)(1),
(2) Date: Oct. 28, 2020

(87) PCT Pub. No.: WO2019/211472
PCT Pub. Date: Nov. 7, 2019

(65) Prior Publication Data
US 2021/0238296 A1 Aug. 5, 2021

(30) Foreign Application Priority Data

May 3, 2018 (DK) .......................... PA 2018 00195
Sep. 26, 2018 (DK) .......................... PA 2018 00644

(51) Int. Cl.
*A61K 39/395* (2006.01)
*A61K 45/06* (2006.01)
*C07K 16/28* (2006.01)

(52) U.S. Cl.
CPC .......... *C07K 16/2878* (2013.01); *A61K 45/06* (2013.01); *C07K 16/2809* (2013.01); *C07K 16/2818* (2013.01); *C07K 16/2833* (2013.01); *C07K 16/2887* (2013.01); *C07K 16/2893* (2013.01); *C07K 16/2896* (2013.01); *C07K 2317/565* (2013.01); *C07K 2317/732* (2013.01); *C07K 2317/734* (2013.01)

(58) Field of Classification Search
None
See application file for complete search history.

(56) References Cited

U.S. PATENT DOCUMENTS

| | | |
|---|---|---|
| 10,759,867 B2 | 9/2020 | Parren et al. |
| 10,882,913 B2 | 1/2021 | Overdijk et al. |
| 11,034,772 B2 | 6/2021 | Oostindie et al. |
| 11,180,572 B2 | 11/2021 | De Jong et al. |
| 11,396,553 B2 | 7/2022 | Oostindie et al. |
| 11,512,137 B2 | 11/2022 | Oostindie et al. |
| 12,049,512 B2 | 7/2024 | Parren et al. |
| 2014/0242075 A1 | 8/2014 | Parren et al. |
| 2015/0175707 A1 | 6/2015 | De Jong et al. |
| 2019/0144554 A1 | 5/2019 | Overdijk et al. |
| 2019/0202926 A1 | 7/2019 | Beurskens et al. |
| 2019/0315877 A1 | 10/2019 | Overdijk et al. |
| 2020/0181277 A1 | 6/2020 | Beurskens et al. |
| 2020/0190200 A1 | 6/2020 | Alfonso Martin et al. |
| 2020/0247897 A1 | 8/2020 | Jensen et al. |
| 2020/0291124 A1 | 9/2020 | Oostindie et al. |
| 2021/0024647 A1 | 1/2021 | Oostindie et al. |
| 2021/0163619 A1 | 6/2021 | Parren et al. |
| 2021/0230301 A1 | 7/2021 | De Jong et al. |
| 2021/0324096 A1 | 10/2021 | Overdijk et al. |
| 2021/0355232 A1 | 11/2021 | Oostindie et al. |
| 2022/0411522 A1 | 12/2022 | Beurskens et al. |
| 2022/0411529 A1 | 12/2022 | De Jong et al. |
| 2023/0399414 A1 | 12/2023 | Oostindie et al. |
| 2024/0076397 A1 | 3/2024 | Oostindie et al. |

FOREIGN PATENT DOCUMENTS

| | | |
|---|---|---|
| WO | 2012/130831 A1 | 10/2012 |
| WO | 2013/004842 A2 | 1/2013 |
| WO | 2014/006217 A1 | 1/2014 |
| WO | 2014/108198 A1 | 7/2014 |
| WO | 2017/117179 A1 | 7/2017 |

OTHER PUBLICATIONS

Oostindie et al. Nature Biotech 40:1509-1519 (Year: 2022).*
Diebolder, C. A. et al: "Complement Is Activated by IgG Hexamers Assembled at the Cell Surface," Science, vol. 343 (6176):1260-1263 (2014).
Taylor, R. et al: "Hexamerization-enhanced CD37 and CD20 antibodies synergize in CDC to kill patient-derived CLL cells with unprecedented potency", Molecular Immunology, Pergamon, vol. 102: 218 (2018).
Wang, X. et al: "IgG Fc engineering to modulate antibody effector functions," Protein & Cell, vol. 9(1): 63-73 (2017).
U.S. Appl. No. 16/921,154, filed Jul. 6, 2020, Paul Parren, US 20210163619.
U.S. Appl. No. 14/130,543, filed May 5, 2014, Paul Parren, now U.S. Pat. No. 10,759,867.

(Continued)

*Primary Examiner* — Meera Natarajan
(74) *Attorney, Agent, or Firm* — Nelson Mullins Riley & Scarborough LLP; Jane E. Remillard, Esq.; Christopher L. Frank

(57) ABSTRACT

Provided herein are combinations of first and second antibodies having modified Fc effector functions resulting from amino acid substitutions in the Fc region, the amino acid substitutions allow for co-dependent activation of effector functions such as CDC and/or ADCC. Also provided are combinations of first and second antibodies having agonistic activity or enhanced agonistic activity resulting from amino acid substitutions in the Fc region where the agonistic activity is co-dependent of both a first and second antibodies.

17 Claims, 92 Drawing Sheets
Specification includes a Sequence Listing.

(56) References Cited

OTHER PUBLICATIONS

U.S. Appl. No. 17/012,102, filed Sep. 4, 2020, Rob N. De Jong, US 20210230301.
U.S. Appl. No. 14/413,178, filed Mar. 17, 2015, Rob N. De Jong, now U.S. Pat. No. 11,180,572.
U.S. Appl. No. 17/896,916, filed Aug. 26, 2022, Paul Parren.
U.S. Appl. No. 14/760,135, filed Jul. 9, 2015, Paul Parren, US 20150353636.
U.S. Appl. No. 18/475,055, filed Sep. 26, 2023, Paul Parren.
U.S. Appl. No. 16/498,104, filed Sep. 26, 2019, Simone Oostindie, US 20200270359.
U.S. Appl. No. 17/066,190, filed Oct. 8, 2020, Simone Oostindie, now U.S. Pat. No. 11,034,772.
U.S. Appl. No. 17/975,333, filed Oct. 27, 2022, Simone Oostindie, US 20230399414.
U.S. Appl. No. 17/534,029, filed Nov. 23, 2021, Simone Oostindie, US 20220251231.
U.S. Appl. No. 17/382,758, filed Jul. 22, 2021, Simone Oostindie, now U.S. Pat. No. 11,396,553.
U.S. Appl. No. 17/975,362, filed Oct. 27, 2022, Simone Oostindie, US 20240117064.
U.S. Appl. No. 16/872,140, filed May 11, 2020, Simone Oostindie, now U.S. Pat. No. 11,512,137.
U.S. Appl. No. 17/975,353, filed Oct. 27, 2023, Simone Oostindie, US 20240076397.
U.S. Appl. No. 16/618,722, filed Dec. 2, 2019, Mette Hamborg Jensen, US20200247897.
U.S. Appl. No. 18/475,842, filed Sep. 27, 2023, Mette Hamborg Jensen.
U.S. Appl. No. 17/972,356, filed Oct. 24, 2022, Mette Hamborg Jensen.
U.S. Appl. No. 15/780,268, filed May 31, 2018, Marije Overdijk, US 20190144554.
U.S. Appl. No. 16/451,714, filed Jun. 25, 2019, Marije Overdijk, now U.S. Pat. No. 10,882,913.
U.S. Appl. No. 17/108,373, filed Dec. 1, 2020, Marije Overdijk, US 20210324096.
U.S. Appl. No. 15/780,285, filed May 31, 2018, Frank Beurskens, US 20190202926.
U.S. Appl. No. 17/684,238, filed Mar. 1, 2022, Frank Beurskens, US 20220411522.
U.S. Appl. No. 16/482,747, filed Aug. 1, 2019, Frank Beurskens, US 20200181277.
U.S. Appl. No. 16/717,189, filed Dec. 17, 2019, Pedro Jose Alfonso, US 20200190200.
U.S. Appl. No. 17/774,333, filed May 4, 2022, Rob De Jong, US 20220411529.

\* cited by examiner

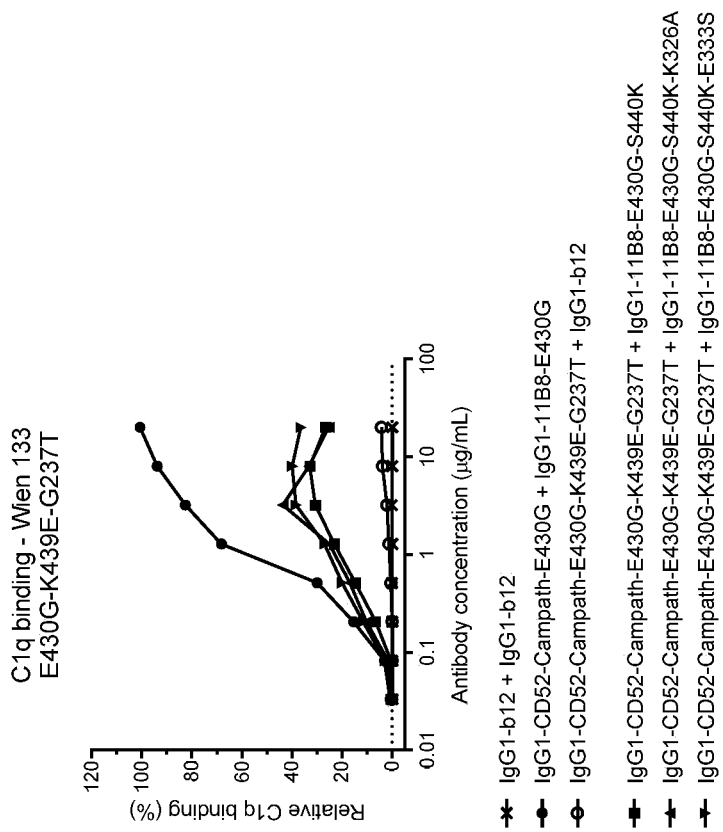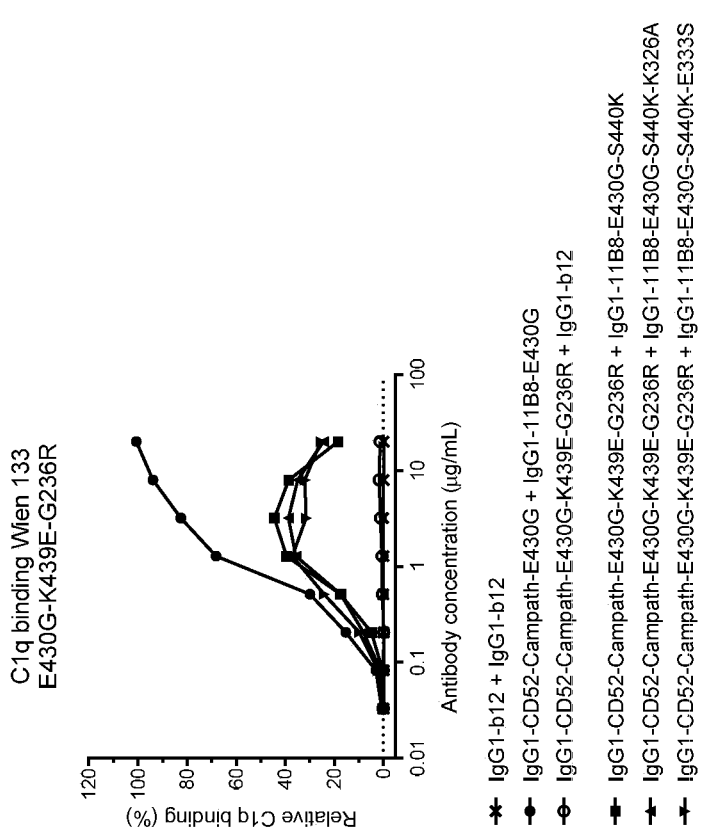

ANTIBODY VARIANT COMBINATIONS AND USES THEREOF

CROSS-REFERENCE TO RELATED APPLICATIONS

This application is a 35 U.S.C. 371 national stage filing of International Application No. PCT/EP2019/061455, filed May 3, 2019, which claims priority to Danish Patent Application Nos. PA 2018 00195, filed May 3, 2018, and PA 2018 00644, filed Sep. 26, 2018. The contents of the aforementioned applications are hereby incorporated by reference.

SEQUENCE LISTING

The instant application contains a Sequence Listing which has been submitted electronically in ASCII format and is hereby incorporated by reference in its entirety. Said ASCII copy, created on Oct. 28, 2020, is named GMI_202US_Sequence_Listing.txt and is 365,700 bytes in size.

FIELD OF THE INVENTION

The present invention relates to antibodies having modified Fc effector functions resulting from amino acid substitutions in the Fc region i.e. such as increased Fc effector functions or decreased Fc effector functions and the use of such antibodies in combination and compositions comprising such antibodies.

BACKGROUND OF THE INVENTION

Fc-mediated effector functions of monoclonal antibodies, such as complement-dependent cytotoxicity (CDC), antibody-dependent cell-mediated cytotoxicity (ADCC) and antibody-dependent cell-mediated phagocytosis (ADCP) contribute to the therapeutic window defined by efficacy and toxicity. CDC is initiated by binding of C1q to the Fc regions of antibodies. C1q is a multimeric protein consisting of six globular binding heads attached to a stalk. The individual globular binding heads have low affinity for IgG; and C1q must gain avidity by binding multiple IgG1 molecules on a cell surface to trigger the classical complement pathway. ADCC and ADCP are initiated by binding of the IgG Fc region to Fcγ receptors (FcγR) on effector cells.

IgG hexamerization upon target binding on the cell surface has been shown to support avid C1q binding. The hexamerization is mediated through intermolecular non-covalent Fc-Fc interactions, and Fc-Fc interactions can be enhanced by point mutations in the CH3 domain, including E345R and E430G.

WO2013/004842 discloses antibodies or polypeptides comprising variant Fc regions having one or more amino acid modifications resulting in modified effector functions such as complement-dependent cytotoxicity (CDC).

WO2014/108198 discloses polypeptides such as antibodies comprising variant Fc regions having one or more amino acid modifications resulting in increased complement-dependent cytotoxicity (CDC).

WO2012/130831 concerns Fc region-containing polypeptides that have altered effector function as a consequence of one or more amino acid substitutions in the Fc region of the polypeptide. These polypeptides exhibit reduced affinity to the human FcγRIIIa and/or FcγRIIa and/or FcγRI compared to a polypeptide comprising the wildtype IgG Fc region, and exhibit reduced ADCC induced by said polypeptide to at least 20% of the ADCC induced by the polypeptide comprising a wild-type human IgG Fc region. WO2012/130831 does not disclose antibodies which have enhanced Fc-Fc interactions and/or enhanced ability to form hexamers.

As described above, previous efforts in enhancing Fc-Fc interactions between antibodies have the effect of enhancing effector functions such as enhanced CDC and/or ADCC, which may lead to cell death of the target cell to which the antibody binds.

However, if the target antigen is ubiquitously expressed in the body both on healthy cells and on disease causing cells, then the antibody may become toxic by killing healthy cells. Therefore, there is a need for making effector functions of the antibody with enhanced effector functions dependent on another antibody, the combination of which is selective for disease causing cells thereby preventing killing of healthy cells.

OBJECTS OF THE INVENTION

Individually acting antibodies with enhanced effector functions rely solely on the antigen binding region of the antibody to achieve specificity for their target cell, which may limit suitable targets to those targets that are highly selectively expressed on diseased cells. Individually acting antibodies with effector function decreasing mutations may spare healthy cells expressing the antigen target of those antibodies, but their potency may be limited by the effector function decreasing mutations. Therefore, there is a clear need for making combinations of antibodies of which each individual antibody may bind both disease causing cells and healthy cells, but of which enhanced effector functions are only or preferentially activated if both antibodies have bound the same disease causing cell. This decoupling of effector function activation from individual target binding enables the creation of antibodies that bind targets that until now could not be used optimally for antibody therapy due to undesirable toxicity on healthy cells, or due to a lack of potency on disease cells, provided the activation of effector function is selective for cells simultaneously bound by combinations of antibodies.

Accordingly, it is an object of the present invention to provide a first antibody and a second antibody that are engineered to provide maximal activity on target cells bound by both antibodies simultaneously, wherein the first antibody provides no or minimal activity on target cells bound only by the first antibody, and wherein the second antibody provides minimal or reduced activity on target cells bound only by the second antibody, compared to the activity on cells bound by both antibodies simultaneously.

It is a further object of the present invention to provide a first antibody and a second antibody both comprising an Fc region of a human IgG and an antigen binding region, which both have a substitution which increases Fc-Fc interactions, a self-oligomerization inhibiting substitution and the first antibody further has a substitution for reduced effector functions such as CDC and/or ADCC, where the first antibody has reduced effector functions such as CDC and/or ADCC compared to a first parent antibody without said substitution for reduced effector functions, where the combination of the first and second antibody has enhanced effector functions compared to the first and second antibody individually.

It is another object of the present invention to provide a first antibody comprising an Fc region of a human IgG and an antigen binding region, which antibody has a substitution which increases Fc-Fc interactions, a self-oligomerization inhibiting substitution and a substitution for reduced effector functions such as CDC and/or ADCC compared to a first parent antibody and a second antibody comprising an Fc region of a human IgG and an antigen binding region, which second antibody has a substitution which increases Fc-Fc interactions, a self-oligomerization inhibiting substitution and a substitution for enhanced effector functions such as CDC and/or ADCC compared to a second parent antibody, where the activity of the first antibody and the second antibody are made co-dependent by complementary the self-oligomerization inhibiting substitutions.

It is a further object of the present invention to provide a first antibody comprising an Fc region of a human IgG and an antigen binding region, which antibody has a substitution which increases Fc-Fc interactions, a self-oligomerization inhibiting substitution and a substitution for reduced effector functions such as CDC and/or ADCC compared to a first parent antibody and a second antibody comprising an Fc region of a human IgG and an antigen binding region, which second antibody has a substitution which increases Fc-Fc interactions, a self-oligomerization inhibiting substitution and a substitution inducing agonistic activity, such as increased activation of a target receptor upon binding, when compared to a second parent antibody, where the activity of the first and the second antibody are made co-dependent by complementary self-oligomerization inhibiting substitutions.

It is a further object of the present invention to provide a first antibody comprising an Fc region of a human IgG and an antigen binding region, which antibody has a substitution which increases Fc-Fc interactions, a self-oligomerization inhibiting substitution and a substitution for reduced agonistic activity, such as reduced activation of a target receptor upon binding compared to a first parent antibody and a second antibody comprising an Fc region of a human IgG and an antigen binding region, which second antibody has a substitution which increases Fc-Fc interactions, a self-oligomerization inhibiting substitution and a substitution for reduced agonistic activity, such as reduced activation of a target receptor upon binding compared to a second parent antibody, where the first and the second antibody in combination have enhanced agonistic activity made co-dependent by complementary self-oligomerization inhibiting substitutions.

It is a further object of the present invention to provide a first antibody comprising an Fc region of a human IgG and an antigen binding region, which antibody has a substitution which increased Fc-Fc interactions, a self-oligomerization inhibiting substitution and a substitution which reduces effector functions such as CDC and/or ADCC compared to a first parent antibody and a second antibody comprising an Fc region of a human IgG and an antigen binding region, which antibody has a self-oligomerization inhibiting substitution, a substitution which increased Fc-Fc interactions and activates signaling, optionally induces enhanced signaling, when the antigen binding region of the antibody is bound to the corresponding antigen compared to a second parent antibody, where the activity of the first and the second antibody are made co-dependent by complementary self-oligomerization inhibiting substitutions.

SUMMARY OF THE INVENTION

As described herein, the present invention relates to a combination of a first antibody having an Fc region and an antigen binding region, where the Fc region has one Fc-Fc enhancing substitution and one or more substitution which reduced effector functions such as CDC and/or ADCC and a second antibody having an Fc region and an antigen binding region, where the Fc region has one Fc-Fc enhancing substitution and optionally has one or more substitutions which enhances Fc effector functions such as CDC and/or ADCC. The first and the second antibody further have a complementary self-oligomerization-inhibiting substitution which makes the hetero-oligomerization of the first and the second antibody co-dependent.

Without being limited to theory, it is believed that a combination of a first antibody and a second antibody of the invention having complementary substitutions that make the effector functions or signaling functions e.g. agonistic activity of the first and second antibody co-dependent is able to reduce the toxicity of the combination and increase the therapeutic window of the combination. Further, a combination of a first antibody and a second antibody of the present invention may be used to specifically deplete cell populations which express the antigens recognized by the first antibody and the second antibody. Thus, a combination of a first antibody and a second antibody of the present invention may be used to specifically deplete tumor cell populations expressing the first and second antigens recognized by the first and second antibody, while not depleting healthy cell populations or tissue expressing only the first or the second antigen recognized by the first and second antibody.

In one aspect the present invention provides a first antibody comprising a first Fc region of a human IgG and a first antigen-binding region capable of binding to a first antigen, for use as a medicament in combination with a second antibody comprising a second Fc region of a human IgG and a second antigen-binding region capable of binding to a second antigen, wherein said first Fc region comprises a. one substitution of an amino acid at a position selected from the group consisting of: E430, E345 and S440, with the proviso that the substitution in S440 is S440Y or S440W, and b. a K439E or S440K substitution, with the proviso that the substitution is not S440K if the substitution in (a) is S440Y or S440W, and c. one substitution of the amino acid at position G237 or, one or more substitutions selected from the group consisting of: G236R, G236K, K322A, E269K, K322E and P329R;

and said second Fc region comprises d. one substitution of an amino acid at a position selected from the group consisting of: E430, E345 and S440, with the proviso that the substitution in S440 is S440Y or S440W, and e. a K439E or S440K substitution, with the proviso that the substitution is not S440K if the substitution in (d) is S440Y or S440W and f. one or more substitutions selected from the group consisting of: K326A, K326W, E333A and E333S if the first Fc region comprises a K322E or P329R substitution;

wherein the first Fc region has a K439E substitution and the second Fc region has a S440K substitution or, the first Fc region has a S440K substitution and the second Fc region has a K439E substitution; wherein the amino acid positions correspond to human IgG1 according to EU numbering system (Edelman et al., Proc Natl Acad Sci USA. 1969 May; 63(1):78-85; Kabat et al., Sequences of Proteins of Immunological Interest, Fifth Edition. 1991 NIH Publication No. 91-3242).

In one aspect the present invention provides a first antibody comprising a first Fc region of a human IgG and a first antigen-binding region capable of binding to a first antigen, for use as a medicament in combination with a second antibody comprising a second Fc region of a human IgG and a second antigen-binding region capable of binding to a second antigen, wherein said first Fc region comprises
  a. one substitution of an amino acid at a position selected from the group consisting of: E430, E345 and S440, with the proviso that the substitution in S440 is S440Y or S440W, and
  b. a K439E or S440K substitution, with the proviso that the substitution is not S440K if the substitution in (a) is S440Y or S440W, and
  c. one or more amino acid substitutions selected from the group consisting of: L234, L235, G237, G236 or, one or more substitutions selected from the group consisting of: K322A and E269K;
  and said second Fc region comprises
  d. one substitution of an amino acid at a position selected from the group consisting of: E430, E345 and S440, with the proviso that the substitution in S440 is S440Y or S440W, and
  e. a K439E or S440K substitution, with the proviso that the substitution is not S440K if the substitution in (d) is S440Y or S440W;
wherein the first Fc region has a K439E substitution and the second Fc region has a S440K substitution or, the first Fc region has a S440K substitution and the second Fc region has a K439E substitution; wherein the amino acid positions correspond to human IgG1 according to Eu numbering system.

In one aspect the present invention provides a first antibody comprising a first Fc region of a human IgG and a first antigen-binding region capable of binding to a first antigen, for use as a medicament in combination with a second antibody comprising a second Fc region of a human IgG and a second antigen-binding region capable of binding to a second antigen, wherein said first Fc region comprises
  a. one substitution of an amino acid at a position selected from the group consisting of: E430, E345 and S440, with the proviso that the substitution in S440 is S440Y or S440W, and
  b. a K439E or S440K substitution, with the proviso that the substitution is not S440K if the substitution in (a) is S440Y or S440W, and
  c. one substitution of the amino acid at position G237 or, one or more substitutions selected from the group consisting of: G236R, G236K, K322A, E269K, L234A, L234F, L235A, L235Q, and L235E;
  and said second Fc region comprises
  d. one substitution of an amino acid at a position selected from the group consisting of: E430, E345 and S440, with the proviso that the substitution in S440 is S440Y or S440W, and
  e. a K439E or S440K substitution, with the proviso that the substitution is not S440K if the substitution in (d) is S440Y or S440W;
wherein the first Fc region has a K439E substitution and the second Fc region has a S440K substitution or, the first Fc region has a S440K substitution and the second Fc region has a K439E substitution; wherein the amino acid positions correspond to human IgG1 according to Eu numbering system.

In one aspect the present invention provides a first antibody comprising a first Fc region of a human IgG and a first antigen-binding region capable of binding to a first antigen, for use as a medicament in combination with a second antibody comprising a second Fc region of a human IgG and a second antigen-binding region capable of binding to a second antigen, wherein said first Fc region comprises
  a. one substitution of an amino acid at a position selected from the group consisting of: E430, E345 and S440, with the proviso that the substitution in S440 is S440Y or S440W, and
  b. a K439E or S440K substitution, with the proviso that the substitution is not S440K if the substitution in (a) is S440Y or S440W, and
  c. one substitution of the amino acid at position P329 or, a K322E substitution;
  and said second Fc region comprises
  d. one substitution of an amino acid at a position selected from the group consisting of: E430, E345 and S440, with the proviso that the substitution in S440 is S440Y or S440W, and
  e. a K439E or S440K substitution, with the proviso that the substitution is not S440K if the substitution in (d) is S440Y or S440W and
  f. one or more substitutions selected from the group consisting of: K326A, K326W, E333A and E333S;
    wherein the first Fc region has a K439E substitution and the second Fc region has a S440K substitution or, the first Fc region has a S440K substitution and the second Fc region has a K439E substitution; wherein the amino acid positions correspond to human IgG1 according to EU numbering system.

In another aspect the present invention provides a first antibody comprising a first Fc region of a human IgG and a first antigen-binding region capable of binding to a first antigen, for use as a medicament in combination with a second antibody comprising a second Fc region of a human IgG and a second antigen-binding region capable of binding to a second antigen, wherein said first Fc region comprises
  a. a K248E and a T437R substitution, and
  b. a K439E or S440K substitution, and
  c. one substitution of the amino acid at position G237 or P329, or one or more substitutions selected from the group consisting of: G236R, G236K, K322A, K332E, E269K, L234A, L234F, L235A, L235Q, and L235E;
  and said second Fc region comprises
  d. a K248E and a T437R substitution, and
  e. a K439E or S440K substitution,
  wherein the first Fc region has a K439E substitution and the second Fc region has a S440K substitution or, the first Fc region has a S440K substitution and the second Fc region has a K439E substitution; wherein the amino acid positions correspond to human IgG1 according to Eu numbering system.

A substitution at a position corresponding to E430, E345 or a S440Y or S440W substitution is considered an Fc-Fc enhancing substitution according to the present invention.

A K439E or a S440K substitution is considered a complementary self-oligomerization-inhibiting substitution according to the present invention. That is a first antibody having an e.g. K439E may not form oligomers with another antibody having a K439E substitution, however an antibody having a K439E substitution may form oligomers with another antibody having a S440K substitution. An antibody having an S440K substitution may not form oligomers with another antibody having an S440K substitution.

A substitution of the amino acid at position G237 or, one or more substitutions selected from the group consisting of: G236R, G236K, K322A, E269K, K322E, P329R, L234A, L234F, L235A, L235Q, and L235E, are considered C1q binding site modulation substitution(s) according to the present invention and reduced effector functions such as CDC and/or ADCC.

One or more substitutions selected from the group consisting of: K326A, K326W, E333A and E333S are considered C1q binding site modulation substitution(s) according to the present invention and increase effector functions such as CDC and/or ADCC.

In one embodiment the second Fc region comprises a G237A substitution.

A G237A substitution is considered an Fc-gamma receptor modulation substitution according to the present invention and decreases Fc-gamma receptor binding.

That is, the inventors of the present invention in a first aspect of the invention found that by combining a first antibody and a second antibody where the first antibody has an Fc-Fc enhancing substitution, a self-oligomerization-inhibiting substitution and one or more substitutions which reduce effector functions such as CDC and/or ADCC, and the second antibody has an Fc-Fc enhancing substitution, a self-oligomerization-inhibiting substitution and optionally one or more substitutions which enhance effector functions such as CDC and/or ADCC, and where the first and the second antibody have complementary oligomerization-inhibiting substitutions thereby making the hetero-oligomerization of the first and the second antibody co-dependent.

It may be possible to improve the safety margin between the effector function activity on diseased cells versus the effector function activity on healthy cells for the antibody combination, when compared to a combination of antibodies with Fc-Fc enhancing and self-oligomerization inhibiting substitutions but without C1q modulating substitutions.

In a further aspect the present invention provides for an antibody comprising an Fc region of a human IgG and an antigen-binding region capable of binding to an antigen, wherein said Fc region comprises
  a. one substitution of an amino acid at a position selected from the group consisting of: E430, E345 and S440, with the proviso that the substitution in S440 is S440Y or S440W, and
  b. a K439E or S440K substitution, with the proviso that the substitution is not S440K if the substitution in (a) is S440Y or S440W, and
  c. one substitution of the amino acid at position G237 or, one or more substitutions selected from the group consisting of: G236R, G236K, K322A, E269K, L234A, L234F, L235A, L235Q, and L235E.

In another aspect the present invention provides for an antibody comprising an Fc region of a human IgG and an antigen-binding region capable of binding to an antigen, wherein said Fc region comprises
  a. a K248E and a T437R substitution, and
  b. a K439E or S440K substitution, and
  c. one substitution of the amino acid at position G237 or P329, or one or more substitutions selected from the group consisting of: G236R, G236K, K322A,
  d. K332E, E269K, L234A, L234F, L235A, L235Q, L235E, K326A, K326W, E333A and E333S.

In one aspect the present invention provides a composition comprising a first and a second antibody wherein the first antibody comprises a first antigen-binding region and a first Fc region according to any embodiment or aspect described herein, and the second antibody comprises a second antigen-binding region and a second Fc region according to any embodiment or aspect described herein.

In one aspect the present invention provides a composition comprising a first and a second antibody, wherein the first antibody comprises a first antigen-binding region capable of binding to a first antigen and a first Fc region of a human IgG, and the second antibody comprises a second antigen-binding region capable of binding to a second antigen and a second Fc region of a human IgG, wherein said first Fc region comprises
  a. one substitution of an amino acid at a position selected from the group consisting of: E430, E345 and S440, with the proviso that the substitution in S440 is S440Y or S440W, and
  b. a K439E or S440K substitution, with the proviso that the substitution is not S440K if the substitution in (a) is S440Y or S440W, and
  c. one substitution of the amino acid at position G237 or, one or more substitutions selected from the group consisting of: G236R, G236K, K322A, E269K, K322E and P329R;
and said second Fc region comprises
  d. one substitution of an amino acid at a position selected from the group consisting of: E430, E345 and S440, with the proviso that the substitution in S440 is S440Y or S440W, and
  e. a K439E or S440K substitution, with the proviso that the substitution is not S440K if the substitution in (d) is S440Y or S440W, and
  f. one or more substitutions selected from the group consisting of: K326A, K326W, E333A and E333S if the first Fc region comprises a K322E or P329R substitution,
wherein the first Fc region has a K439E substitution and the second Fc region has a S440K substitution or, the first Fc region has a S440K substitution and the second Fc region has a K439E substitution, wherein the amino acid positions correspond to human IgG1 according to EU numbering system.

In one aspect the present invention provides a composition comprising a first and a second antibody, wherein the first antibody comprises a first antigen-binding region capable of binding to a first antigen and a first Fc region of a human IgG, and the second antibody comprises a second antigen-binding region capable of binding to a second antigen and a second Fc region of a human IgG, wherein said first Fc region comprises
  a. one substitution of an amino acid at a position selected form the group consisting of: E430, E345 and S440, with the proviso that the substitution in S440 is S440Y or S440W, and
  b. a K439E or S440K substitution, with the proviso that the substitution is not S440K if the substitution in (a) is S440Y or S440W, and
  c. one substitution of the amino acid at position G237 or, one or more substitutions selected from the group consisting of: G236R, G236K, K322A, E269K, L234A, L234F, L235A, L235Q, and L235E;
and said second Fc region comprises
  d. one substitution of an amino acid at a position selected form the group consisting of: E430, E345 and S440, with the proviso that the substitution in S440 is S440Y or S440W, and
  e. a K439E or S440K substitution, with the proviso that the substitution is not S440K if the substitution in (d) is S440Y or S440W,
wherein the first Fc region has a K439E substitution and the second Fc region has a S440K substitution or, the first Fc region has a S440K substitution and the second Fc region has a K439E substitution, wherein the amino acid positions correspond to human IgG1 according to EU numbering system.

In one aspect the present invention provides a composition comprising a first and a second antibody, wherein the first antibody comprises a first antigen-binding region capable of binding to a first antigen and a first Fc region of a human IgG, and the second antibody comprises a second antigen-binding region capable of binding to a second antigen and a second Fc region of a human IgG, wherein said first Fc region comprises
- a. one substitution of an amino acid at a position selected form the group consisting of: E430, E345 and S440, with the proviso that the substitution in S440 is S440Y or S440W, and
- b. a K439E or S440K substitution, with the proviso that the substitution is not S440K if the substitution in (a) is S440Y or S440W, and
- c. one substitution of the amino acid at position P329 or, a K322E substitution;

and said second Fc region comprises
- d. one substitution of an amino acid at a position selected form the group consisting of: E430, E345 and S440, with the proviso that the substitution in S440 is S440Y or S440W, and
- e. a K439E or S440K substitution, with the proviso that the substitution is not S440K if the substitution in (d) is S440Y or S440W, and
- f. one or more substitutions selected from the group consisting of: K326A, K326W, E333A and E333S, wherein the first Fc region has a K439E substitution and the second Fc region has a S440K substitution or, the first Fc region has a S440K substitution and the second Fc region has a K439E substitution, wherein the amino acid positions correspond to human IgG1 according to Eu numbering system.

In another aspect the present invention provides for a composition comprising a first and a second antibody, wherein the first antibody comprises a first antigen-binding region capable of binding to a first antigen and a first Fc region of a human IgG, and the second antibody comprises a second antigen-binding region capable of binding to a second antigen and a second Fc region of a human IgG, wherein said first Fc region comprises
- a. a K248E and a T437R substitution, and
- b. a K439E or S440K substitution, and
- c. one substitution of the amino acid at position G237 or P329, or one or more substitutions selected from the group consisting of: G236R, G236K, K322A, K332E, E269K, L234A, L234F, L235A, L235Q, and L235E;

and said second Fc region comprises
- d. a K248E and a T437R substitution, and
- e. one K439E or S440K substitution, wherein the first Fc region has a K439E substitution and the second Fc region has a S440K substitution or, the first Fc region has a S440K substitution and the second Fc region has a K439E substitution; wherein the amino acid positions correspond to human IgG1 according to Eu numbering system.

In another aspect the present invention relates to a method of depleting a cell population expressing a first antigen and a second antigen, which method comprises contacting said cell population with a first and second antibody or composition according to any first and second antibody or composition as defined herein.

In another aspect the present invention relates to a method of treating an individual having a disease comprising administering to said individual an effective amount of a first and a second antibody according to claims as described herein or an effective amount of a composition as described herein.

In another aspect the present invention relates to a kit comprising a first container comprising a first antibody as defined herein and a second container comprising a second antibody as defined herein.

In another aspect the present invention relates to a first and second antibody or a composition as described herein for use in the treatment of cancer, autoimmune disease, inflammatory disease or infectious disease.

In another aspect the present invention relates to a method of treating an individual having a disease comprising administering to said individual an effective amount of a first and second antibody or composition as described herein.

These and other aspects of the invention, particularly various uses and therapeutic applications for the first and second antibody, are described in further detail below.

BRIEF DESCRIPTION OF THE DRAWINGS

(FIG. 8A, FIG. 8B) An ADCC reporter Bioassay was performed, in which Raji target cells were co-incubated with antibody dilution series and Jurkat human T cells stably expressing high affinity FcγRIIIa (V158) and an NFAT-response element driving expression of firefly luciferase. Luciferase production was quantified by luminescence readout. (FIG. 8C, FIG. 8D) An in vitro Europium TDA (EuTDA) ADCC assay was performed, in which Wien 133 target cells were co-incubated with antibody dilution series and human PBMC (E:T 100:1). Cell lysis was determined by measuring the signal of EuTDA fluorescent chelate in the supernatant.

(FIGS. 16A-16C) Total human IgG in plasma samples was determined by ELISA and plotted in a concentration versus time curve for (FIG. 16A) IgG1-CAMPATH-1H variants, (FIG. 16B) IgG1-11B8 variants, and (FIG. 16C) combinations of IgG1-CAMPATH-1H variants+IgG1-11B8 variants. Each data point represents the mean+/−standard deviation of triplicate samples. (FIG. 16D) Clearance until day 21 after administration of the antibody was determined following the formula D*1,000/AUC with D, injected dose and AUC, area under the curve of the concentration-time curve.

(FIG. 19A) Selective activity of IgG1-CAMPATH-1H-G236R-E430G-K439E mixed with IgG1-11B8-G237A-E430G-S440K. (FIG. 19B) Selective activity of IgG1-CAMPATH-1H-E430G-K439E variants containing an additional G237 mutation, mixed with IgG1-11B8-G237A-E430G-S440K. (FIG. 19C) Selective activity of IgG1-CAMPATH-1H-E430G-K439E variants containing an additional G236R or G237 mutation, mixed with IgG1-11B8-G237A-E430G-S440K containing an additional C1q-binding enhancing E333S mutation. (FIG. 19D) Depth of B-cell depletion by different B-cell targeting antibodies compared to co-dependent antibody combinations of IgG1-CAMPATH-1H-E430G-K439E with additional mutations G236R, G237Q, or G237R, mixed with IgG1-11B8-G237A-E430G-S440K. Y-axis: log scale representation of fraction B-cells determined as above.

(FIG. 21A) Daudi cells and (FIG. 21B) WIL2-S cells were incubated with antibody concentration series in the presence of 20% NHS. CDC efficacy is presented as the normalized AUC of the percentage PI-positive cells, and as lysis at 40 µg/mL IgG. Normalization was performed to non-binding control antibody IgG1-b12 (0%) and the mixture of IgG1-CD37-37.3-E430G+IgG1-11B8-E430G (100%).

(FIG. 22B) Maximal binding (Bmax) to Raji cells by the IgG1-Campath-1H antibody variants with mutations E430G and K439E, in combination with any of the C1q binding modulating mutations G236R, G237A, or G237T is shown normalized relative to the binding of wild type IgG1-Campath-1H (FIG. 22C) Apparent $K_d$ values of IgG1-Campath-1H antibody variants with mutations E430G and S440K, in combination with any of the C1q binding modulating mutations G236R, G237A, or G237T binding to Raji cells.

(FIG. 23C, FIG. 23D) Maximal binding (Bmax) to Raji cells by the IgG1-11B8 antibody variants with mutations E430G and S440K, in combination with any of the C1q binding modulating mutations K326A or E333A (FIG. 23C) or E333S, G237A or G237A-E333S (FIG. 23D) is shown normalized relative to the binding of wild type IgG1-11B8 (FIG. 23E, FIG. 23F) Apparent $K_d$ values of IgG1-11B8 antibody variants with mutations E430G and S440K, in combination with any of the C1q binding modulating mutations K326A or E333A (FIG. 23E) or E333S, G237A or G237A-E333S (FIG. 23F) binding to Raji cells.

(FIG. 24A, FIG. 24C) Binding to human FcRn is shown for variants of anti-CD52 antibody IgG1-CAMPATH-1H with Fc-Fc interaction enhancing mutation E430G, self-oligomerization inhibiting mutation K439E and C1q-binding modulating mutations G237A or G237T using a 40 µg/ml antibody concentration at (FIG. 24A) pH 6.0, or (FIG. 24C) pH 7.4. (FIG. 24B, FIG. 24D) Binding to human FcRn by variants of anti-CD20 antibody IgG1-11B8 with Fc-Fc interaction enhancing mutation E430G, self-oligomerization inhibiting mutation S440K and C1q-binding modulating mutations K326A, E333A, G237A or G237A-E333S using a 40 µg/ml antibody concentration at (FIG. 24B) pH 6.0, or (FIG. 24D) pH 7.4. An FcRn ELISA was performed with 2 µg/mL coated recombinant extracellular domain of human FcRn (FcRnECDHis-B2M-BIO) and antibody dilution series. The amount of bound antibodies was determined with an HRP-conjugated goat anti-human IgG1 antibody and the chemiluminescent substrate ABTS. Absorbance was measured at 405 nm.

(FIG. 25A) Total hIgG concentration in blood samples collected from mice injected with wild-type IgG1-CAMPATH-1H, IgG1-CAMPATH-1H-E430G-K439E-G237Q or IgG1-CAMPATH-1H-E430G-K439E-G236R. (FIG. 25B) Total hIgG concentration in blood samples collected from mice injected with wild-type IgG1-11B8, IgG1-11B8-E430G-S440K-G237A or IgG1-11B8-E430G-S440K-E333S. (FIG. 25C) Total hIgG concentration in blood samples collected from mice injected with mixtures of wild-type IgG1-CAMPATH-1H+IgG1-11B8 or mixtures of IgG1-CAMPATH-1H and IgG1-11B8 antibody variants harboring the mutations as in (FIG. 25A) and (FIG. 25B). In all figures, the dotted line represents the predicted IgG1 concentration in time for wild-type IgG1 antibodies in SCID mice. (FIG. 25D) Clearance until day 21 after administration of the antibody was determined following the formula D*1000/AUC with D, injected dose and AUC, area under the curve of the concentration-time curve.

FIGS. 27A-27D show C1q binding to Wien 133 cells incubated on ice with normal human serum as a source of complement, after opsonization with variants of antibodies IgG1-CAMPATH-1H, IgG1-11B8 and IgG1-b12 harboring mutations E430G, K439E or S440K and G236R, G237T, K326A or E333S, detected by flow cytometry. Mean fluorescence intensity values were normalized to control reactions without antibody (0%) and the top level of a mixture of IgG1-CAMPATH-1H-E430G+IgG1-11B8-E430G (100%), estimated by fitting a log agonist response model. (FIG. 27A) C1q binding of control reactions. (FIGS. 27B-27D) C1q binding of (FIG. 27B) IgG1-CAMPATH-E430G-K439E, (FIG. 27C) IgG1-CAMPATH-E430G-K439E-G236R, and (FIG. 27D) IgG1-CAMPATH-E430G-K439E-G237R, mixed with non-binding control IgG1-b12 or different IgG1-11B8 variants.

(FIGS. 28A-28E) Binding of immobilized antibody variants to dimeric His-tagged biotinylated ECDs as tested in ELISA assays, of (FIG. 28A) high affinity allotype FcγRIIA 131H, (FIG. 28B) low affinity allotype FcγRIIA 131R, (FIG. 28C) FcγRIIB, (FIG. 28D) high affinity allotype FcγRIIIA 158V, or (FIG. 28E) low affinity allotype FcγRIIIA 158F. (FIG. 28F) Binding of immobilized FcγRIa to antibody variants tested in ELISA. Binding is presented for 20 µg/mL antibody samples and was normalized per experiment after subtraction of the signals in wells incubated without primary antibody relative to the averaged signal observed for wild type IgG1-CAMPATH-1H (100%). Detection was performed using Streptavidin-polyHRP and ABTS.

(FIG. 32A) Co-dependent CDC induced by mixtures containing equimolar and non-equimolar concentration ratios of IgG1-CAMPATH-1H-E430G-K439E-G236R and IgG1-11B8-E430G-S440K-G237A. (FIG. 32B) Co-dependent CDC induced by mixtures containing equimolar and non-equimolar concentration ratios of IgG1-CAMPATH-1H-E430G-K439E-G237Q and IgG1-11B8-E430G-S440K-G237A.

(FIG. 35A) CDC efficacy of antibody variants of IgG1-CAMPATH-1H and IgG1-11B8 as a single agent or mixtures thereof harboring Fc-Fc interaction enhancing mutations E430G, E430N, E430T, E430V, E430Y, E345A, E345K, E345Q, E345R or E345Y, self-oligomerization inhibiting mutations K439E or S440K and C1q-binding inhibiting mutations G236R or G237A. (FIG. 35B) CDC efficacy of antibody variants of IgG1-CAMPATH-1H and IgG1-11B8 as a single agent or mixtures thereof harboring Fc-Fc interaction enhancing mutations E430G, E430N, E430T, E430V, E430Y, E345A, E345Q, E345V or E345Y, self-oligomerization inhibiting mutations K439E or S440K and C1q-binding inhibiting mutations G236R or G237A. (FIG. 35C) CDC efficacy of antibody variants of IgG1-CAMPATH-1H and IgG1-11B8 as a single agent or mixtures thereof harboring matching Fc-Fc interaction enhancing mutations E430G, E430N, E430T, E430V, E430Y, E345A, E345Q, E345V or E345Y, self-oligomerization inhibiting mutations K439E or S440K and C1q-binding inhibiting mutations G236R or G237A. (FIG. 35D) CDC efficacy of antibody variants of IgG1-CAMPATH-1H and IgG1-11B8 as a single agent or mixtures thereof harboring Fc-Fc interaction enhancing mutations E430G or K248E-T437R, self-oligomerization inhibiting mutations K439E or S440K and C1q-binding modulating mutations G236R, G237A or E333S. CDC efficacy is presented as the AUC normalized to non-binding control antibody IgG1-b12 (0%) and the mixture of IgG1-CAMPATH-1H-E430G+IgG1-11B8-E430G (100%).

(FIG. 36A) Relative areas-under-the-curve (AUC), normalized to minimal lysis (0% with IgG1-b12) and maximal lysis (100% with the mixture of IgG1-CD37-37-3-E430G+IgG1-11B8-E430G), of cell lysis induced by the indicated antibody variants in dilution, or mixtures thereof. (FIG. 36B) Maximal percentage of lysis induced by the indicated antibody variants and mixtures thereof.

(FIG. 39A) Viability of BxPC-3 human pancreatic cancer cells after a 72 h incubation with the indicated antibody variants. (FIG. 39B) Viability of COLO 205 human colon cancer cells after a 72 h incubation with the indicated antibody variants. The percentage viable cells was calculated using the following formula: % viable cells=[(luminescence antibody sample–luminescence staurosporine sample)/(luminescence no antibody sample–luminescence staurosporine sample)]* 100.

DETAILED DESCRIPTION OF THE INVENTION

Figure 1A:
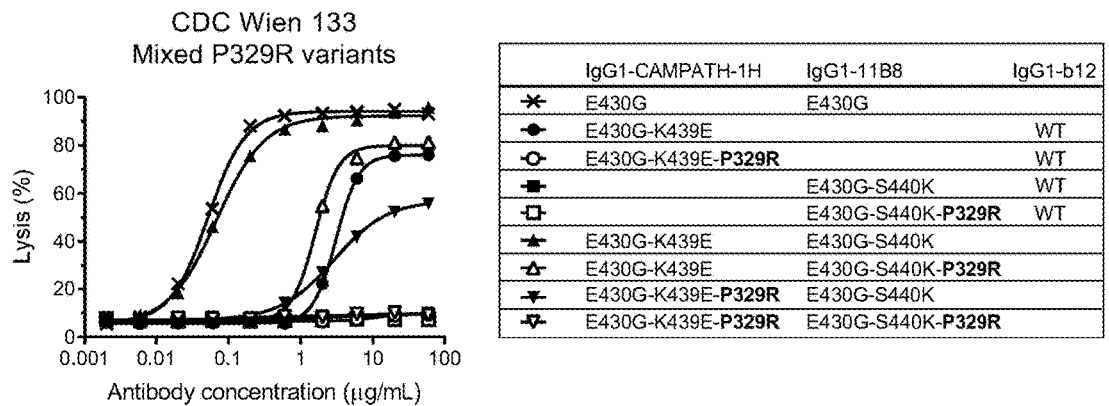
FIGS. 1A and 1B show selectivity of CDC activity by mixed antibody variants of anti-CD52 IgG1-CAMPATH-1H-E430G-K439E+anti-CD20 IgG1-11B8-E430G-S440K by introduction of the P329R mutation. Wien 133 cells were incubated with concentration antibody concentration series in the presence of 20% pooled normal human serum (NHS). CDC efficacy is presented as (FIG. 1A) percentage lysis determined by the percentage propidium iodide (PI)-positive cells and (FIG. 1B) the area under the dose response-response curves (AUC), normalized to non-binding control antibody IgG1-b12 (0%) and the mixture of IgG1-CAMPATH-1H-E430G+IgG1-11B8-E430G (100%).

In describing the embodiments of the invention specific terminology will be resorted to for the sake of clarity. However, the invention is not intended to be limited to the specific terms so selected, and it is understood that each specific term includes all technical equivalents which operate in a similar manner to accomplish a similar purpose.

Definitions

The term "parent antibody", is to be understood as an antibody, which is identical to an antibody according to the invention, but where the parent antibody does not have a C1q binding modulating substitution according to the present invention. Thus a parent antibody may have an Fc-Fc enhancing substitution and a self-oligomerization-inhibiting substitution. The term "C1q binding modulating substitution" is to be understood as a substitution that may inhibit C1q binding such as one substitution of the amino acid at position G237 or, one or more substitutions selected from the group consisting of: G236R, G236K, K322A, E269K, K322E and P329R or a substitution that may enhance C1q binding such as one or more substitutions selected from the group consisting of: K326A, K326W, E333A and E333S.

The term "polypeptide comprising an Fc-region of an immunoglobulin and a binding region" refers in the context of the present invention to a polypeptide which comprises an Fc-region of an immunoglobulin and a binding region which is a capable of binding to any molecule, such as a polypeptide, e.g. present on a cell, bacterium, or virion. The Fc-region of an immunoglobulin is defined as the fragment of an antibody which would be typically generated after digestion of an antibody with papain (which is known for someone skilled in the art) which includes the two CH2-CH3 regions of an immunoglobulin and a connecting region, e.g. a hinge region. The constant domain of an antibody heavy chain defines the antibody isotype, e.g. IgG1, IgG2, IgG3, IgG4, IgA1, IgA2, IgM, IgD, or IgE. The Fc-region mediates the effector functions of antibodies with cell surface receptors called Fc receptors and proteins of the complement system. The binding region may be a polypeptide sequence, such as a protein, protein ligand, receptor, an antigen-binding region, or a ligand-binding region capable of binding to a cell, bacterium, or virion. If the binding region is e.g. a receptor, the "polypeptide comprising an Fc-region of an immunoglobulin and a binding region" may have been prepared as a fusion protein of Fc-region of an immunoglobulin and said binding region. If the binding region is an antigen-binding region the "polypeptide comprising an Fc-region of an immunoglobulin and a binding region" may be an antibody, like a chimeric, humanized, or human antibody or a heavy chain only antibody or a ScFv-Fc-fusion. The polypeptide comprising an Fc-region of an immunoglobulin and a binding region may typically comprise a connecting region, e.g. a hinge region, and two CH2-CH3 regions of the heavy chain of an immunoglobulin, thus the "polypeptide comprising an Fc-region of an immunoglobulin and a binding region" may be a "polypeptide comprising at least an Fc-region of an immunoglobulin and a binding region". The term "Fc-region of an immunoglobulin" means in the context of the present invention that a connecting region, e.g. hinge depending on the subtype of antibody, and the CH2 and CH3 region of an immunoglobulin are present, e.g. a human IgG1, IgG2, IgG3, IgG4, IgD, IgA1, IgGA2, IgM, or IgE. The polypeptide is not limited to human origin but can be of any origin, such as e.g. mouse or cynomolgus origin. The term "wild type Fc-region" means in the context of the present invention an immunoglobulin Fc region with an amino acid sequence as it occurs in nature.

The term "hinge region" as used herein is intended to refer to the hinge region of an immunoglobulin heavy chain. Thus, for example the hinge region of a human IgG1 antibody corresponds to amino acids 216-230 according to the EU numbering.

The term "CH2 region" or "CH2 domain" as used herein is intended to refer to the CH2 region of an immunoglobulin heavy chain. Thus, for example the CH2 region of a human IgG1 antibody corresponds to amino acids 231-340 according to the EU numbering. However, the CH2 region may also be any of the other subtypes as described herein.

The term "CH3 region" or "CH3 domain" as used herein is intended to refer to the CH3 region of an immunoglobulin heavy chain. Thus, for example the CH3 region of a human IgG1 antibody corresponds to amino acids 341-447 according to the EU numbering. However, the CH3 region may also be any of the other subtypes as described herein.

The term "immunoglobulin" refers to a class of structurally related glycoproteins consisting of two pairs of polypeptide chains, one pair of light (L) low molecular weight chains and one pair of heavy (H) chains, all four potentially inter-connected by disulfide bonds. The structure of immunoglobulins has been well characterized. See for instance Fundamental Immunology Ch. 7 (Paul, W., ed., 2nd ed. Raven Press, N.Y. (1989)). Briefly, each heavy chain typically is comprised of a heavy chain variable region (abbreviated herein as VH) and a heavy chain constant region. The heavy chain constant region typically is comprised of three domains, CH1, CH2, and CH3. The heavy chains are inter-connected via disulfide bonds in the so-called "hinge region". Each light chain typically is comprised of a light chain variable region (abbreviated herein as VL) and a light chain constant region. The light chain constant region typically is comprised of one domain, CL. The VH and VL regions may be further subdivided into regions of hyper-variability (or hypervariable regions which may be hyper-variable in sequence and/or form of structurally defined loops), also termed complementarity determining regions (CDRs), interspersed with regions that are more conserved, termed framework regions (FRs). Each VH and VL is typically composed of three CDRs and four FRs, arranged from amino-terminus to carboxy-terminus in the following order: FR1, CDR1, FR2, CDR2, FR3, CDR3, FR4 (see also Chothia and Lesk J. Mol. Biol. 196, 901 917 (1987)). Unless otherwise stated or contradicted by context, CDR sequences herein are identified according to IMGT rules using DomainGapAlign (Lefranc M P., Nucleic Acids Research 1999; 27:209-212 and Ehrenmann F., Kaas Q. and Lefranc M.-P. Nucleic Acids Res., 38, D301-307 (2010); see also internet http address www.imgt.org/. Unless otherwise stated or contradicted by context, reference to amino acid positions in the Fc region/Fc domain in the present invention is according to the EU-numbering (Edelman et al., Proc Natl Acad Sci USA. 1969 May; 63(1):78-85; Kabat et al., Sequences of proteins of immunological interest. 5th Edition—1991 NIH Publication No. 91-3242).

The term "antibody" (Ab) in the context of the present invention refers to an immunoglobulin molecule, a fragment of an immunoglobulin molecule, or a derivative of either thereof, which has the ability to specifically bind to an antigen. The antibody of the present invention comprises an Fc-domain of an immunoglobulin and an antigen-binding region. An antibody generally contains two CH2-CH3 regions and a connecting region, e.g. a hinge region, e.g. at least an Fc-domain. Thus, the antibody of the present invention may comprise an Fc region and an antigen-binding region. The variable regions of the heavy and light chains of the immunoglobulin molecule contain a binding domain that interacts with an antigen. The constant or "Fc" regions of the antibodies may mediate the binding of the immunoglobulin to host tissues or factors, including various cells of the immune system (such as effector cells) and components of the complement system such as C1q, the first component in the classical pathway of complement activation. An antibody may also be a multispecific antibody, such as a bispecific antibody or similar molecule. The term "bispecific antibody" refers to an antibody having specificities for at least two different, typically non-overlapping, epitopes.

Such epitopes may be on the same or different targets. If the epitopes are on different targets, such targets may be on the same cell or different cells or cell types. As indicated above, unless otherwise stated or clearly contradicted by the context, the term antibody herein includes fragments of an antibody which comprise at least a portion of an Fc-region and which retain the ability to specifically bind to the antigen. Such fragments may be provided by any known technique, such as enzymatic cleavage, peptide synthesis and recombinant expression techniques. It has been shown that the antigen-binding function of an antibody may be performed by fragments of a full-length antibody. Examples of binding fragments encompassed within the term "Ab" or "antibody" include, without limitation, monovalent antibodies (described in WO2007059782 by Genmab); heavy-chain antibodies, consisting only of two heavy chains and naturally occurring in e.g. camelids (e.g., Hamers-Casterman (1993) Nature 363:446); ThioMabs (Roche, WO2011069104), strand-exchange engineered domain (SEED or Seed-body) which are asymmetric and bispecific antibody-like molecules (Merck, WO2007110205); Triomab (Pharma/Fresenius Biotech, Lindhofer et al. 1995 J Immunol 155:219; WO2002020039); FcΔAdp (Regeneron, WO2010151792), Azymetric Scaffold (Zymeworks/Merck, WO2012/058768), mAb-Fv (Xencor, WO2011/028952), Xmab (Xencor), Dual variable domain immunoglobulin (Abbott, DVD-Ig, U.S. Pat. No. 7,612,181); Dual domain double head antibodies (Unilever; Sanofi Aventis, WO20100226923), Di-diabody (ImClone/Eli Lilly), Knobs-into-holes antibody formats (Genentech, WO9850431); DuoBody (Genmab, WO 2011/131746); Bispecific IgG1 and IgG2 (Pfizer/Rinat, WO11143545), DuetMab (MedImmune, US2014/0348839), Electrostatic steering antibody formats (Amgen, EP1870459 and WO 2009089004; Chugai, US201000155133; Oncomed, WO2010129304A2); bispecific IgG1 and IgG2 (Rinat neurosciences Corporation, WO11143545), CrossMAbs (Roche, WO2011117329), LUZ-Y (Genentech), Biclonic (Merus, WO2013157953), Dual Targeting domain antibodies (GSK/Domantis), Two-in-one Antibodies or Dual action Fabs recognizing two targets (Genentech, NovImmune, Adimab), Cross-linked Mabs (Karmanos Cancer Center), covalently fused mAbs (AIMM), CovX-body (CovX/Pfizer), FynomAbs (Covagen/Janssen ilag), DutaMab (Dutalys/Roche), iMab (MedImmune), IgG-like Bispecific (ImClone/Eli Lilly, Shen, J., et al. J Immunol Methods, 2007. 318(1-2): p. 65-74), TIG-body, DIG-body and PIG-body (Pharmabcine), Dual-affinity retargeting molecules (Fc-DART or Ig-DART, by Macrogenics, WO/2008/157379, WO/2010/080538), BEAT (Glenmark), Zybodies (Zyngenia), approaches with common light chain (Crucell/Merus, U.S. Pat. No. 7,262,028) or common heavy chains (KBodies by NovImmune, WO2012023053), as well as fusion proteins comprising a polypeptide sequence fused to an antibody fragment containing an Fc-region like scFv-fusions, like BsAb by ZymoGenetics/BMS, HERCULES by Biogen Idec (US007951918), SCORPIONS by Emergent BioSolutions/Trubion and Zymogenetics/BMS, Ts2Ab (MedImmune/AZ (Dimasi, N., et al. J Mol Biol, 2009. 393(3): p. 672-92), scFv fusion by Genetech/Roche, scFv fusion by Novartis, scFv fusion by Immunomedics, scFv fusion by Changzhou Adam Biotech Inc (CN 102250246), TvAb by Roche (WO 2012025525, WO 2012025530), mAb$^2$ by f-Star (WO2008/003116), and dual scFv-fusions. It also should be understood that the term antibody, unless specified otherwise, also includes polyclonal antibodies, monoclonal antibodies (such as human monoclonal antibodies), antibody mixtures (recombinant polyclonals) for instance generated by technologies exploited by Symphogen and Merus (Oligoclonics), multimeric Fc proteins as described in WO2015/158867, fusion proteins as described in WO2014/031646 and antibody-like polypeptides, such as chimeric antibodies and humanized antibodies. An antibody as generated can potentially possess any isotype.

The term "full-length antibody" when used herein, refers to an antibody (e.g., a parent antibody) which contains all heavy and light chain constant and variable domains corresponding to those that are normally found in a wild-type antibody of that isotype.

The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations, insertions or deletions introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

The term "chimeric antibody", as used herein, refers to an antibody in which both chain types i.e. heavy chain and light chain are chimeric as a result of antibody engineering. A chimeric chain is a chain that contains a foreign variable domain (originating from a non-human species, or synthetic or engineered from any species including human) linked to a constant region of human origin.

The term "humanized antibody, as used herein, refers to an antibody in which both chain types are humanized as a result of antibody engineering. A humanized chain is typically a chain in which the complementarity determining regions (CDR) of the variable domains are foreign (originating from a species other than human, or synthetic) whereas the remainder of the chain is of human origin. Humanization assessment is based on the resulting amino acid sequence, and not on the methodology per se, which allows protocols other than grafting to be used.

The terms "monoclonal antibody", "monoclonal Ab", "monoclonal antibody composition", "mAb", or the like, as used herein refer to a preparation of Ab molecules of single molecular composition. A monoclonal antibody composition displays a single binding specificity and affinity for a particular epitope. Accordingly, the term "human monoclonal antibody" refers to Abs displaying a single binding specificity which have variable and constant regions derived from human germline immunoglobulin sequences. The human mAbs may be generated by a hybridoma which includes a B cell obtained from a transgenic or trans-chromosomal non-human animal, such as a transgenic mouse, having a genome comprising a human heavy chain transgene repertoire and a light chain transgene repertoire, rearranged to produce a functional human antibody and fused to an immortalized cell.

The term "isotype" as used herein, refers to the immunoglobulin class (for instance IgG1, IgG2, IgG3, IgG4, IgD, IgA1, IgGA2, IgE, or IgM or any allotypes thereof such as IgG1m(za) and IgG1m(f)) that is encoded by heavy chain constant region genes. Further, each heavy chain isotype can be combined with either a kappa (κ) or lambda (k) light chain. The term "mixed isotype" used herein refers to Fc region of an immunoglobulin generated by combining structural features of one isotype with the analogous region from another isotype thereby generating a hybrid isotype. A mixed isotype may comprise an Fc region having a sequence comprised of two or more isotypes selected from the following IgG1, IgG2, IgG3, IgG4, IgD, IgA1, IgGA2, IgE, or IgM thereby generating combinations such as e.g. IgG1/IgG3, IgG1/IgG4, IgG2/IgG3, IgG2/IgG4 or IgG1/IgA.

The term "antigen-binding region", "antigen binding region", "binding region" or antigen binding domain, as used herein, refers to a region of an antibody which is capable of binding to the antigen. This binding region is typically defined by the VH and VL domains of the antibody which may be further subdivided into regions of hypervariability (or hypervariable regions which may be hypervariable in sequence and/or form of structurally defined loops), also termed complementarity determining regions (CDRs), interspersed with regions that are more conserved, termed framework regions (FRs). The antigen can be any molecule, such as a polypeptide, e.g. present on a cell, bacterium, or virion.

The term "target", as used herein, refers to a molecule to which the antigen binding region of the antibody binds. The target includes any antigen towards which the raised antibody is directed. The term "antigen" and "target" may in relation to an antibody be used interchangeably and constitute the same meaning and purpose with respect to any aspect or embodiment of the present invention.

The term "epitope" means a molecular determinant capable of specific binding to an antibody variable domain. Epitopes usually consist of surface groupings of molecules such as amino acids, sugar side chains or a combination thereof and usually have specific three-dimensional structural characteristics, as well as specific charge characteristics. Conformational and non-conformational epitopes are distinguished in that the binding to the former but not the latter is lost in the presence of denaturing solvents. The epitope may comprise amino acid residues directly involved in the binding (also called immunodominant component of the epitope) and other amino acid residues, which are not directly involved in the binding.

An "antibody" or "antibody variant" or a "variant of a parent antibody" of the present invention is an antibody molecule which comprises one or more mutations as compared to a "parent antibody". The different terms may be used interchangeably and constitute the same meaning and purpose with respect to any aspect or embodiment of the present invention. Exemplary parent antibody formats include, without limitation, a wild-type antibody, a full-length antibody or Fc-containing antibody fragment, a bispecific antibody, a human antibody, humanized antibody, chimeric antibody or any combination thereof. The different terms may be used interchangeably and constitute the same meaning and purpose with respect to any aspect or embodiment of the present invention. Amino acid substitutions may exchange a native amino acid for another naturally-occurring amino acid, or for a non-naturally-occurring amino acid derivative. The amino acid substitution may be conservative or non-conservative. In the context of the present invention, conservative substitutions may be defined by substitutions within the classes of amino acids reflected in one or more of the following three tables:

| Amino acid residue classes for conservative substitutions | |
|---|---|
| Acidic Residues | Asp (D) and Glu (E) |
| Basic Residues | Lys (K), Arg (R), and His (H) |
| Hydrophilic Uncharged Residues | Ser (S), Thr (T), Asn (N), and Gln (Q) |
| Aliphatic Uncharged Residues | Gly (G), Ala (A), Val (V), Leu (L), and Ile (I) |
| Non-polar Uncharged Residues | Cys (C), Met (M), and Pro (P) |
| Aromatic Residues | Phe (F), Tyr (Y), and Trp (W) |

| Alternative conservative amino acid residue substitution classes | | | |
|---|---|---|---|
| 1 | A | S | T |
| 2 | D | E | |
| 3 | N | Q | |
| 4 | R | K | |
| 5 | I | L | M |
| 6 | F | Y | W |

| Alternative Physical and Functional Classifications of Amino Acid Residues | |
|---|---|
| Alcohol group-containing residues | S and T |
| Aliphatic residues | I, L, V, and M |
| Cycloalkenyl-associated residues | F, H, W, and Y |
| Hydrophobic residues | A, C, F, G, H, I, L, M, R, T, V, W, and Y |
| Negatively charged residues | D and E |
| Polar residues | C, D, E, H, K, N, Q, R, S, and T |
| Positively charged residues | H, K, and R |
| Small residues | A, C, D, G, N, P, S, T, and V |
| Very small residues | A, G, and S |
| Residues involved in turn formation | A, C, D, E, G, H, K, N, Q, R, S, P, and T |
| Flexible residues | Q, T, K, S, G, N, D, E, and R |

In the context of the present invention, a substitution in a variant is indicated as:

Original amino acid—position—substituted amino acid;

The three letter code, or one letter code, are used, including the codes Xaa and X to indicate amino acid residue. Accordingly, the notation "E345R" or "Glu345Arg" means, that the variant comprises a substitution of Glutamic acid with Arginine in the variant amino acid position corresponding to the amino acid in position 345 in the parent antibody.

Where a position as such is not present in an antibody, but the variant comprises an insertion of an amino acid, for example:

Position—substituted amino acid; the notation, e.g., "448E" is used.

Such notation is particular relevant in connection with modification(s) in a series of homologous polypeptides or antibodies.

Similarly when the identity of the substitution amino acid residues(s) is immaterial:

Original amino acid—position; or "E345".

For a modification where the original amino acid(s) and/or substituted amino acid(s) may comprise more than one, but not all amino acid(s), the substitution of Glutamic acid for Arginine, Lysine or Tryptophan in position 345:

"Glu345Arg, Lys,Trp" or "E345R,K,W" or "E345R/K/W" or "E345 to R, K or W" may be used interchangeably in the context of the invention.

Furthermore, the term "a substitution" embraces a substitution into any one of the other nineteen natural amino acids, or into other amino acids, such as non-natural amino acids. For example, a substitution of amino acid E in position 345 includes each of the following substitutions:

345A, 345C, 345D, 345G, 345H, 345F, 345I, 345K, 345L, 345M, 345N, 345P, 345Q, 345R, 345S, 345T, 345V, 345W, and 345Y. This is equivalent to the designation 345X, wherein the X designates any amino acid. These substitutions can also be designated E345A, E345C, etc, or E345A, C, etc, or E345A/C/etc. The same applies to analogy to each and every position mentioned herein, to specifically include herein any one of such substitutions.

As used herein, the term "effector cell" refers to an immune cell which is involved in the effector phase of an immune response, as opposed to the recognition and activation phases of an immune response. Exemplary immune cells include a cell of a myeloid or lymphoid origin, for instance lymphocytes (such as B cells and T cells including cytolytic T cells (CTLs)), killer cells, natural killer cells, macrophages, monocytes, eosinophils, polymorphonuclear cells, such as neutrophils, granulocytes, mast cells, and basophils. Some effector cells express Fc receptors (FcRs) or complement receptors and carry out specific immune functions. In some embodiments, an effector cell such as, e.g., a natural killer cell, is capable of inducing ADCC. For example, monocytes, macrophages, neutrophils, dendritic cells and Kupffer cells which express FcRs, are involved in specific killing of target cells and presenting antigens to other components of the immune system, or binding to cells that present antigens. In some embodiments the ADCC can be further enhanced by antibody driven classical complement activation resulting in the deposition of activated C3 fragments on the target cell. C3 cleavage products are ligands to complement receptors (CRs), such as CR3, expressed on myeloid cells. The recognition of complement fragments by CRs on effector cells may promote enhanced Fc receptor-mediated ADCC. In some embodiments antibody driven classical complement activation leads to C3 fragments on the target cell. These C3 cleavage products may promote direct complement-dependent cellular cytotoxicity (CDCC). In some embodiments, an effector cell may phagocytose a target antigen, target particle or target cell. The expression of a particular FcR or complement receptor on an effector cell may be regulated by humoral factors such as cytokines. For example, expression of FcγRI has been found to be up-regulated by interferon γ (IFN γ) and/or G-CSF. This enhanced expression increases the cytotoxic activity of FcγRI-bearing cells against targets. An effector cell can phagocytose a target antigen or phagocytose or lyse a target cell. In some embodiments antibody driven classical complement activation leads to C3 fragments on the target cell. These C3 cleavage products may promote direct phagocytosis by effector cells or indirectly by enhancing antibody mediated phagocytosis.

The term "Fc effector functions," or "Fc-mediated effector functions," as used herein, is intended to refer to functions that are a consequence of binding a polypeptide or antibody to its target, such as an antigen, on a cell membrane wherein the Fc effector function is attributable to the Fc region of the polypeptide or antibody. Examples of Fc effector functions include (i) C1q-binding, (ii) complement activation, (iii) complement-dependent cytotoxicity (CDC), (iv) antibody-dependent cell-mediated cytotoxicity (ADCC), (v) Fc-gamma receptor-binding, (vi) antibody-dependent cellular phagocytosis (ADCP), (vii) complement-dependent cellular cytotoxicity (CDCC), (viii) complement-enhanced cytotoxicity, (ix) binding to complement receptor of an opsonized antibody mediated by the antibody, (x) opsonisation, and (xi) a combination of any of (i) to (x).

The term "clustering-dependent functions," as used herein, is intended to refer to functions that are a consequence of the formation of antigen complexes after oligomerization of polypeptides or antibodies bound to their antigens, optionally on a cell, on a cell membrane, on a virion, or on another particle. Examples of clustering-dependent effector functions include (i) antibody oligomer formation, (ii) antibody oligomer stability, (iii) antigen oligomer formation, (iv) antigen oligomer stability, (v) induction of apoptosis, (vi) proliferation modulation, such as proliferation reduction, inhibition or stimulation, and (vii) a combination of any of (i) to (vi).

The term "agonistic", as used herein, is understood as stimulation or activation of a receptor on a cell membrane resulting in a biological response such as, intracellular signaling. Such an agonistic effect could result in, induction of apoptosis (programmed cell death) or activation of immune cells, or activation of an intracellular pathway.

Agonistic activity or increased agonistic activity may be determined in a viability assay for antibodies directed to targets expressing an intracellular death domain, as described in Example 16 using the following steps of:
  i) Seed a cell line expressing a target corresponding to an antibody e.g. DR5 in polystyrene 96-well flat-bottom plate overnight 37° C.,
  ii) Add a serial dilution of the antibody e.g. an anti-DR5 antibody in a range (0.0003 to 20,000 ng/mL) and incubate for 3 days at 37° C.,
  iii) Determine cell viability by quantifying the presence of ATP e.g. by use of CellTiter-Glo luminescent cell viability assay,
  iv) Calculate the viable cells using the following formula: % viable cells=[(luminescence antibody sample−luminescence staurosporine sample)/(luminescence no antibody sample−luminescence staurosporine sample)]* 100.

Agonistic activity or increased agonistic activity may be determined in a reporter assay for antibodies directed to targets activating intracellular signaling pathway, as described in Example 29, 30, 31 and 32 using the following steps of:
  i) Seed Jurkat cells stably transfected with the target and a luciferase reporter gene downstream of an NFAT response element expressing, the cells are incubated in a 96-well flat-bottom plate overnight 37° C.,
  ii) Add a serial dilution of the antibody e.g. an antibody in a range e.g. 19.5 to 5,000 ng/mL and incubate for 5 hours,
  iii) Add a firefly luciferase substrate (5'-fluoroluciferin) to the cells and incubate for 5-10 minutes,
  iv) Determine the luminescence using an Envision MultiLable Plate reader.

The term "vector," as used herein, is intended to refer to a nucleic acid molecule capable of inducing transcription of a nucleic acid segment ligated into the vector. One type of vector is a "plasmid", which is in the form of a circular double stranded DNA loop. Another type of vector is a viral vector, wherein the nucleic acid segment may be ligated into the viral genome. Certain vectors are capable of autonomous replication in a host cell into which they are introduced (for instance bacterial vectors having a bacterial origin of replication and episomal mammalian vectors). Other vectors (such as non-episomal mammalian vectors) may be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the present invention is intended to include such other forms of expression vectors, such as viral vectors (such as replication defective retroviruses, adenoviruses and adeno-associated viruses), which serve equivalent functions.

The term "recombinant host cell" (or simply "host cell"), as used herein, is intended to refer to a cell into which an expression vector has been introduced. It should be understood that such terms are intended to refer not only to the particular subject cell, but also to the progeny of such a cell. Because certain modifications may occur in succeeding generations due to either mutation or environmental influences, such progeny may not, in fact, be identical to the parent cell, but are still included within the scope of the term "host cell" as used herein. Recombinant host cells include, for example, transfectomas, such as CHO cells, HEK-293 cells, PER.C6, NS0 cells, and lymphocytic cells, and prokaryotic cells such as E. coli and other eukaryotic hosts such as plant cells and fungi.

The term "transfectoma", as used herein, includes recombinant eukaryotic host cells expressing the Ab or a target antigen, such as CHO cells, PER.C6, NS0 cells, HEK-293 cells, plant cells, or fungi, including yeast cells.

The term "preparation" refers to preparations of antibody variants and mixtures of different antibody variants which can have an increased ability to form oligomers when interacting with antigen associated with a cell (e.g., an antigen expressed on the surface of the cell), a cell membrane, a virion or other structure, which may result in enhanced signaling and/or activation by the antigen.

As used herein, the term "affinity" is the strength of binding of one molecule, e.g. an antibody, to another, e.g. a target or antigen, at a single site, such as the monovalent binding of an individual antigen binding site of an antibody to an antigen.

As used herein, the term "avidity" refers to the combined strength of multiple binding sites between two structures, such as between multiple antigen binding sites of antibodies simultaneously interacting with a target or e.g. between antibody and C1q. When more than one binding interactions are present, the two structures will only dissociate when all binding sites dissociate, and thus, the dissociation rate will be slower than for the individual binding sites, and thereby providing a greater effective total binding strength (avidity) compared to the strength of binding of the individual binding sites (affinity).

As used herein, the term "oligomer" refers to a molecule that consists of more than one but a limited number of monomer units (e.g. antibodies) in contrast to a polymer that, at least in principle, consists of an unlimited number of monomers. Exemplary oligomers are dimers, trimers, tetramers, pentamers and hexamers. Greek prefixes are often used to designate the number of monomer units in the oligomer, for example a tetramer being composed of four units and a hexamer of six units.

The term "oligomerization", as used herein, is intended to refer to a process that converts monomers to a finite degree of polymerization. Herein, it is observed, that, antibodies comprising target-binding regions according to the invention can form oligomers, such as hexamers, via non-covalent association of Fc-regions after target binding, e.g., at a cell surface. In the context of the present application, "self-oligomerization", or "auto-oligomerization" is intended to refer to a process of oligomerization between antibody molecules that have identical protein sequences disregarding post-translational modifications. The term "hetero-oligomerization", as used herein, is intended to refer to a process of oligomerization between antibody molecules that have different protein sequences disregarding post-translational modifications. Different antibodies participating in hetero-oligomerization could for instance bind different antigens, such as different target proteins, glycoproteins, glycans, or glycolipids.

The term "self-oligomerization inhibiting substitution" or ""self-oligomerization inhibiting-substitution"" is intended to refer to a substitution in an antibody comprising an Fc region of an immunoglobulin and an antigen binding region, that inhibits the process of oligomerization between antibody molecules that have identical protein sequences disregarding post-translational modifications. Inhibition of self-oligomerization can for example result in an increased EC50 of CDC activity or a reduction in maximal CDC lysis activity of the polypeptide, measured according to the methods described in examples 2 and 15. Examples of self-oligomerization inhibiting substitutions are K439E and S440K.

The term "clustering", as used herein, is intended to refer to oligomerization of antibodies, polypeptides, antigens or other proteins through non-covalent interactions.

The term "Fc-Fc enhancing", as used herein, is intended to refer to increasing the binding strength between, or stabilizing the interaction between, the Fc regions of two Fc-region containing antibodies or polypeptides so that the polypeptides form oligomers upon target binding.

Fc-Fc enhancing substitutions, as used herein refer to substitutions in the following positions corresponding to human IgG1 according to EU numbering E430, E345 or S440 with the proviso that the substitutions in position S440 is S440Y or S440W. Thus, Fc-Fc enhancing substitutions as used herein refer to the following amino acid substitutions E430G, E345K, E430S, E430F, E430T, E345Q, E345R, E345Y, S440W and S440Y. In a preferred embodiment the Fc-Fc enhancing substitution is E430G, E345K or E345R.

When used herein in the context of two antigens, the term "co-located" or grammatical variations thereof, is intended to refer, on one hand, to situations where the two antigens are co-expressed on the same cell. The antigens may already be adjacent to each other on the cell or the antigens may be brought together via oligomerization of the binding polypeptides, e.g. antibodies, of the invention. Furthermore, the term "co-located" is also intended to refer to situations wherein the two antigens are expressed on different cells, but wherein such cells are located in close proximity to each other. The term "co-dependent", as used herein, is intended to refer to a functional effect that is dependent on the simultaneous binding of two or more different Fc-domain containing polypeptides with self-oligomerization inhibiting substitutions to the same target, cell, or virion. In the context of the present invention, functional effects that can be co-dependent include clustering-dependent functions, Fc-mediated effector functions, and the binding of effector molecules such as FcγR or C1, but not necessarily the individual binding of Fc-domain containing polypeptides to their target antigens. As used herein, different Fc-domain containing polypeptides with self-oligomerization inhibiting substitutions may each individually bind different targets, cells, or virions, but the co-dependent functional outcome is dependent on simultaneous binding of two or more different components to the same target, cell or virion. As used herein, co-dependent functional effects are recovered specifically by the two or more different Fc-domain containing polypeptides with self-oligomerization inhibiting substitutions by virtue of the restoration of non-covalent Fc-Fc interactions between different components in the co-dependent Fc-containing polypeptide mixture.

The term "safety margin", as used herein, is intended to refer to the index of the drug's effectiveness and safety and is defined as the range between the minimal therapeutic dose (efficacy on diseased tissue) and the minimal toxic dose (efficacy on healthy tissue) of the drug.

The term "C1q binding" as used herein, is intended to refer to the direct interaction between C1q and antibody. Direct C1q binding can be evaluated for example by using immobilized antibody on artificial surface. The multivalent interaction resulting in high avidity binding of C1q to an antibody oligomer can be evaluated when bound to a predetermined antigen on a cellular or virion surface.

C1q binding to a polypeptide or an antibody may be demined in an ELISA assay using the following steps i) coat a 96-well Microlon ELISA plate with the 1 µg/mL of polypeptide or antibody in 100 µl PBS at 4° C. overnight, ii) incubate the plate with 100 µL/well of a serial dilution series of C1q, final C1q concentration range 30-0.01 µg/mL in 3 fold dilutions for 1 h at 37 C, iii) incubate the plate with 100 µl/well of rabbit anti-human C1q for 1 h at RT, iv) incubate the plate with 100 µl/well swine anti-rabbit IgG-HRP for 1 h at RT, v) incubate the plate with 100 µL/well of substrate with 1 mg/mL 2,2'-azino-bis (3-ethylbenzothiazoline-6-sulfonic acid) for 15 min at RT, vi) the reaction is stopped by adding 100 µL 2% oxalic acid/well. The absorbance is measured at 405 nm in a BioTek EL808 Microplate reader.

The term C1q binding substitution as used herein, is intended to refer to a substitution in a polypeptide comprising an Fc region of an immunoglobulin and an antigen binding region, that enhances the direct interaction with C1q. Enhanced C1q binding can for example result in a decreased EC50 of the interaction between C1q and the polypeptide comprising an Fc region of an immunoglobulin and an antigen binding region, measured according to the method to determine C1q binding described above.

As used herein, the term "complement activation" refers to the activation of the classical complement pathway, which is initiated by a large macromolecular complex called C1 binding to antibody-antigen complexes on a surface. C1 is a complex, which consists of 6 recognition proteins C1q and a hetero-tetramer of serine proteases, C1r2C1s2. C1 is the first protein complex in the early events of the classical complement cascade that involves a series of cleavage reactions that starts with the cleavage of C4 into C4a and C4b and C2 into C2a and C2b. C4b is deposited and forms together with C2a an enzymatic active convertase called C3 convertase, which cleaves complement component C3 into C3b and C3a, which forms a C5 convertase. This C5 convertase splits C5 in C5a and C5b and the last component is deposited on the membrane and that in turn triggers the late events of complement activation in which terminal complement components C5b, C6, C7, C8 and C9 assemble into the membrane attack complex (MAC). The complement cascade results in the creation of pores in the cell membrane which causes lysis of the cell, also known as complement-dependent cytotoxicity (CDC). Complement activation can be evaluated by using C1q efficacy, CDC kinetics CDC assays (as described in WO2013/004842, WO2014/108198) or by the method Cellular deposition of C3b and C4b described in Beurskens et al. in Journal of Immunology, 2012 vol. 188 no. 7, April 1, 3532-3541.

The term "complement-dependent cytotoxicity" ("CDC"), as used herein, is intended to refer to the process of antibody-mediated complement activation leading to lysis of the cell or virion when the antibody bound to its target on a cell or virion as a result of pores in the membrane that are created by MAC assembly.

The term "antibody-dependent cell-mediated cytotoxicity" ("ADCC") as used herein, is intended to refer to a mechanism of killing of antibody-coated target cells or virions by cells expressing Fc receptors that recognize the constant region of the bound antibody. The term "antibody-dependent cellular phagocytosis" ("ADCP") as used herein is intended to refer to a mechanism of elimination of antibody-coated target cells or virions by internalization by phagocytes. The internalized antibody-coated target cells or virions are contained in a vesicle called a phagosome, which then fuses with one or more lysosomes to form a phagolysosome. ADCP may be evaluated by using an in vitro cytotoxicity assay with macrophages as effector cells and video microscopy as described by van Bij et al. in Journal of Hepatology Volume 53, Issue 4, October 2010, Pages 677-685.

The term "complement-dependent cellular cytotoxicity" ("CDCC") as used herein is intended to refer to a mechanism of killing of target cells or virions by cells expressing complement receptors that recognize complement 3 (C3) cleavage products that are covalently bound to the target cells or virions as a result of antibody-mediated complement activation. CDCC may be evaluated in a similar manner as described for ADCC.

The term "plasma half-life" as used herein indicates the time it takes to reduce the concentration of polypeptide in the blood plasma to one half of its initial concentration during elimination (after the distribution phase). For antibodies the distribution phase will typically be 1-3 days during which phase there is about 50% decrease in blood plasma concentration due to redistribution between plasma and tissues. The plasma half-life can be measured by methods well-known in the art.

The term "plasma clearance rate" as used herein is a quantitative measure of the rate at which a polypeptide is removed from the blood upon administration to a living organism. The plasma clearance rate may be calculated as the dose/AUC (mL/day/kg), wherein the AUC value (area under the curve) is determined from a concentration-time curve.

The term "antibody-drug conjugate", as used herein refers to an antibody or Fc-containing polypeptide having specificity for at least one type of malignant cell, a drug, and a linker coupling the drug to e.g. the antibody. The linker is cleavable or non-cleavable in the presence of the malignant cell; wherein the antibody-drug conjugate kills the malignant cell.

The term "antibody-drug conjugate uptake", as used herein refers to the process in which antibody-drug conjugates are bound to a target on a cell followed by uptake/engulfment by the cell membrane and thereby are drawn into the cell. Antibody-drug conjugate uptake may be evaluated as "antibody-mediated internalization and cell killing by anti-TF ADC in an in vitro killing assay" as described in WO 2011/157741.

The term "apoptosis", as used herein refers to the process of programmed cell death (PCD) that may occur in a cell. Biochemical events lead to characteristic cell changes (morphology) and death. These changes include blebbing, cell shrinkage, nuclear fragmentation, chromatin condensation, and chromosomal DNA fragmentation. Binding of an antibody to a certain receptor may induce apoptosis.

The term "programmed cell-death" or "PCD", as used herein refers to the death of a cell in any form mediated by an intracellular program. Different forms of PCD exist, the various types of PCD have in common that they are executed by active cellular processes that can be intercepted by interfering with intracellular signaling. In a particular embodiment, the occurrence of any form of PCD in a cell or tissue may be determined by staining the cell or tissue with conjugated Annexin V, correlating to phosphatidylserine exposure.

The term "Annexin V", as used herein, refers to a protein of the annexin group that binds phosphatidylserine (PS) on the cell surface.

The term "FcRn", as used herein is intended to refer to neonatal Fc receptor which is an Fc receptor. It was first discovered in rodents as a unique receptor capable of transporting IgG from mother's milk across the epithelium of newborn rodent's gut into the newborn's bloodstream. Further studies revealed a similar receptor in humans. In humans, however, it is found in the placenta to help facilitate transport of mother's IgG to the growing fetus and it has also been shown to play a role in monitoring IgG turnover. FcRn binds IgG at acidic pH of 6.0-6.5 but not at neutral or higher pH. Therefore, FcRn can bind IgG from the intestinal lumen (the inside of the gut) at a slightly acidic pH and ensure efficient unidirectional transport to the basolateral side (inside the body) where the pH is neutral to basic (pH 7.0-7.5). This receptor also plays a role in adult salvage of IgG through its occurrence in the pathway of endocytosis in endothelial cells. FcRn receptors in the acidic endosomes bind to IgG internalized through pinocytosis, recycling it to the cell surface, releasing it at the basic pH of blood, thereby preventing it from undergoing lysosomal degradation. This mechanism may provide an explanation for the greater half-life of IgG in the blood compared to other isotypes.

The term "Protein A", as used herein is intended to refer to a 56 kDa MSCRAMM surface protein originally found in the cell wall of the bacterium *Staphylococcus aureus*. It is encoded by the spa gene and its regulation is controlled by DNA topology, cellular osmolarity, and a two-component system called ArlS-ArlR. It has found use in biochemical research because of its ability to bind immunoglobulins. It is composed of five homologous Ig-binding domains that fold into a three-helix bundle. Each domain is able to bind proteins from many of mammalian species, most notably IgGs. It binds the heavy chain Fc region of most immunoglobulins (overlapping the conserved binding site of FcRn receptors) and also interacts with the Fab region of the human VH3 family. Through these interactions in serum, IgG molecules bind the bacteria via their Fc region instead of solely via their Fab regions, by which the bacteria disrupts opsonization, complement activation and phagocytosis.

The term "Protein G", as used herein is intended to refer to an immunoglobulin-binding protein expressed in group C and G Streptococcal bacteria much like Protein A but with differing specificities. It is a 65-kDa (G148 protein G) and a 58 kDa (C40 protein G) cell surface protein that has found application in purifying antibodies through its binding to the Fc region.

SPECIFIC EMBODIMENTS OF THE INVENTION

As described herein, in a first aspect, the invention relates to a first antibody for use as a medicament in combination with a second antibody, wherein the activity of the first and second antibody is co-dependent and the first antibody has an Fc region having one Fc-Fc enhancing, a self-oligomerization-inhibiting substitution and one or more substitution(s) which reduces effector functions such as CDC and/or ADCC and the second antibody has an Fc region having one Fc-Fc enhancing self-oligomerization-inhibiting substitution and optionally one or more substitution(s) which enhances Fc effector functions such as CDC and/or ADCC. Thus, such a combination of a first and a second antibody where the effect of the first antibody is dependent on the presence of the second antibody and the effect of the second antibody is dependent on the presence of the first antibody may increase the safety margin for the use of such a combination of a first and second antibody.

As shown by the inventors of the present invention a first antibody which has an Fc region having one Fc-Fc enhancing substitution and one or more substitution(s) which reduces effector functions such as CDC and/or ADCC and a complementary self-oligomerization-inhibiting substitution shows no or only very limited CDC activity when used as a single antibody. Similar a second antibody according to the invention which has an Fc region having one Fc-Fc enhancing substitution and one or more substitution(s) which enhances Fc effector functions such as CDC and/or ADCC and a complementary self-oligomerization-inhibiting substitution shows only a limited CDC activity when used as a single antibody. However, surprisingly the combination of a first and a second antibody according to the invention is able to restore the induced CDC level while the single agents showed no or limited ability to induce CDC.

In one aspect the present invention provides a first antibody comprising a first Fc region of a human IgG and a first antigen-binding region capable of binding to a first antigen, for use as a medicament in combination with a second antibody comprising a second Fc region of a human IgG and a second antigen-binding region capable of binding to a second antigen, wherein said first Fc region comprises
  a. one substitution of an amino acid at a position selected from the group consisting of: E430, E345 and S440, with the proviso that the substitution in S440 is S440Y or S440W, and
  b. a K439E or S440K substitution, with the proviso that the substitution is not S440K if the substitution in (a) is S440Y or S440W, and
  c. one or more amino acid substitutions selected from the group consisting of: L234, L235, G237, G236 or, one or more substitutions selected from the group consisting of: K322A and E269K;
  and said second Fc region comprises
  d. one substitution of an amino acid at a position selected from the group consisting of: E430, E345 and S440, with the proviso that the substitution in S440 is S440Y or S440W, and
  e. a K439E or S440K substitution, with the proviso that the substitution is not S440K if the substitution in (d) is S440Y or S440W;
wherein the first Fc region has a K439E substitution and the second Fc region has a S440K substitution or, the first Fc region has a S440K substitution and the second Fc region has a K439E substitution; wherein the amino acid positions correspond to human IgG1 according to Eu numbering system.

In another aspect the present invention provides a first antibody comprising a first Fc region of a human IgG and a first antigen-binding region capable of binding to a first antigen, for use as a medicament in combination with a second antibody comprising a second Fc region of a human IgG and a second antigen-binding region capable of binding to a second antigen, wherein said first Fc region comprises
a. one substitution of an amino acid at a position selected from the group consisting of: E430, E345 and S440, with the proviso that the substitution in S440 is S440Y or S440W, and
b. a K439E or S440K substitution, with the proviso that the substitution is not S440K if the substitution in (a) is S440Y or S440W, and
c. one substitution of the amino acid at position G237 or, one or more substitutions selected from the group consisting of: G236R, G236K, K322A, E269K, K322E, P329R, L234A, L234F, L235A, L235Q, and L235E;

and said second Fc region comprises
d. one substitution of an amino acid at a position selected from the group consisting of: E430, E345 and S440, with the proviso that the substitution in S440 is S440Y or S440W, and
e. a K439E or S440K substitution, with the proviso that the substitution is not S440K if the substitution in (d) is S440Y or S440W and
f. one or more substitutions selected from the group consisting of: K326A, K326W, E333A and E333S if the first Fc region comprises a K322E or P329R substitution;

wherein the first Fc region has a K439E substitution and the second Fc region has a S440K substitution or, the first Fc region has a S440K substitution and the second Fc region has a K439E substitution; wherein the amino acid positions correspond to human IgG1 according to EU numbering system (Edelman et al., Proc Natl Acad Sci USA. 1969 May; 63(1):78-85; Kabat et al., Sequences of Proteins of Immunological Interest, Fifth Edition. 1991 NIH Publication No. 91-3242).

In one aspect the present invention provides a first antibody comprising a first Fc region of a human IgG and a first antigen-binding region capable of binding to a first antigen, for use as a medicament in combination with a second antibody comprising a second Fc region of a human IgG and a second antigen-binding region capable of binding to a second antigen, wherein said first Fc region comprises
a. one substitution of an amino acid at a position selected from the group consisting of: E430, E345 and S440, with the proviso that the substitution in S440 is S440Y or S440W, and
b. a K439E or S440K substitution, with the proviso that the substitution is not S440K if the substitution in (a) is S440Y or S440W, and
c. one substitution of the amino acid at position G237 or, one or more substitutions selected from the group consisting of: G236R, G236K, K322A, E269K, L234A, L234F, L235A, L235Q, and L235E;

and said second Fc region comprises
d. one substitution of an amino acid at a position selected from the group consisting of: E430, E345 and S440, with the proviso that the substitution in S440 is S440Y or S440W, and
e. a K439E or S440K substitution, with the proviso that the substitution is not S440K if the substitution in (d) is S440Y or S440W;

wherein the first Fc region has a K439E substitution and the second Fc region has a S440K substitution or, the first Fc region has a S440K substitution and the second Fc region has a K439E substitution; wherein the amino acid positions correspond to human IgG1 according to Eu numbering system.

In one aspect the present invention provides a first antibody comprising a first Fc region of a human IgG and a first antigen-binding region capable of binding to a first antigen, for use as a medicament in combination with a second antibody comprising a second Fc region of a human IgG and a second antigen-binding region capable of binding to a second antigen, wherein said first Fc region comprises
a. one substitution of an amino acid at a position selected from the group consisting of: E430, E345 and S440, with the proviso that the substitution in S440 is S440Y or S440W, and
b. a K439E or S440K substitution, with the proviso that the substitution is not S440K if the substitution in (a) is S440Y or S440W, and
c. one substitution of the amino acid at position P329 or, a K322E substitution; and said second Fc region comprises
d. one substitution of an amino acid at a position selected from the group consisting of: E430, E345 and S440, with the proviso that the substitution in S440 is S440Y or S440W, and
e. a K439E or S440K substitution, with the proviso that the substitution is not S440K if the substitution in (d) is S440Y or S440W and
f. one or more substitutions selected from the group consisting of: K326A, K326W, E333A and E333S;

wherein the first Fc region has a K439E substitution and the second Fc region has a S440K substitution or, the first Fc region has a S440K substitution and the second Fc region has a K439E substitution; wherein the amino acid positions correspond to human IgG1 according to EU numbering system.

A substitution at a position corresponding to E430, E345 or a S440Y or S440W substitution is considered an Fc-Fc enhancing substitution according to the present invention, such a substitution introduces the effect of enhanced Fc-Fc interactions and oligomerization in the polypeptide or antibody. The enhanced oligomerization occurs when the antigen binding region of the antibody is bound to the corresponding target antigen. The enhanced oligomerization generates oligomers such as e.g. hexamers. The generation of oligomeric structures, such as hexamers has the effect of increasing Fc effector functions e.g. CDC by increasing C1q binding avidity of the polypeptide.

In one embodiment the first antibody comprises at most one substitution at a position corresponding to E430, E345 or a S440Y or S440W substitution. In one embodiment the second antibody comprises at most one substitution at a position corresponding to E430, E345 or a S440Y or S440W substitution. Thus, in one embodiment the Fc region comprises at most one substitution at a position corresponding to E430, E345 or a S440Y or S440W substitution. In one embodiment of the invention the first Fc and second Fc region comprises a substitution selected from the group consisting of: E430G, E345K, E430S, E430F, E430T, E345Q, E345R, E345Y, S440W and S440Y. Thus, in one embodiment the first Fc region may have an E430G substitution and the second Fc region may have an E345K substitution. In another embodiment the first Fc region may have an E345K substitution and the second antibody may have an E430G substitution. The substitution in the first and the second Fc region may be selected independently form the group of Fc-Fc enhancing substitutions.

In one embodiment of the invention the first and second Fc region comprises a substitution selected from the group consisting of: E430G, E345K and E345R.

In one embodiment of the invention the first and second Fc region comprises an E430G substitution. In one embodiment of the invention the first and second Fc region comprises an E345K substitution. In one embodiment of the invention the first and second Fc region comprises an E345R substitution. In one embodiment of the invention the first and second Fc region comprises a S440Y substitution.

The first and the second Fc region further comprise a K439E or a S440K substitution which is considered complementary oligomerization-inhibiting substitutions according to the present invention. That is a first antibody having an e.g. K439E may not form oligomers with another antibody having a K439E substitution, however an antibody having a K439E substitution may form oligomers with another antibody having a S440K substitution. An antibody having an S440K substitution may not form oligomers with another antibody having an S440K substitution, but may form oligomers with an antibody having a K439E substitution. Thus, in one embodiment of the invention the first Fc region comprises a K439E substitution and the second Fc region comprises a S440K substitution. In one embodiment of the invention the first Fc region comprises a S440K substitution and the second Fc region comprises a K439E substitution. When an Fc region comprises a S440K oligomerization inhibition substitution then the Fc region may not comprise a S440Y or S440W Fc-Fc enhancing substitution. Thus, an Fc region having a S440K oligomerization inhibition substitution may have an Fc-Fc enhancing substitution in an amino acid positon corresponding to E430 or E345.

In another aspect the present invention provides a first antibody comprising a first Fc region of a human IgG and a first antigen-binding region capable of binding to a first antigen, for use as a medicament in combination with a second antibody comprising a second Fc region of a human IgG and a second antigen-binding region capable of binding to a second antigen, wherein said first Fc region comprises
 a. a K248E and a T437R substitution, and
 b. a K439E or S440K substitution, and
 c. one substitution of the amino acid at position G237 or P329, or one or more substitutions selected from the group consisting of: G236R, G236K, K322A, K332E, E269K, L234A, L234F, L235A, L235Q, and L235E;
and said second Fc region comprises
 d. a K248E and a T437R substitution, and
 e. a K439E or S440K substitution,
 wherein the first Fc region has a K439E substitution and the second Fc region has a S440K substitution or, the first Fc region has a S440K substitution and the second Fc region has a K439E substitution; wherein the amino acid positions correspond to human IgG1 according to Eu numbering system.

An Fc-Fc enhancing substitution at a position corresponding to E430, E345 or a S440Y or S440W substitution according to any aspect or embodiment herein, may be substituted for the following two substitutions T248E and T437R.

In one embodiment of the invention the first Fc region comprises a substitution which reduced effector functions such as CDC and/or ADCC. Thus, in one embodiment of the invention the first Fc region comprises a substitution which reduces CDC. In one embodiment of the invention the first Fc region comprises a substitution which reduces ADCC. In one embodiment of the invention the first Fc region comprises a substitution which reduces CDC and ADCC.

In one embodiment of the invention the first Fc region comprises one amino acid substitution at position G237. A substitution in amino acid position G237 may have the effect of reducing the antibodies ability to induce CDC. Herby embodiments are provided wherein the first Fc region comprises a substitution which in addition to reducing CDC activity may also reduce Fc-gamma receptor binding and thereby Fc-gamma receptor mediated effector functions.

In one embodiment of the invention the first Fc region comprises one substitution selected from the group consisting of: G237A, G237T, G237Q, G237R, G237S, G237N, G237D, G237E, G237K, G237V, G237M, G237I, G237L, G237H, G237F, G237Y, G237W and G237P.

The inventors found that by substituting glycine in the position corresponding to 237 in human IgG1, with amino acid such as alanine, threonine, glutamine or arginine which represents various classes of natural occurring amino acids the ability of the antibody to induce CDC was reduced. Thus, it is believed that any substitution of G237 with another natural amino acid will reduce the antibodies ability to induce CDC. A substitution in amino acid position G237 may reduce the ability of an antibody having an Fc-Fc enhancing substitution and a self-oligomerization-inhibiting substitution to induce CDC on its own.

In one embodiment of the invention the first Fc region comprises one substitution selected from the group consisting of: G237T, G237A, G237Q and G237R. In one embodiment the first Fc region comprises a G237T substitution. In one embodiment of the invention the first Fc region comprises a G237A substitution. In one embodiment of the invention the first Fc region comprises a G237S substitution. In one embodiment of the invention the first Fc region comprises a G237Q substitution. In one embodiment of the invention the first Fc region comprises a G237R substitution.

In one embodiment of the invention the first Fc region comprises one or more substitutions selected from the group consisting of: G236R, G236K, E269K and P329R. In one embodiment of the invention the first Fc region comprises an L234F and an L235E substitution. Herby embodiments are provided wherein the first Fc region comprises a substitution which in addition to reducing CDC activity may also reduce Fc-gamma receptor binding and thereby Fc-gamma receptor mediated effector functions.

In one embodiment of the invention the first Fc region comprises one or more substitutions selected from the group consisting of: G236R, G236K and E269K. In one embodiment of the invention the first Fc region comprises one or more substitutions selected from the group consisting of: G236R and E269K. In one embodiment of the invention the first Fc region comprises a G263R or a G236K substitution. In one embodiment of the invention the first Fc region comprises a G236R substitution. In one embodiment of the invention the first Fc region comprises a G236K substitution. In one embodiment of the invention the first Fc region comprises a G269K substitution.

In one embodiment of the invention the first Fc region comprises one substitution selected from the group consisting of: K322A and K322E. Herby embodiment is provided wherein the first Fc region comprises a substitution which may reduce the antibodies ability to induce CDC activity while retaining the antibodies ability to bind Fc-gamma receptors.

In one embodiment of the invention the first Fc region comprises a K322A substitution. In one embodiment of the invention the first Fc region comprises a K322E substitution.

In one embodiment of the invention the first Fc region comprises an amino acid substitution at positon P329.

In one embodiment of the invention the first Fc region comprises on substitution selected from the group consisting of: P329R, P329K, P329E, P329D, and P329A. In one embodiment of the invention the first Fc region comprises a P329R substitution. In one embodiment of the invention the first Fc region comprises a P329R substitution. In one embodiment of the invention the first Fc region comprises a P329K substitution. In one embodiment of the invention the first Fc region comprises a P329E substitution. In one embodiment of the invention the first Fc region comprises a P329D substitution. In one embodiment of the invention the first Fc region comprises a P329A substitution.

Hereby embodiments are provided wherein the first antibody comprises a first Fc region which has an Fc-Fc enhancing substitution which introduces the effect of enhanced Fc-Fc interactions and oligomerization of the antibody. The enhanced oligomerization occurs when the antigen binding region of the antibody is bound to the corresponding target antigen. The enhanced oligomerization generates oligomers such as e.g. hexamers. The generation of oligomeric structures, such as hexamers has the effect of increasing Fc effector functions e.g. CDC by increasing C1q binding avidity of the antibody. However, by introducing a self-oligomerization inhibiting substitution and a substitution which reduces effector functions such as CDC and/or ADCC an antibody is generated which has decreased effector functions such as CDC and/or ADCC, which may allow for improved control of the toxic profile of the antibody in combination with a second antibody. That the first antibody has decreased effector functions such as CDC and/or ADCC is to be understood as when the first antibody is compared to a parent antibody having the same Fc-Fc enhancing substitution and self-oligomerization inhibiting substitution, but not a substitution which reduces effector functions.

In one embodiment of the invention the second Fc region comprises a substitution which increases effector functions such as CDC and/or ADCC. Thus, in one embodiment the second Fc region comprises a substitution which increases CDC. In one embodiment the second Fc region comprises a substitution which increases ADCC. In one embodiment the second Fc region comprises a substitution which increases CDC and ADCC. That the second antibody has increased effector functions such as CDC and/or ADCC is to be understood as when the second antibody is compared to a parent antibody having the same Fc-Fc enhancing substitution and self-oligomerization inhibiting substitution, but not a substitution which enhances effector functions.

In one embodiment of the invention the second Fc region comprises one or more substitution(s) selected from the group consisting of: G237A, K326A, K326W, E333A and E333S.

In one embodiment of the invention the second Fc region comprises a G237A substitution. In one embodiment of the invention the second Fc region comprises a substitution which reduced Fc-gamma Receptor binding, such as G237A.

In one embodiment of the invention the second Fc region comprises one or more substitution(s) selected from the group consisting of: K326A, K326W, E333A and E333S.

In one embodiment of the invention the second Fc region comprises one substitution selected from the group consisting of: K326A, K326W, E333A and E333S.

In one embodiment of the invention the second Fc region comprises one substitution selected from the group consisting of: K326A, K326W, E333A and E333S. In one embodiment of the invention the second Fc region comprises a K326A substitution. In one embodiment of the invention the second Fc region comprises a K326W substitution. In one embodiment of the invention the second Fc region comprises a E333A substitution. In one embodiment of the invention the second Fc region comprises an E333S substitution.

In one embodiment of the invention the second Fc region comprises two substitutions selected from the group consisting of: K326A, K326W, E333A and E333S.

In one embodiment of the invention the second Fc region comprises a K326W and E333S substitution. In one embodiment of the invention the second Fc region comprises a K326A and E333A substitution.

In one embodiment of the invention the second Fc region comprises a G237A and an E333S substitution.

In one embodiment of the invention the second Fc region comprises a K326A substitution.

In one embodiment of the invention the second Fc region comprises a E333S substitution.

Hereby embodiments are provided wherein the second antibody comprises a second Fc region which has an Fc-Fc enhancing substitution which introduces the effect of enhanced Fc-Fc interactions and oligomerization of the antibody. The enhanced oligomerization occurs when the antigen binding region of the antibody is bound to the corresponding target antigen. The enhanced oligomerization generates oligomers such as e.g. hexamers. The generation of oligomeric structures, such as hexamers has the effect of increasing Fc effector functions e.g. CDC by increasing C1q binding avidity of the antibody. However, by introducing a substitution which increases effector functions such as CDC and/or ADCC an antibody is generated which has increased oligomerization and increased effector functions such as CDC and/or ADCC, which may allow for improved potency of the antibody in combination with a first antibody. That the second antibody has increased effector functions such as CDC and/or ADCC is to be understood as when the second antibody is compared to a parent antibody having the same Fc-Fc enhancing substitution and self-oligomerization inhibiting substitution, but not a substitution which increases effector functions.

The following Table provides a non-limiting list of embodiments, describing combinations of a first polypeptide and a second polypeptide with specific substitutions, Thus, for example, embodiment 1 of the Table below is a combination of a first antibody comprising substitutions at positions corresponding to E430G, K439E and G236R, respectively, in human IgG, with a second antibody comprising E430G and S440K substitutions, respectively, in human IgG. As described herein, the first and second antibody of all of the embodiments 1 to 177 can optionally comprise further substitutions.

| Embodiment | First antibody mutations | Second antibody mutations |
| --- | --- | --- |
| 1 | E430G K439E G236R | E430G S440K |
| 2 | E430G K439E G236K | E430G S440K |
| 3 | E430G K439E G237A | E430G S440K |
| 4 | E430G K439E G237T | E430G S440K |
| 5 | E430G K439E G237Q | E430G S440K |
| 6 | E430G K439E G237R | E430G S440K |
| 7 | E430G K439E G237S | E430G S440K |
| 8 | E430G K439E G237N | E430G S440K |
| 9 | E430G K439E G237D | E430G S440K |
| 10 | E430G K439E G237E | E430G S440K |
| 11 | E430G K439E G237K | E430G S440K |
| 12 | E430G K439E G237V | E430G S440K |
| 13 | E430G K439E G237M | E430G S440K |
| 14 | E430G K439E G237I | E430G S440K |
| 15 | E430G K439EG237L | E430G S440K |
| 16 | E430G K439E G237H | E430G S440K |

| Embodiment | First antibody mutations | Second antibody mutations |
|---|---|---|
| 17 | E430G K439E G237F | E430G S440K |
| 18 | E430G K439E G237Y | E430G S440K |
| 19 | E430G K439E G237W | E430G S440K |
| 20 | E430G K439E G237P | E430G S440K |
| 21 | E430G K439E E269K | E430G S440K |
| 22 | E430G K439E K322A | E430G S440K |
| 23 | E430G K439E K322E | E430G S440K |
| 24 | E430G K439E L234F L235E | E430G S440K |
| 25 | E430G K439E L234F L235A | E430G S440K |
| 26 | E430G K439E L234F L235Q | E430G S440K |
| 27 | E430G K439E L234A L235E | E430G S440K |
| 28 | E430G K439E L234A L235A | E430G S440K |
| 29 | E430G K439E L234A L235Q | E430G S440K |
| 30 | E430G K439E | E430G S440K G236R |
| 31 | E430G K439E | E430G S440K G236K |
| 32 | E430G K439E | E430G S440K G237A |
| 33 | E430G K439E | E430G S440K G237T |
| 34 | E430G K439E | E430G S440K G237Q |
| 35 | E430G K439E | E430G S440K G237R |
| 36 | E430G K439E | E430G S440K G237S |
| 37 | E430G K439E | E430G S440K G237N |
| 38 | E430G K439E | E430G S440K G237D |
| 39 | E430G K439E | E430G S440K G237E |
| 40 | E430G K439E | E430G S440K G237K |
| 41 | E430G K439E | E430G S440K G237V |
| 42 | E430G K439E | E430G S440K G237M |
| 43 | E430G K439E | E430G S440K G237I |
| 44 | E430G K439E | E430G S440K G237L |
| 45 | E430G K439E | E430G S440K G237H |
| 46 | E430G K439E | E430G S440K G237F |
| 47 | E430G K439E | E430G S440K G237Y |
| 48 | E430G K439E | E430G S440K G237W |
| 49 | E430G K439E | E430G S440K G237P |
| 50 | E430G K439E | E430G S440K E269K |
| 51 | E430G K439E | E430G S440K K322A |
| 52 | E430G K439E | E430G S440K K322E |
| 53 | E430G K439E | E430G S440K L234F L235E |
| 54 | E430G K439E | E430G S440K L234F L235A |
| 55 | E430G K439E | E430G S440K L234F L235Q |
| 56 | E430G K439E | E430G S440K L234A L235E |
| 57 | E430G K439E | E430G S440K L234A L235A |
| 58 | E430G K439E | E430G S440K L234A L235Q |
| 59 | E430G K439E G236R | E430G S440K G237A |
| 60 | E430G K439E G236R | E430G S440K K326A |
| 61 | E430G K439E G236R | E430G S440K K326W |
| 62 | E430G K439E G236R | E430G S440K E333A |
| 63 | E430G K439E G236R | E430G S440K E333S |
| 64 | E430G K439E G236R | E430G S440K G237A E333S |
| 65 | E430G K439E G236R | E430G S440K K326W E333S |
| 66 | E430G K439E G236R | E430G S440K K326W E333A |
| 67 | E430G K439E G237A | E430G S440K G236R |
| 68 | E430G K439E K326A | E430G S440K G236R |
| 69 | E430G K439E K326W | E430G S440K G236R |
| 70 | E430G K439E E333A | E430G S440K G236R |
| 71 | E430G K439E E333S | E430G S440K G236R |
| 72 | E430G K439E G237A E333S | E430G S440K G236R |
| 73 | E430G K439E K326W E333S | E430G S440K G236R |
| 74 | E430G K439E K326W E333A | E430G S440K G236R |
| 75 | E430G K439E G237T | E430G S440K G237A |
| 76 | E430G K439E G237T | E430G S440K K326A |
| 77 | E430G K439E G237T | E430G S440K K326W |
| 78 | E430G K439E G237T | E430G S440K E333A |
| 79 | E430G K439E G237T | E430G S440K E333S |
| 80 | E430G K439E G237T | E430G S440K G237A E333S |
| 81 | E430G K439E G237T | E430G S440K K326W E333S |
| 82 | E430G K439E G237T | E430G S440K K326W E333A |
| 83 | E430G K439E G237A | E430G S440K G237T |
| 84 | E430G K439E K326A | E430G S440K G237T |
| 85 | E430G K439E K326W | E430G S440K G237T |
| 86 | E430G K439E E333A | E430G S440K G237T |
| 87 | E430G K439E E333S | E430G S440K G237T |
| 88 | E430G K439E G237A E333S | E430G S440K G237T |
| 89 | E430G K439E K326W E333S | E430G S440K G237T |
| 90 | E430G K439E K326W E333A | E430G S440K G237T |
| 91 | E430G K439E G237A | E430G S440K G237A |
| 92 | E430G K439E G237A | E430G S440K K326A |
| 93 | E430G K439E G237A | E430G S440K K326W |
| 94 | E430G K439E G237A | E430G S440K E333A |
| 95 | E430G K439E G237A | E430G S440K E333S |
| 96 | E430G K439E G237A | E430G S440K G237A E333S |
| 97 | E430G K439E G237A | E430G S440K K326W E333S |
| 98 | E430G K439E G237A | E430G S440K K326W E333A |
| 99 | E430G K439E K326A | E430G S440K G237A |
| 100 | E430G K439E K326W | E430G S440K G237A |
| 101 | E430G K439E E333A | E430G S440K G237A |
| 102 | E430G K439E E333S | E430G S440K G237A |
| 103 | E430G K439E G237A E333S | E430G S440K G237A |
| 104 | E430G K439E K326W E333S | E430G S440K G237A |
| 105 | E430G K439E K326W E333A | E430G S440K G237A |
| 106 | E430G K439E G237Q | E430G S440K G237A |
| 107 | E430G K439E G237Q | E430G S440K K326A |
| 108 | E430G K439E G237Q | E430G S440K K326W |
| 109 | E430G K439E G237Q | E430G S440K E333A |
| 110 | E430G K439E G237Q | E430G S440K E333S |
| 111 | E430G K439E G237Q | E430G S440K G237A E333S |
| 112 | E430G K439E G237Q | E430G S440K K326W E333S |
| 113 | E430G K439E G237Q | E430G S440K K326W E333A |
| 114 | E430G K439E G237A | E430G S440K G237Q |
| 115 | E430G K439E K326A | E430G S440K G237Q |
| 116 | E430G K439E K326W | E430G S440K G237Q |
| 117 | E430G K439E E333A | E430G S440K G237Q |
| 118 | E430G K439E E333S | E430G S440K G237Q |
| 119 | E430G K439E G237A E333S | E430G S440K G237Q |
| 120 | E430G K439E K326W E333S | E430G S440K G237Q |
| 121 | E430G K439E K326W E333A | E430G S440K G237Q |
| 122 | E430G K439E G237R | E430G S440K G237A |
| 123 | E430G K439E G237R | E430G S440K K326A |
| 124 | E430G K439E G237R | E430G S440K K326W |
| 125 | E430G K439E G237R | E430G S440K E333A |
| 126 | E430G K439E G237R | E430G S440K E333S |
| 127 | E430G K439E G237R | E430G S440K G237A E333S |
| 128 | E430G K439E G237R | E430G S440K K326W E333S |
| 129 | E430G K439E G237R | E430G S440K K326W E333A |
| 130 | E430G K439E G237A | E430G S440K G237R |
| 131 | E430G K439E K326A | E430G S440K G237R |
| 132 | E430G K439E K326W | E430G S440K G237R |
| 133 | E430G K439E E333A | E430G S440K G237R |
| 134 | E430G K439E E333S | E430G S440K G237R |
| 135 | E430G K439E G237A E333S | E430G S440K G237R |
| 136 | E430G K439E K326W E333S | E430G S440K G237R |
| 137 | E430G K439E K326W E333A | E430G S440K G237R |
| 138 | E430G K439E G237S | E430G S440K G237A |
| 139 | E430G K439E G237S | E430G S440K K326A |
| 140 | E430G K439E G237S | E430G S440K K326W |
| 141 | E430G K439E G237S | E430G S440K E333A |
| 142 | E430G K439E G237S | E430G S440K E333S |
| 143 | E430G K439E G237S | E430G S440K G237A E333S |
| 144 | E430G K439E G237S | E430G S440K K326W E333S |
| 145 | E430G K439E G237S | E430G S440K K326W E333A |
| 146 | E430G K439E G237A | E430G S440K G237S |
| 147 | E430G K439E K326A | E430G S440K G237S |
| 148 | E430G K439E K326W | E430G S440K G237S |
| 149 | E430G K439E E333A | E430G S440K G237S |
| 150 | E430G K439E E333S | E430G S440K G237S |
| 151 | E430G K439E G237A E333S | E430G S440K G237S |
| 152 | E430G K439E K326W E333S | E430G S440K G237S |
| 153 | E430G K439E K326W E333A | E430G S440K G237S |
| 154 | E345K K439E G236R | E345K S440K |
| 155 | E345K K439E G236R | E345K S440K G237A |
| 156 | E345K K439E G236R | E345K S440K E333S |
| 157 | E345K K439E G237Q | E345K S440K |

-continued

| Embodiment | First antibody mutations | Second antibody mutations |
| --- | --- | --- |
| 158 | E345K K439E G237Q | E345K S440K G237A |
| 159 | E345K K439E G237Q | E345K S440K E333S |
| 160 | E345R K439E G236R | E345K S440K |
| 161 | E345R K439E G236R | E345K S440K G237A |
| 162 | E345R K439E G236R | E345K S440K E333S |
| 163 | E345R K439E G237Q | E345K S440K |
| 164 | E345R K439E G237Q | E345K S440K G237A |
| 165 | E345R K439E G237Q | E345K S440K E333S |
| 166 | E345K K439E | E345K S440K G236R |
| 167 | E345K K439E G237A | E345K S440K G236R |
| 168 | E345K K439E E333S | E345K S440K G236R |
| 169 | E345K K439E | E345K S440K G237Q |
| 170 | E345K K439E G237A | E345K S440K G237Q |
| 171 | E345K K439E E333S | E345K S440K G237Q |
| 172 | E345R K439E | E345R S440K G236R |
| 173 | E345R K439E G237A | E345R S440K G236R |
| 174 | E345R K439E E333S | E345R S440K G236R |
| 175 | E345R K439E | E345R S440K G237Q |
| 176 | E345R K439E G237A | E345R S440K G237Q |
| 177 | E345R K439E E333S | E345R S440K G237Q |

The following Table provides a preferred list of embodiments, describing combinations of a first antibody and a second antibody with specific substitutions, Thus, for example, embodiment 1 of the Table below is a combination of a first antibody comprising substitutions at positions corresponding to E430G, K439E and G236R, respectively, in human IgG, with a second antibody comprising E430G and S440K substitutions, respectively, in human IgG. As described herein, the first and second antibody of all of the below embodiments 1 to 36 can optionally comprise further substitutions.

| Embodiment | First antibody mutations | Second antibody mutations |
| --- | --- | --- |
| 1 | E430G K439E G236R | E430G S440K |
| 2 | E430G K439E G237Q | E430G S440K |
| 3 | E430G K439E | E430G S440K G236R |
| 4 | E430G K439E | E430G S440K G237Q |
| 5 | E430G K439E G236R | E430G S440K G237A |
| 6 | E430G K439E G236R | E430G S440K E333S |
| 7 | E430G K439E G237A | E430G S440K G236R |
| 8 | E430G K439E E333S | E430G S440K G236R |
| 9 | E430G K439E G237Q | E430G S440K G237A |
| 10 | E430G K439E G237Q | E430G S440K E333S |
| 11 | E430G K439E G237A | E430G S440K G237Q |
| 12 | E430G K439E E333S | E430G S440K G237Q |
| 13 | E345K K439E G236R | E345K S440K |
| 14 | E345K K439E G236R | E345K S440K G237A |
| 15 | E345K K439E G236R | E345K S440K E333S |
| 16 | E345K K439E G237Q | E345K S440K |
| 17 | E345K K439E G237Q | E345K S440K G237A |
| 18 | E345K K439E G237Q | E345K S440K E333S |
| 19 | E345K K439E G236R | E345K S440K |
| 20 | E345K K439E G236R | E345K S440K G237A |
| 21 | E345R K439E G236R | E345K S440K E333S |
| 22 | E345K K439E G237Q | E345K S440K |
| 23 | E345K K439E G237Q | E345K S440K G237A |
| 24 | E345R K439E G237Q | E345K S440K E333S |
| 25 | E345K K439E | E345K S440K G236R |
| 26 | E345K K439E G237A | E345K S440K G236R |
| 27 | E345K K439E E333S | E345K S440K G236R |
| 28 | E345K K439E | E345K S440K G237Q |
| 29 | E345K K439E G237A | E345K S440K G237Q |
| 30 | E345K K439E E333S | E345K S440K G237Q |
| 31 | E345R K439E | E345R S440K G236R |
| 32 | E345R K439E G237A | E345R S440K G236R |
| 33 | E345R K439E E333S | E345R S440K G236R |
| 34 | E345R K439E | E345R S440K G237Q |
| 35 | E345R K439E G237A | E345R S440K G237Q |
| 36 | E345R K439E E333S | E345R S440K G237Q |

In one embodiment the first Fc region comprises an E430G, a K439E and a G236R substitution and the second Fc region comprises an E430G and S440K substitution. In one embodiment the first Fc region comprises an E430G, a K439E and a G237Q substitution and the second Fc region comprises an E430G and S440K substitution. In one embodiment the first Fc region comprises an E430G and a K439E substitution and the second Fc region comprises an E430G, S440K and G236R substitution. In one embodiment the first Fc region comprises an E430G and a K439E substitution and the second Fc region comprises an E430G, S440K and G237Q substitution. In one embodiment the first Fc region comprises an E430G, a K439E and a G236R substitution and the second Fc region comprises an E430G, S440K and G237A substitution. In one embodiment the first Fc region comprises an E430G, a K439E and a G236R substitution and the second Fc region comprises an E430G, S440K and E333S substitution. In one embodiment the first Fc region comprises an E430G, a K439E and a G237A substitution and the second Fc region comprises an E430G, S440K and G236R substitution. In one embodiment the first Fc region comprises an E430G, a K439E and an E333S substitution and the second Fc region comprises an E430G, S440K and G236R substitution. In one embodiment the first Fc region comprises an E430G, a K439E and a G237Q substitution and the second Fc region comprises an E430G, S440K and G237A substitution. In one embodiment the first Fc region comprises an E430G, a K439E and a G237Q substitution and the second Fc region comprises an E430G, S440K and E333S substitution. In one embodiment the first Fc region comprises an E430G, a K439E and a G237A substitution and the second Fc region comprises an E430G, S440K and a G237Q substitution. In one embodiment the first Fc region comprises an E430G, a K439E and an E333S substitution and the second Fc region comprises an E430G, S440K and a G237Q substitution. In one embodiment the first Fc region comprises an E345K, a K439E and a G236R substitution and the second Fc region comprises an E345K, S440K and an E333S substitution. In one embodiment the first Fc region comprises an E345R, a K439E and a G236R substitution and the second Fc region comprises an E345K, S440K and an E333S substitution. In one embodiment the first Fc region comprises an E345R, a K439E and a G237Q substitution and the second Fc region comprises an E345K and S440K substitution.

In one embodiment of the invention the first and/or second antibody is human, humanized or chimeric. In one embodiment of the invention the first and second antibody is human, humanized or chimeric. In one embodiment of the invention the first and second antibody is human. In one embodiment of the invention the first and second antibody is humanized. In one embodiment of the invention the first antibody is human and the second antibody is humanized. In one embodiment of the invention the first antibody is humanized and the second antibody is human.

In one embodiment of the invention the first and/or second antibody is a monoclonal antibody. In one embodiment of the invention the first and second antibody is a monoclonal antibody. In one embodiment of the invention the first and second antibody is a bispecific antibody. In one embodiment the first antibody is a monoclonal antibody and the second antibody is a bispecific antibody. In one embodiment the first antibody is a bispecific antibody and the second antibody is a monoclonal antibody.

It is to be understood that the embodiments described herein with reference to an antibody refers to an antibody comprising an Fc region of an immunoglobulin and an antigen-binding region, an antibody may also be a multispecific antibody such as a bispecific antibody having a first Fc region of an immunoglobulin and a first antigen-binding region, and a second polypeptide or antibody having a second Fc region of an immunoglobulin and a second antigen-binding region.

In one embodiment of the invention the first and/or second antibody is an IgG1, IgG2, IgG3 or IgG4 isotype. In one embodiment of the invention the first and second antibody is an IgG1, IgG2, IgG3 or IgG4 isotype. In one embodiment of the invention the first and second antibody is a human IgG1, IgG2, IgG3 or IgG4 isotype. In one embodiment of the invention the first and second antibody is an IgG1, IgG2 or IgG4 isotype. In one embodiment of the invention the first and second antibody is a human IgG1, IgG2 or IgG4 isotype. In one embodiment of the invention the first and/or second antibody is an IgG1 isotype. In one embodiment of the invention the first and/or second antibody is a human IgG1 isotype. In one embodiment of the invention the first and second antibody is an IgG1 isotype. In one embodiment the first and second antibody is an IgG2 isotype. In on embodiment of the invention the first and second antibody is an IgG4 isotype. In one embodiment of the invention the first antibody is an IgG1 isotype and the second antibody is an IgG2 isotype. In one embodiment of the invention the first antibody is an IgG2 isotype and the second antibody is an IgG1 isotype.

In one embodiment of the invention the first antibody comprises a heavy chain of an IgG1 isotype. In one embodiment of the invention the second antibody comprises a heavy chain of an IgG1 isotype. In one embodiment of the invention the first antibody comprises a heavy chain of an IgG2 isotype. In one embodiment of the invention the second antibody comprises a heavy chain of an IgG2 isotype. In one embodiment of the invention the first antibody comprises a heavy chain of an IgG3 isotype. In one embodiment of the invention the second antibody comprises a heavy chain of an IgG3 isotype. In one embodiment of the invention the first antibody comprises a heavy chain of an IgG4 isotype. In one embodiment of the invention the second antibody comprises a heavy chain of an IgG4 isotype.

In one embodiment of the invention the first antibody comprises a heavy chain of an IgG1 isotype and the second antibody comprises a heavy chain of an IgG1 isotype.

In a preferred embodiment, said first antibody comprises a first Fc region of a human IgG1 isotype and/or said second antibody comprises a second Fc region of a human IgG1 isotype.

In one embodiment of the invention, the antibody, or the first and/or second antibody comprises a first and/or second constant region comprising a sequence selected from table 1.

In one embodiment of the invention, the antibody, or the first and/or second antibody comprises a first and/or second constant region comprising a sequence selected from the group consisting of SEQ ID NO: 63 to 122, 135-138, 140-145.

In one embodiment of the invention, the first and/or second antibody comprises a first and/or second heavy chain constant region comprising a sequence selected from the group consisting of SEQ ID NO: 63 to 122, 135-138, 140-145, wherein the first and second heavy chain sequence are selected independently from the group.

In one embodiment of the invention, the antibody, or the first and/or second antibody comprises a first and/or second constant region comprising a sequence selected from the group consisting of SEQ ID NO: 63 to 122, 135-138 and 140-145, wherein at most 5 additional substitutions are introduced, such as at most 4 additional substitutions, such as at most 3 additional substitutions, such as at most 2 additional substitutions, such as at most 1 additional substitution.

In one embodiment of the invention the antibody, e.g. the first or second antibody comprises a constant region comprising a sequence set forth in SEQ ID NO: 84. In one embodiment of the invention the antibody, e.g. the first or second antibody comprises a constant region comprising a sequence set forth in SEQ ID NO: 87. In one embodiment of the invention the antibody, e.g. the first or second antibody comprises a constant region comprising a sequence set forth in SEQ ID NO: 101. In one embodiment of the invention the antibody, e.g. the first or second antibody comprises a constant region comprising a sequence set forth in SEQ ID NO: 107. In one embodiment of the invention the antibody, e.g. the first or second antibody comprises a constant region comprising a sequence set forth in SEQ ID NO: 105. In one embodiment of the invention the antibody, e.g. the first or second antibody comprises a constant region comprising a sequence set forth in SEQ ID NO: 103. In one embodiment of the invention the antibody, e.g. the first or second antibody comprises a constant region comprising a sequence set forth in SEQ ID NO: 85. In one embodiment of the invention the antibody, e.g. the first or second antibody comprises a constant region comprising a sequence set forth in SEQ ID NO: 104. In one embodiment of the invention the antibody, e.g. the first or second antibody comprises a constant region comprising a sequence set forth in SEQ ID NO: 82. In one embodiment of the invention the antibody, e.g. the first or second antibody comprises a constant region comprising a sequence set forth in SEQ ID NO: 66. In one embodiment of the invention the antibody, e.g. the first or second antibody comprises a constant region comprising a sequence set forth in SEQ ID NO: 68. In one embodiment of the invention the antibody, e.g. the first or second antibody comprises a constant region comprising a sequence set forth in SEQ ID NO: 73.

In one embodiment of the invention the first and second antigens are both cell surface-exposed molecules. In one embodiment the first and second antigens are expressed on the same cell. In one embodiment the first and second antigens are expressed in the same tissue.

In one embodiment of the invention the first and second antigens are co-located in cells or tissues that are target cells or target tissue for the disease or disorder to be treated. In one embodiment of the invention the first and second antigens are not identical.

In one embodiment of the invention the first and second antibody depletes a cell population expressing the first and second antigen.

In one embodiment of the invention the cell population is a tumor cell.

In one embodiment of the invention the cell population is a hematological tumor cell or a solid tumor cell.

In one embodiment of the invention the cell population is a leukocyte, such as a leukocyte cell population.

In one embodiment of the invention the cell population is a lymphocyte, such as a lymphocyte cell population.

In one embodiment of the invention the cell population is a B cell, such as a B cell population. In one embodiment of the invention the cell population is a subset of a B cell population.

In one embodiment of the invention the cell population is a T cell, such as a T cell population. In one embodiment of the invention the cell population is a subset of a T cell population. In one embodiment of the invention the cell population is a regulatory T cell.

In one embodiment of the invention the cell population is a NK cell. In one embodiment of the invention the cell population is a myeloid derived suppressor cell. In one embodiment of the invention cell population is a tumor associated macrophage.

Hereby embodiments are described wherein the first antibody and second antibody according to the invention is used as a medicament to deplete a specific cell population expressing a first and second antigen recognized by the first and second antibody. Thus, a first and second antibody according to the present invention may be used to deplete tumor cells that express a first and second antigen recognized by the first and second antibody, while the first and second antibody may not deplete the healthy tissue expressing only the first or the second antigen. A first and second antibody according to the present invention may also be particularly useful in depleting specific cell populations of the immune system, such as specific subsets of lymphocytes e.g. B cells or T cells or even subsets of B cells or subsets of T cells.

In one embodiment of the invention the antibody is a monospecific antibody, bispecific antibody or multispecific antibody. In one embodiment of the invention is a natural antibody.

The antibody which has a natural, e.g. a human Fc domain may also be an antibody having other mutations than those of the present invention, such as e.g. mutations that affect glycosylation or enables the antibody to be a bispecific antibody. By the term "natural antibody" is meant any antibody which does not comprise any genetically introduced mutations. An antibody which comprises naturally occurring modifications, e.g. different allotypes, is thus to be understood as a "natural antibody" in the sense of the present invention, and can thereby be understood as a parent antibody. A natural antibody may serve as a template for the at least three substitutions in the first antibody or the at least two substitutions in the second antibody according to the present invention, and thereby providing the first and second antibody of the invention. An example of a parent antibody comprising other substitutions than those of the present invention is the bispecific antibody as described in WO2011/131746 (Genmab), utilizing reducing conditions to promote half-molecule exchange of two antibodies comprising IgG4-like CH3 regions, thus forming bispecific antibodies without concomitant formation of aggregates. Other examples of parent antibodies include but are not limited to bispecific antibodies such as heterodimeric bispecifics: Triomabs (Fresenius); bispecific IgG1 and IgG2 (Rinat neurosciences Corporation); FcΔAdp (Regeneron); Knobs-into-holes (Genentech); Electrostatic steering (Amgen, Chugai, Oncomed); SEEDbodies (Merck); Azymetric scaffold (Zymeworks); mAb-Fv (Xencor); and LUZ-Y (Genentech). Other exemplary parent antibody formats include, without limitation, a wild type antibody, a full-length antibody or Fc-containing antibody fragment, a human antibody, humanized antibody, chimeric antibody or any combination thereof.

In one aspect of the invention the antibody comprises an Fc region of a human IgG and an antigen-binding region capable of binding to an antigen, wherein said Fc region comprises one substitution of an amino acid at a position selected from the group consisting of: E430, E345 and S440, with the proviso that the substitution in S440 is S440Y or S440W, and a K439E or S440K substitution, with the proviso that the substitution is not S440K if the substitution in (a) is S440Y or S440W, and one substitution of the amino acid at position G237 or, one or more substitutions selected from the group consisting of: G236R, G236K, K322A, E269K, L234A, L234F, L235A, L235Q, and L235E.

In another aspect the antibody comprising an Fc region of a human IgG and an antigen-binding region capable of binding to an antigen, wherein said Fc region comprises a K248E and a T437R substitution, and a K439E or S440K substitution, and one substitution of the amino acid at position G237 or P329, or one or more substitutions selected from the group consisting of: G236R, G236K, K322A, K332E, E269K, L234A, L234F, L235A, L235Q, L235E, K326A, K326W, E333A and E333S.

In one embodiment of the invention the Fc region comprises a substitution selected from the group consisting of: E430G, E345K, E430S, E430F, E430T, E345Q, E345R, E345Y, S440W and S440Y.

In one embodiment of the invention the Fc region comprises a substitution selected from the group consisting of: E430G, E345K and E345R.

In one embodiment of the invention the Fc region comprises an E430G substitution.

In one embodiment of the invention the Fc region comprises at most one substitution at a position selected from the group consisting of: E430, E345 and S440, with the proviso that the substitution in S440 is S440Y or S440W.

In one embodiment of the invention the Fc region comprises one substitution selected from the group consisting of: G237A, G237T, G237Q, G237R, G237S, G237N, G237D, G237E, G237K, G237V, G237M, G237I, G237L, G237H, G237F, G237Y, G237W, G237P.

In one embodiment of the invention the Fc region comprises one substitution selected from the group consisting of: G237A, G237T, G237S, G237Q, G237R. In one embodiment of the invention the Fc region comprises a G237Q substitution.

In one embodiment of the invention the Fc region comprises one or more substitutions selected from the group consisting of: G236R and E269K.

In one embodiment of the invention the Fc region comprises a G236R substitution.

In one embodiment of the invention wherein the Fc region comprises an E269K substitution.

In one embodiment of the invention the Fc region comprises a K322A substitution.

Targets and Method of Use

The first and/or second antibody according to the present invention may bind a target are expressed on the same cell. In one embodiment the target is a target that activates, inhibits, modulates and/or regulates a signal transduction pathway.

Examples of targets that may be particularly suitable as targets according to the present invention are cell surface receptors and ligands.

The following protein classes may also be particular suitable as antigen binding target for the first and/or second antibody according to the invention, tumor necrosis receptor super family, GPI-anchored proteins, Lipidated proteins, Hydrolases (EC 3.) and regulators superfamilies, B7 family-related protein, immunoglobulin superfamily, interleukin receptor family, Integrins, Ig-like cell adhesion molecule family, Receptor type Protein Tyrosine Phosphatases, C-type lectins, Tetraspanins, Membrane spanning 4-domains, Activating leukocyte immunoglobulin like receptors, C-C motif chemokine receptors, G protein-coupled receptors, Toll like receptors, Receptor Tyrosine Kinases. In one embodiment of the invention the first and second antigen binding regions is capable of binding to a target antigen form the same protein class. In one embodiment of the invention the first and second antigen binding regions is capable of binding to a target antigen form a different protein classes.

In one embodiment of the invention the first antigen binding region is capable of binding to a target antigen from the protein class of GPI-anchored proteins and the second antigen binding region is capable of binding to a target antigen from the protein class of Tetraspanins. In one embodiment of the invention the first antigen binding region is capable of binding to a target antigen from the protein class of Tetraspanins and the second antigen binding region is capable of binding to a target antigen from the protein class of GPI-anchored proteins.

In one embodiment of the invention the first antigen binding region is capable of binding to a target antigen from the protein class of GPI-anchored proteins and the second antigen binding region is capable of binding to a target antigen from the protein class of Membrane spanning 4-domains. In one embodiment of the invention the first antigen binding region is capable of binding to a target antigen from the protein class of Membrane spanning 4-domains and the second antigen binding region is capable of binding to a target antigen from the protein class of GPI-anchored proteins.

In one embodiment of the invention the first antigen binding region is capable of binding to a target antigen from the protein class of tumor necrosis receptor super family and the second antigen binding region is capable of binding to a target antigen from the protein class of tumor necrosis receptor super family.

In one embodiment of the invention the first antigen binding region is capable of binding to a target antigen from the protein class of tumor necrosis receptor super family and the second antigen binding region is capable of binding to a target antigen from the protein class of immunoglobulin superfamily.

Cell surface receptors include, for example, receptors that belong to receptor families such as the hematopoietic factor receptor family, cytokine receptor family, tyrosine kinase receptor family, serine/threonine kinase receptor family, TNF receptor family, G protein-coupled receptor family, GPI-anchored receptor family, tyrosine phosphatase receptor family, adhesion factor family, and hormone receptor family.

Various references that relate to receptors belonging to these receptor families and their characteristics are available and include, for example, Cooke B A., King R J B., van der Molen H J. ed. New Comprehensive Biochemistry Vol. 18B "Hormones and their Actions Part II" pp. 1-46 (1988) Elsevier Science Publishers BV., New York, USA; Patthy L. (1990) Cell, 61: 13-14; Ullrich A., et al. (1990) Cell, 61: 203-212; Massagul J. (1992) Cell, 69: 1067-1070; Miyajima A., et al. (1992) Annu. Rev. Immunol., 10: 295-331; Taga T. and Kishimoto T. (1992) FASEB J., 7: 3387-3396; Fantl W I., et al. (1993) Annu. Rev. Biochem., 62: 453-481; Smith C A., et al. (1994) Cell, 76: 959-962; Flower D R. (1999) Biochim. Biophys. Acta, 1422: 207-234; and M. Miyasaka ed., Cell Technology, supplementary volume, Handbook series, "Handbook for Adhesion Factors" (1994) (Shujun-sha, Tokyo, Japan).

In one embodiment of the invention the antibody comprises an antigen binding region wherein the antigen binding region binds to a member of the tumor necrosis factor receptor super family (TNFR-SF) or G-protein Coupled Receptor (GPCR) superfamily.

In one embodiment of the invention the first and/or second antibody binds to a cell surface receptor, for example, hormone receptors and cytokine receptors. Exemplary cytokine receptors include, for example, hematopoietic factor receptor, lymphokine receptor, growth factor receptor, differentiation control factor receptor and the like.

Examples of cytokine receptors are erythropoietin (EPO) receptor, thrombopoietin (TPO) receptor, granulocyte colony stimulating factor (G-CSF) receptor, macrophage colony stimulating factor (M-CSF) receptor, granular macrophage colony stimulating factor (GM-CSF) receptor, tumor necrosis factor (TNF) receptor, interleukin-1 (IL-1) receptor, interleukin-2 (IL-2) receptor, interleukin-3 (IL-3) receptor, interleukin-4 (IL-4) receptor, interleukin-5 (IL-5) receptor, interleukin-6 (IL-6) receptor, interleukin-7 (IL-7) receptor, interleukin-9 (IL-9) receptor, interleukin-10 (IL-10) receptor, interleukin-11 (IL-11) receptor, interleukin-12 (IL-12) receptor, interleukin-13 (IL-13) receptor, interleukin-15 (IL-15) receptor, interferon-alpha (IFN-alpha) receptor, interferon-beta (IFN-beta) receptor, interferon-gamma (IFN-gamma) receptor, growth hormone (GH) receptor, insulin receptor, blood stem cell proliferation factor (SCF) receptor, vascular epidermal growth factor (VEGF) receptor, epidermal cell growth factor (EGF) receptor, nerve growth factor (NGF) receptor, fibroblast growth factor (FGF) receptor, platelet-derived growth factor (PDGF) receptor, transforming growth factor-beta (TGF-beta) receptor, leukocyte migration inhibitory factor (LIF) receptor, ciliary neurotrophic factor (CNTF) receptor, oncostatin M (OSM) receptor, and Notch family receptor.

The tumor necrosis factor receptor superfamily (TNFRSF) is a group of receptors characterized by the ability to bind ligands of the tumor necrosis factor superfamily (TNFSF) via an extracellular cysteine-rich domain. The TNF receptors form trimeric complexes in the plasma membrane. The TNFRSF include the following list of 29 proteins; TNFR1 (Uniprot P19438), FAS (Uniprot P25445), DR3 (Uniprot Q93038), DR4 (Uniprot O00220), DR5 (Uniprot O14763), DR6 (Uniprot O75509), NGFR (Uniprot P08138), EDAR (Uniprot Q9UNE0), DcR1 (Uniprot O14798), DcR2 (Uniprot Q9UBN6), DcR3 (Uniprot O95407), OPG (Uniprot O00300), TROY (Uniprot Q9NS68), XEDAR (Uniprot Q9HAV5), LTbR (Uniprot P36941), HVEM (Uniprot Q92956), TWEAKR (Uniprot Q9NP84), CD120b (Uniprot P20333), OX40 (Uniprot P43489), CD40 (Uniprot P25942), CD27 (Uniprot P26842), CD30 (Uniprot P28908), 4-1BB (Uniprot Q07011), RANK (Uniprot Q9Y6Q6), TACI (Uniprot O14836), BLySR (Uniprot Q96RJ3), BCMA (Uniprot Q02223), GITR (Uniprot Q9Y5U5), RELT (Uniprot Q969Z4).

In one embodiment of the invention the antibody, the first and/or second antibody comprises an antigen-binding region capable of binding to an antigen selected from the group consisting of: DR4, DR5, CD20, CD37, CD52, HLA-DR, CD3 and CD5.

In one embodiment the antigen-binding region is capable of binding to DR4. In one embodiment the antigen-binding region is capable of binding to DR5. In one embodiment the antigen-binding region is capable of binding to CD20. In one embodiment the antigen-binding region is capable of binding to CD37. In one embodiment the antigen-binding region is capable of binding to CD52. In one embodiment the antigen-binding region is capable of binding to HLA-DR. In one embodiment the antigen-binding region is capable of binding to CD3. In one embodiment the antigen-binding region is capable of binding to CD5.

In one embodiment of the invention the antibody, or the first and/or second antibody comprises an antigen-binding region comprising:
- a VH region comprising a CDR1 sequence as set forth in SEQ ID NO: 196, a CDR2 sequence as set forth in SEQ ID NO:196 and a CDR3 sequence as set forth SEQ ID NO: 198, and a VL region comprising a CDR1 sequence as set forth in SEQ ID NO:200, a CDR2 sequence as set forth in: AAT and a CDR3 sequence as set forth SEQ ID NO:201 [DR4];
- a VH region comprising a CDR1 sequence as set forth in SEQ ID NO:50, a CDR2 sequence as set forth in SEQ ID NO:51 and a CDR3 sequence as set forth SEQ ID NO:52, and a VL region comprising a CDR1 sequence as set forth in SEQ ID NO:54, a CDR2 sequence as set forth in: FAS and a CDR3 sequence as set forth SEQ ID NO:55 [DR5-01-G56T];
- a VH region comprising a CDR1 sequence as set forth in SEQ ID NO:57, a CDR2 sequence as set forth in SEQ ID NO:58 and a CDR3 sequence as set forth SEQ ID NO:59, and a VL region comprising a CDR1 sequence as set forth in SEQ ID NO:61, a CDR2 sequence as set forth in: RTS and a CDR3 sequence as set forth SEQ ID NO:62 [DR5-05];
- a VH region comprising a CDR1 sequence as set forth in SEQ ID NO:36, a CDR2 sequence as set forth in SEQ ID NO:37 and a CDR3 sequence as set forth SEQ ID NO:38, and a VL region comprising a CDR1 sequence as set forth in SEQ ID NO:40, a CDR2 sequence as set forth in: DAS and a CDR3 sequence as set forth SEQ ID NO:41 [CD20, 7D8];
- a VH region comprising a CDR1 sequence as set forth in SEQ ID NO:9, a CDR2 sequence as set forth in SEQ ID NO:10 and a CDR3 sequence as set forth SEQ ID NO: 11, and a VL region comprising a CDR1 sequence as set forth in SEQ ID NO: 13, a CDR2 sequence as set forth in: DAS and a CDR3 sequence as set forth SEQ ID NO:14 [CD20, 11B8];
- a VH region comprising a CDR1 sequence as set forth in SEQ ID NO:43, a CDR2 sequence as set forth in SEQ ID NO:44 and a CDR3 sequence as set forth SEQ ID NO:45, and a VL region comprising a CDR1 sequence as set forth in SEQ ID NO:47, a CDR2 sequence as set forth in: VAT and a CDR3 sequence as set forth SEQ ID NO:48 [CD37];
- a VH region comprising a CDR1 sequence as set forth in SEQ ID NO:2, a CDR2 sequence as set forth in SEQ ID NO:3 and a CDR3 sequence as set forth SEQ ID NO:4, and a VL region comprising a CDR1 sequence as set forth in SEQ ID NO:6, a CDR2 sequence as set forth in: NTN, and a CDR3 sequence as set forth SEQ ID NO:7 [CD52, CAMPATH-1H];
- a VH region comprising a CDR1 sequence as set forth in SEQ ID NO: 161, a CDR2 sequence as set forth in SEQ ID NO:162, and a CDR3 sequence as set forth SEQ ID NO: 163, and a VL region comprising a CDR1 sequence as set forth in SEQ ID NO: 165, a CDR2 sequence as set forth in: LVS and a CDR3 sequence as set forth SEQ ID NO:166 [CD52, h2E8];
- a VH region comprising a CDR1 sequence as set forth in SEQ ID NO: 168, a CDR2 sequence as set forth in SEQ ID NO:169 and a CDR3 sequence as set forth SEQ ID NO: 170, and a VL region comprising a CDR1 sequence as set forth in SEQ ID NO: 172, a CDR2 sequence as set forth in SEQ ID NO:AAS and a CDR3 sequence as set forth SEQ ID NO: 173 [HLA-DR, huI243];
- a VH region comprising a CDR1 sequence as set forth in SEQ ID NO: 175, a CDR2 sequence as set forth in SEQ ID NO:176 and a CDR3 sequence as set forth SEQ ID NO: 177, and a VL region comprising a CDR1 sequence as set forth in SEQ ID NO: 179, a CDR2 sequence as set forth in: DNN and a CDR3 sequence as set forth SEQ ID NO:180 [HLA-DR, 1D09C3];
- a VH region comprising a CDR1 sequence as set forth in SEQ ID NO: 182, a CDR2 sequence as set forth in SEQ ID NO:183 and a CDR3 sequence as set forth SEQ ID NO: 184, and a VL region comprising a CDR1 sequence as set forth in SEQ ID NO: 186, a CDR2 sequence as set forth in SEQ ID NO:DTS and a CDR3 sequence as set forth SEQ ID NO: 187 [CD3, huCLB T3/4];
- a VH region comprising a CDR1 sequence as set forth in SEQ ID NO: 189, a CDR2 sequence as set forth in SEQ ID NO:190 and a CDR3 sequence as set forth SEQ ID NO: 191, and a VL region comprising a CDR1 sequence as set forth in SEQ ID NO: 193, a CDR2 sequence as set forth in: ATS and a CDR3 sequence as set forth SEQ ID NO: 194 [CD5].

In one aspect the present invention relates to a composition comprising a first and a second antibody wherein the first antibody comprises a first antigen-binding region and a first Fc region according to any embodiment disclosed herein and the second antibody comprises a second antigen-binding region and a second Fc region according to any aspect or embodiment disclosed herein.

In another aspect the present invention relates to a composition comprising a first and a second antibody, wherein the first antibody comprises a first antigen-binding region capable of binding to a first antigen and a first Fc region of a human IgG, and the second antibody comprises a second antigen-binding region capable of binding to a second antigen and a second Fc region of a human IgG, wherein said first Fc region comprises
- one substitution of an amino acid at a position selected form the group consisting of: E430, E345 and S440, with the proviso that the substitution in S440 is S440Y or S440W, and
- a K439E or S440K substitution, with the proviso that the substitution is not S440K if the substitution in (a) is S440Y or S440W, and
- one substitution of the amino acid at position G237 or, one or more substitutions selected from the group consisting of: G236R, G236K, K322A, E269K, K322E, P329R, L234A, L234F, L235A, L235Q, and L235E;

and said second Fc region comprises
- one substitution of an amino acid at a position selected form the group consisting of: E430, E345 and S440, with the proviso that the substitution in S440 is S440Y or S440W, and
- a K439E or S440K substitution, with the proviso that the substitution is not S440K if the substitution in (d) is S440Y or S440W, and
- one or more substitutions selected from the group consisting of: K326A, K326W, E333A and E333S if the first Fc region comprises a K322E or P329R substitution,
- wherein the first Fc region has a K439E substitution and the second Fc region has a S440K substitution or, the first Fc region has a S440K substitution and the second Fc region has a K439E substitution, wherein the amino acid positions correspond to human IgG1 according to EU numbering system.

In one aspect the present invention provides a composition comprising a first and a second antibody, wherein the first antibody comprises a first antigen-binding region capable of binding to a first antigen and a first Fc region of a human IgG, and the second antibody comprises a second antigen-binding region capable of binding to a second antigen and a second Fc region of a human IgG, wherein said first Fc region comprises
- one substitution of an amino acid at a position selected form the group consisting of: E430, E345 and S440, with the proviso that the substitution in S440 is S440Y or S440W, and
- a K439E or S440K substitution, with the proviso that the substitution is not S440K if the substitution in (a) is S440Y or S440W, and
- one substitution of the amino acid at position G237 or, one or more substitutions selected from the group consisting of: G236R, G236K, K322A, E269K, L234A, L234F, L235A, L235Q, and L235E;

and said second Fc region comprises
- one substitution of an amino acid at a position selected form the group consisting of: E430, E345 and S440, with the proviso that the substitution in S440 is S440Y or S440W, and
- a K439E or S440K substitution, with the proviso that the substitution is not S440K if the substitution in (d) is S440Y or S440W, wherein the first Fc region has a K439E substitution and the second Fc region has a S440K substitution or, the first Fc region has a S440K substitution and the second Fc region has a K439E substitution, wherein the amino acid positions correspond to human IgG1 according to EU numbering system.

In one aspect the present invention provides a composition comprising a first and a second antibody, wherein the first antibody comprises a first antigen-binding region capable of binding to a first antigen and a first Fc region of a human IgG, and the second antibody comprises a second antigen-binding region capable of binding to a second antigen and a second Fc region of a human IgG, wherein said first Fc region comprises
- one substitution of an amino acid at a position selected form the group consisting of: E430, E345 and S440, with the proviso that the substitution in S440 is S440Y or S440W, and
- a K439E or S440K substitution, with the proviso that the substitution is not S440K if the substitution in (a) is S440Y or S440W, and
- one substitution of the amino acid at position P329 or, a K322E substitution; and said second Fc region comprises
- one substitution of an amino acid at a position selected form the group consisting of: E430, E345 and S440, with the proviso that the substitution in S440 is S440Y or S440W, and
- a K439E or S440K substitution, with the proviso that the substitution is not S440K if the substitution in (d) is S440Y or S440W, and
- one or more substitutions selected from the group consisting of: K326A, K326W, E333A and E333S, wherein the first Fc region has a K439E substitution and the second Fc region has a S440K substitution or, the first Fc region has a S440K substitution and the second Fc region has a K439E substitution, wherein the amino acid positions correspond to human IgG1 according to EU numbering system.

In one embodiment of the invention the composition comprising a first and second Fc region comprises a substitution selected from the group consisting of: E430G, E345K, E430S, E430F, E430T, E345Q, E345R, E345Y, S440W and S440Y.

In one embodiment of the invention the composition comprising a first and second Fc region comprises a substitution selected form the group consisting of: E430G, E345K and E345R.

In on embodiment of the invention the composition comprising a first and second Fc region comprises an E430G substitution.

In one embodiment of the invention the composition comprising a first Fc region comprises one substitution selected from the group consisting of: G237A, G237T, G237Q, G237R, G237S, G237N, G237D, G237E, G237K, G237V, G237M, G237I, G237L, G237H, G237F, G237Y, G237W and G237P.

In one embodiment of the invention the composition comprising a first Fc region comprises one substitution selected from the group consisting of: G237A, G237T, G237Q, G237R and G237S.

In one embodiment of the invention the composition comprising a first Fc region comprises one substitution selected from the group consisting of: G237A, G237T, G237Q and G237R.

In one embodiment of the invention, the first Fc region comprises a G237Q substitution.

In one embodiment of the invention, the first Fc region comprises a G237T substitution.

In one embodiment of the invention the composition comprising a first Fc region comprises one or more substitutions selected from the group consisting of: G236R, and G236K.

In one embodiment of the invention the composition comprising a first Fc region comprises s one or more substitutions selected from the group consisting of: G236R, G236K and E269K. In one embodiment of the invention the composition comprising a first Fc region comprises one or more substitutions selected from the group consisting of: G236R and E269K. In one embodiment of the invention the composition comprising a first Fc region comprises a G263R or a G236K substitution.

In one embodiment of the invention the composition comprising a first Fc region comprises one substitution selected from the group consisting of: K322E and K322A.

In one embodiment of the invention the composition comprising a first Fc region comprises a P329R substitution.

In one embodiment of the invention the composition comprising a first Fc region comprises a G236R substitution.

In one embodiment of the invention the composition comprising a first Fc region comprises one substitution of the amino acid at position P329.

In one embodiment of the invention the composition comprising a first Fc region comprises one substitution selected from the group consisting of: P329R, P329A, P329T, P329Q, P329R, P329S, P329N, P329D, P329E, P329K, P329V, P329M, P329I, P329L, P329H, P329F, P329Y, P329W and P329P.

In one embodiment of the invention the composition comprising a first Fc region comprises one substitution selected from the group consisting of: P329R, P329K, P329E, P329D and P329A.

In one embodiment of the invention the composition comprising a first Fc region comprises a P329R substitution.

In one embodiment of the invention the composition comprising a first Fc region comprises a K322A substitution.

In one embodiment of the invention the composition comprising a first Fc region comprises an E269K substitution.

In one embodiment of the invention the composition comprising a second Fc region comprises one or more substitution(s) selected from the group consisting of: G237A, K326A, K326W, E333A and E333S.

In one embodiment of the invention the composition comprising a second Fc region comprises one or more substitution(s) selected from the group consisting of: K326A, K326W, E333A and E333S.

In one embodiment of the invention the composition comprising a second Fc region comprises one substitution selected from the group consisting of: K326A, K326W, E333A and E333S.

In one embodiment of the invention the composition comprising a second Fc region comprises a G237A substitution.

In one embodiment of the invention the composition comprising a second Fc region comprises a K326A substitution.

In one embodiment of the invention the composition comprising a second Fc region comprises a E333S substitution.

In one embodiment of the invention the composition comprising a second Fc region comprises two substitutions selected from the group consisting of: K326A, K326W, E333A and E333S.

In one embodiment of the invention the composition comprising second Fc region comprises a K326W and E333S substitution.

In one embodiment of the invention the composition comprising a second Fc region comprises a K326A and E333A substitution.

In one embodiment of the invention the composition comprising a second Fc region comprises a G237A and E333S substitution.

In one embodiment of the present invention the composition comprising a first and second antibody are present in the composition at a 1:50 to 50:1 molar ratio, such as a 1:1 molar ratio, a 1:2 molar ratio, a 1:3 molar ratio, a 1:4 molar ratio, a 1:5 molar ratio, a 1:6 molar ratio, a 1:7 molar ratio, a 1:8 molar ratio, a 1:9 molar ratio, a 1:10 molar ratio, a 1:15 molar ratio, a 1:20 molar ratio, a 1:25 molar ratio, a 1:30 molar ratio, a 1:35 molar ratio, a 1:40 molar ratio, a 1:45 molar ratio, a 1:50 molar ratio, a 50:1 molar ratio, a 45:1 molar ratio, a 40:1 molar ratio, a 35:1 molar ratio, a 30:1 molar ratio, a 25:1 molar ratio, a 20:1 molar ratio, a 15:1 molar ratio, a 10:1 molar ratio, a 9:1 molar ratio, a 8:1 molar ratio, a 7:1 molar ratio, a 6:1 molar ratio, a 5:1 molar ratio, a 4:1 molar ratio, a 3:1 molar ratio, a 2:1 molar ratio.

In one embodiment of the present invention the composition comprising a first antibody and a second antibody are present in the composition at molar ratio of about a 1:50 to 50:1, such as a molar ratio of about 1:40 to 40:1, such as a molar ratio of about 1:30 to 30:1, such as a molar ratio of about 1:20 to 20:1, such as a molar ratio of about 1:10 to 10:1, such as a molar ratio of about 1:9 to 9:1, such as a molar ratio of about 1:5 to 5:1.

In one embodiment of the present invention the composition comprising a first and a second antibody and/or any additional polypeptide are present in the composition at an equimolar ratio.

In one embodiment of the present invention the composition according to any aspect or embodiment is a pharmaceutical composition.

In one aspect the present invention relates to a method of depleting a cell population expressing a first antigen and a second antigen, which method comprises contacting said cell population with a first and second antibody or composition according to any aspect or embodiment disclosed herein.

In one embodiment of the present invention the cell population is a tumor cell population, such as a hematological tumor cell population or a solid tumor cell population.

In one embodiment of the invention the cell population is a present in the blood.

In one embodiment of the invention the cell population is a leukocyte, such as a leukocyte cell population.

In one embodiment of the invention the cell population is a subset of a leukocyte cell population.

In one embodiment of the invention the cell population is a lymphocyte cell population.

In one embodiment of the invention the cell population is a B cell population. In one embodiment of the invention the cell population is a subset of a B cell population.

In one embodiment of the invention the cell population is a T cell population. In one embodiment of the invention the cell population is a subset of a T cell population. In one embodiment of the invention the cell population is a regulatory T cell, such as a regulatory T cell population.

In one embodiment of the invention the cell population is a NK cell population.

In one embodiment of the invention the cell population is myeloid derived suppressor cell.

Therapeutic Applications

The first and second antibody, bispecific antibodies or compositions according to any aspect or embodiment of the present invention may be used as a medicament, i.e. for therapeutic applications.

In one aspect the present invention provides a first and second antibody or a composition according to any aspect or embodiment disclosed herein for use as a medicament.

In another aspect the present invention provides an antibody or a composition according to any aspect or embodiment disclosed herein for use in the treatment of cancer, autoimmune disease, inflammatory disease or infectious disease.

In another aspect the present invention relates to a method of treating an individual having a disease comprising administering to the individual an effective amount of a first and second antibody or composition according to any aspect or embodiment disclosed herein.

In aspect the invention relates to a method of treating an individual having a disease comprising administering to said individual an effective amount of a first and a second antibody according to any aspect or embodiment described herein or an effective amount of a composition according to any aspect or embodiment described herein.

In one embodiment of the invention the disease is selected from the group of: cancer, autoimmune disease, inflammatory disease and infectious disease.

In one embodiment of the invention the method comprises administering an additional therapeutic agent.

In one embodiment of the invention the method according to any aspect or embodiment disclosed herein relates to further administering an additional therapeutic agent.

In one embodiment of the invention the additional therapeutic agent is one or more anti-cancer agent(s) selected from the group consisting of chemotherapeutics (including but not limited to paclitaxel, temozolomide, cisplatin, carboplatin, oxaliplatin, irinotecan, doxorubicin, gemcitabine, 5-fluorouracil, pemetrexed), kinase inhibitors (including but not limited to sorafenib, sunitinib or everolimus), apoptosis-modulating agents (including but not limited to recombinant human TRAIL or birinapant), RAS inhibitors, proteasome inhibitors (including but not limited to bortezomib), histon deacetylase inhibitors (including but not limited to vorinostat), nutraceuticals, cytokines (including but not limited to IFN-γ), antibodies or antibody mimetics (including but not limited to anti-EGFR, anti-IGF-1R, anti-VEGF, anti-CD20, anti-CD38, anti-HER2, anti-PD-1, anti-PD-L1, anti-CTLA4, anti-CD40, anti-CD137, anti-GITR antibodies and antibody mimetics), antibody-drug conjugates.

Kit-of-Parts

It is to be understood that the embodiments described below with reference to a first and second antibody refers to antibodies comprising an Fc region of an immunoglobulin and an antigen-binding region.

The invention also relates to kit-of-parts for simultaneous, separate or sequential use in therapy comprising a first and second antibody as described herein. Furthermore, such first and second may be obtained according to any method described herein.

In one aspect the present invention relates to a kit of parts comprising an antibody or composition according to any aspect or embodiment described herein, wherein said first and second antibody or composition is in one or more containers such as vials.

In one embodiment of the present invention the kit of parts comprises a first and second antibody or a composition according to any aspect or embodiment described herein, for simultaneous, separate or sequential use in therapy.

In another aspect, the present invention relates to use of a first and second antibody, a composition or kit-of-parts according to any of the embodiments herein described for use in a diagnostic method.

In another aspect, the present invention relates to a diagnostic method comprising administering a first and second antibody, a composition or a kit-of-parts according to any embodiments herein described to at least a part of the body of a human or other mammal.

In another aspect, the present invention relates to use of a first and second antibody, a composition or kit-of-parts according to any of the embodiments herein described in imaging at least a part of the body of a human or other mammal.

In another aspect, the present invention relates to a method for imaging of at least a part of the body of a human or other mammal, comprising administering a first and second antibody, a composition or a kit-of-parts according to any embodiments herein described.

Further Uses

It is to be understood that the embodiments described below with reference to a first and second antibody refer to a first and second antibody each comprising an Fc region of an immunoglobulin and an antigen-binding region.

In a further aspect, the invention relates to a first and second antibody of the invention as described above for use as a medicament, in particular for use as a medicament for the treatment of diseases or disorders. Examples of such diseases and disorders include, without limitation, cancer, autoimmune diseases, inflammatory diseases, infectious diseases, bacterial, viral or fungal infections.

In another aspect, the present invention relates to a first and second antibody, bispecific antibodies, compositions and kit-of-parts described herein, for treatment of a disease, such as cancer.

In another aspect, the present invention relates to a method for treatment of a human disease, comprising administration of a first and second antibody, a composition or a kit-of-parts described herein.

In another aspect, the present invention relates to a method for treatment of cancer in a human comprising administration of a first and second antibody, a composition or a kit-of-parts.

"Treatment" refers to the administration of an effective amount of a therapeutically active compound of the present invention with the purpose of easing, ameliorating, arresting or eradicating (curing) symptoms or disease states.

An "effective amount" or "therapeutically effective amount" refers to an amount effective, at dosages and for periods of time necessary, to achieve a desired therapeutic result. A therapeutically effective amount of an antibody may vary according to factors such as the disease state, age, sex, and weight of the individual, and the ability of the antibody to elicit a desired response in the individual. A therapeutically effective amount is also one in which any toxic or detrimental effects of the antibody or antibody portion are outweighed by the therapeutically beneficial effects.

Dosages

It is to be understood that the embodiments described below with reference to an antibody refers to an antibody comprising an Fc region of an immunoglobulin and an antigen-binding region, an antibody may also be a multi-specific antibody such as a bispecific antibody having a first Fc region of an immunoglobulin and a first antigen-binding region, and a second polypeptide or antibody having a second Fc region of an immunoglobulin and a second antigen-binding region.

Efficient dosages and the dosage regimens for an antibody depend on the disease or condition to be treated and may be determined by the persons skilled in the art. An exemplary, non-limiting range for a therapeutically effective amount of an antibody of the present invention is about 0.1 to 100 mg/kg, such as about 0.1 to 50 mg/kg, for example about 0.1 to 20 mg/kg, such as about 0.1 to 10 mg/kg, for instance about 0.5, about such as 0.3, about 1, about 3, about 5, or about 8 mg/kg.

Antibodies of the present invention may also be administered in combination therapy, i.e., combined with other therapeutic agents relevant for the disease or condition to be treated. Accordingly, in one embodiment, the antibody-containing medicament is for combination with one or more further therapeutic agents, such as a cytotoxic, chemotherapeutic or anti-angiogenic agents. Such combined administration may be simultaneous, separate or sequential.

In a further embodiment, the present invention provides a method for treating or preventing disease, such as cancer, which method comprises administration to a subject in need thereof of a therapeutically effective amount of a variant or pharmaceutical composition of the present invention, in combination with radiotherapy and/or surgery.

Method of Preparation

It is to be understood that the embodiments described below with reference to an antibody refer to an antibody comprising an Fc region of an immunoglobulin and an antigen-binding region, an antibody may also be a multi-specific antibody having a first Fc region of an immunoglobulin and a first antigen-binding region, and a second antibody having a second Fc region of an immunoglobulin and a second antigen-binding region.

The invention also provides isolated nucleic acids and vectors encoding an antibody according to any one of the aspects described above, as well as vectors and expression systems encoding the antibodies. Suitable nucleic acid constructs, vectors and expression systems for antibodies and variants thereof are known in the art, and described in the Examples. In embodiments where the variant antibody comprises not only a heavy chain (or Fc-containing fragment thereof) but also a light chain, the nucleotide sequences encoding the heavy and light chain portions may be present on the same or different nucleic acids or vectors.

The invention also provides a method for producing, in a host cell, an antibody according to any one of the aspects described above, wherein said polypeptide or antibody comprises at least the Fc region of a heavy chain, said method comprising the following steps:
a) providing a nucleotide construct encoding said Fc region of said variant,
b) expressing said nucleotide construct in a host cell, and
c) recovering said antibody variant from a cell culture of said host cell.

In some embodiments, the antibody is a heavy-chain antibody. In most embodiments, however, the antibody will also contain a light chain and thus said host cell further expresses a light-chain-encoding construct, either on the same or a different vector.

Host cells suitable for the recombinant expression of antibodies are well-known in the art, and include CHO, HEK-293, Expi293, PER-C6, NS/0 and Sp2/0 cells. In one embodiment, said host cell is a cell which is capable of Asn-linked glycosylation of proteins, e.g. an eukaryotic cell, such as a mammalian cell, e.g. a human cell. In a further embodiment, said host cell is a non-human cell which is genetically engineered to produce glycoproteins having human-like or human glycosylation. Examples of such cells are genetically-modified *Pichia pastoris* (Hamilton et al., Science 301 (2003) 1244-1246; Potgieter et al., J. Biotechnology 139 (2009) 318-325) and genetically-modified *Lemna minor* (Cox et al., Nature Biotechnology 12 (2006) 1591-1597).

In one embodiment, said host cell is a host cell which is not capable of efficiently removing C-terminal lysine K447 residues from antibody heavy chains. For example, Table 2 in Liu et al. (2008) J Pharm Sci 97: 2426 (incorporated herein by reference) lists a number of such antibody production systems, e.g. Sp2/0, NS/0 or transgenic mammary gland (goat), wherein only partial removal of C-terminal lysines is obtained. In one embodiment, the host cell is a host cell with altered glycosylation machinery. Such cells have been described in the art and can be used as host cells in which to express variants of the invention to thereby produce an antibody with altered glycosylation. See, for example, Shields, R. L. et al. (2002) J. Biol. Chem. 277: 26733-26740; Umana et al. (1999) Nat. Biotech. 17:176-1, as well as EP1176195; WO03/035835; and WO99/54342. Additional methods for generating engineered glycoforms are known in the art, and include but are not limited to those described in Davies et al., 2001, Biotechnol Bioeng 74:288-294; Shields et al, 2002, J Biol Chem 277:26733-26740; Shinkawa et al., 2003, J Biol Chem 278:3466-3473), U.S. Pat. No. 6,602,684, WO00/61739A1; WO01/292246A1; WO02/311140A1; WO 02/30954A1; Potelligent™ technology (Biowa, Inc. Princeton, N.J.); GlycoMAb™ glycosylation engineering technology (GLYCART biotechnology AG, Zurich, Switzerland); US 20030115614; Okazaki et al., 2004, JMB, 336: 1239-49.

The invention also relates to an antibody obtained or obtainable by the method of the invention described above.

In a further aspect, the invention relates to a host cell capable of producing an antibody of the invention. In one embodiment, the host cell has been transformed or transfected with a nucleotide construct of the invention.

The present invention is further illustrated by the following examples which should not be construed as further limiting.

TABLE 1

SEQUENCE LIST

| SEQ ID NO | Name | Sequence |
|---|---|---|
| SEQ ID NO 1 | VH CAMPATH-1H | QVQLQESGPGLVRPSQTLSLTCTVSGFTFTDFY MNWVRQPPGRGLEWIGFIRDKAKGYTTEYNPS VKGRVTMLVDTSKNQFSLRLSSVTAADTAVYYC AREGHTAAPFDYWGQGSLVTVSS |
| SEQ ID NO 2 | VH CAMPATH-1H CDR1 | GFTFTDFY |
| SEQ ID NO 3 | VH CAMPATH-1H CDR2 | IRDKAKGYTT |
| SEQ ID NO 4 | VH CAMPATH-1H CDR3 | AREGHTAAPFDY |
| SEQ ID NO 5 | VL CAMPATH-1H | DIQMTQSPSSLSASVGDRVTITCKASQNIDKYL NWYQQKPGKAPKLLIYNTNNLQTGVPSRFSGSG SGTDFTFTISSLQPEDIATYYCLQHISRPRTFGQ GTKVEIK |

TABLE 1-continued

SEQUENCE LIST

| SEQ ID NO | Name | Sequence |
|---|---|---|
| SEQ ID NO 6 | VL CAMPAT H-1H CDR1 | QNIDKY |
| | VL CAMPAT H-1H CDR2 | NTN |
| SEQ ID NO 7 | VL CAMPAT H-1H CDR3 | LQHISRPRT |
| SEQ ID NO 8 | VH CD20-11B8 | EVQLVQSGGGLVHPGGSLRLSCTGSGFTFSYH AMHWVRQAPGKGLEWVSIIGTGGVTYYADSVK GRFTISRDNVKNSLYLQMNSLRAEDMAVYYCAR DYYGAGSFYDGLYGMDVWGQGTTVTVSS |
| SEQ ID NO 9 | VH CD20-11B8 CDR1 | GFTFSYHA |
| SEQ ID NO 10 | VH CD20-11B8 CDR2 | IGTGGVT |
| SEQ ID NO 11 | VH CD20-11B8 CDR3 | ARDYYGAGSFYDGLYGMDV |
| SEQ ID NO 12 | VL CD20-11B8 | EIVLTQSPATLSLSPGERATLSCRASQSVSSYLA WYQQKPGQAPRLLIYDASNRATGIPARFSGSGS GTDFTLTISSLEPEDFAVYYCQQRSDWPLTFGG GTKVEIK |
| SEQ ID NO 13 | VL CD20-11B8 CDR1 | QSVSSY |
| | VL CD20-11B8 CDR2 | DAS |
| SEQ ID NO 14 | VL CD20-11B8 CDR3 | QQRSDWPLT |
| SEQ ID NO 15 | VH gp120-b12 | QVQLVQSGAEVKKPGASVKVSCQASGYRFSNF VIHWVRQAPGQRFEWMGWINPYNGNKEFSAK FQDRVTFTADTSANTAYMELRSLRSADTAVYYCA RVGPYSWDDSPQDNYYMDVWGKGTTVIVSS |
| SEQ ID NO 16 | VH gp120-b12 CDR1 | GYRFSNFV |
| SEQ ID NO 17 | VH gp120-b12 CDR2 | INPYNGNK |
| SEQ ID NO 18 | VH gp120-b12 CDR3 | ARVGPYSWDDSPQDNYYMDV |
| SEQ ID NO 19 | VL gp120-b12 | EIVLTQSPGTLSLSPGERATFSCRSSHSIRSRRV AWYQHKPGQAPRVIHGVSNRASGISDRFSGSG SGTDFTLTITRVEPEDFALYYCQVYGASSYTFGQ GTKLERK |

TABLE 1-continued

SEQUENCE LIST

| SEQ ID NO | Name | Sequence |
|---|---|---|
| SEQ ID NO 20 | VL gp120-b12 CDR1 | HSIRSRR |
| | VL gp120-b12 CDR2 | GVS |
| SEQ ID NO 21 | VL gp120-b12-CDR3 | QVYGASSYT |
| SEQ ID NO 22 | constant region human HC IgG1m(f) | ASTKGPSVFPLAPSSKSTSGGTAALGCLVKDYFP EPVTVSWNSGALTSGVHTFPAVLQSSGLYSLSSV VTVPSSSLGTQTYICNVNHKPSNTKVDKRVEPKS CDKTHTCPPCPAPELLGGPSVFLFPPKPKDTLMIS RTPEVTCVVVDVSHEDPEVKFNWYVDGVEVHNA KTKPREEQYNSTYRVVSVLTVLHQDWLNGKEYK CKVSNKALPAPIEKTISKAKGQPREPQVYTLPPSR EEMTKNQVSLTCLVKGFYPSDIAVEWESNGQPE NNYKTTPPVLDSDGSFFLYSKLTVDKSRWQQGN VFSCSVMHEALHNHYTQKSLSLSPGK |
| SEQ ID NO 23 | constant region human HC IgG1m(z) | ASTKGPSVFPLAPSSKSTSGGTAALGCLVKDYFP EPVTVSWNSGALTSGVHTFPAVLQSSGLYSLSSV VTVPSSSLGTQTYICNVNHKPSNTKVDKKVEPKS CDKTHTCPPCPAPELLGGPSVFLFPPKPKDTLMIS RTPEVTCVVVDVSHEDPEVKFNWYVDGVEVHNA KTKPREEQYNSTYRVVSVLTVLHQDWLNGKEYK CKVSNKALPAPIEKTISKAKGQPREPQVYTLPPSR EEMTKNQVSLTCLVKGFYPSDIAVEWESNGQPE NNYKTTPPVLDSDGSFFLYSKLTVDKSRWQQGN VFSCSVMHEALHNHYTQKSLSLSPGK |
| SEQ ID NO 24 | constant region human HC IgG1m(a) | ASTKGPSVFPLAPSSKSTSGGTAALGCLVKDYFP EPVTVSWNSGALTSGVHTFPAVLQSSGLYSLSSV VTVPSSSLGTQTYICNVNHKPSNTKVDKPVEPKS CDKTHTCPPCPAPELLGGPSVFLFPPKPKDTLMIS RTPEVTCVVVDVSHEDPEVKFNWYVDGVEVHNA KTKPREEQYNSTYRVVSVLTVLHQDWLNGKEYK CKVSNKALPAPIEKTISKAKGQPREPQVYTLPPSR DELTKNQVSLTCLVKGFYPSDIAVEWESNGQPE NNYKTTPPVLDSDGSFFLYSKLTVDKSRWQQGN VFSCSVMHEALHNHYTQKSLSLSPGK |
| SEQ ID NO 25 | constant region human HC IgG1m(x) | ASTKGPSVFPLAPSSKSTSGGTAALGCLVKDYFP EPVTVSWNSGALTSGVHTFPAVLQSSGLYSLSSV VTVPSSSLGTQTYICNVNHKPSNTKVDKPVEPKS CDKTHTCPPCPAPELLGGPSVFLFPPKPKDTLMIS RTPEVTCVVVDVSHEDPEVKFNWYVDGVEVHNA KTKPREEQYNSTYRVVSVLTVLHQDWLNGKEYK CKVSNKALPAPIEKTISKAKGQPREPQVYTLPPSR EEMTKNQVSLTCLVKGFYPSDIAVEWESNGQPE NNYKTTPPVLDSDGSFFLYSKLTVDKSRWQQGN VFSCSVMHEGLHNHYTQKSLSLSPGK |
| SEQ ID NO 26 | constant region human HC IgG1m(f)-E430G | ASTKGPSVFPLAPSSKSTSGGTAALGCLVKDYFP EPVTVSWNSGALTSGVHTFPAVLQSSGLYSLSSV VTVPSSSLGTQTYICNVNHKPSNTKVDKRVEPKS CDKTHTCPPCPAPELLGGPSVFLFPPKPKDTLMIS RTPEVTCVVVDVSHEDPEVKFNWYVDGVEVHNA KTKPREEQYNSTYRVVSVLTVLHQDWLNGKEYK CKVSNKALPAPIEKTISKAKGQPREPQVYTLPPSR EEMTKNQVSLTCLVKGFYPSDIAVEWESNGQPE NNYKTTPPVLDSDGSFFLYSKLTVDKSRWQQGN VFSCSVMHGALHNHYTQKSLSLSPGK |

TABLE 1-continued

SEQUENCE LIST

| SEQ ID NO | Name | Sequence |
|---|---|---|
| SEQ ID NO 27 | constant region human HC IgG1m(f)-E345K | ASTKGPSVFPLAPSSKSTSGGTAALGCLVKDYFP EPVTVSWNSGALTSGVHTFPAVLQSSGLYSLSSV VTVPSSSLGTQTYICNVNHKPSNTKVDKRVEPKS CDKTHTCPPCPAPELLGGPSVFLFPPKPKDTLMIS RTPEVTCVVVDVSHEDPEVKFNWYVDGVEVHNA KTKPREEQYNSTYRVVSVLTVLHQDWLNGKEYK CKVSNKALPAPIEKTISKAKGQPRKPQVYTLPPSR EEMTKNQVSLTCLVKGFYPSDIAVEWESNGQPE NNYKTTPPVLDSDGSFFLYSKLTVDKSRWQQGN VFSCSVMHEALHNHYTQKSLSLSPGK |
| SEQ ID NO 28 | constant region human HC IgG1m(f)-E345R | ASTKGPSVFPLAPSSKSTSGGTAALGCLVKDYFP EPVTVSWNSGALTSGVHTFPAVLQSSGLYSLSSV VTVPSSSLGTQTYICNVNHKPSNTKVDKRVEPKS CDKTHTCPPCPAPELLGGPSVFLFPPKPKDTLMIS RTPEVTCVVVDVSHEDPEVKFNWYVDGVEVHNA KTKPREEQYNSTYRVVSVLTVLHQDWLNGKEYK CKVSNKALPAPIEKTISKAKGQPRRPQVYTLPPSR EEMTKNQVSLTCLVKGFYPSDIAVEWESNGQPE NNYKTTPPVLDSDGSFFLYSKLTVDKSRWQQGN VFSCSVMHEALHNHYTQKSLSLSPGK |
| SEQ ID NO 29 | constant region human HC IgG1m(f)-K439E | ASTKGPSVFPLAPSSKSTSGGTAALGCLVKDYFP EPVTVSWNSGALTSGVHTFPAVLQSSGLYSLSSV VTVPSSSLGTQTYICNVNHKPSNTKVDKRVEPKS CDKTHTCPPCPAPELLGGPSVFLFPPKPKDTLMIS RTPEVTCVVVDVSHEDPEVKFNWYVDGVEVHNA KTKPREEQYNSTYRVVSVLTVLHQDWLNGKEYK CKVSNKALPAPIEKTISKAKGQPREPQVYTLPPSR EEMTKNQVSLTCLVKGFYPSDIAVEWESNGQPE NNYKTTPPVLDSDGSFFLYSKLTVDKSRWQQGN VFSCSVMHEALHNHYTQESLSLSPGK |
| SEQ ID NO 30 | constant region human HC IgG1m(f)-S440K | ASTKGPSVFPLAPSSKSTSGGTAALGCLVKDYFP EPVTVSWNSGALTSGVHTFPAVLQSSGLYSLSSV VTVPSSSLGTQTYICNVNHKPSNTKVDKRVEPKS CDKTHTCPPCPAPELLGGPSVFLFPPKPKDTLMIS RTPEVTCVVVDVSHEDPEVKFNWYVDGVEVHNA KTKPREEQYNSTYRVVSVLTVLHQDWLNGKEYK CKVSNKALPAPIEKTISKAKGQPREPQVYTLPPSR EEMTKNQVSLTCLVKGFYPSDIAVEWESNGQPE NNYKTTPPVLDSDGSFFLYSKLTVDKSRWQQGN VFSCSVMHEALHNHYTQKKLSLSPGK |
| SEQ ID NO 31 | constant region human HC IgG2 | ASTKGPSVFPLAPCSRSTSESTAALGCLVKDYFPE PVTVSWNSGALTSGVHTFPAVLQSSGLYSLSSVV TVPSSNFGTQTYTCNVDHKPSNTKVDKTVERKC CVECPPCPAPPVAGPSVFLFPPKPKDTLMISRTPE VTCVVVDVSHEDPEVQFNWYVDGVEVHNAKTKP REEQFNSTFRVVSVLTVVHQDWLNGKEYKCKVS NKGLPAPIEKTISKTKGQPREPQVYTLPPSREEMT KNQVSLTCLVKGFYPSDIAVEWESNGQPENNYK TTPPMLDSDGSFFLYSKLTVDKSRWQQGNVFSC SVMHEALHNHYTQKSLSLSPGK |
| SEQ ID NO 32 | constant region human HC IgG3 | ASTKGPSVFPLAPCSRSTSGGTAALGCLVKDYFP EPVTVSWNSGALTSGVHTFPAVLQSSGLYSLSSV VTVPSSSLGTQTYTCNVNHKPSNTKVDKRVELKT PLGDTTHTCPRCPEPKSCDTPPPCPRCPEPKSCD TPPPCPRCPEPKSCDTPPPCPRCPAPELLGGPSVF LFPPKPKDTLMISRTPEVTCVVVDVSHEDPEVQF KWYVDGVEVHNAKTKPREEQYNSTFRVVSVLTV LHQDWLNGKEYKCKVSNKALPAPIEKTISKTKGQ PREPQVYTLPPSREEMTKNQVSLTCLVKGFYPSDI AVEWESSGQPENNYNTTPPMLDSDGSFFLYSKL TVDKSRWQQGNIFSCSVMHEALHNRFTQKSLSL SPGK |
| SEQ ID NO 33 | constant region human HC IgG4 | ASTKGPSVFPLAPCSRSTSESTAALGCLVKDYFPE PVTVSWNSGALTSGVHTFPAVLQSSGLYSLSSVV TVPSSSLGTKTYTCNVDHKPSNTKVDKRVESKY GPPCPSCPAPEFLGGPSVFLFPPKPKDTLMISRTP EVTCVVVDVSQEDPEVQFNWYVDGVEVHNAKT KPREEQFNSTYRVVSVLTVLHQDWLNGKEYKCK |

TABLE 1-continued

SEQUENCE LIST

| SEQ ID NO | Name | Sequence |
|---|---|---|
|  |  | VSNKGLPSSIEKTISKAKGQPREPQVYTLPPSQEE MTKNQVSLTCLVKGFYPSDIAVEWESNGQPENN YKTTPPVLDSDGSFFLYSRLTVDKSRWQEGNVFS CSVMHEALHNHYTQKSLSLSLGK |
| SEQ ID NO 34 | Constant region human kappa LC | RTVAAPSVFIFPPSDEQLKSGTASVVCLLNNFYPR EAKVQWKVDNALQSGNSQESVTEQDSKDSTYS LSSTLTLSKADYEKHKVYACEVTHQGLSSPVTKS FNRGEC |
| SEQ ID NO 35 | VH CD20-7D8 | EVQLVESGGGLVQPDRSLRLSCAASGFTFHDYA MHWVRQAPGKGLEWVSTISWNSGTIGYADSV KGRFTISRDNAKNSLYLQMNSLRAEDTALYYCAK DIQYGNYYYGMDVWGQGTTVTVSS |
| SEQ ID NO 36 | VH CD20-7D8 CDR1 | GFTFHDYA |
| SEQ ID NO 37 | VH CD20-7D8 CDR2 | ISWNSGTI |
| SEQ ID NO 38 | VH CD20-7D8 CDR3 | AKDIQYGNYYYGMDV |
| SEQ ID NO 39 | VL CD20-7D8 | EIVLTQSPATLSLSPGERATLSCRASQSVSSYLA WYQQKPGQAPRLLIYDASNRATGIPARFSGSGS GTDFTLTISSLEPEDFAVYYCQQRSNWPITFGQ GTRLEIK |
| SEQ ID NO 40 | VL CD20-7D8 CDR1 | QSVSSY |
|  | VL CD20-7D8 CDR2 | DAS |
| SEQ ID NO 41 | VL CD20-7D8 CDR3 | QQRSNWPIT |
| SEQ ID NO 42 | VH CD37-37-3 | QVQVKESGPGLVAPSQSLSITCTVSGFSLTTSG VSWVRQPPGKGLEWLGVIWGDGSTNYHSALK SRLSIKKDHSKSQVFLKLNSLQTDDTATYYCAKG GYSLAHWGQGTLVTVSA |
| SEQ ID NO 43 | VH CD37-37-3 CDR1 | GFSLTTSG |
| SEQ ID NO 44 | VH CD37-37-3 CDR2 | IWGDGST |
| SEQ ID NO 45 | VH CD37-37-3 CDR3 | AKGGYSLAH |
| SEQ ID NO 46 | VL CD37-37-3 | DIQMTQSPASLSVSVGETVTITCRASENIRSNLA WYQQKQGKSPQLLVNVATNLADGVPSRFSGSG SGTQYSLKINSLQSEDFGTYYCQHYWGTTWTF GGGTKLEIK |

TABLE 1-continued

SEQUENCE LIST

| SEQ ID NO | Name | Sequence |
|---|---|---|
| SEQ ID NO 47 | VL CD37-37-3 CDR1 | ENIRSN |
| | VL CD37-37-3 CDR2 | VAT |
| SEQ ID NO 48 | VL CD37-37-3 CDR3 | QHYWGTTWT |
| SEQ ID NO 49 | VH hDR5-01-G56T | EVQLQQSGAEVVKPGASVKLSCKASGFNIKDTF IHWVKQAPGQGLEWIGRIDPANTNTKYDPKFQ GKATITTDTSSNTAYMELSSLRSEDTAVYYCVRG LYTYYFDYWGQGTLVTVSS |
| SEQ ID NO 50 | VH hDR5-01-G56T CDR1 | GFNIKDTF |
| SEQ ID NO 51 | VH hDR5-01-G56T CDR2 | IDPANTNT |
| SEQ ID NO 52 | VH hDR5-01-G56T CDR3 | VRGLYTYYFDY |
| SEQ ID NO 53 | VL hDR5-01-G56T | EIVMTQSPATLSVSPGERATLSCRASQSISNNLH WYQQKPGQAPRLLIKFASQSITGIPARFSGSGS GTEFTLTISSLQSEDFAVYYCQQGNSWPYTFGQ GTKLEIK |
| SEQ ID NO 54 | VL hDR5-01-G56T CDR1 | QSISNN |
| | VL hDR5-01-G56T CDR2 | FAS |
| SEQ ID NO 55 | VL hDR5-01-G56T CDR3 | QQGNSWPYT |
| SEQ ID NO 56 | VH hDR5-05 | QVQLVQSGAEVKKPGASVKVSCKASGFNIKDT HMHWVRQAPGQRLEWIGRIDPANGNTEYDQK FQGRVTITVDTSASTAYMELSSLRSEDTAVYYCA RWGTNVYFAYWGQGTLVTVSS |
| SEQ ID NO 57 | VH hDR5-05 CDR1 | GFNIKDTH |
| SEQ ID NO 58 | VH hDR5-05 CDR2 | IDPANGNT |
| SEQ ID NO 59 | VH hDR5-05 CDR3 | ARWGTNVYFAY |
| SEQ ID NO 60 | VL hDR5-05 | DIQLTQSPSSLSASVGDRVTITCSASSSVSYMY WYQQKPGKAPKPWIYRTSNLASGVPSRFSGSGS GTDPFTLTISSLQPEDFATYYCQQYHSYPPTFGG GTKVEIK |
| SEQ ID NO 61 | VL hDR5-05 CDR1 | SSVSY |
| | VL hDR5-05 CDR2 | RTS |

TABLE 1-continued

SEQUENCE LIST

| SEQ ID NO | Name | | Sequence |
|---|---|---|---|
| SEQ ID NO 62 | VL hDR5-05 CDR3 | | QQYHSYPPT |
| SEQ ID NO 63 | constant region human HC IgG1m(f)-A327K-E430G | constant region human HC IgG1m(f)-A327K-E430G | ASTKGPSVFPLAPSSKSTSGGTAALGCLVKDYFP EPVTVSWNSGALTSGVHTFPAVLQSSGLYSLSSV VTVPSSSLGTQTYICNVNHKPSNTKVDKRVEPKS CDKTHTCPPCPAPELLGGPSVFLFPPKPKDTLMIS RTPEVTCVVVDVSHEDPEVKFNWYVDGVEVHNA KTKPREEQYNSTYRVVSVLTVLHQDWLNGKEYK CKVSNKKLPAPIEKTISKAKGQPREPQVYTLPPSR EEMTKNQVSLTCLVKGFYPSDIAVEWESNGQPE NNYKTTPPVLDSDGSFFLYSKLTVDKSRWQQGN VFSCSVMHGALHNHYTQKSLSLSPGK |
| SEQ ID NO 64 | constant region human HC IgG1m(f)-E345A-K439E-G236R | constant region human HC IgG1m(f)-G236R-E345A-K439E | ASTKGPSVFPLAPSSKSTSGGTAALGCLVKDYFP EPVTVSWNSGALTSGVHTFPAVLQSSGLYSLSSV VTVPSSSLGTQTYICNVNHKPSNTKVDKRVEPKS CDKTHTCPPCPAPELLRGPSVFLFPPKPKDTLMIS RTPEVTCVVVDVSHEDPEVKFNWYVDGVEVHNA KTKPREEQYNSTYRVVSVLTVLHQDWLNGKEYK CKVSNKALPAPIEKTISKAKGQPRAPQVYTLPPSR EEMTKNQVSLTCLVKGFYPSDIAVEWESNGQPE NNYKTTPPVLDSDGSFFLYSKLTVDKSRWQQGN VFSCSVMHEALHNHYTQESLSLSPGK |
| SEQ ID NO 65 | constant region human HC IgG1m(f)-E345A-S440K-G237A | constant region human HC IgG1m(f)-G237A-E345A-S440K | ASTKGPSVFPLAPSSKSTSGGTAALGCLVKDYFP EPVTVSWNSGALTSGVHTFPAVLQSSGLYSLSSV VTVPSSSLGTQTYICNVNHKPSNTKVDKRVEPKS CDKTHTCPPCPAPELLGAPSVFLFPPKPKDTLMIS RTPEVTCVVVDVSHEDPEVKFNWYVDGVEVHNA KTKPREEQYNSTYRVVSVLTVLHQDWLNGKEYK CKVSNKALPAPIEKTISKAKGQPRAPQVYTLPPSR EEMTKNQVSLTCLVKGFYPSDIAVEWESNGQPE NNYKTTPPVLDSDGSFFLYSKLTVDKSRWQQGN VFSCSVMHEALHNHYTQKKLSLSPGK |
| SEQ ID NO 66 | constant region human HC IgG1m(f)-E345K-K439E-G236R | constant region human HC IgG1m(f)-G236R-E345K-K439E | ASTKGPSVFPLAPSSKSTSGGTAALGCLVKDYFP EPVTVSWNSGALTSGVHTFPAVLQSSGLYSLSSV VTVPSSSLGTQTYICNVNHKPSNTKVDKRVEPKS CDKTHTCPPCPAPELLRGPSVFLFPPKPKDTLMIS RTPEVTCVVVDVSHEDPEVKFNWYVDGVEVHNA KTKPREEQYNSTYRVVSVLTVLHQDWLNGKEYK CKVSNKALPAPIEKTISKAKGQPRKPQVYTLPPSR EEMTKNQVSLTCLVKGFYPSDIAVEWESNGQPE NNYKTTPPVLDSDGSFFLYSKLTVDKSRWQQGN VFSCSVMHEALHNHYTQESLSLSPGK |
| SEQ ID NO 67 | constant region human HC IgG1m(f)-E345K-K439E-K322A | constant region human HC IgG1m(f)-K322A-E345K-K439E | ASTKGPSVFPLAPSSKSTSGGTAALGCLVKDYFP EPVTVSWNSGALTSGVHTFPAVLQSSGLYSLSSV VTVPSSSLGTQTYICNVNHKPSNTKVDKRVEPKS CDKTHTCPPCPAPELLGGPSVFLFPPKPKDTLMIS RTPEVTCVVVDVSHEDPEVKFNWYVDGVEVHNA KTKPREEQYNSTYRVVSVLTVLHQDWLNGKEYK CAVSNKALPAPIEKTISKAKGQPRKPQVYTLPPS REEMTKNQVSLTCLVKGFYPSDIAVEWESNGQP ENNYKTTPPVLDSDGSFFLYSKLTVDKSRWQQG NVFSCSVMHEALHNHYTQESLSLSPGK |
| SEQ ID NO 68 | constant region human HC IgG1m(f)-E345K-S440K-E333S | constant region human HC IgG1m(f)-E333S-E345K-S440K | ASTKGPSVFPLAPSSKSTSGGTAALGCLVKDYFP EPVTVSWNSGALTSGVHTFPAVLQSSGLYSLSSV VTVPSSSLGTQTYICNVNHKPSNTKVDKRVEPKS CDKTHTCPPCPAPELLGGPSVFLFPPKPKDTLMIS RTPEVTCVVVDVSHEDPEVKFNWYVDGVEVHNA KTKPREEQYNSTYRVVSVLTVLHQDWLNGKEYK CKVSNKALPAPISKTISKAKGQPRKPQVYTLPPS REEMTKNQVSLTCLVKGFYPSDIAVEWESNGQP ENNYKTTPPVLDSDGSFFLYSKLTVDKSRWQQG NVFSCSVMHEALHNHYTQKKLSLSPGK |

TABLE 1-continued

SEQUENCE LIST

| SEQ ID NO | Name | | Sequence |
|---|---|---|---|
| SEQ ID NO 69 | constant region human HC IgG1m(f)- E345Q- K439E- G236R | region human HC IgG1m (f)- G236R- E345Q- K439E | ASTKGPSVFPLAPSSKSTSGGTAALGCLVKDYFP EPVTVSWNSGALTSGVHTFPAVLQSSGLYSLSSV VTVPSSSLGTQTYICNVNHKPSNTKVDKRVEPKS CDKTHTCPPCPAPELLRGPSVFLFPPKPKDTLMIS RTPEVTCVVVDVSHEDPEVKFNWYVDGVEVHNA KTKPREEQYNSTYRVVSVLTVLHQDWLNGKEYK CKVSNKALPAPIEKTISKAKGQPRQPQVYTLPPS REEMTKNQVSLTCLVKGFYPSDIAVEWESNGQP ENNYKTTPPVLDSDGSFFLYSKLTVDKSRWQQG NVFSCSVMHEALHNHYTQESLSLSPGK |
| SEQ ID NO 70 | constant region human HC IgG1m(f)- E345Q- S440K- G237A | constant region human HC IgG1m (f)- G237A- E345Q- S440K | ASTKGPSVFPLAPSSKSTSGGTAALGCLVKDYFP EPVTVSWNSGALTSGVHTFPAVLQSSGLYSLSSV VTVPSSSLGTQTYICNVNHKPSNTKVDKRVEPKS CDKTHTCPPCPAPELLGAPSVFLFPPKPKDTLMIS RTPEVTCVVVDVSHEDPEVKFNWYVDGVEVHNA KTKPREEQYNSTYRVVSVLTVLHQDWLNGKEYK CKVSNKALPAPIEKTISKAKGQPRQPQVYTLPPS REEMTKNQVSLTCLVKGFYPSDIAVEWESNGQP ENNYKTTPPVLDSDGSFFLYSKLTVDKSRWQQG NVFSCSVMHEALHNHYTQKKLSLSPGK |
| SEQ ID NO 71 | constant region human HC IgG1m(f)- E345R- E430G- K439E- G236R | constant region human HC IgG1m (f)- G236R- E345R- E430G- K439E | ASTKGPSVFPLAPSSKSTSGGTAALGCLVKDYFP EPVTVSWNSGALTSGVHTFPAVLQSSGLYSLSSV VTVPSSSLGTQTYICNVNHKPSNTKVDKRVEPKS CDKTHTCPPCPAPELLRGPSVFLFPPKPKDTLMIS RTPEVTCVVVDVSHEDPEVKFNWYVDGVEVHNA KTKPREEQYNSTYRVVSVLTVLHQDWLNGKEYK CKVSNKALPAPIEKTISKAKGQPRRPQVYTLPPSR EEMTKNQVSLTCLVKGFYPSDIAVEWESNGQPE NNYKTTPPVLDSDGSFFLYSKLTVDKSRWQQGN VFSCSVMHGALHNHYTQESLSLSPGK |
| SEQ ID NO 72 | constant region human HC IgG1m(f)- E345R- E430G- S440K- E333S | constant region human HC IgG1m (f)- E333S- E345R- E430G- S440K | ASTKGPSVFPLAPSSKSTSGGTAALGCLVKDYFP EPVTVSWNSGALTSGVHTFPAVLQSSGLYSLSSV VTVPSSSLGTQTYICNVNHKPSNTKVDKRVEPKS CDKTHTCPPCPAPELLGGPSVFLFPPKPKDTLMIS RTPEVTCVVVDVSHEDPEVKFNWYVDGVEVHNA KTKPREEQYNSTYRVVSVLTVLHQDWLNGKEYK CKVSNKALPAPISKTISKAKGQPRRPQVYTLPPS REEMTKNQVSLTCLVKGFYPSDIAVEWESNGQP ENNYKTTPPVLDSDGSFFLYSKLTVDKSRWQQG NVFSCSVMHGALHNHYTQKKLSLSPGK |
| SEQ ID NO 73 | constant region human HC IgG1m(f)- E345R- K439E- G236R | constant region human HC IgG1m (f)- G236R- E345R- K439E | ASTKGPSVFPLAPSSKSTSGGTAALGCLVKDYFP EPVTVSWNSGALTSGVHTFPAVLQSSGLYSLSSV VTVPSSSLGTQTYICNVNHKPSNTKVDKRVEPKS CDKTHTCPPCPAPELLRGPSVFLFPPKPKDTLMIS RTPEVTCVVVDVSHEDPEVKFNWYVDGVEVHNA KTKPREEQYNSTYRVVSVLTVLHQDWLNGKEYK CKVSNKALPAPIEKTISKAKGQPRRPQVYTLPPSR EEMTKNQVSLTCLVKGFYPSDIAVEWESNGQPE NNYKTTPPVLDSDGSFFLYSKLTVDKSRWQQGN VFSCSVMHEALHNHYTQESLSLSPGK |
| SEQ ID NO 74 | constant region human HC IgG1m(f)- E345R- K439E- K322A | constant region human HC IgG1m (f)- K322A- E345R- K439E | ASTKGPSVFPLAPSSKSTSGGTAALGCLVKDYFP EPVTVSWNSGALTSGVHTFPAVLQSSGLYSLSSV VTVPSSSLGTQTYICNVNHKPSNTKVDKRVEPKS CDKTHTCPPCPAPELLGGPSVFLFPPKPKDTLMIS RTPEVTCVVVDVSHEDPEVKFNWYVDGVEVHNA KTKPREEQYNSTYRVVSVLTVLHQDWLNGKEYK CAVSNKALPAPIEKTISKAKGQPRRPQVYTLPPS REEMTKNQVSLTCLVKGFYPSDIAVEWESNGQP ENNYKTTPPVLDSDGSFFLYSKLTVDKSRWQQG NVFSCSVMHEALHNHYTQESLSLSPGK |

TABLE 1-continued

SEQUENCE LIST

| SEQ ID NO | Name | | Sequence |
|---|---|---|---|
| SEQ ID NO 75 | constant region human HC IgG1m(f)-E345V-K439E-G236R | constant region human HC IgG1m(f)-G236R-E345V-K439E | ASTKGPSVFPLAPSSKSTSGGTAALGCLVKDYFP EPVTVSWNSGALTSGVHTFPAVLQSSGLYSLSSV VTVPSSSLGTQTYICNVNHKPSNTKVDKRVEPKS CDKTHTCPPCPAPELLRGPSVFLFPPKPKDTLMIS RTPEVTCVVVDVSHEDPEVKFNWYVDGVEVHNA KTKPREEQYNSTYRVVSVLTVLHQDWLNGKEYK CKVSNKALPAPIEKTISKAKGQPRVPQVYTLPPSR EEMTKNQVSLTCLVKGFYPSDIAVEWESNGQPE NNYKTTPPVLDSDGSFFLYSKLTVDKSRWQQGN VFSCSVMHEALHNHYTQESLSLSPGK |
| SEQ ID NO 76 | constant region human HC IgG1m(f)-E345V-S440K-G237A | constant region human HC IgG1m(f)-G237A-E345V-S440K | ASTKGPSVFPLAPSSKSTSGGTAALGCLVKDYFP EPVTVSWNSGALTSGVHTFPAVLQSSGLYSLSSV VTVPSSSLGTQTYICNVNHKPSNTKVDKRVEPKS CDKTHTCPPCPAPELLGAPSVFLFPPKPKDTLMIS RTPEVTCVVVDVSHEDPEVKFNWYVDGVEVHNA KTKPREEQYNSTYRVVSVLTVLHQDWLNGKEYK CKVSNKALPAPIEKTISKAKGQPRVPQVYTLPPSR EEMTKNQVSLTCLVKGFYPSDIAVEWESNGQPE NNYKTTPPVLDSDGSFFLYSKLTVDKSRWQQGN VFSCSVMHEALHNHYTQKKLSLSPGK |
| SEQ ID NO 77 | constant region human HC IgG1m(f)-E345Y-K439E-G236R | constant region human HC IgG1m(f)-G236R-E345Y-K439E | ASTKGPSVFPLAPSSKSTSGGTAALGCLVKDYFP EPVTVSWNSGALTSGVHTFPAVLQSSGLYSLSSV VTVPSSSLGTQTYICNVNHKPSNTKVDKRVEPKS CDKTHTCPPCPAPELLRGPSVFLFPPKPKDTLMIS RTPEVTCVVVDVSHEDPEVKFNWYVDGVEVHNA KTKPREEQYNSTYRVVSVLTVLHQDWLNGKEYK CKVSNKALPAPIEKTISKAKGQPRYPQVYTLPPSR EEMTKNQVSLTCLVKGFYPSDIAVEWESNGQPE NNYKTTPPVLDSDGSFFLYSKLTVDKSRWQQGN VFSCSVMHEALHNHYTQESLSLSPGK |
| SEQ ID NO 78 | constant region human HC IgG1m(f)-E345Y-S440K-G237A | constant region human HC IgG1m(f)-G237A-E345Y-S440K | ASTKGPSVFPLAPSSKSTSGGTAALGCLVKDYFP EPVTVSWNSGALTSGVHTFPAVLQSSGLYSLSSV VTVPSSSLGTQTYICNVNHKPSNTKVDKRVEPKS CDKTHTCPPCPAPELLGAPSVFLFPPKPKDTLMIS RTPEVTCVVVDVSHEDPEVKFNWYVDGVEVHNA KTKPREEQYNSTYRVVSVLTVLHQDWLNGKEYK CKVSNKALPAPIEKTISKAKGQPRYPQVYTLPPSR EEMTKNQVSLTCLVKGFYPSDIAVEWESNGQPE NNYKTTPPVLDSDGSFFLYSKLTVDKSRWQQGN VFSCSVMHEALHNHYTQKKLSLSPGK |
| SEQ ID NO 79 | constant region human HC IgG1m(f)-E430G | constant region human HC IgG1m(f)-E430G | ASTKGPSVFPLAPSSKSTSGGTAALGCLVKDYFP EPVTVSWNSGALTSGVHTFPAVLQSSGLYSLSSV VTVPSSSLGTQTYICNVNHKPSNTKVDKRVEPKS CDKTHTCPPCPAPELLGGPSVFLFPPKPKDTLMIS RTPEVTCVVVDVSHEDPEVKFNWYVDGVEVHNA KTKPREEQYNSTYRVVSVLTVLHQDWLNGKEYK CKVSNKALPAPIEKTISKAKGQPREPQVYTLPPSR EEMTKNQVSLTCLVKGFYPSDIAVEWESNGQPE NNYKTTPPVLDSDGSFFLYSKLTVDKSRWQQGN VFSCSVMHGALHNHYTQKSLSLSPGK |
| SEQ ID NO 80 | constant region human HC IgG1m(f)-E430G-K439E | constant region human HC IgG1m(f)-E430G-K439E | ASTKGPSVFPLAPSSKSTSGGTAALGCLVKDYFP EPVTVSWNSGALTSGVHTFPAVLQSSGLYSLSSV VTVPSSSLGTQTYICNVNHKPSNTKVDKRVEPKS CDKTHTCPPCPAPELLGGPSVFLFPPKPKDTLMIS RTPEVTCVVVDVSHEDPEVKFNWYVDGVEVHNA KTKPREEQYNSTYRVVSVLTVLHQDWLNGKEYK CKVSNKALPAPIEKTISKAKGQPREPQVYTLPPSR EEMTKNQVSLTCLVKGFYPSDIAVEWESNGQPE NNYKTTPPVLDSDGSFFLYSKLTVDKSRWQQGN VFSCSVMHGALHNHYTQESLSLSPGK |

TABLE 1-continued

SEQUENCE LIST

| SEQ ID NO | Name | | Sequence |
|---|---|---|---|
| SEQ ID NO 81 | constant region human HC IgG1m(f)- E430G- K439E- E269K | constant region human HC IgG1m (f)- E269K- E430G- K439E | ASTKGPSVFPLAPSSKSTSGGTAALGCLVKDYFP EPVTVSWNSGALTSGVHTFPAVLQSSGLYSLSSV VTVPSSSLGTQTYICNVNHKPSNTKVDKRVEPKS CDKTHTCPPCPAPELLGGPSVFLFPPKPKDTLMIS RTPEVTCVVVDVSHKDPEVKFNWYVDGVEVHNA KTKPREEQYNSTYRVVSVLTVLHQDWLNGKEYK CKVSNKALPAPIEKTISKAKGQPREPQVYTLPPSR EEMTKNQVSLTCLVKGFYPSDIAVEWESNGQPE NNYKTTPPVLDSDGSFFLYSKLTVDKSRWQQGN VFSCSVMHGALHNHYTQESLSLSPGK |
| SEQ ID NO 82 | constant region human HC IgG1m(f)- E430G- K439E- E333S | constant region human HC IgG1m (f)- E333S- E430G- K439E | ASTKGPSVFPLAPSSKSTSGGTAALGCLVKDYFP EPVTVSWNSGALTSGVHTFPAVLQSSGLYSLSSV VTVPSSSLGTQTYICNVNHKPSNTKVDKRVEPKS CDKTHTCPPCPAPELLGGPSVFLFPPKPKDTLMIS RTPEVTCVVVDVSHEDPEVKFNWYVDGVEVHNA KTKPREEQYNSTYRVVSVLTVLHQDWLNGKEYK CKVSNKALPAPISKTISKAKGQPREPQVYTLPPSR EEMTKNQVSLTCLVKGFYPSDIAVEWESNGQPE NNYKTTPPVLDSDGSFFLYSKLTVDKSRWQQGN VFSCSVMHGALHNHYTQESLSLSPGK |
| SEQ ID NO 83 | constant region human HC IgG1m(f)- E430G- K439E- G236K | constant region human HC IgG1m (f)- G236K- E430G- K439E | ASTKGPSVFPLAPSSKSTSGGTAALGCLVKDYFP EPVTVSWNSGALTSGVHTFPAVLQSSGLYSLSSV VTVPSSSLGTQTYICNVNHKPSNTKVDKRVEPKS CDKTHTCPPCPAPELLKGPSVFLFPPKPKDTLMIS RTPEVTCVVVDVSHEDPEVKFNWYVDGVEVHNA KTKPREEQYNSTYRVVSVLTVLHQDWLNGKEYK CKVSNKALPAPIEKTISKAKGQPREPQVYTLPPSR EEMTKNQVSLTCLVKGFYPSDIAVEWESNGQPE NNYKTTPPVLDSDGSFFLYSKLTVDKSRWQQGN VFSCSVMHGALHNHYTQESLSLSPGK |
| SEQ ID NO 84 | constant region human HC IgG1m(f)- E430G- K439E- G236R | constant region human HC IgG1m (f)- G236R- E430G- K439E | ASTKGPSVFPLAPSSKSTSGGTAALGCLVKDYFP EPVTVSWNSGALTSGVHTFPAVLQSSGLYSLSSV VTVPSSSLGTQTYICNVNHKPSNTKVDKRVEPKS CDKTHTCPPCPAPELLRGPSVFLFPPKPKDTLMIS RTPEVTCVVVDVSHEDPEVKFNWYVDGVEVHNA KTKPREEQYNSTYRVVSVLTVLHQDWLNGKEYK CKVSNKALPAPIEKTISKAKGQPREPQVYTLPPSR EEMTKNQVSLTCLVKGFYPSDIAVEWESNGQPE NNYKTTPPVLDSDGSFFLYSKLTVDKSRWQQGN VFSCSVMHGALHNHYTQESLSLSPGK |
| SEQ ID NO 85 | constant region human HC IgG1m(f)- E430G- K439E- G237A | constant region human HC IgG1m (f)- G237A- E430G- K439E | ASTKGPSVFPLAPSSKSTSGGTAALGCLVKDYFP EPVTVSWNSGALTSGVHTFPAVLQSSGLYSLSSV VTVPSSSLGTQTYICNVNHKPSNTKVDKRVEPKS CDKTHTCPPCPAPELLGAPSVFLFPPKPKDTLMIS RTPEVTCVVVDVSHEDPEVKFNWYVDGVEVHNA KTKPREEQYNSTYRVVSVLTVLHQDWLNGKEYK CKVSNKALPAPIEKTISKAKGQPREPQVYTLPPSR EEMTKNQVSLTCLVKGFYPSDIAVEWESNGQPE NNYKTTPPVLDSDGSFFLYSKLTVDKSRWQQGN VFSCSVMHGALHNHYTQESLSLSPGK |
| SEQ ID NO 86 | constant region human HC IgG1m(f)- E430G- K439E- G237A- K322A | constant region human HC IgG1m- (f)- G237A- K322A- E430G- K439E | ASTKGPSVFPLAPSSKSTSGGTAALGCLVKDYFP EPVTVSWNSGALTSGVHTFPAVLQSSGLYSLSSV VTVPSSSLGTQTYICNVNHKPSNTKVDKRVEPKS CDKTHTCPPCPAPELLGAPSVFLFPPKPKDTLMIS RTPEVTCVVVDVSHEDPEVKFNWYVDGVEVHNA KTKPREEQYNSTYRVVSVLTVLHQDWLNGKEYK CAVSNKALPAPIEKTISKAKGQPREPQVYTLPPSR EEMTKNQVSLTCLVKGFYPSDIAVEWESNGQPE NNYKTTPPVLDSDGSFFLYSKLTVDKSRWQQGN VFSCSVMHGALHNHYTQESLSLSPGK |

TABLE 1-continued

SEQUENCE LIST

| SEQ ID NO | Name | | Sequence |
|---|---|---|---|
| SEQ ID NO 87 | constant region human HC IgG1m(f)-E430G-K439E-G237Q | constant region human HC IgG1m (f)-G237Q-E430G-K439E | ASTKGPSVFPLAPSSKSTSGGTAALGCLVKDYFP EPVTVSWNSGALTSGVHTFPAVLQSSGLYSLSSV VTVPSSSLGTQTYICNVNHKPSNTKVDKRVEPKS CDKTHTCPPCPAPELLGQPSVFLFPPKPKDTLMIS RTPEVTCVVVDVSHEDPEVKFNWYVDGVEVHNA KTKPREEQYNSTYRVVSVLTVLHQDWLNGKEYK CKVSNKALPAPIEKTISKAKGQPREPQVYTLPPSR EEMTKNQVSLTCLVKGFYPSDIAVEWESNGQPE NNYKTTPPVLDSDGSFFLYSKLTVDKSRWQQGN VFSCSVMHGALHNHYTQESLSLSPGK |
| SEQ ID NO 88 | constant region human HC IgG1m(f)-E430G-K439E-G237R | constant region human HC IgG1m (f)-G237R-E430G-K439E | ASTKGPSVFPLAPSSKSTSGGTAALGCLVKDYFP EPVTVSWNSGALTSGVHTFPAVLQSSGLYSLSSV VTVPSSSLGTQTYICNVNHKPSNTKVDKRVEPKS CDKTHTCPPCPAPELLGRPSVFLFPPKPKDTLMIS RTPEVTCVVVDVSHEDPEVKFNWYVDGVEVHNA KTKPREEQYNSTYRVVSVLTVLHQDWLNGKEYK CKVSNKALPAPIEKTISKAKGQPREPQVYTLPPSR EEMTKNQVSLTCLVKGFYPSDIAVEWESNGQPE NNYKTTPPVLDSDGSFFLYSKLTVDKSRWQQGN VFSCSVMHGALHNHYTQESLSLSPGK |
| SEQ ID NO 89 | constant region human HC IgG1m(f)-E430G-K439E-G237T | constant region human HC IgG1m (f)-G237T-E430G-K439E | ASTKGPSVFPLAPSSKSTSGGTAALGCLVKDYFP EPVTVSWNSGALTSGVHTFPAVLQSSGLYSLSSV VTVPSSSLGTQTYICNVNHKPSNTKVDKRVEPKS CDKTHTCPPCPAPELLGTPSVFLFPPKPKDTLMIS RTPEVTCVVVDVSHEDPEVKFNWYVDGVEVHNA KTKPREEQYNSTYRVVSVLTVLHQDWLNGKEYK CKVSNKALPAPIEKTISKAKGQPREPQVYTLPPSR EEMTKNQVSLTCLVKGFYPSDIAVEWESNGQPE NNYKTTPPVLDSDGSFFLYSKLTVDKSRWQQGN VFSCSVMHGALHNHYTQESLSLSPGK |
| SEQ ID NO 90 | constant region human HC IgG1m(f)-E430G-K439E-K322A | constant region human HC IgG1m (f)-K322A-E430G-K439E | ASTKGPSVFPLAPSSKSTSGGTAALGCLVKDYFP EPVTVSWNSGALTSGVHTFPAVLQSSGLYSLSSV VTVPSSSLGTQTYICNVNHKPSNTKVDKRVEPKS CDKTHTCPPCPAPELLGGPSVFLFPPKPKDTLMIS RTPEVTCVVVDVSHEDPEVKFNWYVDGVEVHNA KTKPREEQYNSTYRVVSVLTVLHQDWLNGKEYK CAVSNKALPAPIEKTISKAKGQPREPQVYTLPPSR EEMTKNQVSLTCLVKGFYPSDIAVEWESNGQPE NNYKTTPPVLDSDGSFFLYSKLTVDKSRWQQGN VFSCSVMHGALHNHYTQESLSLSPGK |
| SEQ ID NO 91 | constant region human HC IgG1m(f)-E430G-K439E-K322E | constant region human HC IgG1m (f)-K322E-E430G-K439E | ASTKGPSVFPLAPSSKSTSGGTAALGCLVKDYFP EPVTVSWNSGALTSGVHTFPAVLQSSGLYSLSSV VTVPSSSLGTQTYICNVNHKPSNTKVDKRVEPKS CDKTHTCPPCPAPELLGGPSVFLFPPKPKDTLMIS RTPEVTCVVVDVSHEDPEVKFNWYVDGVEVHNA KTKPREEQYNSTYRVVSVLTVLHQDWLNGKEYK CEVSNKALPAPIEKTISKAKGQPREPQVYTLPPSR EEMTKNQVSLTCLVKGFYPSDIAVEWESNGQPE NNYKTTPPVLDSDGSFFLYSKLTVDKSRWQQGN VFSCSVMHGALHNHYTQESLSLSPGK |
| SEQ ID NO 92 | constant region human HC IgG1m(f)-E430G-K439E-L234A | constant region human HC IgG1m (f)-L234A-E430G-K439E | ASTKGPSVFPLAPSSKSTSGGTAALGCLVKDYFP EPVTVSWNSGALTSGVHTFPAVLQSSGLYSLSSV VTVPSSSLGTQTYICNVNHKPSNTKVDKRVEPKS CDKTHTCPPCPAPEALGGPSVFLFPPKPKDTLMIS RTPEVTCVVVDVSHEDPEVKFNWYVDGVEVHNA KTKPREEQYNSTYRVVSVLTVLHQDWLNGKEYK CKVSNKALPAPIEKTISKAKGQPREPQVYTLPPSR EEMTKNQVSLTCLVKGFYPSDIAVEWESNGQPE NNYKTTPPVLDSDGSFFLYSKLTVDKSRWQQGN VFSCSVMHGALHNHYTQESLSLSPGK |

TABLE 1-continued

SEQUENCE LIST

| SEQ ID NO | Name | | Sequence |
|---|---|---|---|
| SEQ ID NO 93 | constant region human HC IgG1m(f)- E430G- K439E- L234A- L235A | constant region human HC IgG1m (f)- L234A- L235A- E430G- K439E | ASTKGPSVFPLAPSSKSTSGGTAALGCLVKDYFP EPVTVSWNSGALTSGVHTFPAVLQSSGLYSLSSV VTVPSSSLGTQTYICNVNHKPSNTKVDKRVEPKS CDKTHTCPPCPAPEAAGGPSVFLFPPKPKDTLMI SRTPEVTCVVVDVSHEDPEVKFNWYVDGVEVHN AKTKPREEQYNSTYRVVSVLTVLHQDWLNGKEY KCKVSNKALPAPIEKTISKAKGQPREPQVYTLPPS REEMTKNQVSLTCLVKGFYPSDIAVEWESNGQP ENNYKTTPPVLDSDGSFFLYSKLTVDKSRWQQG NVFSCSVMHGALHNHYTQESLSLSPGK |
| SEQ ID NO 94 | constant region human HC IgG1m(f)- E430G- K439E- L234F | constant region human HC IgG1m (f)- L234F- E430G- K439E | ASTKGPSVFPLAPSSKSTSGGTAALGCLVKDYFP EPVTVSWNSGALTSGVHTFPAVLQSSGLYSLSSV VTVPSSSLGTQTYICNVNHKPSNTKVDKRVEPKS CDKTHTCPPCPAPEFLGGPSVFLFPPKPKDTLMIS RTPEVTCVVVDVSHEDPEVKFNWYVDGVEVHNA KTKPREEQYNSTYRVVSVLTVLHQDWLNGKEYK CKVSNKALPAPIEKTISKAKGQPREPQVYTLPPSR EEMTKNQVSLTCLVKGFYPSDIAVEWESNGQPE NNYKTTPPVLDSDGSFFLYSKLTVDKSRWQQGN VFSCSVMHGALHNHYTQESLSLSPGK |
| SEQ ID NO 95 | constant region human HC IgG1m(f)- E430G- K439E- L234F- L235E | constant region human HC IgG1m (f)- L234F- L235E- E430G- K439E | ASTKGPSVFPLAPSSKSTSGGTAALGCLVKDYFP EPVTVSWNSGALTSGVHTFPAVLQSSGLYSLSSV VTVPSSSLGTQTYICNVNHKPSNTKVDKRVEPKS CDKTHTCPPCPAPEFEGGPSVFLFPPKPKDTLMIS RTPEVTCVVVDVSHEDPEVKFNWYVDGVEVHNA KTKPREEQYNSTYRVVSVLTVLHQDWLNGKEYK CKVSNKALPAPIEKTISKAKGQPREPQVYTLPPSR EEMTKNQVSLTCLVKGFYPSDIAVEWESNGQPE NNYKTTPPVLDSDGSFFLYSKLTVDKSRWQQGN VFSCSVMHGALHNHYTQESLSLSPGK |
| SEQ ID NO 96 | constant region human HC IgG1m(f)- E430G- K439E- L235A | constant region human HC IgG1m (f)- L235A- E430G- K439E | ASTKGPSVFPLAPSSKSTSGGTAALGCLVKDYFP EPVTVSWNSGALTSGVHTFPAVLQSSGLYSLSSV VTVPSSSLGTQTYICNVNHKPSNTKVDKRVEPKS CDKTHTCPPCPAPELAGGPSVFLFPPKPKDTLMIS RTPEVTCVVVDVSHEDPEVKFNWYVDGVEVHNA KTKPREEQYNSTYRVVSVLTVLHQDWLNGKEYK CKVSNKALPAPIEKTISKAKGQPREPQVYTLPPSR EEMTKNQVSLTCLVKGFYPSDIAVEWESNGQPE NNYKTTPPVLDSDGSFFLYSKLTVDKSRWQQGN VFSCSVMHGALHNHYTQESLSLSPGK |
| SEQ ID NO 97 | constant region human HC IgG1m(f)- E430G- K439E- L235E | constant region human HC IgG1m (f)- L235E- E430G- K439E | ASTKGPSVFPLAPSSKSTSGGTAALGCLVKDYFP EPVTVSWNSGALTSGVHTFPAVLQSSGLYSLSSV VTVPSSSLGTQTYICNVNHKPSNTKVDKRVEPKS CDKTHTCPPCPAPELEGGPSVFLFPPKPKDTLMIS RTPEVTCVVVDVSHEDPEVKFNWYVDGVEVHNA KTKPREEQYNSTYRVVSVLTVLHQDWLNGKEYK CKVSNKALPAPIEKTISKAKGQPREPQVYTLPPSR EEMTKNQVSLTCLVKGFYPSDIAVEWESNGQPE NNYKTTPPVLDSDGSFFLYSKLTVDKSRWQQGN VFSCSVMHGALHNHYTQESLSLSPGK |
| SEQ ID NO 98 | constant region human HC IgG1m(f)- E430G- K439E- L235Q | constant region human HC IgG1m (f)- L235Q- E430G- K439E | ASTKGPSVFPLAPSSKSTSGGTAALGCLVKDYFP EPVTVSWNSGALTSGVHTFPAVLQSSGLYSLSSV VTVPSSSLGTQTYICNVNHKPSNTKVDKRVEPKS CDKTHTCPPCPAPELQGGPSVFLFPPKPKDTLMIS RTPEVTCVVVDVSHEDPEVKFNWYVDGVEVHNA KTKPREEQYNSTYRVVSVLTVLHQDWLNGKEYK CKVSNKALPAPIEKTISKAKGQPREPQVYTLPPSR EEMTKNQVSLTCLVKGFYPSDIAVEWESNGQPE NNYKTTPPVLDSDGSFFLYSKLTVDKSRWQQGN VFSCSVMHGALHNHYTQESLSLSPGK |

TABLE 1-continued

SEQUENCE LIST

| SEQ ID NO | Name | | Sequence |
|---|---|---|---|
| SEQ ID NO 99 | constant region human HC IgG1m(f)-E430G-K439E-N297Q | constant region human IgG1m (f)-N297Q-E430G-K439E | ASTKGPSVFPLAPSSKSTSGGTAALGCLVKDYFP EPVTVSWNSGALTSGVHTFPAVLQSSGLYSLSSV VTVPSSSLGTQTYICNVNHKPSNTKVDKRVEPKS CDKTHTCPPCPAPELLGGPSVFLFPPKPKDTLMIS RTPEVTCVVVDVSHEDPEVKFNWYVDGVEVHNA KTKPREEQYQSTYRVVSVLTVLHQDWLNGKEYK CKVSNKALPAPIEKTISKAKGQPREPQVYTLPPSR EEMTKNQVSLTCLVKGFYPSDIAVEWESNGQPE NNYKTTPPVLDSDGSFFLYSKLTVDKSRWQQGN VFSCSVMHGALHNHYTQESLSLSPGK |
| SEQ ID NO 100 | constant region human HC IgG1m(f)-E430G-K439E-P329R | constant region human IgG1m (f)-P329R-E430G-K439E | ASTKGPSVFPLAPSSKSTSGGTAALGCLVKDYFP EPVTVSWNSGALTSGVHTFPAVLQSSGLYSLSSV VTVPSSSLGTQTYICNVNHKPSNTKVDKRVEPKS CDKTHTCPPCPAPELLGGPSVFLFPPKPKDTLMIS RTPEVTCVVVDVSHEDPEVKFNWYVDGVEVHNA KTKPREEQYNSTYRVVSVLTVLHQDWLNGKEYK CKVSNKALRAPIEKTISKAKGQPREPQVYTLPPSR EEMTKNQVSLTCLVKGFYPSDIAVEWESNGQPE NNYKTTPPVLDSDGSFFLYSKLTVDKSRWQQGN VFSCSVMHGALHNHYTQESLSLSPGK |
| SEQ ID NO 101 | constant region human HC IgG1m(f)-E430G-S440K | constant region human IgG1m (f)-E430G-S440K | ASTKGPSVFPLAPSSKSTSGGTAALGCLVKDYFP EPVTVSWNSGALTSGVHTFPAVLQSSGLYSLSSV VTVPSSSLGTQTYICNVNHKPSNTKVDKRVEPKS CDKTHTCPPCPAPELLGGPSVFLFPPKPKDTLMIS RTPEVTCVVVDVSHEDPEVKFNWYVDGVEVHNA KTKPREEQYNSTYRVVSVLTVLHQDWLNGKEYK CKVSNKALPAPIEKTISKAKGQPREPQVYTLPPSR EEMTKNQVSLTCLVKGFYPSDIAVEWESNGQPE NNYKTTPPVLDSDGSFFLYSKLTVDKSRWQQGN VFSCSVMHGALHNHYTQKKLSLSPGK |
| SEQ ID NO 102 | constant region human HC IgG1m(f)-E430G-S440K-E333A | constant region human IgG1m (f)-E333A-E430G-S440K | ASTKGPSVFPLAPSSKSTSGGTAALGCLVKDYFP EPVTVSWNSGALTSGVHTFPAVLQSSGLYSLSSV VTVPSSSLGTQTYICNVNHKPSNTKVDKRVEPKS CDKTHTCPPCPAPELLGGPSVFLFPPKPKDTLMIS RTPEVTCVVVDVSHEDPEVKFNWYVDGVEVHNA KTKPREEQYNSTYRVVSVLTVLHQDWLNGKEYK CKVSNKALPAPIAKTISKAKGQPREPQVYTLPPSR EEMTKNQVSLTCLVKGFYPSDIAVEWESNGQPE NNYKTTPPVLDSDGSFFLYSKLTVDKSRWQQGN VFSCSVMHGALHNHYTQKKLSLSPGK |
| SEQ ID NO 103 | constant region human HC IgG1m(f)-E430G-S440K-E333S | constant region human IgG1m (f)-E333S-E430G-S440K | ASTKGPSVFPLAPSSKSTSGGTAALGCLVKDYFP EPVTVSWNSGALTSGVHTFPAVLQSSGLYSLSSV VTVPSSSLGTQTYICNVNHKPSNTKVDKRVEPKS CDKTHTCPPCPAPELLGGPSVFLFPPKPKDTLMIS RTPEVTCVVVDVSHEDPEVKFNWYVDGVEVHNA KTKPREEQYNSTYRVVSVLTVLHQDWLNGKEYK CKVSNKALPAPISKTISKAKGQPREPQVYTLPPSR EEMTKNQVSLTCLVKGFYPSDIAVEWESNGQPE NNYKTTPPVLDSDGSFFLYSKLTVDKSRWQQGN VFSCSVMHGALHNHYTQKKLSLSPGK |
| SEQ ID NO 104 | constant region human HC IgG1m(f)-E430G-S440K-G236R | constant region human IgG1m (f)-G236R-E430G-S440K | ASTKGPSVFPLAPSSKSTSGGTAALGCLVKDYFP EPVTVSWNSGALTSGVHTFPAVLQSSGLYSLSSV VTVPSSSLGTQTYICNVNHKPSNTKVDKRVEPKS CDKTHTCPPCPAPELLRGPSVFLFPPKPKDTLMIS RTPEVTCVVVDVSHEDPEVKFNWYVDGVEVHNA KTKPREEQYNSTYRVVSVLTVLHQDWLNGKEYK CKVSNKALPAPIEKTISKAKGQPREPQVYTLPPSR EEMTKNQVSLTCLVKGFYPSDIAVEWESNGQPE NNYKTTPPVLDSDGSFFLYSKLTVDKSRWQQGN VFSCSVMHGALHNHYTQKKLSLSPGK |

TABLE 1-continued

SEQUENCE LIST

| SEQ ID NO | Name | | Sequence |
|---|---|---|---|
| SEQ ID NO 105 | constant region human HC IgG1m(f)-E430G-S440K-G237A | constant region human HC IgG1m (f)-G237A-E430G-S440K | ASTKGPSVFPLAPSSKSTSGGTAALGCLVKDYFP EPVTVSWNSGALTSGVHTFPAVLQSSGLYSLSSV VTVPSSSLGTQTYICNVNHKPSNTKVDKRVEPKS CDKTHTCPPCPAPELLGAPSVFLFPPKPKDTLMIS RTPEVTCVVVDVSHEDPEVKFNWYVDGVEVHNA KTKPREEQYNSTYRVVSVLTVLHQDWLNGKEYK CKVSNKALPAPIEKTISKAKGQPREPQVYTLPPSR EEMTKNQVSLTCLVKGFYPSDIAVEWESNGQPE NNYKTTPPVLDSDGSFFLYSKLTVDKSRWQQGN VFSCSVMHGALHNHYTQKKLSLSPGK |
| SEQ ID NO 106 | constant region human HC IgG1m(f)-E430G-S440K-G237A-E333S | constant region human HC IgG1m (f)-G237A-E333S-E430G-S440K | ASTKGPSVFPLAPSSKSTSGGTAALGCLVKDYFP EPVTVSWNSGALTSGVHTFPAVLQSSGLYSLSSV VTVPSSSLGTQTYICNVNHKPSNTKVDKRVEPKS CDKTHTCPPCPAPELLGAPSVFLFPPKPKDTLMIS RTPEVTCVVVDVSHEDPEVKFNWYVDGVEVHNA KTKPREEQYNSTYRVVSVLTVLHQDWLNGKEYK CKVSNKALPAPISKTISKAKGQPREPQVYTLPPSR EEMTKNQVSLTCLVKGFYPSDIAVEWESNGQPE NNYKTTPPVLDSDGSFFLYSKLTVDKSRWQQGN VFSCSVMHGALHNHYTQKKLSLSPGK |
| SEQ ID NO 107 | constant region human HC IgG1m(f)-E430G-S440K-G237Q | constant region human HC IgG1m (f)-G237Q-E430G-S440K | ASTKGPSVFPLAPSSKSTSGGTAALGCLVKDYFP EPVTVSWNSGALTSGVHTFPAVLQSSGLYSLSSV VTVPSSSLGTQTYICNVNHKPSNTKVDKRVEPKS CDKTHTCPPCPAPELLGQPSVFLFPPKPKDTLMIS RTPEVTCVVVDVSHEDPEVKFNWYVDGVEVHNA KTKPREEQYNSTYRVVSVLTVLHQDWLNGKEYK CKVSNKALPAPIEKTISKAKGQPREPQVYTLPPSR EEMTKNQVSLTCLVKGFYPSDIAVEWESNGQPE NNYKTTPPVLDSDGSFFLYSKLTVDKSRWQQGN VFSCSVMHGALHNHYTQKKLSLSPGK |
| SEQ ID NO 108 | constant region human HC IgG1m(f)-E430G-S440K-G237R | constant region human HC IgG1m (f)-G237R-E430G-S440K | ASTKGPSVFPLAPSSKSTSGGTAALGCLVKDYFP EPVTVSWNSGALTSGVHTFPAVLQSSGLYSLSSV VTVPSSSLGTQTYICNVNHKPSNTKVDKRVEPKS CDKTHTCPPCPAPELLGRPSVFLFPPKPKDTLMIS RTPEVTCVVVDVSHEDPEVKFNWYVDGVEVHNA KTKPREEQYNSTYRVVSVLTVLHQDWLNGKEYK CKVSNKALPAPIEKTISKAKGQPREPQVYTLPPSR EEMTKNQVSLTCLVKGFYPSDIAVEWESNGQPE NNYKTTPPVLDSDGSFFLYSKLTVDKSRWQQGN VFSCSVMHGALHNHYTQKKLSLSPGK |
| SEQ ID NO 109 | constant region human HC IgG1m(f)-E430G-S440K-K322E | constant region human HC IgG1m (f)-K322E-E430G-S440K | ASTKGPSVFPLAPSSKSTSGGTAALGCLVKDYFP EPVTVSWNSGALTSGVHTFPAVLQSSGLYSLSSV VTVPSSSLGTQTYICNVNHKPSNTKVDKRVEPKS CDKTHTCPPCPAPELLGGPSVFLFPPKPKDTLMIS RTPEVTCVVVDVSHEDPEVKFNWYVDGVEVHNA KTKPREEQYNSTYRVVSVLTVLHQDWLNGKEYK CEVSNKALPAPIEKTISKAKGQPREPQVYTLPPSR EEMTKNQVSLTCLVKGFYPSDIAVEWESNGQPE NNYKTTPPVLDSDGSFFLYSKLTVDKSRWQQGN VFSCSVMHGALHNHYTQKKLSLSPGK |
| SEQ ID NO 110 | constant region human HC IgG1m(f)-E430G-S440K-K326A | constant region human HC IgG1m (f)-K326A-E430G-S440K | ASTKGPSVFPLAPSSKSTSGGTAALGCLVKDYFP EPVTVSWNSGALTSGVHTFPAVLQSSGLYSLSSV VTVPSSSLGTQTYICNVNHKPSNTKVDKRVEPKS CDKTHTCPPCPAPELLGGPSVFLFPPKPKDTLMIS RTPEVTCVVVDVSHEDPEVKFNWYVDGVEVHNA KTKPREEQYNSTYRVVSVLTVLHQDWLNGKEYK CKVSNAALPAPIEKTISKAKGQPREPQVYTLPPSR EEMTKNQVSLTCLVKGFYPSDIAVEWESNGQPE NNYKTTPPVLDSDGSFFLYSKLTVDKSRWQQGN VFSCSVMHGALHNHYTQKKLSLSPGK |

TABLE 1-continued

SEQUENCE LIST

| SEQ ID NO | Name | | Sequence |
|---|---|---|---|
| SEQ ID NO 111 | constant region human HC IgG1m(f)- E430G- S440K- K326A- E333A | constant region human HC IgG1m (f)- K326A- E333A- E430G- S440K | ASTKGPSVFPLAPSSKSTSGGTAALGCLVKDYFP EPVTVSWNSGALTSGVHTFPAVLQSSGLYSLSSV VTVPSSSLGTQTYICNVNHKPSNTKVDKRVEPKS CDKTHTCPPCPAPELLGGPSVFLFPPKPKDTLMIS RTPEVTCVVVDVSHEDPEVKFNWYVDGVEVHNA KTKPREEQYNSTYRVVSVLTVLHQDWLNGKEYK CKVSNAALPAPIAKTISKAKGQPREPQVYTLPPS REEMTKNQVSLTCLVKGFYPSDIAVEWESNGQP ENNYKTTPPVLDSDGSFFLYSKLTVDKSRWQQG NVFSCSVMHGALHNHYTQKKLSLSPGK |
| SEQ ID NO 112 | constant region human HC IgG1m(f)- E430G- S440K- K326W | constant region human HC IgG1m (f)- K326W- E430G- S440K | ASTKGPSVFPLAPSSKSTSGGTAALGCLVKDYFP EPVTVSWNSGALTSGVHTFPAVLQSSGLYSLSSV VTVPSSSLGTQTYICNVNHKPSNTKVDKRVEPKS CDKTHTCPPCPAPELLGGPSVFLFPPKPKDTLMIS RTPEVTCVVVDVSHEDPEVKFNWYVDGVEVHNA KTKPREEQYNSTYRVVSVLTVLHQDWLNGKEYK CKVSNWALPAPIEKTISKAKGQPREPQVYTLPPS REEMTKNQVSLTCLVKGFYPSDIAVEWESNGQP ENNYKTTPPVLDSDGSFFLYSKLTVDKSRWQQG NVFSCSVMHGALHNHYTQKKLSLSPGK |
| SEQ ID NO 113 | constant region human HC IgG1m(f)- E430G- S440K- | constant region human HC IgG1m (f)- N297Q- E430G- S440K | ASTKGPSVFPLAPSSKSTSGGTAALGCLVKDYFP EPVTVSWNSGALTSGVHTFPAVLQSSGLYSLSSV VTVPSSSLGTQTYICNVNHKPSNTKVDKRVEPKS CDKTHTCPPCPAPELLGGPSVFLFPPKPKDTLMIS RTPEVTCVVVDVSHEDPEVKFNWYVDGVEVHNA KTKPREEQYNSTYRVVSVLTVLHQDWLNGKEYK CKVSNKALPAPIEKTISKAKGQPREPQVYTLPPSR EEMTKNQVSLTCLVKGFYPSDIAVEWESNGQPE NNYKTTPPVLDSDGSFFLYSKLTVDKSRWQQGN VFSCSVMHGALHNHYTQKKLSLSPGK |
| SEQ ID NO 114 | constant region human HC IgG1m(f)- E430G- S440K- P329R | constant region human HC IgG1m (f)- P329R- E430G- S440K | ASTKGPSVFPLAPSSKSTSGGTAALGCLVKDYFP EPVTVSWNSGALTSGVHTFPAVLQSSGLYSLSSV VTVPSSSLGTQTYICNVNHKPSNTKVDKRVEPKS CDKTHTCPPCPAPELLGGPSVFLFPPKPKDTLMIS RTPEVTCVVVDVSHEDPEVKFNWYVDGVEVHNA KTKPREEQYNSTYRVVSVLTVLHQDWLNGKEYK CKVSNKALRAPIEKTISKAKGQPREPQVYTLPPSR EEMTKNQVSLTCLVKGFYPSDIAVEWESNGQPE NNYKTTPPVLDSDGSFFLYSKLTVDKSRWQQGN VFSCSVMHGALHNHYTQKKLSLSPGK |
| SEQ ID NO 115 | constant region human HC IgG1m(f)- E430N- K439E- G236R | constant region human HC IgG1m (f)- G236R- E430N- K439E | ASTKGPSVFPLAPSSKSTSGGTAALGCLVKDYFP EPVTVSWNSGALTSGVHTFPAVLQSSGLYSLSSV VTVPSSSLGTQTYICNVNHKPSNTKVDKRVEPKS CDKTHTCPPCPAPELLRGPSVFLFPPKPKDTLMIS RTPEVTCVVVDVSHEDPEVKFNWYVDGVEVHNA KTKPREEQYNSTYRVVSVLTVLHQDWLNGKEYK CKVSNKALPAPIEKTISKAKGQPREPQVYTLPPSR EEMTKNQVSLTCLVKGFYPSDIAVEWESNGQPE NNYKTTPPVLDSDGSFFLYSKLTVDKSRWQQGN VFSCSVMHNALHNHYTQESLSLSPGK |
| SEQ ID NO 116 | constant region human HC IgG1m(f)- E430N- S440K- G237A | constant region human HC IgG1m (f)- G237A- E430N- S440K | ASTKGPSVFPLAPSSKSTSGGTAALGCLVKDYFP EPVTVSWNSGALTSGVHTFPAVLQSSGLYSLSSV VTVPSSSLGTQTYICNVNHKPSNTKVDKRVEPKS CDKTHTCPPCPAPELLGAPSVFLFPPKPKDTLMIS RTPEVTCVVVDVSHEDPEVKFNWYVDGVEVHNA KTKPREEQYNSTYRVVSVLTVLHQDWLNGKEYK CKVSNKALPAPIEKTISKAKGQPREPQVYTLPPSR EEMTKNQVSLTCLVKGFYPSDIAVEWESNGQPE NNYKTTPPVLDSDGSFFLYSKLTVDKSRWQQGN VFSCSVMHNALHNHYTQKKLSLSPGK |

TABLE 1-continued

SEQUENCE LIST

| SEQ ID NO | Name | | Sequence |
|---|---|---|---|
| SEQ ID NO 117 | constant region human HC IgG1m(f)-E430T-K439E-G236R | constant region human HC IgG1m (f)-G236R-E430T-K439E | ASTKGPSVFPLAPSSKSTSGGTAALGCLVKDYFP EPVTVSWNSGALTSGVHTFPAVLQSSGLYSLSSV VTVPSSSLGTQTYICNVNHKPSNTKVDKRVEPKS CDKTHTCPPCPAPELLRGPSVFLFPPKPKDTLMIS RTPEVTCVVVDVSHEDPEVKFNWYVDGVEVHNA KTKPREEQYNSTYRVVSVLTVLHQDWLNGKEYK CKVSNKALPAPIEKTISKAKGQPREPQVYTLPPSR EEMTKNQVSLTCLVKGFYPSDIAVEWESNGQPE NNYKTTPPVLDSDGSFFLYSKLTVDKSRWQQGN VFSCSVMHTALHNHYTQESLSLSPGK |
| SEQ ID NO 118 | constant region human HC IgG1m(f)-E430T-S440K-G237A | constant region human HC IgG1m (f)-G237A-E430T-S440K | ASTKGPSVFPLAPSSKSTSGGTAALGCLVKDYFP EPVTVSWNSGALTSGVHTFPAVLQSSGLYSLSSV VTVPSSSLGTQTYICNVNHKPSNTKVDKRVEPKS CDKTHTCPPCPAPELLGAPSVFLFPPKPKDTLMIS RTPEVTCVVVDVSHEDPEVKFNWYVDGVEVHNA KTKPREEQYNSTYRVVSVLTVLHQDWLNGKEYK CKVSNKALPAPIEKTISKAKGQPREPQVYTLPPSR EEMTKNQVSLTCLVKGFYPSDIAVEWESNGQPE NNYKTTPPVLDSDGSFFLYSKLTVDKSRWQQGN VFSCSVMHTALHNHYTQKKLSLSPGK |
| SEQ ID NO 119 | constant region human HC IgG1m(f)-E430V-K439E-G236R | constant region human HC IgG1m (f)-G236R-E430V-K439E | ASTKGPSVFPLAPSSKSTSGGTAALGCLVKDYFP EPVTVSWNSGALTSGVHTFPAVLQSSGLYSLSSV VTVPSSSLGTQTYICNVNHKPSNTKVDKRVEPKS CDKTHTCPPCPAPELLRGPSVFLFPPKPKDTLMIS RTPEVTCVVVDVSHEDPEVKFNWYVDGVEVHNA KTKPREEQYNSTYRVVSVLTVLHQDWLNGKEYK CKVSNKALPAPIEKTISKAKGQPREPQVYTLPPSR EEMTKNQVSLTCLVKGFYPSDIAVEWESNGQPE NNYKTTPPVLDSDGSFFLYSKLTVDKSRWQQGN VFSCSVMHVALHNHYTQESLSLSPGK |
| SEQ ID NO 120 | constant region human HC IgG1m(f)-E430V-S440K-G237A | constant region human HC IgG1m (f)-G237A-E430V-S440K | ASTKGPSVFPLAPSSKSTSGGTAALGCLVKDYFP EPVTVSWNSGALTSGVHTFPAVLQSSGLYSLSSV VTVPSSSLGTQTYICNVNHKPSNTKVDKRVEPKS CDKTHTCPPCPAPELLGAPSVFLFPPKPKDTLMIS RTPEVTCVVVDVSHEDPEVKFNWYVDGVEVHNA KTKPREEQYNSTYRVVSVLTVLHQDWLNGKEYK CKVSNKALPAPIEKTISKAKGQPREPQVYTLPPSR EEMTKNQVSLTCLVKGFYPSDIAVEWESNGQPE NNYKTTPPVLDSDGSFFLYSKLTVDKSRWQQGN VFSCSVMHVALHNHYTQKKLSLSPGK |
| SEQ ID NO 121 | constant region human HC IgG1m(f)-E430Y-K439E-G236R | constant region human HC IgG1m (f)-G236R-E430Y-K439E | ASTKGPSVFPLAPSSKSTSGGTAALGCLVKDYFP EPVTVSWNSGALTSGVHTFPAVLQSSGLYSLSSV VTVPSSSLGTQTYICNVNHKPSNTKVDKRVEPKS CDKTHTCPPCPAPELLRGPSVFLFPPKPKDTLMIS RTPEVTCVVVDVSHEDPEVKFNWYVDGVEVHNA KTKPREEQYNSTYRVVSVLTVLHQDWLNGKEYK CKVSNKALPAPIEKTISKAKGQPREPQVYTLPPSR EEMTKNQVSLTCLVKGFYPSDIAVEWESNGQPE NNYKTTPPVLDSDGSFFLYSKLTVDKSRWQQGN VFSCSVMHYALHNHYTQESLSLSPGK |
| SEQ ID NO 122 | constant region human HC IgG1m(f)-E430Y-S440K-G237A | constant region human HC IgG1m (f)-G237A-E430Y-S440K | ASTKGPSVFPLAPSSKSTSGGTAALGCLVKDYFP EPVTVSWNSGALTSGVHTFPAVLQSSGLYSLSSV VTVPSSSLGTQTYICNVNHKPSNTKVDKRVEPKS CDKTHTCPPCPAPELLGAPSVFLFPPKPKDTLMIS RTPEVTCVVVDVSHEDPEVKFNWYVDGVEVHNA KTKPREEQYNSTYRVVSVLTVLHQDWLNGKEYK CKVSNKALPAPIEKTISKAKGQPREPQVYTLPPSR EEMTKNQVSLTCLVKGFYPSDIAVEWESNGQPE NNYKTTPPVLDSDGSFFLYSKLTVDKSRWQQGN VFSCSVMHYALHNHYTQKKLSLSPGK |

TABLE 1-continued

SEQUENCE LIST

| SEQ ID NO | Name | | Sequence |
|---|---|---|---|
| SEQ ID NO 123 | constant region human HC IgG1m(f)- G236R- E430G | constant region human HC IgG1m (f)- G236R- E430G | ASTKGPSVFPLAPSSKSTSGGTAALGCLVKDYFP EPVTVSWNSGALTSGVHTFPAVLQSSGLYSLSSV VTVPSSSLGTQTYICNVNHKPSNTKVDKRVEPKS CDKTHTCPPCPAPELLRGPSVFLFPPKPKDTLMIS RTPEVTCVVVDVSHEDPEVKFNWYVDGVEVHNA KTKPREEQYNSTYRVVSVLTVLHQDWLNGKEYK CKVSNKALPAPIEKTISKAKGQPREPQVYTLPPSR EEMTKNQVSLTCLVKGFYPSDIAVEWESNGQPE NNYKTTPPVLDSDGSFFLYSKLTVDKSRWQQGN VFSCSVMHGALHNHYTQKSLSLSPGK |
| SEQ ID NO 124 | constant region human HC IgG1m(f)- G237A- E430G | constant region human HC IgG1m (f)- G237A- E430G | ASTKGPSVFPLAPSSKSTSGGTAALGCLVKDYFP EPVTVSWNSGALTSGVHTFPAVLQSSGLYSLSSV VTVPSSSLGTQTYICNVNHKPSNTKVDKRVEPKS CDKTHTCPPCPAPELLGAPSVFLFPPKPKDTLMIS RTPEVTCVVVDVSHEDPEVKFNWYVDGVEVHNA KTKPREEQYNSTYRVVSVLTVLHQDWLNGKEYK CKVSNKALPAPIEKTISKAKGQPREPQVYTLPPSR EEMTKNQVSLTCLVKGFYPSDIAVEWESNGQPE NNYKTTPPVLDSDGSFFLYSKLTVDKSRWQQGN VFSCSVMHGALHNHYTQKSLSLSPGK |
| SEQ ID NO 125 | constant region human HC IgG1m(f)- G237Q- E430G | constant region human HC IgG1m (f)- G237Q- E430G | ASTKGPSVFPLAPSSKSTSGGTAALGCLVKDYFP EPVTVSWNSGALTSGVHTFPAVLQSSGLYSLSSV VTVPSSSLGTQTYICNVNHKPSNTKVDKRVEPKS CDKTHTCPPCPAPELLGQPSVFLFPPKPKDTLMIS RTPEVTCVVVDVSHEDPEVKFNWYVDGVEVHNA KTKPREEQYNSTYRVVSVLTVLHQDWLNGKEYK CKVSNKALPAPIEKTISKAKGQPREPQVYTLPPSR EEMTKNQVSLTCLVKGFYPSDIAVEWESNGQPE NNYKTTPPVLDSDGSFFLYSKLTVDKSRWQQGN VFSCSVMHGALHNHYTQKSLSLSPGK |
| SEQ ID NO 126 | constant region human HC IgG1m(f)- G237R- E430G | constant region human HC IgG1m (f)- G237R- E430G | ASTKGPSVFPLAPSSKSTSGGTAALGCLVKDYFP EPVTVSWNSGALTSGVHTFPAVLQSSGLYSLSSV VTVPSSSLGTQTYICNVNHKPSNTKVDKRVEPKS CDKTHTCPPCPAPELLGRPSVFLFPPKPKDTLMIS RTPEVTCVVVDVSHEDPEVKFNWYVDGVEVHNA KTKPREEQYNSTYRVVSVLTVLHQDWLNGKEYK CKVSNKALPAPIEKTISKAKGQPREPQVYTLPPSR EEMTKNQVSLTCLVKGFYPSDIAVEWESNGQPE NNYKTTPPVLDSDGSFFLYSKLTVDKSRWQQGN VFSCSVMHGALHNHYTQKSLSLSPGK |
| SEQ ID NO 127 | constant region human HC IgG1m(f)- G237T- E430G | constant region human HC IgG1m (f)- G237T- E430G | ASTKGPSVFPLAPSSKSTSGGTAALGCLVKDYFP EPVTVSWNSGALTSGVHTFPAVLQSSGLYSLSSV VTVPSSSLGTQTYICNVNHKPSNTKVDKRVEPKS CDKTHTCPPCPAPELLGTPSVFLFPPKPKDTLMIS RTPEVTCVVVDVSHEDPEVKFNWYVDGVEVHNA KTKPREEQYNSTYRVVSVLTVLHQDWLNGKEYK CKVSNKALPAPIEKTISKAKGQPREPQVYTLPPSR EEMTKNQVSLTCLVKGFYPSDIAVEWESNGQPE NNYKTTPPVLDSDGSFFLYSKLTVDKSRWQQGN VFSCSVMHGALHNHYTQKSLSLSPGK |
| SEQ ID NO 128 | constant region human HC IgG1m(f)- K248E- T437R- K439E- G236R | constant region human HC IgG1m (f)- G236R- K248E- T437R- K439E | ASTKGPSVFPLAPSSKSTSGGTAALGCLVKDYFP EPVTVSWNSGALTSGVHTFPAVLQSSGLYSLSSV VTVPSSSLGTQTYICNVNHKPSNTKVDKRVEPKS CDKTHTCPPCPAPELLRGPSVFLFPPKPEDTLMIS RTPEVTCVVVDVSHEDPEVKFNWYVDGVEVHNA KTKPREEQYNSTYRVVSVLTVLHQDWLNGKEYK CKVSNKALPAPIEKTISKAKGQPREPQVYTLPPSR EEMTKNQVSLTCLVKGFYPSDIAVEWESNGQPE NNYKTTPPVLDSDGSFFLYSKLTVDKSRWQQGN VFSCSVMHEALHNHYRQESLSLSPGK |

TABLE 1-continued

SEQUENCE LIST

| SEQ ID NO | Name | | Sequence |
|---|---|---|---|
| SEQ ID NO 129 | constant region human HC IgG1m(f)-K248E-T437R-K439E-G237Q | constant region human HC IgG1m(f)-G237Q-K248E-T437R-K439E | ASTKGPSVFPLAPSSKSTSGGTAALGCLVKDYFP EPVTVSWNSGALTSGVHTFPAVLQSSGLYSLSSV VTVPSSSLGTQTYICNVNHKPSNTKVDKRVEPKS CDKTHTCPPCPAPELLGQPSVFLFPPKPEDTLMIS RTPEVTCVVVDVSHEDPEVKFNWYVDGVEVHNA KTKPREEQYNSTYRVVSVLTVLHQDWLNGKEYK CKVSNKALPAPIEKTISKAKGQPREPQVYTLPPSR EEMTKNQVSLTCLVKGFYPSDIAVEWESNGQPE NNYKTTPPVLDSDGSFFLYSKLTVDKSRWQQGN VFSCSVMHEALHNHYRQESLSLSPGK |
| SEQ ID NO 130 | constant region human HC IgG1m(f)-K248E-T437R-S440K-E333S | constant region human HC IgG1m(f)-K248E-E333S-T437R-S440K | ASTKGPSVFPLAPSSKSTSGGTAALGCLVKDYFP EPVTVSWNSGALTSGVHTFPAVLQSSGLYSLSSV VTVPSSSLGTQTYICNVNHKPSNTKVDKRVEPKS CDKTHTCPPCPAPELLGGPSVFLFPPKPEDTLMIS RTPEVTCVVVDVSHEDPEVKFNWYVDGVEVHNA KTKPREEQYNSTYRVVSVLTVLHQDWLNGKEYK CKVSNKALPAPISKTISKAKGQPREPQVYTLPPSR EEMTKNQVSLTCLVKGFYPSDIAVEWESNGQPE NNYKTTPPVLDSDGSFFLYSKLTVDKSRWQQGN VFSCSVMHEALHNHYRQKKLSLSPGK |
| SEQ ID NO 131 | constant region human HC IgG1m(f)-K248E-T437R-S440K-G237A | constant region human HC IgG1m(f)-G237A-K248E-T437R-S440K | ASTKGPSVFPLAPSSKSTSGGTAALGCLVKDYFP EPVTVSWNSGALTSGVHTFPAVLQSSGLYSLSSV VTVPSSSLGTQTYICNVNHKPSNTKVDKRVEPKS CDKTHTCPPCPAPELLGAPSVFLFPPKPEDTLMIS RTPEVTCVVVDVSHEDPEVKFNWYVDGVEVHNA KTKPREEQYNSTYRVVSVLTVLHQDWLNGKEYK CKVSNKALPAPIEKTISKAKGQPREPQVYTLPPSR EEMTKNQVSLTCLVKGFYPSDIAVEWESNGQPE NNYKTTPPVLDSDGSFFLYSKLTVDKSRWQQGN VFSCSVMHEALHNHYRQKKLSLSPGK |
| SEQ ID NO 132 | constant region human HC IgG1m(f)-K322E-E430G | constant region human HC IgG1m(f)-K322E-E430G | ASTKGPSVFPLAPSSKSTSGGTAALGCLVKDYFP EPVTVSWNSGALTSGVHTFPAVLQSSGLYSLSSV VTVPSSSLGTQTYICNVNHKPSNTKVDKRVEPKS CDKTHTCPPCPAPELLGGPSVFLFPPKPKDTLMIS RTPEVTCVVVDVSHEDPEVKFNWYVDGVEVHNA KTKPREEQYNSTYRVVSVLTVLHQDWLNGKEYK CEVSNKALPAPIEKTISKAKGQPREPQVYTLPPSR EEMTKNQVSLTCLVKGFYPSDIAVEWESNGQPE NNYKTTPPVLDSDGSFFLYSKLTVDKSRWQQGN VFSCSVMHGALHNHYTQKSLSLSPGK |
| SEQ ID NO 133 | constant region human HC IgG1m(f)-P329R-E430G | constant region human HC IgG1m(f)-P329R-E430G | ASTKGPSVFPLAPSSKSTSGGTAALGCLVKDYFP EPVTVSWNSGALTSGVHTFPAVLQSSGLYSLSSV VTVPSSSLGTQTYICNVNHKPSNTKVDKRVEPKS CDKTHTCPPCPAPELLGGPSVFLFPPKPKDTLMIS RTPEVTCVVVDVSHEDPEVKFNWYVDGVEVHNA KTKPREEQYNSTYRVVSVLTVLHQDWLNGKEYK CKVSNKALRAPI EKTISKAKGQPREPQVYTLPPSR EEMTKNQVSLTCLVKGFYPSDIAVEWESNGQPE NNYKTTPPVLDSDGSFFLYSKLTVDKSRWQQGN VFSCSVMHGALHNHYTQKSLSLSPGK |
| SEQ ID NO 134 | constant region human HC IgG2-E430G | constant region human HC IgG2-E430G | ASTKGPSVFPLAPCSRSTSESTAALGCLVKDYFPE PVTVSWNSGALTSGVHTFPAVLQSSGLYSLSSVV TVPSSNFGTQTYTCNVDHKPSNTKVDKTVERKC CVECPPCPAPPVAGPSVFLFPPKPKDTLMISRTPE VTCVVVDVSHEDPEVQFNWYVDGVEVHNAKTKP REEQFNSTFRVVSVLTVVHQDWLNGKEYKCKVS NKGLPAPIEKTISKTKGQPREPQVYTLPPSREEMT KNQVSLTCLVKGFYPSDIAVEWESNGQPENNYK TTPPMLDSDGSFFLYSKLTVDKSRWQQGNVFSC SVMHGALHNHYTQKSLSLSPGK |

TABLE 1-continued

SEQUENCE LIST

| SEQ ID NO | Name | | Sequence |
|---|---|---|---|
| SEQ ID NO 135 | constant region human HC IgG2-E430G-K439E | constant region human HC IgG2-E430G-K439E | ASTKGPSVFPLAPCSRSTSESTAALGCLVKDYFPE PVTVSWNSGALTSGVHTFPAVLQSSGLYSLSSVV TVPSSNFGTQTYTCNVDHKPSNTKVDKTVERKC CVECPPCPAPPVAGPSVFLFPPKPKDTLMISRTPE VTCVVVDVSHEDPEVQFNWYVDGVEVHNAKTKP REEQFNSTFRVVSVLTVVHQDWLNGKEYKCKVS NKGLPAPIEKTISKTKGQPREPQVYTLPPSREEMT KNQVSLTCLVKGFYPSDIAVEWESNGQPENNYK TTPPMLDSDGSFFLYSKLTVDKSRWQQGNVFSC SVMHGALHNHYTQESLSLSPGK |
| SEQ ID NO 136 | constant region human HC IgG2-E430G-K439E-G236R | constant region human HC IgG2-G236R-E430G-K439E | ASTKGPSVFPLAPCSRSTSESTAALGCLVKDYFPE PVTVSWNSGALTSGVHTFPAVLQSSGLYSLSSVV TVPSSNFGTQTYTCNVDHKPSNTKVDKTVERKC CVECPPCPAPPVARPSVFLFPPKPKDTLMISRTPE VTCVVVDVSHEDPEVQFNWYVDGVEVHNAKTKP REEQFNSTFRVVSVLTVVHQDWLNGKEYKCKVS NKGLPAPIEKTISKTKGQPREPQVYTLPPSREEMT KNQVSLTCLVKGFYPSDIAVEWESNGQPENNYK TTPPMLDSDGSFFLYSKLTVDKSRWQQGNVFSC SVMHGALHNHYTQESLSLSPGK |
| SEQ ID NO 137 | constant region human HC IgG2-E430G-S440K | constant region human HC IgG2-E430G-S440K | ASTKGPSVFPLAPCSRSTSESTAALGCLVKDYFPE PVTVSWNSGALTSGVHTFPAVLQSSGLYSLSSVV TVPSSNFGTQTYTCNVDHKPSNTKVDKTVERKC CVECPPCPAPPVAGPSVFLFPPKPKDTLMISRTPE VTCVVVDVSHEDPEVQFNWYVDGVEVHNAKTKP REEQFNSTFRVVSVLTVVHQDWLNGKEYKCKVS NKGLPAPIEKTISKTKGQPREPQVYTLPPSREEMT KNQVSLTCLVKGFYPSDIAVEWESNGQPENNYK TTPPMLDSDGSFFLYSKLTVDKSRWQQGNVFSC SVMHGALHNHYTQKKLSLSPGK |
| SEQ ID NO 138 | constant region human HC IgG2-E430G-S440K-E333S | constant region human HC IgG2-E333S-E430G-S440K | ASTKGPSVFPLAPCSRSTSESTAALGCLVKDYFPE PVTVSWNSGALTSGVHTFPAVLQSSGLYSLSSVV TVPSSNFGTQTYTCNVDHKPSNTKVDKTVERKC CVECPPCPAPPVAGPSVFLFPPKPKDTLMISRTPE VTCVVVDVSHEDPEVQFNWYVDGVEVHNAKTKP REEQFNSTFRVVSVLTVVHQDWLNGKEYKCKVS NKGLPAPISKTISKTKGQPREPQVYTLPPSREEMT KNQVSLTCLVKGFYPSDIAVEWESNGQPENNYK TTPPMLDSDGSFFLYSKLTVDKSRWQQGNVFSC SVMHGALHNHYTQKKLSLSPGK |
| SEQ ID NO 139 | constant region human HC IgG3-E430G | constant region human HC IgG3-E430G | ASTKGPSVFPLAPCSRSTSGGTAALGCLVKDYFP EPVTVSWNSGALTSGVHTFPAVLQSSGLYSLSSVV VTVPSSSLGTQTYTCNVNHKPSNTKVDKRVELKT PLGDTTHTCPRCPEPKSCDTPPPCPRCPEPKSCD TPPPCPRCPEPKSCDTPPPCPRCPAPELLGGPSVF LFPPKPKDTLMISRTPEVTCVVVDVSHEDPEVQF KWYVDGVEVHNAKTKPREEQYNSTFRVVSVLTV LHQDWLNGKEYKCKVSNKALPAPIEKTISKTKGQ PREPQVYTLPPSREEMTKNQVSLTCLVKGFYPSDI AVEWESSGQPENNYNTTPPMLDSDGSFFLYSKL TVDKSRWQQGNIFSCSVMHGALHNRFTQKSLSL SPGK |
| SEQ ID NO 140 | constant region human HC IgG3-E430G-K439E | constant region human HC IgG3-E430G-K439E | ASTKGPSVFPLAPCSRSTSGGTAALGCLVKDYFP EPVTVSWNSGALTSGVHTFPAVLQSSGLYSLSSVV VTVPSSSLGTQTYTCNVNHKPSNTKVDKRVELKT PLGDTTHTCPRCPEPKSCDTPPPCPRCPEPKSCD TPPPCPRCPEPKSCDTPPPCPRCPAPELLGGPSVF LFPPKPKDTLMISRTPEVTCVVVDVSHEDPEVQF KWYVDGVEVHNAKTKPREEQYNSTFRVVSVLTV LHQDWLNGKEYKCKVSNKALPAPIEKTISKTKGQ PREPQVYTLPPSREEMTKNQVSLTCLVKGFYPSDI AVEWESSGQPENNYNTTPPMLDSDGSFFLYSKL TVDKSRWQQGNIFSCSVMHGALHNRFTQESLSL SPGK |

TABLE 1-continued

SEQUENCE LIST

| SEQ ID NO | Name | | Sequence |
|---|---|---|---|
| SEQ ID NO 141 | constant region human HC IgG3-E430G-K439E-G236R | constant region human HC IgG3-G236R-E430G-K439E | ASTKGPSVFPLAPCSRSTSGGTAALGCLVKDYFP EPVTVSWNSGALTSGVHTFPAVLQSSGLYSLSSV VTVPSSSLGTQTYTCNVNHKPSNTKVDKRVELKT PLGDTTHTCPRCPEPKSCDTPPPCPRCPEPKSCD TPPPCPRCPEPKSCDTPPPCPRCPAPELLRGPSVF LFPPKPKDTLMISRTPEVTCVVVDVSHEDPEVQF KWYVDGVEVHNAKTKPREEQYNSTFRVVSVLTV LHQDWLNGKEYKCKVSNKALPAPIEKTISKTKGQ PREPQVYTLPPSREEMTKNQVSLTCLVKGFYPSDI AVEWESSGQPENNYNTTPPMLDSDGSFFLYSKL TVDKSRWQQGNIFSCSVMHGALHNRFTQESLSL SPGK |
| SEQ ID NO 142 | constant region human HC IgG3-E430G-S440K | constant region human HC IgG3-E430G-S440K | ASTKGPSVFPLAPCSRSTSGGTAALGCLVKDYFP EPVTVSWNSGALTSGVHTFPAVLQSSGLYSLSSV VTVPSSSLGTQTYTCNVNHKPSNTKVDKRVELKT PLGDTTHTCPRCPEPKSCDTPPPCPRCPEPKSCD TPPPCPRCPEPKSCDTPPPCPRCPAPELLGGPSVF LFPPKPKDTLMISRTPEVTCVVVDVSHEDPEVQF KWYVDGVEVHNAKTKPREEQYNSTFRVVSVLTV LHQDWLNGKEYKCKVSNKALPAPIEKTISKTKGQ PREPQVYTLPPSREEMTKNQVSLTCLVKGFYPSDI AVEWESSGQPENNYNTTPPMLDSDGSFFLYSKL TVDKSRWQQGNIFSCSVMHGALHNRFTQKKLS LSPGK |
| SEQ ID NO 143 | constant region human HC IgG3-E430G-S440K-E333S | constant region human HC IgG3-E333S-E430G-S440K | ASTKGPSVFPLAPCSRSTSGGTAALGCLVKDYFP EPVTVSWNSGALTSGVHTFPAVLQSSGLYSLSSV VTVPSSSLGTQTYTCNVNHKPSNTKVDKRVELKT PLGDTTHTCPRCPEPKSCDTPPPCPRCPEPKSCD TPPPCPRCPEPKSCDTPPPCPRCPAPELLGGPSVF LFPPKPKDTLMISRTPEVTCVVVDVSHEDPEVQF KWYVDGVEVHNAKTKPREEQYNSTFRVVSVLTV LHQDWLNGKEYKCKVSNKALPAPISKTISKTKGQ PREPQVYTLPPSREEMTKNQVSLTCLVKGFYPSDI AVEWESSGQPENNYNTTPPMLDSDGSFFLYSKL TVDKSRWQQGNIFSCSVMHGALHNRFTQKKLS LSPGK |
| SEQ ID NO 144 | constant region human HC IgG4-E430G-S228P | constant region human HC IgG4-S228P-E430G | ASTKGPSVFPLAPCSRSTSESTAALGCLVKDYFPE PVTVSWNSGALTSGVHTFPAVLQSSGLYSLSSVV TVPSSSLGTKTYTCNVDHKPSNTKVDKRVESKY GPPCPPCPAPEFLGGPSVFLFPPKPKDTLMISRTP EVTCVVVDVSQEDPEVQFNWYVDGVEVHNAKT KPREEQFNSTYRVVSVLTVLHQDWLNGKEYKCK VSNKGLPSSIEKTISKAKGQPREPQVYTLPPSQEE MTKNQVSLTCLVKGFYPSDIAVEWESNGQPENN YKTTPPVLDSDGSFFLYSRLTVDKSRWQEGNVFS CSVMHGALHNHYTQKSLSLSLGK |
| SEQ ID NO 145 | constant region human HC IgG4-E430G-K439E-S228P | constant region human HC IgG4-S228P-E430G-K439E | ASTKGPSVFPLAPCSRSTSESTAALGCLVKDYFPE PVTVSWNSGALTSGVHTFPAVLQSSGLYSLSSVV TVPSSSLGTKTYTCNVDHKPSNTKVDKRVESKY GPPCPPCPAPEFLGGPSVFLFPPKPKDTLMISRTP EVTCVVVDVSQEDPEVQFNWYVDGVEVHNAKT KPREEQFNSTYRVVSVLTVLHQDWLNGKEYKCK VSNKGLPSSIEKTISKAKGQPREPQVYTLPPSQEE MTKNQVSLTCLVKGFYPSDIAVEWESNGQPENN YKTTPPVLDSDGSFFLYSRLTVDKSRWQEGNVFS CSVMHGALHNHYTQESLSLSLGK |
| SEQ ID NO 146 | constant region human HC IgG4-E430G-K439E-S228P-G236R | constant region human HC IgG4-S228P-G236R-E430G-K439E | ASTKGPSVFPLAPCSRSTSESTAALGCLVKDYFPE PVTVSWNSGALTSGVHTFPAVLQSSGLYSLSSVV TVPSSSLGTKTYTCNVDHKPSNTKVDKRVESKY GPPCPPCPAPEFLRGPSVFLFPPKPKDTLMISRTP EVTCVVVDVSQEDPEVQFNWYVDGVEVHNAKT KPREEQFNSTYRVVSVLTVLHQDWLNGKEYKCK VSNKGLPSSIEKTISKAKGQPREPQVYTLPPSQEE MTKNQVSLTCLVKGFYPSDIAVEWESNGQPENN YKTTPPVLDSDGSFFLYSRLTVDKSRWQEGNVFS CSVMHGALHNHYTQESLSLSLGK |

TABLE 1-continued

SEQUENCE LIST

| SEQ ID NO | Name | | Sequence |
|---|---|---|---|
| SEQ ID NO 147 | constant region human HC IgG4-E430G-S440K-S228P | constant region human HC IgG4-S228P-E430G-S440K | ASTKGPSVFPLAPCSRSTSESTAALGCLVKDYFPE PVTVSWNSGALTSGVHTFPAVLQSSGLYSLSSVV TVPSSSLGTKTYTCNVDHKPSNTKVDKRVESKY GPPCPPCPAPEFLGGPSVFLFPPKPKDTLMISRTP EVTCVVVDVSQEDPEVQFNWYVDGVEVHNAKT KPREEQFNSTYRVVSVLTVLHQDWLNGKEYKCK VSNKGLPSSIEKTISKAKGQPREPQVYTLPPSQEE MTKNQVSLTCLVKGFYPSDIAVEWESNGQPENN YKTTPPVLDSDGSFFLYSRLTVDKSRWQEGNVFS CSVMHGALHNHYTQKKLSLSLGK |
| SEQ ID NO 148 | constant region human HC IgG4-E430G-S440K-S228P-E333S | constant region human HC IgG4-S228P-E333S-E430G-S440K | ASTKGPSVFPLAPCSRSTSESTAALGCLVKDYFPE PVTVSWNSGALTSGVHTFPAVLQSSGLYSLSSVV TVPSSSLGTKTYTCNVDHKPSNTKVDKRVESKY GPPCPPCPAPEFLGGPSVFLFPPKPKDTLMISRTP EVTCVVVDVSQEDPEVQFNWYVDGVEVHNAKT KPREEQFNSTYRVVSVLTVLHQDWLNGKEYKCK VSNKGLPSSISKTISKAKGQPREPQVYTLPPSQE EMTKNQVSLTCLVKGFYPSDIAVEWESNGQPEN NYKTTPPVLDSDGSFFLYSRLTVDKSRWQEGNVF SCSVMHGALHNHYTQKKLSLSLGK |
| SEQ ID NO 149 | FCGR1AE CDHis | | MWFLTTLLLWVPVDGQVDTTKAVITLQPPWVSV FQEETVTLHCEVLHLPGSSSTQWFLNGTATQTST PSYRITSASVNDSGEYRCQRGLSGRSDPIQLEIH RGWLLLQVSSRVFTEGEPLALRCHAWKDKLVYN VLYYRNGKAFKFFHWNSNLTILKTNISHNGTYHC SGMGKHRYTSAGISVTVKELFPAPVLNASVTSPL LEGNLVTLSCETKLLLQRPGLQLYFSFYMGSKTLR GRNTSSEYQILTARREDSGLYWCEAATEDGNVL KRSPELELQVLGLQLPTPVWFHHHHHH |
| SEQ ID NO 150 | diFCGR2 AH-HisBAP | | METQMSQNVCPRNLWLLQPLTVLLLLASADSQA AAPPKAVLKLEPPWINVLQEDSVTLTCQGARSPE SDSIQWFHNGNLIPTHTQPSYRFKANNNDSGEY TCQTGQTSLSDPVHLTVLSEWLVLQTPHLEFQEG ETIMLRCHSWKDKPLVKVTFFQNGKSQKFSHLD PTFSIPQANHSHSGDYHCTGNIGYTLFSSKPVTIT VQVPSMGSSSPVAPPKAVLKLEPPWINVLQEDSV TLTCQGARSPESDSIQWFHNGNLIPTHTQPSYRF KANNNDSGEYTCQTGQTSLSDPVHLTVLSEWLV LQTPHLEFQEGETIMLRCHSWKDKPLVKVTFFQN GKSQKFSHLDPTFSIPQANHSHSGDYHCTGNIG YTLFSSKPVTITVQVPSMGPGSSSHHHHHHPGG GLNDIFEAQKIEWHE |
| SEQ ID NO 151 | diFCGR2 AR-HisBAP | | MVLSLLYLLTALPGILSAAPPKAVLKLEPPWINVLQ EDSVTLTCQGARSPESDSIQWFHNGNLIPTHTQP SYRFKANNNDSGEYTCQTGQTSLSDPVHLTVLS EWLVLQTPHLEFQEGETIMLRCHSWKDKPLVKVT FFQNGKSQKFSRLDPTFSIPQANHSHSGDYHCT GNIGYTLFSSKPVTITVQVPSMGSSSPAAPPKAVL KLEPPWINVLQEDSVTLTCQGARSPESDSIQWF HNGNLIPTHTQPSYRFKANNNDSGEYTCQTGQT SLSDPVHLTVLSEWLVLQTPHLEFQEGETIMLRC HSWKDKPLVKVTFFQNGKSQKFSRLDPTFSIPQA NHSHSGDYHCTGNIGYTLFSSKPVTITVQVPSMG SSSPGSSSHHHHHHPGGGLNDIFEAQKIEWHE |
| SEQ ID NO 152 | diFCGR2 B-HisBAP | | MVLSLLYLLTALPGILSAAPPKAVLKLEPQWINVL QEDSVTLTCRGTHSPESDSIQWFHNGNLIPTHT QPSYRFKANNNDSGEYTCQTGQTSLSDPVHLTV LSEWLVLQTPHLEFQEGETIVLRCHSWKDKPLVK VTFFQNGKSKKFSRDPNFSIPQANHSHSGDYH CTGNIGYTLYSSKPVTITVQAPSSSPMGPAAPPK AVLKLEPQWINVLQEDSVTLTCRGTHSPESDSIQ WFHNGNLIPTHTQPSYRFKANNNDSGEYTCQTG QTSLSDPVHLTVLSEWLVLQTPHLEFQEGETIVLR CHSWKDKPLVKVTFFQNGKSKKFSRDPNFSIP QANHSHSGDYHCTGNIGYTLYSSKPVTITVQAPS SSPMGPGSSSHHHHHHPGGGLNDIFEAQKIEW HE |

TABLE 1-continued

SEQUENCE LIST

| SEQ ID NO | Name | | Sequence |
|---|---|---|---|
| SEQ ID NO 153 | diFCGR3 AF-HisBAP | | MVLSLLYLLTALPGISTEDLPKAVVFLEPQWYRVL EKDSVTLKCQGAYSPEDNSTQWFHNESLISSQA SSYFIDAATVDDSGEYRCQTNLSTLSDPVQLEVH IGWLLLQAPRWVFKEEDPIHLRCHSWKNTALHK VTYLQNGKGRKYFHHNSDFYIPKATLKDSGSYFC RGLFGSKNVSSETVNITITQGPSMGSSSPSEDLP KAVVFLEPQWYRVLEKDSVTLKCQGAYSPEDNS TQWFHNESLISSQASSYFIDAATVDDSGEYRCQ TNLSTLSDPVQLEVHIGWLLLQAPRWVFKEEDPI HLRCHSWKNTALHKVTYLQNGKGRKYFHHNSDF YIPKATLKDSGSYFCRGLFGSKNVSSETVNITITQ GPSMGSSSPGPGSSSHHHHHHPGGGLNDIFEA QKIEWHE |
| SEQ ID NO 154 | diFCGR3 AV-HisBAP | | MVLSLLYLLTALPGISTEDLPKAVVFLEPQWYRVL EKDSVTLKCQGAYSPEDNSTQWFHNESLISSQA SSYFIDAATVDDSGEYRCQTNLSTLSDPVQLEVH IGWLLLQAPRWVFKEEDPIHLRCHSWKNTALHK VTYLQNGKGRKYFHHNSDFYIPKATLKDSGSYFC RGLVGSKNVSSETVNITITQGPSMGSSSPSEDLP KAVVFLEPQWYRVLEKDSVTLKCQGAYSPEDNS TQWFHNESLISSQASSYFIDAATVDDSGEYRCQ TNLSTLSDPVQLEVHIGWLLLQAPRWVFKEEDPI HLRCHSWKNTALHKVTYLQNGKGRKYFHHNSDF YIPKATLKDSGSYFCRGLVGSKNVSSETVNITITQ GPSMGSSSPGPGSSSHHHHHHPGGGLNDIFEA QKIEWHE |
| SEQ ID NO 155 | FcRnECD His | | AESHLSLLYHLTAVSSPAPGTPAFWVSGWLGPQ QYLSYNSLRGEAEPCGAWVWENQVSWYWEKET TDLRIKEKLFLEAFKALGGKGPYTLQGLLGCELGP DNTSVPTAKFALNGEEFMNFDLKQGTWGGDWP EALAISQRWQQQDKAANKELTFLLFSCPHRLREH LERGRGNLEWKEPPSMRLKARPSSPGFSVLTCSA FSFYPPELQLRFLRNGLAAGTGQGDFGPNSDGSF HASSSLTVKSGDEHHYCCIVQHAGLAQPLRVELE SPAKSSHHHHHH |
| SEQ ID NO 156 | Beta2-microglobulin B2M | | IQRTPKIQVYSRHPAENGKSNFLNCYVSGFHPSD IEVDLLKNGERIEKVEHSDLSFSKDWSFYLLYTE FTPTEKDEYACRVNHVTLSQPKIVKWDRDM |
| SEQ ID NO 157 | constant region human HC IgG1m(f)-E430G-S440K-K326W-E333S | constant region human HC IgG1m(f)-K326W-E333S-E430G-S440K | ASTKGPSVFPLAPSSKSTSGGTAALGCLVKDYFP EPVTVSWNSGALTSGVHTFPAVLQSSGLYSLSSV VTVPSSSLGTQTYICNVNHKPSNTKVDKRVEPKS CDKTHTCPPCPAPELLGGPSVFLFPPKPKDTLMIS RTPEVTCVVVDVSHEDPEVKFNWYVDGVEVHNA KTKPREEQYNSTYRVVSVLTVLHQDWLNGKEYK CKVSNWALPAPISKTISKAKGQPREPQVYTLPPS REEMTKNQVSLTCLVKGFYPSDIAVEWESNGQP ENNYKTTPPVLDSDGSFFLYSKLTVDKSRWQQG NVFSCSVMHGALHNHYTQKKLSLSPGK |
| SEQ ID NO 158 | constant region human HC IgG1m(f)-E345R-E430G-S440Y | constant region human HC IgG1m(f)-E345R-E430G-S440Y | ASTKGPSVFPLAPSSKSTSGGTAALGCLVKDYFP EPVTVSWNSGALTSGVHTFPAVLQSSGLYSLSSV VTVPSSSLGTQTYICNVNHKPSNTKVDKRVEPKS CDKTHTCPPCPAPELLGGPSVFLFPPKPKDTLMIS RTPEVTCVVVDVSHEDPEVKFNWYVDGVEVHNA KTKPREEQYNSTYRVVSVLTVLHQDWLNGKEYK CKVSNKALPAPIEKTISKAKGQPRRPQVYTLPPSR EEMTKNQVSLTCLVKGFYPSDIAVEWESNGQP ENNYKTTPPVLDSDGSFFLYSKLTVDKSRWQQGN VFSCSVMHGALHNHYTQKYLSLSPGK |
| SEQ ID NO 159 | Her2ECD His (TX1014-Her2ECD His) | | MELAALCRWGLLLALLPPGAASTQVCTGTDMKLR LPASPETHLDMLRHLYQGCQVVQGNLELTYLPTN ASLSFLQDIQEVQGYVLIAHNQVRQVPLQRLRIV RGTQLFEDNYALAVLDNGDPLNNTTPVTGASPG GLRELQLRSLTEILKGGVLIQRNPQLCYQDTILWK DIFHKNNQLALTLIDTNRSRACHPCSPMCKGSRC WGESSEDCQSLTRTVCAGGCARCKGPLPTDCCH EQCAAGCTGPKHSDCLACLHFNHSGICELHCPAL VTYNTDTFESMPNPEGRYTFGASCVTACPYNYLS TDVGSCTLVCPLHNQEVTAEDGTQRCEKCSKPC |

TABLE 1-continued

SEQUENCE LIST

| SEQ ID NO | Name | Sequence |
|---|---|---|
| | | ARVCYGLGMEHLREVRAVTSANIQEFAGCKKIFG SLAFLPESFDGDPASNTAPLQPEQLQVFETLEEIT GYLYISAWPDSLPDLSVFQNLQVIRGRILHNGAY SLTLQGLGISWLGLRSLRELGSGLALIHHNTHLCF VHTVPWDQLFRNPHQALLHTANRPEDECVGEGL ACHQLCARGHCWGPGPTQCVNCSQFLRGQECV EECRVLQGLPREYVNARHCLPCHPECQPQNGSV TCFGPEADQCVACAHYKDPPFCVARCPSGVKPD LSYMPIWKFPDEEGACQPCPINCTHSCVDLDDK GCPAEQRHHHHHH |
| SEQ ID NO 160 | VH h2E8 (CD52) | EVHLVESGGGLVQPGGSLRLSCAASGFTFSRYG MSWVRQAPGKGLELVAMMKTKGGRTYYPDSV KGRFTISRDNAKNSLYLQMNSLRAEDTAIYYCAS DGYYWGQGTTVTVSS |
| SEQ ID NO 161 | VH h2E8 CDR1 | GFTFSRYG |
| SEQ ID NO 162 | VH h2E8 CDR2 | MKTKGGRT |
| SEQ ID NO 163 | VH h2E8 CDR3 | ASDGYY |
| SEQ ID NO 164 | VL h2E8 | DVVMTQTPLSLSVTLGQPASISCKSSQSLLHSD GKTYLNWLQQRPGQSPRRLIYLVSKLDSGVPDR FSGSGSGTDFTLKISRVEAEDVGIYYCWQGTHL WTFGGGTKVEIK |
| SEQ ID NO 165 | VL h2E8 CDR1 | QSLLHSDGKTY |
| | VL h2E8 CDR2 | LVS |
| SEQ ID NO 166 | VL h2E8 CDR3 | WQGTHLWT |
| SEQ ID NO 167 | VH HLA-DR-hu1243 | QVQLQQSGSELKKPGASVKVSCKASGFTFTNY GMNWVKQAPGQGLKWMGWINTYTREPTYAD DFKGRFAFSLDTSVSTAYLQISSLKADDTAVYFC ARDITAVVPTGFDYWGQGSLVTVSS |
| SEQ ID NO 168 | VH HLA-DR-hu1243 CDR1 | GFTFTNYG |
| SEQ ID NO 169 | VH HLA-DR-hu1243 CDR2 | INTYTREP |
| SEQ ID NO 170 | VH HLA-DR-hu1243 CDR3 | ARDITAVVPTGFDY |
| SEQ ID NO 171 | VL HLA-DR-hu1243 | DIQLTQSPSSLSASVGDRVTITCRASENIYSNLA WYRQKPGKAPKLLVFAASNLADGVPSRFSGSGS GTDYTFTISSLQPEDIATYYCQHFWTTPWAFGG GTKLQIK |
| SEQ ID NO 172 | VL HLA-DR-hu1243 CDR1 | ENIYSN |
| | VL HLA-DR-hu1243 CDR2 | AAS |

TABLE 1-continued

SEQUENCE LIST

| SEQ ID NO | Name | Sequence |
|---|---|---|
| SEQ ID NO 173 | VL HLA-DR-hu1243 CDR3 | QHFWTTPWA |
| SEQ ID NO 174 | VH HLA-DR-1D09C3 | QVQLKESGPALVKPTQTLTLTCTFSGFSLSTSGV GVGWIRQPPGKALEWLALIDWDDDKYYSTSLK TRLTISKDTSKNQVVLTMTNMDPVDTATYYCAR SPRYRGAFDYWGQGTLVTVSS |
| SEQ ID NO 175 | VH HLA-DR-1D09C3 CDR1 | GFSLSTSGVG |
| SEQ ID NO 176 | VH HLA-DR-1D09C3 CDR2 | IDWDDDK |
| SEQ ID NO 177 | VH HLA-DR-1D09C3 CDR3 | ARSPRYRGAFDY |
| SEQ ID NO 178 | VL HLA-DR-1D09C3 | DIVLTQPPSVSGAPGQRVTISCSGSESNIGNNY VQWYQQLPGTAPKLLIYDNNQRPSGVPDRFSGS KSGTSASLAITGLQSEDEADYYCQSYDMNVHV FGGGTKLTVL |
| SEQ ID NO 179 | VL HLA-DR-1D09C3 CDR1 | ESNIGNNY |
|  | VL HLA-DR-1D09C3 CDR2 | DNN |
| SEQ ID NO 180 | VL HLA-DR-1D09C3 CDR3 | QSYDMNVHV |
| SEQ ID NO 181 | VH huCLB-T3/4 | EVQLVESGGGLVKPGGSLRLSCAASGFTFSSYG MFWVRQAPGKGLEWVATISRYSRYIYYPDSVK GRFTISRDNAKNSLYLQMNSLRAEDTAVYYCAR RPLYGSSPDYWGQGTLVTVSS |
| SEQ ID NO 182 | VH huCLB-T3/4 CDR1 | GFTFSSYG |
| SEQ ID NO 183 | VH huCLB-T3/4 CDR2 | ISRYSRYI |
| SEQ ID NO 184 | VH huCLB-T3/4 CDR3 | ARRPLYGSSPDY |
| SEQ ID NO 185 | VL huCLB-T3/4 | EIVLTQSPATLSLSPGERATLSCSASSSVTYVHW YQQKPGQAPRLLIYDTSKLASGIPARFSGSGSGT DFTLTISSLEPEDFAVYYCFQGSGYPLTFSGTK LEMR |

TABLE 1-continued

SEQUENCE LIST

| SEQ ID NO | Name | Sequence |
|---|---|---|
| SEQ ID NO 186 | VL huCLB-T3/4 CDR1 | SSVTY |
| | VL huCLB-T3/4 CDR2 | DTS |
| SEQ ID NO 187 | VL huCLB-T3/4 CDR3 | FQGSGYPLT |
| SEQ ID NO 188 | VH CD5 INSERM | EVQLQESGPGLVKPSQTLSLTCSVTGYSITSGY YWHWIRQFPGNKLEWMGYISYSGFTNYKTSLI NRISITHDTSENQFFLNLNSVTTEDTATYYCAGD RTGSWFAYWGQGTLVTVSS |
| SEQ ID NO 189 | VH CD5 INSERM CDR1 | GYSITSGYY |
| SEQ ID NO 190 | VH CD5 INSERM CDR2 | ISYSGFT |
| SEQ ID NO 191 | VH CD5 INSERM CDR3 | AGDRTGSWFAY |
| SEQ ID NO 192 | VL CD5 INSERM | DIQVTQSPSSLSASLGERISLTCRTSQDISNYLN WFQQKPDGTFKRLIYATSSLDSGVPKRFSGSGS GSDYSLTISSLESEDFADYYCLQYASYPFTFGS GTKLEIK |
| SEQ ID NO 193 | VL CD5 INSERM CDR1 | QDISNY |
| | VL CD5 INSERM CDR2 | ATS |
| SEQ ID NO 194 | VL CD5 INSERM CDR3 | LQYASYPFT |
| SEQ ID NO 195 | VH DR4-chCTB007 | EVQLQQSGAELVKPGASVKLSCTASGFNIKDTY MHWVKQRPEQGLEWIGRIDPANGNTKYDPKF QGKATITADTSSNTAYLQLSSLTSEDTAVYYCAY YYVSNAWFTYWGQGTLVTVSA |
| SEQ ID NO 196 | VH DR4-chCTB007 CDR1 | GFNIKDTY |
| SEQ ID NO 197 | VH DR4-chCTB007 CDR2 | IDPANGNT |
| SEQ ID NO 198 | VH DR4-chCTB007 CDR3 | AYYYVSNAWFTY |
| SEQ ID NO 199 | VL DR4-chCTB007 | DIQMTQSPASLSVSVGETVTITCRASENIYSNLE WYQQKQGKSPQLLVYAATNLADGVPSRFSGSG SGTQYSLKINSLQSEDFGSYYCQHFWGTWTFG GGTKLEIK |

TABLE 1-continued

SEQUENCE LIST

| SEQ ID NO | Name | Sequence |
|---|---|---|
| SEQ ID NO 200 | VL DR4-chCTB007 CDR1 | ENIYSN |
| | VL DR4-chCTB007 CDR2 | AAT |
| SEQ ID NO 201 | VL DR4-chCTB007 CDR3 | QHFWGTWT |

Table defining substitutions that were tested in examples 5-23.

| Substitution | Purpose |
|---|---|
| G4-S228P | IgG4-specific substitution that stabilizes G4 hinge region (inhibits reduction) |
| K248E | Stimulation of self-oligomerization |
| L234A | Inhibition of FcGammaR binding; mild inhibition of C1q binding |
| L234F | Inhibition of FcGammaR binding; weak inhibition of C1q binding |
| L235A | Inhibition of FcGammaR binding; mild inhibition of C1q binding |
| L235Q | Inhibition of FcGammaR binding; mild inhibition of C1q binding |
| L234A-L235A | Inhibition of FcGammaR binding; mild inhibition of C1q binding |
| L234F-L235E | Inhibition of FcGammaR binding; mild inhibition of C1q binding |
| G236R | Inhibition of FcGammaR binding; mild inhibition of C1q binding |
| G236K | Inhibition of FcGammaR binding; mild inhibition of C1q binding |
| G237A | Inhibition of FcGammaR binding; weak inhibition of C1q binding |
| G237T | Inhibition of FcGammaR binding; weak inhibition of C1q binding |
| G237Q | Inhibition of FcGammaR binding; mild inhibition of C1q binding |
| G237R | Inhibition of FcGammaR binding; intermediate inhibition of C1q binding |
| K322A | Mild inhibition of C1q binding |
| K322E | Strong inhibition of C1q binding |
| K326A | Stimulation of C1q binding |
| K326W | Stimulation of C1q binding |
| K326A-E333A | Stimulation of C1q binding |
| K326W-E333S | Stimulation of C1q binding |
| A327K | Inhibition of FcGammaR binding; intermediate inhibition of C1q binding |
| P329R | Inhibition of FcGammaR binding; strong inhibition of C1q binding |
| E333A | Stimulation of C1q binding |
| E333S | Stimulation of C1q binding |
| E345K | Stimulation of self-oligomerization |
| E345R | Stimulation of self-oligomerization |
| E345A | Stimulation of self-oligomerization |
| E345Q | Stimulation of self-oligomerization |
| E345V | Stimulation of self-oligomerization |
| E345Y | Stimulation of self-oligomerization |
| E430G | Stimulation of self-oligomerization |
| E430N | Stimulation of self-oligomerization |
| E430T | Stimulation of self-oligomerization |
| E430V | Stimulation of self-oligomerization |
| E430Y | Stimulation of self-oligomerization |
| T437R | Stimulation of self-oligomerization |
| K439E | Inhibition of self-oligomerization |
| S440K | Inhibition of self-oligomerization |

Table defining self-oligomerization inhibiting substitutions.

| First Fc-region containing polypeptide | Second Fc-region containing polypeptide |
|---|---|
| K439E | S440K |
| S440K | K439E |

| Table defining FcGammaR binding-inhibiting and C1q-binding inhibiting substitutions. | |
|---|---|
| Substitution | Purpose |
| L234A | Inhibition of FcGammaR binding; mild inhibition of C1q binding |
| L234F | Inhibition of FcGammaR binding; weak inhibition of C1q binding |
| L235A | Inhibition of FcGammaR binding; mild inhibition of C1q binding |
| L235Q | Inhibition of FcGammaR binding; mild inhibition of C1q binding |
| L234A-L235A | Inhibition of FcGammaR binding; mild inhibition of C1q binding |
| L234F-L235E | Inhibition of FcGammaR binding; mild inhibition of C1q binding |
| G236R | Inhibition of FcGammaR binding; mild inhibition of C1q binding |
| G236K | Inhibition of FcGammaR binding; mild inhibition of C1q binding |
| G237A | Inhibition of FcGammaR binding; weak inhibition of C1q binding |
| G237T | Inhibition of FcGammaR binding; weak inhibition of C1q binding |
| G237Q | Inhibition of FcGammaR binding; mild inhibition of C1q binding |
| G237R | Inhibition of FcGammaR binding; intermediate inhibition of C1q binding |
| A327K | Inhibition of FcGammaR binding; intermediate inhibition of C1q binding |
| P329R | Inhibition of FcGammaR binding; strong inhibition of C1q binding |

EXAMPLES

Example 1

Antibody Expression Constructs

For the expression of human and humanized antibodies used herein, variable heavy (VH) chain and variable light (VL) chain sequences were prepared by gene synthesis (GeneArt Gene Synthesis; ThermoFisher Scientific) and cloned in pcDNA3.3 expression vectors (ThermoFisher Scientific) containing a constant region of a human IgG heavy chain (HC) (constant region human IgG1m(f) HC: SEQ ID NO 22; constant region human IgG2 HC: SEQ ID NO 31; constant region human IgG3 HC: SEQ ID NO 32; or constant region human IgG4 HC: SEQ ID NO 33) and or the constant region of the human kappa light chain (LC): SEQ ID NO 34. Desired mutations were introduced by gene synthesis. CD20 antibody variants in this application have VH and VL sequences derived from previously described CD20 antibody IgG1-CD20-11B8 (WO2004/035607; VH: SEQ ID NO 8; VL: SEQ ID NO 12). CD52 antibody variants in this application have VH and VL sequences derived from previously described CD52 antibody CAMPATH-1H (Crowe et al., 1992 Clin Exp Immunol. 87(1):105-110; VH: SEQ ID NO 1; VL: SEQ ID NO 5) and from previously described CD52 antibody h2E8 (US2014/0127236; VH: SEQ ID NO 160; VL: SEQ ID NO 164). CD37 antibody variants in this application have VH and VL sequences derived from previously described CD37 antibody IgG1-CD37-37.3 (WO2011/112978; VH: SEQ ID NO 42; VL: SEQ ID NO 46). DR4 antibody variants in this application have VH and VL sequences derived from previously described DR4 antibody DR4-chCTB007 (US2009/0136503A1; VH: SEQ ID NO 200; VL: SEQ ID NO 204). DR5 antibody variants in this application have VH and VL sequences derived from previously described DR5 antibody DR5-01-G56T (WO 2017/093447; VH: SEQ ID NO 49; VL: SEQ ID NO 53) and DR5-05 (WO2014/009358; VH: SEQ ID NO 56; VL: SEQ ID NO 60). HLA-DR antibody variants in this application have VH and VL sequences derived from previously described HLA-DR antibody HLA-DR-hu243 (U.S. Pat. No. 8,722,047B2; VH: SEQ ID NO 168; VL: SEQ ID NO 172) and from previously described HLA-DR antibody HLA-DR-1D09C3 (U.S. Pat. No. 7,521,047B2; VH: SEQ ID NO 176; VL: SEQ ID NO 180). CD3 antibody variants in this application have VH and VL sequences derived from previously described CD3 antibody huCLB-T3/4 (Parren et al., Res. Immunol 1991 November-December; 142(9):749-63; VH: SEQ ID NO 184; VL: SEQ ID NO 188). CD5 antibody variants in this application have VH and VL sequences derived from previously described CD5 antibody CD5-INSERM (WO2010145895; VH: SEQ ID NO 192; VL: SEQ ID NO 196). The human IgG1 antibody b12, an HIV gp120-specific antibody was used as a negative control in some experiments (Barbas et al., J Mol Biol. 1993 Apr. 5; 230(3):812-23; VH: SEQ ID NO 15; VL: SEQ ID NO 19).

Transient Expression Antibody Constructs

Plasmid DNA mixtures encoding both heavy and light chains of antibodies were transiently transfected in Expi293F cells (Gibco, Cat No A14635) using 293fectin (Life Technologies) essentially as described by Vink et al. (Vink et al., 2014 Methods 65(1):5-10). Antibody concentrations in the supernatants were measured by absorbance at 280 nm. Antibody-containing supernatants were either directly used in in vitro assays, or antibodies were purified as described below.

Antibody Purification and Quality Assessment

Antibodies were purified by Protein A affinity chromatography. Culture supernatants were filtered over a 0.20 μM dead-end filter and loaded on 5 mL MabSelect SuRe columns (GE Healthcare), washed and eluted with 0.02 M sodium citrate-NaOH, pH 3. The eluates were loaded on a HiPrep Desalting column (GE Healthcare) immediately after purification and the antibodies were buffer exchanged into 12.6 mM NaH2PO4, 140 mM NaCl, pH 7.4 buffer (B.Braun or Thermo Fisher). After buffer exchange, samples were sterile filtered over 0.2 μm dead-end filters. Purified proteins were analyzed by a number of bioanalytical assays including capillary electrophoresis on sodium dodecyl sulfate-polyacrylamide gels (CE-SDS) and high-performance size exclusion chromatography (HP-SEC). Concentration was measured by absorbance at 280 nm. Purified antibodies were stored at 2-8° C.

Example 2: Selectivity of CDC Activity by Mixed Antibody Variants by Introduction of the P329R Mutation in Anti-CD52 IgG1-CAMPATH-1H-K439E+Anti-CD20 IgG1-11B8-S440K with an E430G Fc-Fc Interaction Enhancing Mutation The effect of mutation P329R on in vitro CDC efficacy was tested using mixtures of variants of anti-CD20 antibody IgG1-11B8 and anti-CD52 antibody IgG1-CAMPATH-1H. Different concentrations of purified antibodies (range 0.001-60.0 μg/mL final concentrations) were tested in an in vitro CDC assay on Wien 133 cells with 20% NHS. Different mutations were introduced in antibodies IgG1-11B8 and IgG1-CAMPATH-1H: E430G, which induces enhanced Fc-Fc interactions; P329R, which inhibits direct C1q binding to antibodies; and either of the mutations K439E or S440K, which inhibit the formation of homo-hexameric antibody complexes through inhibition of the intermolecular Fc-Fc interactions and promote the formation of hetero-hexameric antibody complexes through cross-complementary Fc-Fc interactions. As controls, single antibodies were also mixed 1:1 with non-binding isotype control antibodies IgG1-b12 or IgG1-b12-E430G to enable direct comparison of the concentrations of individual components and mixtures composed thereof. For the CDC assay, $0.1 \times 10^6$ Wien 133 cells (kindly provided by Dr. Geoff Hale, BioAnaLab Limited, Oxford, UK) in RPMI (Lonza, Cat No. BE12-115F) with 0.2% bovine serum albumin (BSA; Roche, Cat No. 10735086001) were pre-incubated in polystyrene round-bottom 96-well plates (Greiner bio-one Cat #650101) with concentration series of purified antibodies in a total volume of 80 µL for 15 min on a shaker at RT. Next, 20 µL normal human serum (NHS; Sanquin, Reference No. M0008) was added as a source of complement and incubated in a 37° C. incubator for 45 min (20% final NHS concentration; 0.001-10.0 µg/mL final antibody concentrations in 3-fold dilutions). The reaction was stopped by putting the plates on ice before pelleting the cells by centrifugation and replacing the supernatant replaced by 20 µL of 2 µg/mL propidium iodide solution (PI; Sigma Aldrich, Cat No. P4170). The number of PI-positive cells was determined by flow cytometry on an Intellicyt iQue screener (Westburg) and the percentage lysis was calculated as (number of PI-positive cells/total number of cells)×100%. The data were analyzed using best-fit values of a non-linear dose-response fit using log-transformed concentrations in GraphPad PRISM and the area under the dose-response curves of three experimental replicates was calculated. Relative areas under the curve (AUC) values represent normalization to minimal lysis (0% with IgG1-b12) and maximal lysis (100% with the mixture of IgG1-CAMPATH-1H-E430G+IgG1-11B8-E430G).

Figure 1B:
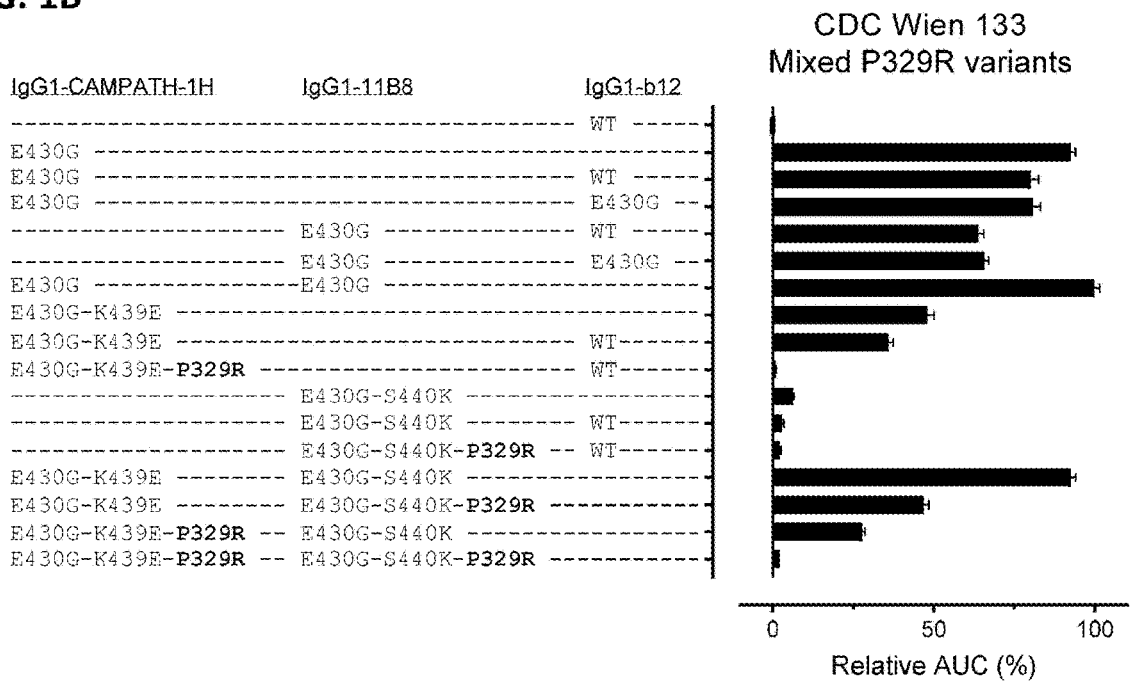

A 1:1 mixture of anti-CD52 IgG1-CAMPATH-1H-E430G+anti-CD20 IgG1-11B8-E430G (both containing SEQ ID NO 26) induced efficient cell lysis of Wiens 133 cells (FIG. 1A; set to 100% in FIG. 1B), which was found to be more efficient than the single antibodies separately (FIG. 1B). When IgG1-CAMPATH-1H-E430G was tested as a single agent, introduction of the K439E mutation (SEQ ID NO 80) resulted in decreased CDC efficacy, and K439E-P329R (SEQ ID NO 100) resulted in complete loss of CDC activity (FIG. 1A-B). For IgG1-11B8-E430G, introduction of either the S440K mutation (SEQ ID NO 101) or S440K-P329R (SEQ ID NO 114) resulted in loss of CDC efficacy (FIG. 1A-B).

The mixture of anti-CD20 IgG1-11B8-E430G-S440K (no single agent CDC activity)+anti-CD52 IgG1-CAMPATH-1H-E430G-K439E (partial single agent CDC activity) completely restored maximal CDC activity on Wien 133, similar to the level of the CD20- and CD52-targeting mixture IgG1-CAMPATH-1H-E430G+IgG1-11B8-E430G (similar dose-response in FIG. 1A; 100% in FIG. 1B). Adding anti-CD20 IgG1-11B8-E430G-S440K (no single agent CDC activity) to anti-CD52 IgG1-CAMPATH-1H-P329R-E430G-K439E (no single agent CDC activity), partially recovered cell lysis on Wien 133 (56% at saturating target binding in FIG. 1A; 28% in FIG. 1B).

Adding anti-CD20 IgG1-11B8-P329R-E430G-S440K (no single agent CDC activity) to anti-CD52 IgG1-CAMPATH-1H-E430G-K439E (partial single agent CDC activity), partially restored CDC activity on Wien 133 to a level lower than the mixture IgG1-CAMPATH-1H-E430G+IgG1-11B8-E430G (higher EC50 and lower maximal kill in FIG. 1A; 47% in FIG. 1B), but moderately higher than the mixture of anti-CD52 IgG1-CAMPATH-1H-E430G-K439E+control antibody (IgG1-b12), which has a similar maximal kill but higher EC50 (FIG. 1A) and lower relative AUC (36% in FIG. 1B). In contrast, adding anti-CD20 IgG1-11B8-P329R-E430G-S440K (no single agent CDC activity) to anti-CD52 IgG1-CAMPATH-1H-P329R-E430G-K439E (no single agent CDC activity) did not restore any CDC activity (FIG. 1A-B).

Figure 2A:
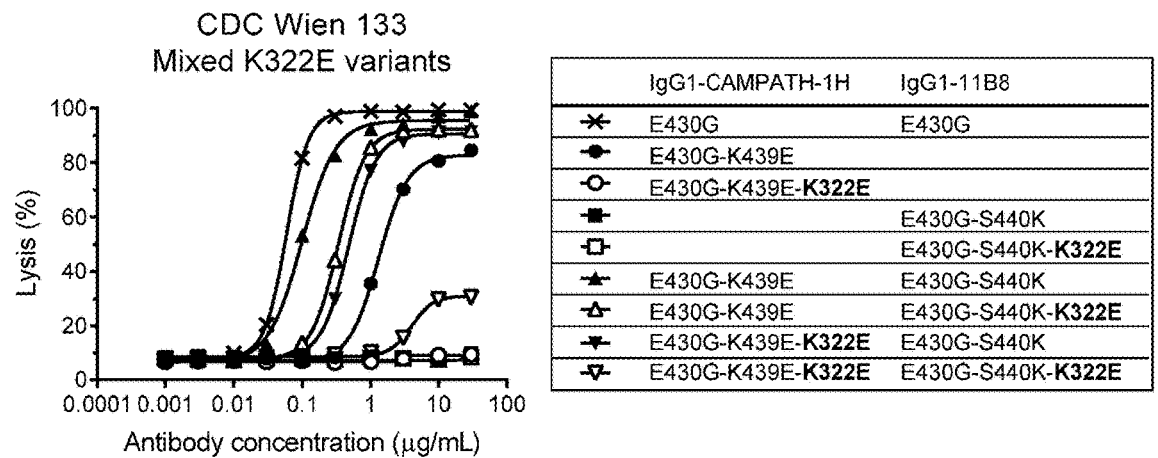
FIGS. 2A and 2B show selectivity of CDC activity by mixed antibody variants of anti-CD52 IgG1-CAMPATH-1H-E430G-K439E+anti-CD20 IgG1-11B8-E430G-S440K by introduction of the K322E mutation. Wien 133 cells were incubated with antibody concentration series in the presence of 20% NHS. CDC efficacy is presented as (FIG. 2A) percentage lysis determined by the percentage PI-positive cells and (FIG. 2B) the AUC normalized to non-binding control antibody IgG1-b12 (0%) and the mixture of IgG1-CAMPATH-1H-E430G+IgG1-11B8-E430G (100%).
Figure 2B:
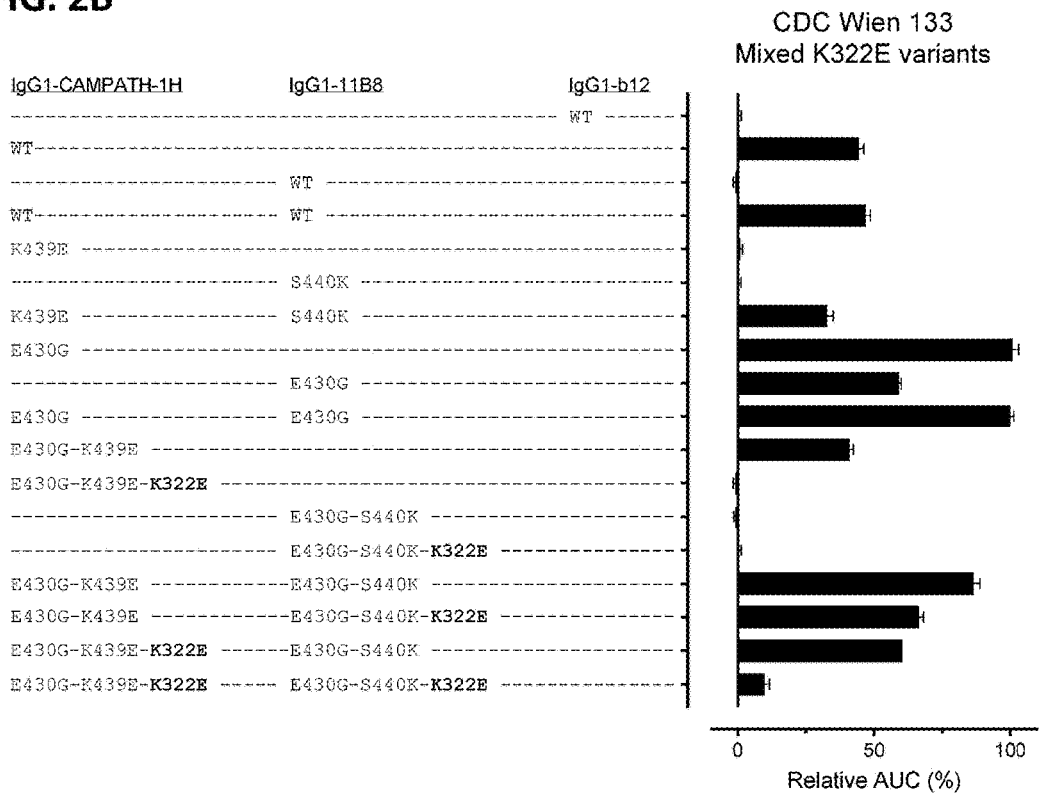
Figure 3A:
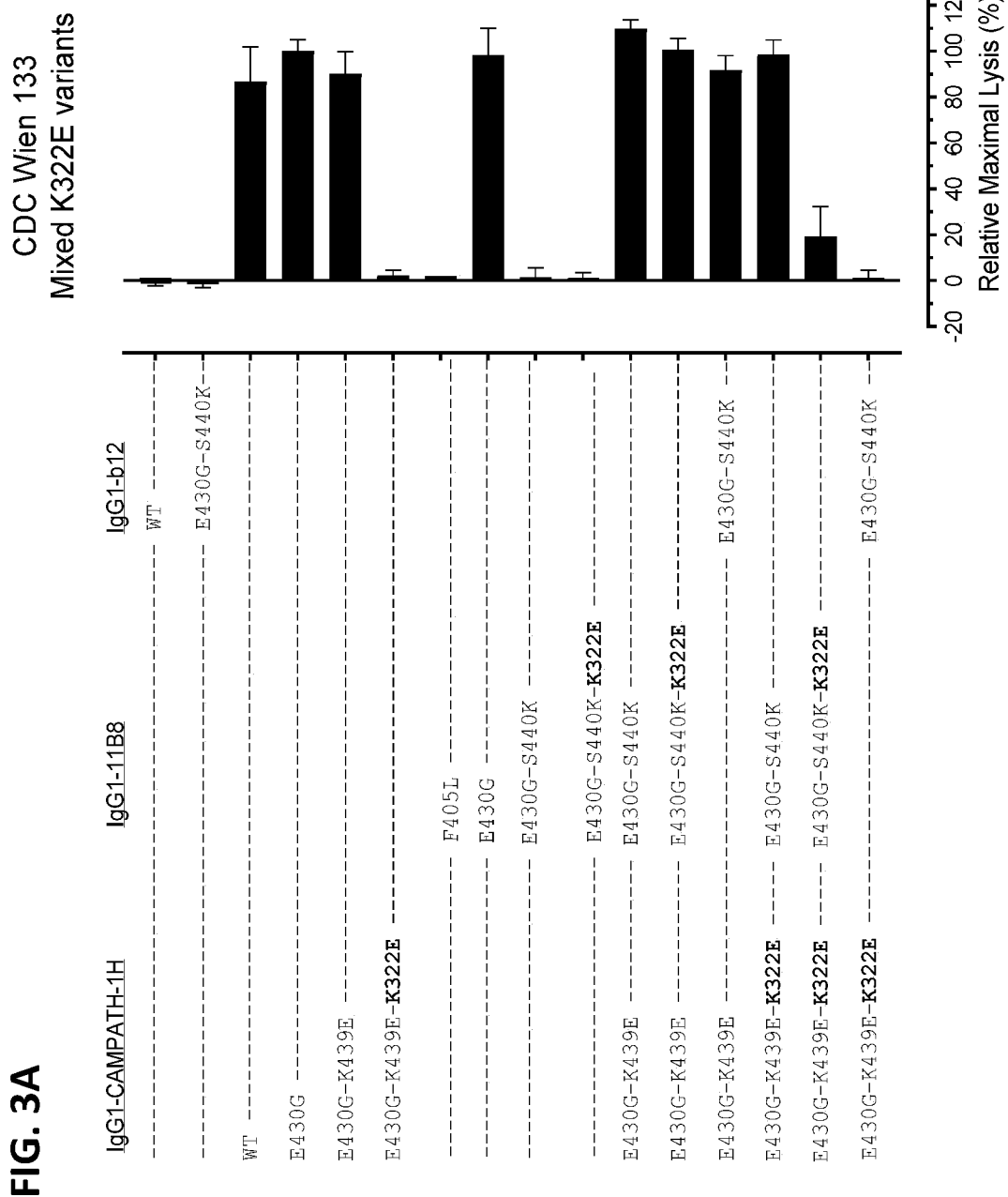
FIGS. 3A-3G show the selectivity of CDC activity by introduction of the K322E mutation in mixed antibody variants of anti-CD52 IgG1-CAMPATH-1H-E430G-K439E+anti-CD20-11B8-E430G-S440K on different cell lines. In vitro CDC assays were performed with 30 µg/mL antibody in the presence of 20% NHS using Burkitt's lymphoma cell lines Wien 133 (FIG. 3A), Daudi (FIG. 3B), Raji (FIG. 3C) and Ramos (FIG. 3D), acute lymphoblastic lymphoma (ALL) cell line REH (FIG. 3E), myeloma cell line U266B1 (FIG. 3F), and B cell lymphoma cell line U-698-M (FIG. 3G). CDC activity is presented as the percentage lysis determined by the percentage PI-positive cells normalized per cell line to non-binding control antibody IgG1-b12 (0%) and IgG1-CAMPATH-1H-E430G (100%) for REH, U266B1, and Wien 133 or IgG1-11B8-E430G (100%) for Daudi, Raji, Ramos, and U-698-M.
Figure 3B:
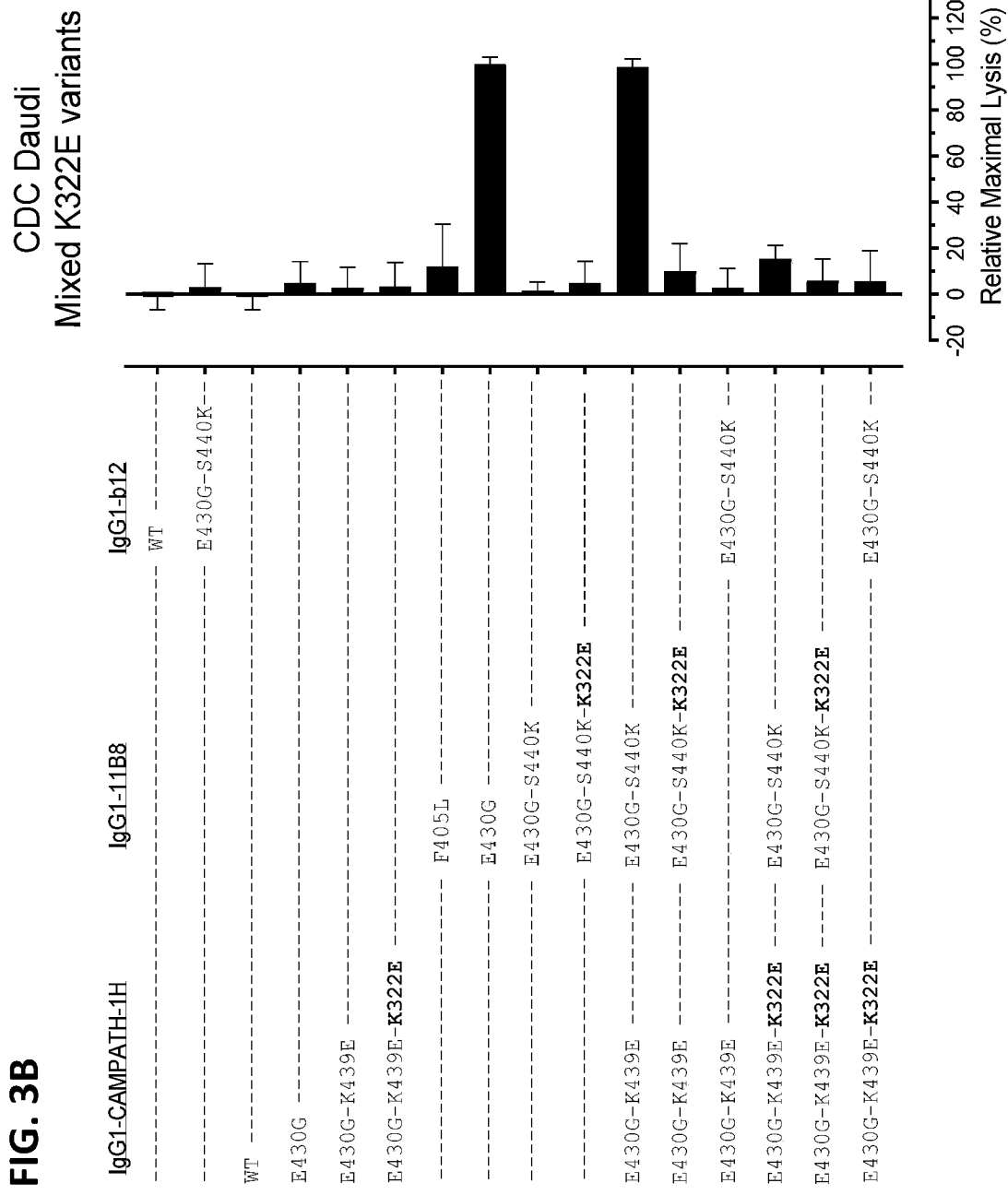
Figure 3C:
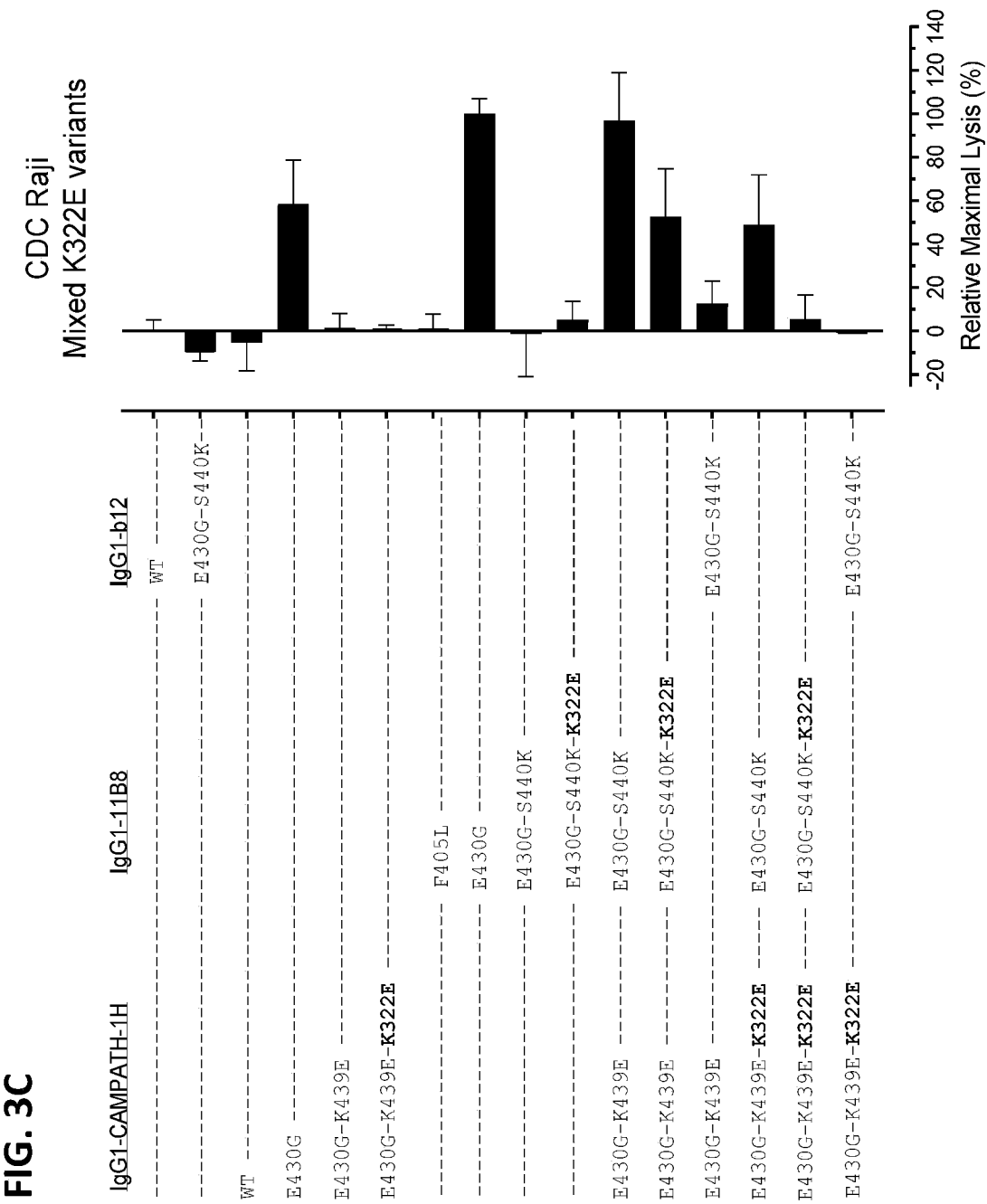
Figure 3D:
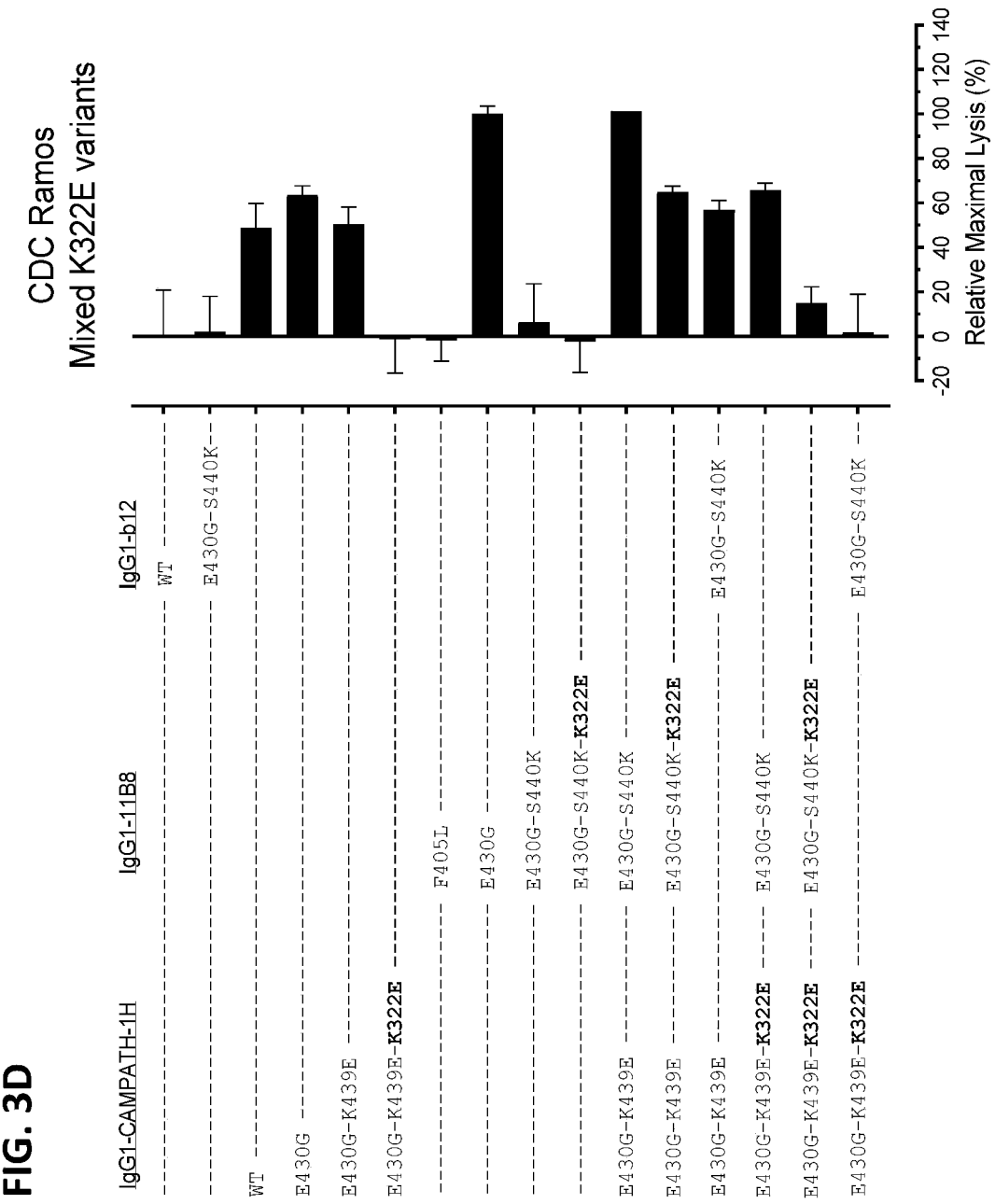
Figure 3E:
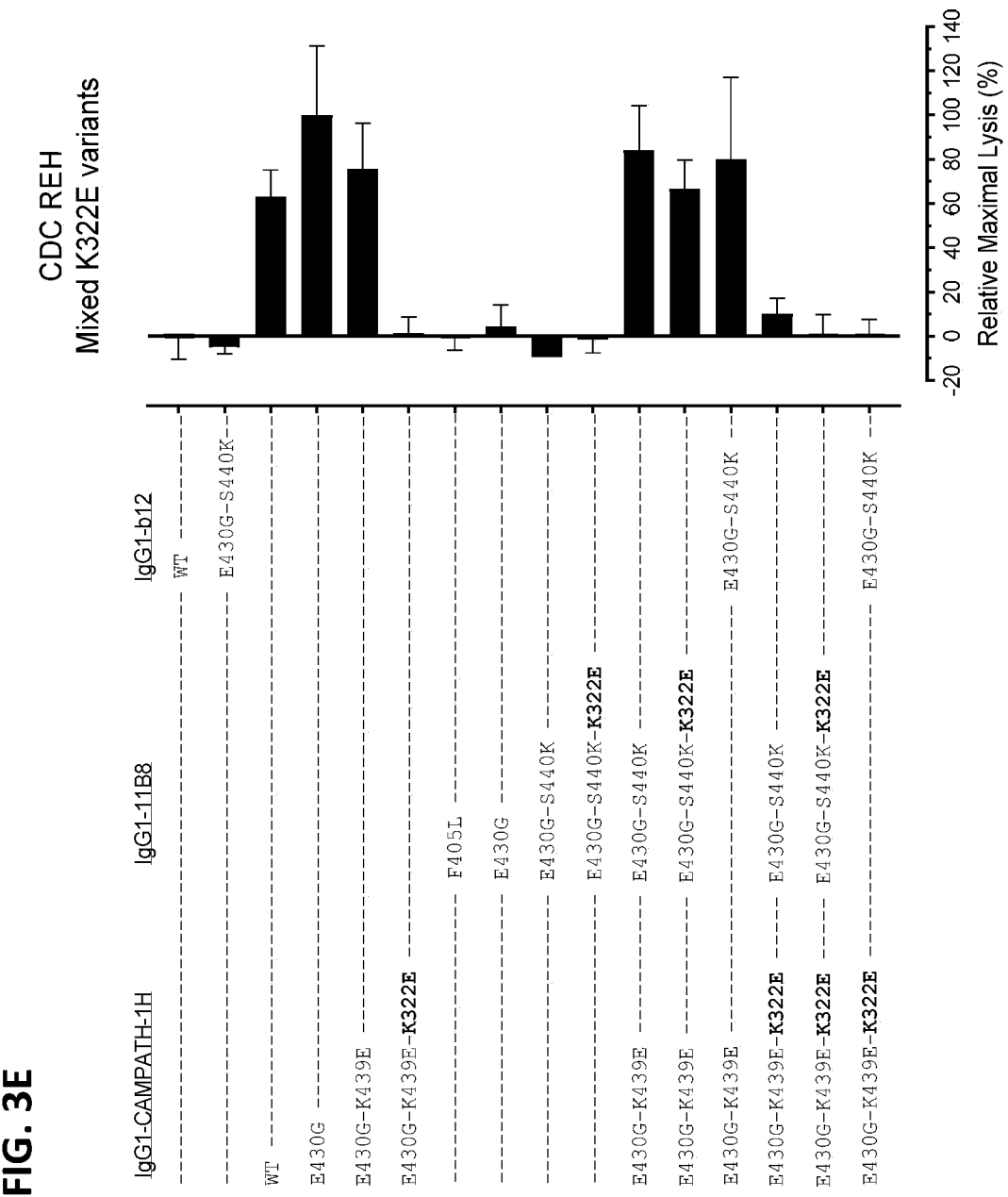
Figure 3F:
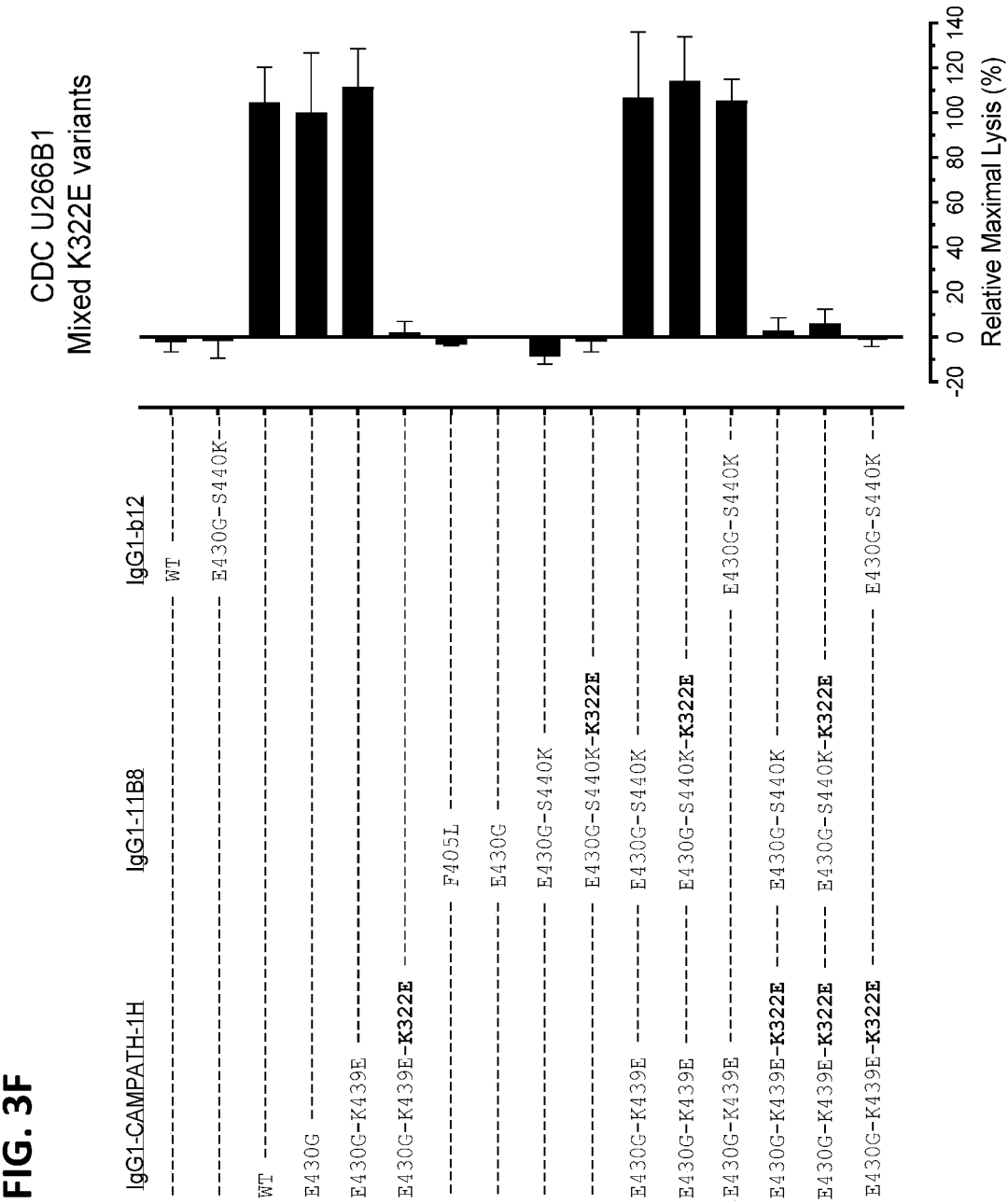
Figure 3G:
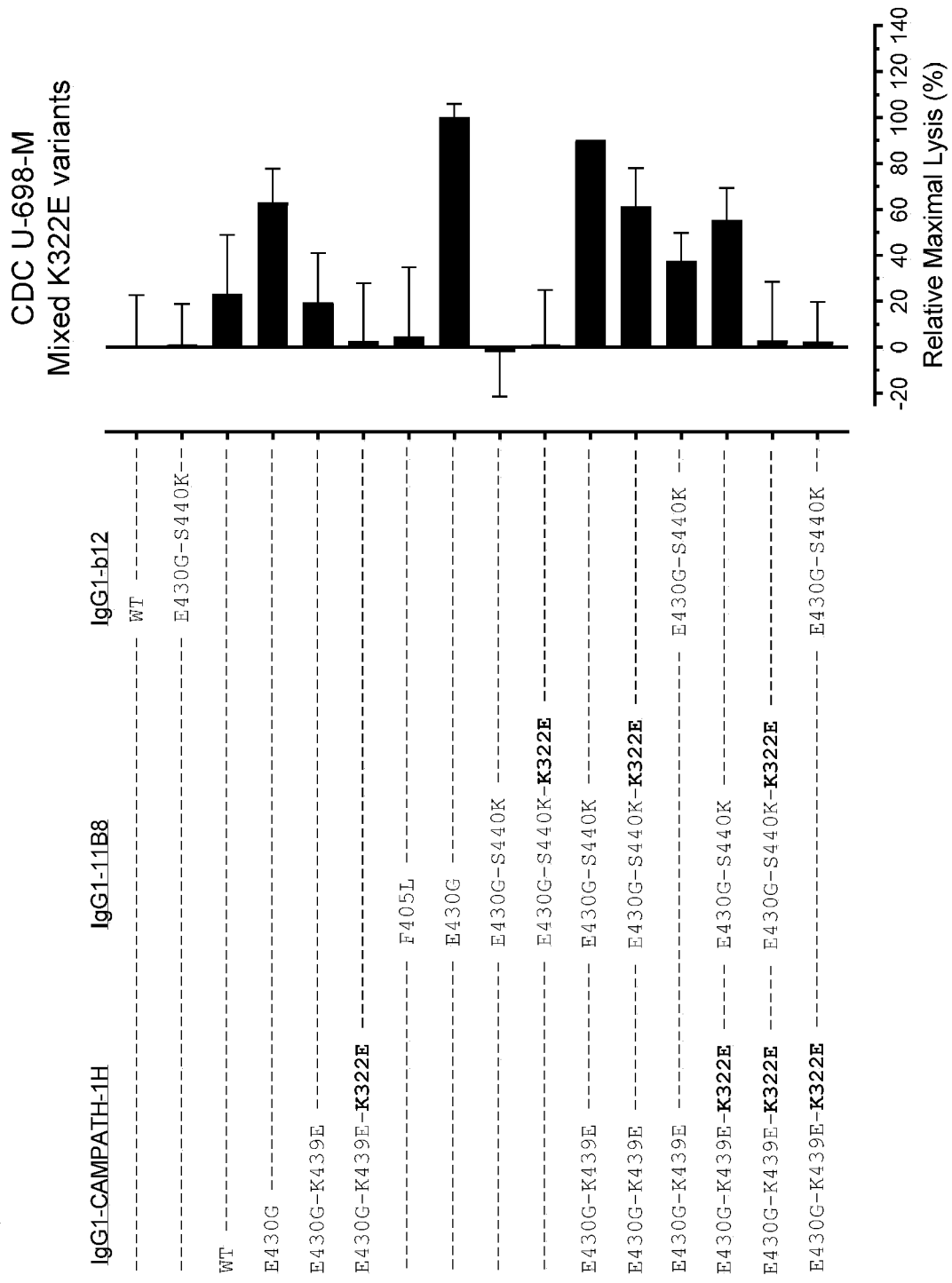
Figure 4:
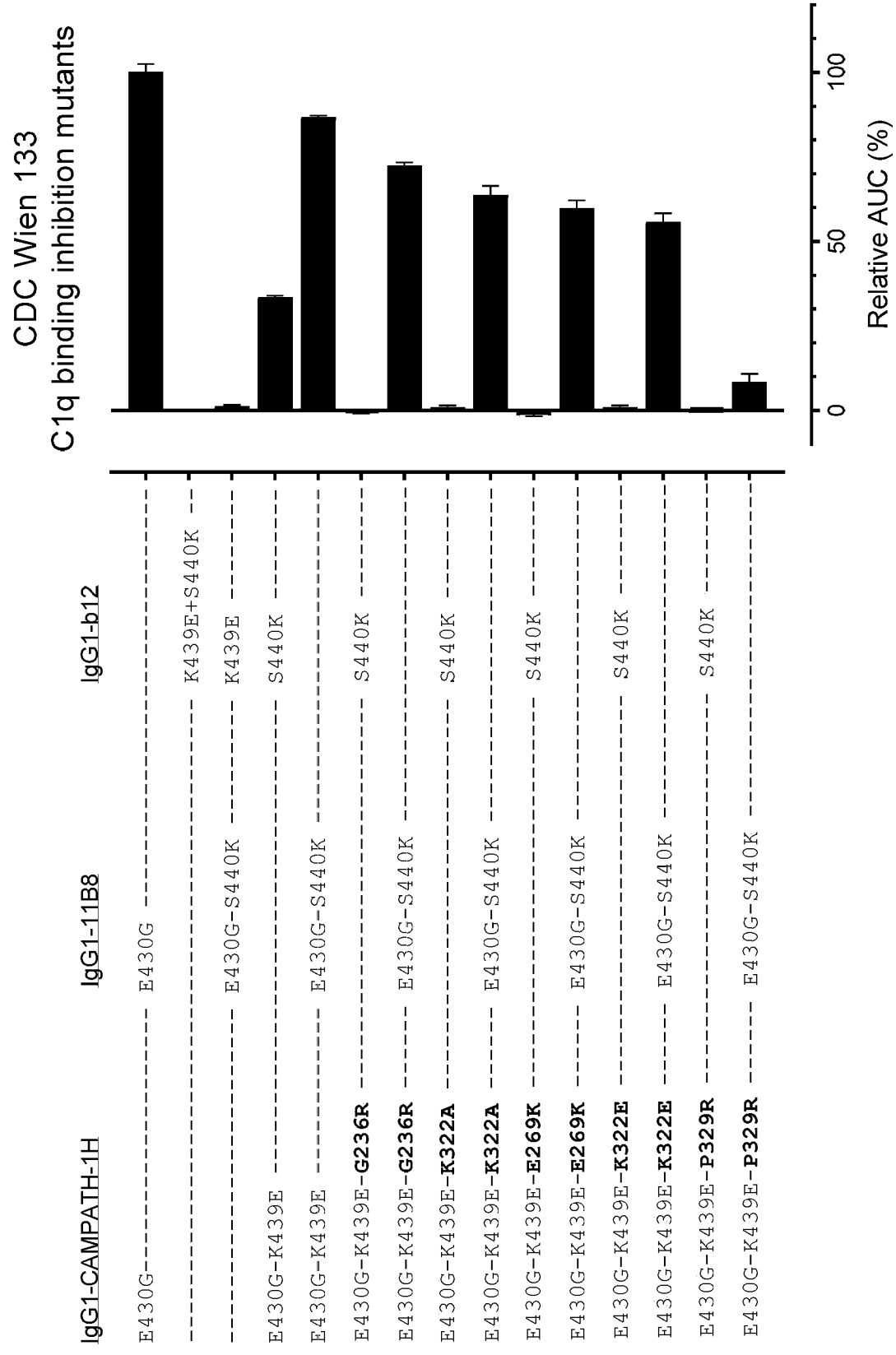
FIG. 4 shows selectivity of CDC activity by mixed antibody variants of anti-CD52 IgG1-CAMPATH-1H-E430G-K439E with a C1q binding inhibition mutation (G236R, K322A, E269K, K322E or P329R)+anti-CD20 IgG1-11B8-E430G-S440K. Wien 133 cells were incubated with antibody concentration series in the presence of 20% NHS. CDC efficacy is presented as the normalized AUC of the percentage PI-positive cells. Normalization was performed to non-binding control antibody mix IgG1-b12-K439E+IgG1-b12-S440K (0%) and the mixture of IgG1-CAMPATH-1H-E430G+IgG1-11B8-E430G (100%).

These data illustrate that the introduction of mutation P329R, which inhibits direct C1q binding, could further suppress the CDC activity of individual components in K439E+S440K antibody mixtures with enhanced Fc-Fc interactions (E430G). Surprisingly, it was observed that for two antibodies against two different targets that both did not show detectable CDC activity as a single agent, CDC activity could be partially restored for mixtures in which only one of the two antibodies contained the P329R C1q binding inhibition mutation. These data indicate that a mixture of anti-CD20 IgG-E430G-S440K+anti-CD52 IgG-E430G-K439E antibodies could be applied to create selectivity of CDC activity on cells simultaneously expressing the two different targets by introduction of the C1q binding inhibition mutation P329R to decrease or inhibit single agent activity. Without being limited by theory, the avidity of C1q for C1q binding sites in three of the antibodies in hetero-hexameric IgG assemblies may be sufficiently high to recover partial CDC activity. In contrast, the loss of all six C1q binding sites in all six antibodies, e.g. in mixtures of two antibodies that both contain the P329R mutation, resulted in loss of CDC activity.

Example 3: Selectivity of CDC Activity by Mixed Antibody Variants by Introduction of the K322E Mutation in Anti-CD52 IgG1-CAMPATH-1H-K439E+Anti-CD20 IgG1-11B8-S440K with an E430G Fc-Fc Interaction Enhancing Mutation The effect of mutation K322E on in vitro CDC efficacy was tested using mixtures of variants of anti-CD20 antibody IgG1-11B8 and anti-CD52 antibody IgG1-CAMPATH-1H. Different concentrations of purified antibodies (range 0.001-30.0 μg/mL final concentrations) were tested in an in vitro CDC assay on Wien 133 cells with 20% NHS, essentially as described in Example 2. Different mutations were introduced in antibodies IgG1-11B8 and IgG1-CAMPATH-1H: E430G, which induces enhanced Fc-Fc interactions; K322E, which inhibits direct C1q binding to antibodies; and either of the mutations K439E or S440K, which inhibit the formation of homo-hexameric antibody complexes through inhibition of the intermolecular Fc-Fc interactions and promote the formation of hetero-hexameric antibody complexes through cross-complementary Fc-Fc interactions. The percentage lysis was calculated from the number of PI-positive cells. Data were analyzed using best-fit values of a non-linear dose-response fit using log-transformed concentrations and the area under the dose-response curves of three experimental replicates was calculated. Relative areas under the curve (AUC) values represent normalization to minimal lysis (0% with IgG1-b12) and maximal lysis (100% with the mixture of IgG1-CAMPATH-1H-E430G+IgG1-11B8-E430G).

A 1:1 mixture of anti-CD52 IgG1-CAMPATH-1H-E430G+anti-CD20 IgG1-11B8-E430G induced efficient cell lysis of Wien 133 cells (FIG. 2A; set to 100% in FIG. 2B). When IgG1-CAMPATH-1H-E430G was tested as a single agent, introduction of the K439E mutation resulted in decreased CDC efficacy, and K439E-K322E (SEQ ID NO 91) resulted in complete loss of CDC activity (FIG. 2A-B). For IgG1-11B8-E430G, introduction of either the S440K mutation or S440K-K322E (SEQ ID NO 109) resulted in loss of CDC efficacy FIG. 2A-B).

The mixture of anti-CD20 IgG1-11B8-E430G-S440K (no single agent CDC activity)+anti-CD52 IgG1-CAMPATH-1H-E430G-K439E (partial single agent CDC activity) restored high CDC activity on Wien 133 cells, comparable to the level of the to the CD20- and CD52-targeting mixture IgG1-CAMPATH-1H-E430G+IgG1-11B8-E430G (comparable dose-response in FIG. 2A; 87% in FIG. 2B). Adding anti-CD20 IgG1-11B8-E430G-S440K (no single agent CDC activity) to anti-CD52 IgG1-CAMPATH-1H-K322E-E430G-K439E (no single agent CDC activity), partially recovered cell lysis on Wien 133 (higher EC50 than the mixture IgG1-CAMPATH-1H-E430G+IgG1-11B8-E430G in FIG. 2A; 60% in FIG. 2B).

Adding anti-CD20 IgG1-11B8-K322E-E430G-S440K (no single agent CDC activity) to anti-CD52 IgG1-CAMPATH-1H-E430G-K439E (partial single agent CDC activity), partially restored CDC activity on Wien 133 (higher EC50 than the mixture IgG1-CAMPATH-1H-E430G+IgG1-11B8-E430G in FIG. 2A; 66% in FIG. 2B). In contrast, adding anti-CD20 IgG1-11B8-K322E-E430G-S440K (no single agent CDC activity) to anti-CD52 IgG1-CAMPATH-1H-K322E-E430G-K439E (no single agent CDC activity) only restored minimal CDC activity (high EC50 and maximal kill of approximately 31% in FIG. 2A; 10% in FIG. 2B).

These data illustrate that the introduction of mutation K322E, which inhibits direct C1q binding, could further suppress the CDC activity of individual components in K439E+S440K antibody mixtures with enhanced Fc-Fc interactions (E430G). Surprisingly, it was observed that for two antibodies against two different targets that both did not show detectable CDC activity as a single agent, CDC activity could be restored to near-maximal cell lysis for mixtures in which only one of the two antibodies contained the K322E C1q binding inhibition mutation. These data indicate that a mixture of anti-CD20 IgG-E430G-S440K+anti-CD52 IgG-E430G-K439E antibodies could be applied to create selectivity of CDC activity on cells simultaneously expressing the two different targets by introduction of the C1q binding inhibition mutation K322E to decrease or inhibit single agent activity.

Example 4: Selectivity of CDC Activity on Different Cell Lines by Mixed Antibody Variants by Introduction of the K322E Mutation in Anti-CD20+Anti-CD52 Antibodies with an E430G Fc-Fc Interaction Enhancing Mutation Example 2 and Example 3 describe that specific combinations of Fc-Fc interaction-enhanced anti-CD20 and anti-CD52 antibodies show most efficient CDC activity on Wien 133 cells if both components were simultaneously present, provided each of the antibodies contained either a K439E or an S440K mutation that blocks homo-oligomerization via Fc-Fc interactions. The selective activity of the mixture compared to its individual components was improved by introduction of the P329R (Example 2) or K322E (Example 3) C1q binding inhibition mutation in the anti-CD52 antibody IgG1-CAPMATH-1H-E430G-S440K to suppress its residual CDC activity as a single component. Here, selectivity of CDC activity by mixtures of the anti-CD20 IgG1-11B8-E430G-S440K+anti-CD52 IgG1-CAMPATH-1H-E430G-K439E antibody variants with a K322E mutation for cells expressing sufficient levels of both CD20 and CD52 on the cell surface was tested on seven different human cell lines: Burkitt's lymphoma cell lines Wien 133, Daudi (ATCC, Cat No. CCL-213), Raji (ATCC, Cat No. CCL-86) and Ramos (ATCC, Cat No. CRL-1596), acute lymphoblastic lymphoma (ALL) cell line REH (DSMZ, Cat No. ACC-22), myeloma cell line U266B1 (ATCC, Cat No. TIB-196), and B cell lymphoma cell line U-698-M (DSMZ, Cat No. ACC-4). The in vitro CDC assays were performed with 20% NHS and final antibody concentrations of 30.0 μg/mL, essentially as described in Example 2. Cell lysis was calculated from the number of PI-positive cells, averaged from three experimental replicates and normalized per cell line relative to the cell lysis measured for negative control antibody IgG1-b12 (0%) and for IgG1-CAMPATH-1H-E430G (100%, for REH, U266B1, and Wien 133) or IgG1-11B8-E430G (100%, for Daudi, Raji, Ramos, and U-698-M), depending on which antibody induced the highest lysis.

Cell surface expression levels of CD52 and CD20 were determined by indirect immunofluorescence using the Human IgG Calibrator Kit (Biocytex, Cat No. CP010). 100,000 cells per well were seeded in polystyrene 96-well round-bottom plates (Greiner Bio-One, Cat No. 650101). The next steps were performed at 4° C. Cells were pelleted by centrifugation for 3 minutes at 300×g and resuspended in 50 μL PBS (B Braun, Cat No. 3623140) containing saturating concentrations of 10 μg/mL IgG1-CAMPATH-1H (anti-CD52) or IgG1-11B8 (anti-CD20). After an incubation of 30 minutes at 4° C., cells were pelleted by centrifugation at 300×g for 3 minutes and resuspended in 150 μL FACS buffer (PBS+0.1% (w/v) bovine serum albumin (BSA)+0.02% (w/v) sodium azide). Set-up and Calibration Beads were added to the plate according to the manufacturer's instructions. Cells and beads in parallel were washed two more times with 150 μL FACS buffer, resuspended in 50 μL FITC-conjugated mouse-IgG absorbed goat anti-human IgG (BioCytex) and incubated for 30 minutes at 4° C. Cells and beads were washed twice and resuspended in 150 μL FACS buffer. Cells were resuspended in Fixative (BioCytex) and incubated between 5 and 60 minutes at 4° C. protected from light. Immunofluorescence was measured by flow cytometry on a FACS Canto II (BD Biosciences) by recording 10,000 events within the population of viable cells. The Geometric mean of fluorescence intensity of the Calibration Beads was used to calculate the calibration curve that was forced to go through zero intensity and zero concentration using GraphPad Prism software. For each cell line, the antibody binding capacities (ABC) of IgG1-CAMPATH-1H and IgG1-11B8, representative of the CD52 and CD20 cell surface expression, respectively, were calculated using the Geometric mean fluorescence intensity, based on the equation of the calibration curve (interpolation of unknowns from the standard curve) using GraphPad Software, followed by subtraction of the background determined for wells incubated without primary antibody. The ABC values were averaged from two independent experiments and (summarized in Table 2).

FIG. 3 shows that the CDC activity at target saturation of IgG1-CAMPATH-1H-E430G and IgG1-11B8-E430G varied with the target expression levels: U266B1 (CD20 ABC<20,000; CD52 ABC>$1\times10^6$) and REH (CD20 ABC<20,000; CD52 ABC>100,000) cells were resilient to lysis by anti-CD20 antibody IgG1-11B8-E430G, but sensitive to anti-CD52 antibody IgG1-CAMPATH-1H-E430G.

Vice versa, Daudi cells (CD52 ABC<75,000; CD20 ABC>100,000) were resilient to IgG1-CAMPATH-1H-E430G, but sensitive to IgG1-11B8-E430G. The other four tested cell lines were sensitive to both IgG1-CAMPATH-1H-E430G and IgG1-11B8-E430G: Wien 133 (CD20 ABC>100,000; CD52 ABC>300,000), Raji (CD20 ABC>100,000; CD52 ABC>85,000), U-698-M (CD20 ABC>70,000; CD52: ABC>90,000) and Ramos (CD20 ABC>80,000; CD52 ABC>175,000).

For IgG1-CAMPATH-1H-E430G, introduction of the K439E mutation resulted in reduced single agent CDC activity on U-698-M and Raji cells (CD52 ABC<100,000), but had no significant effect on cell lines U266B1 (CD52 ABC>1×10⁶) cells, Wien 133 (CD52 ABC>300,000), Ramos (CD52 ABC>175,000), and REH cells (CD52 ABC>135,000). C1q binding inhibition by introduction of the K322E in IgG1-CAMPATH-1H-E430G-K439E further eliminated single agent CDC activity on all tested cell lines that were responsive to IgG1-CAMPATH-1H-E430G. For IgG1-11B8-E430G, introduction of only the S440K mutation or introduction of both the S440K and K322E mutations resulted in complete inhibition of single agent CDC activity on all tested cell lines that were sensitive to IgG1-11B8-E430G: Daudi (CD20 ABC<115,000), Wien 133 (CD20 ABC<110,000), Raji (CD20 ABC<120,000), U-698-M (CD20 ABC<75,000) and Ramos (CD20 ABC<85,000).

The mixture of IgG1-CAMPATH-1H-E430G-K439E+IgG1-11B8-E430G-S440K showed CDC activity on all tested cell lines, irrespective of the CD20 and CD52 surface expression levels (FIG. 3). In stark contrast, a mixture of IgG1-CAMPATH-1H-E430G-K439E-K322E+IgG1-11B8-E430G-S440K showed selective lysis of only those cell lines that displayed sufficient surface expression levels of both CD20 and CD52: Wien 133 (CD20 ABC>100,000; CD52 ABC>300,000), Ramos (CD20 ABC>80,000; CD52 ABC>175,000), U-698-M (CD20 ABC>70,000; CD52 ABC>90,000), and Raji (CD20 ABC>100,000; CD52 ABC>85,000).

When CD20 or CD52 was only expressed at very low levels, no CDC activity was observed with the mixture of IgG1-CAMPATH-1H-E430G-K439E-K322E+IgG1-11B8-E430G-S440K: Daudi (CD52 ABC<75,000), U266B1 U266B1 (CD20 ABC<20,000) and REH (CD20 ABC<20,000). When the K322E C1q binding inhibition mutation was introduced in both antibodies (IgG1-CAMPATH-1H-E430G-K439E-K322E+IgG1-11B8-E430G-S440K-K322E), no CDC activity was observed. Together, these data suggest that the recruitment of C1q and CDC efficacy by IgG1-CAMPATH-1H-E430G-K439E-K322E is dependent on its hetero-oligomerization with IgG1-11B8-E430G-S440K.

In conclusion, selective killing of cells expressing sufficient levels of both CD20 and CD52 could be achieved using a mixture of IgG1-CAMPATH-1H-E430G-K439E-K322E+ IgG1-11B8-E430G-S440K; in contrast, this mixture displayed background lysis levels on cell lines that expressed such low expression levels of either CD20 or CD52 that they could not be killed by single agent CDC activity of IgG1-11B8-E430G-S440K and IgG1-CAMPATH-1H-E430G-K439E-K322E, respectively.

TABLE 2

Cell surface expression of CD52 and CD20 on hematological cancer cell lines.

| | ABC[1] | | | | | | |
|---|---|---|---|---|---|---|---|
| Target | U266B1 | Wien 133 | Ramos | REH | U-698-M | Raji | Daudi |
| CD52 IgG1-CAMPATH-1H | 1,455,918 | 332,343 | 178,794 | 135,088 | 93,651 | 85,514 | 7,275 |
| CD20 IgG1-11B8 | 18,544 | 101,937 | 81,198 | 13,031 | 70,047 | 115,310 | 110,004 |

[1]Cell surface expression is expressed as the number of specific antibody binding capacities (ABC) per cell, determined using the Human IgG Calibrator Kit (Biocytex).

Example 5: Analysis of the Effect of Different C1q Binding Inhibition Mutations in Anti-CD52 Antibody IgG1-CAMPATH-1H-E430G-K439E on the Selective CDC Activity of Antibody Mixtures with Anti-CD20 Antibody IgG1-11B8-E430G-S440K It was described above that introduction of the P329R (Example 2) or K322E (Example 3) C1q binding inhibition mutation resulted in inhibition of residual CDC activity of IgG1-CAMPATH-1H-E430G-K439E on Wien 133 cells, while CDC activity was either completely, partially or not at all recovered when mixed with IgG1-11B8-E430G-S440K, depending on the cell line tested (Example 4). Here, the effects of different C1q binding inhibition mutations were compared in in vitro CDC assays using Wien 133 cells with IgG1-CAMPATH-1H-E430G-K439E variants containing the G236R (SEQ ID NO 84), K322A (SEQ ID NO 90), E269K (SEQ ID NO 81), K322E or P329R C1q binding inhibition mutation (listed here by expected decreasing C1q binding affinity) in a mixture with IgG1-11B8-E430G-S440K. The in vitro CDC assay using Wien 33 cells was performed with 20% NHS and serial dilution antibody concentrations (range 0.002-40.0 μg/mL final concentrations in 4-fold dilutions), essentially as described in Example 2. Cell lysis was calculated from the number of PI-positive cells as measured by flow cytometry on an Intellicyt iQue™ screener, averaged from three experimental replicates. Relative areas under the curve (AUC) values represent normalization to minimal lysis (0% with negative control IgG1-b12-K439E+IgG1-b12-S440K) and maximal lysis (100% with the mixture of IgG1-CAMPATH-1H-E430G+IgG1-11B8-E430G). FIG. 4 shows bar diagrams for the AUC values of the dose-response CDC activity curves on Wien 133 cells. Introduction of either one of the C1q binding inhibition mutations (G236R, K322A, E269K, K322E or P329R) resulted in complete inhibition of residual single agent CDC activity by IgG1-CAMPATH-1H-E430G-K439E on Wien 133. In a mixture with IgG1-11B8-E430G-S440K, increasing levels of CDC activity recovery were observed with IgG1-CAMPATH-1H-E430G-K439E variants containing the single C1q binding inhibition mutation P329R, K322E, E269K, K322A, or G236R. These data suggest that there was a direct correlation between the C1q binding affinity of the IgG1-CAMPATH-1H-E430G-K439E variants (P329R, K322E, E269K, K322A, or G236R) and the recovery of CDC activity for the mixtures with IgG1-11B8-E430G-S440K.

Figure 5:
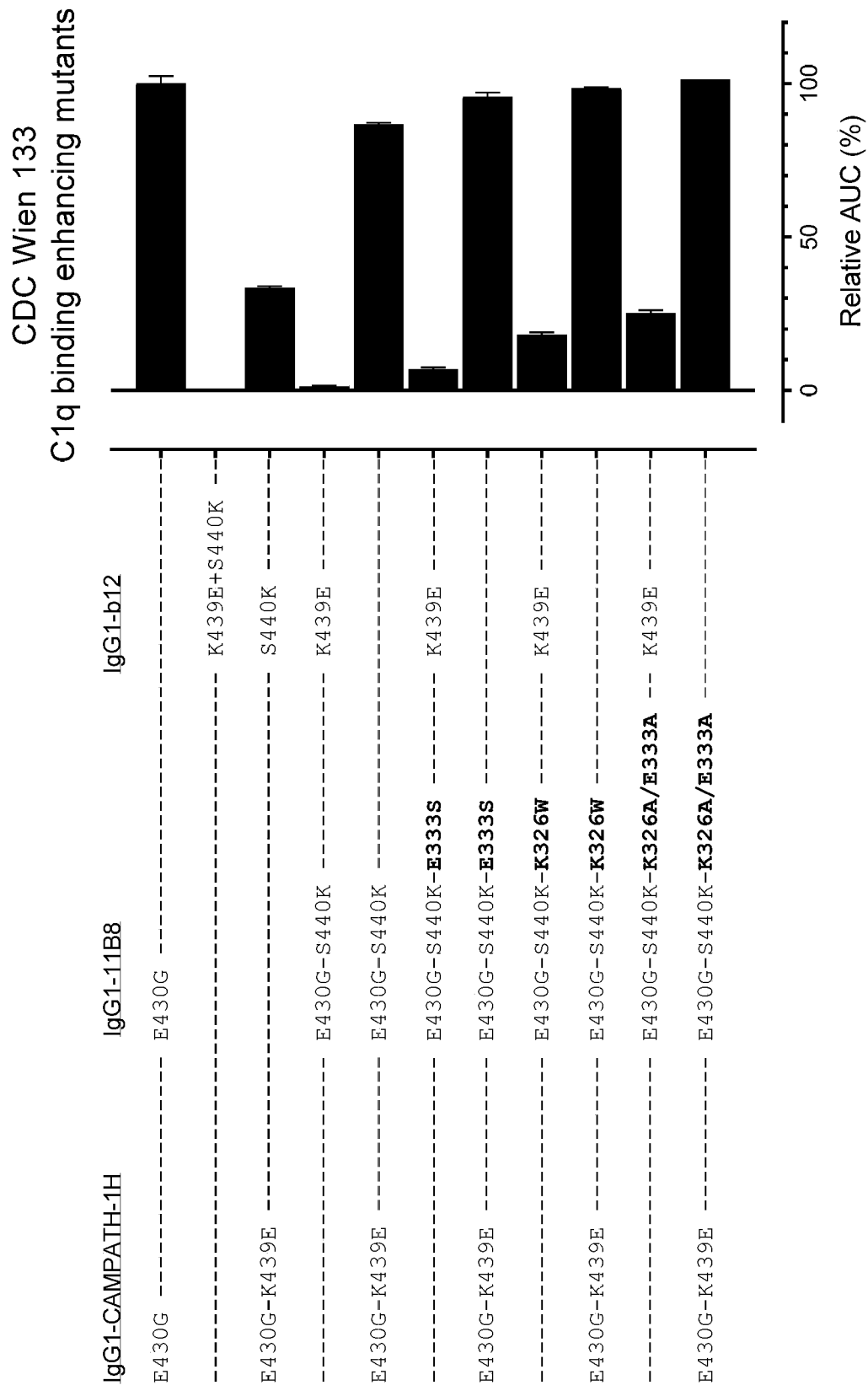
FIG. 5 shows selectivity of CDC activity by mixed antibody variants of anti-CD52 IgG1-CAMPATH-1H-E430G-K439E+anti-CD20 IgG1-11B8-E430G-S440K with a C1q binding enhancing mutation (E333S, K326W or K326A/E333A). Wien 133 cells were incubated with antibody concentration series in the presence of 20% NHS. CDC efficacy is presented as the normalized AUC of the percentage PI-positive cells. Normalization was performed to non-binding control antibody mix IgG1-b12-K439E+IgG1-b12-S440K (0%) and the mixture of IgG1-CAMPATH-1H-E430G+IgG1-11B8-E430G (100%).
Figure 6A:
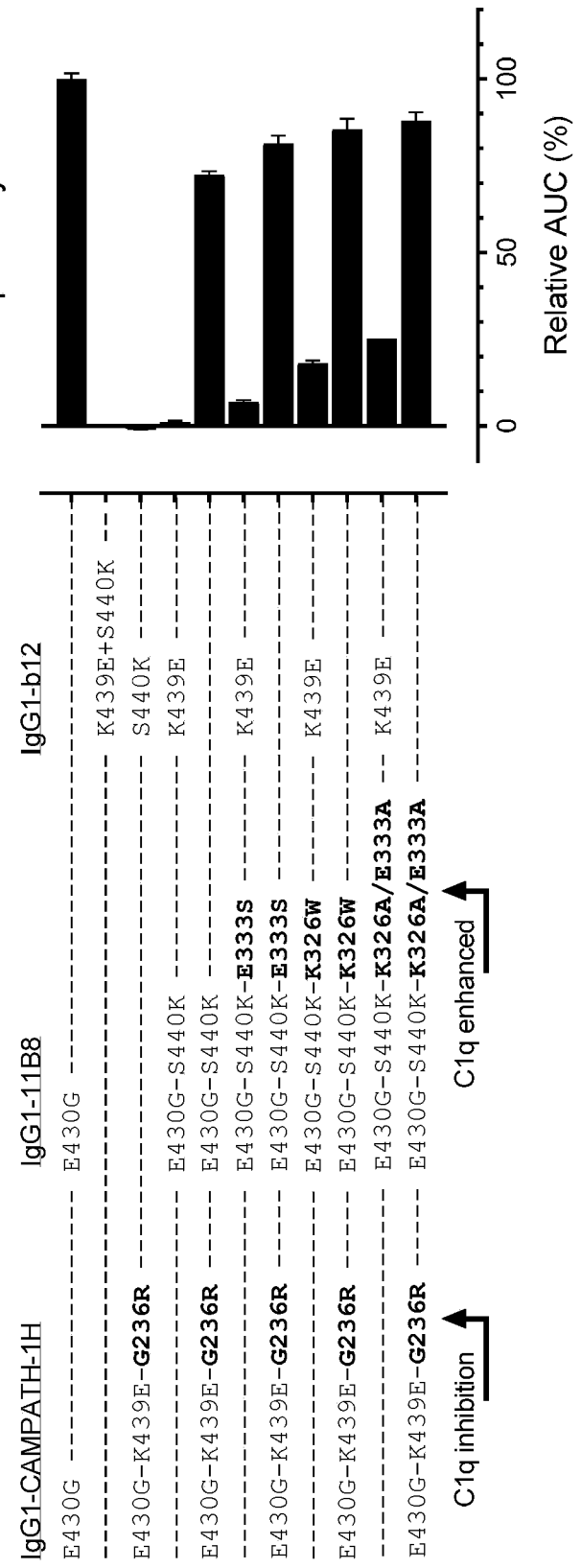
FIGS. 6A-6E show selectivity of CDC activity by mixed antibody variants of anti-CD52 IgG1-CAMPATH-1H-E430G-K439E with the C1q binding inhibition mutation G236R (FIG. 6A), K322A (FIG. 6B), E269K (FIG. 6C), K322E (FIG. 6D) or P329R (FIG. 6E)+anti-CD20 IgG1-11B8-E430G-S440K with a C1q binding enhancing mutation (E333S, K326W or K326A/E333A). Wien 133 cells were incubated with antibody concentration series in the presence of 20% NHS. CDC efficacy is presented as the normalized AUC of the percentage PI-positive cells. Normalization was performed to non-binding control antibody mix IgG1-b12-K439E+IgG1-b12-S440K (0%) and the mixture of IgG1-CAMPATH-1H-E430G+IgG1-11B8-E430G (100%).
Figure 6B:
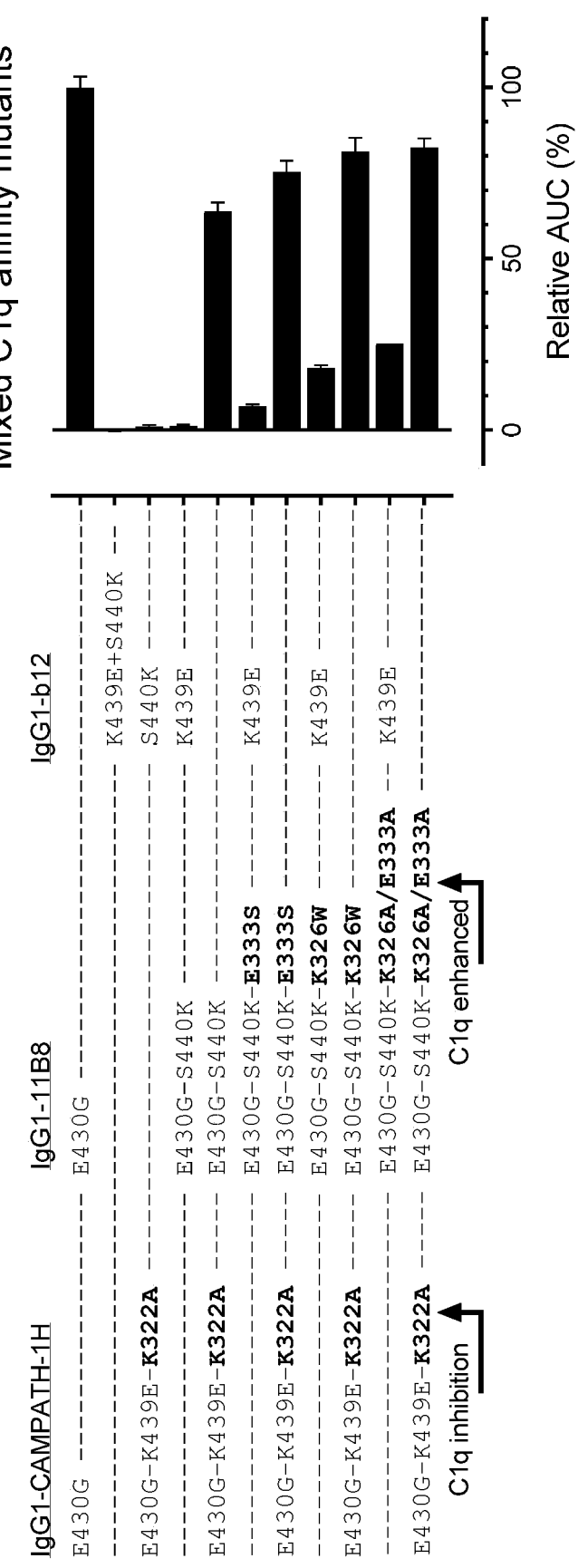
Figure 6C:
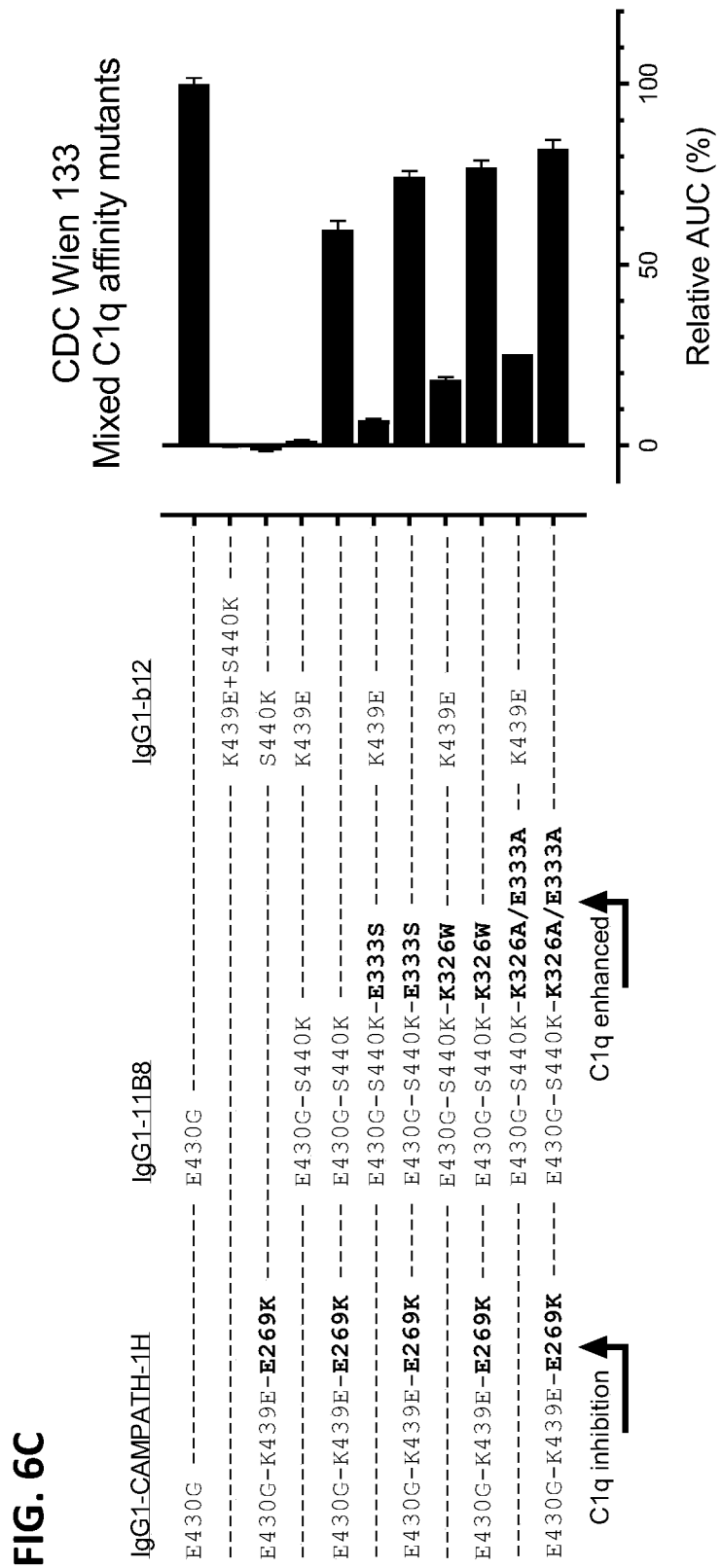
Figure 6D:
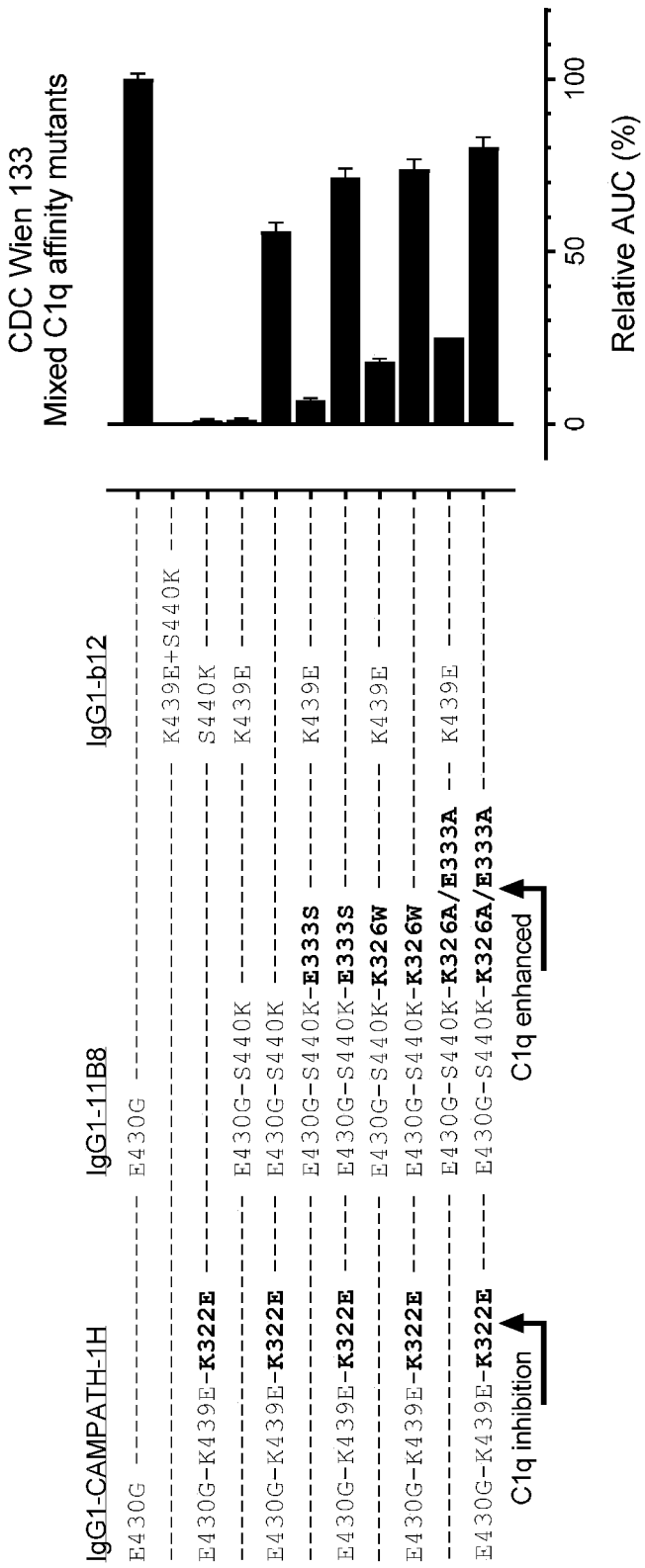
Figure 6E:
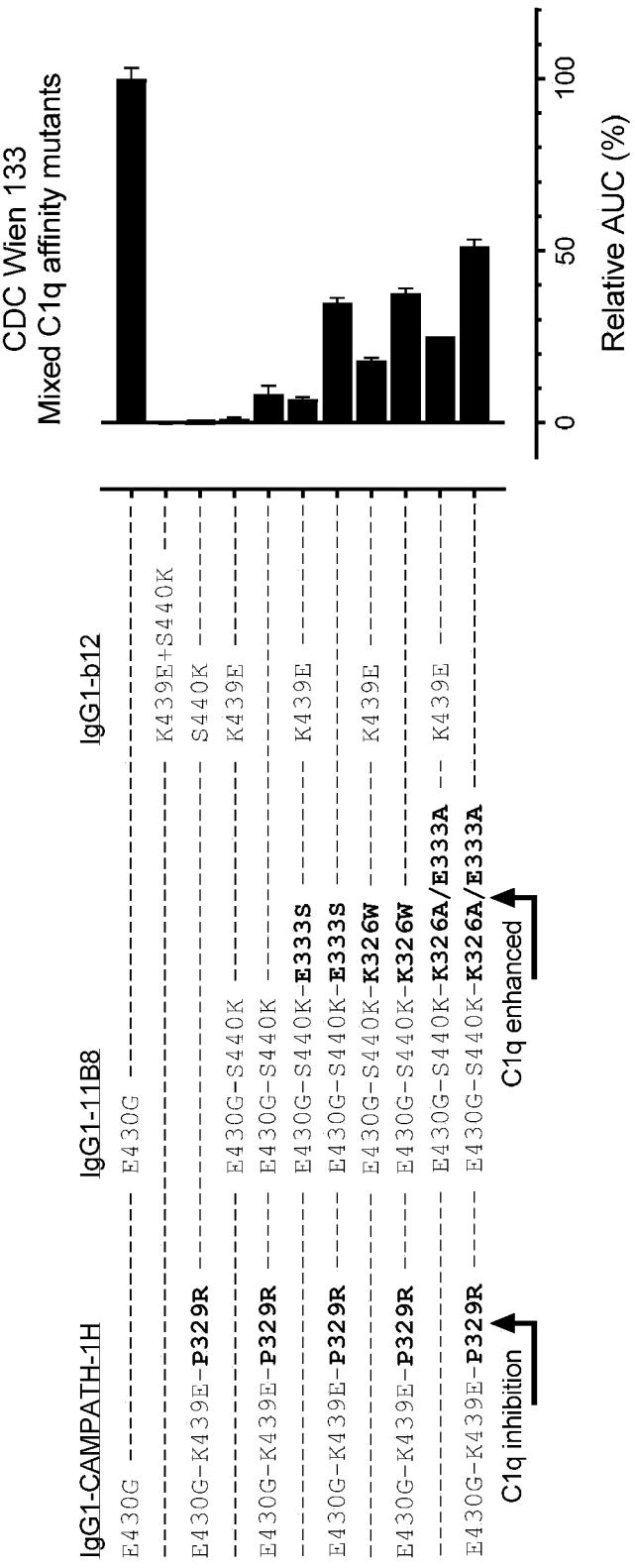

Example 6: Analysis of the Effect of Different C1q Binding Enhancing Mutations in Anti-CD20 Antibody IgG1-11B8-E430G-S440K on the Selective CDC Activity of Antibody Mixtures with Anti-CD52 Antibody IgG1-CAMPATH-1H-E430G-K439E The effects of different C1q binding enhancing mutations were compared in in vitro CDC assays using Wien 133 cells with IgG1-11B8-E430G-S440K variants containing the C1q binding enhancing mutations E333S (SEQ ID NO 103), K326W (SEQ ID NO 112) or K326A/E333A (SEQ ID NO 111; listed here by expected increasing C1q binding affinity) in a mixture with IgG1-CAMPATH-1H-E430G-K439E. The in vitro CDC assay using Wien 133 cells was performed with 20% NHS and serial dilution antibody concentrations (range 0.002-40.0 µg/mL final concentrations in 4-fold dilutions), essentially as described in Example 2. Cell lysis was calculated from the number of PI-positive cells as measured by flow cytometry on an Intellicyt iQue™ screener, averaged from three experimental replicates. Relative areas under the curve (AUC) values represent normalization to minimal lysis (0% with negative control IgG1-b12-K439E+IgG1-b12-S440K) and maximal lysis (100% with the mixture of IgG1-CAMPATH-1H-E430G+IgG1-11B8-E430G). FIG. 5 shows bar diagrams for the AUC values of the dose-response CDC activity curves on Wien 133 cells. Introduction of the C1q binding enhancing mutations E333S, K326W or K326A/E333A resulted in increasing single agent CDC activity by IgG1-11B8-E430G-S440K on Wien 133 (7% for E333S; 18% for K326W; 25% for K326A/E333A compared to 1% without a C1q binding enhancing mutation). In a mixture with IgG1-CAMPATH-1H-E430G-K439E, increasing levels of CDC activity were observed with IgG1-11B8-E430G-S440K variants containing the C1q binding enhancing mutations K326A/E333A, K326W or E333S. These data suggest that there was a direct correlation between the C1q binding affinity of the IgG1-11B8-E430G-S440K variants (K326A/E333A, K326W or E333S) and the CDC activity for the mixtures with IgG1-CAMPATH-1H-E430G-K439E.

Example 7: Analysis of the Effect of Different C1q Binding Inhibition Mutations in Anti-CD52 Antibody IgG1-CAMPATH-1H-E430G-K439E and C1q Binding Enhancing Mutations in Anti-CD20 Antibody IgG1-11B8-E430G-S440K on the Selective CDC Activity of Antibody Mixtures of the Anti-CD52 and Anti-CD20 Antibody Variants The effects of different mutations that affect the C1q binding affinity were compared in in vitro CDC assays using Wien 133 cells with an IgG1-CAMPATH-1H-E430G-K439E variant containing the G236R, K322A, E269K, K322E or P329R C1q binding inhibition mutation (described in Example 5) in mixtures with an IgG1-11B8-E430G-S440K variant containing the C1q binding enhancing mutations E333S, K326W or K326A/E333A (described in Example 6). The in vitro CDC assay using Wien 133 cells was performed with 20% NHS and serial dilution antibody concentrations (range 0.002-40.0 µg/mL final concentrations in 4-fold dilutions), essentially as described in Example 2. Cell lysis was calculated from the number of PI-positive cells as measured by flow cytometry on an Intellicyt iQue™ screener, averaged from three experimental replicates. Relative areas under the curve (AUC) values represent normalization to minimal lysis (0% with negative control IgG1-b12-K439E+IgG1-b12-S440K) and maximal lysis (100% with the mixture of IgG1-CAMPATH-1H-E430G+IgG1-11B8-E430G). FIG. 6 shows bar diagrams for the AUC values of the dose-response CDC activity curves on Wien 133 cells. The mixtures of anti-CD20 IgG1-11B8-E430G-S440K with a C1q binding enhancing mutation in a mixture with anti-CD52 IgG1-CAMPATH-1H-E430G-K439E antibody variants with a C1q binding inhibition mutation G236R or K322A showed improved recovery of CDC activity on Wien 133 cells compared to the mixtures with IgG1-11B8-E430G-S440K without a C1q binding enhancing mutation. There was a correlation between the expected strength of C1q binding affinity in the IgG1-11B8-E430G-S440K variant (K326A/E333A>K326W>E333S) and the level of CDC activity recovery when mixed with a IgG1-CAMPATH-1H-E430G-K439E variant containing a C1q binding inhibition mutation, with slightly enhanced maximal lysis recovery for G236R (FIG. 6A; Table 3), maximal lysis recovery with increased EC50 values for K322A (FIG. 6B; Table 3), E269K (FIG. 6C; Table 3), K322E (FIG. 6D; Table 3) or maximal lysis remained reduced with increased EC50 values for P329R (FIG. 6E; Table 3).

TABLE 3

| IgG1-CAMPATH-1H | IgG1-11B8 | IgG1-b12 | Mean | Stand. dev. | n= |
|---|---|---|---|---|---|
| E430G | E430G | | 96.7 | 0.14 | 2 |
| | | K439E + S440K | 4.81 | 0.56 | 3 |
| | E430G-S440K | K439E | 6.01 | 1.13 | 3 |
| | E430G-S440K-K326W | K439E | 44.1 | 2.42 | 3 |
| | E430G-S440K-E333S | K439E | 23.3 | 2.50 | 3 |
| | E430G-S440K-K326A-E333A | K439E | 59.5 | 1.50 | 3 |
| E430G-K439E-K322E | S440K | | 7.03 | 0.71 | 3 |
| E430G-K439E-K322E | E430G-S440K | | 89.3 | 1.22 | 3 |
| E430G-K439E-K322E | E430G-S440K-K326W | | 95.9 | 0.81 | 3 |
| E430G-K439E-K322E | E430G-S440K-E333S | | 95.4 | 0.92 | 3 |
| E430G-K439E-K322E | E430G-S440K-K326A-E333A | | 96.6 | 1.05 | 3 |
| E430G | E430G | | 95.9 | 0.92 | 2 |
| E430G-K439E-P329R | | S440K | 5.47 | 1.83 | 3 |
| E430G-K439E-P329R | E430G-S440K | | 27.5 | 13.6 | 3 |

TABLE 3-continued

| IgG1-CAMPATH-1H----IgG1-11B8----------------IgG1-b12----- | Mean | Stand. dev. | n= |
|---|---|---|---|
| E430G-K439E-P329R--E430G-S440K-K326W--------------------- | 77.2 | 5.80 | 3 |
| E430G-K439E-P329R--E430G-S440K-E333S--------------------- | 75.0 | 5.61 | 3 |
| E430G-K439E-P329R--E430G-S440K-K326A-E333A--------------- | 86.6 | 2.87 | 3 |
| E430G-K439E-K322A--------------------------S440K-------- | 5.95 | 1.38 | 3 |
| E430G-K439E-K322A--E430G-S440K--------------------------- | 90.4 | 1.07 | 3 |
| E430G-K439E-K322A--E430G-S440K-K326W--------------------- | 95.5 | 1.32 | 3 |
| E430G-K439E-K322A--E430G-S440K-E333S--------------------- | 95.8 | 1.16 | 3 |
| E430G-K439E-K322A--E430G-S440K-K326A-E333A--------------- | 96.4 | 1.46 | 3 |
| E430G--------------E430G--------------------------------- | 95.1 | 0.28 | 2 |
| E430G-K439E-G236R--------------------------S440K-------- | 5.52 | 1.42 | 3 |
| E430G-K439E-G236R--E430G-S440K--------------------------- | 91.4 | 1.93 | 3 |
| E430G-K439E-G236R--E430G-S440K-K326W--------------------- | 95.6 | 1.12 | 3 |
| E430G-K439E-G236R--E430G-S440K-E333S--------------------- | 95.3 | 1.00 | 3 |
| E430G-K439E-G236R--E430G-S440K-K326A-E333A--------------- | 96.4 | 0.95 | 3 |
| E430G-K439E-E269K--------------------------S440K-------- | 4.93 | 1.44 | 3 |
| E430G-K439E-E269K--E430G-S440K--------------------------- | 89.3 | 1.00 | 3 |
| E430G-K439E-E269K--E430G-S440K-K326W--------------------- | 95.6 | 1.45 | 3 |
| E430G-K439E-E269K--E430G-S440K-E333S--------------------- | 95.0 | 1.19 | 3 |
| E430G-K439E-E269K--E430G-S440K-K326A-E333A--------------- | 95.7 | 1.35 | 3 |
| E430G--------------E430G--------------------------------- | 96.2 | 0.92 | 2 |
| E430G---------------------------------------------------- | 90.9 | 0.42 | 3 |
| E430G-K439E---------------------------------------------- | 75.1 | 1.98 | 2 |
| E430G-K439E--------------------------------------S440K-------- | 69.9 | 1.06 | 2 |
| E430G-K439E--------E430G-S440K--------------------------- | 93.7 | 1.06 | 2 |
| E430G-K439E--------E430G-S440K-K326W--------------------- | 96.4 | 0.78 | 2 |
| E430G-K439E--------E430G-S440K-E333S--------------------- | 96.3 | 0.92 | 2 |
| E430G-K439E--------E430G-S440K-K326A-E333A--------------- | 96.3 | 0.85 | 2 |
| -----------------E430G---------------------------------- | 76.8 | 2.95 | 3 |

Example 8: Target Binding of Anti-CD52 IgG1-CAMPATH-1H Antibody Variants and Anti-CD20 IgG1-11B8 Antibody Variants on Cells Binding to Wien 133 and Raji lymphoma cells was analyzed by flow cytometry for anti-CD52 IgG1-CAMPATH-1H with E430G, K439E and C1q binding inhibiting mutations G236R or K322A and anti-CD20 IgG1-11B8 with E430G, S440K and C1q binding-enhancing mutation E333S. Cell suspensions were washed with FACS buffer and resuspended in FACS buffer [PBS+0.1% (w/v) bovine serum albumin (BSA)+0.02% (w/v) sodium azide] at a concentration of $2.5 \times 10^6$ cells/mL. 40 µL cell suspension samples (100,000 cells per well) were seeded in polystyrene 96-well round-bottom plates (Greiner Bio-One; Cat nr 650101) and incubated with 40 µL antibody samples (final concentrations 0.001-30 µg/mL in 3-fold dilutions) for 30 minutes at 4° C. Cells were pelleted by centrifugation at 300×g for 3 minutes at 4° C. and washed twice with 150 µL FACS buffer. Cells were incubated with 50 µL secondary antibody R-phycoerythrin (R-PE)-conjugated goat-anti-human IgG F(ab')2 (Jackson ImmunoResearch, Cat No. 109-116-098, 1:100) for 30 minutes at 4° C., protected from light. Cells were washed twice with 150 µL FACS buffer, resuspended in 150 µL FACS buffer, and antibody binding was analyzed by flow cytometry on an Intellicyt iQue screener. Binding curves were analyzed using non-linear regression analysis (sigmoidal dose-response with variable slope) using GraphPad Prism software.

Figure 7A:
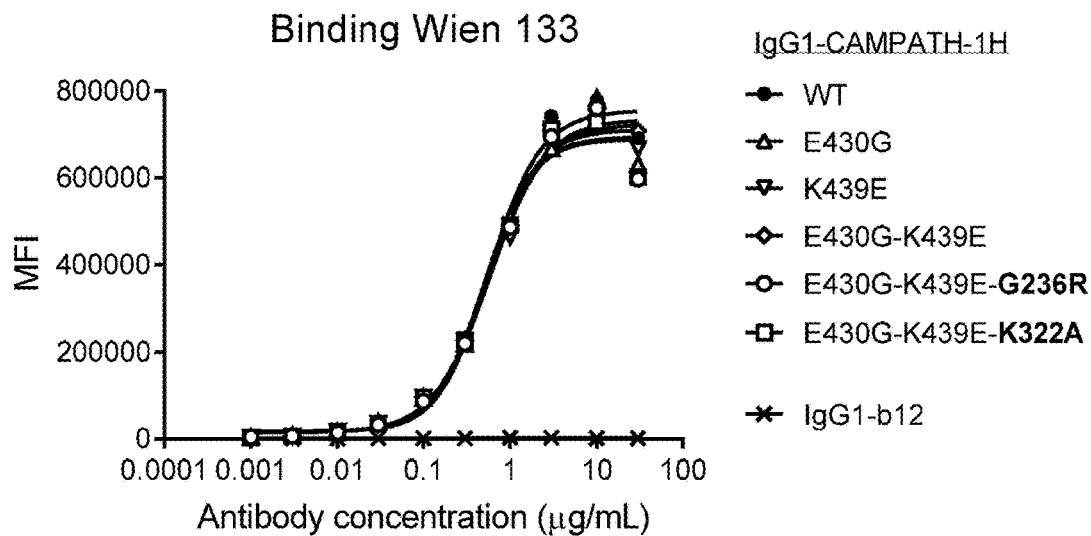
FIGS. 7A-7D show binding of antibody variants of anti-CD52 IgG1-CAMPATH-1H-E430G-K439E with the C1q binding inhibition mutation G236R or K322A (FIG. 7A, FIG. 7B) and antibody variants of anti-CD20 IgG1-11B8-E430G-S440K with the C1q binding enhancing mutation E333S (FIG. 7C, FIG. 7D) to human lymphoma cell lines Wien 133 (FIG. 7A, FIG. 7C) and Raji (FIG. 7B, FIG. 7D). Antibody binding was tested by flow cytometry. Binding is expressed as geometric mean of fluorescence intensity (MFI). As a negative control for binding, a sample without primary antibody or non-binding anti-gp120 antibody IgG1-b12 was used.
Figure 7B:
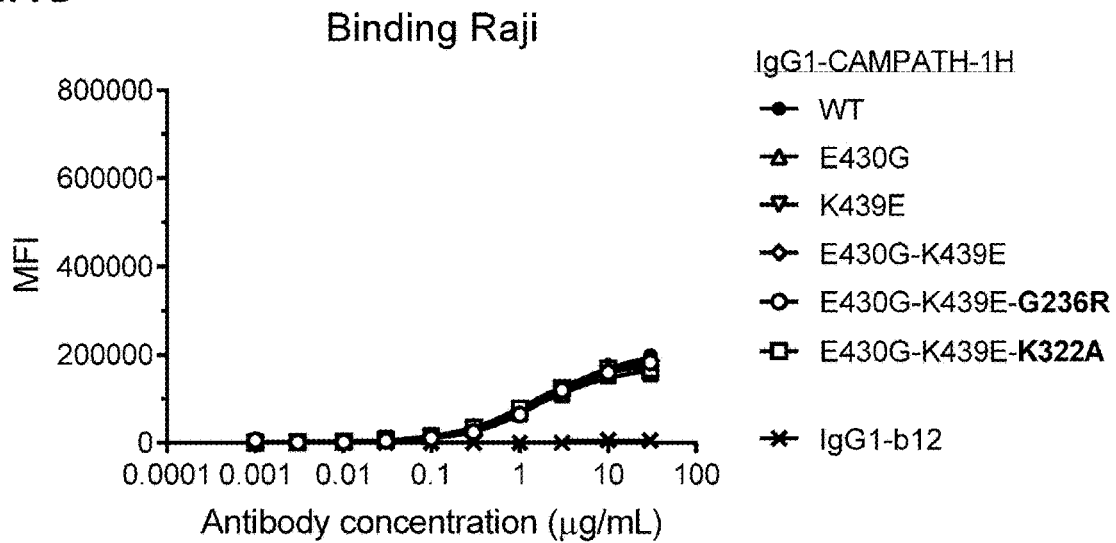
Figure 7C:
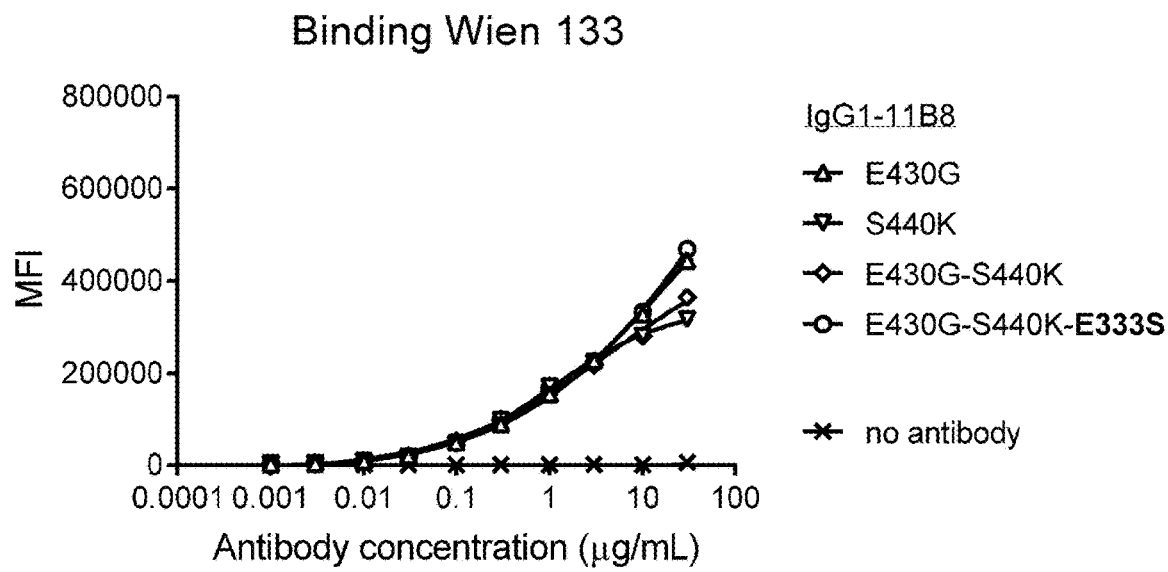

FIG. 7 shows that for IgG1-CAMPATH-1H, all tested antibody variants showed similar dose-dependent binding to both Wien 133 (FIG. 7A) and Raji cells (FIG. 7B). These data indicate that introduction of the single mutations E430G and K439E, and the double mutation E430G-K439E had no effect on target binding on the cell surface. Also introduction of an additional mutation G236R or K322A had no effect on CD52 target binding on the cell surface.

Figure 7D:
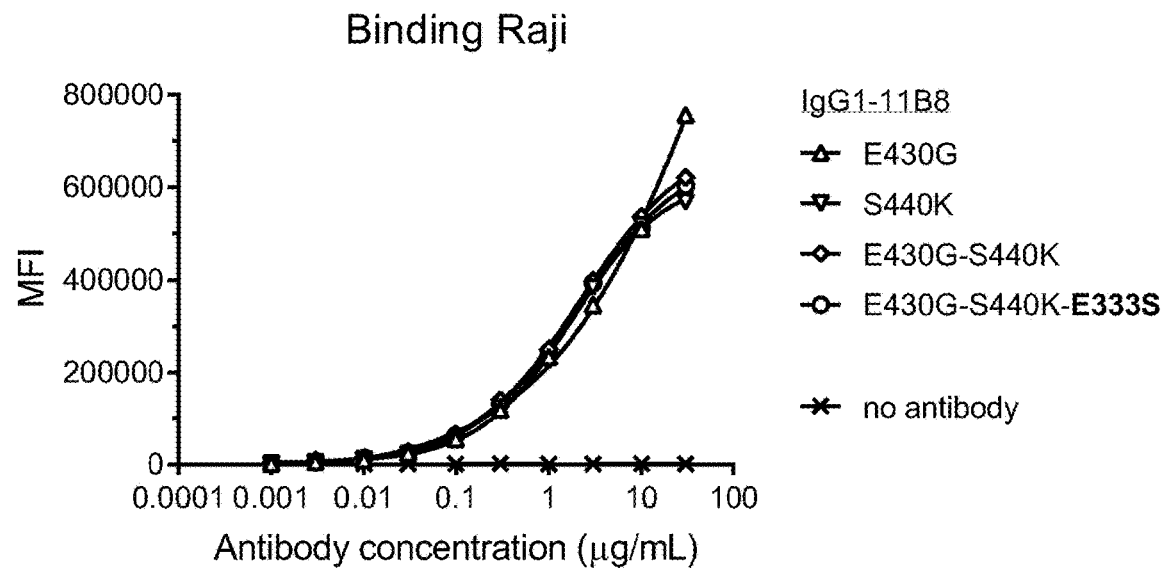

FIG. 7 shows that for IgG1-11B8, all tested antibody variants showed similar dose-dependent binding to both Wien 133 (FIG. 7C) and Raji cells (FIG. 7D). These data indicate that introduction of the single mutations E430G and S440K, and the double mutation E430G-S440K had no effect on target binding on the cell surface. Also introduction of an additional mutation E333S had no effect on CD20 target binding on the cell surface.

Example 9: Analysis of the Effect of C1q Binding Inhibition Mutations in Anti-CD52 Antibody IgG1-CAMPATH-1H-E430G-K439E and a C1q Binding Enhancing Mutation in Anti-CD20 Antibody IgG1-11B8-E430G-S440K on the FcγR-Mediated Effector Functions Using Mixtures of the Anti-CD52 and Anti-CD20 Antibody Variants The effects of the introduction of C1q binding inhibiting mutations G236R or K322A in IgG1-CAMPATH-1H-E430G-K439E variants and of the C1q binding enhancing mutation E333S in IgG1-11B-E430G-S440K on antibody-dependent cellular cytotoxicity (ADCC) were tested in an ADCC reporter bioassay on Raji cells and in an in vitro Europium TDA (EuTDA) ADCC assay with human peripheral blood mononuclear cells (PBMC) on Wien 133 cells.

For the ADCC reporter bioassay, variants of IgG1-CAMPATH-1H (WT, E430G, K439E (SEQ ID NO 29), E430G-K439E, E430G-K439E-G236R and E430G-K439E-K322A) and IgG1-11B8 (WT, E430G. S440K (SEQ ID NO 30), E430G-S440K, E430G-S440K-E333S) were tested using the Bio-Glo Luciferase Assay System (Promega, Cat No. G7940) on Raji cells. As effector cells, the kit contains Jurkat human T cells that are engineered to stably express high affinity FcγRIIIa (V158) and a nuclear factor of activated T cells (NFAT)-response element driving expression of firefly luciferase. Briefly, Raji cells (5.000 cells/well) were seeded in 384-Wells white OptiPlates (Perkin Elmer Cat No. 6007290) in ADCC Assay Buffer [RPMI-1640 medium (Lonza, Cat No. BE12-115F) supplemented with 4% Low IgG Serum (Promega, Cat No. G711A)] and incubated for 6 hours at 37° C./5% CO2 in a total volume of 30 µL containing antibody concentration series (0.4-10,000 ng/mL final concentrations in 3.5-fold dilutions) and thawed ADCC Bioassay Effector Cells (Promega, Cat No. G701A). After incubating the plates for 15 minutes at room temperature (RT), 30 µL Bio Glo Assay Luciferase Reagent [Bio-Glo Luciferase Assay Substrate (Promega Cat No. G720A) in Bio-Glo Luciferase Assay Buffer (Promega, Cat No. G719A)] was added and incubated for 5 minutes at RT. Luciferase production was quantified by luminescence readout on an EnVision Multilabel Reader (Perkin Elmer).

Figure 8A:
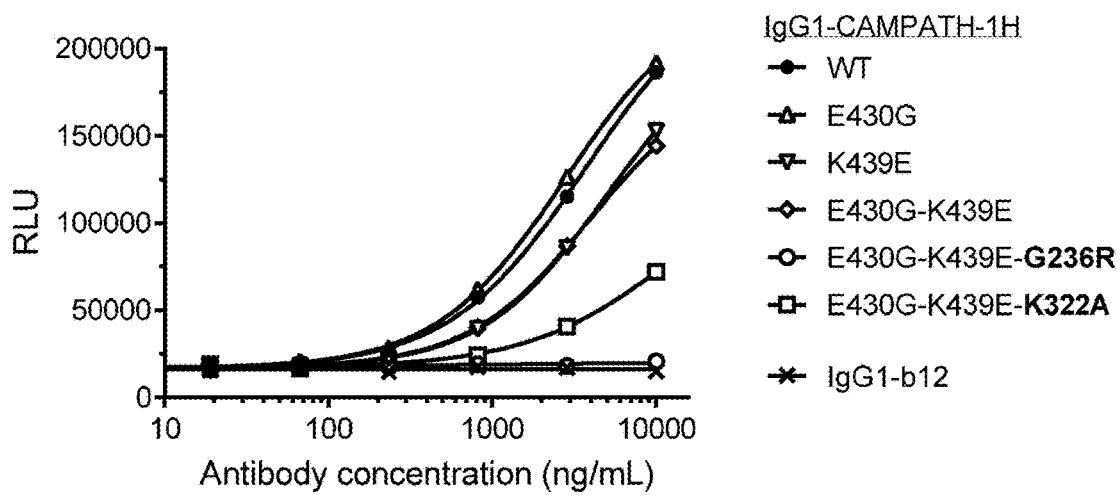
FIGS. 8A-8D show the ADCC capacity of antibody variants of anti-CD52 IgG1-CAMPATH-1H-E430G-K439E with the C1q binding inhibition mutation G236R or K322A (FIG. 8A, FIG. 8C) and antibody variants of anti-CD20 IgG1-11B8-E430G-S440K with the C1q binding enhancing mutation E333S (FIG. 8B, FIG. 8D).
Figure 8B:
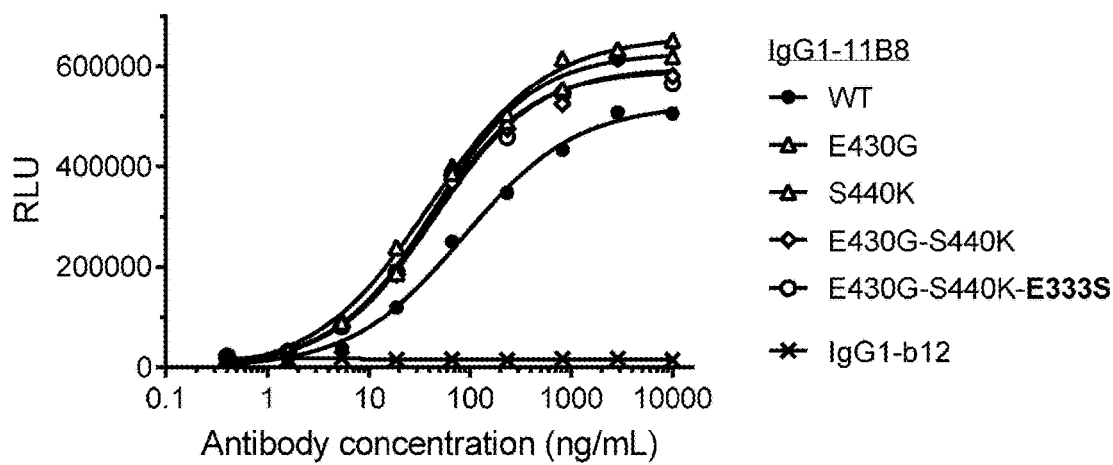

Introduction of the C1q binding inhibiting mutation G236R in IgG1-CAMPATH-E430G-K439E resulted in complete inhibition of FcγRIIIa activation in the effector cells after binding of the single anti-CD52 antibody on Raji cells, whereas C1q binding inhibiting mutation K322A resulted in partial inhibition of FcγRIIIa activation in the ADCC reporter bioassay (FIG. 8A). All tested IgG1-11B8 antibody variants showed considerable FcγRIIIa activation in the effector cells after binding of the single anti-CD20 antibodies on Raji cells, with no significant differences between the IgG1-11B8 variants containing the S440K and/or E430G and/or E333S mutations (FIG. 8B).

The in vitro EuTDA ADCC assay (DELFIA EuTDA Cytotoxicity Assay, Perkin Elmer, Cat No. AD0116) was performed on Wien 133 cells with freshly isolated PBMCs from three different healthy donors as effector cells to test the ADCC activity of IgG1-CAMPATH-1H antibody variants (WT, K439E, E430G-K439E, G236R-E430G-K439E, and K322A-E430G-K439E) and IgG1-11B8 antibody variants (WT, S440K, E430G-S440K, and E333S-E430G-S440K) as single agents or in combinations (IgG1-CAMPATH-1H-G236R-E430G-K439E or -K322A-E430G-K439E with IgG1-11B8-E333S-E430G-S440K). PBMC were isolated from buffy coats (Sanquin, Amsterdam, The Netherlands) using Lymphocyte Separation Medium (Lonza, Cat No. 17-829E) for standard Ficoll density centrifugation, according to the manufacturer's instructions. After resuspension of cells in RPMI-1640 medium (Lonza, Cat No. BE12-115F) supplemented with 10% Donor Bovine Serum with Iron (DBSI, ThermoFischer, Cat No. 10371029) and Penicillin/Streptomycin (Pen/Strep, Lonza, Cat No. DE17-603E), cells were counted by trypan blue (Sigma Aldrich, Cat No. T8154) exclusion and concentrated to $2 \times 10^7$ cells/mL.

Wien 133 cells were harvested, washed (twice in PBS, 1,200 rpm, 5 min), collected in RPMI-1640 medium supplemented with 10% DBSI and Pen/Strep at a concentration of $1 \times 10^6$ cells/mL, to which 15 µL DELFIA BATDA Reagent (Perkin Elmer, Cat No. C136-100, 5 µL/$3 \times 10^6$ cells) was added. The mixture was incubated in a water bath for 20 minutes at 37° C. After washing of the cells (five times in 50 mL PBS, 1,200 rpm, 5 min), the cells were resuspended in RPMI-1640 medium supplemented with 10% DBSI and Pen/Strep, counted by trypan blue exclusion, and diluted to a concentration of $2 \times 10^5$ cells/mL.

For the ADCC experiment, 50 µL of BATDA-labelled Wien 133 cells (10,000 cells/well) were pre-incubated with a concentration series (0.01-10,000 ng/mL final concentrations in 10-fold dilutions) of IgG1-CAMPATH-1H and/or IgG1-11B8 antibody variants in a total volume of 150 µL RPMI-1640 medium supplemented with 10% DBSI and Pen/Strep in 96-well V-bottom microtiter plates (Greiner Bio-One; Cat No. 651101). After 15 min at RT, 50 µL PBMC ($1 \times 10^6$ cells) were added, resulting in an effector to target ratio (E:T) of 100:1, and incubated for 2 hours at 37° C./5% C02. To determine the maximum amount of cell lysis, 50 µL of BATDA-labelled Wien 133 cells (10,000 cells/well) were incubated with 150 µL RPMI-1640 medium supplemented with 10% DBSI, Pen/Strep, and DELFIA Lysis Buffer (0.03% Digitonin and 19% DMSO, Perkin Elmer, Cat No. AD0116-A) according to the manufacturers' recommendations. To determine the amount of spontaneous lysis, 50 µL of BATDA-labelled Wien 133 cells (10,000 cells/well) were incubated in 150 µL medium without any antibody or effector cells.

To measure the amount of released BATDA Reagent, plates were centrifuged (500×g, 10 min), 20 µL of supernatant was transferred to a DELFIA Microtitration plate, and 200 µL of DELFIA Europium Solution (Perkin Elmer, Cat No. AD0116-B) was added. Subsequently, plates were incubated at RT for 15 minutes while shaking. Europium-BATDA (EuTDA) was measured on a time-resolved fluorometer (Perkin Elmer EnVision 2104 Multi Detection Microplate Reader) and used to calculate the percentage of antibody-mediated lysis as follows: (release sample−spontaneous release)/(maximal release−spontaneous release)×100%.

Figure 8C:
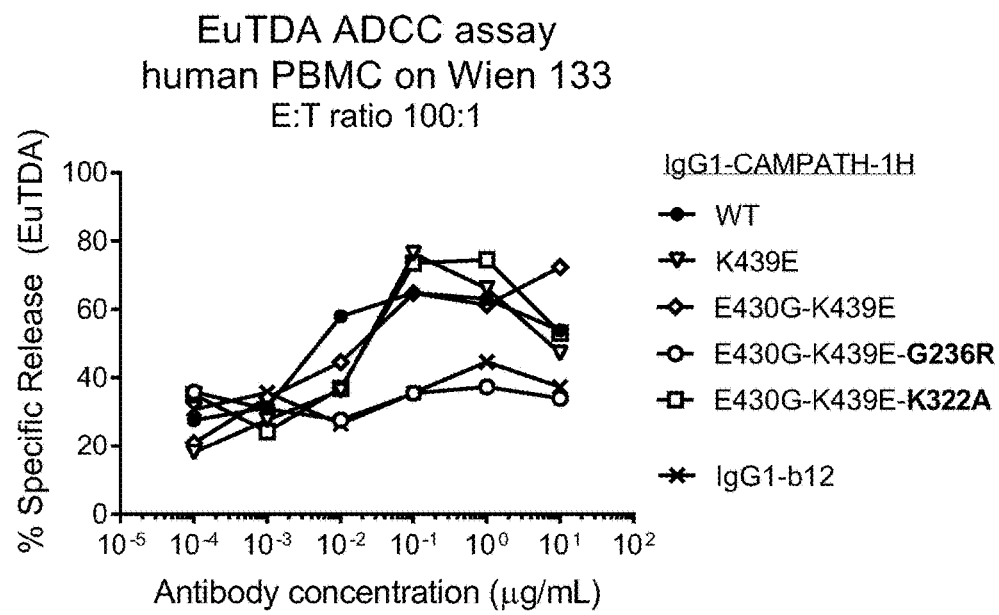
Figure 8D:
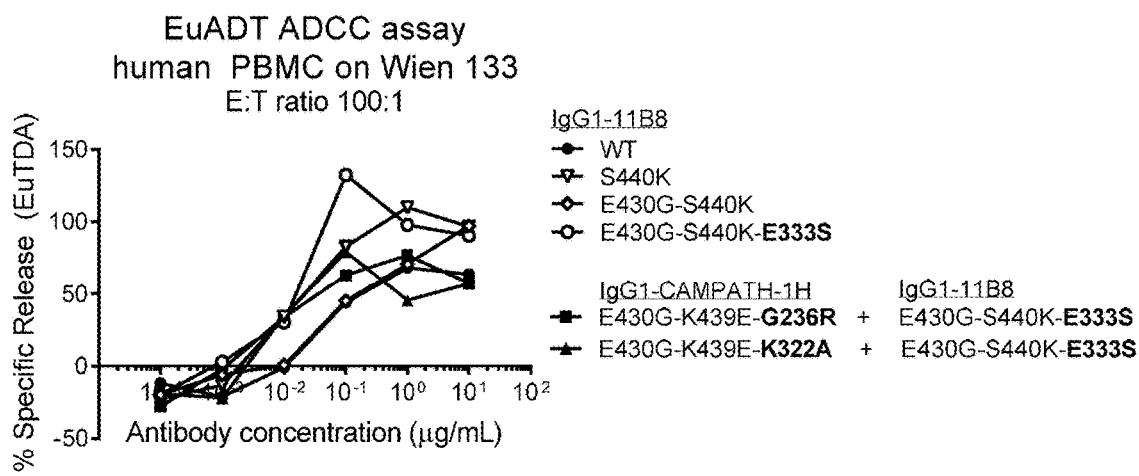

Introduction of the E430G and/or the K439E mutation in WT IgG1-CAMPATH-1H had no effect on the dose-responsive ADCC-mediated killing of Wien 133 cells when tested as single agents (FIG. 8C). Introduction of the C1q binding inhibiting mutation G236R in IgG1-CAMPATH-E430G-K439E resulted in complete inhibition of ADCC activity of the single agent, whereas C1q binding inhibiting mutation K322A had no effect on the ADCC activity of single agent IgG1-CAMPATH-E430G-K439E on Wien 133 cells (FIG. 8C). All tested IgG1-11B8 antibody variants showed considerable ADCC efficacy on Wien 133 cells when tested as single agents, with no significant differences between the IgG1-11B8 variants containing the S440K and/or E430G and/or E333S mutations (FIG. 8D). Mixtures of IgG1-11B8-E333S-E430G-S440K with IgG1-CAMPATH-1H-G236R-E430G-K439E or IgG1-CAMPATH-1H-K322A-E430G-K439E both showed considerable ADCC efficacy on Wien 133 cells (FIG. 8D).

In conclusion, mutation G236R strongly inhibited ADCC activity of IgG-CAMPATH-E430G-K439E in both the luminescence ADCC reporter bioassay and the in vitro EuTDA ADCC assay. IgG-CAMPATH-E430G-K439E with the K322A mutation showed reduced activity in the luminescence ADCC reporter bioassay, but showed retained substantial ADCC activity in the in vitro EuTDA ADCC assay.

Example 10: Analysis of Different Fc-Fc Interaction Enhancing Mutations for Selective CDC Activity of Mixtures of IgG1-CAMPATH-K439E Variants with a C1q Binding Inhibition Mutation and IgG1-11B8-S440K Variants with or without a C1q Binding Enhancing Mutation on Wien 133 Cells It was described in Example 5 that introduction of a C1q binding inhibition mutation (G236R, K322A, E269K, K322E or P329R) in IgG1-CAMPATH-1H-E430G-K439E resulted in complete inhibition of single agent CDC activity on Wien 133, and recovery of CDC activity when in a mixture with IgG1-11B8-E430G-S440K. It was described in Example 6 that an IgG1-11B8-E430G-S440K containing a C1q binding enhancing mutation, such as E333S, showed very limited CDC activity when tested as a single agent in an in vitro CDC assay using Wien 133 cells, but showed recovery of CDC activity in a mixture with IgG1-CAMPATH-1H-E430G-K439E. It was described in Example 7 that the combinations of anti-CD52 antibody IgG1-CAMPATH-1H-E430G-K439E containing the C1q binding inhibition mutation G236R or K322A with anti-CD20 antibody IgG1-11B8-E430G-S440K containing the C1q binding enhancing mutation E333S showed selective CDC activity on Wien 133 cells, while no CDC activity was observed for the single agents. Here, this principle of selective induction of CDC activity by the mixture of an IgG1-CAMPATH-1H variant with an Fc-Fc-enhancing mutation (such as E430G), the K439E mutation and a C1q binding enhancing mutation (such as G236R or K322A) with an IgG1-11B8 antibody variant with an Fc-Fc-enhancing mutation (such as E430G), the S440K mutation and optionally a C1q binding enhancing mutation (such as E333S) was analyzed for other Fc-Fc enhancing mutations such as E345K, E345R and E345R-E430G in an in vitro CDC assay on Wien 133 cells. The in vitro CDC assay using Wien 133 cells was performed with 20% NHS and antibody concentration series (final concentration range 0.003-10.0 µg/mL in 3-fold dilutions), essentially as described in Example 2. Cell lysis and relative area under the curve (AUC) values were calculated from the number of PI-positive cells as described in Example 2, from two experimental replicates. AUC was normalized to the values for negative control antibody IgG1-b12 (0%) and for positive control IgG1-CAMPATH-1H-E430G+IgG1-11B8-E430G (100%), while maximal lysis data presented reflects un-normalized cell lysis at 10 µg/mL IgG.

Figure 9A:
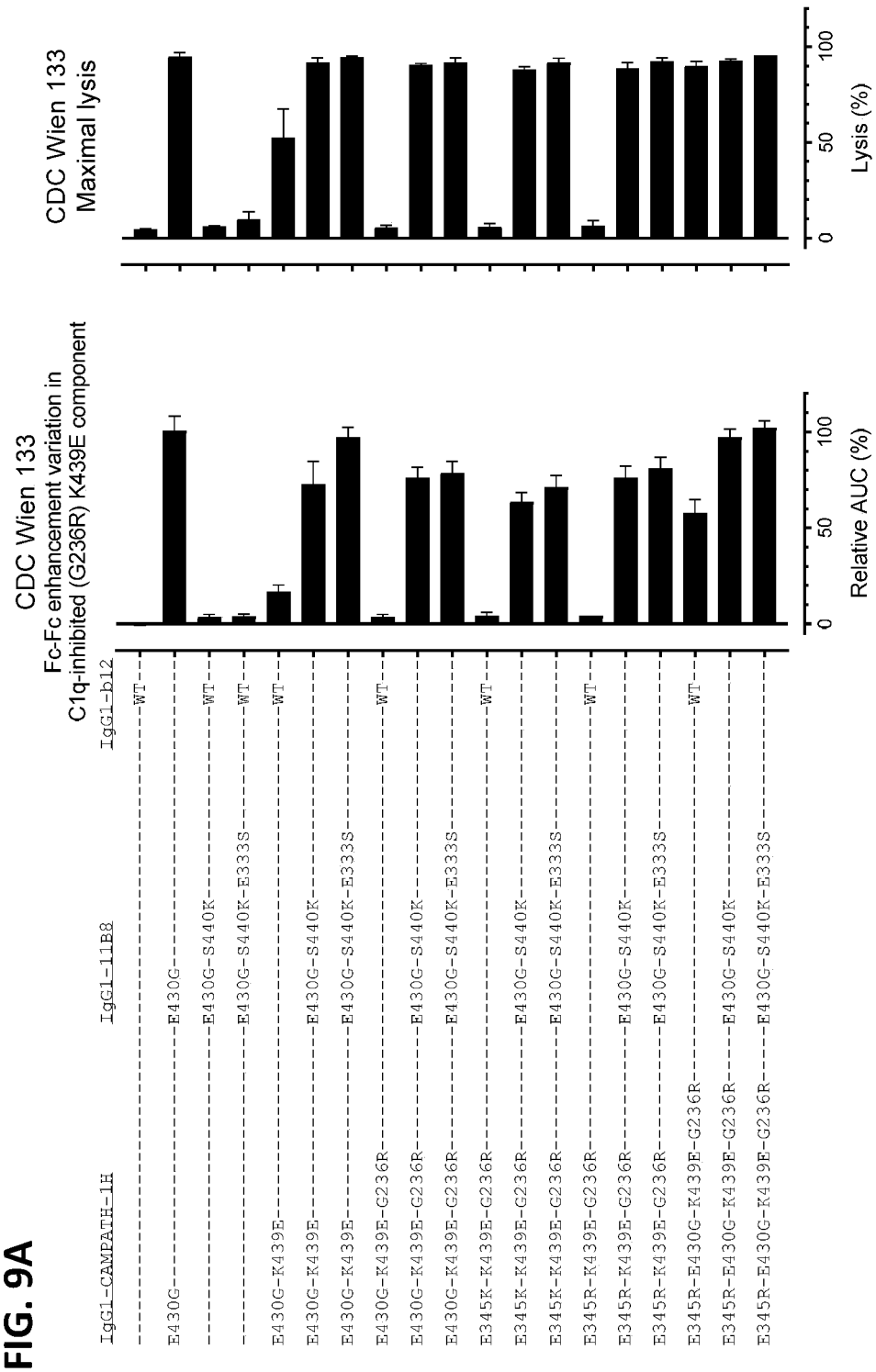
FIGS. 9A-9C show selectivity of CDC activity by mixed antibody variants of Fc-Fc interaction enhanced anti-CD52 IgG1-CAMPATH-1H-K439E with C1q binding inhibition mutation G236R or K322A+variants of Fc-Fc interaction enhanced anti-CD20 IgG1-11B8-S440K with or without C1q binding enhancing mutation E333S. The tested Fc-Fc interaction enhancing mutations were E430G, E345K, E345R and E345R-E430G. Wien 133 cells were incubated with antibody concentration series in the presence of 20% NHS. CDC efficacy is presented as the normalized AUC of the percentage PI-positive cells and maximal lysis. Normalization was performed to non-binding control antibody IgG1-b12 (0%) and the mixture of IgG1-CAMPATH-1H-E430G+IgG1-11B8-E430G (100%).
Figure 9B:
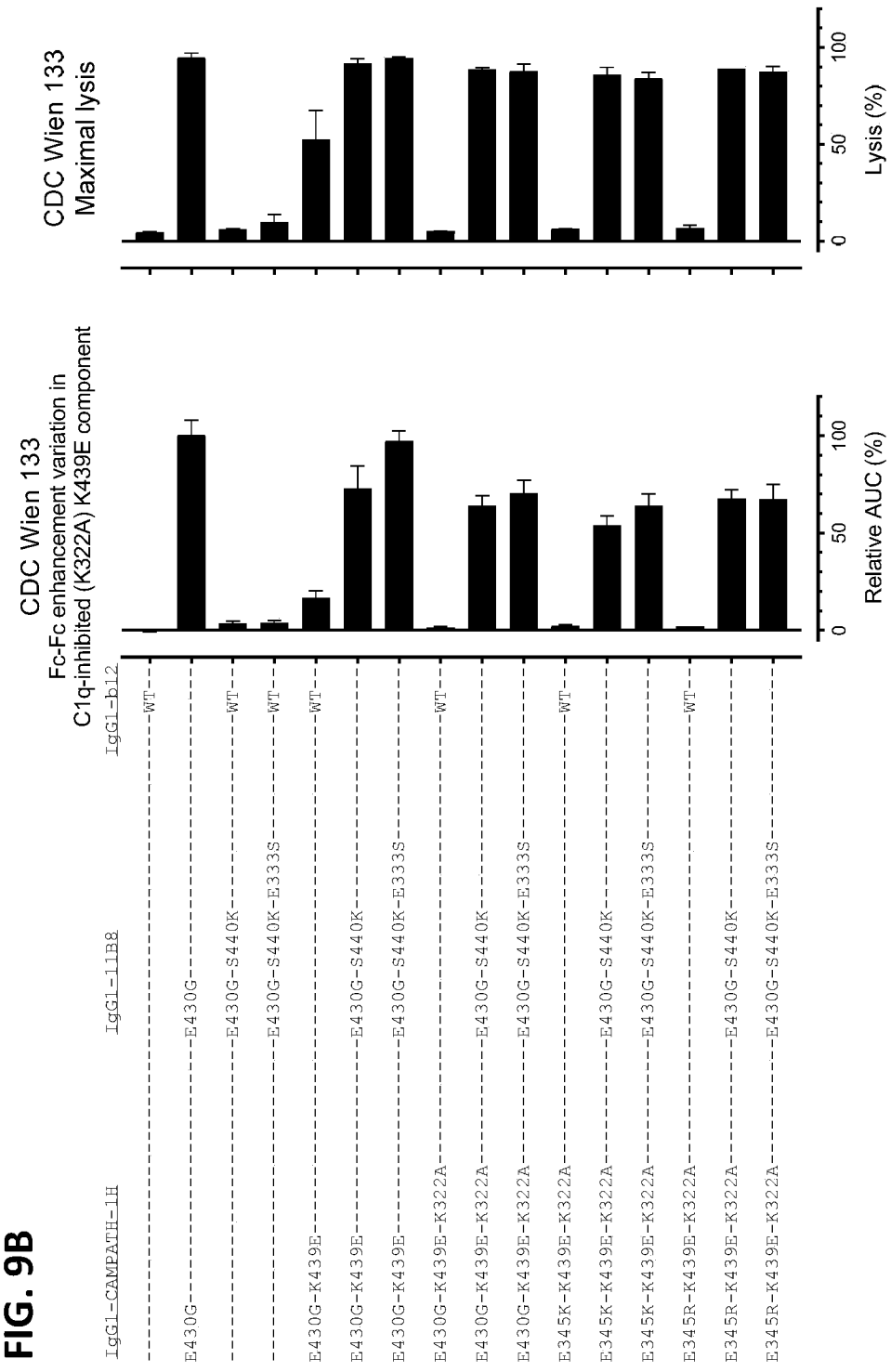
Figure 9C:
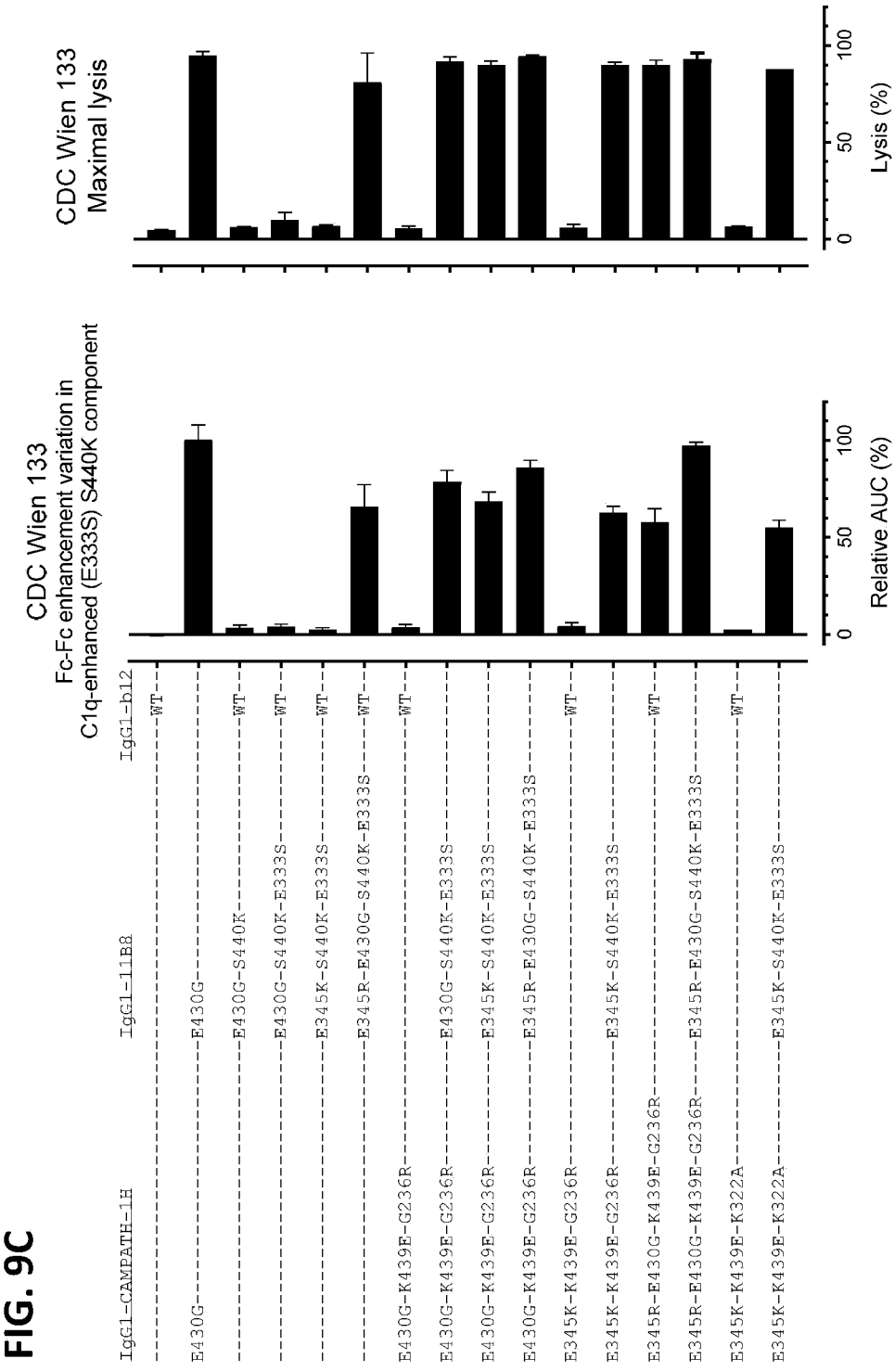

FIG. 9 shows bar diagrams for the AUC values of the dose-response CDC activity curves and the maximal lysis on Wien 133 cells. Introduction of the C1q binding inhibition mutation G236R (FIG. 9A) or K322A (FIG. 9B) in IgG1-CAMPATH-1H-K439E with either one of the Fc-Fc interaction enhancing mutations E430G, E345K (SEQ ID NO: 66 or 67, respectively) or E345R (SEQ ID NO: 74 or 73, respectively) resulted in loss of CDC activity when tested as a single targeting agent on Wien 133 cells. In contrast, the IgG1-CAMPATH-1H-K439E variant with the two Fc-Fc interactions enhancing mutations E345R-E430G and the C1q binding inhibition mutation G236R (SEQ ID NO: 71) showed residual single agent CDC activity on Wien 133 cells (FIG. 9A). The mixtures of IgG1-CAMPATH-1H-K439E-G236R (FIG. 9A) or IgG1-CAMPATH-1H-K439E-K322A (FIG. 9B) containing either the E430G, E345K or E345R Fc-Fc interaction enhancing mutation with IgG1-11B8-E430G-S440K or IgG1-11B8-E430G-S440K-E333S showed recovery of CDC activity on Wien 133 cells, whereas all these variants did not induce any CDC as single agents. IgG1-11B8-S440K-E333S antibody variants containing either the E430G or E345K (SEQ ID NO: 68) Fc-Fc interaction enhancing mutation did not induce significant CDC activity when tested as single agents in an in vitro CDC assay using Wien 133 cells, whereas single agent activity was observed with IgG1-11B8-E345R-E430G-S440K-E333S (SEQ ID NO: 72) containing two Fc-Fc interactions enhancing mutations E345R-E430G (FIG. 9C). The mixtures of IgG1-11B8-S440K-E333S containing either the E345K or E430G Fc-Fc interaction enhancing mutation with IgG1-CAMPATH-1H-E430G-K439E-G236R showed recovery of CDC activity on Wien 133 cells, whereas all these variants did not induce any CDC as single agents (FIG. 9C). Similarly, the mixtures of IgG1-11B8-E345K-S440K-E333S with IgG1-CAMPATH-1H-E345K-K439E-G236R or IgG1-CAMPATH-1H-E345K-K439E-K322A, all containing the E345K Fc-Fc interaction enhancing mutation, showed recovery of CDC activity on Wien 133 cells, whereas the single agents did not induce CDC (FIG. 9C).

Together, these data indicate that selective CDC activity on CD52-positive/CD20-positive Wien 133 cells can be achieved by compositions of an IgG1-CAMPATH-1H-K439E variant containing one of the Fc-Fc interaction enhancing mutations such as E430G, E345K or E345R, and a G236R or K322A C1q binding inhibition mutation, mixed with an IgG1-11B8-S440K variant containing one of the Fc-Fc interaction enhancing mutations with or without a C1q binding enhancing mutation such as E333S. In conclusion, the CDC activity of individual antibodies with different Fc-Fc interaction enhancing mutations can be controlled by introduction of a self-oligomerization inhibiting mutation combined with modulation of the C1q binding strength. Complement activity is restored after mixing two such antibodies with complementary self-oligomerization-inhibiting mutations, which allows for selective hetero-oligomerization on cells bound by both antibodies simultaneously.

Example 11: Analysis of Different C1q Binding Modulating Mutations for Selective CDC Activity of Mixtures of Anti-CD52 IgG1-CAMPATH-E430G-K439E and Anti-CD20 IgG1-11B8-E430G-S440K Antibody Variants on Wien 133 Cells It was described in Example 7 that the combinations of anti-CD52 antibody IgG1-CAMPATH-1H-E430G-K439E containing a C1q binding inhibition mutation such as G236R or K322A with anti-CD20 antibody IgG1-11B8-E430G-S440K containing C1q binding enhancing mutations such as E333S, K326W or K326A-E333A showed selective CDC activity on Wien 133 cells, while little to no CDC activity was observed for the single agents. Here, alternative C1q binding modulating mutations were tested in different combinations of IgG1-CAMPATH-1H-E430G-K439E and IgG1-11B8-E430G-S440K antibody variants, with the aim to suppress CDC activity of the single agents, and enable maximal recovery of selective CDC activity by mixtures of anti-CD52 and anti-CD20 antibody variants. The in vitro CDC assay using Wien 133 cells was performed with 20% NHS and antibody concentration series (final concentration range 0.003-10.0 µg/mL in 3-fold dilutions), essentially as described in Example 2. Cell lysis and relative AUC values were calculated from the number of PI-positive cells as described in Example 2, from two experimental replicates. AUC was normalized to the values for negative control antibody IgG1-b12 (0%) and for positive control IgG1-CAMPATH-1H-E430G+IgG1-11B8-E430G (100%), while maximal lysis data presented reflects un-normalized cell lysis at 10 µg/mL IgG.

Figure 10A:
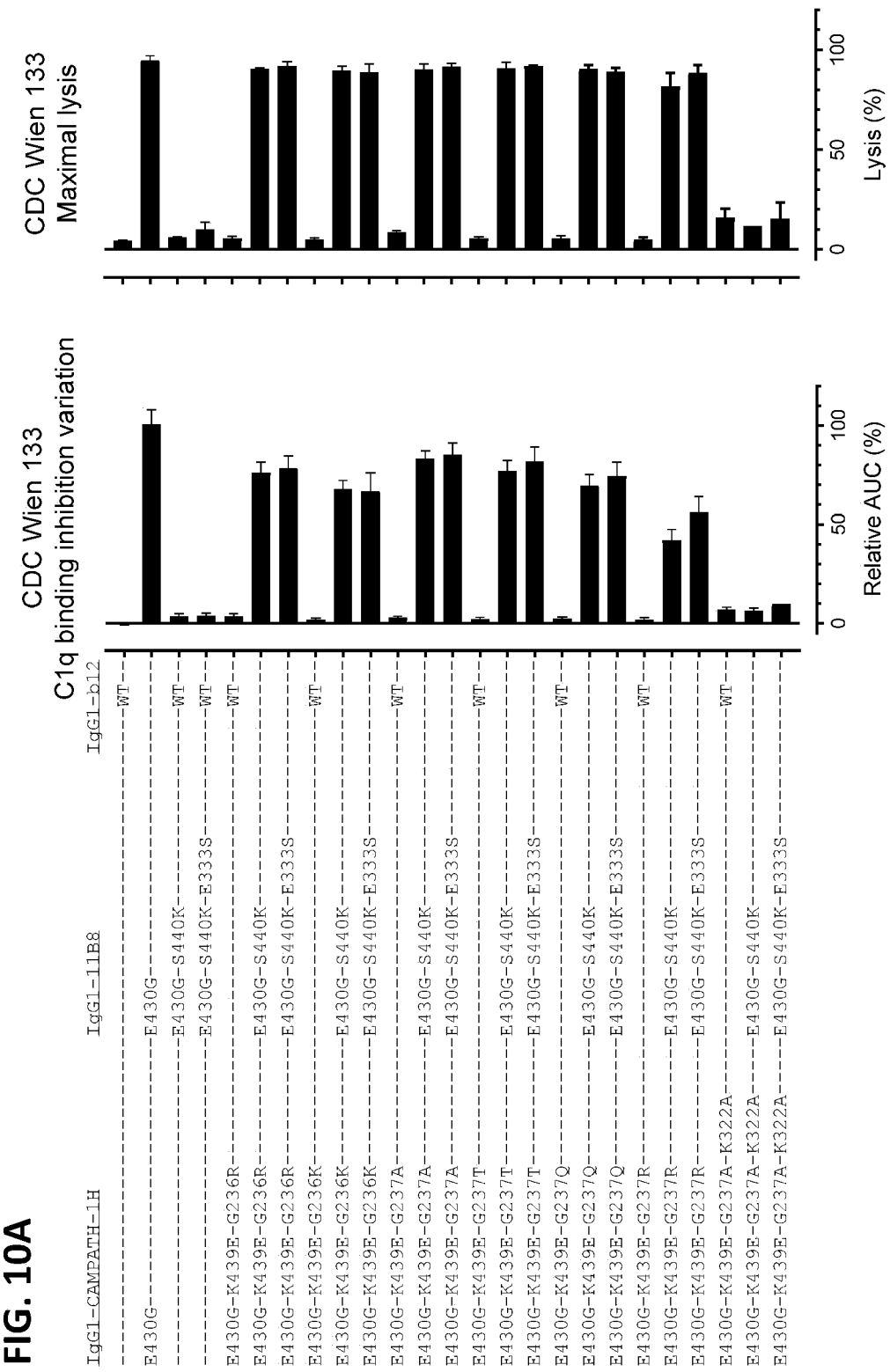
FIGS. 10A and 10B show selectivity of CDC activity by mixed antibody variants of anti-CD52 IgG1-CAMPATH-1H-E430G-K439E with C1q binding modulating mutations at position G236 (G236R or G236K) or position G237 (G237A, G237T, G237Q or G237R), or the double mutation G237A-K322A+anti-CD20 IgG1-11B8-E430G-S440K with or without C1q binding modulating mutation E333S, E333A, K326A, K326W-E333S, G237A or G237A-E333S. Wien 133 cells were incubated with antibody concentration series in the presence of 20% NHS. CDC efficacy is presented as the normalized AUC of the percentage PI-positive cells and maximal lysis. Normalization was performed to non-binding control antibody IgG1-b12 (0%) and the mixture of IgG1-CAMPATH-1H-E430G+IgG1-11B8-E430G (100%).

First, IgG1-CAMPATH-1H-E430G-K439E antibody variants containing a substitution at amino acid position G236 (G236R or G236K (SEQ ID NO 83)) or position G237 (G237A (SEQ ID NO 85), G237T (SEQ ID NO 89), G237Q (SEQ ID NO 87) or G237R (SEQ ID NO 88)) or the double mutation G237A-K322A (SEQ ID NO 86) were combined with IgG1-11B8-E430G-S440K with or without the C1q binding enhancing mutation E333S. As shown in FIG. 10A, all tested C1q binding modulating mutations at position G236 or G237 in IgG1-CAMPATH-1H-E430G-K439E resulted in selective CDC activity in the mixtures with IgG1-11B8-E430G-S440K with or without the C1q binding enhancing mutation E333S, while showing little to no CDC activity as single agents on Wien 133 cells. In contrast, the mixture of IgG1-CAMPATH-1H-E430G-K439E variant containing the double mutation G237A-K322A did not show recovery of CDC activity when combined with the IgG1-11B8-E430G-S440K with or without the C1q binding enhancing mutation E333S.

Figure 10B:
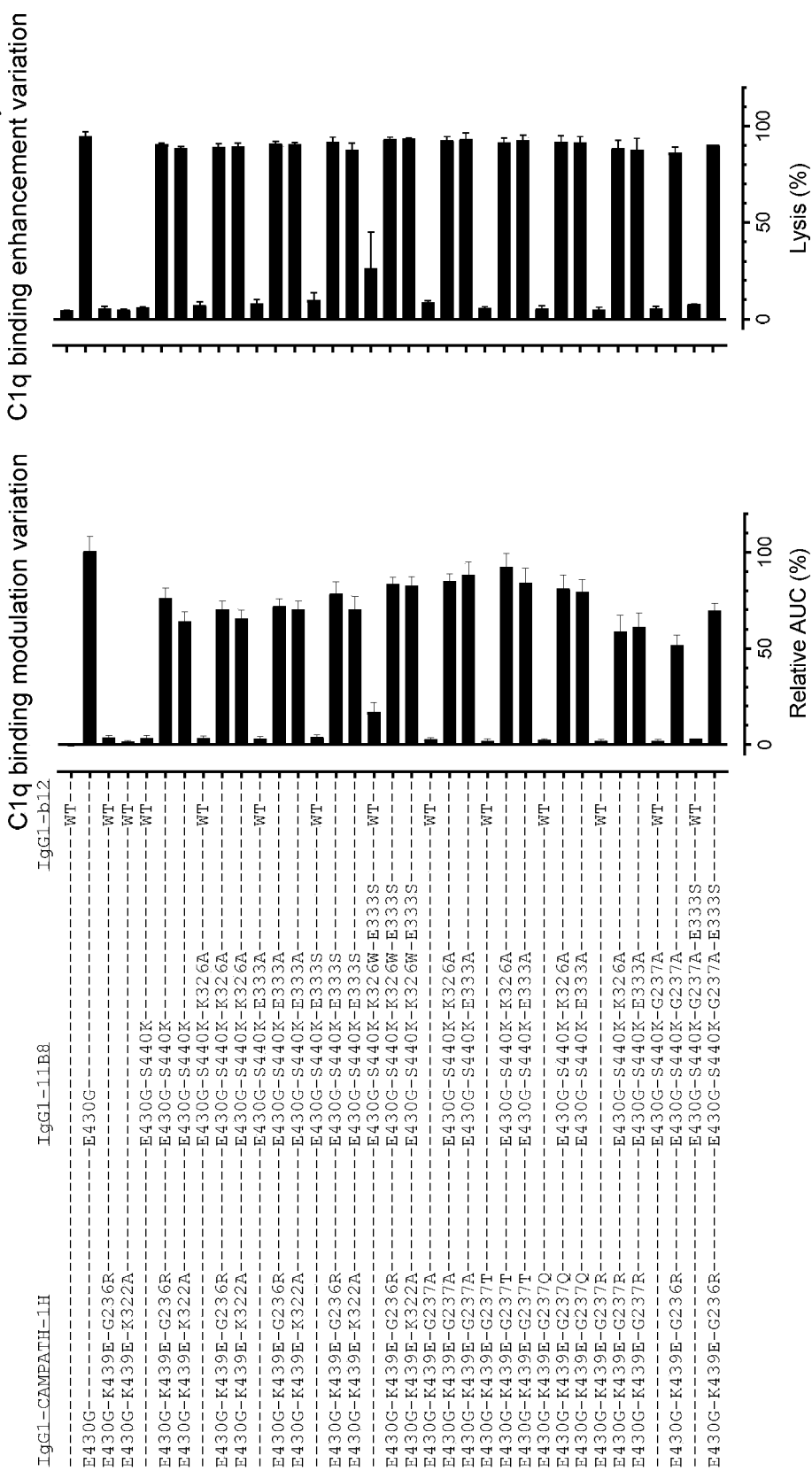

Next, IgG1-11B8-E430G-S440K antibody variants containing the C1q binding enhancing mutation(s) K326A (SEQ ID NO 110), E333A (SEQ ID NO 102), E333S or K236W-E333S (SEQ ID NO 157) were combined with IgG1-CAMPATH-1H-E430G-K439E containing the C1q binding inhibition mutation G236R or K322A. As shown in FIG. 10B, IgG1-11B8-E430G-S440K antibody variants containing the single C1q binding enhancing mutation K326A, E333A or E333S retained lack of CDC activity as single agents on Wien 133 cells, whereas the IgG1-11B8-E430G-S440K variant containing the double mutation K236W-E333S showed significantly more CDC activity as a single agent. All tested combinations of IgG1-11B8-E430G-S440K antibody variants containing the single C1q binding enhancing mutation K326A, E333A or E333S with the IgG1-CAMPATH-1H-E430G-K439E variants containing the C1q binding inhibition mutation G236R or K322A showed recovery of CDC activity, while showing little to no CDC activity as single agents on Wien 133 cells.

IgG1-11B8-E430G-S440K antibody variants containing the C1q binding enhancing mutation K326A or E333A were also combined with IgG1-CAMPATH-1H-E430G-K439E containing a C1q binding modulating mutation at position G237 (G237A, G237T, G237Q or G237R). As shown in FIG. 10B, all tested combinations of IgG1-11B8-E430G-S440K-K326A or IgG1-11B8-E430G-S440K-E333A with IgG1-CAMPATH-1H-E430G-K439E antibody variants containing one of the tested mutations at position G237 resulted in selective CDC activity, while all single agents showed little to no CDC activity on Wien 133 cells.

Mutation G237A was introduced in IgG1-11B8-E430G-S440K antibody variants to suppress FcγR-mediated effector functions in the S440K component (SEQ ID NO 105). To compensate for potentially decreased C1q binding, G237A was tested in combination with C1q binding enhancing mutation E333S (SEQ ID NO 106). IgG1-11B8 variants were combined with IgG1-CAMPATH-1H-E430G-K439E-G236R. As shown in FIG. 10B, these combinations also showed selective CDC activity, while the single agents showed little to no CDC activity on Wien 133 cells.

In conclusion, the CDC activity of individual antibodies with Fc-Fc interaction enhancing mutation E430G could be controlled by introduction of a self-oligomerization inhibiting mutation combined with different mutations inhibiting C1q binding. Maximal recovery of complement activity using such antibodies was achieved by mixing with antibodies containing different C1q binding enhancing mutations and complementary self-oligomerization inhibiting mutations, which allowed for selective hetero-oligomerization on cells bound by both antibodies simultaneously.

Example 12: Analysis of Selective CDC Activity on Wien 133 Cells for Mixtures of Anti-CD52 Antibody and Anti-CD20 Antibody Variants in Different Human IgG Isotype Backbones The VH sequences of anti-CD52 CAMPATH-1H were cloned in human IgG1, IgG2, IgG3 and hinge-stabilized IgG4 (S228P) Fc backbones containing the E430G-K439E-G236R mutations, and the VH sequences of anti-CD20 11B8 were cloned in human IgG1, IgG2, IgG3 and hinge-stabilized IgG4 (S228P) Fc backbones containing the E430G-S440K-E333S mutations. Different combinations of these anti-CD52 and anti-CD20 isotype variants were tested for selective CDC activity. An in vitro CDC assay using Wien 133 cells was performed with 20% NHS and antibody concentration series (final concentration range 0.003-10.0 µg/mL in 3-fold dilutions), essentially as described in Example 2. Cell lysis and relative AUC values were calculated from the number of PI-positive cells as described in Example 2, from two experimental replicates. AUC was normalized to the values for negative control antibody IgG1-b12 (0%) and for positive control IgG1-CAMPATH-1H-E430G+IgG1-11B8-E430G (100%), while maximal lysis data presented reflects un-normalized cell lysis at 10 µg/mL IgG.

Figure 11:
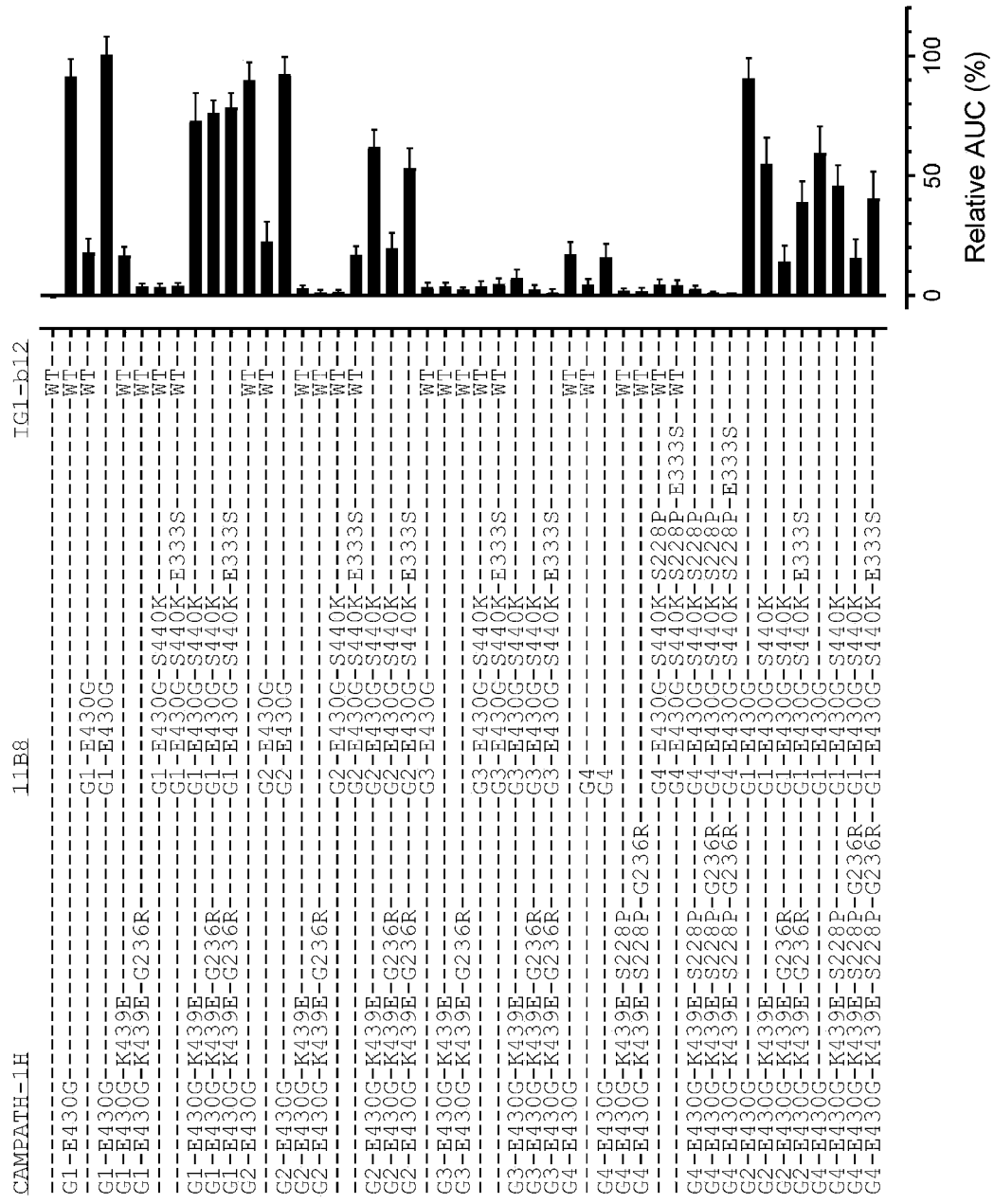
FIG. 11 shows selectivity of CDC activity by mixed antibody isotype variants (IgG1, IgG2, IgG3 and hinge-stabilized IgG4) of anti-CD52 CAMPATH-1H-E430G-K439E with or without C1q binding inhibition mutation G236R+anti-CD20 11B8-E430G-S440K with or without C1q binding enhancing mutation E333S. Wien 133 cells were incubated with antibody concentration series in the presence of 20% NHS. CDC efficacy is presented as the normalized AUC of the percentage PI-positive cells. Normalization was performed to non-binding control antibody IgG1-b12 (0%) and the mixture of IgG1-CAMPATH-1H-E430G+IgG1-11B8-E430G (100%).

Mixtures of IgG2-CAMPATH-1H-E430G-K439E-G236R and IgG2-11B8-E430G-S440K or IgG2-11B8-E430G-S440K-E333S showed recovery of CDC activity, however, with reduced CDC potency (AUC) compared to the mixture of the corresponding IgG1 antibody variants (FIG. 11). IgG2-CAMPATH-1H-E430G-K439E-G236R and IgG2-11B8-E430G-S440K showed no single agent CDC activity, while introduction of the C1q binding enhancing mutation E333S in IgG2-11B8-E430G-S440K-E333S resulted in the induction of some CDC activity by the single agent on Wien 133 cells (FIG. 11).

No CDC activity was observed for any of the tested single agents or mixtures of IgG3 isotype variants (FIG. 11). Also for the tested single agents or mixtures of IgG4 isotype variants, no CDC activity was observed (FIG. 11).

Surprisingly, mixtures of IgG2-CAMPATH-1H-E430G-K439E-G236R with IgG1-11B8-E430G-S440K-E333S and mixtures of hinge-stabilized IgG4-CAMPATH-1H-E430G-K439E-G236R (SEQ ID NO 146) with IgG1-11B8-E430G-S440K-E333S showed partial recovery of CDC potency, while the respective single agents did not induce CDC on Wien 133 cells (FIG. 11).

In conclusion, the CDC activity of individual antibodies with different IgG backbones containing Fc-Fc interaction enhancing mutation E430G could be controlled by introduction of a self-oligomerization inhibiting mutation combined with mutations modulating C1q binding. By mixing such antibodies containing complementary self-oligomerization inhibiting mutations, the CDC activity of such antibodies could be restored by selective hetero-oligomerization on cells bound by both antibodies simultaneously.

Figure 12A:
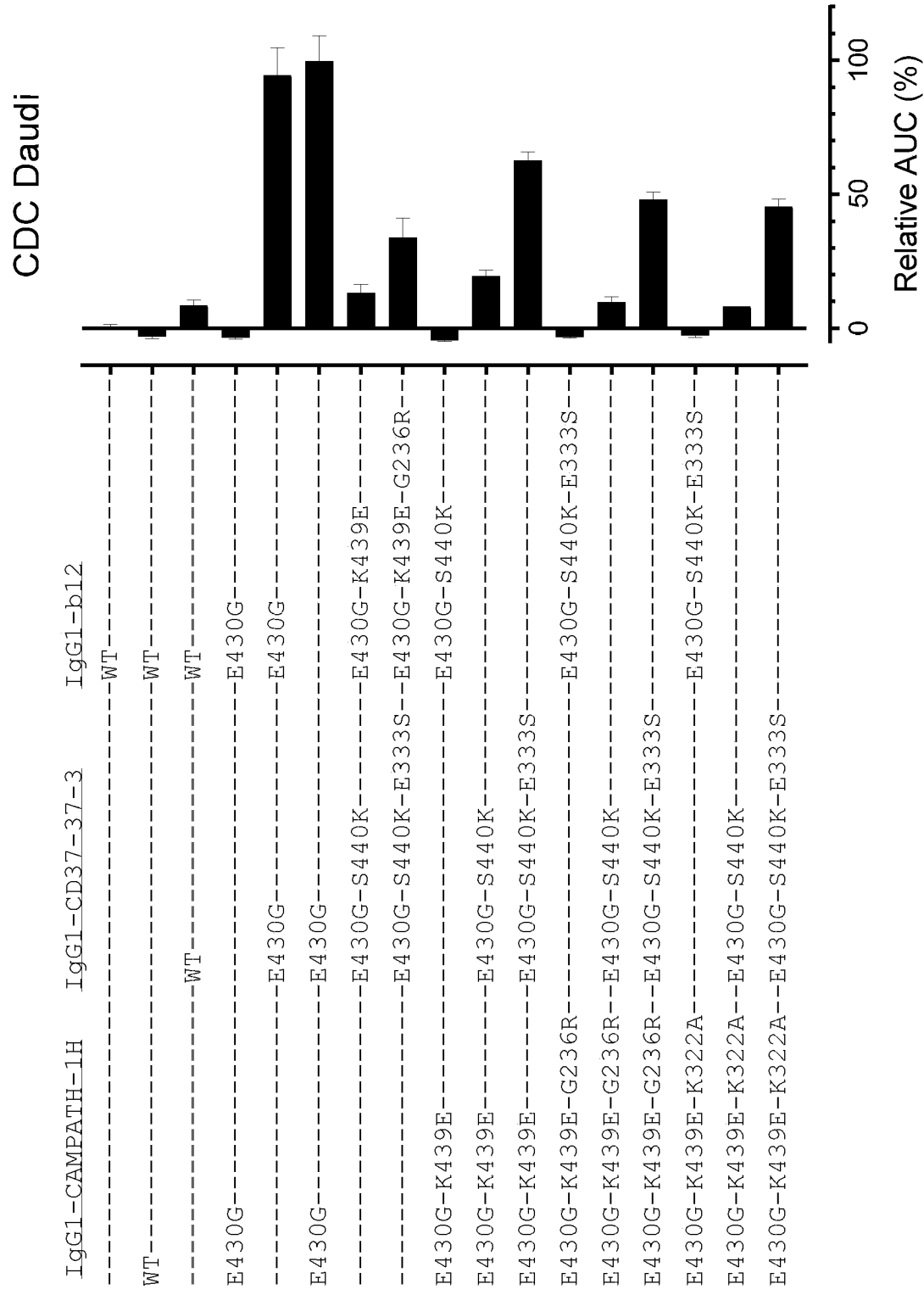
FIGS. 12A and 12B show selectivity of CDC activity by mixed antibody variants of anti-CD52 IgG1-CAMPATH-1H-E430G-K439E with or without C1q binding inhibition mutation G236R or K322A+anti-CD37 IgG1-CD37-37.3-E430G-S440K with or without C1q binding enhancing mutation E333S on (FIG. 12A) Daudi and (FIG. 12B) Wien 133 cells. Target cells were incubated with antibody concentration series in the presence of 20% NHS. CDC efficacy is presented as the normalized AUC of the percentage PI-positive cells. Normalization was performed to non-binding control antibody IgG1-b12 (0%) and the mixture of IgG1-CAMPATH-1H-E430G+IgG1-CD37-37.3-E430G (100%).

Example 13: Selectivity of CDC Activity by Mixtures of Anti-CD52 IgG1-CAMPATH-1H Antibody Variants and Anti-CD37 IgG1-CD37-37.3 Antibody Variants on Cell Lines with Different Target Expression Levels As described in Example 4, selective CDC activity by the mixture of IgG1-CAMPATH-1H-E430G-K439E-K322E+IgG1-11B8-E430G-S440K could only be achieved on cells expressing sufficient levels of both targets, i.e. CD20 and CD52. Furthermore, in Example 7 it is described that maximal killing of Wien 133 cells with preserved selectivity for the antibody combination was achieved using IgG1-CAMPATH-1H-E430G-K439E containing a C1q binding inhibition mutation, such as G236R or K322A, and IgG1-11B8-E430G-S440K containing a C1q binding enhancing mutation, such as E333S. Here, selective CDC activity was tested for a combination of anti-CD52 antibody variants and anti-CD37 antibody variants in in vitro CDC assays using Daudi and Wien 133 cells. The in vitro CDC assays using Daudi and Wien 133 cells were performed with 20% NHS and antibody concentration series (final concentration range 0.003-10.0 µg/mL in 3-fold dilutions), essentially as described in Example 2. Cell lysis and relative AUC values were calculated from the number of PI-positive cells as described in Example 2, from two experimental replicates (Daudi) and one experiment (Wien 133). AUC was normalized to the values for negative control antibody IgG1-b12 (0%) and for positive control IgG1-CAMPATH-1H-E430G+ IgG1-11B8-E430G (100%). Daudi cells, expressing low CD52 levels (Table 2), were found to be resilient to CDC induction by all IgG1-CAMPATH-1H variants (WT, E430G, E430G-K439E, E430G-K439E-G236R and E430G-K439E-K322A) when tested as single agents (FIG. 12A). CDC activity by IgG1-CD37-37.3-E430G on Daudi cells (expressing high CD37 levels, data not shown) was inhibited by introduction of the S440K mutation, and partially recovered by the additional introduction of the E333S C1q binding enhancing mutation. WT IgG1-CD37-37.3 did not induce CDC activity on Daudi cells. For the mixtures of IgG1-CD37-37.3-E430G-S440K with IgG1-CAMPATH-1H-E430G-K439E variants containing G236R or K322A, the observed CDC activity was similar to that of the single agent IgG1-CD37-37.3-E430G-S440K, demonstrating a lack of cooperativity with the IgG1-CAMPATH-1H variants at low CD52 expression. Low cooperativity was observed for mixtures of IgG1-CD37-37.3-E430G-S440K-E333S with variants of IgG1-CAMPATH-1H-E430G-K439E variants containing C1q-inhibiting mutation G236R or K322A. These data demonstrated that C1q binding inhibiting mutation G236R in IgG1-CAMPATH-1H-E430G-K439E suppressed spurious co-activation at cells expressing low levels of CD52.

Figure 12B:
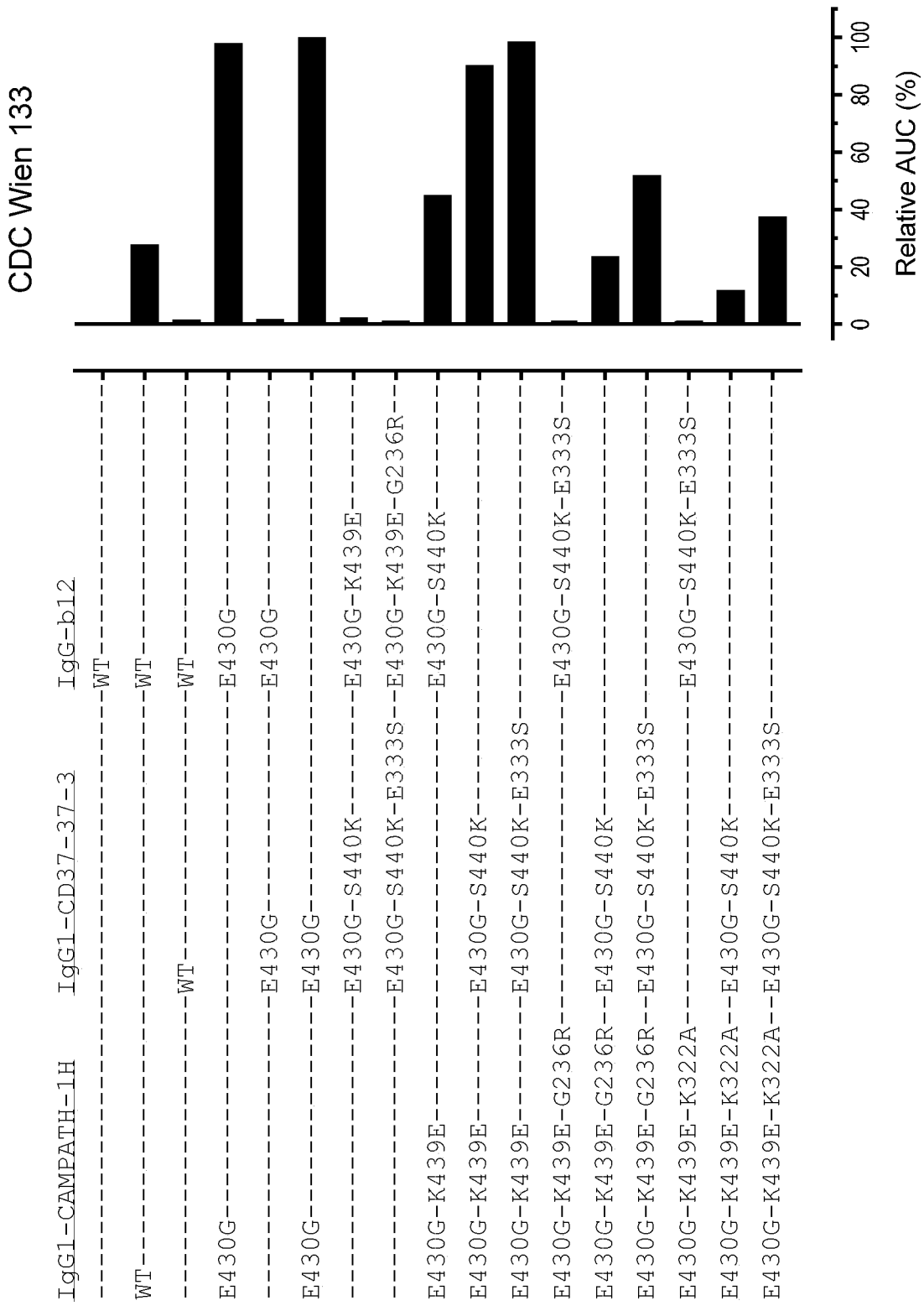

Wien 133 cells, expressing modest CD37 levels (data not shown), were found to be resilient to CDC induction by all IgG1-CD37-37.3 variants (WT, E430G, E430G-S440K, E430G-S440K-E333S) when tested as single agents (FIG. 12B). CDC activity by IgG1-CAMPATH-1H-E430G on Wien 133 cells, expressing high CD52 levels (ABC>300,000; Table 2), was reduced to the levels of WT IgG1-CAMPATH-1H by introduction of the K439E mutation. Further introduction of a C1q binding inhibition mutation (IgG1-CAMPATH-1H-E430G-K439E-G236R and IgG1-CAMPATH-1H-E430G-K439E-K322A) resulted in complete inhibition of CDC activity for the single agents on Wien 133 cells. For the mixtures of IgG1-CAMPATH-1H-E430G-K439E-G236R or IgG1-CAMPATH-1H-E430G-K439E-K322A with IgG1-CD37-37.3-E430G-S440K or IgG1-CD37-37.3-E430G-S440K-E333S, recovery of CDC activity was observed to levels superior to that of WT IgG1-CAMPATH-1H, while all these variants did not show CDC activity on Wien 133 cells as single agents.

In conclusion, selective recovery of CDC efficacy for mixtures of IgG1-CAMPATH-1H-E430G and IgG1-CD37-37.3-E430G antibody variants could be established on Wien 133 cells expressing appreciable levels of both CD37 and CD52, while Daudi cells expressing low levels of CD52 could be protected from the presence of IgG1-CAMPATH-1H-E430G variants containing both a self-oligomerization inhibitory mutation and C1q-binding inhibitory mutation G236R or K322A.

Example 14: Selective DR5 Agonist Activity of a Mixture of Two Non-Crossblocking Anti-DR5 Antibodies on BxPC-3 Cells The mixture of the two non-crossblocking anti-death receptor 5 (DR5) antibodies IgG1-DR5-01-G56T-E430G+ IgG1-DR5-05-E430G act as a DR5 agonist to induce killing of DR5-positive cancer cells (WO17093447). Here, a viability assay was performed to study the capacity of combinations of IgG1-DR5-01-G56T-E430G antibody variants (K439E, K439E-G236R) with IgG1-DR5-05-E430G antibody variants (S440K, S440K-E333S) to induce killing of human BxPC-3 pancreatic cancer cells (ATCC, Cat No. CRL-1687), which express low levels of DR5 (data not shown). BxPC-3 cells were harvested by trypsinization and passed through a cell strainer. Cells were pelleted by centrifugation for 5 minutes at 1,200 rpm and resuspended in culture medium at a concentration of $0.5 \times 10^5$ cells/mL (RPMI 1640 with 25 mM Hepes and L-Glutamine (Lonza)+ 10% DBSI (Life Technologies Cat No. 10371-029)+Pen/Strep). 100 µL of the single cell suspensions (5,000 cells/well) were seeded in polystyrene 96-well flat-bottom plates (Greiner Bio-One, Cat No. 655182) and allowed to adhere overnight at 37° C. The next day, 50 µL samples of an antibody dilution series (final concentration range 0.003-20 µg/mL in 3-fold dilutions) and 10 µL purified human C1q stock solution (Quidel, Cat No. A400, 2.5 µg/mL final concentration) were added and incubated for 3 days at 37° C. As a positive control, cells were incubated with 5 µM staurosporine (Sigma Aldrich, Cat No. S6942). The viability of the cell cultures was determined in a CellTiter-Glo luminescent cell viability assay (Promega, Cat No. G7571) that quantifies the ATP present, which is an indicator of metabolically active cells. From the kit, 15 µL Luciferin Solution Reagent was added per well and mixed by shaking the plate for 2 minutes at 500 rpm. Next, plates were incubated for 1.5 hours at 37° C. 100 µL supernatant was transferred to a white OptiPlate-96 (Perkin Elmer, Cat No. 6005299) and luminescence was measured on an EnVision Multilabel Reader (PerkinElmer). Data were analyzed and plotted using non-linear regression (sigmoidal dose-response with variable slope) using GraphPad Prism software. The percentage viable cells was calculated using the following formula: % viable cells=[(luminescence antibody sample–luminescence staurosporine sample)/(luminescence no antibody sample–luminescence staurosporine sample)]* 100.

Figure 13A:
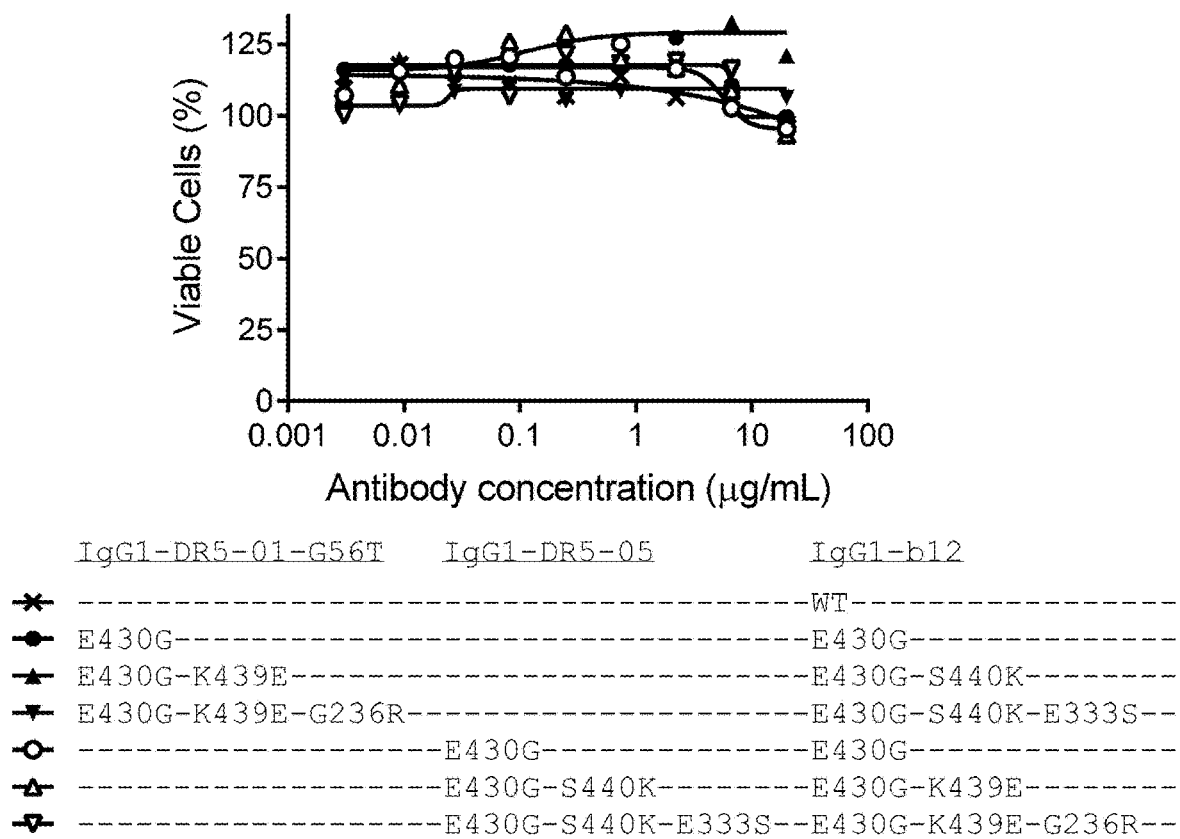
FIGS. 13A and 13B show DR5-mediated cytotoxicity of (FIG. 13A) single antibody variants or (FIG. 13B) an agonist mixture of antibody variants of anti-DR5 IgG1-DR5-01-G56T-E430G-K439E with or without C1q binding inhibition mutation G236R+IgG1-DR5-05-E430G-S440K with or without C1q binding enhancing mutation E333S on BxPC-3 human pancreatic cancer cells. A three-day viability assay was performed and cell viability was determined using the CellTiter-Glo kit.
Figure 13B:
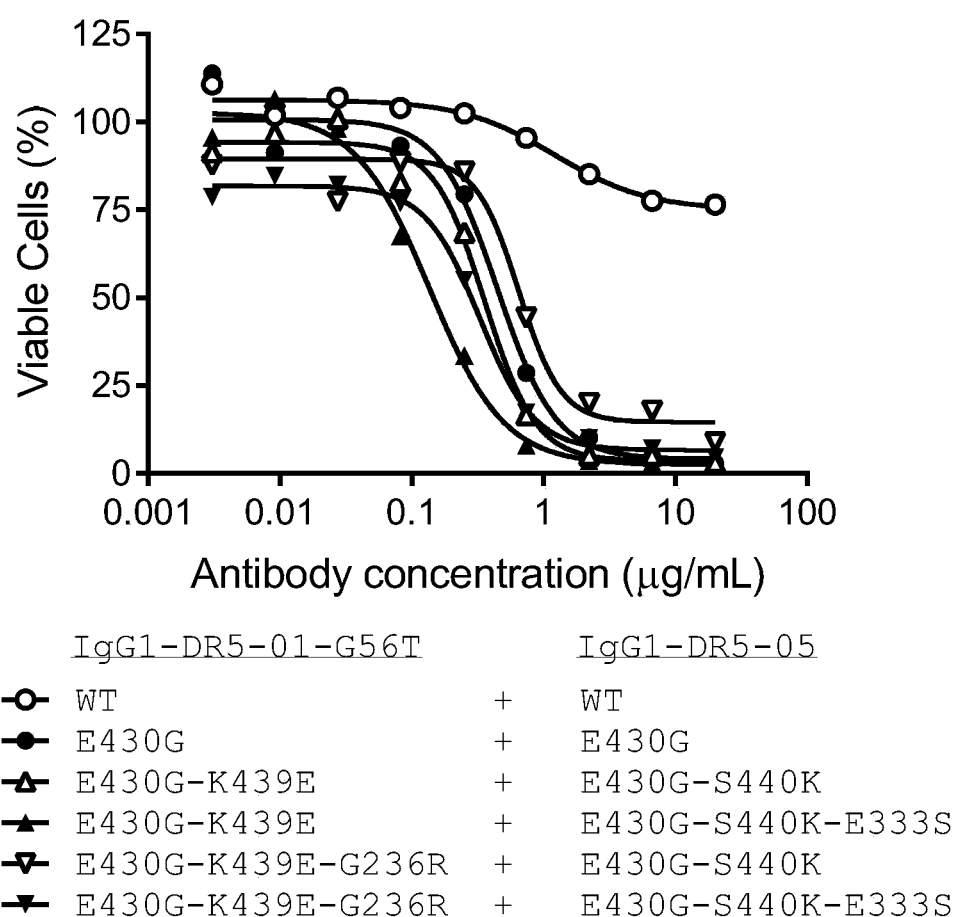

None of the tested single agents induced killing of BxPC-3 cells (FIG. 13A), whereas the combination of IgG1-DR5-01-G56T-E430G+IgG1-DR5-05-E430G induced dose-dependent killing of BxPC-3 cells (FIG. 13B). This selective killing was retained in the combination of IgG1-DR5-01-G56T-E430G-K439E+IgG1-DR5-05-E430G-S440K, indicating that both antibodies form heterohexamers. By modulating the C1q binding sites, it was observed that the induction of killing of BxPc-3 cells by DR5 agonist activity was most efficient with the combination of IgG1-DR5-01-G56T-E430G-K439E (no C1q binding inhibition mutation)+IgG1-DR5-05-E430G-S440K-E333S (with E333S C1q binding enhancing mutation), and somewhat reduced with the combination of IgG1-DR5-01-G56T-E430G-K439E-G236R (with the G236R C1q binding inhibition mutation)+IgG1-DR5-05-E430G+S440K (no C1q binding enhancing mutation). The other tested combination of IgG1-DR5-01-G56T-E430G-K439E-E333S (with C1q binding inhibition mutation)+IgG1-DR5-05-E430G-S440K-E333S (with E333S C1q binding enhancing mutation) showed similar efficacy as IgG1-DR5-01-G56T-E430G+ IgG1-DR5-05-E430G.

In conclusion, the introduction of C1q-modulatory mutations did not compromise the selective killing of BxPC-3 cells by hetero-oligomerizing mixtures of anti-DR5 antibodies. Rather, the potency of the mixture was proportional to that of the expected combined C1q binding avidity of the hetero-oligomeric antibody structure formed at BxPC-3 cells after DR5 binding.

Figure 14:
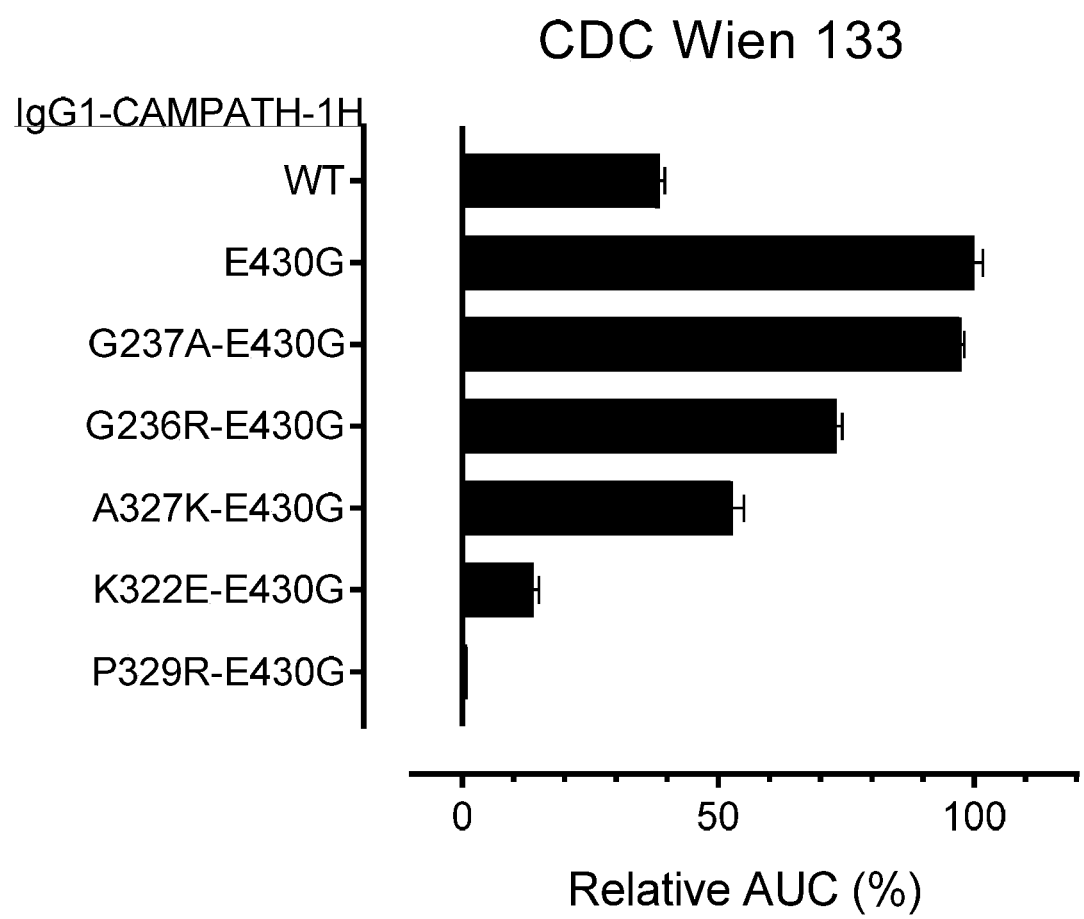
FIG. 14 shows CDC activity by antibody variants of anti-CD52 IgG1-CAMPATH-1H-E430G with the C1q binding modulating mutation G237A, G236R, A327K, K322E or P329R. Wien 133 cells were incubated with antibody concentration series in the presence of 20% NHS. CDC efficacy is presented as the normalized AUC of the percentage PI-positive cells. Normalization was performed to non-binding control antibody IgG1-b12-S440K (0%; not shown) and IgG1-CAMPATH-1H-E430G (100%).

Example 15: Analysis of the Effect of Different C1q Binding Inhibition Mutations in Anti-CD52 Antibody IgG1-CAMPATH-1H-E430G on CDC Activity The effects of introducing different C1q binding inhibition mutations in IgG1-CAMPATH-1H-E430G (G237A, G236R, A327K, K322E or P329R) were compared in in vitro CDC assays using Wien 133 cells. The in vitro CDC assay using Wien 133 cells was performed with 20% NHS and serial dilution antibody concentrations (range 0.002-40.0 µg/mL final concentrations in 4-fold dilutions), essentially as described in Example 2. Cell lysis was calculated from the number of PI-positive cells as measured by flow cytometry on an Intellicyt iQue™ screener, averaged from three experimental replicates. Relative areas under the curve (AUC) values represent normalization to minimal lysis (0% with negative control IgG1-b12-K439E+IgG1-b12-S440K (not shown)) and maximal lysis (100% with IgG1-CAMPATH-1H-E430G). FIG. 14 shows that the G237A mutation (SEQ ID NO: 124) had no effect on the CDC potency of IgG1-CAMPATH-1H-E430G on Wien 133 cells. Introduction of the G236R (SEQ ID NO: 123) or A327K (SEQ ID NO: 63) mutation resulted in partially decreased CDC activity, while the K322E (SEQ ID NO: 132) mutation resulted in decreased CDC activity to a residual level below that for WT IgG1-CAMPATH-1H. Only the P329R mutation (SEQ ID NO: 133) resulted in complete inhibition of CDC activity by IgG1-CAMPATH-1H-E430G-P329R on Wien 133 cells.

Example 16: FcRn Binding of Anti-CD52 IgG1-CAMPATH-1H Antibody Variants and Anti-CD20 IgG1-11B8 Antibody Variants The neonatal Fc receptor (FcRn) is responsible for the long plasma half-life of IgG by protecting IgG from degradation. After internalization of the antibody, FcRn binds to antibody Fc regions in endosomes, where the interaction is stable in the mildly acidic environment (pH 6.0). Upon recycling to the plasma membrane, where the environment is neutral (pH 7.4), the interaction is lost and the antibody is released back into the circulation. This influences the plasma half-life of IgG.

An FcRn binding enzyme-linked immunosorbent assay (ELISA) was performed to evaluate binding of human FcRn to anti-CD52 IgG1-CAMPATH-1H with E430G, K439E and C1q binding inhibiting mutations G236R or K322A and anti-CD20 IgG1-11B8 with E430G, S440K and C1q binding-enhancing mutation E333S. Streptawell 96 well plates (Roche, Cat No. 1734776001) were coated with 5 µg/mL (100 µL/well) recombinantly produced biotinylated extracellular domain of human FcRn [FcRnhsECDHis-B2M-BIO, i.e. the extracellular domain of human FcRn with a C-terminal His tag (FcRnhsECDHis; SEQ ID NO 155) as dimer with beta2microglobulin (B2M; SEQ ID NO 156)], diluted in PBS supplemented with 0.05% Tween 20 (PBST) plus 0.2% BSA for 2 hours while shaking at room temperature (RT). Plates were washed three times with PBST. Serially diluted antibody samples (Range 0.0005-40 µg/mL final concentrations in 5-fold dilutions in PBST/0.2% BSA, pH 6.0 or pH 7.4) were added and incubated for 1 hour at RT while shaking. Plates were washed with PBST/0.2% BSA, pH 6.0 or pH 7.4. Horseradish Peroxidase (HRP)-conjugated polyclonal Goat-anti-Human kappa light chain (1:5,000; Sigma, Cat No. A-7164) diluted in PBST/0.2% BSA, pH 6.0 or pH 7.4 was added, and plates were incubated for 1 hour at RT while shaking. After washing with PBST/0.2% BSA, pH 6.0 or pH 7.4, 100 µL 2,2'-Azino-bis(3-ethylbenzthiazoline-6-sulfonic acid (ABTS; 1 mg/mL; Roche Cat No. 11112422001 and 11112597001) was added as substrate and plates were incubated for 10 minutes at RT protected from light. The reaction was stopped using 100 µL 2% oxalic acid (Riedel de Haen, Cat No. 33506), incubated for 10 minutes at RT and absorbance was measured at 405 nm using an ELISA reader. Log-transformed data were analyzed by fitting sigmoidal dose-response curves with variable slope using GraphPad Prism software.

Figure 15A:
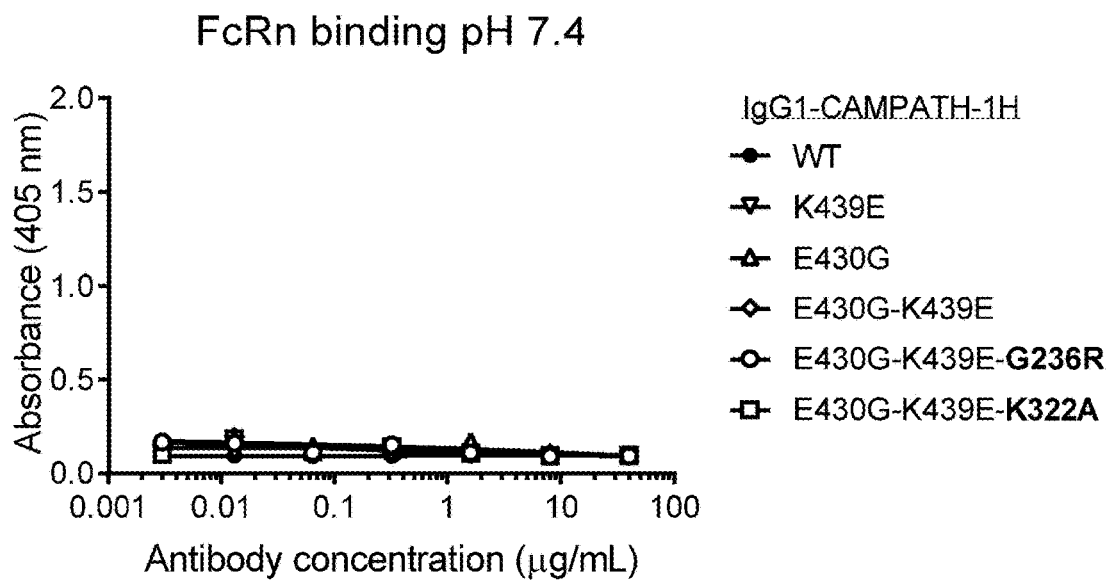
FIGS. 15A-15F show binding of antibody variants of anti-CD52 IgG1-CAMPATH-1H-E430G-K439E with the C1q binding inhibition mutation G236R or K322A (FIG. 15A, FIG. 15B, FIG. 15C) and antibody variants of anti-CD20 IgG1-11B8-E430G-S440K with the C1q binding enhancing mutation E333S (FIG. 15D, FIG. 15E, FIG. 15F) to human FcRn. An FcRn ELISA was performed with 5 µg/mL coated recombinant extracellular domain of human FcRn (FcRnhsECDHis-B2M-BIO) and antibody dilution series. The amount of bound antibodies was determined with an HRP-conjugated goat anti-human IgG1 antibody and the chemiluminescent substrate ABTS. Absorbance was measured at 405 nm.
Figure 15B:
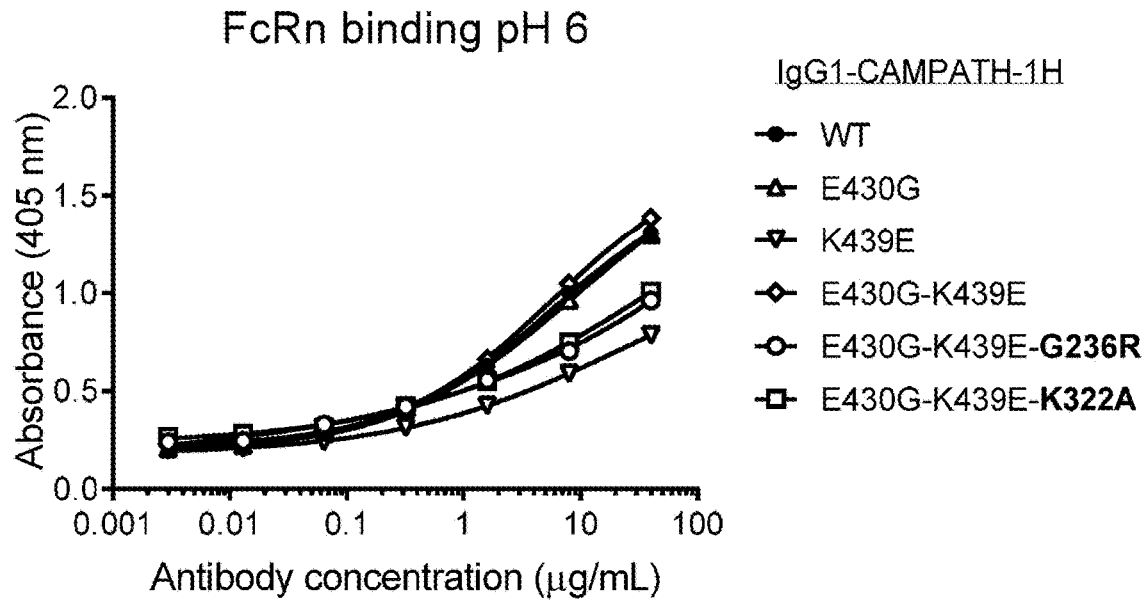
Figure 15C:
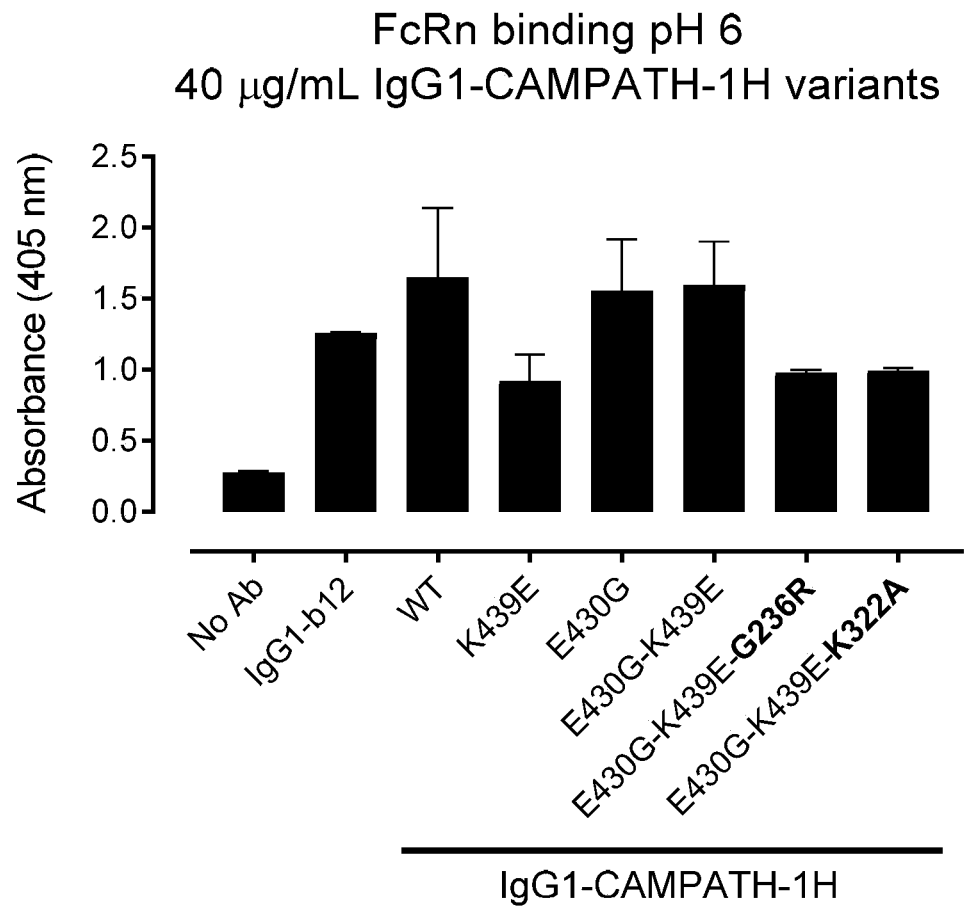
Figure 15D:
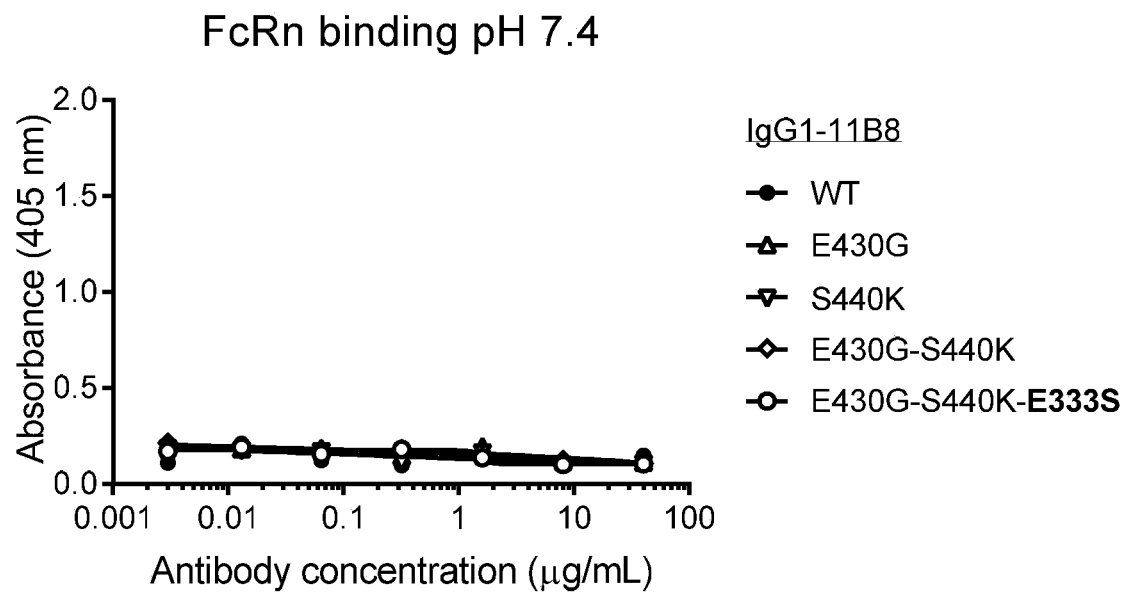
Figure 15E:
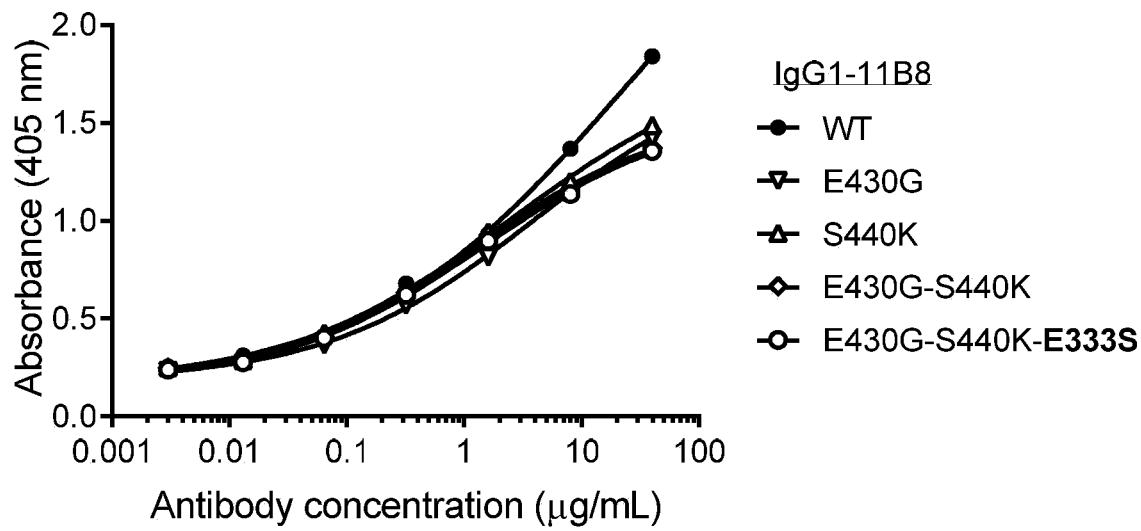
Figure 15F:
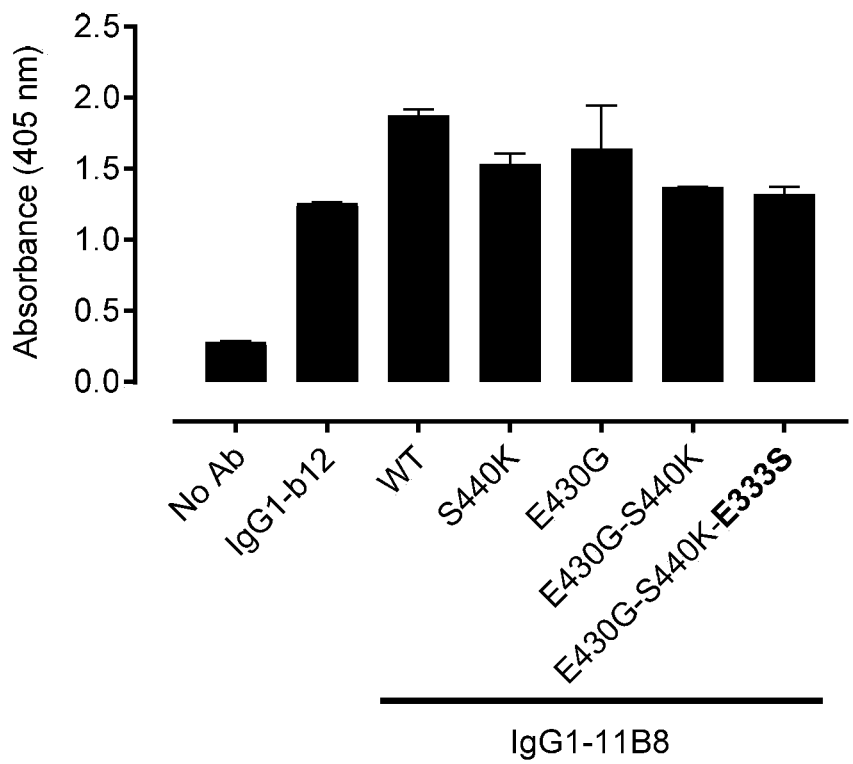

All tested IgG1-CAMPATH-1H antibody variants showed no binding to human FcRn at pH 7.4 (FIG. 15A), and efficient FcRn binding at pH 6.0 (FIG. 15B). The apparent differences in binding between tested IgG1-CAMPATH-1H variants were interpreted as insignificant, given the spread between the binding curves of IgG1-CAMPATH-1H variants K439E (apparent lower end) and variant E430G-K439E (apparent top end) and the spread between the maximal FcRn binding of IgG1-b12 and IgG1-CAMPATH-1H with wild type Fc domains harboring the FcRn binding site (FIG. 15B,C). All tested IgG1-11B8 antibody variants showed no binding to human FcRn at pH 7.4 (FIG. 15D), and efficient FcRn binding at pH 6.0 (FIG. 15E). Introduction of the C1q binding enhancing mutation E333S in IgG1-11B8-E430G-S440K had no effect on the binding to human FcRn (FIG. 15E,F). Together, these data showed that anti-CD52 IgG1-CAMPATH-1H with E430G, K439E and C1q binding inhibiting mutations G236R or K322A and anti-CD20 IgG1-11B8 with E430G, S440K and C1q binding-enhancing mutation E333S showed normal binding to human FcRn.

Figure 16A:
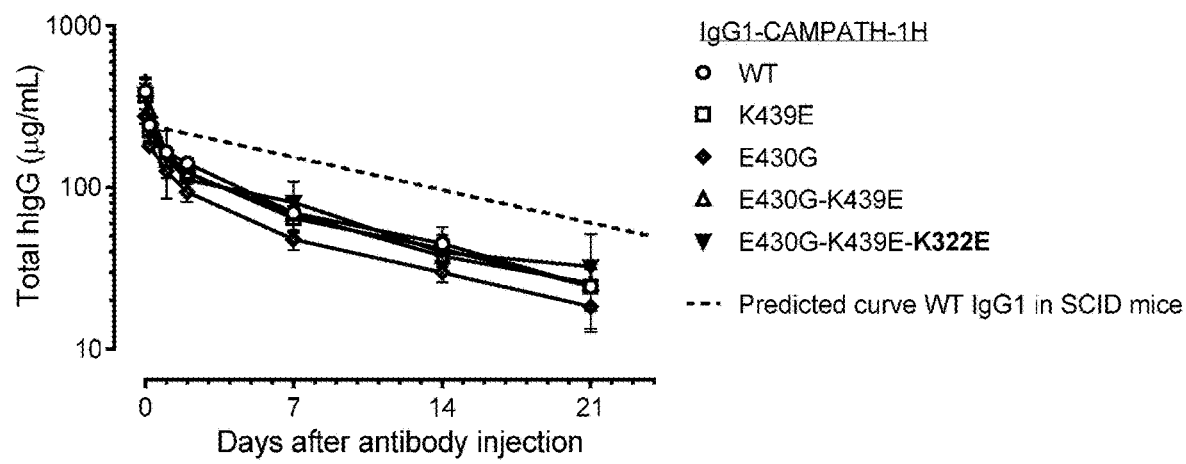
FIGS. 16A-16D show the clearance rate of 500 µg intravenously administered antibody in SCID mice.
Figure 16B:
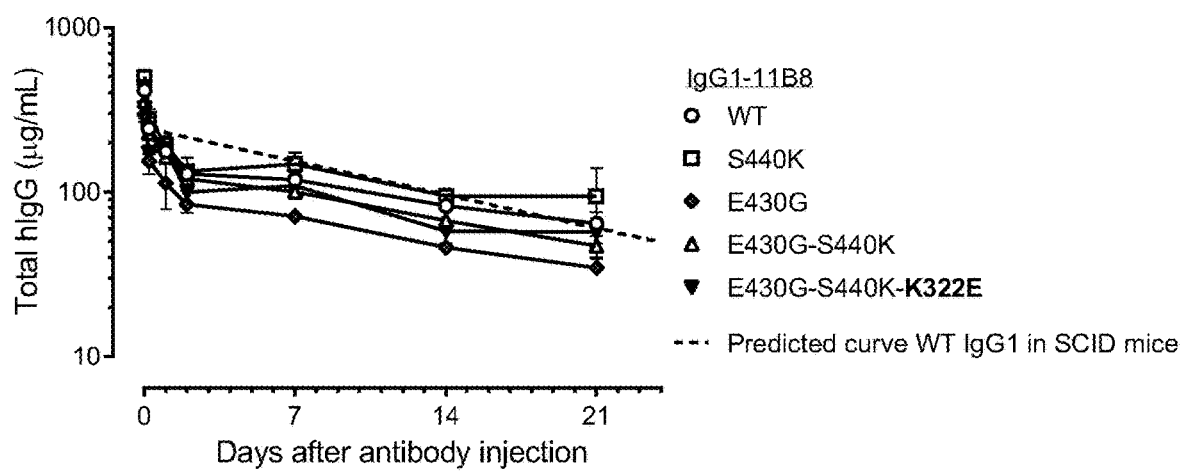
Figure 16C:
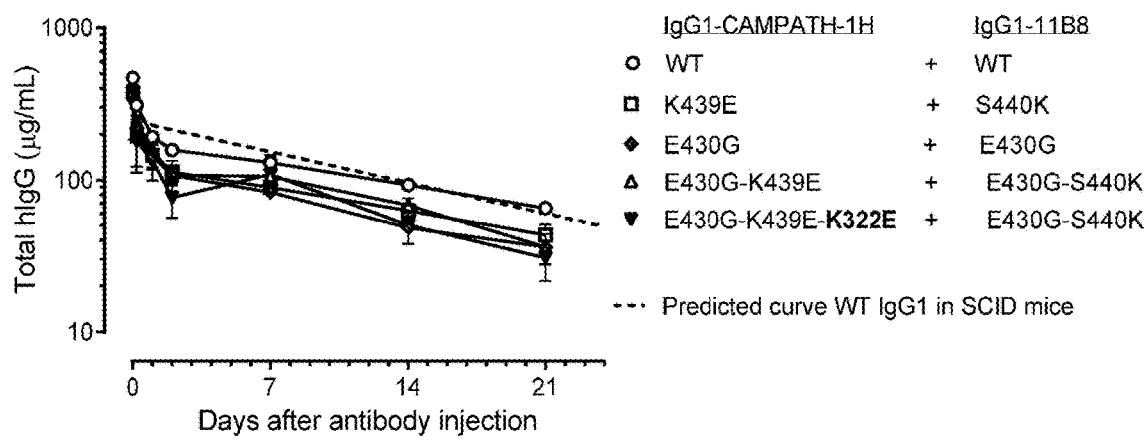
Figure 16D:
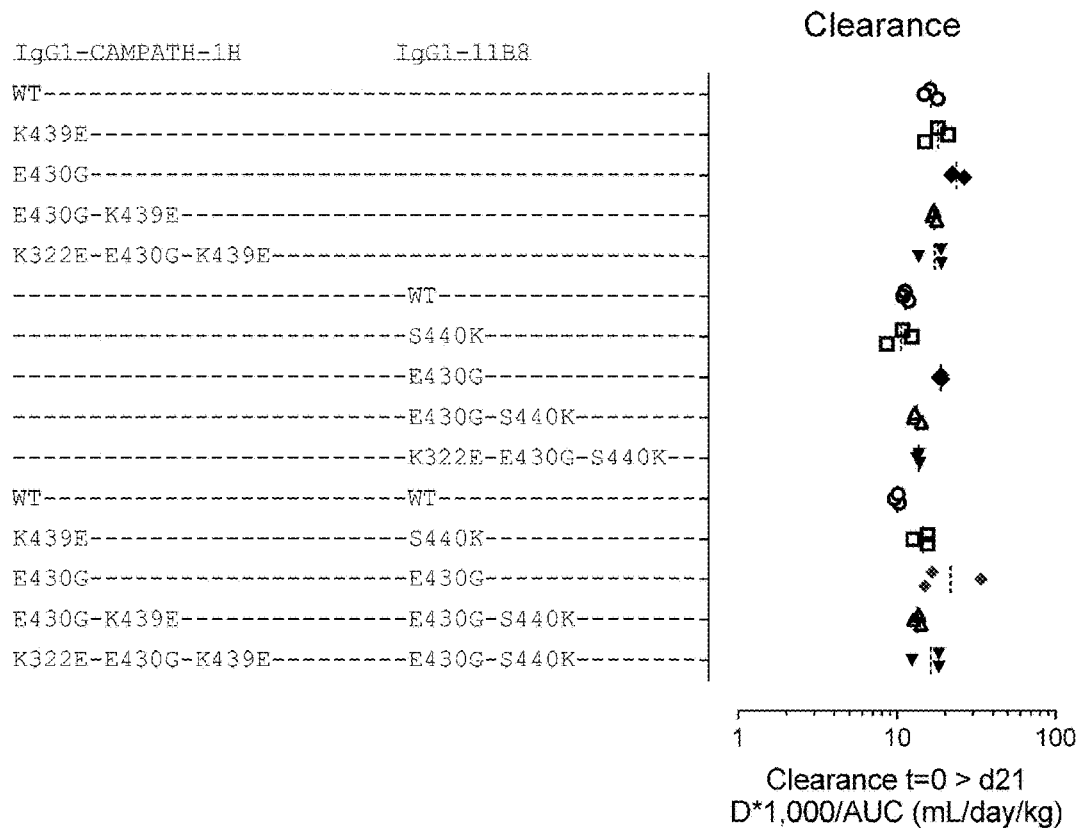
Figure 17A:
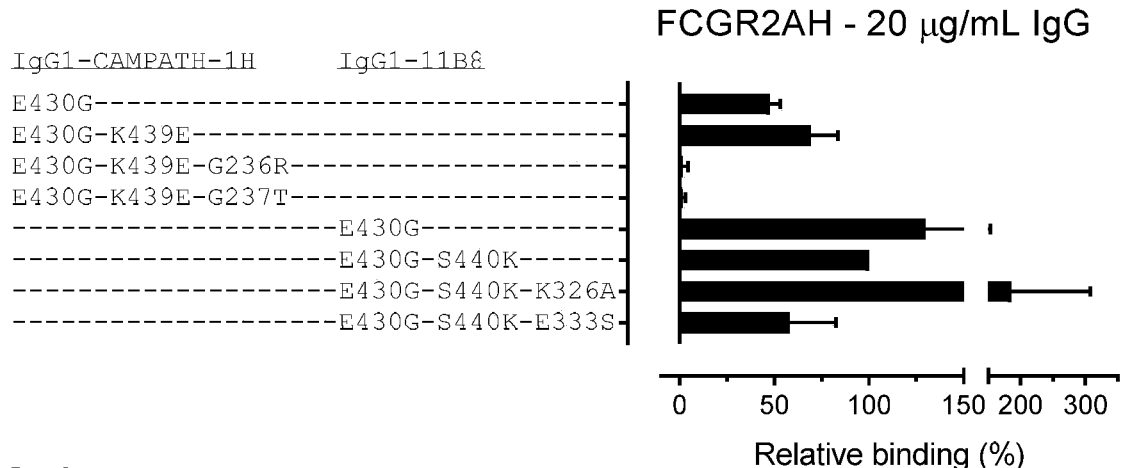
FIGS. 17A-17E show binding of immobilized IgG1-CAMPATH-1H-E430G-K439E variants with the C1q binding inhibition mutations G236R or G237T and IgG1-11B8-E430G-S440K variants with the C1q binding enhancing mutations K326A or E333S to dimeric His-tagged biotinylated ECD's of FcγRIIA allotype 131H (FIG. 17A), FcγRIIA allotype 131R (FIG. 17B), FcγRIIB (FIG. 17C), FcγRIIIA allotype 158V (FIG. 17D) and FcγRIIIA allotype 158F (FIG. 17E) as tested in ELISA assays. Binding is presented for 20 µg/mL antibody samples relative to no antibody control (background) and binding to IgG1-11B8-E430G-S440K (100%). Detection was performed using Streptavidin-polyHRP and ABTS.
Figure 17B:
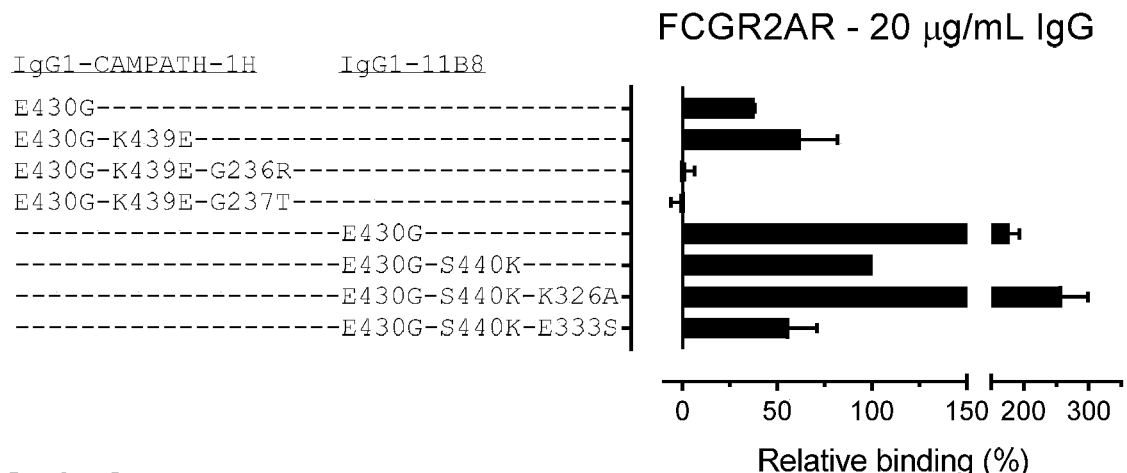
Figure 17C:
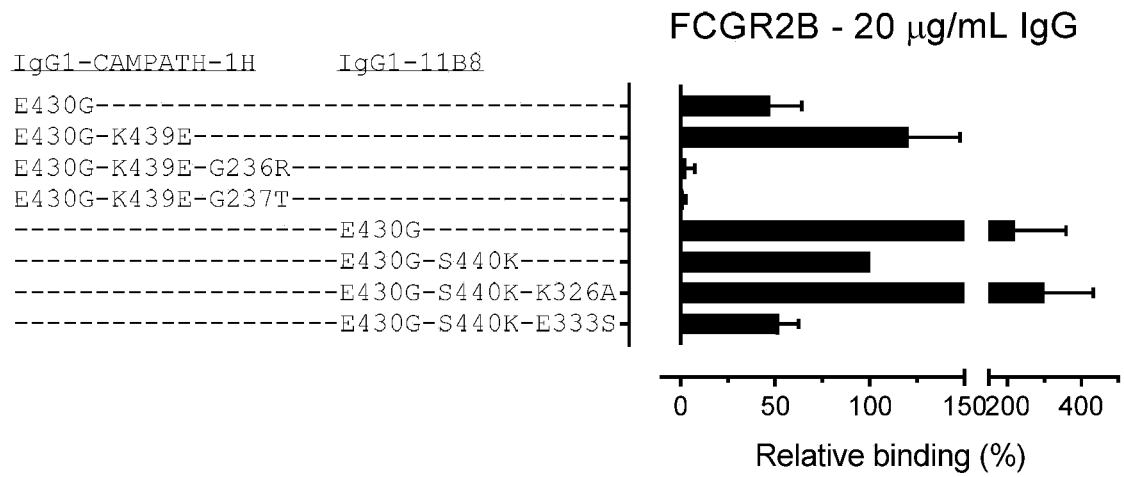
Figure 17D:
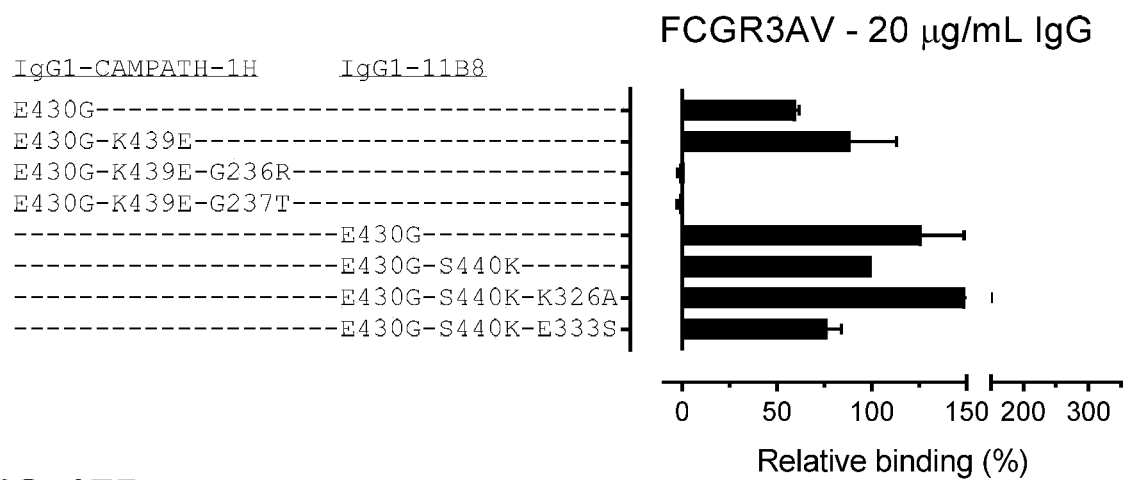
Figure 17E:
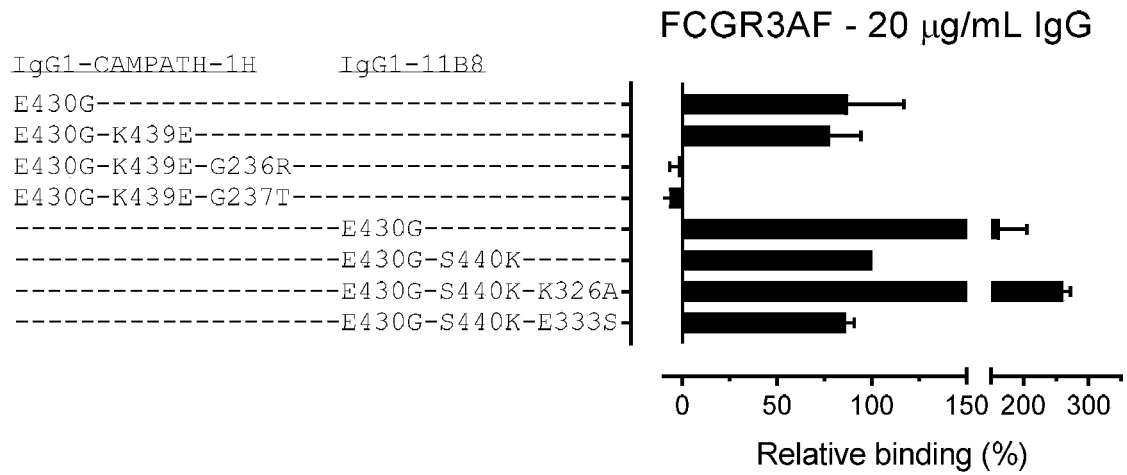

Example 17: Pharmacokinetic (PK) Analysis of IgG1-CAMPATH-1H and IgG1-11B8 Antibody Variants Containing the E430G, K439E, S440K and/or K322E Mutations and Combinations Thereof The effect of the K439E, S440K, E430G and K322E mutation on the clearance rate of IgG1-CAMPATH-1H and/or IgG1-11B8 was studied in a PK experiment in SCID mice. The clearance rate of IgG1-CAMPATH-1H-E430G, -K439E, -E430G-K439E and -K322-E430G-K439E was compared to that of WT IgG1-CAMPATH-1H, and the clearance rate of IgG1-11B8-E430G, -S440K, -E430G-S440K and -K322-E430G-S440K was compared to that of WT IgG1-11B8. Furthermore, the clearance rate of combinations of the IgG1-CAMPATH-1H antibody variants with the IgG1-11B8 antibody variants as indicated in FIG. 16C and FIG. 16D was also determined and compared to the clearance of the combination of WT IgG1-CAMPATH-1H with WT IgG1-11B8.

The mice in this study were housed in the Central Laboratory Animal Facility (Utrecht, The Netherlands) and handled in accordance with good animal practice as defined by FELASA, in an AAALAC and ISO 9001:2000 accredited animal facility (GDL). All experiments were performed in compliance with the Dutch animal protection law (WoD) translated from the directives (2010/63/EU) and approved by the Dutch animal ethics committees (CCD) and by the local Animal Welfare Body. 11-12 weeks old female SCID (C.B-17/IcrHan®Hsd-Prkdc$^{scid}$, Envigo) mice (3 mice per group) were injected intravenously with 500 µg antibody (500 µg for a single agent; 250 µg+250 µg for an antibody mixture) (25 mg/kg) in a 200 µL injection volume. 50 µL blood samples were collected from the saphenous vein alternating with cheek vein puncture at 10 minutes, 4 hours, 1 day, 2 days, 7 days, 14 days and 21 days after antibody administration. Blood was collected into heparin-containing vials and centrifuged for 10 minutes at 14,000×g. 20 µL plasma samples were diluted with 380 µL PBS and stored at −20° C. until determination of antibody concentrations. Total human IgG concentrations were determined using a sandwich ELISA. Mouse anti-human IgG-kappa mAb clone MH16 (CLB Sanquin, Cat No. M1268) was used as capturing antibody and coated in 100 µL overnight at 4° C. to 96-well ELISA microplates (Greiner, Cat No. 655092) at a concentration of 2 µg/mL in PBS. Plates were blocked by incubating on a plate shaker for 1 h at RT with PBS supplemented with 0.2% BSA. After washing, 100 µL of the diluted plasma samples were added and incubated on a plate shaker for 1 h at RT. Plates were washed three times with 300 µL PBST and subsequently incubated on a plate shaker for 1 h at RT with 100 µL peroxidase-labeled goat anti-human IgG immunoglobulin (Jackson, Cat No. 109-035-098; 1:10.000 in PBST supplemented with 0.2% BSA). Plates were washed again three times with 300 µL PBST before incubation for 15 minutes at RT with 100 µL substrate ABTS protected from light. The reaction was stopped by adding 100 µL 2% oxalic acid and incubation for 10 minutes at RT. Absorbance was measured in a microplate reader (Biotek, Winooski, VT) at 405 nm. Concentration was calculated by using the injected material as a reference curve. As a plate control human myeloma protein containing IgG1 kappa (The Binding Site, Cat No. BP078) was included. Human IgG concentrations (in µg/mL) were plotted (FIG. 16A for IgG1-CAMPATH-1H variants, FIG. 16B for the IgG1-11B8 variants and FIG. 16C for the combinations) and Area under the curve (AUC) was calculated using Graphpad Prism software. Clearance rates until the last day of blood sampling (day 21) were determined by the formula D*1,000/AUC, in which D is the dose of injection (25 mg/kg) (FIG. 16D).

The clearance rate of all IgG1-CAMPATH-1 variants, including WT, was a bit faster than the clearance of the IgG1-11B8 variants and the predicted IgG1 curve (based on the 2-compartment model).

Introduction of the E430G mutation in both IgG1-CAMPATH-1H and IgG1-11B8 resulted in a small increase in the clearance rate of these antibodies. Introduction of the K439E or S440K and/or K322E mutations in IgG1-CAMPATH-1H-E430G and IgG1-11B8-E430G led to a clearance rate comparable to that of WT IgG1-CAMPATH-1H and WT IgG1-11B8, respectively (FIG. 16D). All tested combinations of IgG1-CAMPATH-1H variants with IgG1-11B8-variants showed clearance rates that were comparable to that of the combination of the WT IgG1-CAMPATH-1H+IgG1-11B8 antibodies.

Together, these data indicated that anti-CD52 IgG1-CAMPATH-1H with E430G, K439E, E430G-K439E or E430G-K439E-K322E mutations and anti-CD20 IgG1-11B8 with E430G, S440K, E430G-S440K or E430G-S440K-K322E mutations and mixtures thereof, showed clearance rates similar to that of WT IgG1 antibodies.

Example 18: The Effect of G236R, G237T, K326A, or E333S Mutations on the In Vitro FcγR Binding of Anti-CD52 or Anti-CD20 Antibodies with a Hexamerization Enhancing Mutation and K439E or S440K Using purified antibodies, binding of IgG1-CAMPATH-1H or IgG1-11B8 antibody variants to dimeric ECD's of FcγRIIA allotype 131H, FcγRIIA allotype 131R, FcγRIIB, FcγRIIIA allotype 158F, and FcγRIIIA allotype 158V was tested in ELISA assays. To detect binding to dimeric FcγR variants, 96-well Microlon ELISA plates (Greiner, Germany) were coated overnight at 4° C. with goat F(ab')2-anti-human-IgG-F(ab')2 (Jackson Laboratory, 109-006-097, 1 µg/mL) in PBS, washed and blocked with 200 µL/well PBS/0.2% BSA for 1 h at room temperature (RT). With washings in between incubations, plates were sequentially incubated with 100 µL/well of a dilution series of IgG1-CAMPATH-1H or IgG1-11B8 antibody variants (0.0013-20 µg/mL in five-fold steps) in PBST/0.2% BSA for 1 h at RT, 100 µL/well of dimeric, His-tagged, C-terminally biotinylated FcγR ECD variants (1 µg/mL) in PBST/0.2% BSA for 1 h at RT, and with 100 µL/well Streptavidin-polyHRP (CLB, M2032, 1:10.000) in PBST/0.2% BSA as detecting antibody for 30 min at RT. Development was performed for circa 20 (IIA-131H) or 30 (IIA-131R, IIB, IIIA-158V, IIIA-158F) min with 1 mg/mL ABTS (Roche, Mannheim, Germany). To stop the reactions, 100 µL of 2% oxalic acid was added. Absorbances were measured at 405 nm in a microplate reader (BioTek, Winooski, VT). FcγR binding at 20 µg/mL antibody concentration was plotted. Data is based on three independent replicates, normalized per experiment relative to background signal in ELISA (no antibody control, 0%) and an internal standard, IgG1-11B8-E430G-S440K, set to 100%.

Because FcγR-mediated effector functions may be less sensitive to regulation by IgG hexamerization than CDC, full selectivity of cytotoxicity for co-dependent mixtures regulated by hexamerization may require suppression of FcγR binding to each individual antibody in the mixture, particularly in the presence of effector cells expressing FcγR receptors. When mutations G236R or G237T inhibiting C1q binding were introduced into antibody IgG1-CAMPATH-1H-E430G-K439E, binding to FcγR variants IIA, IIB, and IIIA was strongly inhibited, as detected by ELISA (FIG. 17). When mutations K326A or E333S enhancing C1q binding were introduced into IgG1-11B8-E430G-S440K, mutation K326A resulted in increased binding to all FcγR variants tested, while mutation E333S reduced binding to FcγR variants IIA/B and IIIA by ~50 and ~20% respectively (FIG. 17). A further suppression of FcγR-binding to IgG1-11B8-E430G-S440K, IgG1-11B8-K326A-E430G-S440K, or IgG1-11B8-E333S-E430G-S440K may require additional mutations, such as mutation G237A tested in Example 19.

In conclusion, whereas IgG1-11B8-E430G-S440K variants with K326A or E333S mutations retain FcγR-binding, IgG1-CAMPATH-1H-E430G-K439E variants containing G236R or G237T mutations did not show detectable binding to FcγR variants IIA, IIB, and IIIA.

Example 19: Analysis of Different C1q Binding Modulating Mutations for Selective CDC Activity of Mixtures of Anti-CD52 IgG1-CAMPATH-1H-E430G-K439E and Anti-CD20 IgG1-11B8-E430G-S440K-G237A Antibody Variants on Wien 133 Cells In Example 11, it was shown that introduction of the FcγR binding inhibiting mutation G237A in IgG1-11B8-E430G-S440K variants with or without the C1q binding enhancing mutation E333S did not compromise CDC activity at 10 µg/mL IgG when combined with the IgG1-CAMPATH-1H-E430G-K439E variant containing the C1q binding inhibiting mutation G236R. Here, another C1q binding inhibition mutation (G237T) was introduced in IgG1-CAMPATH-1H-

E430G-K439E and tested in combination with IgG1-11B8-E430G-S440K-G237A and IgG1-11B8-E430G-S440K-G237A-E333S. The in vitro CDC assay using Wien 133 cells was performed with 20% NHS and antibody concentration series (final concentration range 0.01-40.0 µg/mL in 3.3-fold dilutions), essentially as described in Example 2. Cell lysis and relative AUC values were calculated from the number of PI-positive cells as described in Example 2, from three experimental replicates. AUC was normalized to the values for negative control antibody IgG1-b12 (0%) and for positive control IgG1-CAMPATH-1H-E430G+IgG1-11B8-E430G (100%), while maximal lysis data presented reflects un-normalized cell lysis at 40 µg/mL IgG.

Figure 18:
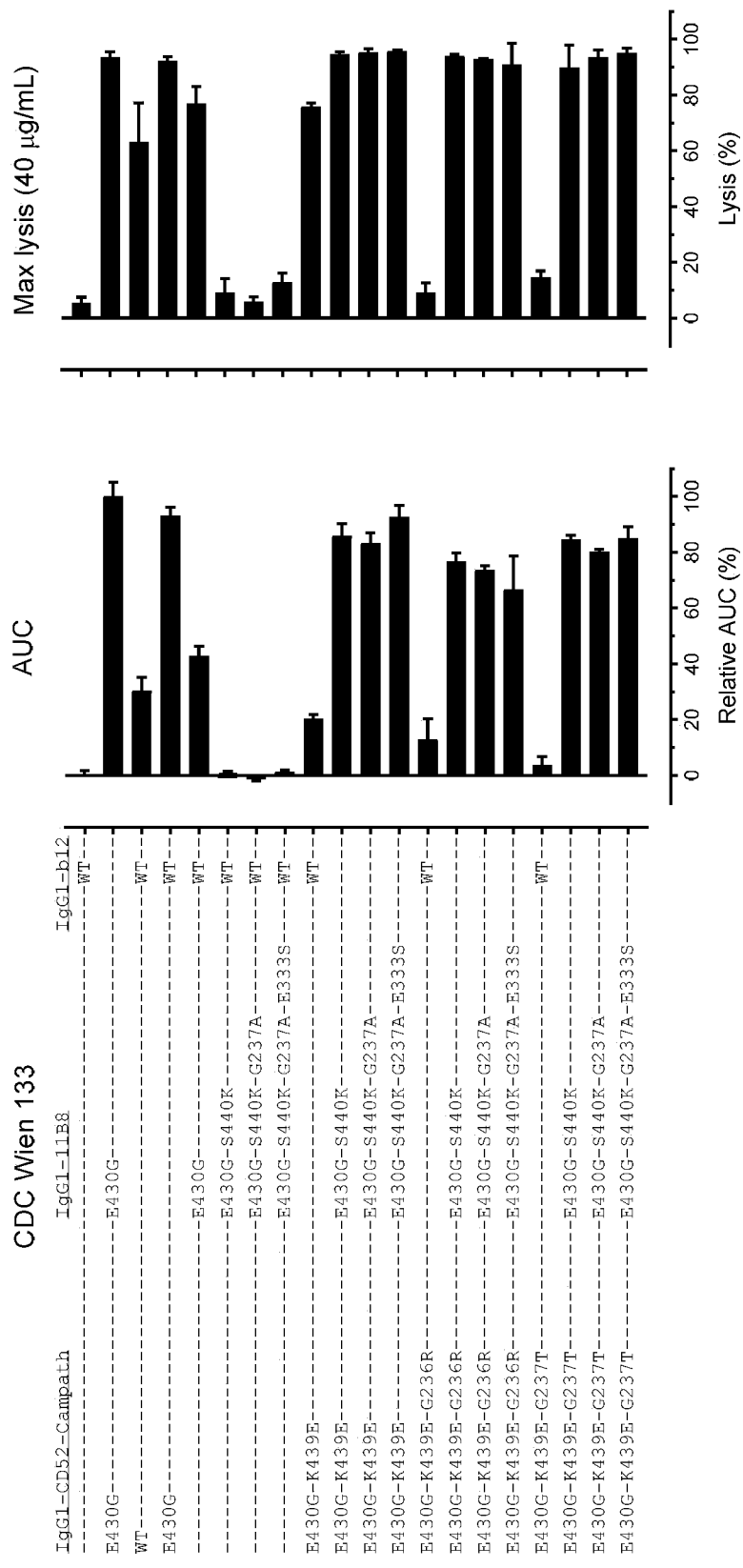
FIG. 18 shows selectivity of CDC activity by mixed antibody variants of anti-CD52 IgG1-CAMPATH-1H-E430G-K439E with or without a C1q binding inhibiting mutation (G236R or G237T)+anti-CD20 IgG1-11B8-E430G-S440K with FcγR binding inhibiting mutation G237A with or without the C1q binding enhancing mutation E333S. Wien 133 cells were incubated with antibody concentration series in the presence of 20% NHS. CDC efficacy is presented as the normalized AUC of the percentage PI-positive cells, and as lysis at 40 µg/mL IgG. Normalization was performed to non-binding control antibody IgG1-b12 (0%) and the mixture of IgG1-CAMPATH-1H-E430G+ IgG1-11B8-E430G (100%).

Because FcγR-mediated effector functions may be less sensitive to regulation by IgG hexamerization than CDC, full selectivity of cytotoxicity for co-dependent mixtures regulated by hexamerization may require suppression of FcγR binding to each individual antibody in the mixture, particularly in the presence of effector cells expressing FcγR receptors. The introduction of mutation G236R and G237T into IgG1-Campath-E430G-K439E strongly suppressed FcγR binding (Example 18), but IgG1-11B8-E430G-S440K showed regular FcγR binding. To suppress FcγR binding of the 11B8 component in the tested mixtures, mutation G237A was introduced into antibody IgG1-11B8-E430G-S440K with or without additional E333S mutation. As shown in FIG. 18, introduction of the C1q binding inhibition mutation G237R or G237T reduced the single agent activity of the IgG1-CAMPATH-1H-E430G-K439E component efficiently, while retaining full CDC activity in combination with IgG1-11B8-E430G-S440K-G237A or IgG1-11B8-E430G-S440K-G237A-E333S on Wien 133 cells.

In conclusion, the selectivity of the CDC activity of the anti-CD52 IgG1-CAMPATH-1H+anti-CD20 IgG1-11B8-G237A antibody variants with Fc-Fc interaction enhancing mutation E430G and the self-oligomerization inhibiting mutation K439E or S440K, respectively, was increased by introduction of the C1q binding inhibiting mutation G236R or G237T in the anti-CD52 K439E component. Introduction of the C1q binding enhancing mutation E333S in the 11B8 variant did not increase the recovery of CDC activity in the combinations, as maximal recovery of complement activity was already achieved with IgG1-11B8-E430G-S440K-G237A (with G237A for FcγR binding inhibition).

Example 20: Depletion of a Subset of Hematological Cells by Co-Dependent Antibody Combinations In Example 19, CDC activity was shown on Wien 133 cells for mixtures of anti-CD52 and anti-CD20 antibody variants designed to work in co-dependent fashion. The specificity of co-dependent antibody mixtures was tested in whole blood cytotoxicity assays. CD52 is expressed on both T-cells and B-cells, while CD20 is expressed on B-cells, but not substantially on T-cells. A mixture of independently acting CD52 and CD20 targeting antibodies would therefore be expected to eliminate both T-cells and B-cells, while a strictly-co-dependent Ab mixture would be expected to exclusively deplete B-cells, since they express both CD52 and CD20. The aim of the experiment was therefore to test which mixtures of anti-CD52 and anti-CD20 antibody variants could deplete B-cells without affecting the T-cell population.

Anonymous hirudin-treated blood samples were obtained at the University Medical Center Utrecht. During the first day, mixtures of CD52, CD20 and gp120 directed antibodies were prepared in RPMI 1640 medium supplemented with 0.2% BSA. Antibodies were transferred to plates containing 30 µL hirudin-treated blood in RPMI/0.2% BSA in an end volume of 100 µL, at a final antibody concentration of 10 µg/mL, and incubated at 37° C. and 5% CO2 for 18 hours. The second day, an equal volume of red blood cell (RBC) lysis buffer was added to the mixtures, after which the cells were collected by centrifugation (3 minutes at 300 rcf). This step was repeated until all red blood cells were lysed, which was assessed by the transparency of the mixture.

Subsequently, a mixture of detection antibodies directed against different hematological subsets labeled with fluorescent dyes was added and the mixtures were incubated for 30 minutes at 4° C. After three washing steps performed with FACS buffer, cells were re-suspended in FACS buffer and the relative abundances of remaining cell populations were determined by flow cytometry using an LSR Fortessa X20 FACS (BD). In parallel, the procedures for the staining of compensation control beads (UltraComp eBeads, Thermo Scientific cat. nr. 01-2222) using individual immuno-detection reagents or fixable viability stain (FVS) were performed and detected by flow cytometry. All steps were performed on ice. Detection reagents used were anti-CD3 labeled with efluor 450 (e-biosciences cat. nr. 48-0037), CD19 labeled with BV711 (Biolegend cat. nr. 302245), CD66b labeled with PE-Cy7 (Biolegend cat. nr. 305115), and FVS viability stain BV510 (BD cat. nr. 564406). In brief, viable cells were gated by exclusion of FVS positive cells and doublets. Within the viable cell population, myeloid cells were gated by $CD66b^{high}$ expression, while lymphoid cells were separated into T-cells by $CD3^{high}/CD19^{low}/CD66b^{low}$ expression and B-cells by $CD3^{low}/CD19^{high}/CD66b^{low}$ expression; the remaining $CD3^{low}/CD19^{low}/CD66b^{low}$ lymphoid cells may contain NK-cells, but were not further characterized in these experiments. Blood samples of five different healthy donors were tested in three independent experiments.

Figure 19A:
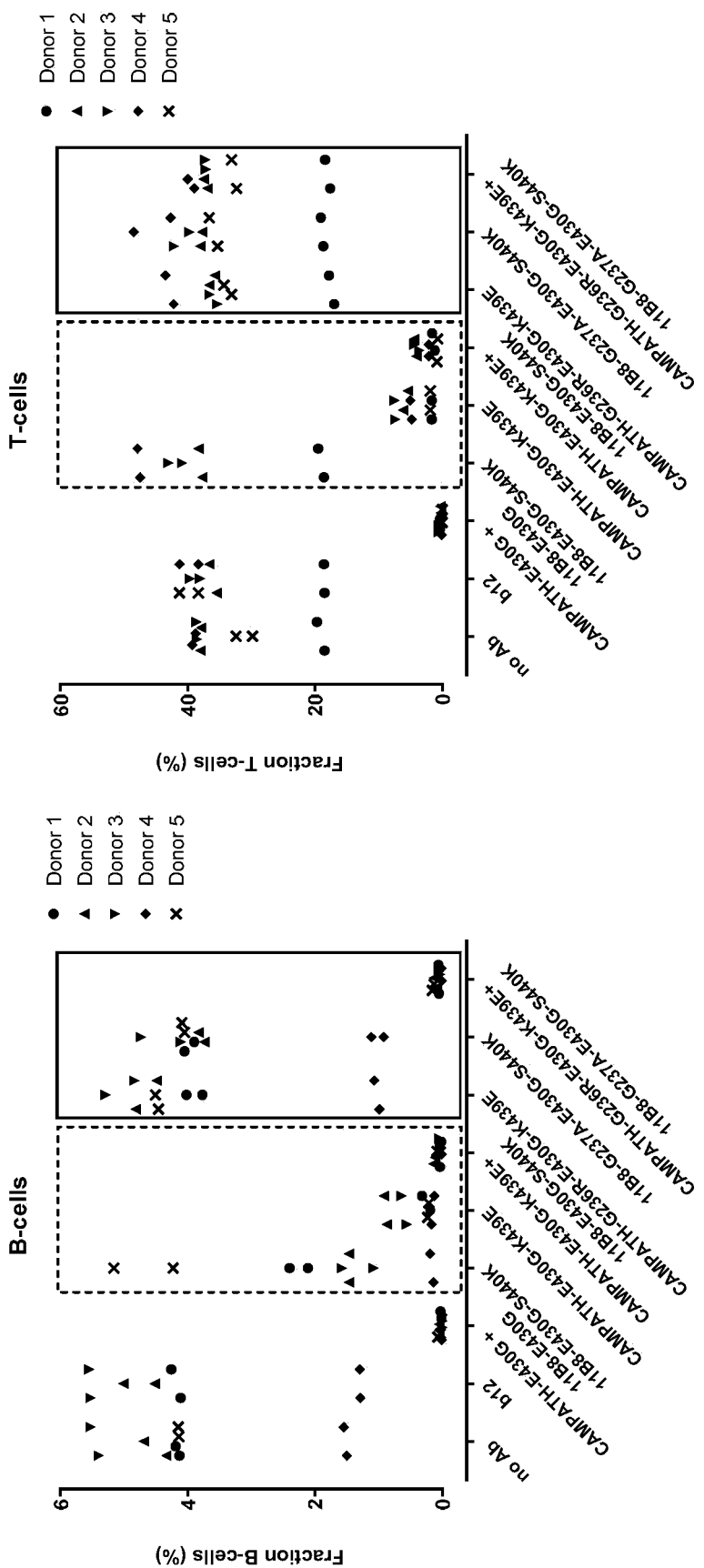
FIGS. 19A-19D show selective activity of combinations of variants of IgG1-CAMPATH-1H and IgG1-11B8 in whole blood, determined by flow cytometry analysis of blood cells. Y-axes: Fraction B-cells (CD19-positive/CD3-negative), or Fraction T-cells (CD19-negative/CD3-positive) of total lymphocyte population (CD66b-negative), after o/n incubation in the presence of effector cells. X-axes: different treatment groups. Symbols represent cells from five different healthy donors, tested in two separate incubations per donor.

In contrast to CDC assays on tumor cell lines, whole blood assays are performed in the presence of FcγR-expressing effector cells that can mediate ADCC and ADCP, so the depletion of blood cells can be mediated by different effector mechanisms besides CDC. Because FcγR-mediated effector functions may be less sensitive to IgG hexamerization than CDC, additional suppression of FcγR-mediated effector functions may be required to make cytotoxicity co-dependent on the binding of two hetero-hexamer forming antibody reagents in close proximity. The relative abundance of B-cells and T-cells within the lymphocyte population ranged from approximately 1.5-6% and 20-40% respectively, in different donors (FIG. 19A). Indeed, a mixture of CD52-directed IgG1-Campath-1H-E430G and CD20-directed IgG1-11B8-E430G depleted all T-cells (expressing CD52) and B-cells (expressing CD52 and CD20). A mixture of IgG1-Campath-1H-E430G-K439E+IgG1-11B8-E430G-S440K, based on the mutations disclosed in WO2013004842 was not co-dependent in this assay setup (FIG. 19A). IgG1-Campath-1H-E430G-K439E displayed substantial single agent activity on both B-cells and T-cells, which may be explained both by FcγR-mediated activity and by residual CDC activity as observed on tumor cell lines at high IgG concentrations (Example 4). IgG1-11B8-E430G-S440K displayed single agent activity on B-cells, likely explained by FcγR-mediated activity. Indeed, the mixture of IgG1-Campath-1H-E430G-K439E+IgG1-11B8-E430G-S440K caused substantial depletion of both B-cells and T-cells. In stark contrast, a mixture of IgG1-Campath-1H-G236R-E430G-K439E+IgG1-11B8-G237A-E430G-S440K showed selective depletion of only B-cells, not T-cells, in a stringently co-dependent fashion (FIG. 19A). Indeed, IgG1-Campath-1H-G236R-E430G-K439E did not show appreciable single agent activity on either B- or T-cells, demonstrating that the introduction of mutation G236R eliminated both FcγR-mediated activity, as expected from example 18, in addition to suppressing single agent CDC activity as observed in e.g. previous examples 5, 7, and 19. The introduction of mutation G237A present in IgG1-11B8-G237A-E430G-S440K eliminated residual single agent activity on B-cells, most likely by a suppression of residual FcγR-mediated activity.

Figure 19B:
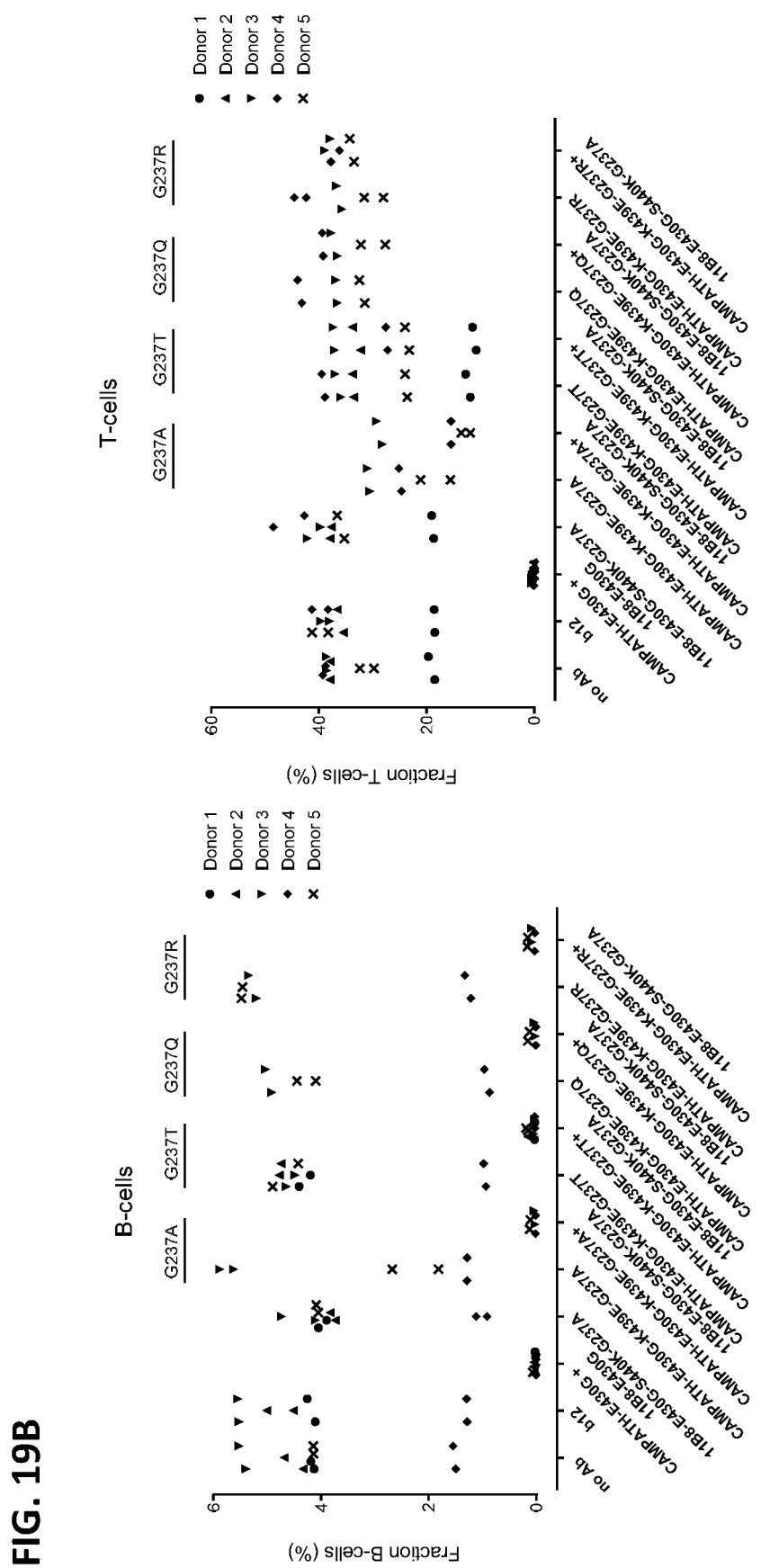

Variants of IgG1-CD52-Campath-E430G-K439E containing additional mutations at position G237, i.e. G237A, G237T, G237Q, or G237R, displayed varying levels of single agent activity (FIG. 19B). Variants IgG1-CD52-Campath-G237A-E430G-K439E and IgG1-CD52-Campath-G237T-E430G-K439E induced a reduction of the number of T-cells as single agents. In contrast, variants IgG1-CD52-Campath-G237Q-E430G-K439E and IgG1-CD52-Campath-G237R-E430G-K439E did not show appreciable single agent activity, neither on B-cells, nor on T-cells. When IgG1-11B8-G237A-E430G-S440K, devoid of single agent activity, was mixed with IgG1-CD52-Campath-G237Q-E430G-K439E, or with IgG1-CD52-Campath-G237R-E430G-K439E, a potent and selective depletion of B-cells, not T-cells was observed (FIG. 19B).

Figure 19C:
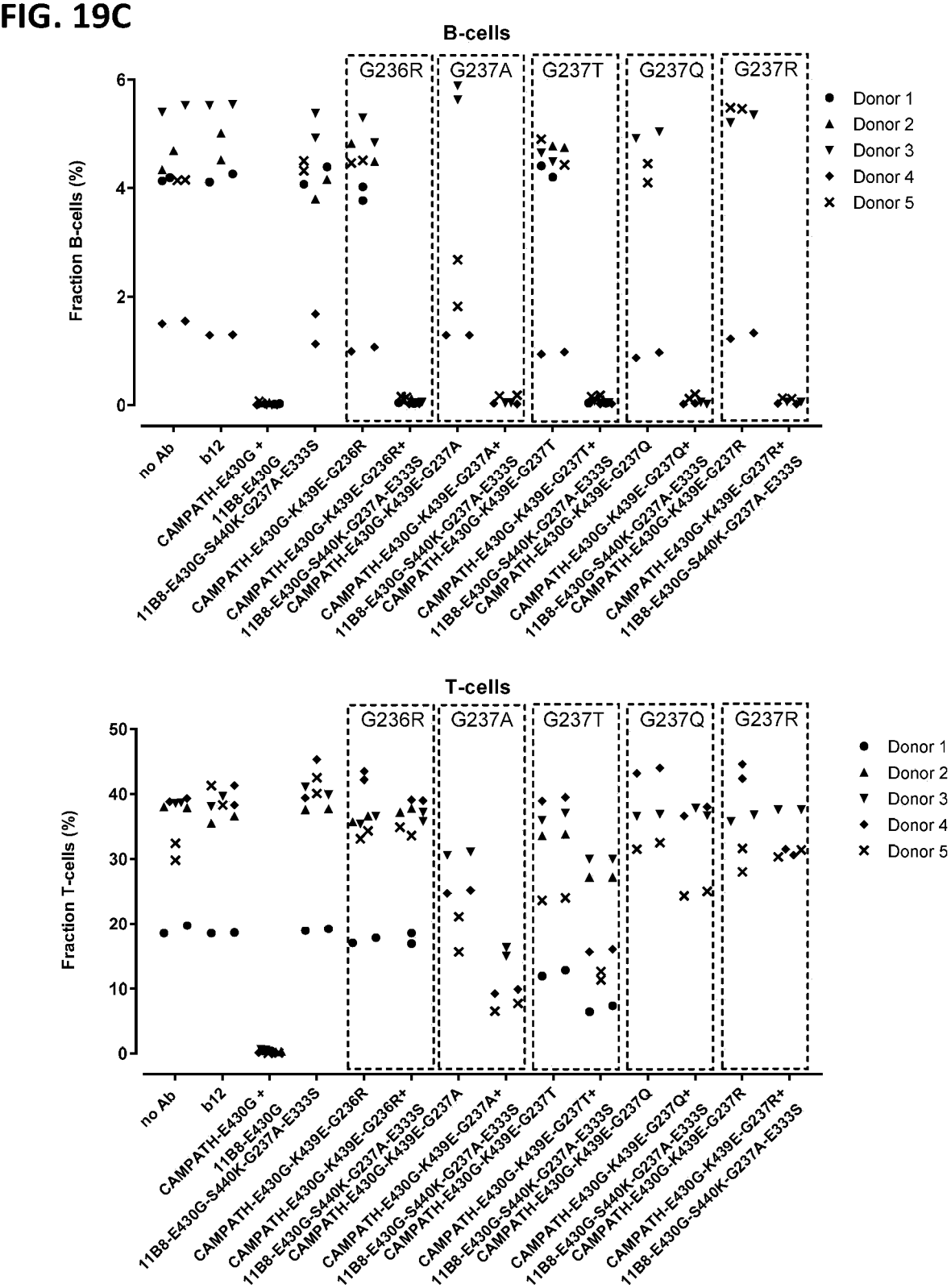

Similar results were obtained in the presence of IgG1-11B8-G237A-E333S-E430G-S440K containing mutation E333S enhancing C1q affinity: this component did not show appreciable single agent activity on B-cells nor on T-cells, while mixing with IgG1-CD52-Campath-G236R-E430G-K439E, IgG1-CD52-Campath-G237Q-E430G-K439E, or IgG1-CD52-Campath-G237R-E430G-K439E resulted in a potent and selective depletion of B-cells, not T-cells (FIG. 19C). In contrast, when IgG1-11B8-G237A-E333S-E430G-S440K was mixed with IgG1-CD52-Campath-G237A-E430G-K439E or IgG1-CD52-Campath-G237T-E430G-K439E, detectable T-cell depletion was observed (FIG. 19C), consistent with the results in FIG. 19B.

Figure 19D:
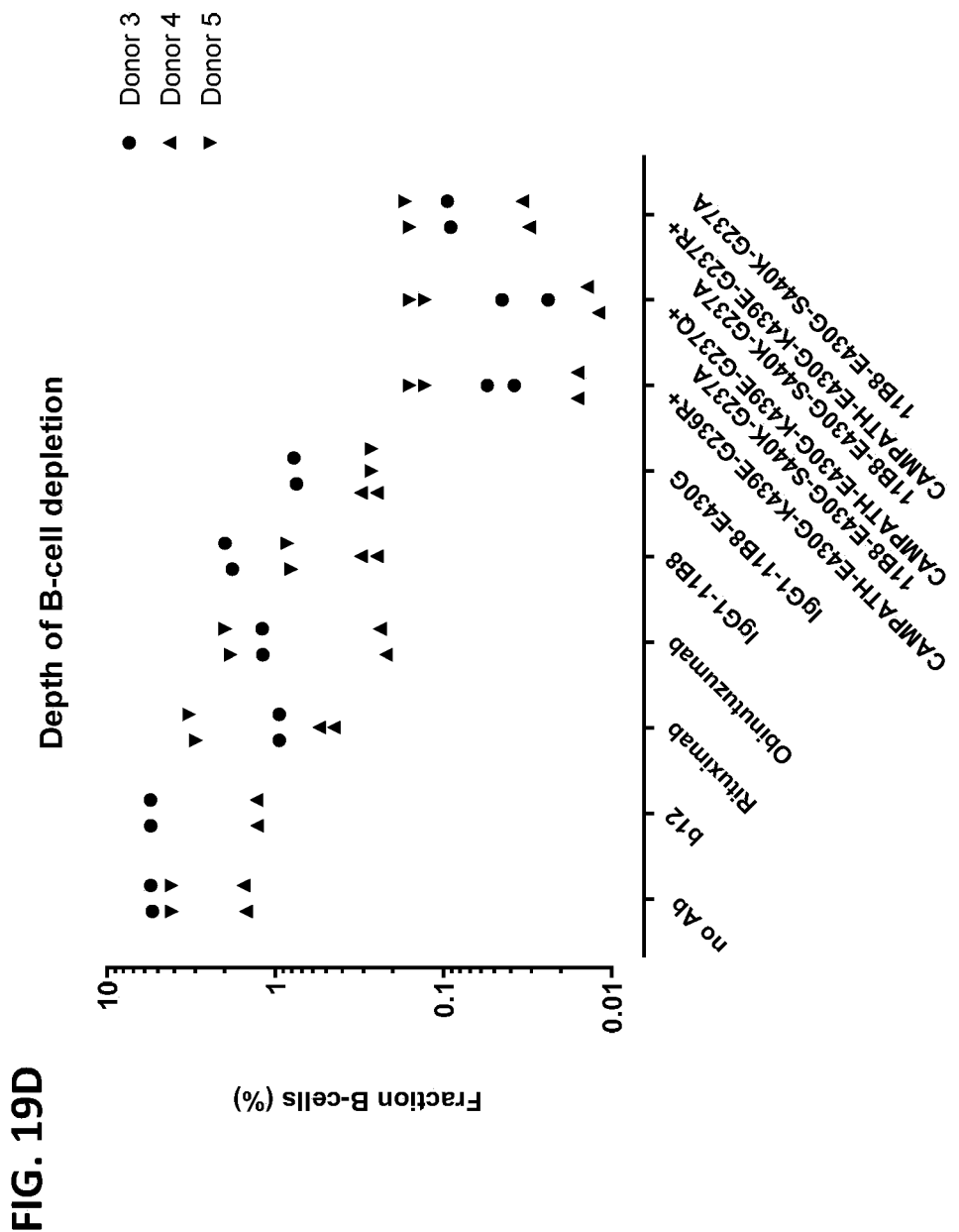

The potency of co-dependent antibody mixtures targeting B-cells expressing both CD52 and CD20 was also compared to independently B-cell targeting antibodies rituximab, obinutuzumab, IgG1-11B8 and IgG1-11B8-E430G. Interestingly, the depth of B-cell depletion of strictly co-dependent antibody mixtures targeting both CD52 and CD20 exceeded that by rituximab, obinutuzumab, IgG1-11B8 and IgG1-11B8-E430G (FIG. 19D). This was true for the mixtures of IgG1-11B8-G237A-E430G-S440K with IgG1-CD52-Campath-G236R-E430G-K439E, IgG1-CD52-Campath-G237Q-E430G-K439E, or IgG1-CD52-Campath-G237R-E430G-K439E, all of which showed selective depletion of B-cells, not T-cells (FIGS. 19A/B).

In conclusion, these data demonstrated that combinations of two antibodies targeting two different cell surface targets could be forced to work in a strictly co-dependent fashion. As a consequence, the selective depletion of a hematological subset, here B-cells expressing CD20, was achieved from the total population of CD52 expressing cells. These strictly co-dependent antibody combinations were composed of one antibody with Fc-domain mutations E430G and K439E in addition to mutation of G236R, G237Q, or G237T, and one antibody with Fc-domain mutations G237A, E430G, and S440K, with optional additional mutation E333S.

Example 21: Enhanced Selectivity of CDC Activity on Multiple Cell Lines by Mixed Antibody Variants by Introduction of the C1q Binding Inhibition Mutations G236R or G237T in Anti-CD52 IgG1-CAMPATH-1H-E430G K439E when Combined with an Anti-CD20 IgG1-11B8-E430G-S440K Variant In previous examples, enhanced selectivity of CDC activity was shown by introduction of C1q binding inhibiting mutations in IgG1-CAMPATH-1H-E430G-K439E (K322E in Example 3, G236R or G237T in Example 19) in the combination with IgG1-11B8-E430G-S440K antibody variants with or without C1q binding enhancing mutation(s) E333S and/or FcγR binding inhibiting mutation G237A. Here, the selectivity of CDC activity on CD20/CD52 double positive cells after introduction of the C1q binding inhibiting mutations G236R or G237T into IgG1-CAMPATH-1H-E430G-K439E was tested on human tumor cell lines with different expression levels of CD52 and CD20 (see Table 4 below). In vitro CDC assays using Daudi, Raji, Ramos, REH and U-698-M cell lines were performed with 20% NHS and antibody concentration series (final concentration range 0.01-40.0 μg/mL in 3.3-fold dilutions), essentially as described in Example 2. Cell lysis and relative AUC values were calculated from the number of PI-positive cells as described in Example 2, from three experimental replicates. AUC was normalized to the values for negative control antibody IgG1-b12 (0%) and for positive control IgG1-CAMPATH-1H-E430G+IgG1-11B8-E430G (100%), while maximal lysis data presented reflects un-normalized cell lysis at 40 μg/mL IgG.

TABLE 4

CD20 and CD52 expression levels on different cell lines

| Antibody (target) | ABC* | | | | |
|---|---|---|---|---|---|
| | Daudi | Raji | Ramos | REH | U-698-M |
| IgG1-CAMPATH-1H (CD52) | $1.0 \times 10^4$ | $1.3 \times 10^5$ | $2.7 \times 10^5$ | $1.9 \times 10^5$ | $1.4 \times 10^5$ |
| IgG1-11B8 (CD20) | $1.7 \times 10^5$ | $1.7 \times 10^5$ | $1.1 \times 10^5$ | $1.9 \times 10^4$ | $1.0 \times 10^5$ |

*ABC antibody Binding Capacity as determined by QIFIKIT analysis (data not shown)

Figure 20A:
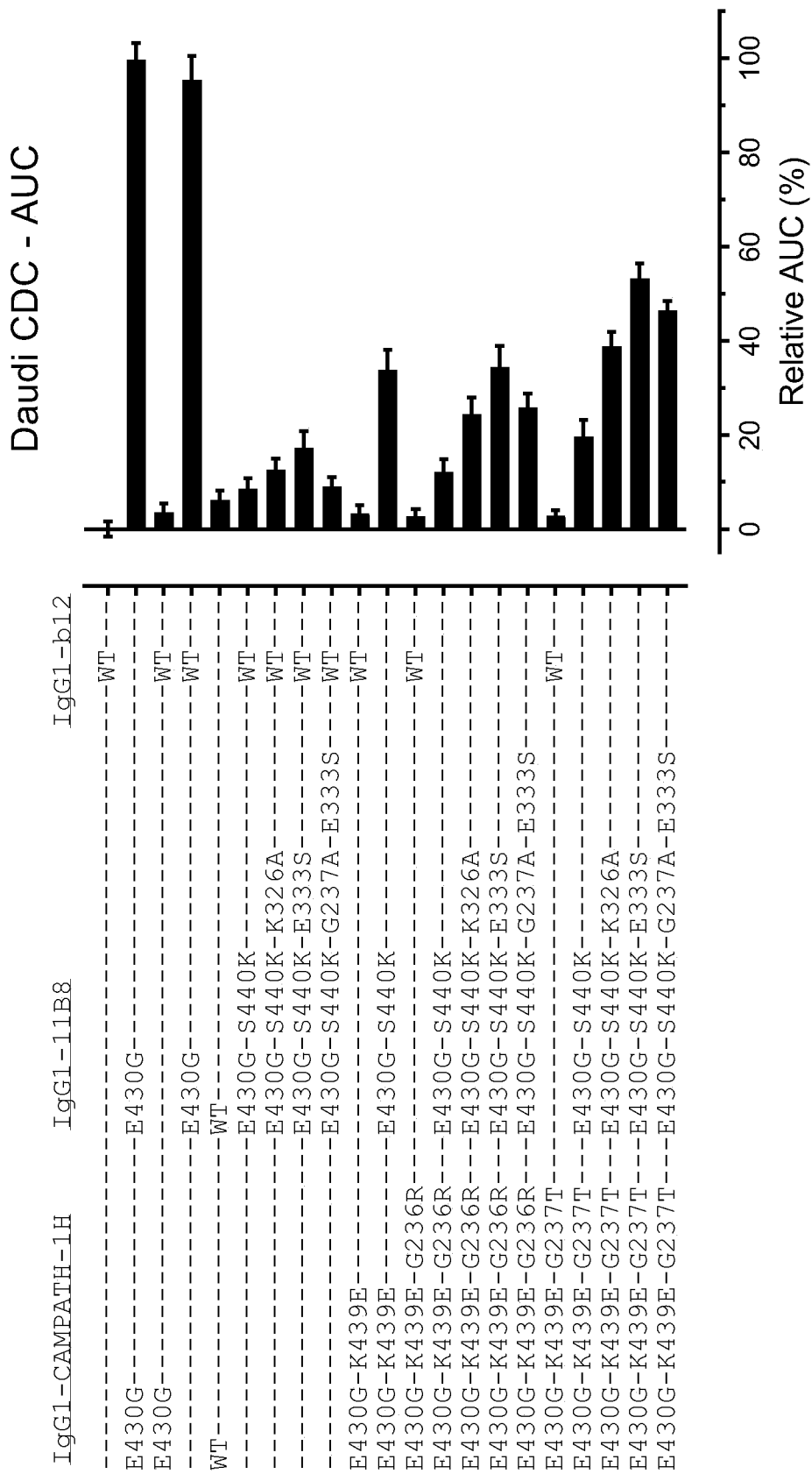
FIGS. 20A-20E show selectivity of CDC activity on different cell lines with different expression levels of CD20 and CD52 by the combination of IgG1-CAMPATH-1H-E430G-K439E and IgG1-11B8-E430G-S440K antibody variants with a C1q binding inhibiting mutation in the anti-CD52 component and a C1q binding enhancing mutation in the anti-CD20 component. In vitro CDC assays were performed with 0.01-40 µg/mL antibody in the presence of 20% NHS using Burkitt's lymphoma cell lines Daudi (FIG. 20A), Raji (FIG. 20B) and Ramos (FIG. 20C), ALL cell line REH (FIG. 20D), and B cell lymphoma cell line U-698-M (FIG. 20E). CDC efficacy is presented as the normalized AUC of the percentage PI-positive cells and as maximal lysis. Normalization was performed to non-binding control antibody IgG1-b12 (0%) and the mixture of IgG1-CAMPATH-1H-E430G+IgG1-11B8-E430G (100%).
Figure 20A:
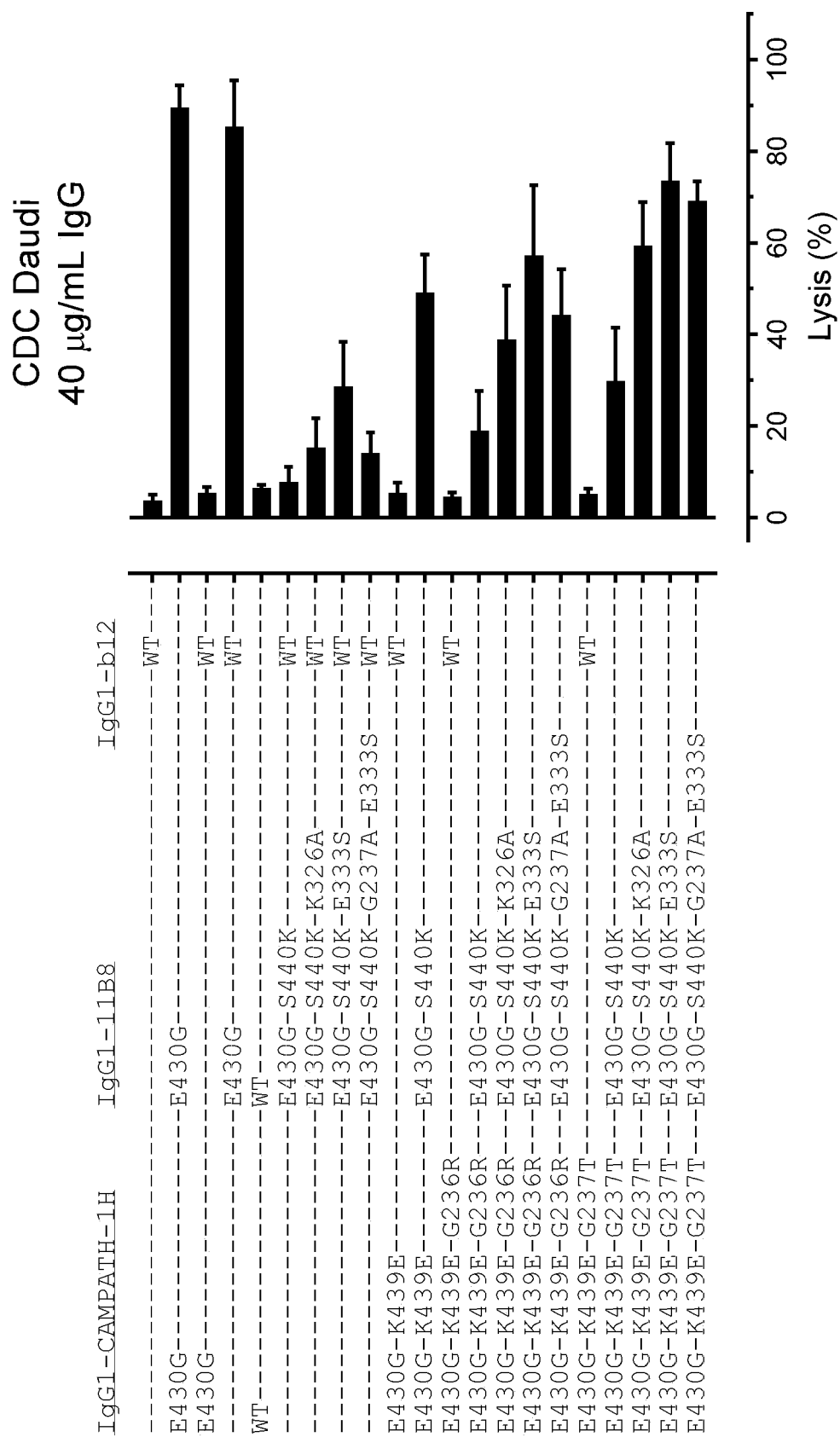
Figure 20B:
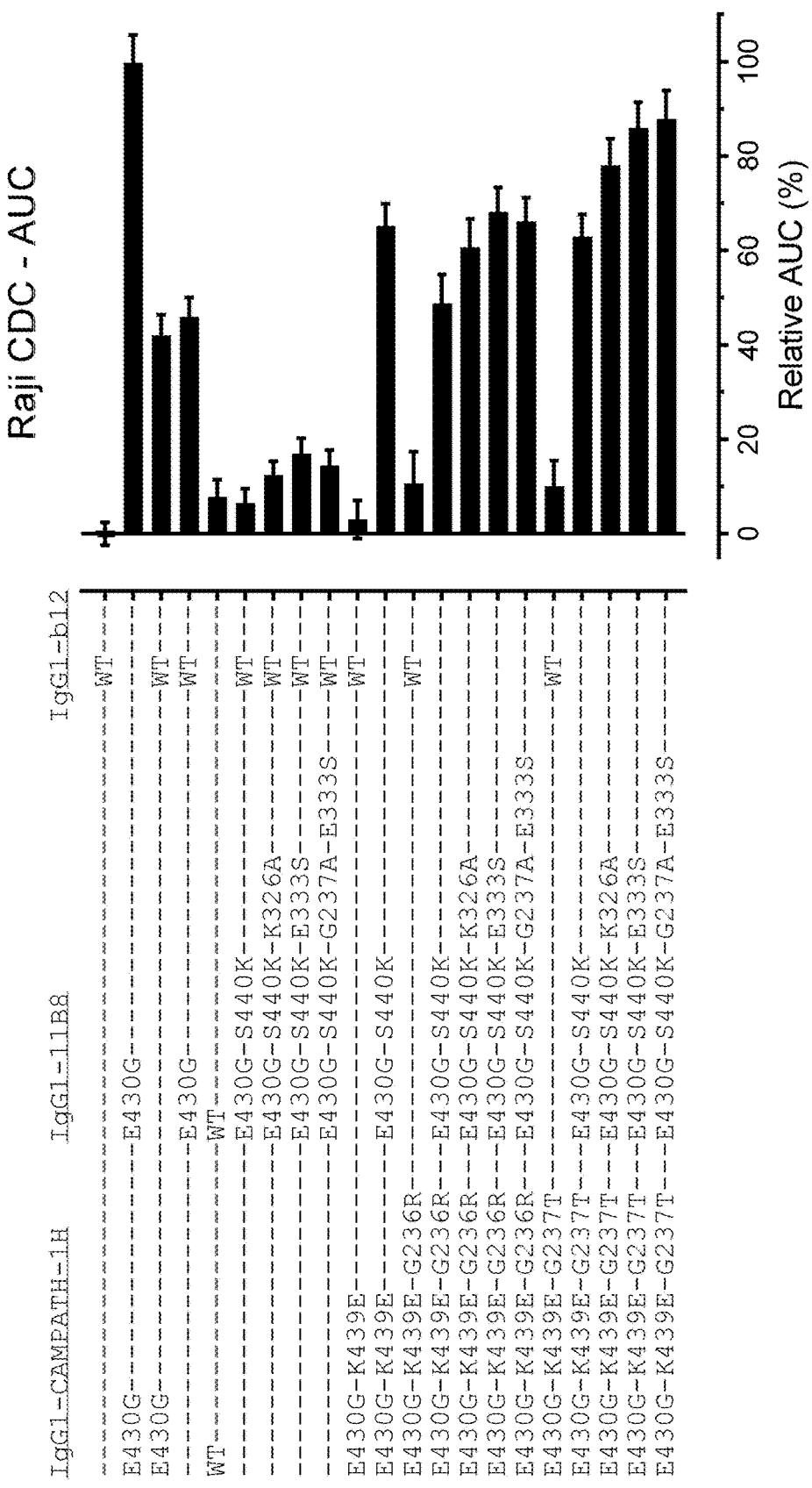
Figure 20B:
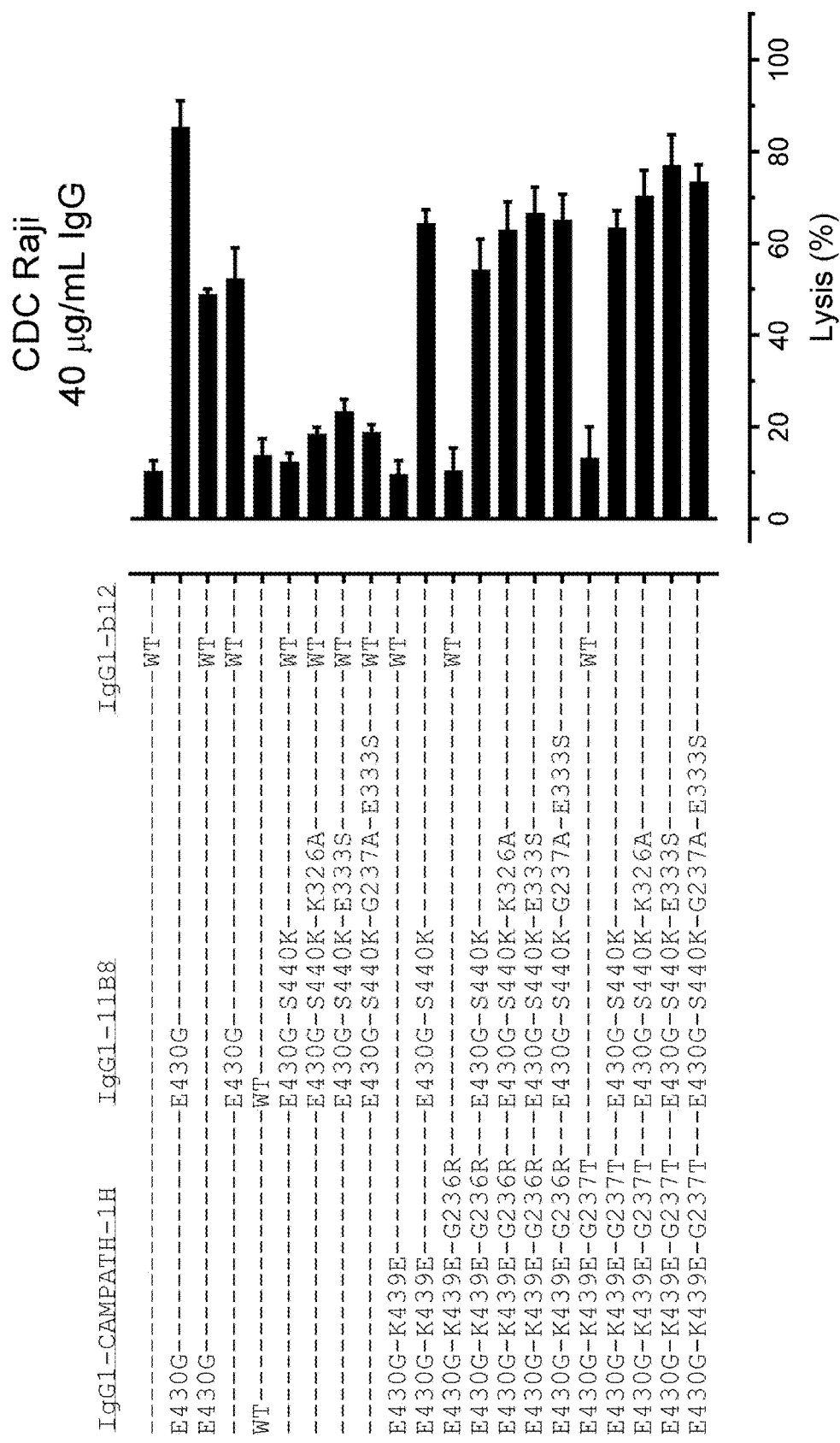
Figure 20C:
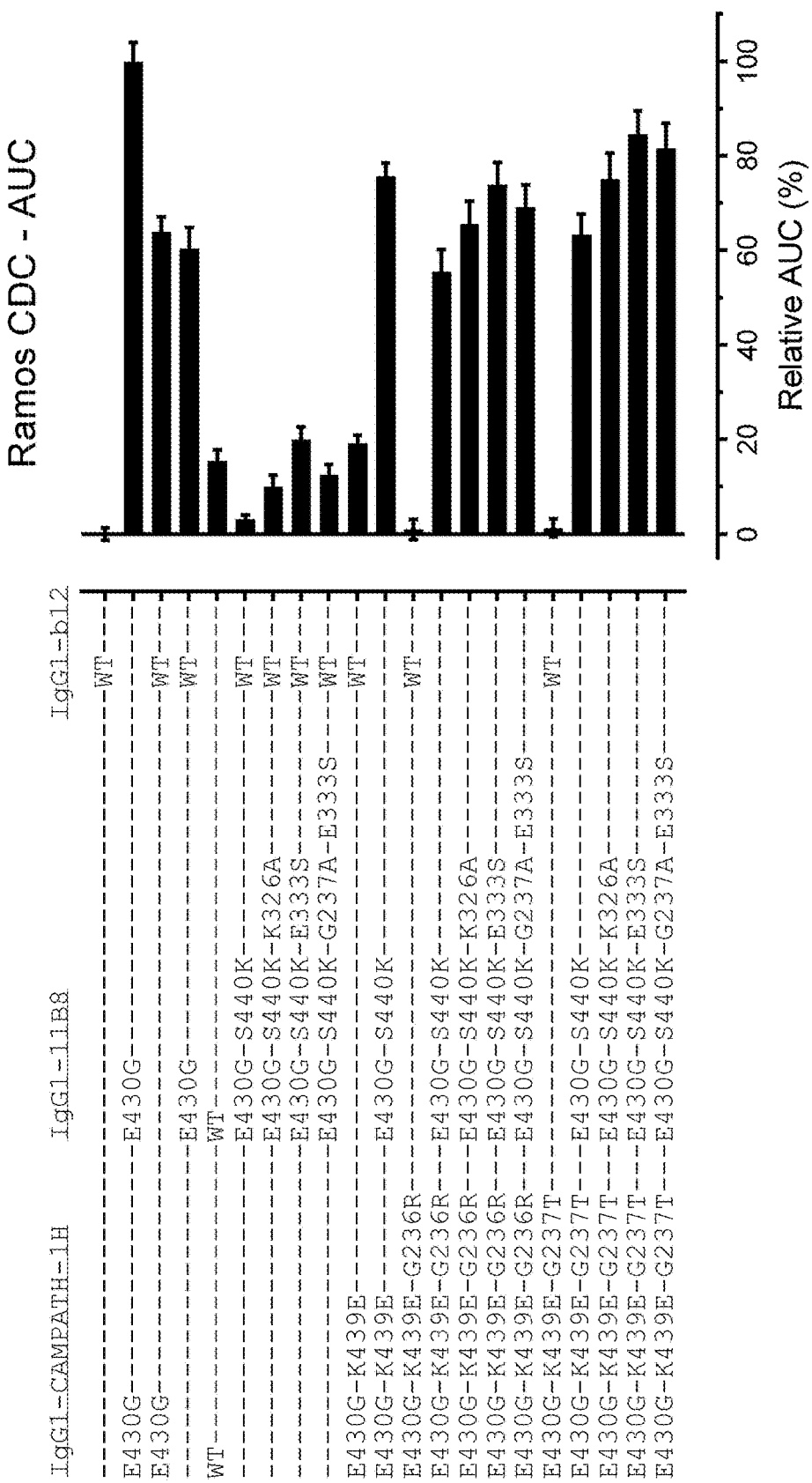
Figure 20C:
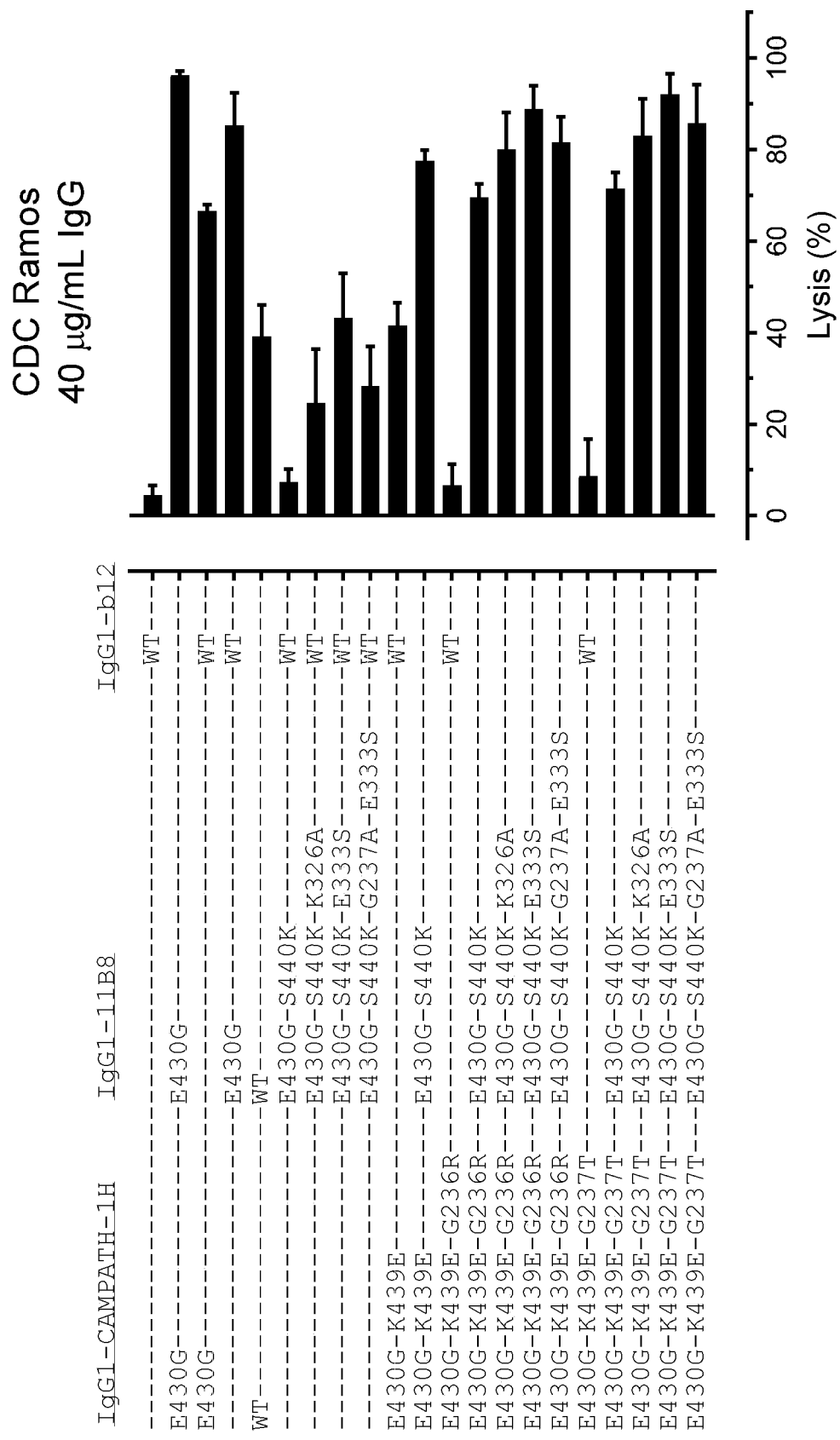
Figure 20D:
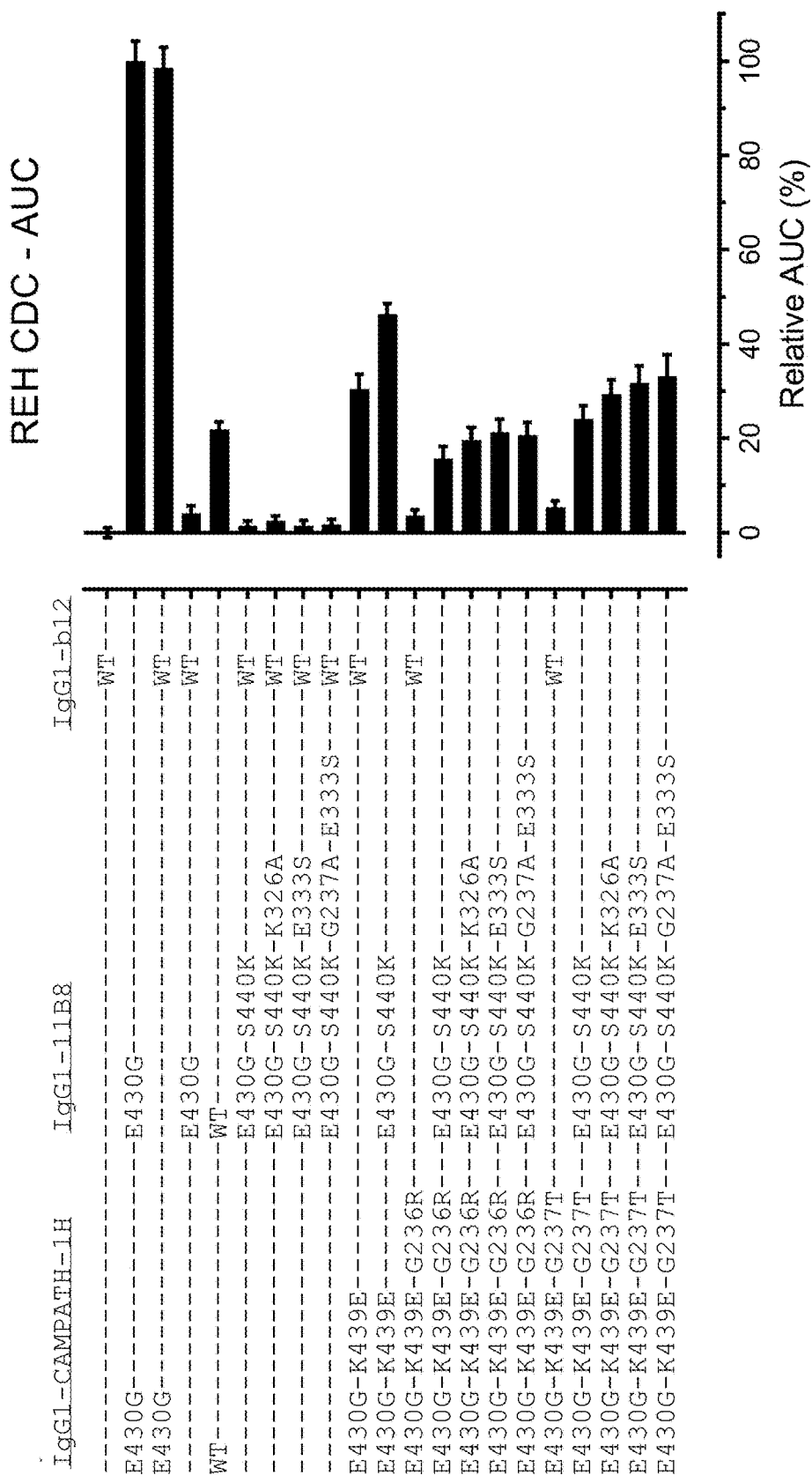
Figure 20D:
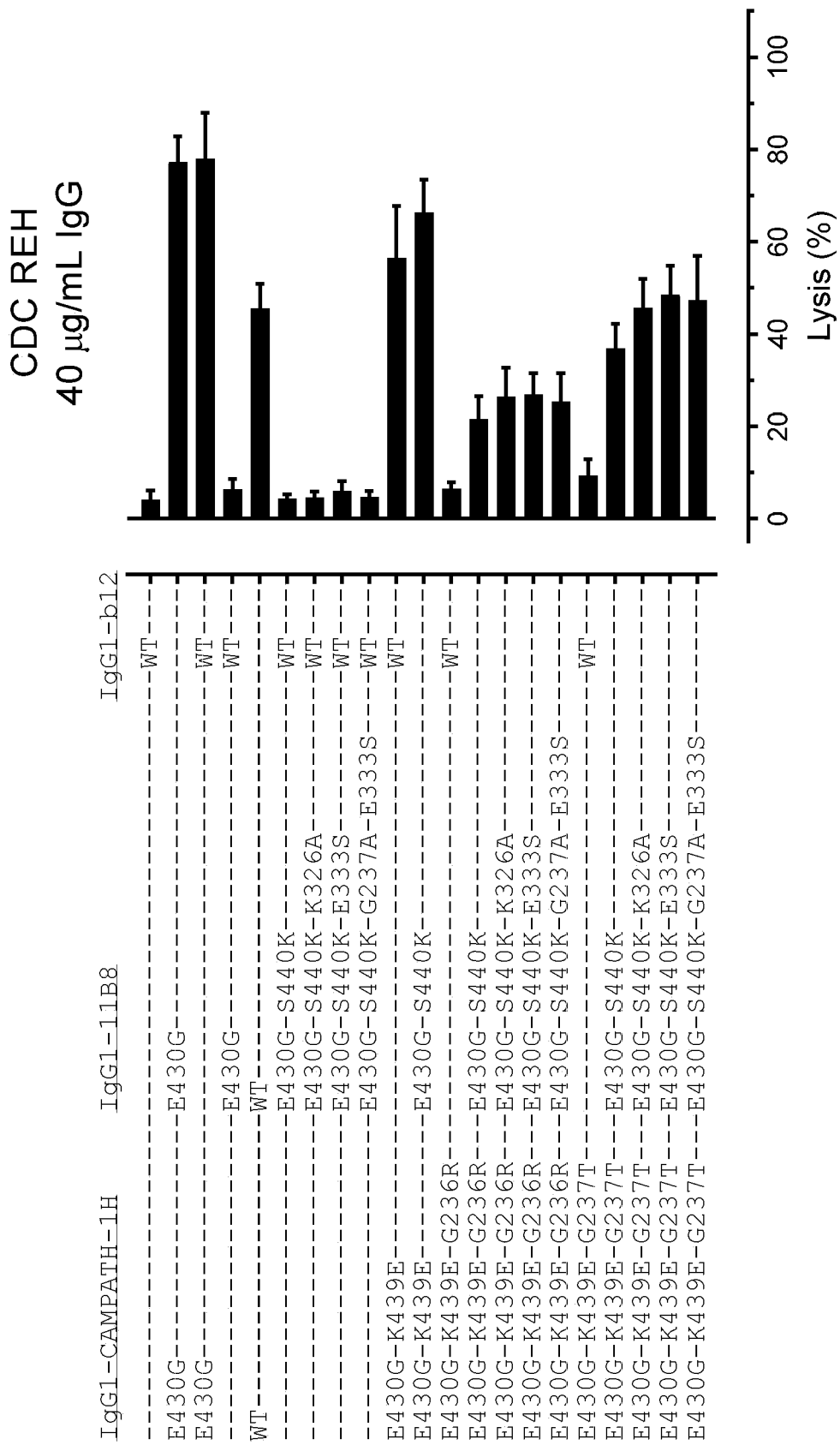
Figure 20E:
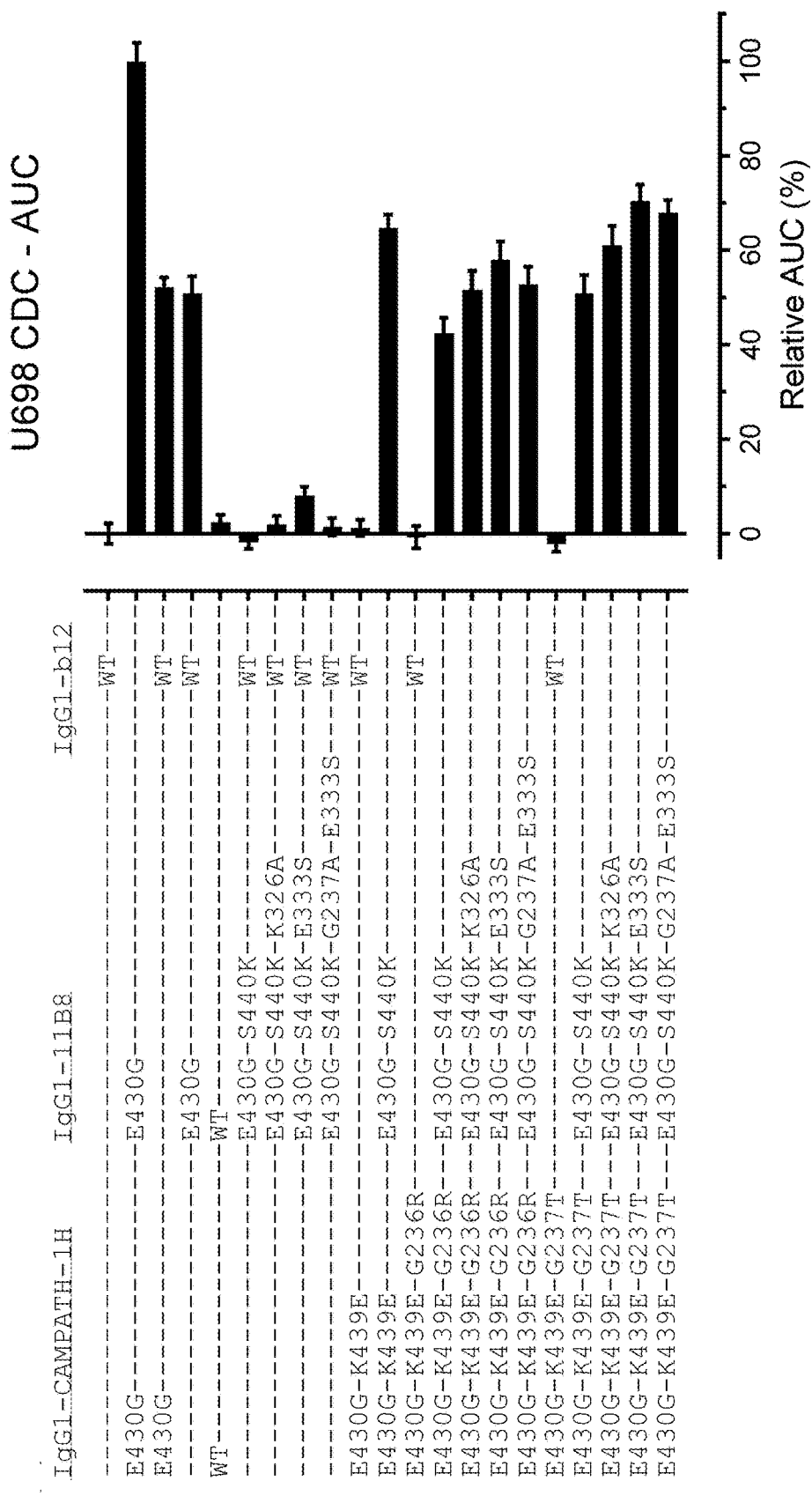
Figure 20E:
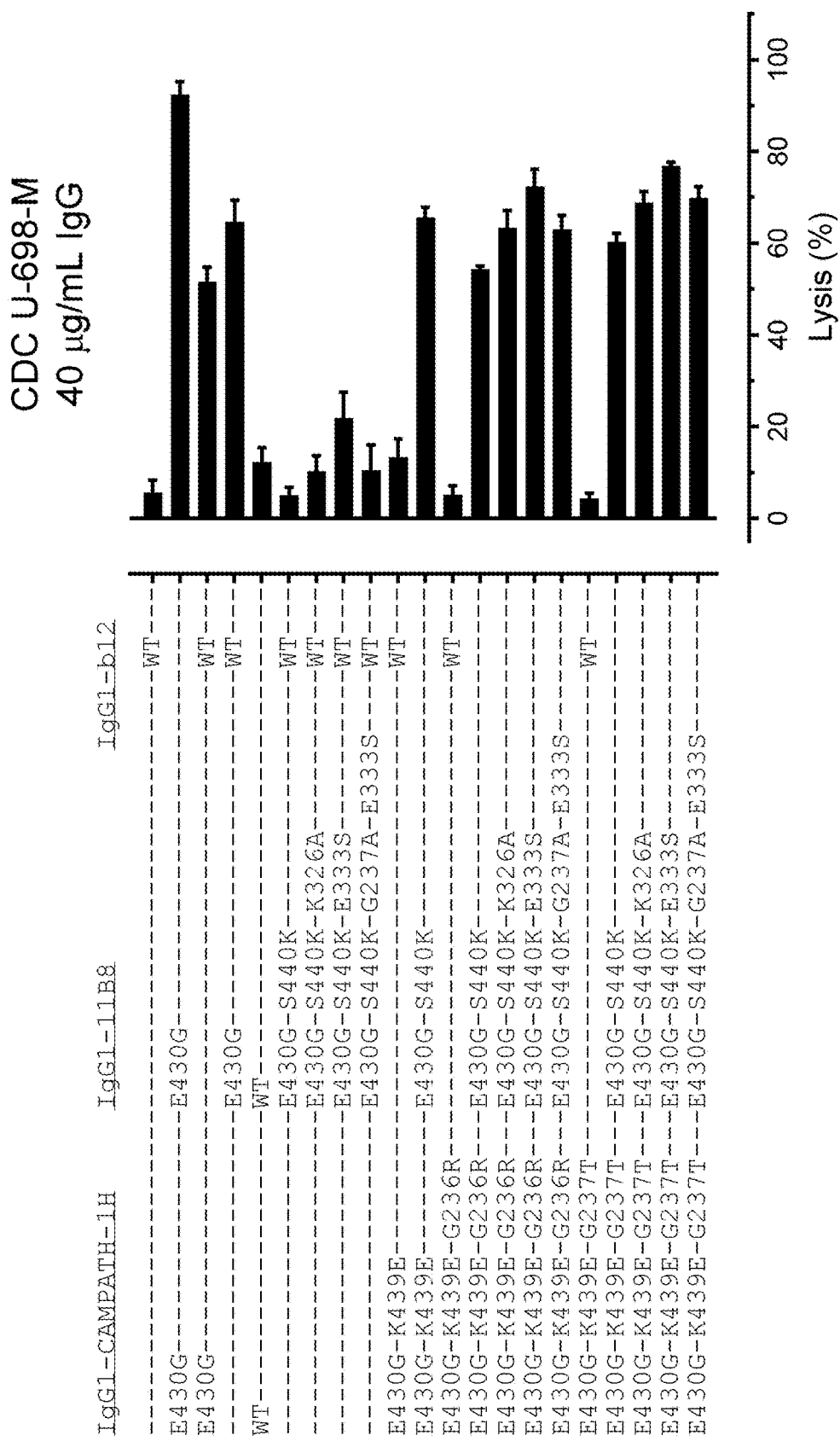

The IgG1-CAMPATH-1H-E430G-K439E variants with the C1q binding inhibition mutation G237R or G237T showed no single agent activity (comparable to background levels) on all tested cell lines with different CD52 expression levels: Daudi (FIG. 20A), Raji (FIG. 20B), Ramos (FIG. 20C), REH (FIG. 20D) and U-698-M (FIG. 20E). For cell lines Daudi, Ramos, Raji, and U-698-M, increased recovery of CDC activity was observed when combined with IgG1-11B8-E430G-S440K antibody variants with the tested C1q binding enhancing mutation E333S (with or without FcγR inhibiting mutation G237A) or K326A. The effect of C1q enhancing mutations K326A or E333S in CD20 targeted 11B8 was less prominent when CD20 expression levels were lower (REH: 19,000 ABC CD20). Consistent with target expression levels, CDC of low CD20 expressing cell line REH was highly dependent on the presence of a CD52-targeting agent, while CDC of low CD52 expressing cell line Daudi was highly dependent on the presence of a CD20 targeting agent. Indeed, the CDC AUC and maximal lysis induced by IgG1-G236R-E430G-K439E+IgG1-11B8-E430G-S440K on cell lines REH and Daudi was substantially lower than that induced by the combination of IgG1-Campath-1H-E430G+IgG1-11B8-E430G, illustrating the relative selectivity of this mixture for CD20/CD52 double-positive cell lines Ramos, Raji and U-698-M. The CDC sensitivity of low CD52 expressing Daudi cells was modulated by the presence of C1q enhancing mutation K326A, E333S, or G237A-E333S introduced in the CD20 targeting agent.

In conclusion, selectivity of CDC activity for the combination of IgG1-CAMPATH-1H-E430G-K439E and IgG1-11B8-E430G-S440K could be established independent of the target expression levels in different cell lines by introduction of a C1q binding inhibiting mutation such as G236R or G237T in the anti-CD52 E430G-K439E component; the potency of the mixture was modulated by introduction of a C1q binding enhancing mutation such as E333S or K326A in the anti-CD20 E430G-S440K component.

Example 22: Selectivity of CDC Activity by Mixtures of Anti-CD37 IgG1-CD37-37.3 Antibody Variants and Anti-CD20 IgG1-11B8 Antibody Variants on Cell Lines with Different Target Expression Levels In previous examples, selective CDC activity was shown for combinations of anti-CD52 with anti-CD20 antibody variants (Example 7, Example 11, Example 12) and anti-CD52 with anti-CD37 antibody variants (Example 14). Here, selective CDC activity was tested for a combination of anti-CD37 antibody variants with anti-CD20 antibody variants in in vitro CDC assays using Daudi and WIL2-S cells. The in vitro CDC assays using Daudi and B lymphoblast WIL2-S cells (ATCC, CRL-8885) were performed with 20% NHS and antibody concentration series (final concentration range 0.005-10.0 µg/mL in 3-fold dilutions), essentially as described in Example 2. Culture medium for the WIL2-S cells was composed of RPMI 1640 with 25 mM Hepes and L-Glutamine (Lonza, Cat No BE12-115F) supplemented with +10% heat inactivated DBSI, 1 mM Sodium Pyruvate (Lonza, Cat No. BE13-115E) and 50 U/mL Pen/Strep. Cell lysis was calculated from the number of PI-positive cells, averaged from three experimental replicates and normalized to the cell lysis measured for negative control antibody IgG1-b12 (0%) and for 10 µg/mL IgG1-CAMPATH-1H-E430G+IgG1-11B8-E430G (100%).

Figure 21A:
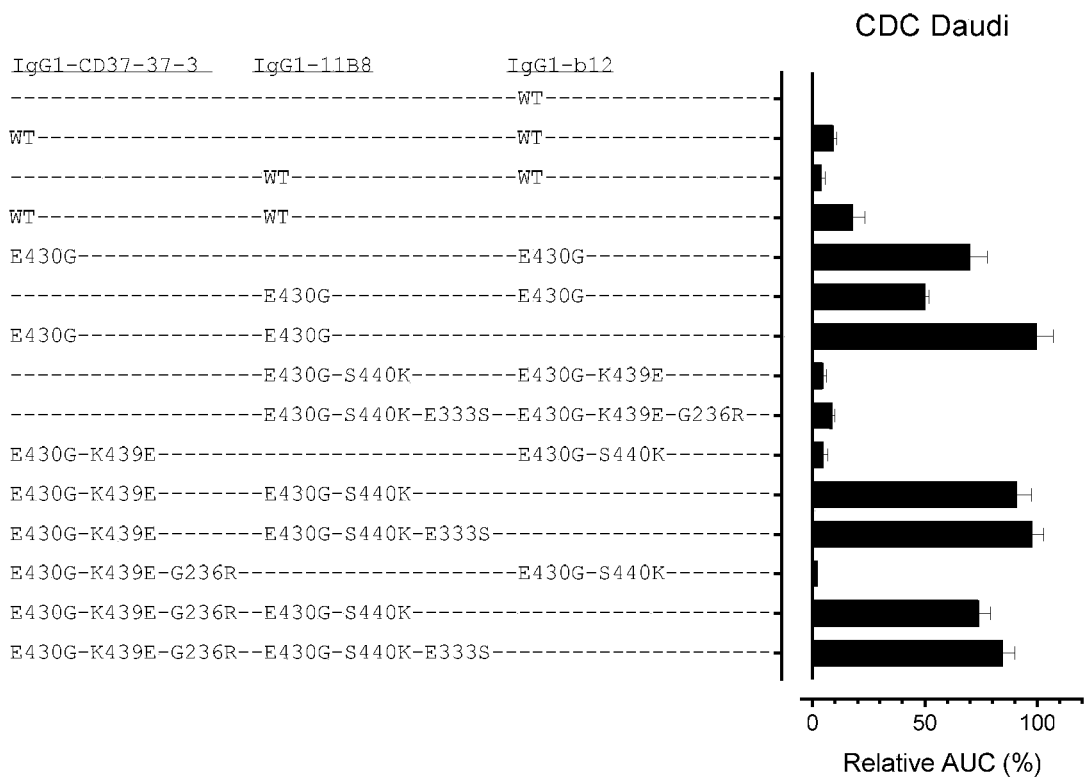
FIGS. 21A and 21B show selectivity of CDC activity by mixed antibody variants of anti-CD37 IgG1-CD37-37.3-E430G-K439E with or without a G236R C1q binding inhibiting mutation+anti-CD20 IgG1-11B8-E430G-S440K with or without the C1q binding enhancing mutation E333S.

Daudi cells were resilient to CDC induction by WT anti-CD37 antibody IgG1-CD37-37.3 and WT Type II anti-CD20 antibody IgG1-11B8 when tested as single agents, while some CDC activity was observed for the mixture of the two WT antibodies (FIG. 21A). Introduction of the Fc-Fc interaction enhancing mutation resulted in the induction of CDC activity for both antibodies when tested as single agents and strong CDC activity when tested as a mixture. Single agent CDC activity by IgG1-CD37-37.3-E430G was strongly inhibited by introduction of the K439E mutation, and completely inhibited by the additional introduction of the G236R C1q binding inhibition mutation. Single agent CDC activity by IgG1-11B8-E430G was inhibited by introduction of the S440K mutation, also in presence of the additional C1q binding-enhancing mutation E333S. For all tested mixtures of IgG1-CD37-37.3 antibody mutants (containing E430G, E430G-K439E or E430G-K439E-G326R) with IgG1-11B8 antibody mutants (containing E430G, E430G-S440K or E430G-S440K-E333S), strong CDC activity was observed on Daudi cells.

Figure 21B:
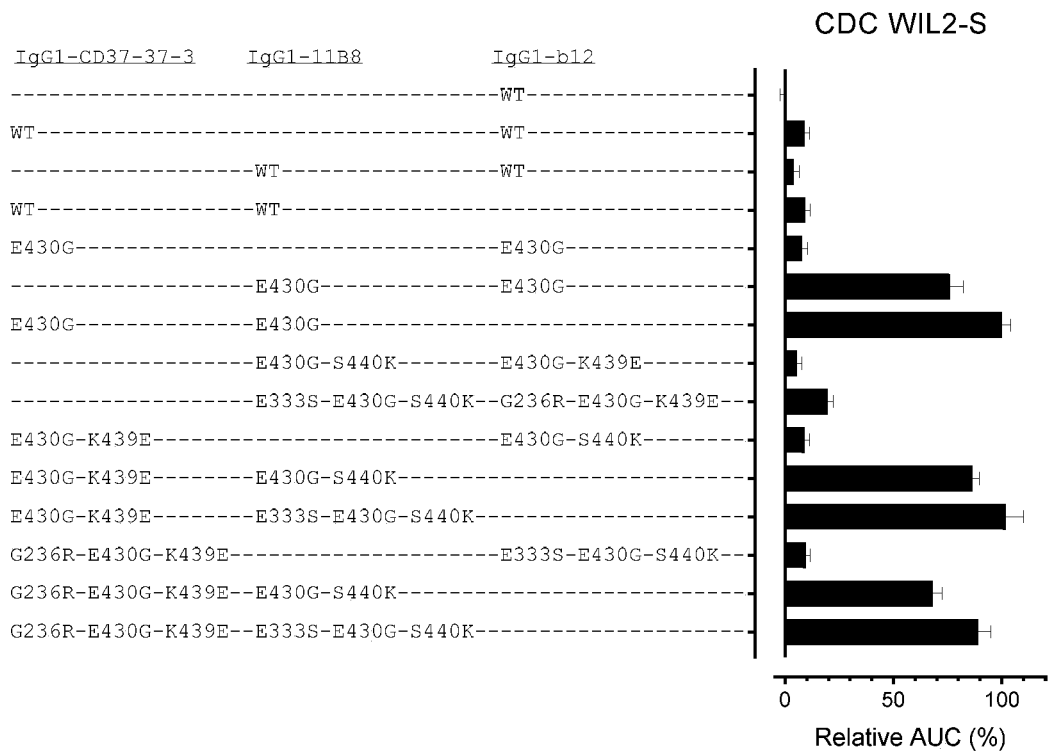

On WIL2-S cells, CDC activity was very low for all IgG1-CD37-37.3 antibody variants (WT, E430G, E430G-K439E and E430G-K439E-E333S) when tested as single agents (FIG. 21B). Introduction of the E430G mutation in Type II anti-CD20 antibody IgG1-11B8 resulted in the induction of CDC activity on WIL2-S cells. Single agent CDC activity by IgG1-11B8-E430G was strongly inhibited by introduction of the S440K mutation, while introduction of the additional C1q binding-enhancing mutation E333S resulted in low CDC activity by IgG1-11B8-E430G-S440K-E333S (FIG. 21B). For all tested mixtures of IgG1-CD37-37.3 antibody mutants (containing E430G, E430G-K439E or E430G-K439E-G326R) with IgG1-11B8 antibody mutants (containing E430G, E430G-S440K or E430G-S440K-E333S), strong CDC activity was observed on WIL2-S cells.

In conclusion, these data demonstrated selective CDC activity on Daudi and WIL2-S cells by the mixtures of the tested IgG1-CD37-37.3-E430G antibody variants (K439E and K439E-G236R) with IgG1-11B8-E430G antibody variants (S440K and S440K-E333S), while little to no CDC activity was observed by the individual antibodies when tested as single agents.

Example 23: CDC Activity on Daudi Cells by Compositions of Anti-CD37 IgG1-CD37-37.3 Antibody Variants and Anti-CD20 IgG1-11B8 Antibody Variants Mixed at Different Ratio's In Example 22, selective CDC activity was shown for anti-CD37 antibody variants mixed with anti-CD20 antibody variants at 1:1 ratio's, in in vitro CDC assays using Daudi cells. Here, the effect of varying the ratio between two co-dependent antibody components present in a mixture was examined. Compositions containing IgG1-CD37-37.3-G236R-E430G-K439E at concentrations ranging from 0.0005-10 µg/mL and IgG1-11B8-E430G-S440K at concentrations ranging from 0.013-10 µg/mL were generated in full factorial design and tested in in vitro CDC assays. The in vitro CDC assays using Daudi cells were performed with 20% NHS, essentially as described in Example 2. Cell lysis was calculated from the number of PI-positive cells.

Daudi cells were lysed by mixtures of IgG1-CD37-37.3-G236R-E430G-K439E and IgG1-11B8-E430G-S440K in a co-dependent fashion. Single agents showed limited activity: maximally 8% lysis was induced by up to 10 µg/mL IgG1-CD37-37.3-G236R-E430G-K439E mixed with non-binding control antibody IgG1-b12, and maximally 7% lysis was induced by up to 10 µg/mL IgG1-11B8-E430G-S440K mixed with IgG1-b12. In contrast, mixtures of IgG1-CD37-37.3-G236R-E430G-K439E and IgG1-11B8-E430G-S440K induced efficient lysis of Daudi cells for compositions representing a wide range of different antibody ratio's (Table 5).

Remarkably, when CD20 binding was saturated by providing IgG1-11B8-E430G-S440K at 10 µg/mL, the addition of >0.12 µg/mL IgG1-CD37-37.3-G236R-E430G-K439E resulted in lysis of >70% of the Daudi cells. Detectable lysis was observed for compositions containing 10 µg/mL IgG1-11B8-E430G-S440K and 0.013 µg/mL IgG1-CD37-37.3-G236R-E430G-K439E. Similarly, when CD37 binding was saturated using 10 µg/mL IgG1-CD37-37.3-G236R-E430G-K439E, >1.1 µg/mL IgG1-11B8-E430G-S440K induced lysis of >69% of Daudi cells. Detectable lysis was observed for compositions containing 10 µg/mL IgG1-CD37-37.3-G236R-E430G-K439E and 0.12 µg/mL IgG1-11B8-E430G-S440K.

This implied that antibody compositions containing IgG1-CD37-37.3-G236R-E430G-K439E and IgG1-11B8-E430G-

S440K at ratio's ranging from approximately 1:1000-1:1, or 1:1-1:100, yielded detectable lysis of Daudi cells, provided binding of at least one of the two targets CD37 and CD20 was saturated. Antibody compositions containing IgG1-CD37-37.3-G236R-E430G-K439E and IgG1-11B8-E430G-S440K at ratio's ranging from approximately 1:100-1:1, or 1:1-1:10, yielded lysis of >69% of Daudi cells, provided binding of at least one of the two targets was saturated.

In conclusion, these data demonstrated that antibody compositions with widely differing ratio's yielded detectable to efficient lysis of Daudi cells by CDC, especially when binding of at least one of the two targets was saturated, while no detectable lysis was observed when the second component was absent or present at low abundance. Table 5 shows CDC activity for compositions containing IgG1-CD37-37.3-G236R-E430G-K439E at concentrations ranging from 0.0005-10 µg/mL and IgG1-11B8-E430G-S440K at concentrations ranging from 0.013-10 µg/mL, mixed in full factorial design. Daudi cells were incubated with antibody mixtures in the presence of 20% NHS. Lysis of Daudi cells was calculated from the fraction PI-positive cells.

ment relative to the maximal binding level (Bmax) calculated for wild type IgG1-11B8.

Figure 22A:
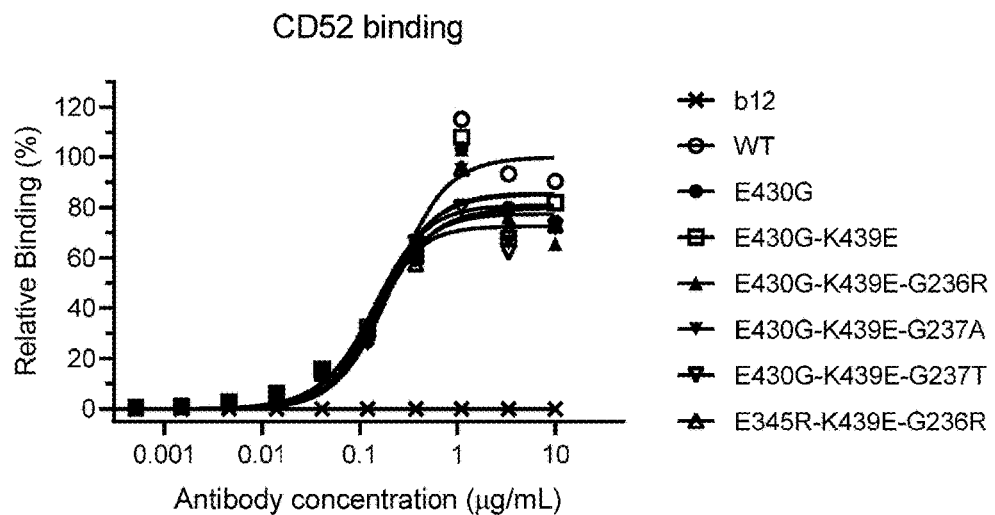
FIGS. 22A-22C show (FIG. 22A) binding of antibody variants of anti-CD52 IgG1-CAMPATH-1H with the Fc:Fc interaction enhancing mutations E430G or E345R, self-oligomerization inhibiting mutation K439E, in combination with any of the FcγR-binding inhibiting and C1q-binding modulating mutations G236R, G237A or G237T to human lymphoma cell line Wien 133. Antibody binding was tested by flow cytometry and is presented normalized relative to the Bmax value of wild type IgG1-Campath-1H (100%). As a negative control for binding, a non-binding anti-gp120 antibody IgG1-b12 was used.
Figure 22B:
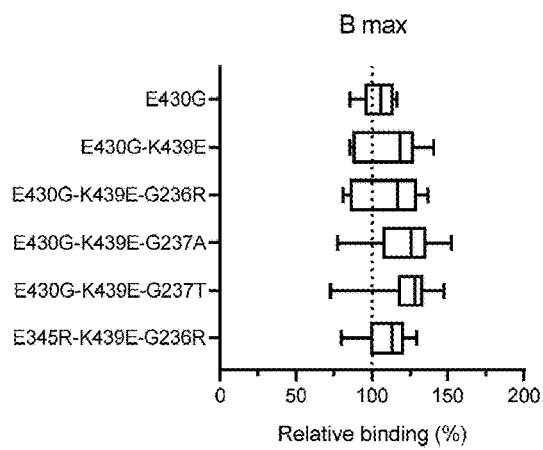
Figure 22C:
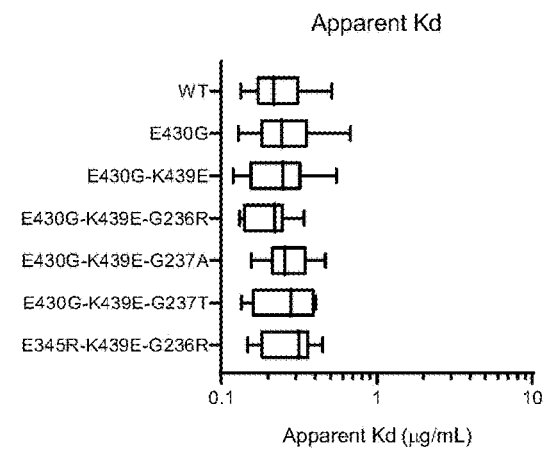

FIG. 22A shows binding observed for IgG1-CAMPATH-1H variants in a representative experiment, in which all tested antibody variants showed similar dose-dependent binding to Wien 133 cells. These data indicate that introduction of the mutations E430G and K439E had no effect on target binding on the cell surface. Comparable target binding was observed when mutation E345R was introduced instead of mutation E430G. Also introduction of either of the additional mutations G236R, G237A or G237T in IgG1-CAMPATH-1H-E430G-K439E had no effect on CD52 target binding on the cell surface. When comparing data collected from three independent experiments, no difference in averaged maximal binding (Bmax; FIG. 22B) was observed, and no difference in averaged apparent Kd (FIG. 22C) was observed for the antibody variants as compared to the wild-type antibodies.

| Lysis (%) | IgG µg/mL | IgG1-CD37-37.3-G236R-E430G-K439E | | | | | | | | | |
|---|---|---|---|---|---|---|---|---|---|---|---|
| | | 10 | 3.3 | 1.1 | 0.37 | 0.12 | 0.041 | 0.013 | 0.0045 | 0.0015 | 0.0005 |
| IgG1-11B8- | 10 | 93 | 92 | 92 | 87 | 70 | 39 | 14 | 6 | 7 | 16 |
| E430G-S440K | 3.3 | 83 | 87 | 86 | 78 | 50 | 28 | 12 | 8 | 6 | 7 |
| | 1.1 | 69 | 63 | 61 | 52 | 35 | 16 | 6 | 6 | 6 | 6 |
| | 0.37 | 36 | 26 | 22 | 18 | 13 | 8 | 5 | 5 | 6 | 16 |
| | 0.12 | 12 | 10 | 9 | 9 | 7 | 6 | 5 | 5 | 4 | 5 |
| | 0.041 | 6 | 6 | 7 | 6 | 5 | 5 | 5 | 6 | 4 | 4 |
| | 0.013 | 5 | 5 | 6 | 6 | 6 | 5 | 5 | 4 | 5 | 5 |

Example 24: Target Binding on Wien 133 Cells of Anti-CD52 IgG1-CAMPATH-1H Antibody Variants Binding to Wien 133 lymphoma cells was analyzed by flow cytometry for anti-CD52 IgG1-CAMPATH-1H antibody variants with Fc-Fc interaction enhancing mutation E430G or E345R, self-oligomerization inhibiting mutation K439E and either of the FcγR-binding inhibiting and C1q-binding modulating mutations G236R, G237A or G237T. Cell suspensions were washed with PBS and resuspended in FACS buffer [PBS+0.1% (w/v) bovine serum albumin (BSA)+0.02% (w/v) sodium azide] at a concentration of 2×10$^6$ cells/mL. 50 µL cell suspension samples (100,000 cells per well) were seeded in polystyrene 96-well round-bottom plates (Greiner Bio-One; Cat nr 650261) and incubated with 50 µL antibody samples (final concentrations 0.0002-10 µg/mL in 3-fold dilutions) for 30 minutes at 4° C. Cells were pelleted by centrifugation at 300×g for 3 minutes at 4° C. and washed three times with 150 µL FACS buffer. Cells were incubated with 50 µL secondary antibody R-phycoerythrin (R-PE)-conjugated goat-anti-human IgG F(ab')2 (Jackson ImmunoResearch, Cat No. 109-116-098, 1:200) for 30 minutes at 4° C., protected from light. Cells were washed twice with 150 µL FACS buffer, resuspended in 30 µL FACS buffer, and antibody binding was analyzed by flow cytometry on an Intellicyt iQue screener. Maximal binding level (Bmax) and apparent Kd were determined by non-linear regression analysis of the binding curves with the specific binding with Hill slope model supplied in GraphPad Prism software version 8, after subtraction of the background signal observed for cells only incubated with secondary antibody. Binding data was normalized per experi- Example 25: Target Binding on Raji Cells of Anti-CD20 IgG1-11B8 Antibody Variants Containing E430G-S440K Mutations Binding of anti-CD20 IgG1-11B8 antibody variants with Fc:Fc interaction enhancing mutation E430G, self-oligomerization inhibiting mutation S440K and C1q-binding modulating mutations to Raji lymphoma cells was analyzed by flow cytometry. The in vitro binding assay using Raji cells was performed with serial dilution antibody concentrations (range 0.0007-40 µg/ml final concentrations in 3-fold dilutions), essentially as described in Example 24. Antibody binding was analyzed by flow cytometry on an Intellicyt iQue screener. Maximal binding level (Bmax) and apparent Kd were determined by non-linear regression analysis of the binding curves with the specific binding with Hill slope model supplied in GraphPad Prism software version 8, after subtraction of the background signal observed for cells only incubated with secondary antibody. Binding data was normalized per experiment relative to the maximal binding level (Bmax) calculated for wild type IgG1-11B8.

Figure 23A:
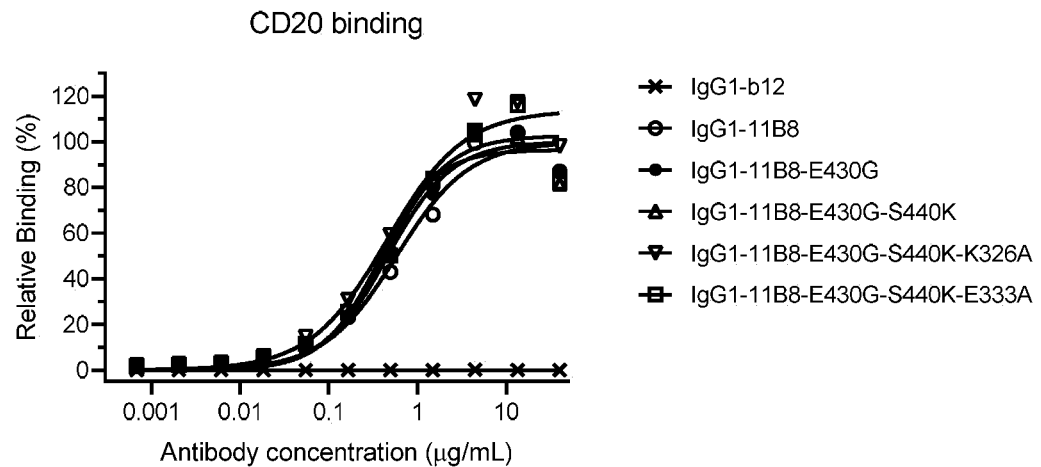
FIGS. 23A-23F show binding of antibody variants of anti-CD20 IgG1-11B8 with the Fc-Fc interaction enhancing mutation E430G, self-oligomerization inhibiting mutation S440K, in combination with any of the C1q binding modulating mutations K326A or E333A (FIG. 23A) or E333S, G237A or G237A-E333S (FIG. 23B) to human lymphoma cell line Raji. Antibody binding was tested by flow cytometry and is presented normalized relative to the Bmax value of wild type IgG1-11B8 (100%). As a negative control for binding, a non-binding anti-gp120 antibody IgG1-b12 was used.
Figure 23B:
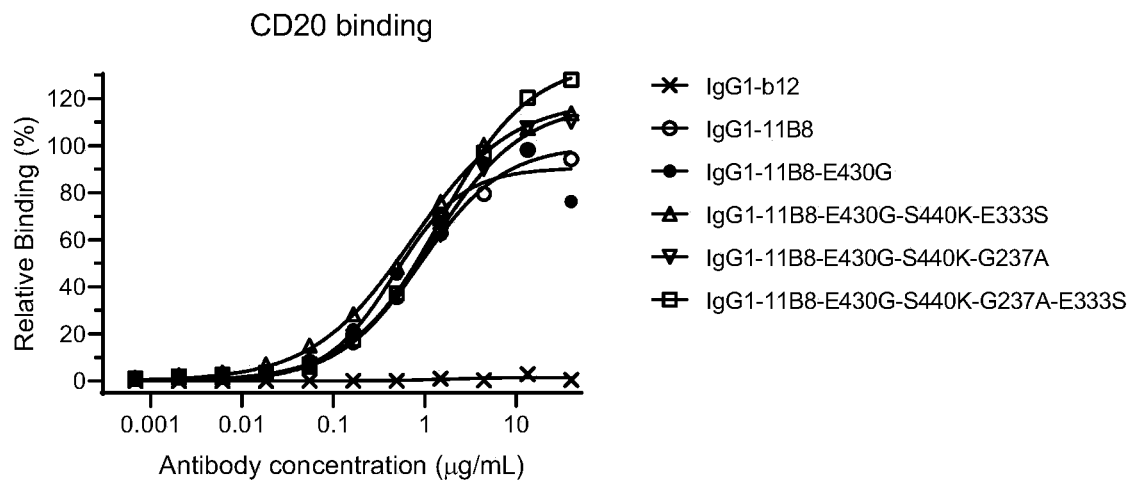
Figure 23C:
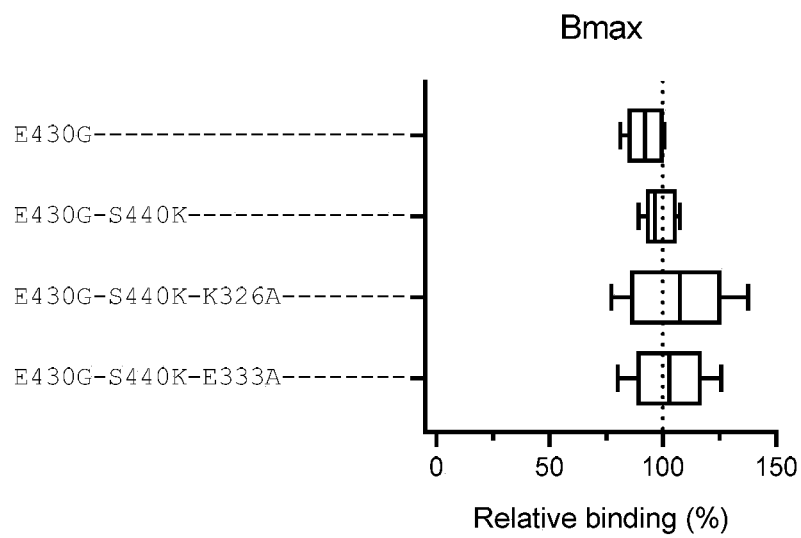
Figure 23D:
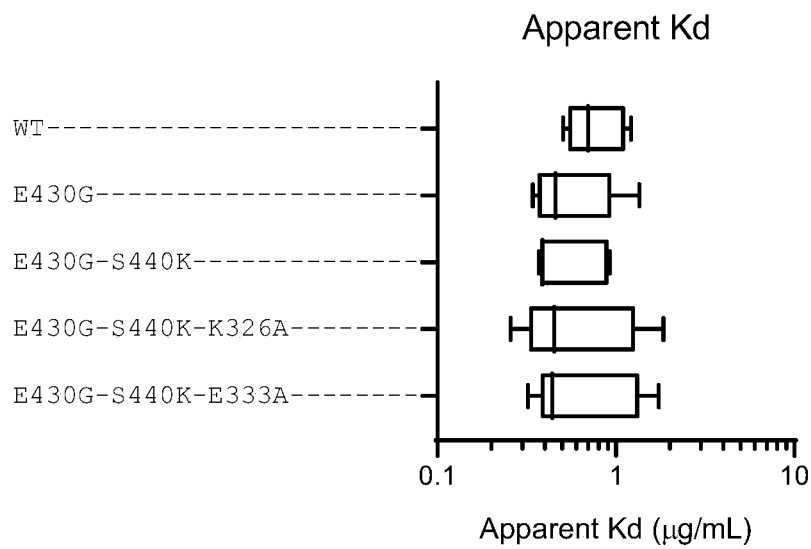
Figure 23E:
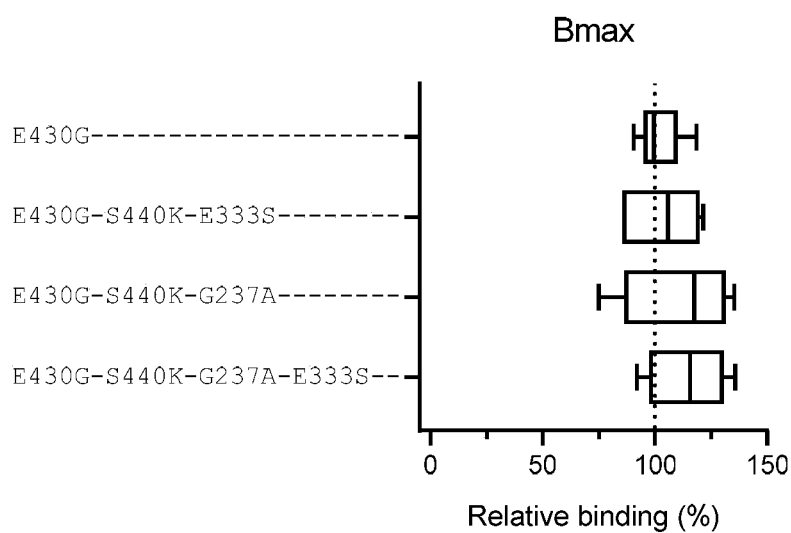
Figure 23F:
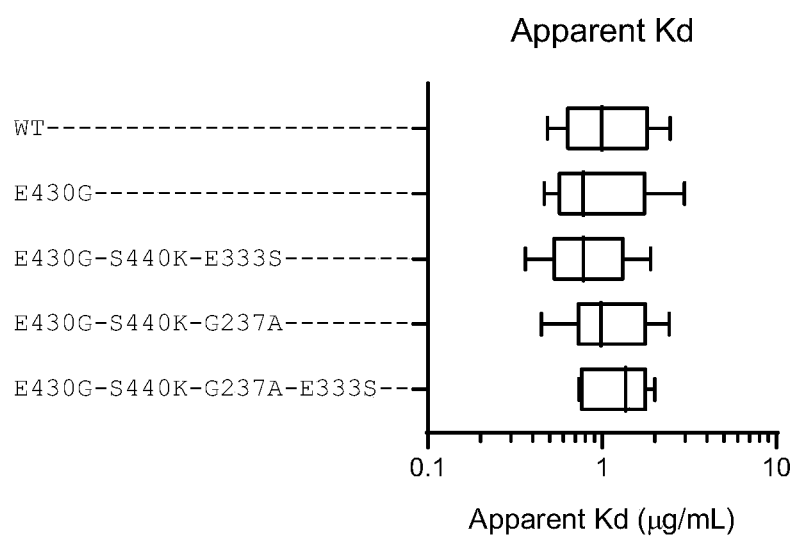

FIGS. 23A and B show a representative binding experiment, demonstrating that all tested IgG1-11B8 antibody variants showed similar dose-dependent binding to Raji cells. When averaged over three independent experiments, the maximal binding (Bmax) values and the averaged apparent $K_d$ values of IgG1-11B8 antibody variants harboring any of the mutations mentioned above were similar to those of wild-type IgG1-11B8 (FIG. 23C-F). These data indicate that introduction of the single or combined mutations E430G and S440K had no effect on target binding on the cell surface.

Introduction of either of the additional C1q-binding enhancing mutations K326A, E333A or E333S, the C1q binding inhibiting mutation G237A, or the combination of C1q binding modulating mutations G237A-E333S in IgG1-11B8-E430G-S440K had no effect on CD20 target binding on the cell surface.

Example 26: FcRn Binding of Anti-CD52 IgG1-CAMPATH-1H and Anti-CD20 IgG1-11B8 Antibody Variants Containing E430G and K439E or S440K Mutations The neonatal Fc receptor (FcRn) is responsible for the long plasma half-life of IgG by protecting IgG from degradation. After internalization of the antibody, FcRn binds to antibody Fc regions in endosomes, where the interaction is stable in the mildly acidic environment (pH 6.0). Upon recycling to the plasma membrane, where the environment is neutral (pH 7.4), the interaction is lost and the antibody is released back into the circulation. This influences the plasma half-life of IgG.

An FcRn binding enzyme-linked immunosorbent assay (ELISA) was performed to evaluate binding of human FcRn to anti-CD52 IgG1-CAMPATH-1H or anti-CD20 IgG1-11B8 with Fc-Fc interaction enhancing mutation E430G, self-oligomerization inhibiting mutation K439E (in the case of IgG1-CAMPATH-1H) or S440K (in the case of IgG1-11B8) and either of the C1q-binding modulating mutations G237A, G237T, K326A, E333A or G237A-E333S. Streptawell 96 well plates (Roche, Cat No. 1734776001) were coated with 2 µg/mL (100 µL/well) recombinantly produced biotinylated extracellular domain of human FcRn [FcRnECDHis-B2M-BIO, i.e. the extracellular domain of human FcRn with a C-terminal His tag (FcRnECDHis; SEQ ID 155) as dimer with beta2microglobulin (B2M; SEQ ID 156)], diluted in PBS for 2 hours while shaking at room temperature (RT). Plates were washed three times with PBST. Antibody samples were added at 40 µg/mL final concentration in PBST/0.2% BSA pH 6.0 or pH 7.4, and incubated for 1 hour at RT while shaking. Plates were washed three times with PBST/0.2% BSA, pH 6.0 or pH 7.4. Horseradish Peroxidase (HRP)-conjugated polyclonal Goat-anti-Human kappa light chain (1:5,000; Sigma, Cat No. A-7164) diluted in PBST/0.2% BSA, pH 6.0 or pH 7.4 was added, and plates were incubated for 1 hour at RT while shaking. After washing three times with PBST/0.2% BSA, pH 6.0 or pH 7.4, 100 µL 2,2'-Azino-bis(3-ethylbenzthiazoline-6-sulfonic acid (ABTS; 1 mg/mL; Roche Cat No. 11112422001) was added as substrate and plates were incubated for 10 minutes at RT protected from light. The reaction was stopped using 100 µL 2% oxalic acid (Riedel de Haen, Cat No. 33506), incubated for 10 minutes at RT and absorbance was measured at 405 nm using an ELISA reader.

Figure 24A:
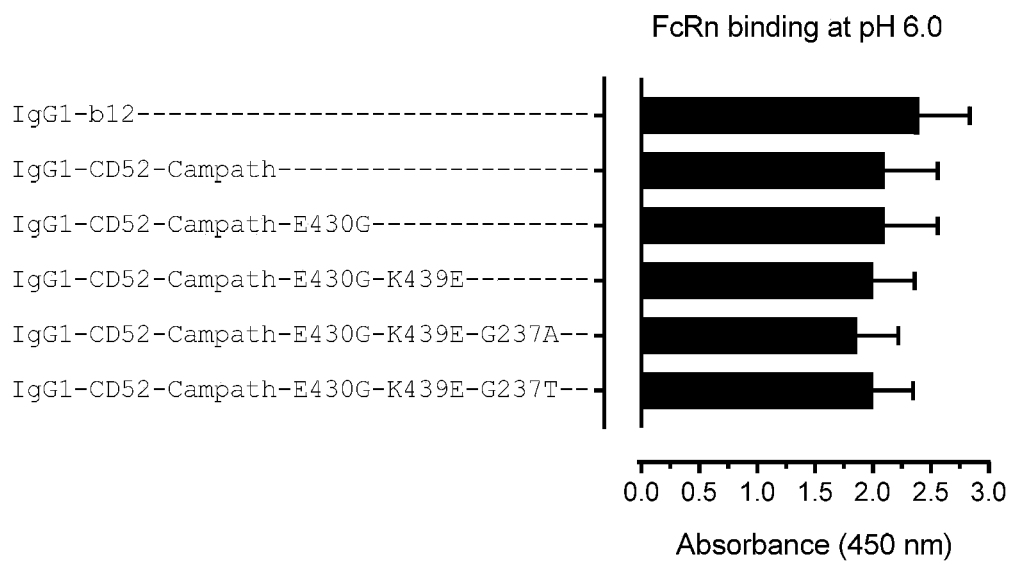
FIGS. 24A-24D show FcRn binding of anti-CD52 IgG1-CAMPATH-1H and anti-CD20 IgG1-11B8 antibody variants.
Figure 24B:
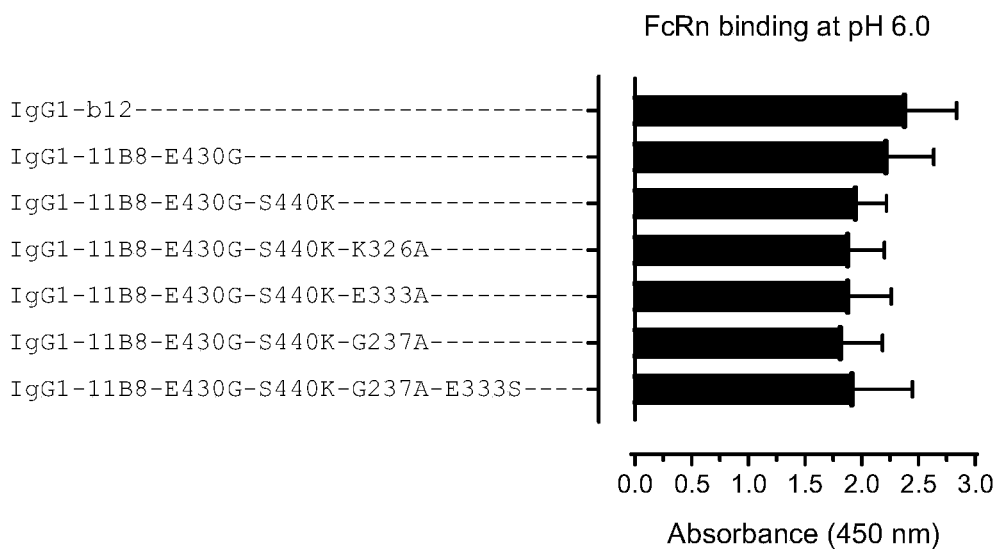
Figure 24C:
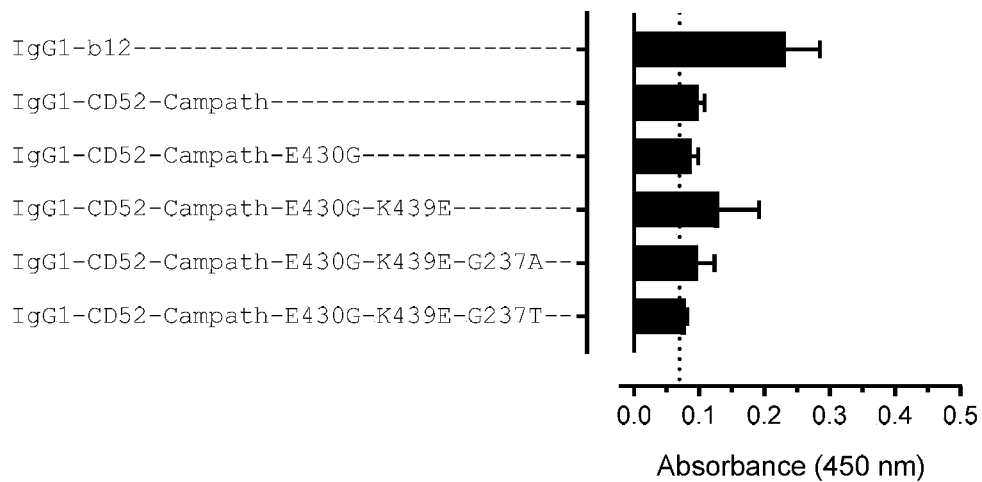
Figure 24D:
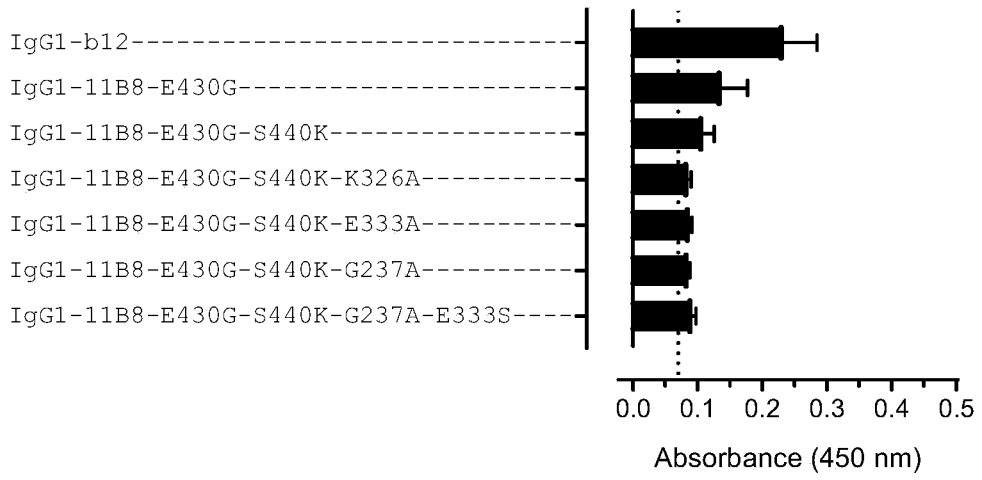

At pH 6.0, highly similar FcRn binding was observed by wild-type IgG1-CAMPATH-1H and IgG1-CAMPATH-1H antibody variants harboring mutations E430G or E430G-K439E, as well as by IgG1-CAMPATH-1H-E430G-K439E antibody variants harboring C1q-binding modulating mutations G237A or G237T (FIG. 24A). Also, wild-type IgG1-11B8, IgG1-11B8 antibody variants harboring mutations E430G or E430G-S440K, and IgG1-11B8-E430G-S440K antibody variants harboring C1q-binding modulating mutations K326A, E333A, G237A or G237A-E333S showed similar FcRn binding at pH 6.0 (FIG. 24B). IgG1-b12 showed low residual binding to FcRn at pH 7.4, in contrast to the other antibodies tested, which all showed binding essentially similar to the background signal recorded for wells incubated without antibody (FIG. 24C, D). Taken together, these results show that anti-CD52 IgG1-CAMPATH-1H and anti-CD20 IgG1-11B8 with hexamerization enhancing mutation E430G, self-oligomerization inhibiting mutations K439E or S440K, and C1q-binding modulating mutations K326A, G237A, G237T, E333A or G237A-E333S showed normal binding to human FcRn.

Example 27: Pharmacokinetic (PK) Analysis of Antibody Variants Harboring Mutations that Enhance Fc-Fc Interactions, Inhibit Self-Oligomerization and Modulate C1q-Binding The pharmacokinetic properties of anti-CD52 IgG1-CAMPATH-1H and anti-CD20 IgG1-11B8 antibody variants harboring an Fc-Fc interaction enhancing mutation, a self-oligomerization inhibiting mutation and a C1q-binding modulating mutation were analyzed in a mouse study. The antibody variants were tested both as single antibodies and as a mixture.

The mice in this study were housed in the Central Laboratory Animal Facility (Utrecht, The Netherlands) and kept in individually ventilated cages with water and food provided ad libitum. All experiments were in compliance with the Dutch animal protection law (WoD) translated from the directives (2010/63/EU) and were approved by the Dutch Central Commission for animal experiments and by the local Ethical committee). SCID mice (C.B-17/IcrHan@Hsd-Prkdc<scid, Envigo) were injected intravenously with 500 µg antibody (wild-type IgG1-CAMPATH-1H, variants thereof harboring the E430G and K439E mutations and either of the G237Q or G236R mutations, wild-type IgG1-11B8, variants thereof harboring the E430G and S440K mutations and either of the G237A or E333S mutations, or combinations of an IgG1-CAMPATH-1H and IgG1-11B8 antibody variant) using 3 mice per group. 50 µL blood samples were collected from the facial vein at 10 minutes, 4 hours, 1 day, 2 days, 7 days, 14 days and 21 days after antibody administration. Blood was collected into heparin containing vials and centrifuged for 5 minutes at 10,000 g. Plasma was stored at −20° C. until determination of antibody concentrations.

Specific human IgG concentrations were determined using a total hIgG ELISA. Mouse anti-human IgG IgG2amm-1015-6A05-Fab (in house generated antibody, batch 3233-025-EP, Genmab, The Netherlands), coated to 96-well Microlon ELISA plates (Greiner, Germany) at a concentration of 2 µg/mL, was used as capturing antibody. After blocking plates with PBS supplemented with 0.2% bovine serum albumin, samples were added, serially diluted in ELISA buffer (PBS supplemented with 0.05% Tween 20 and 0.2% bovine serum albumin), and incubated on a plate shaker for 1 h at room temperature (RT). Plates were subsequently incubated with goat anti-human IgG immunoglobulin (#109-035-098, Jackson, West Grace, PA) and developed with 2,2'-azino-bis (3-ethylbenzthiazoline-6-sulfonic acid) (ABTS; Roche, Mannheim, Germany). The respective materials used for injection were used as the reference curve. Absorbance was measured in a microplate reader (Biotek, Winooski, VT) at 405 nm.

Figure 25A:
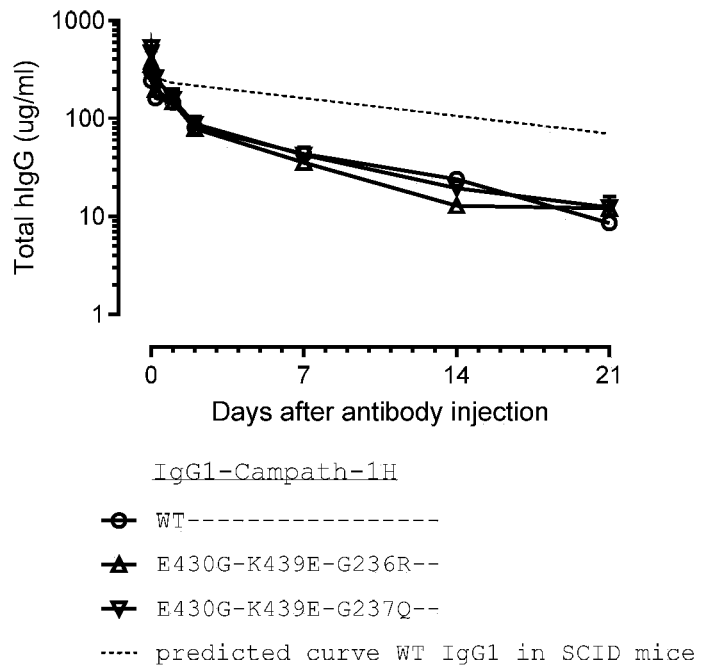
FIGS. 25A-25D show total human IgG (hIgG) concentrations as measured in blood samples collected from mice injected with anti-CD52 IgG1-CAMPATH-1H or anti-IgG1-11B8 antibody variants or mixtures thereof.
Figure 25B:
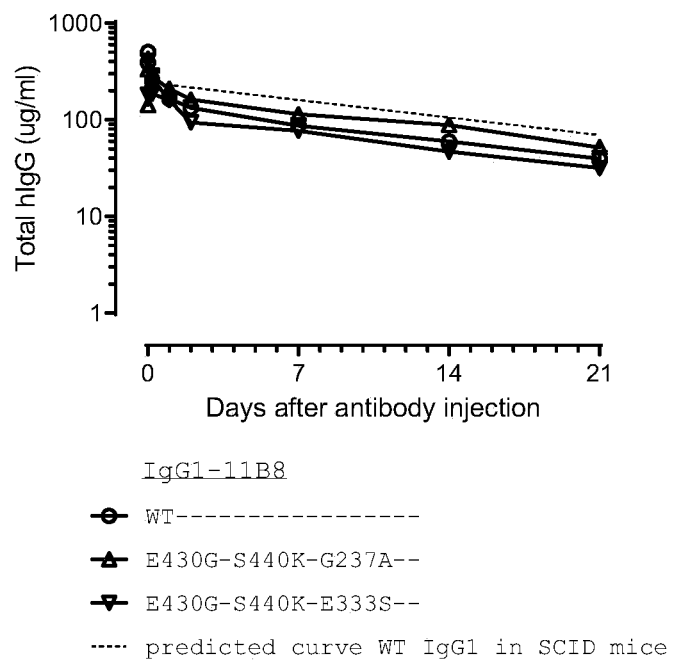
Figure 25C:
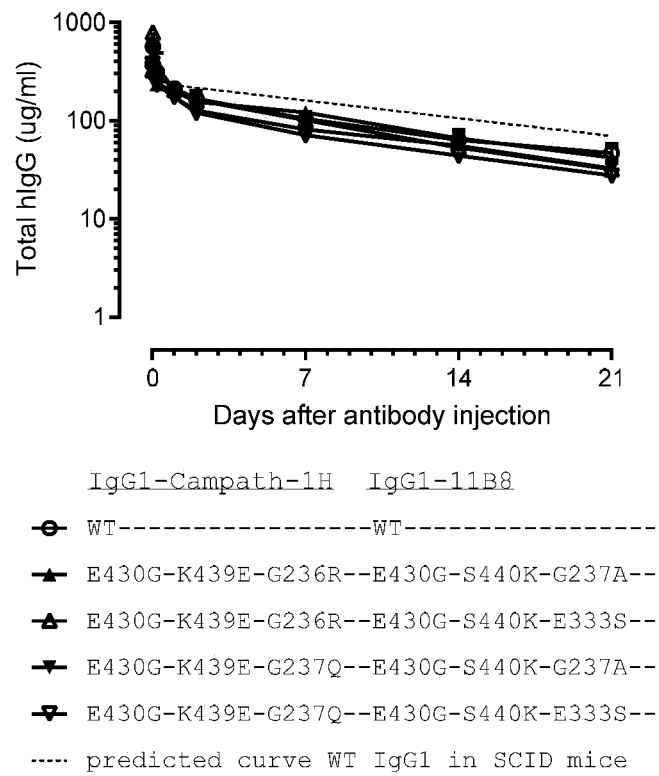

The clearance of wild-type antibody IgG1-CAMPATH-1H and the antibody variants IgG1-CAMPATH-1H-E430G-K439E-G236R and IgG1-CAMPATH-1H-E430G-K439E-G237Q was comparable, although the observed IgG concentrations of all IgG1-CAMPATH-1H antibody variants injected in mice was lower than the expected concentration curve, based on the 2-compartment model, for wild-type IgG1 antibodies in SCID mice (FIG. 25A). The clearance of wild-type antibody IgG1-11B8 and variants thereof, IgG1-11B8-E430G-S440K-G237A and IgG1-11B8-E430G-S440K-E333S, was comparable (FIG. 25B) to each other. In the case of IgG1-11B8 and its variants, the total IgG1 concentration curve was similar to the predicted concentration curve for wild-type IgG1 in SCID mice. Consistent with the observations for single antibodies, the introduction of mutations that enhance Fc-Fc interactions, inhibit self-oligomerization or modulate C1q-binding did not impact the pharmacokinetics of mixtures of IgG1-CAMPATH-1H and IgG1-11B8 antibodies (FIG. 25C). The total IgG concentration curve of mixtures was similar to, though slightly lower than, the predicted concentration curve for wild-type IgG1 in SCID mice.

Figure 25D:
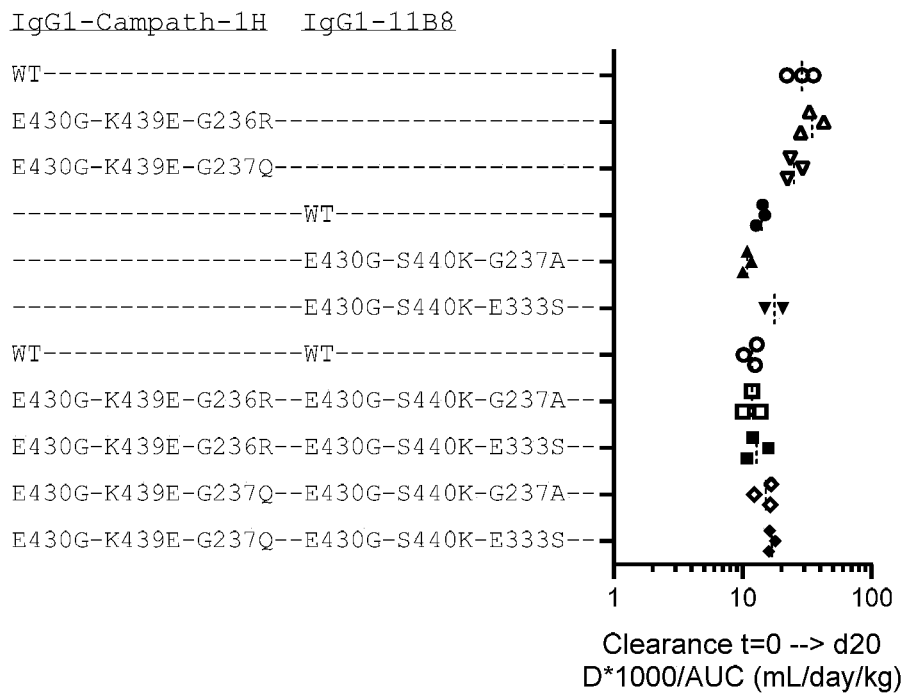

Variants of IgG1-11B8 with mutations E430G-S440K-G237A showed a clearance rate similar to wild type IgG1-11B8 (FIG. 25D). Variants of IgG1-CAMPATH-1H with mutations E430G-K439E-G236R or E430G-K439E-G237Q displayed clearance rates similar to that of wild type IgG1-CAMPATH-1H (FIG. 25D), while the clearance of all IgG1-CAMPATH-1H variants tested was higher than that of the IgG1-11B8 variants tested. All tested combinations of IgG1-CAMPATH-1H variants with IgG1-11B8-variants showed clearance rates that were comparable to that of the combination of the WT IgG1-CAMPATH-1H+IgG1-11B8 antibodies. In conclusion, the introduction of mutations that modulate Fc-Fc interactions, self-oligomerization and C1q-binding did not impact the pharmacokinetic profile of IgG1-CAMPATH-1H and IgG1-11B8 antibodies or mixtures thereof in mice.

Example 28: Fluid Phase Complement Activation by Antibody Variants of IgG1-CAMPATH-1H and IgG1-11B8 Harboring an Fc-Fc Interaction Enhancing Mutation, Self-Oligomerization Inhibiting Mutations and C1q-Binding Modulating Mutations Upon oligomerization of antibodies, complement factor C1 can bind to antibody multimers initiating the further activation of the complement cascade. After activation of the classical complement pathway, activated C1s cleaves C4 into fragments C4a and C4b, which is further processed by Factor I into C4d. Therefore, the serum concentration of C4d can be used as a measure of classical complement pathway activation. Here, C4d serum concentrations were measured after incubation of anti-CD52 IgG1-CAMPATH-1H and anti-CD20 IgG1-11B8 antibody variants in human serum with intact complement (not heat-inactivated) to determine whether the introduction of mutations that enhance Fc-Fc interactions, inhibit self-oligomerization and modulate C1q-binding induce classical complement pathway activation independent of target-binding.

Single antibodies were mixed with 90% normal human AB serum (NHS) at a final total recombinant IgG concentration of 100 µg/ml. The antibodies were then incubated for 60 min at 37° C. and subsequently kept on ice. Next, the samples were diluted 100-fold using specimen diluent (from Quidel, MicroVue Complement C4d Fragment EIA kit). According to the manufacturer's instructions, samples and kit-provided standards were applied to a 96-wells microtiter plate that was pretreated with 3 plate washing steps using 250-300 µl wash buffer and blotting dry after each step. The plates were incubated for 30 minutes at RT on a shaker. Next, the microtiter plates were emptied and washed 5 times using wash buffer and blotted dry after each step. Per well, 50 µl of kit-provided C4d Conjugate was added and incubated for 30 minutes at RT. Again, all wells were washed 5 times using wash buffer and blotted dry after each step. Per well, 100 µl of kit-provided substrate was then added and incubated for 30 minutes at RT. To stop the enzymatic reaction, 50 µl kit-provided stop solution was added to all wells and the absorbance was determined at 405 nm wavelength using an ELISA reader (Biotek, Winooski, VT). Background C4d levels of approximately 11 to 13 µg/ml were detected in the serum used for these assays. Therefore, two samples containing no antibodies were used as negative controls and the average concentration of C4d measured in these samples was subtracted from the C4d concentrations measured in the samples incubated with antibody variants. Sample means and standard deviations were calculated over all values recorded in three independent experiments.

Figure 26A:
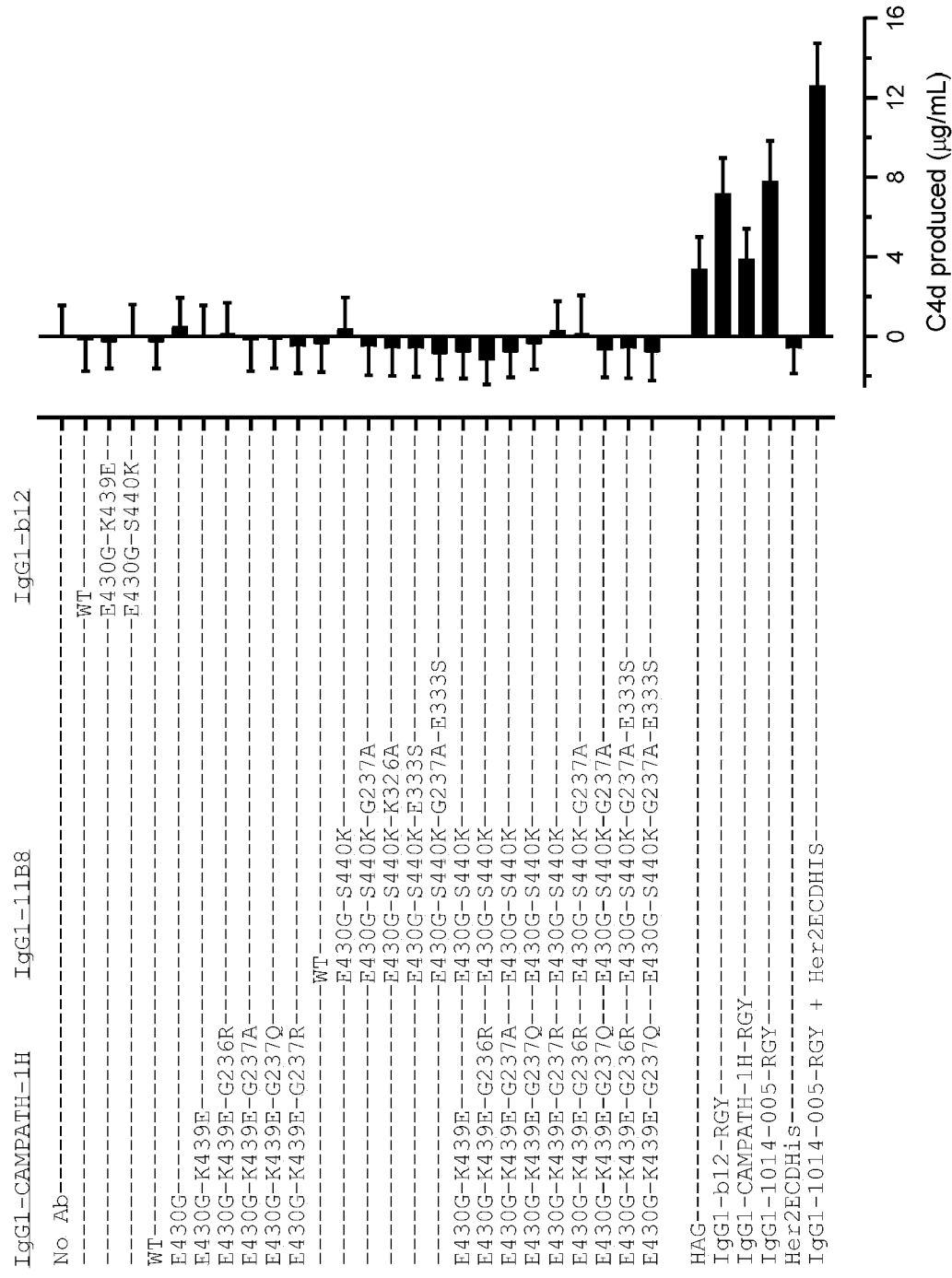
FIGS. 26A and 26B show the concentration of C4d (in µg/ml) detected in samples incubated with antibody variants of IgG1-CAMPATH-1H, IgG1-11B8 and IgG1-b12 harboring mutations E430G, K439E or S440K and G236R, G237A, G237Q or G237R, after subtraction of the average C4d concentration detected in negative control samples containing no antibodies. Positive control samples include antibody variants harboring the E345R, E430G and S440Y Fc-Fc interaction enhancing mutations (RGY).
Figure 26B:
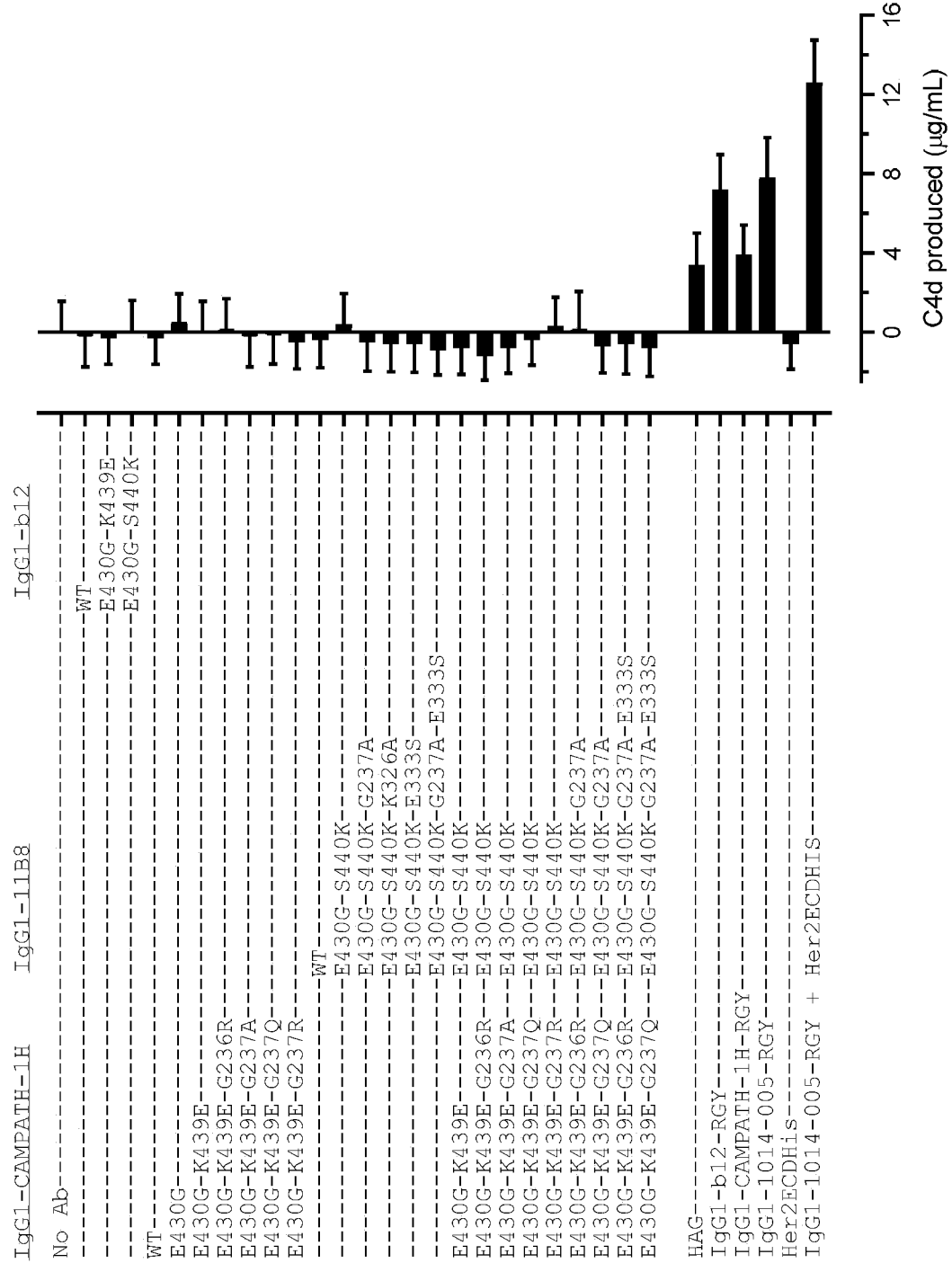

Complement activation as determined by C4d concentrations in serum was detected for antibody variants containing the E345R, E430G, S440Y (RGY) mutations (FIG. 26). The strongest complement activation was detected upon incubation of recombinant Her2ECDHis (SEQ ID NO: 159) and Her2-specific antibody variant IgG1-1014-005-E345R-E430G-S440Y (IgG1-1014-005-RGY; SEQ ID NO: 158) while recombinant Her2ECDHis did not induce complement activation. No concentrations of C4d significantly differing from background C4d levels were detected for any of IgG1-CAMPATH-1H, IgG1-11B8 or IgG1-b12 antibody variants, or mixtures thereof.

In conclusion, the introduction of Fc-Fc interaction enhancing mutation E430G, self-oligomerization inhibiting mutation K439E or S440K and C1q-binding modulating mutations G236R, G237A, G237Q or G237R in antibody variants of IgG1-CAMPATH-1H, IgG1-11B8 or IgG1-b12 did not result in complement activation in solution.

Example 29: C1q Binding on Cells by Antibody Variants Containing E430G, and K439E or S440K Mutations Flow cytometric analysis was performed to analyze C1q binding to Wien 133 cells incubated with anti-CD52 IgG1-CAMPATH-1H and anti-CD20 IgG1-11B8 antibody variants harboring mutations that enhance Fc-Fc interactions, inhibit self-oligomerization or modulate C1q-binding. Per sample, $0.1 \times 10^6$ Wien 133 cells were incubated for 15 minutes at 37° C. with dilutions of the antibody variants in a concentration range of 20 to 0.033 µg/ml in 2.5-fold dilution steps. Next, the plates were cooled on ice to 0° C. for 30 min. Cooled normal human AB serum (NHS) was added to a final concentration of 20% and the plates were incubated for 10-20 minutes on ice at 0° C. The cells were washed twice with ice-cold FACS buffer (PBS+0.1% BSA+0.02% NaN$_3$) and subsequently incubated with 20 µg/ml rabbit anti-human C1q-FITC (Dako; cat nr F0254) for 30 minutes at 4° C. After washing the cells twice in FACS buffer, the cells were suspended in 30 µl FACS buffer and analyzed on an iQue flow cytometer (Intellicyt). C1q-binding measured as mean fluorescence intensity values were fitted with a log agonist response model after log transformation of the concentration axis, and normalized relative to the average MFI of wells incubated without antibody (0%) and the fitted top value of the dose-response curve of positive control IgG1-CAMPATH-1H-E430G+IgG1-11B8-E430G (100%), using GraphPad Prism version 8.

Figure 27B:
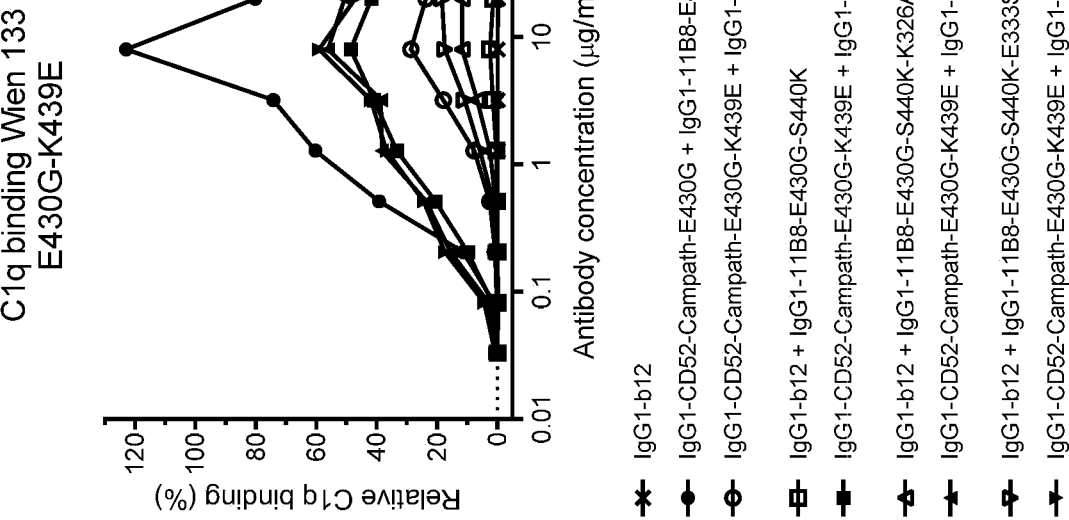
Figure 27A:
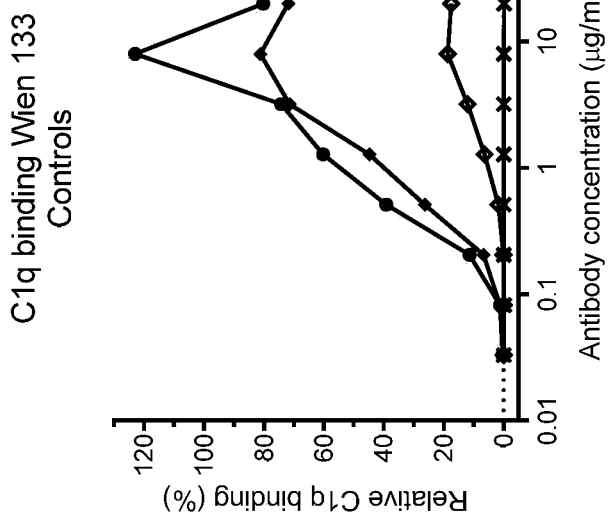
Figure 28A:
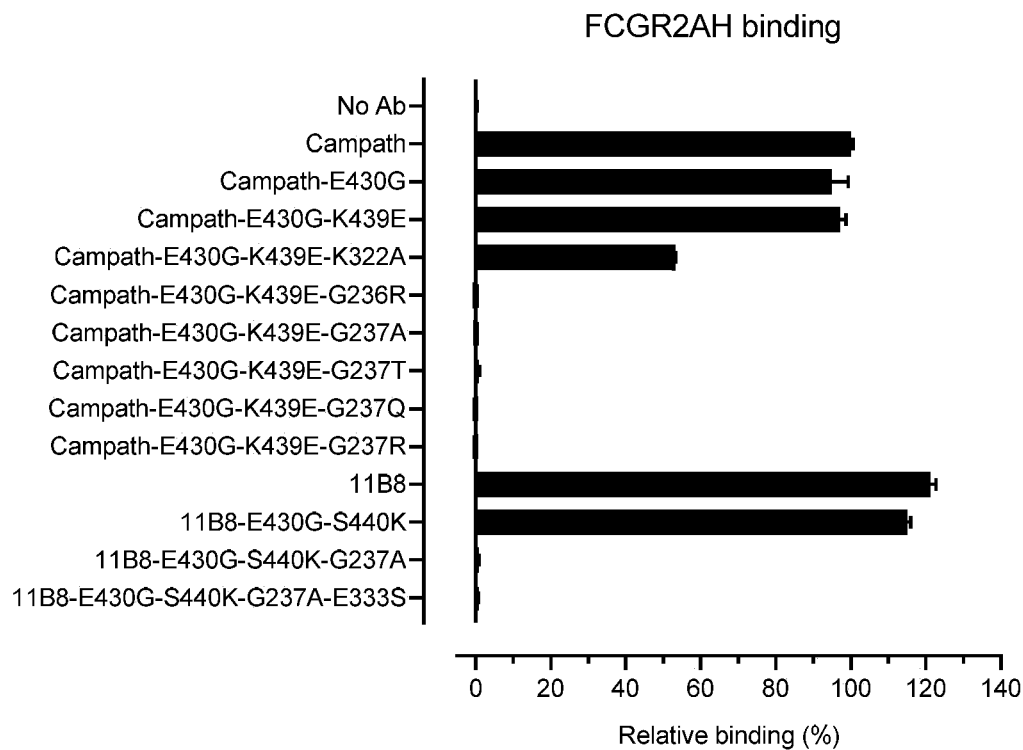
FIGS. 28A-28F show FcγR binding by IgG1-CAMPATH-1H-E430G and IgG1-11B8-E430G antibody variants harboring self-oligomerization inhibiting mutation K439E or S440K and C1q-binding modulating mutations.
Figure 28B:
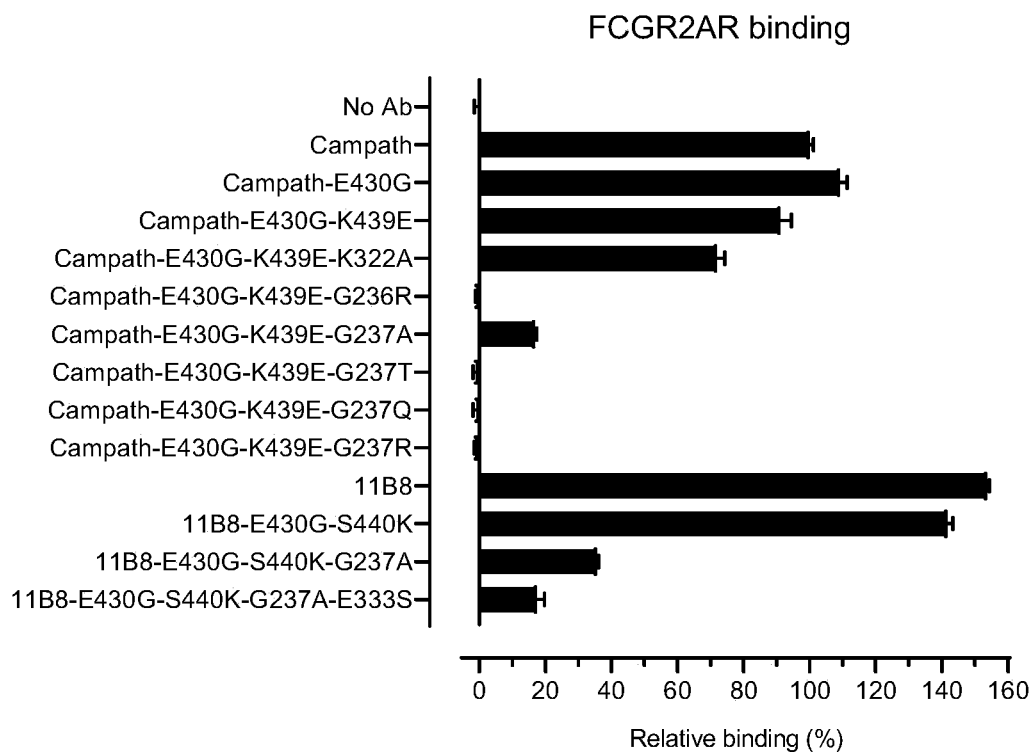
Figure 28C:
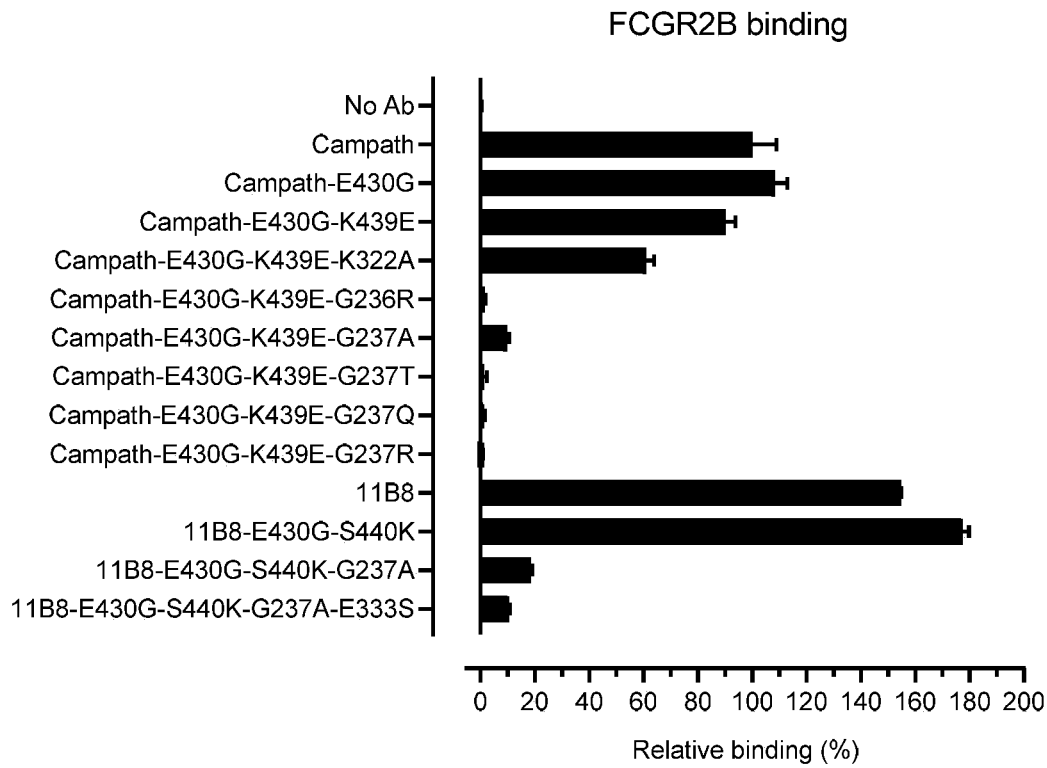
Figure 28D:
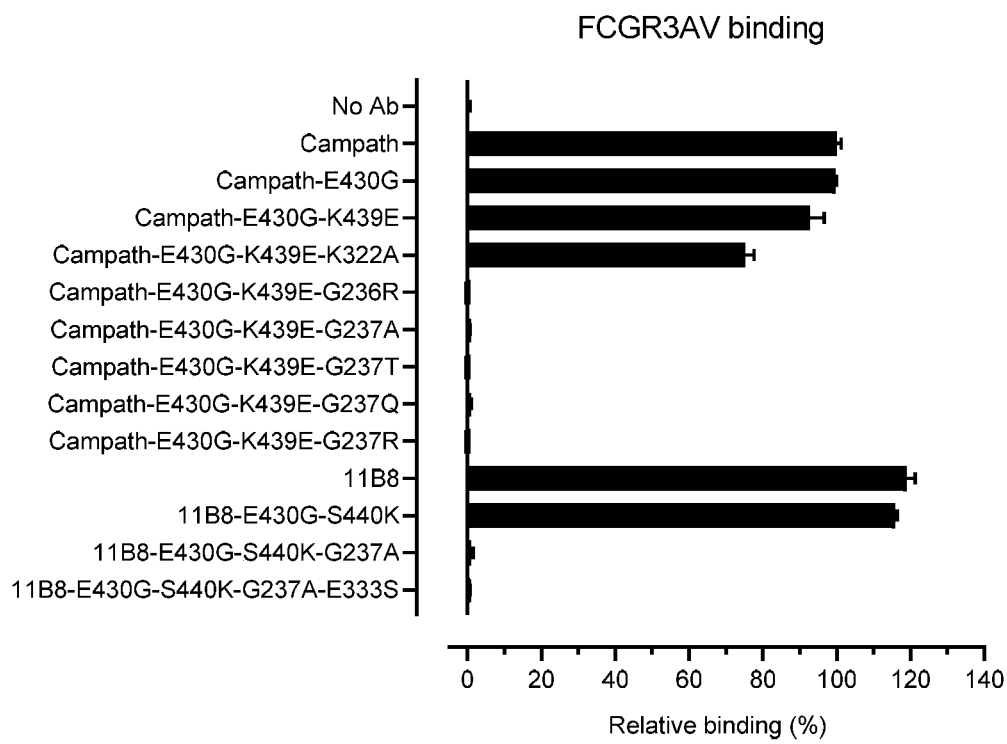
Figure 28E:
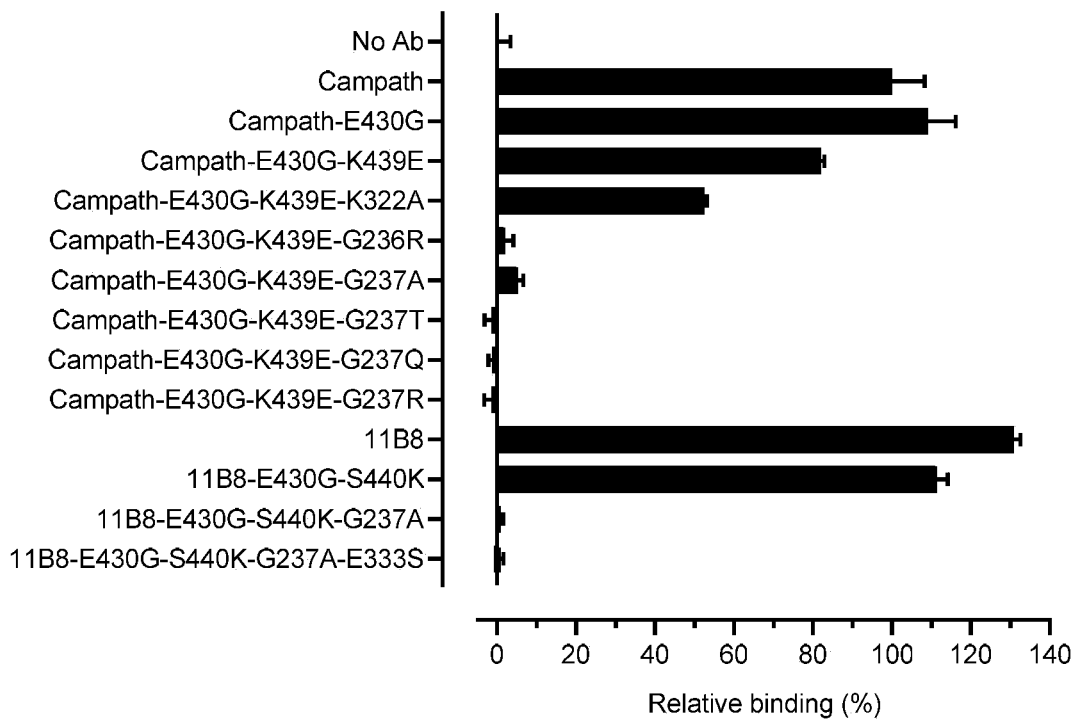
Figure 28F:
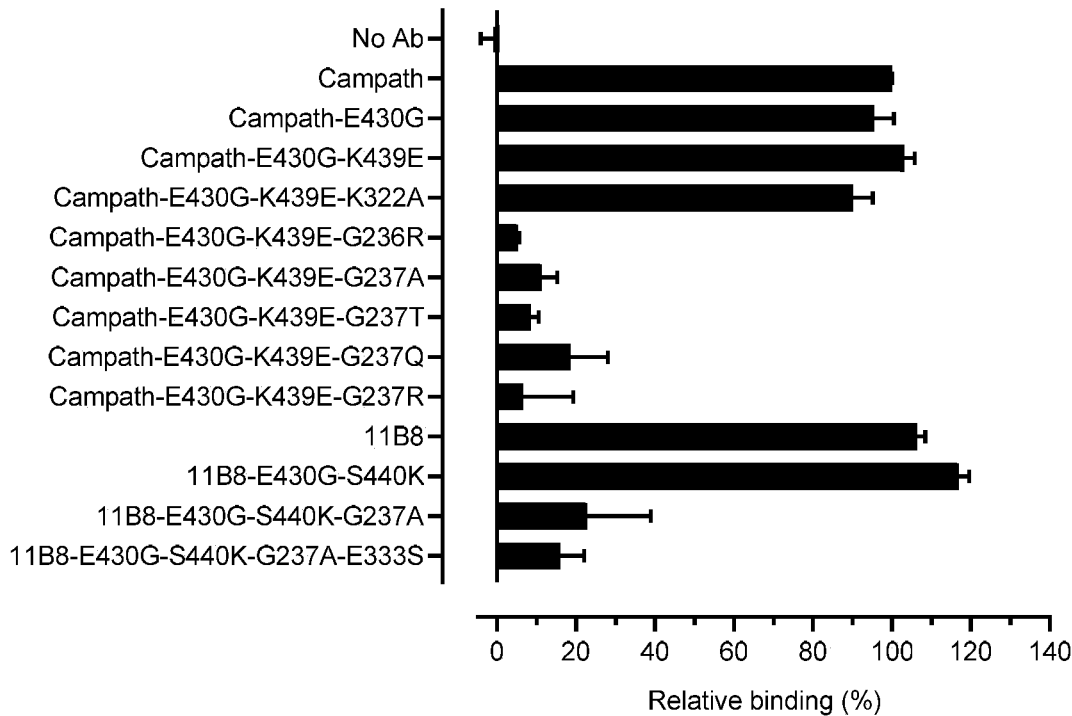

Efficient C1q binding was observed after incubating Wien 133 cells with a mixture of IgG1-CAMPATH-1H-E430G and IgG1-11B8-E430G (FIG. 27A). The single agent C1q- binding activity of IgG1-CAMPATH-1H-E430G was close to the level induced by the positive control mixture, while IgG1-11B8-E430G demonstrated low single agent C1q-binding activity.

The introduction of self-oligomerization inhibiting mutation K439E in IgG1-CAMPATH-1H-E430G resulted in a partial abrogation of the C1q-binding efficiency, while introduction of self-oligomerization inhibiting mutation S440K in IgG1-11B8-E430G resulted in a complete loss of C1q-binding (FIG. 27B). The capacity to bind C1q was restored to intermediate levels, as compared with the positive control mixture, by mixing IgG1-CAMPATH-1H-E430G-K439E and IgG1-11B8-E430G-S440K. A mild recovery of single agent C1q-binding was attained by introduction of C1q-binding enhancing mutation K326A or E333S in IgG1-11B8-E430G-S440K. Mixing either of the latter two antibody variants with IgG1-CAMPATH-1H-E430G-K439E resulted in restoration of C1q-binding similar to the level of a mixture of IgG1-CAMPATH-1H-E430G-K439E+IgG1-11B8-E430G-S440K.

C1q-binding was fully abrogated by introduction of either of the C1q-binding inhibiting mutations G236R (FIG. 27C) or G237T (FIG. 27D) in IgG1-CAMPATH-1H-E430G-K439E. A partial restoration of C1q-binding was observed after mixing IgG1-CAMPATH-1H-E430G-K439E-G236R with IgG1-11B8-E430G antibody variants harboring either of the S440K, S440K-K326A or S440K-E333S mutations (FIG. 27C). Likewise, a partial restoration of C1q-binding was observed by mixing IgG1-CAMPATH-1H-E430G-K439E-G237T with IgG1-11B8-E430G antibody variants harboring either of the S440K, S440K-K326A or S440K-E333S mutations (FIG. 27D).

In conclusion, while introduction of self-oligomerization inhibiting mutations K439E or S440K partially abrogated C1q-binding capacity of antibodies harboring the Fc-Fc enhancing mutation E430G, full abrogation of C1q-binding could be attained by introduction of additional C1q-binding inhibiting mutations. C1q-binding was recovered to different levels by mixing antibodies with complementary mutations K439E and S440K, depending on the C1q modulating mutations introduced in the individual antibodies.

Example 30: The Effect of C1q-Binding Modulating Mutations on the In Vitro FcγR Binding of Anti-CD52 and Anti-CD20 Antibodies with a Hexamerization Enhancing Mutation and a Self-Oligomerization Inhibiting Mutation Using purified antibodies, binding of IgG1-CAMPATH-1H and IgG1-11B8 antibody variants to the monomeric extracellular domain (ECD) of FcγRIA (FCGR1AECDHis; SEQ ID NO 149) and to dimeric extracellular domains of FcγRIIA allotype 131H (diFCGR2AH-HisBAP; SEQ ID NO 150), FcγRIIA allotype 131R (diFCGR2AR-HisBAP; SEQ ID NO 151), FcγRIIB (diFCGR2B-HisBAP; SEQ ID NO 152), FcγRIIIA allotype 158F (diFCGR3AF-HisBAP; SEQ ID NO 153), and FcγRIIIA allotype 158V (diFCGR3AV-HisBAP; SEQ ID NO 154) was tested in ELISA assays. To detect binding to dimeric FcγR variants, 96-well Microlon ELISA plates (Greiner, Germany) were coated overnight at 4° C. with goat F(ab')2-anti-human-IgG-F(ab')2 (Jackson Laboratory, 109-006-097, 1 μg/mL) in PBS, washed and blocked with 200 μL/well PBS/0.2% BSA for 1 h at room temperature (RT). With washings in between incubations, plates were sequentially incubated with 100 μL/well of 20 μg/ml IgG1-CAMPATH-1H antibody variants in PBST/0.2% BSA for 1 hour at RT while shaking, 100 μL/well of dimeric, His-tagged, C-terminally biotinylated FcγR ECD variants (1 μg/mL) in PBST/0.2% BSA for 1 hour at RT while shaking, and with 100 μL/well Streptavidin-polyHRP (CLB, M2032, 1:10.000) in PBST/0.2% BSA as detecting antibody for 30 min at RT while shaking. Development was performed for circa 10 (IIAH, IIAR, IIIAV), 20 (IIIAF), or 30 (IIB) minutes with 1 mg/mL ABTS (Roche, Mannheim, Germany). To stop the reactions, 100 μL/well of 2% oxalic acid was added. Absorbance was measured at 405 nm in a microplate reader (BioTek, Winooski, VT). To detect binding to FcγRIa, 96-well Microlon ELISA plates (Greiner, Germany) were coated overnight at 4° C. with FCGR1AECD-His (1 μg/mL) in PBS, washed and blocked with 200 μL/well PBS/0.2% BSA for 1 h at room temperature (RT). With washings in between incubations, plates were sequentially incubated with 100 μL/well of 20 μg/ml IgG1-CAMPATH-1H antibody variants in PBST/0.2% BSA for 1 h at RT while shaking and 100 μL/well of goat anti-human-kappaLC-HRP (1:5000) in PBST/0.2% BSA for 30 minutes at RT while shaking. Development was performed for circa 10 minutes with 1 mg/mL ABTS (Roche, Mannheim, Germany). To stop the reactions, 100 μL/well of 2% oxalic acid was added. Absorbance was measured at 405 nm in a microplate reader (BioTek, Winooski, VT). Data from three (FcγRI, FcγRIIB, FcγRIIIA) or two (FcγRIIA) independent replicates were combined by normalization per plate relative to the background signal in ELISA (no antibody control, 0%) and an internal standard, IgG1-CAMPATH-1H, set to 100%, and then averaged over all experiments. The mutations introduced to modulate C1q-binding to antibody variants were also expected to affect FcγR binding. Assessment of binding of IgG1-CAMPATH-1H and IgG1-11B8 antibody variants with Fc-Fc interaction enhancing mutation E430G, self-oligomerization inhibiting mutation K439E or S440K and either of the C1q-binding modulating mutations G236R, G237A, K322A, G237T, G237Q, G237R or G237A-E333S to FcγRIIa, FcγRIIb, FcγRIIIa and FcγRIa by ELISA revealed that introduction of mutations G236R, G237A, G237T, G237Q or G237R in IgG1-CAMPATH-1H-E430G-K439E strongly suppressed binding to all tested FcγR variants (FIG. 28A-F). Low residual binding was observed for IgG1-CAMPATH-1H-E430G-G237A to FcγRIIb and the low affinity FcγRIIa and FcγRIIIa receptors. Low residual binding to FcγRIa was also observed for IgG1-CAMPATH-1H-E430G-K439E variants with mutations G236R, G237T, G237Q and G237R. Wild-type IgG1-11B8 and IgG1-11B8-E430G-S440K showed similar strong binding to all tested FcγR, which was suppressed by introduction of G237A or G237A-E333S in IgG1-11B8-E430G-S440K. The latter two antibody variants showed low residual binding to FcγRIa, FcγRIIb and the low affinity FcγRIIa receptors. Introduction of mutation K322A mildly suppressed binding of IgG1-CAMPATH-1H-E430G-K439E to all tested FcγR.

In conclusion, FcγR-binding was strongly inhibited by introduction of C1q-binding modulating mutations G236R, G237A, G237T, G237Q and G237R in IgG1-CAMPATH-1H-E430G-K439E. Similarly, introduction of mutation G237A or G237A-E333S in IgG1-11B8-E430G-S440K strongly suppressed FcγR binding.

Example 31: Selectivity of CDC Activity by Mixed Antibody Variants by Introduction of C1q-Binding Modulating Mutations in Anti-CD52 IgG1-h2E8, IgG1-CAMPATH-1H and Anti-CD20 IgG1-11B8 Antibody Variants with an E430G Fc-Fc Interaction Enhancing Mutation Like IgG1-CAMPATH-1H, the humanized antibody IgG1-h2E8 targets human CD52. Here, the effect on CDC efficacy of the introduction of C1q-binding modulating mutations in IgG1-CAMPATH-1H, IgG1-h2E8, IgG1-11B8 antibody variants harboring an Fc-Fc interaction enhancing mutation and a self-oligomerization inhibiting mutation was studied using Wien 133 lymphoma cells.

Different mutations were introduced in antibodies IgG1-CAMPATH-1H, IgG1-h2E8, IgG1-11B8 and IgG1-b12: E430G, which induces enhanced Fc-Fc interactions; either of the mutations K439E or S440K, which inhibit the formation of homo-hexameric antibody complexes through inhibition of the intermolecular Fc-Fc interactions and promote the formation of hetero-hexameric antibody complexes through cross-complementary Fc-Fc interactions; G236R, G237A, G237R, G237T or G237Q, which suppress binding of C1q to the hetero-hexameric antibody complex and suppress binding to Fcγ receptors. As controls, single antibodies were also mixed 1:1 with non-binding isotype control antibody IgG1-b12 or with IgG1-b12-E430G-S440K to enable direct comparison of the concentrations of individual components and mixtures composed thereof. A range of concentrations of purified antibodies (range 0.009-40.0 μg/mL final concentrations; 3.3-fold dilutions) was tested in an in vitro CDC assay on Wien 133 cells with 20% NHS, essentially as described in Example 2. The percentage of cell lysis was calculated as (number of PI-positive cells/total number of cells)×100%. The data were analyzed using best-fit values of a non-linear agonist response model using log-transformed concentrations in GraphPad PRISM and the area under the dose-response curves of three experimental replicates was calculated. Relative areas under the curve (AUC) values represent normalization to minimal lysis (0% with IgG1-b12) and maximal lysis (100% with the mixture of IgG1-CAMPATH-1H-E430G+IgG1-11B8-E430G).

Figure 29A:
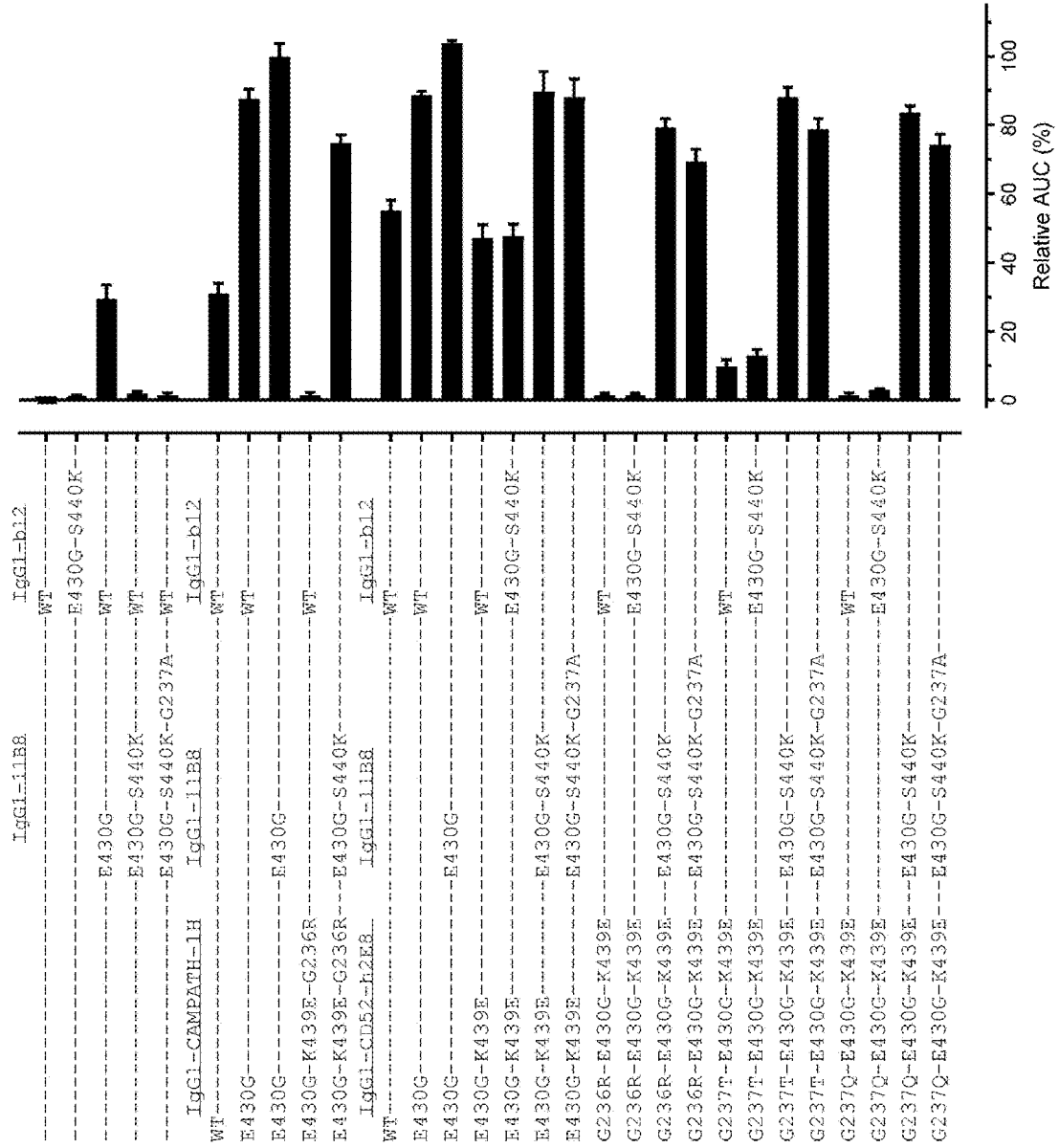
FIGS. 29A and 29B show selectivity of CDC activity by mixed antibody variants of anti-CD52 IgG1-CAMPATH-1H, anti-CD20 IgG1-11B8 and anti-CD52 IgG1-h2E8 by introduction of mutations that enhance Fc-Fc interactions, inhibit self-oligomerization and modulate C1q-binding. Wien 133 cells were incubated with antibody concentration series in the presence of 20% NHS. CDC efficacy was measured in three independent experiments and is presented as (FIG. 29A) the averaged AUC normalized to non-binding control antibody IgG1-b12 (0%) and the mixture of IgG1-CAMPATH-1H-E430G+IgG1-11B8-E430G (100%) and (FIG. 29B) the averaged percentage lysis determined by the propidium iodide positivity at an antibody concentration of 40 µg/ml.

The intermediate single agent CDC efficacy induced by IgG1-11B8-E430G was abrogated by introduction of mutation S440K or double mutation S440K-G237A (FIG. 29A). Compared with IgG1-11B8-E430G, stronger single agent CDC efficacy was induced by IgG1-CAMPATH-1H-E430G, which could be fully abrogated by introduction of mutations K439E-G236R. CDC efficacy could be partially restored by mixing IgG1-CAMPATH-1H-E430G-K439E-G236R with IgG1-11B8-E430G-S440K to approximately 80% of the potency (relative AUC) of the positive control mixture IgG1-CAMPATH-1H-E430G+IgG1-11B8-E430G.

Figure 29B:
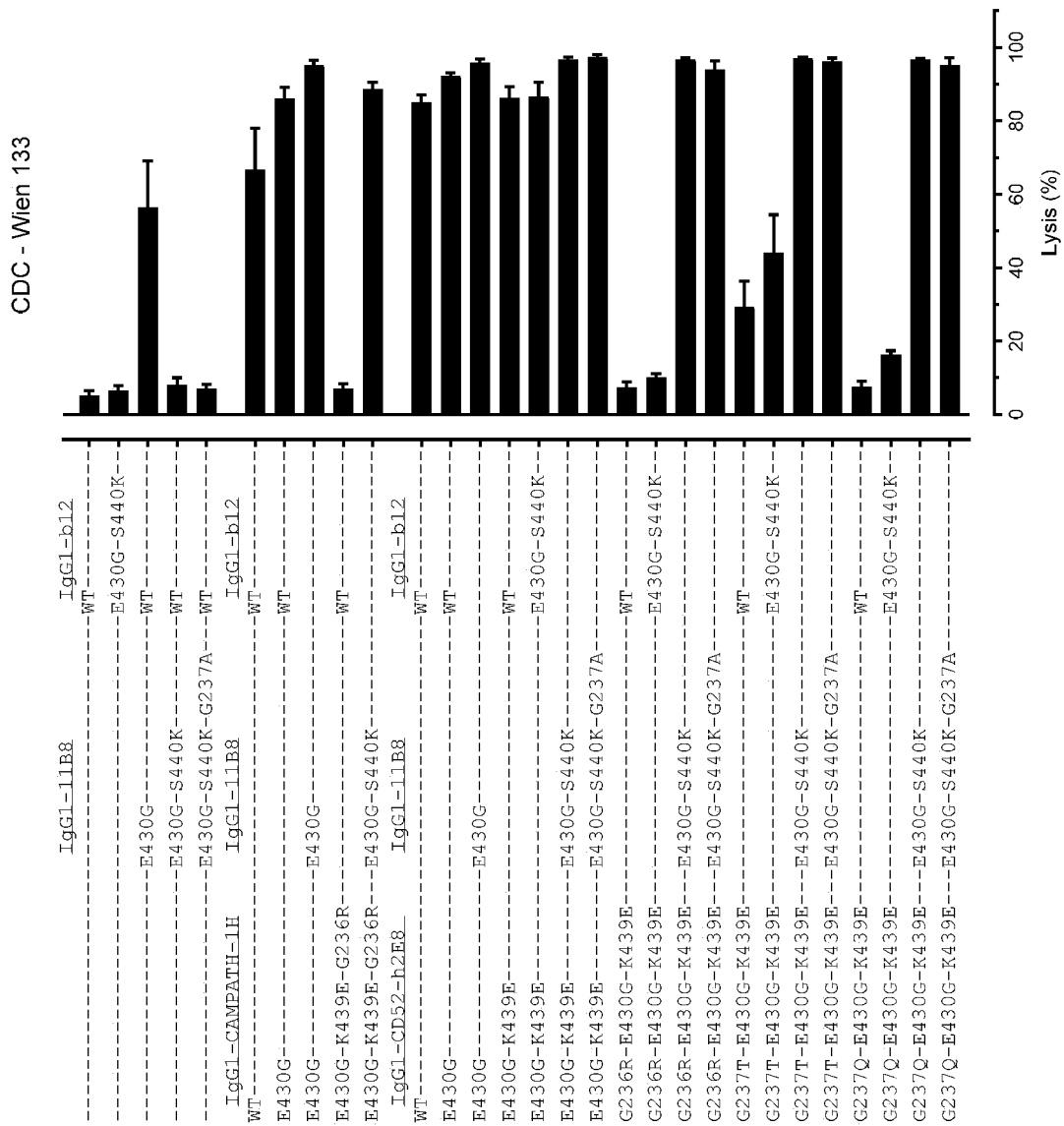

Similar to wild-type IgG1-CAMPATH-1H, wild-type IgG1-h2E8 induced CDC in Wien 133 cells with intermediate efficacy, which could be potentiated by introduction of Fc-Fc interaction enhancing mutation E430G to the same level induced by IgG1-CAMPATH-1H-E430G. Mixing IgG1-h2E8-E430G with IgG1-11B8-E430G induced CDC with an efficiency comparable to a mixture of IgG1-CAMPATH-1H-E430G and IgG1-11B8-E430G. The single agent CDC activity of IgG1-h2E8-E430G could be partially suppressed by introduction of self-oligomerization inhibiting mutation K439E. The maximal lysis induced by single agent IgG1-h2E8-E430G-K439E at 40 μg/ml was close to the level of a mixture of IgG1-h2E8-E430G+IgG1-11B8-E430G (FIG. 29B). CDC efficacy was restored by mixing IgG1-h2E8-E430G-K439E with IgG1-11B8-E430G-S440K (recovering approximately 90% of the potency of the positive control mixture IgG1-CAMPATH-1H-E430G+IgG1-11B8-E430G), but not by mixing with non-antigen binding IgG1-b12-E430G-S440K. The introduction of mutation G237A in IgG1-11B8-E430G-S440K in the latter mixture did not affect CDC efficacy of the mixture, measured either as AUC or as maximal lysis at 40 μg/ml (FIG. 29B).

Introduction of mutation G236R in IgG1-h2E8-E430G-K439E fully abrogated the residual single agent CDC activity, while approximately 79% of the CDC potency compared to the control mixture could be recovered by mixing with IgG1-11B8-E430G-S440K. Introduction of mutation G237A in IgG1-11B8-E430G-S440K mildly suppressed the CDC efficacy recovered after mixing with IgG1-h2E8-E430G-K439E-G236R. Introduction of mutation G237T in IgG1-h2E8-E430G-K439E suppressed, but did not fully abrogate, single agent CDC efficacy. Similar to the mixture of IgG1-h2E8-E430G-K439E-G236R and IgG1-11B8-E430G-S440K antibody variants, CDC efficacy of IgG1-h2E8-E430G-K439E-G237T could be restored by mixing with IgG1-11B8-E430G-S440K to approximately 88% of the control mixture potency, or with IgG1-11B8-E430G-S440K-G237A (to approximately 79% of). Like introduction of mutation G236R, introduction of G237Q in IgG1-h2E8-E430G-K439E fully abrogated the residual single agent CDC activity. CDC efficacy could be restored to approximately 84% of the control mixture potency by mixing with IgG1-11B8-E430G-S440K. Introduction of mutation G237A in IgG1-11B8-E430G-S440K in the latter mixture induced a mild suppression of CDC efficacy to approximately 74% of the control mixture potency. The maximal lysis induced at 40 μg/ml by all antibody mixtures of IgG1-h2E8-E430G-K439E antibody variants with any of the C1q-binding modulating mutations G236R, G237T or G237Q, and either IgG1-11B8-E430G-S440K or IgG1-11B8-E430G-S440K-G237A was comparable to the maximal lysis induced by a mixture of IgG1-h2E8-E430G-K439E and IgG1-11B8-E430G-S440K (FIG. 29B).

In conclusion, variants of the anti-CD52 antibody IgG1-h2E8 harboring the E430G mutation, self-oligomerization inhibiting mutation K439E and a C1q-binding modulating mutation showed comparable selective co-dependent CDC efficacy in Wien 133 cells as IgG1-CAMPATH-1H antibody variants harboring the same mutations, when mixed with anti-CD20 IgG1-11B8 antibody variants, showing that the effects induced by the mutations observed were not specific to IgG1-CAMPATH-1H, but were also applicable to other CD52-targeted antibodies.

Example 32: Target-Binding Independent Recruitment of Antibody Variants Containing Mutations that Enhance Fc-Fc Interactions, Inhibit Self-Oligomerization and Modulate C1q-Binding In the previous Examples, it was demonstrated that single agent CDC activity of antigen-binding antibody variants harboring an Fc-Fc interaction enhancing mutation and a self-oligomerization inhibiting mutation could be further reduced by introducing C1q-binding inhibiting mutations. Recovery of CDC efficacy was observed after mixing antibody variants with reduced single agent activity with complementary antigen-binding antibody variants harboring C1q-binding modulating mutations. Here, we tested whether co-dependent hexamerization and CDC could also be induced by mixing antigen-binding antibody variants with non-binding antibody variants harboring said mutations.

Different mutations were introduced in the anti-CD52 IgG1-CAMPATH-1H antibody, anti-CD20 IgG1-11B8 antibody and non-binding control antibody IgG1-b12: E430G, which induces enhanced Fc-Fc interactions; either of the mutations K439E or S440K, which inhibit the formation of homo-hexameric antibody complexes through inhibition of the intermolecular Fc-Fc interactions and promote the formation of hetero-hexameric antibody complexes through cross-complementary Fc-Fc interactions; G236R or G237A, which suppress binding of C1q to the hetero-hexameric antibody complex. A range of concentrations of purified antibodies (range 0.009-40.0 µg/mL final concentrations; 3.3-fold dilutions) was tested in an in vitro CDC assay on Wien 133 cells with 20% NHS, essentially as described in Example 2. The percentage of cell lysis was calculated as (number of PI-positive cells/total number of cells)×100%. The data were analyzed using best-fit values of a non-linear agonist dose-response model using log-transformed concentrations in GraphPad PRISM and the area under the dose-response curves of three experimental replicates was calculated. Relative areas under the curve (AUC) values represent values normalized to the AUC value observed for isotype control antibody IgG1-b12 (0%) and the AUC value of the mixture of IgG1-CAMPATH-1H-E430G+IgG1-11B8-E430G (100%).

Figure 30A:
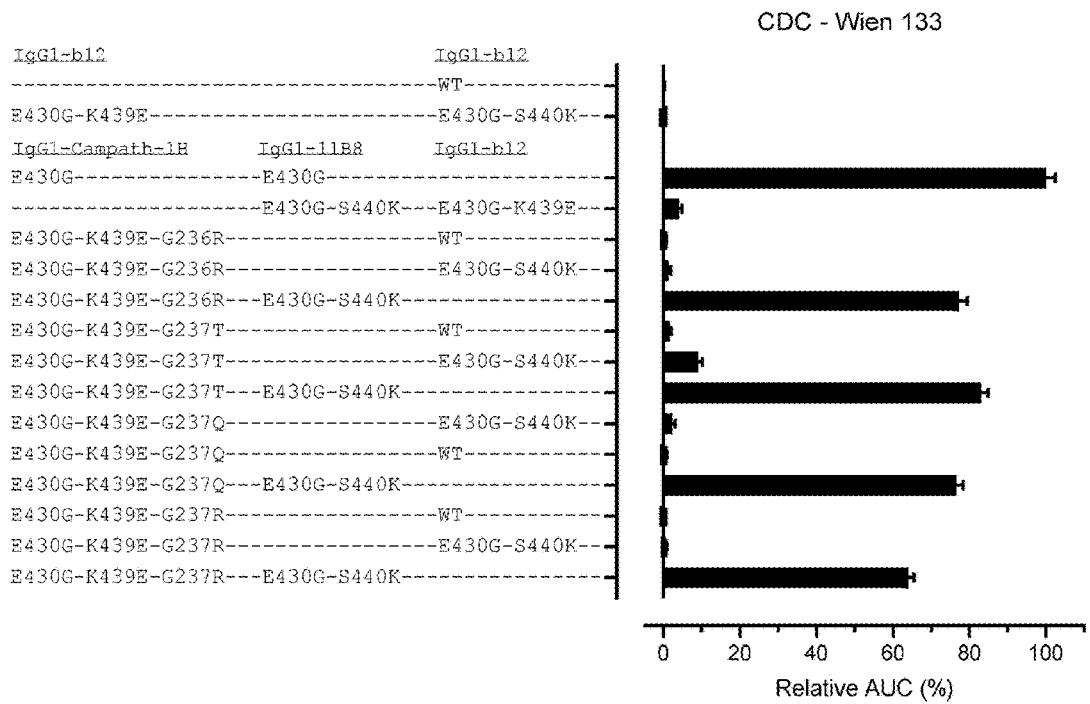
FIGS. 30A-30D show CDC efficacy of single agent and combined anti-CD52 IgG1-CAMPATH-1H-E430G, anti-CD20 IgG1-11B8-E430G, and non-antigen-binding IgG1-b12-E430G antibody variants harboring self-oligomerization inhibiting mutations and C1q-binding modulating mutations as indicated. Wien 133 cells were incubated with antibody concentration series in the presence of 20% NHS. CDC efficacy is presented as the AUC normalized to non-binding control antibody IgG1-b12 (0%) and the mixture of IgG1-CAMPATH-1H-E430G+IgG1-11B8-E430G (100%).
Figure 30B:
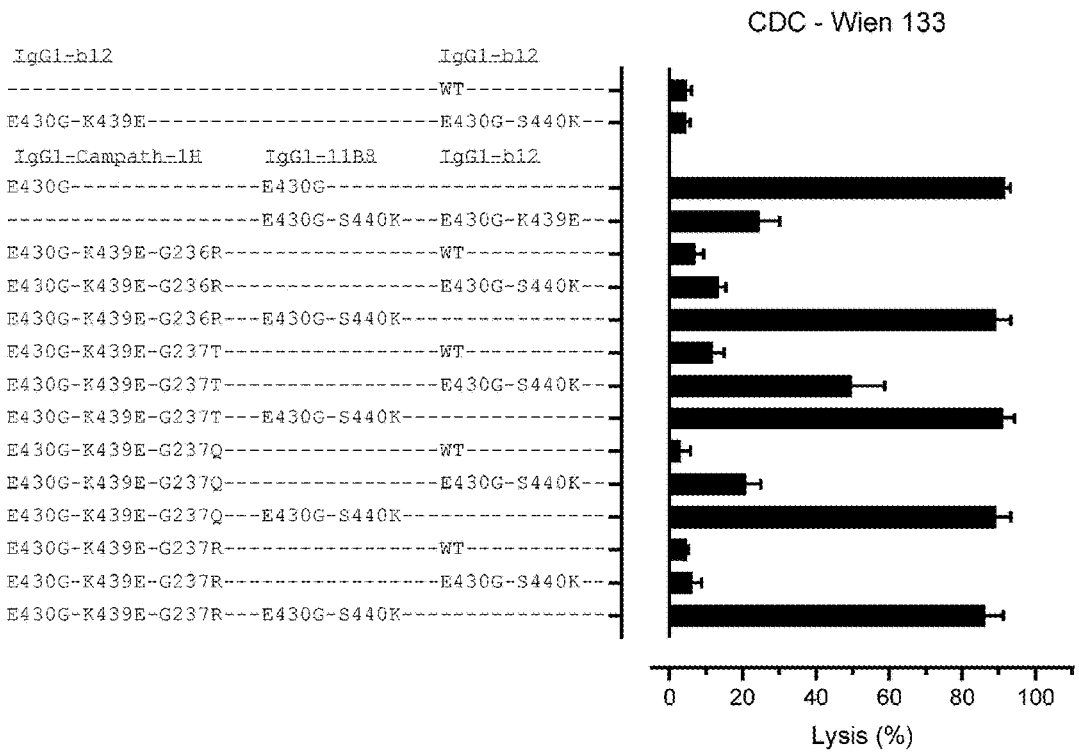

FIG. 30A, B shows that no single agent activity was observed for a mixture of antibody variants of the non-binding control antibody IgG1-b12 harboring the E430G mutation in combination with either of the mutations K439E or S440K. In addition, as described in previous Examples, no single agent activity was observed for antibodies IgG1-CAMPATH-1H-E430G-K439E-G236R, IgG1-CAMPATH-1H-E430G-K439E-G237Q, IgG1-CAMPATH-1H-E430G-K439E-G237R, or IgG1-11B8-E430G-S440K. When IgG1-CAMPATH-1H-E430G-K439E-G237T was mixed with non-antigen binding IgG1-b12-E430G-S440K, CDC was detected with 9% of the potency of that of the positive control mixture (IgG1-CAMPATH-1H-E430G+IgG1-11B8-E430G). When IgG1-11B8-E430G-S440K was incubated with non-binding IgG1-b12-E430G-K439E, modest CDC could be detected. In contrast, all four CAMPATH variants tested could potently recover CDC upon mixing with CD20 antigen-binding IgG1-11B8-E430G-S440K.

Figure 30C:
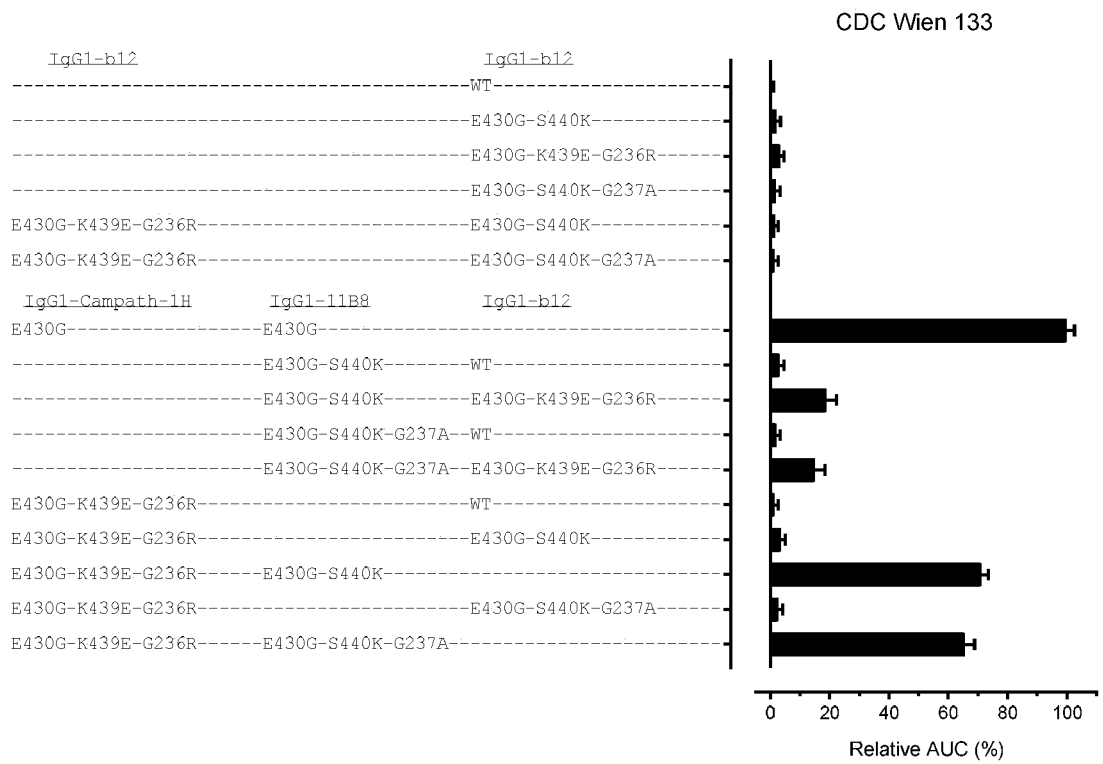
Figure 30D:
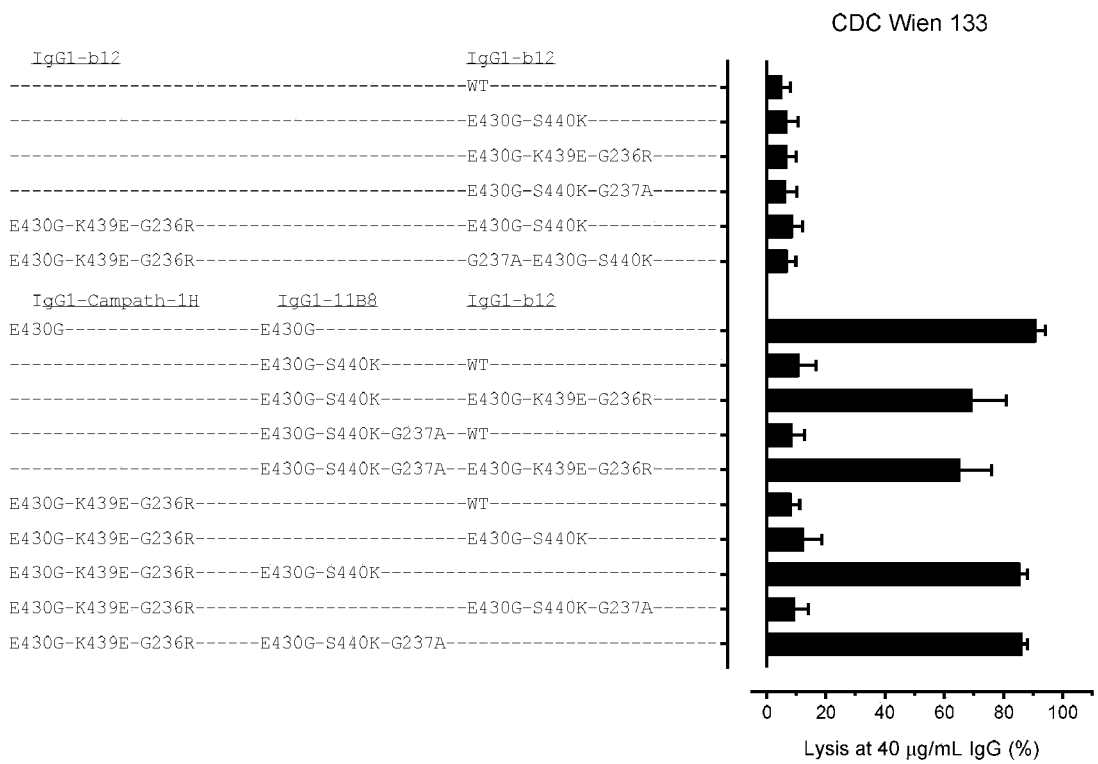

The potential recruitment of non-cell bound antibodies by CD20-directed IgG1-11B8 variants was analyzed in more detail in separate experiments by comparing the CDC efficacy after mixing with variants of CD52-binding antibody IgG1-CAMPATH-1H, or non-binding control antibody IgG1-b12, both containing E430G, K439E and G236R mutations (FIG. 30C, D). No single agent activity was observed for antibody variants of the non-binding control antibody IgG1-b12 harboring the E430G mutation in combination with either of the mutations K439E or S440K and either of the G236R of G237A mutations. Upon mixing two non-antigen binding IgG1-b12 antibody variants which both harbor the E430G mutation, either of the K439E or S440K mutations and either of the G236R or G237A mutations, no CDC efficacy was observed. Partial recovery of CDC efficacy to approximately 15% and 19% of the CDC potency of the positive control mixture was observed after mixing non-antigen binding antibody IgG1-b12-E430G-K439E-G236R with either IgG1-11B8-E430G-S440K or IgG1-11B8-E430G-S440K-G237A, respectively. CDC activity could be recovered to approximately 65% and 71% of the level induced by the positive control mixture by mixing IgG1-CAMPATH-1H-E430G-K439E-G236R with either IgG1-11B8-E430G-S440K or IgG1-11B8-E430G-S440K-G237A, respectively. This recovery was not induced upon mixing IgG1-CAMPATH-1H-E430G-K439E-G236R with either of the non-target binding antibodies IgG1-b12-E430G-S440K or IgG1-b12-E430G-S440K-G237A.

These data indicate that antigen-binding antibody variants harboring Fc-Fc interaction enhancing mutation E430G, self-oligomerization inhibiting mutation S440K and optionally C1q-binding inhibiting mutation G237A can recruit non-antigen bound antibody variants harboring complementary mutations E430G, K439E and G236R, ultimately resulting in the induction of CDC. Antigen-binding independent recruitment of the complementary antibody E430G-S440K was strongly suppressed if the antigen-bound antibody contained in addition to E430G-K439E also either of the C1q-binding inhibiting mutations G236R, G237Q, or G237R, whereas G237T failed to block antigen-binding independent recruitment of the complementary antibody.

Example 33: Capacity to Activate FcγRIIa and FcγRIIIa by Antibody Variants Harboring Mutations that Enhance Fc-Fc Interaction, Inhibit Self-Oligomerization and Modulate C1q-Binding In Example 31, the binding of antibody variants harboring Fc-Fc interaction enhancing mutation E430G, either of self-oligomerization inhibiting mutations K439E or S440K and either of the C1q-binding modulating mutations G236R, G237A, G237T, G237Q, G237R or K322A to FcγRIa, FcγRIIa, FcγRIIb, and FcγRIIIa was studied. Introduction of C1q-binding modulating mutations at the G236 or G237 positions resulted in suppression of FcγR binding. Here, we studied whether introduction of C1q-binding modulating mutations G236R, G237A, G237A-E333S or G237Q in anti-CD52 IgG1-CAMPATH-1H-E430G-K439E and anti-CD20 IgG1-11B8-E430G-S440K affected the induction of ADCC by determining FcγRIIa and FcγRIIIa-mediated activation in a Promega reporter assay using target-expressing Raji cells and a Jurkat reporter cell line expressing the high affinity allotype variants of human FcγRIIa or human FcγRIIIa. Activation of FcγR-mediated signaling by the IgG1-CAMPATH-1H and IgG1-11B8 antibody variants mentioned above was quantified using ADCC Reporter BioAssays (Promega, FcγRIIa: Cat #G9995; FcγRIIIa: Cat #G7018) on Raji cells, according to the manufacturer's recommendations. As effector cells, the kit contains Jurkat human T cells that are engineered to stably express high affinity FcγRIIa (FcγRII-H) or FcγRIIIa (V158) and a nuclear factor of activated T cells (NFAT)-response element driving expression of firefly luciferase. Briefly, Raji cells (5.000 cells/well) were seeded in 384-Wells white Opti-Plates (Perkin Elmer Cat #6007290) in ADCC Assay Buffer (Promega, Cat #G719A) supplemented with 12% Low IgG Serum (Promega; Cat #G711A) and incubated for 6 hours at 37° C./5% CO2 in a total volume of 30 µL containing antibody concentration series (0.0002-40 µg/mL final concentrations in 4-fold dilutions) and thawed ADCC Bioassay Effector Cells. After incubating the plates for 15 minutes at room temperature (RT), 30 µL Bio Glo Assay Luciferase Reagent was added and incubated for 5 minutes at RT. Luciferase production was quantified by luminescence readout on an EnVision Multilabel Reader (Perkin Elmer). Luminescence signals were normalized by subtracting with background luminescence signal determined from medium-only samples (no Raji cells, no antibody, no effector cells). The data were analyzed using best-fit values of a non-linear agonist dose-response model using log-transformed concentrations in GraphPad PRISM and the area under the dose-response curves of three (FcγRIIa) or two (FcγRIIIa) experimental replicates was calculated. AUC values were normalized per experiment relative to the reporter activity observed for cells incubated with non-binding control IgG1-b12 (0%) and the activity of the mixture of wild type IgG1-Campath-1H+wild type IgG1-11B8 (100%), and subsequently averaged over the experimental replicates.

Figure 31A:
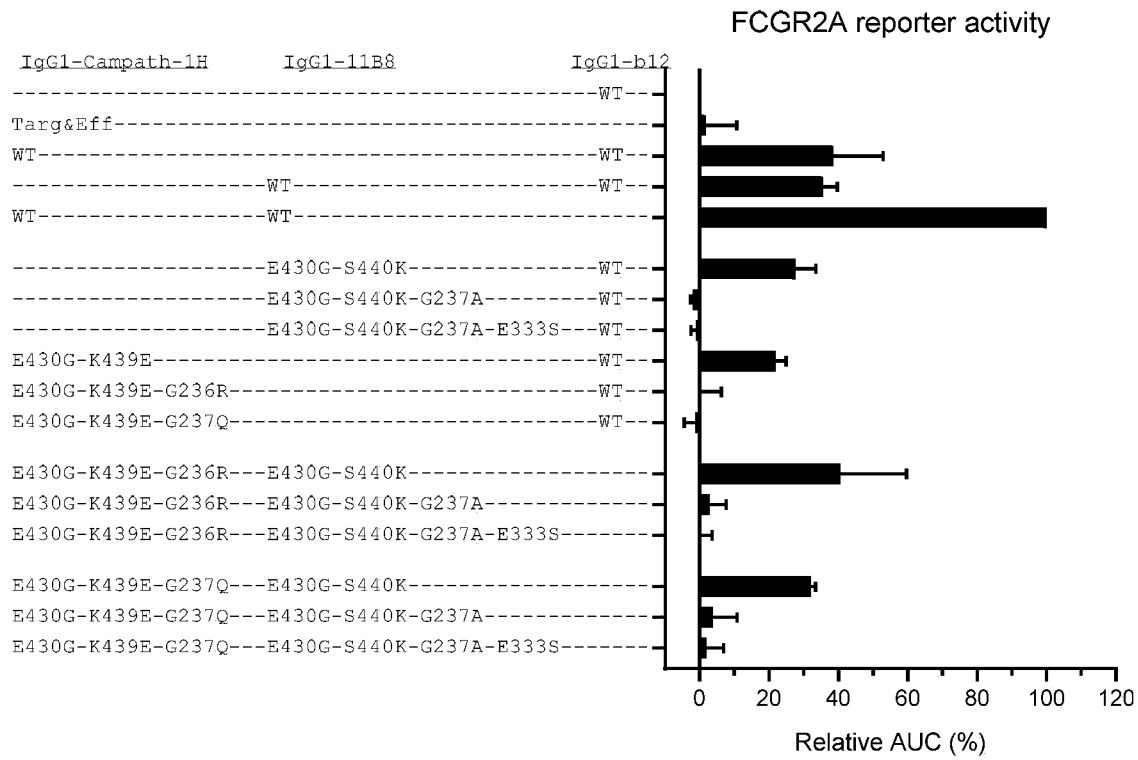
FIGS. 31A and 31B show the activation of Jurkat reporter cell lines stably expressing either (FIG. 31A) FcγRIIa or (FIG. 31B) FcγRIIIa, as measured by the level of luminescence (RLU), upon co-culturing with Raji lymphoma cells and different concentrations of IgG1-CAMPATH-1H and IgG1-11B8 antibody variants. Luminescence values were normalized per experiment relative to those observed for IgG1-b12 (0%) and wild type IgG1-Campath-1H+wild type IgG1-11B8 (100%), before averaging over three (FcγRIIa) or two (FcγRIIIa) experimental replicates.
Figure 31B:
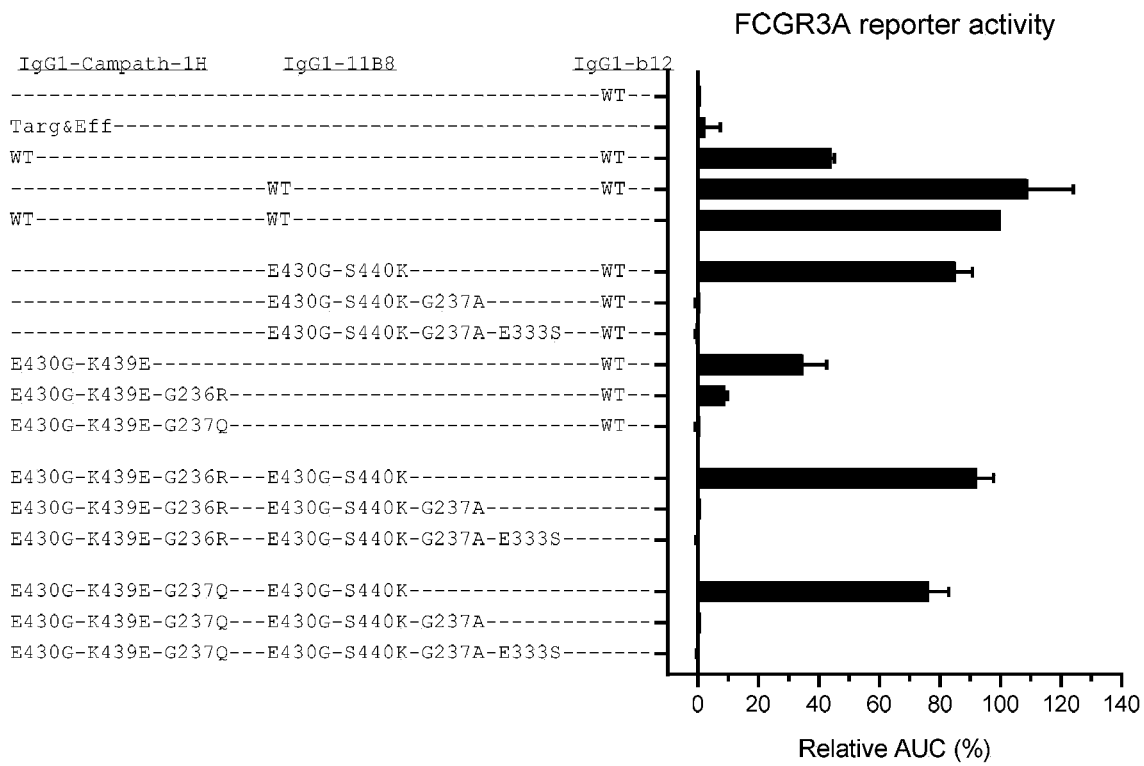

As a single agent, antibody variant IgG1-11B8-E430G-S440K induced FcγRIIa-mediated activation (FIG. 31A), which is in line with the results in Example 31 showing FcγRIIa-binding by this variant. In contrast, no FcγRIIa-mediated activation by single agent antibody variants was observed upon introduction of C1q-binding modulating mutations G236R, or G237Q in IgG1-CAMPATH-1H-E430G-K439E, or mutations G237A, or G237A-E333S in IgG1-11B8-E430G-S440K. Also mixtures of IgG1-CAMPATH-1H-E430G-K439E variants harboring mutation G236R or G237Q and IgG1-11B8-E430G-S440K variants harboring mutations G237A or G237A-E333S did not induce FcγRIIa-mediated activation. However, a mixture of IgG1-11B8-E430G-S440K and either IgG1-CAMPATH-1H-E430G-K439E-G236R or IgG1-CAMPATH-1H-E430G-K439E-G237Q did induce FcγRIIa-mediated activation. The same antibody variants were tested for the capacity to induce FcγRIIIa-mediated activation (FIG. 31B). Here, FcγRIIIa-mediated activation was observed by IgG1-11B8-E430G-S440K alone or when mixed with IgG1-CAMPATH-1H-E430G-K439E variants harboring either the G236R or G237Q mutation. IgG1-CAMPATH-1H-E430G-K439E with or without mutation G236R induced low or intermediate FcγRIIIa-mediated activation, respectively. When IgG1-CAMPATH-1H-E430G-K439E-G236R or IgG1-CAMPATH-1H-E430G-K439E-G237Q were mixed with either of the IgG1-11B8-E430G-S440K variants G237A or G237A-E333S, FcγRIIIa-mediated activation could not be detected.

In conclusion, the capacity to induce FcγRIIa- or FcγRIIIa-mediated activation, used as a surrogate measure for ADCC, by IgG1-CAMPATH-1H and IgG1-11B8 antibody variants harboring an Fc-Fc interaction enhancing and self-oligomerization inhibiting mutation was efficiently abrogated by the introduction of C1q-binding modulating mutations G236R, G237A, G237A-E333S or G237Q.

Example 34: Selectivity of CDC Activity on Wien 133 Cells after Titrating Components of a Mixture of Anti-CD52 IgG1-CAMPATH-1H and Anti-CD20 IgG1-11B8 Antibody Variants with Mutations that Enhance Fc-Fc Interactions, Inhibit Self-Oligomerization and Modulate C1q-Binding In the previous Examples, antibody variants harboring a mutation that enhances Fc-Fc interactions, as well as a mutation that inhibits self-oligomerization and a mutation that modulates C1q-binding were mixed in a 1:1 ratio. Here, we tested whether selective co-dependent CDC activity was also attained by mixing two antibody variants at non-equimolar ratios.

An in vitro CDC assay using Wien 133 cells was performed with 20% NHS, essentially as described in Example 2. Single antibodies were titrated in 3.3-fold dilutions (final concentration range 0.005-20.0 μg/mL). When antibody mixtures were applied, one component was titrated (final concentration range 0.0003-20.0 μg/mL in 5-fold dilutions) and the other component was used at a fixed concentration of 20 μg/mL. Cell lysis was calculated from the number of PI-positive cells as described in Example 2.

Figure 32A:
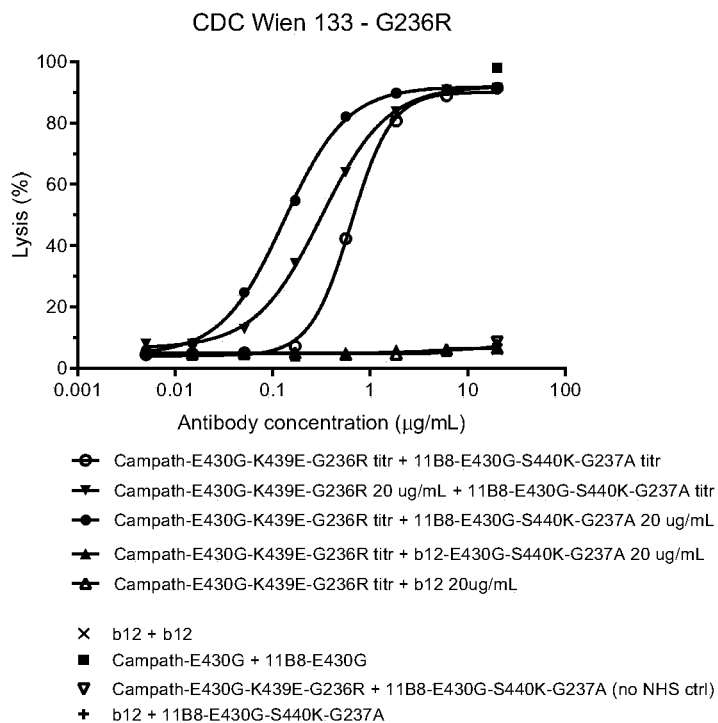
FIGS. 32A and 32B show co-dependent CDC on Wien 133 cells induced by mixtures of IgG1-CAMPATH-1H and IgG1-11B8 antibody variants harboring mutations that enhance Fc-Fc interactions, inhibit self-oligomerization and modulate C1q-binding in non-equimolar ratios.
Figure 32B:
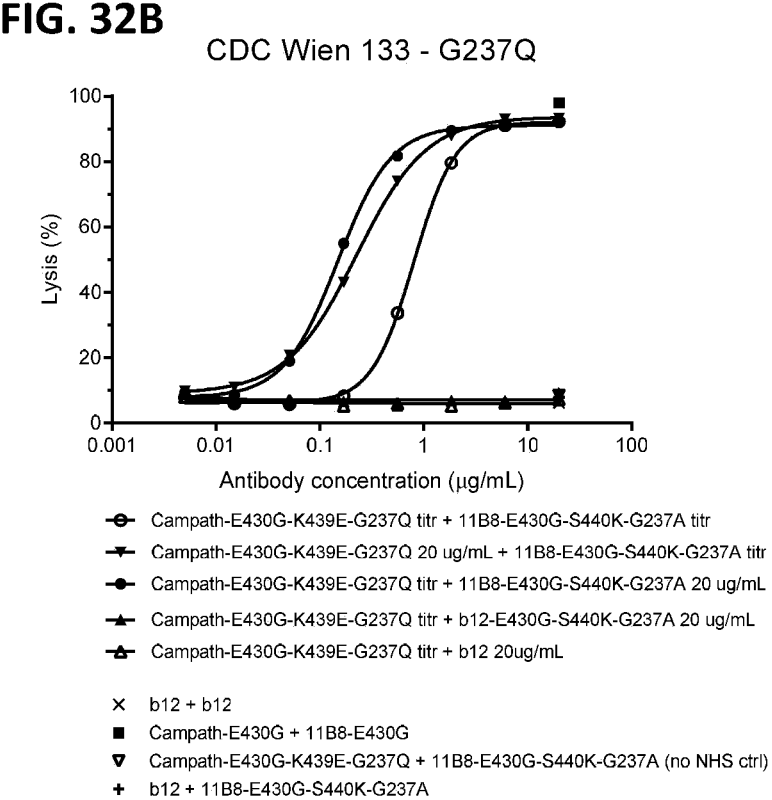

Efficient CDC activity on Wien 133 cells was induced by a titrated mixture (1:1 ratio) of IgG1-CAMPATH-1H-E430G-K439E-G236R and IgG1-11B8-E430G-S440K-G237A (FIG. 32A). CDC was induced even more efficiently upon incubating Wien 133 cells with an antibody variant mixture in which one antibody variant was titrated while the other antibody variant was applied at a fixed concentration of 20 μg/mL. No CDC activity was detected upon mixing titrated IgG1-CAMPATH-1H-E430G-K439E-G236R with 20 μg/mL of non-target binding antibody IgG1-b12 or a variant thereof harboring the E430G-S440K-G237A mutations, indicating that hetero-hexamerization remained target-binding dependent even at IgG concentrations saturating CD20 binding. Also, no CDC was observed upon mixing IgG1-CAMPATH-1H-E430G-K439E-G236R and IgG1-11B8-E430G-S440K-G237A in the absence of serum, indicating C1q is required for stabilization of the hexameric complex. Highly similar results were obtained for mixtures of IgG1-CAMPATH-1H-E430G-K439E-G237Q and IgG1-11B8-E430G-S440K-G237A (FIG. 32B). CDC was only induced by mixtures of IgG1-CAMPATH-1H-E430G-K439E-G237Q and IgG1-11B8-E430G-S440K-G237A, in mixtures in which both antibody variants were titrated or in mixtures in which one antibody variant was titrated and the other antibody variants was applied at a fixed concentration of 20 μg/mL. Mixtures of IgG1-CAMPATH-1H-E430G-K439E-G237Q and non-target binding antibody IgG1-b12 or a variant thereof harboring the E430G-S440K-G237A mutations did not induce CDC.

In conclusion, efficient CDC on Wien 133 cells could be induced co-dependently by antibody variants of IgG1-CAMPATH-1H and IgG1-11B8 harboring the Fc-Fc interaction enhancing mutation E430G, either of the self-oligomerization inhibiting mutations K439E or S440K and either of the C1q-binding modulating mutations G236R, G237A or G237Q over a wide range of non-equimolar ratio's: >50% lysis was observed at CAMPATH:11B8 ratio's ranging from 100:3 down to 1:100, provided binding to at least one of the two targets was saturated.

Example 35: Selectivity of Anti-CD52 and Anti-HLA-DR Antibody Variants Harboring Fc-Fc Interaction Enhancing Mutation E430G, Either of the Self-Oligomerization Inhibiting Mutations K439E or S440K, and C1q-Binding Modulating Mutations P329R or G236R Here, the selective co-dependent CDC efficacy by anti-CD52 and anti-HLA-DR antibody variants harboring an Fc-Fc interaction enhancing mutation, self-oligomerization inhibiting mutations and C1q-binding modulating mutations was studied on Oci-Ly17 lymphoma cells.

Different mutations were introduced in anti-CD52 antibody IgG1-CAMPATH-1H and anti-HLA-DR antibodies IgG1-HLA-DR-huL243 and IgG1-HLA-DR-1D09C3: E430G, which induces enhanced Fc-Fc interactions, either of the self-oligomerization inhibiting mutations K439E or S440K, and either of the mutations G236 or P329R, which suppress binding of C1q. As controls, single antibodies were also mixed 1:1 with non-binding isotype control antibodies IgG1-b12 or IgG1-b12-E430G-S440K to enable direct comparison of the concentrations of individual components and mixtures composed thereof. A range of concentrations of purified antibodies (range 0.009-40.0 μg/mL final concentrations; 3.3-fold dilutions) was tested in an in vitro CDC assay on 30,000 Oci-Ly17 lymphoma cells per condition with 20% NHS, essentially as further described in Example 2. The percentage of cell lysis was calculated as (number of PI-positive cells/total number of cells)×100%. The data were analyzed using best-fit values of a non-linear agonist dose-response model using log-transformed concentrations in GraphPad PRISM and the area under the dose-response curves of three experimental replicates was calculated. Relative areas under the curve (AUC) values represent normalization to minimal lysis (0% with IgG1-b12) and maximal lysis (100% with the mixture of IgG1-CAMPATH-1H-E430G+IgG1-HLA-DR-huL243-E430G in FIG. 33A; or 100% with the mixture of IgG1-CAMPATH-1H-E430G+IgG1-HLA-DR-1D09C3-E430G in FIG. 33B).

Figure 33A:
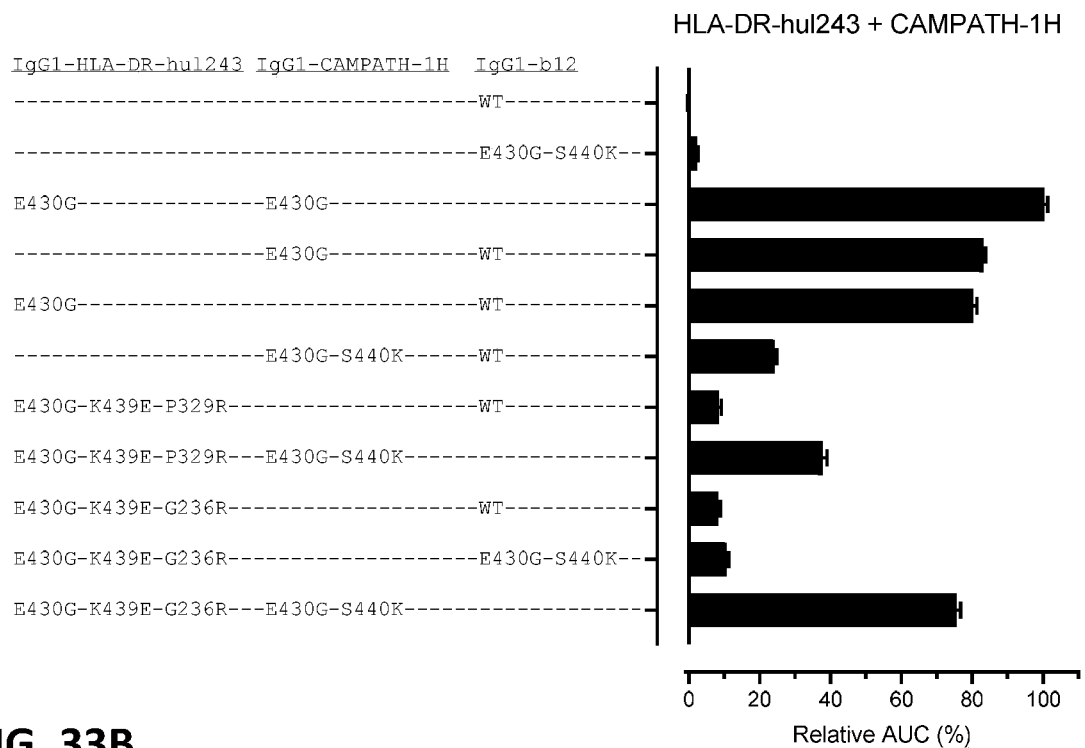
FIGS. 33A and 33B show selectivity of CDC activity by mixtures of antibody variants of anti-CD52 IgG1-CAMPATH-1H with either anti-HLA-DR IgG1-HLA-DR-huL243 variants (FIG. 33A) or anti-HLA-DR IgG1-HLA-DR-1D09C3 variants (FIG. 33B) by introduction of mutations that enhance Fc-Fc interactions, inhibit self-oligomerization and inhibit C1q-binding. Oci-Ly17 cells were incubated with antibody concentration series in the presence of 20% NHS. CDC efficacy is presented as the AUC normalized to non-binding control antibody IgG1-b12 (0%) and the mixture of (FIG. 33A) IgG1-CAMPATH-1H-E430G+IgG1-HLA-DR-huL243-E430G (100%) or (FIG. 33B) IgG1-CAMPATH-1H-E430G+IgG1-HLA-DR-1D09C3-E430G (100%).

A mixture of IgG1-CAMPATH-1H-E430G and IgG1-HLA-DR-huL243-E430G induced efficient CDC of Oci-Ly17 cells (positive control mixture; set at 100%, FIG. 33A). The single agents of the latter mixture induced CDC to approximately 83% (IgG1-CAMPATH-1H-E430G) and 80% (IgG1-HLA-DR-huL243-E430G) of the potency of the positive control mixture. Introduction of mutation S440K in IgG1-CAMPATH-1H-E430G reduced the capacity to induce CDC to approximately 24% of the control mixture potency, while the introduction of double mutation K439E-P329R in IgG1-HLA-DR-huL243-E430G reduced the capacity to induce CDC to approximately 8.5% of the control mixture potency. By mixing IgG1-HLA-DR-huL243-E430G-K439E-P329R and IgG1-CAMPATH-1H-E430G-S440K, the capacity to induce CDC was restored to approximately 38% of the control mixture potency. Single agent CDC efficacy of IgG1-HLA-DR-huL243-E430G was abrogated by introduction of the double mutation K439E-G236R. Restoration of CDC efficacy could be attained by mixing IgG1-HLA-DR-huL243-E430G-K439E-G236R with IgG1-CAMPATH-1H-E430G-S440K to approximately 75% of control mixture potency, but not with the non-target binding antibody variant IgG1-b12-E430G-S440K.

Figure 33B:
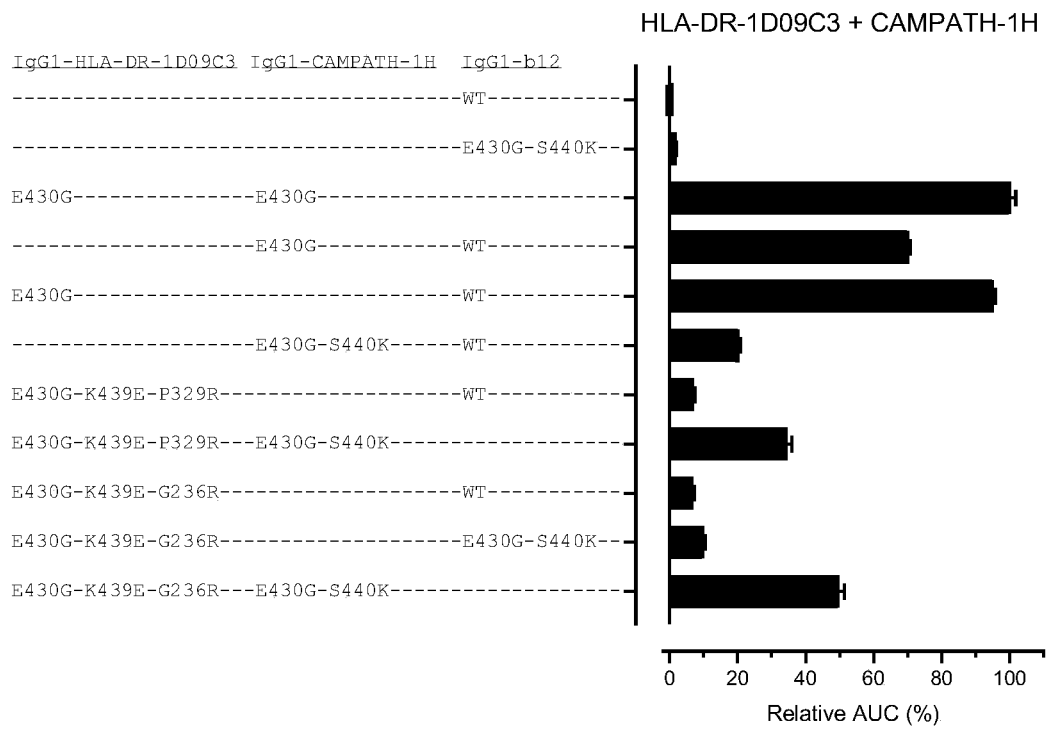

Comparable results were observed when testing variants of anti-HLA-DR antibody IgG1-HLA-DR-1D09C3 instead of IgG1-HLA-DR-huL243 (FIG. 33B). A mixture of IgG1-CAMPATH-1H-E430G and IgG1-HLA-DR-1D09C3-E430G induced efficient CDC of Oci-Ly17 cells (positive control mixture; set at 100%, FIG. 33B). The single agents of the latter mixture induced CDC to approximately 70% (IgG1-CAMPATH-1H-E430G) and 95% (IgG1-HLA-DR-1D09C3-E430G) of the control mixture potency. Introduction of mutation S440K in IgG1-CAMPATH-1H-E430G reduced the capacity to induce CDC to approximately 20% of control mixture potency, while the introduction of double mutation K439E-P329R in IgG1-HLA-DR-1D09C3-E430G reduced the capacity to induce CDC to approximately 7% of control mixture potency. By mixing IgG1-HLA-DR-huL243-E430G-K439E-P329R and IgG1-CAMPATH-1H-E430G-S440K, the capacity to induce CDC was restored to approximately 35% of the level induced by the control mixture potency. Single agent CDC efficacy of IgG1-HLA-DR-1D09C3-E430G was abrogated by introduction of the double mutation K439E-G236R. Restoration of CDC efficacy could be attained by mixing IgG1-HLA-DR-1D09C3-E430G-K439E-G236R with IgG1-CAMPATH-1H-E430G-S440K to approximately 50% of control mixture potency, but not with the non-target binding antibody variant IgG1-b12-E430G-S440K.

In conclusion, these data show that selective, co-dependent CDC of Oci-Ly17 lymphoma cells could be induced by mixing antibody variants of anti-CD52 IgG1-CAMPATH-1H with antibody variants of either anti-HLA-DR IgG1-HLA-DR-huL243 or IgG1-HLA-DR-1D09C3 by introducing Fc-Fc interaction enhancing mutation E430G, self-oligomerization inhibiting mutations K439E or S440K, and C1q-binding inhibiting mutations P329R or G236R.

Example 36: Selectivity of Antibody Variants Containing Mutations at the L234 and L235 Position that Suppress FcγR-Binding and C1q-Binding In Examples 5 and 12, the effect on CDC efficacy upon introduction of mutations that modulate C1q-binding in antibody variants was described. Introduction of mutations G236R and G237Q in IgG1-CAMPATH-1H-E430G-K439E resulted in abrogation of single agent CDC activity on Wien 133 cells. Here, the effects on CDC efficacy on Wien 133 cells were studied for IgG1-CAMPATH-1H-E430G-K439E and IgG1-11B8-E430G-S440K antibody variants upon introduction of C1q-binding modulating mutations at the L234 and L235 position.

Different mutations were introduced in antibodies IgG1-CAMPATH-1H and IgG1-11B8: E430G, which induces enhanced Fc-Fc interactions; either of the self-oligomerization inhibiting mutations K439E or S440K; and L234A, L234A-L235A, L234F, L234F-L235E, L235A, L235Q, G236R or G237Q which suppress binding of C1q to the hetero-hexameric antibody complex. As controls, single antibodies were also mixed 1:1 with non-binding isotype control antibodies IgG1-b12 to enable direct comparison of the concentrations of individual components and mixtures composed thereof. Here, unpurified supernatants from transiently transfected EXPI293 supernatants were used as source of IgG for IgG1-CAMPATH-1H variants containing substitutions in L234, L235 or combinations thereof. A range of concentrations of antibodies (range 0.009-40.0 μg/mL final concentrations; 3.3-fold dilutions) was tested in an in vitro CDC assay on Wien 133 cells with 20% NHS, essentially as described in Example 2. The percentage of cell lysis was calculated as (number of PI-positive cells/total number of cells)×100%. The data were analyzed using best-fit values of a non-linear agonist dose-response model using log-transformed concentrations in GraphPad PRISM and the area under the dose-response curves of three experimental replicates was calculated.

Relative areas under the curve (AUC) values represent normalization to minimal lysis (0% with IgG1-b12) and maximal lysis (100% with the mixture of IgG1-CAMPATH-1H-E430G+IgG1-11B8-E430G).

Figure 34:
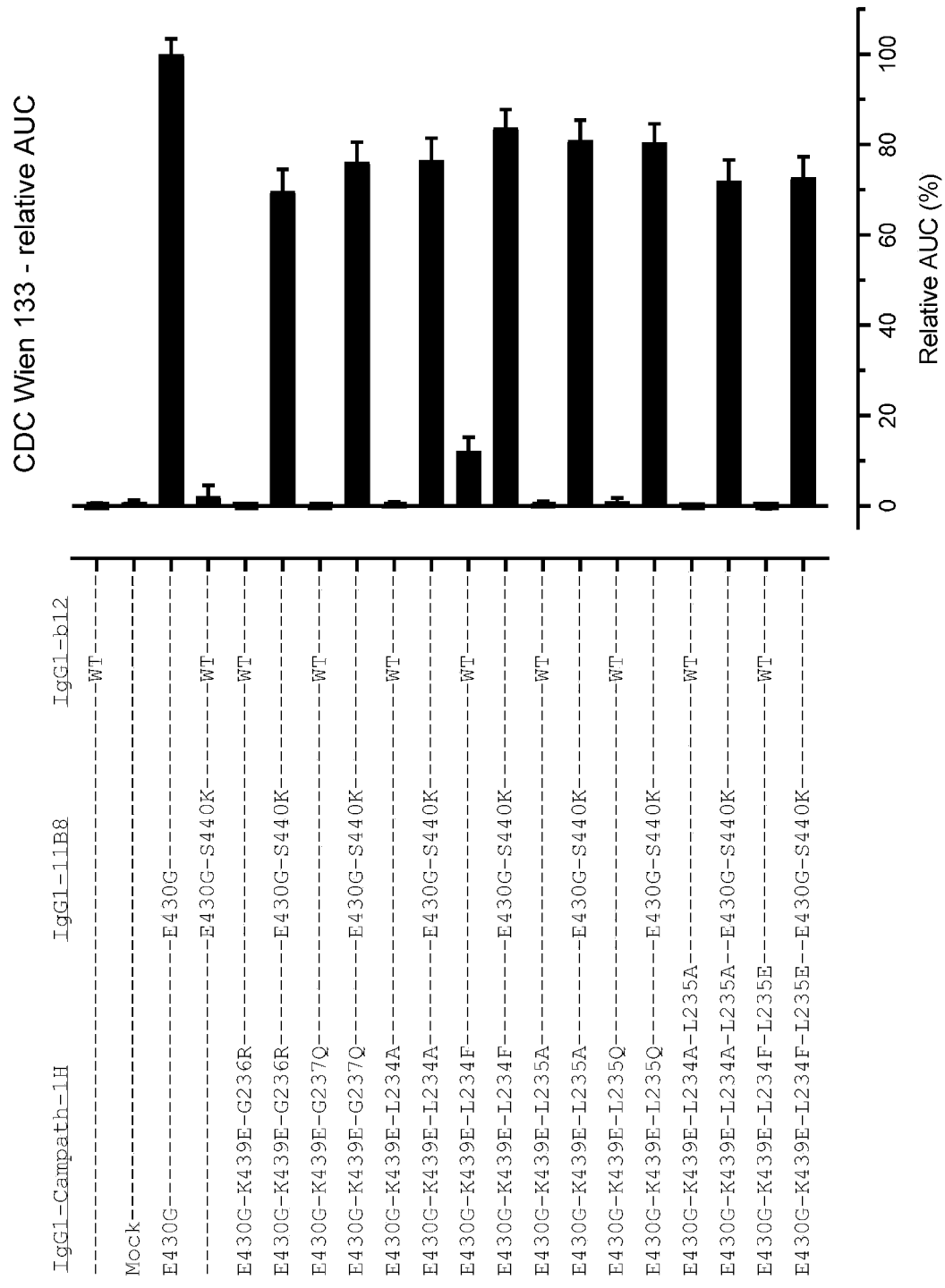
FIG. 34 shows the selective co-dependent CDC activity of mixed antibody variants of anti-CD52 IgG1-CAMPATH-1H and anti-CD20 IgG1-11B8 by introduction of mutations that enhance Fc-Fc interactions, inhibit self-oligomerization and inhibit C1q-binding. CDC efficacy is shown for variants of IgG1-CAMPATH-1H-E430G-K439E with either of the mutations L234A, L234A-L235A, L234F, L234F-L235E, L235A, L235Q, G236R or G237Q and mixtures of these variants with either non-binding control antibody IgG1-b12 or IgG1-11B8-E430G-S440K. CDC efficacy is presented as the AUC normalized to non-binding control antibody IgG1-b12 (0%) and the mixture of IgG1-CAMPATH-1H-E430G+IgG1-11B8-E430G (100%).

Mock-transfected EXPI293 supernatant did not induce lysis of Wien 133 cells, ruling out a contribution by substances in the unpurified supernatants used. The single agent CDC efficacy of IgG1-CAMPATH-1H-E430G-K439E on Wien 133 cells was fully abrogated upon introduction of either of the mutations L234A, L234A-L235A, L234F-L235E, L235A, L235Q, G236R or G237Q, while low residual CDC activity was observed for IgG1-CAMPATH-1H-E430G-K439E-L234F (FIG. 34). For all these antibody variants, CDC efficacy could be partially restored upon mixing with IgG1-11B8-E430G-S440K. The efficiency of CDC recovery ranged from approximately 70% (IgG1-CAMPATH-1H-E430G-K439E-G236R+IgG1-11B8-E430G-S440K) to approximately 84% (IgG1-CAMPATH-1H-E430G-K439E-L234F+IgG1-11B8-E430G-S440K) of the potency defined by the AUC of the positive control mixture IgG1-CAMPATH-1H-E430G+IgG1-11B8-E430G.

In conclusion, single agent activity of IgG1-CAMPATH-1H-E430G-K439E on Wien 133 cells could be abrogated by introduction of C1q-binding inhibiting mutations L234A, L234A-L235A, L234F, L234F-L235E, L235A and L235Q, comparable to the effects of introduction of mutations G236R or G237Q. Recovery of CDC efficacy could be attained by mixing these antibody variants with IgG1-11B8-E430G-S440K. So, it was observed that any of the C1q-binding inhibiting substitutions tested in previous examples and this example could improve the selectivity of the co-dependently acting antibodies of the present invention. Within this large group, G236K/R, G237, L234 and L235 substitutions are preferred substitutions as they modulate C1q binding relatively mildly, while simultaneously inhibiting FcγR-mediated effector functions. Without being limited by theory, this may make it possible to recover potent oligomerization-dependent activity, such as CDC, if the hetero-hexameric complex formed between the two antibodies of the present invention on cells bound by both antibodies has sufficient C1q-binding avidity, thereby selectively displaying maximal activity on cells bound by both antibodies.

Example 37: Selectivity of Antibody Variants with Alternative Fc-Fc Interaction Enhancing Mutations at the E345 and E430 Positions, in Addition to Mutations that Inhibit Self-Oligomerization and Modulate C1q-Binding In previous Examples, the Fc-Fc interaction enhancing mutations E345K, E345R and E430G were introduced in co-dependent antibody variants. Here, we studied whether introduction of alternative substitutions at the E430 and E345 positions in antibody variants of IgG1-CAMPATH-1H and IgG1-11B8 harboring mutations that inhibit self-oligomerization and modulate C1q-binding resulted in co-dependent induction of CDC on Wien 133 cells.

Different mutations were introduced in antibodies IgG1-CAMPATH-1H and IgG1-11B8. E430 substitutions E430G, E430N, E430T, E430V, and E430Y were chosen to represent widely different substitutions, such as small, hydrophilic, hydrophobic, and large/aromatic mutations. Likewise, mutations E345A, E345K, E345Q, E345R, E345V, E345Y introduced into E345 were chosen to represent small, basic/charged, hydrophilic, hydrophobic, and large/aromatic mutations. Mutation combination K248E-T437R was previously suggested to modulate IgG oligomerization via Fc-Fc interactions (WO2018031258). Furthermore, antibodies contained either the self-oligomerization inhibiting mutations K439E or S440K, and/or C1q modulating mutations G236R, G237A or E333S. As controls, single antibodies were also mixed 1:1 with non-binding isotype control antibodies IgG1-b12 to enable direct comparison of the concentrations of individual components and mixtures composed thereof. Here, unpurified supernatants from transiently transfected EXPI293 supernatants were used as source of IgG for antibody variants that did not contain an E430G, E345K, or E345R substitution. A range of concentrations of antibodies (range 0.009-40.0 µg/mL final concentrations; 3.3-fold dilutions) was tested in an in vitro CDC assay on Wien 133 cells with 20% NHS, essentially as described in Example 2. The percentage of cell lysis was calculated as (number of PI-positive cells/total number of cells)×100%. The data were analyzed using best-fit values of a non-linear agonist dose-response model using log-transformed concentrations in GraphPad PRISM and the area under the dose-response curves of two experimental replicates was calculated. CDC potency/efficiency presented as relative areas under the curve (AUC) values represent values normalized per plate relative to minimal lysis (0% with IgG1-b12) and maximal lysis (100% with the mixture of IgG1-CAMPATH-1H-E430G+IgG1-11B8-E430G), that were subsequently averaged over the two independent experimental replicates.

Mock-transfected EXPI293 supernatant did not induce lysis of Wien 133 cells, ruling out a contribution by substances in the unpurified supernatants used. As described in previous Examples, introduction of mutations E430G-S440K or E430G-S440K-G237A in IgG1-11B8 abrogated the single agent CDC efficacy (FIG. 35A), while the single agent CDC activity of IgG1-CAMPATH-1H could be abrogated by introduction of mutations E430G-K439E-G236R. CDC efficacy was restored by mixing IgG1-CAMPATH-1H-E430G-K439E-G236R with IgG1-11B8 antibody variants with either the E430G-S440K or E430G-S440K-G237A mutations to approximately 82% and 91%, respectively, of the potency measured for the positive control mixture IgG1-CAMPATH-1H-E430G+IgG1-11B8-E430G.

When either of the mutations E430N (resulting in SEQ ID NO 115), E430T (resulting in SEQ ID NO 117), E430V (resulting in SEQ ID NO 119), E345A (resulting in SEQ ID NO 64), E345K (resulting in SEQ ID NO 66), E345Q (resulting in SEQ ID NO 69), E345R (resulting in SEQ ID NO 73) or E345Y (resulting in SEQ ID NO 77) was introduced in IgG1-CAMPATH-1H-K439E-G236R instead of E430G, comparable results to those observed for E430G were attained: the single agent CDC activity of IgG1-CAMPATH-1H antibody variants harboring any of the E430 substitutions mentioned was at background level, while recovery of CDC activity was attained by mixing the IgG1-CAMPATH-1H variants with IgG1-11B8-E430G-S440K or IgG1-11B8-E430G-S440K-G237A. The recovery of CDC efficacy by mixtures ranged from approximately 78% (IgG1-CAMPATH-1H-E345Q-K439E-G236R+IgG1-11B8-E430G-S440K) to approximately 92% (IgG1-CAMPATH-1H-E345R-K439E-G236R+IgG1-11B8-E430G-S440K-G237A) of the control mixture potency. Antibody variant IgG1-CAMPATH-1H-E430Y-K439E-G236R (SEQ ID NO 121) induced approximately 44% residual single agent CDC activity of the control mixture potency. CDC efficacy was restored to approximately 94% of the level induced by the positive control mixture by mixing IgG1-CAMPATH-1H-E430Y-K439E-G236R with IgG1-11B8-S440K-G237A.

Figure 35A:
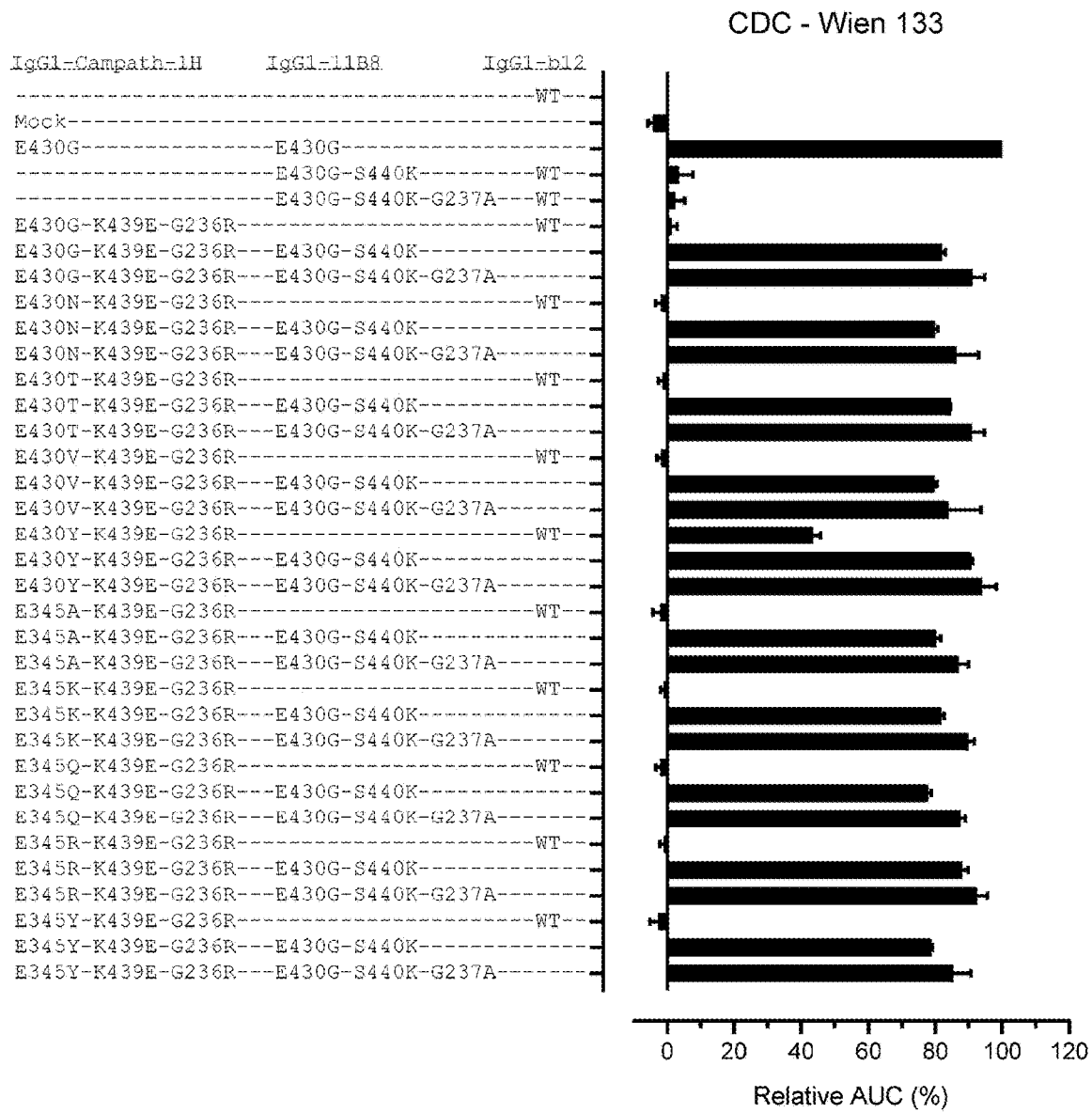
FIGS. 35A-35D show the selective co-dependent CDC activity of mixed antibody variants of anti-CD52 IgG1-CAMPATH-1H and anti-CD20 IgG1-11B8 by introduction of mutations that enhance Fc-Fc interactions, inhibit self-oligomerization and modulate C1q-binding.
Figure 35B:
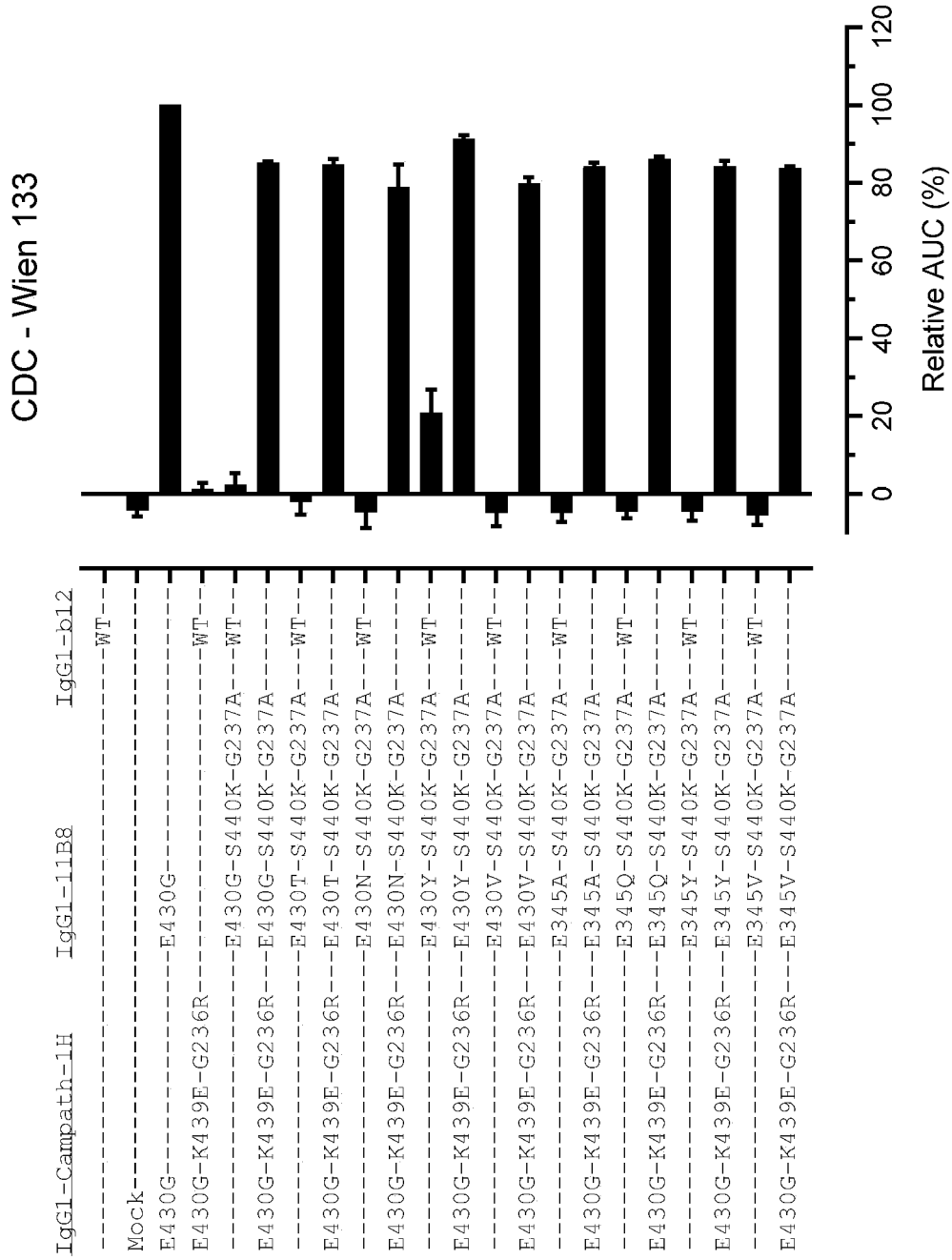

Upon substituting the E430G mutation in IgG1-11B8-E430G-S440K-G237A with either of the mutations E430N (resulting in SEQ ID NO 116), E430T (resulting in SEQ ID NO 118), E430V (resulting in SEQ ID NO 120), E345A (resulting in SEQ ID NO 65), E345Q (resulting in SEQ ID NO 70), E345V (resulting in SEQ ID NO 76) or E345Y (resulting in SEQ ID NO 78), comparable results to those observed for E430G were attained: the single agent CDC activity of IgG1-11B8 antibody variants harboring any of the E430 substitutions mentioned was at background level, while recovery of CDC activity was attained by mixing the IgG1-11B8 variants with IgG1-CAMPATH-1H-E430G-K439E-G236R (FIG. 35B). The recovery of CDC efficacy by mixtures ranged from approximately 80% (IgG1-CAMPATH-1H-E430G-K439E-G236R+IgG1-11B8-E430V-S440K-G237A) to approximately 86% (IgG1-CAMPATH-1H-E430G-K439E-G236R+IgG1-11B8-E345Q-S440K-G237A) of the control mixture potency. Approximately 21% residual single agent CDC activity of the level induced by the positive control mixture was observed for antibody variant IgG1-11B8-E430Y-S440K-G237A (SEQ ID NO 122), while CDC efficacy could be restored to approximately 91% of the level induced by the positive control mixture by mixing IgG1-11B8-E430Y-S440K-G237A with IgG1-CAMPATH-1H-E430G-K439E-G236R.

Figure 35C:
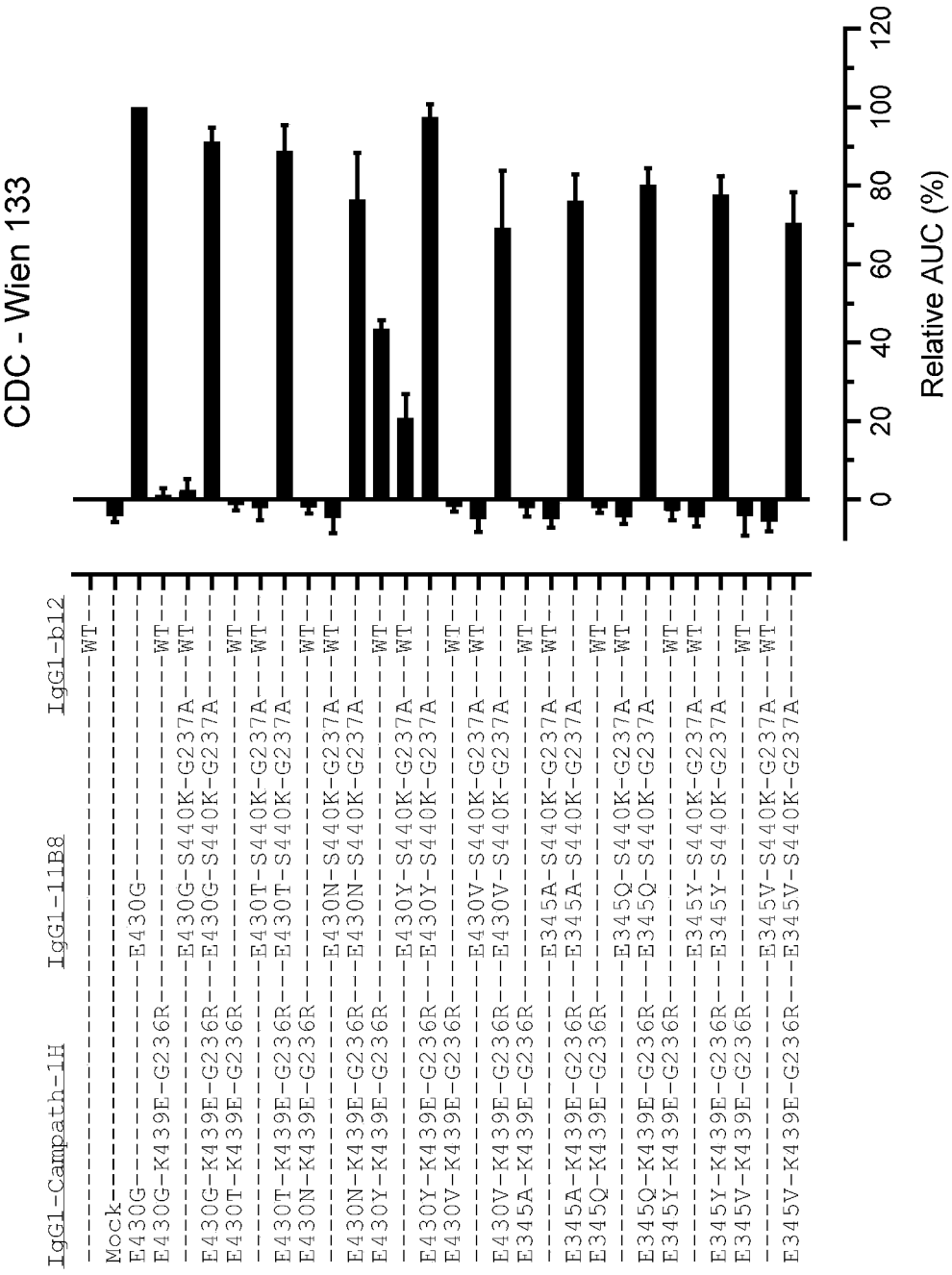

Potent recovery of CDC efficacy was also observed upon mixing an IgG1-CAMPATH-1H-K439E-G236R and IgG1-11B8-S440K-G237A antibody variant in which an identical Fc-Fc interaction modulating mutation was introduced into both antibodies, selected from the following mutations: E430N, E430T, E430V, E345A, E345Q, E345V, E345Y (FIG. 35C). As shown in FIGS. 35A and B, the single agent activity of these antibody variants was at background levels. Recovery of CDC efficacy ranged from approximately 70% (IgG1-CAMPATH-1H-E430V-K439E-G236R+IgG1-11B8-

E430V-S440K-G237A) to approximately 89% (IgG1-CAM-PATH-1H-E430T-K439E-G236R+IgG1-11B8-E430T-S440-G237A) of the level induced by the positive control mixture. The highest recovery of CDC efficacy was attained by a mixture of IgG1-CAMPATH-1H-K439E-G236R and IgG1-11B8-S440K-G237A antibody variants in which the E430Y mutation was introduced (approximately 97% of the level induced by the positive control mixture), while both antibody variants induced residual single agent CDC activity, as described above.

Figure 35D:
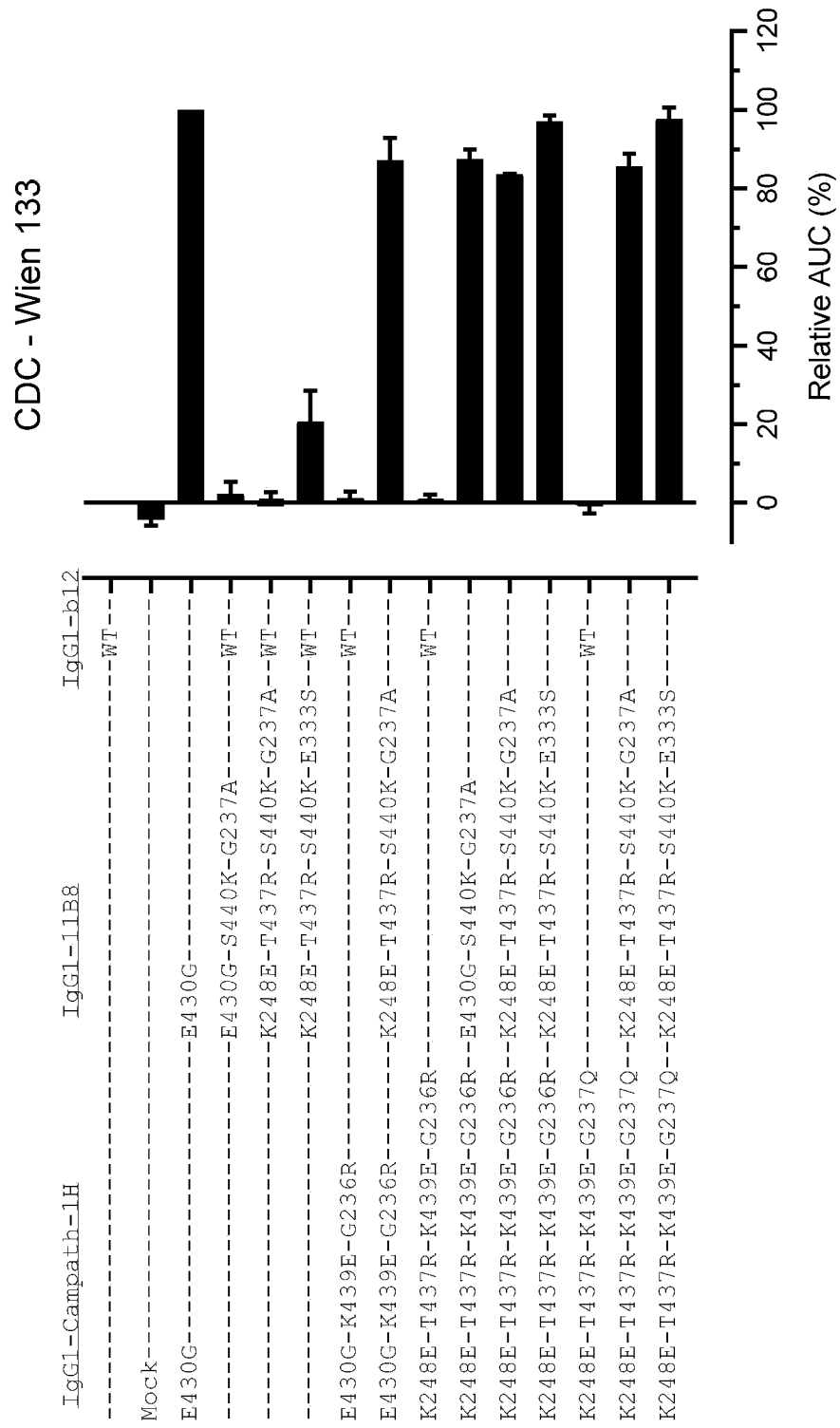

Introduction of the double mutation K248E-T437R in antibody variants has been described to promote Fc-Fc interactions. As shown in FIG. 35D, introduction of mutations S440K-G237A in IgG1-11B8-K248E-T437R (resulting in SEQ ID NO 131) abrogated the single agent CDC efficacy on Wien 133 cells. A partial inhibition of single agent CDC activity was observed upon introduction of mutations S440K-E333S in IgG1-11B8-K248E-T437R (resulting in SEQ ID NO 130). Potent recovery of CDC efficacy was observed when mixing IgG1-11B8-K248E-T437R-S440K-G237A with IgG1-CAMPATH-1H-E430G-K439E-G236R to approximately 87% of the control mixture potency. Furthermore, introduction of mutations K248E-T437R in an IgG1-CAMPATH-1H antibody variant that also harbors the K439E-G236R mutations (resulting in SEQ ID NO 128) resulted in an antibody variant lacking any single agent CDC activity. CDC efficacy could be potently restored by mixing IgG1-CAMPATH-1H-K248E-T437R-K439E-G236R with either of the IgG1-11B8 antibody variants harboring the E430G-S440K-G237A, K248E-T437R-S440K-G237A or K248E-T437R-S440K-E333S mutations, to approximately 87%, 84% and 97% of the control mixture potency, respectively. Likewise, introduction of mutations K248E-T437R in an IgG1-CAMPATH-1H antibody variant that also harbors the K439E-G237Q mutations (resulting in SEQ ID NO 129) resulted in an antibody variant lacking any single agent CDC activity. Recovery of CDC efficacy could be attained by mixing IgG1-CAMPATH-1H-K248E-T437R-K439E-G237Q with IgG1-11B8 antibody variants harboring the K248E-T437R-S440K-G237A or K248E-T437R-S440K-E333S mutations to approximately 86% and 98% of the control mixture potency, respectively.

In conclusion, selective co-dependent CDC efficacy on Wien 133 cells could be attained by mixing IgG1-CAMPATH-1H and IgG1-11B8 antibody variants harboring different Fc-Fc interaction modulating mutations including all tested E430 substitutions (E430G, E430N, E430T, E430V, E430Y), all tested E345 substitutions (E345A, E345K, E345Q, E345R, E345V, E345Y), and K248E-T437R, in addition to mutations that inhibit self-oligomerization and modulate C1q-binding. Furthermore, co-dependent activity was observed when the antibodies mixed contained non-identical Fc-Fc interaction enhancing mutations.

So, it can be expected that any E430 or any E345 substitution could be applied in the co-dependently acting antibodies of the invention, provided they also contain a self-oligomerization inhibiting mutation K439E or S440K, and provided that one antibody also contains a C1q binding modulating mutation, exemplified by G236R, G237Q, or G237A. Fc-Fc interaction enhancing substitutions E430Y and E430F may be less preferred substitutions for the antibodies of the present invention, due to their residual single agent activity.

Example 38: Selectivity of CDC Activity on Raji Lymphoma Cells by Mixtures Consisting of an Antibody Variant Harboring the E430G-S440K Mutations and a C1q-Binding Inhibiting Mutation and an Antibody Variant Harboring the E430G-K439E Mutations and a C1q-Binding Enhancing Mutation In previous Examples, the capacity to induce CDC was measured for co-dependent mixtures containing two antibody variants of which one was an antibody variant harboring an Fc-Fc interaction enhancing mutation and self-oligomerization inhibiting mutation K439E in combination with a C1q-binding inhibiting mutation and the other was an antibody variant harboring an Fc-Fc interaction enhancing mutation and self-oligomerization inhibiting mutation S440K, optionally in combination with a C1q-binding enhancing mutation. Here, we tested whether selective co-dependent CDC induction on Raji cells could also be induced inversely, i.e. by mixing IgG1-CD37-37-3-E430G-K439E antibody variants harboring a mildly C1q-binding inhibiting or enhancing mutation with IgG1-11B8-E430G-S440K antibody variants harboring a C1q-binding inhibiting mutation.

Figure 36A:
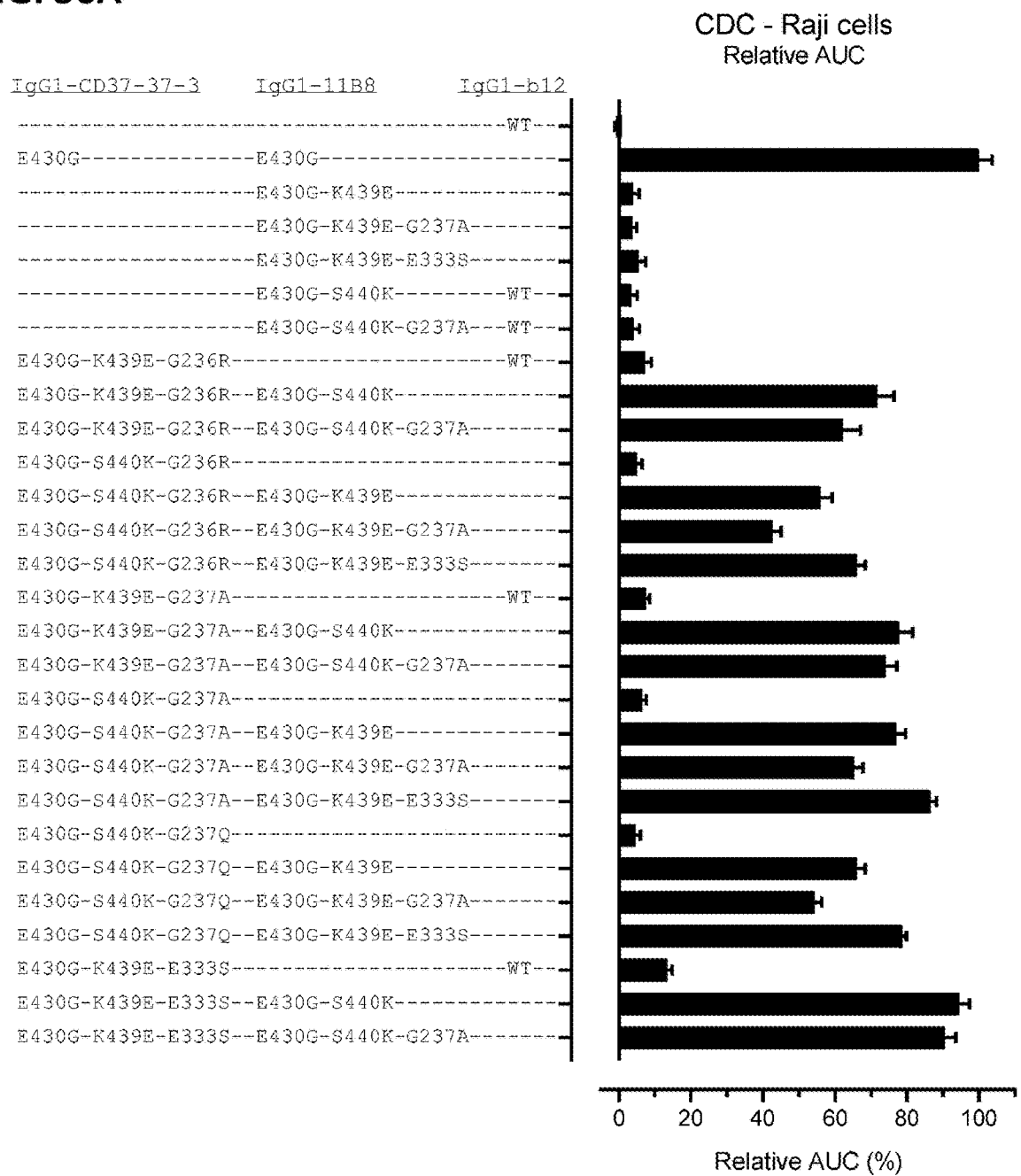
FIGS. 36A and 36B show co-dependent CDC on Raji lymphoma cells induced by mixtures of IgG1-CD37-37-3 and IgG1-11B8 antibody variants harboring mutations that enhance Fc-Fc interactions, inhibit self-oligomerization and modulate C1q-binding.
Figure 36B:
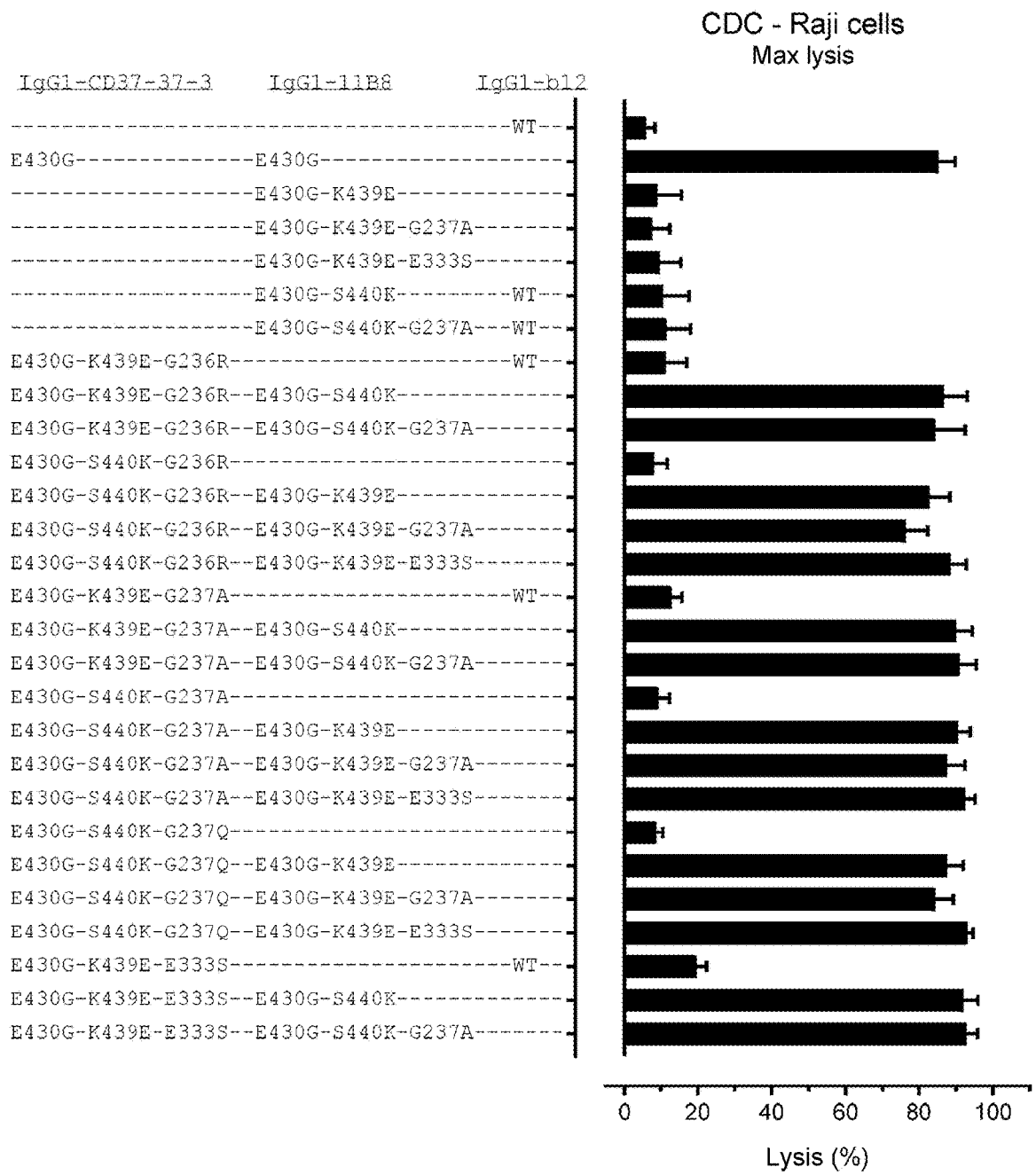

Different mutations were introduced in antibodies IgG1-CD37-37-3 and IgG1-11B8: E430G, which induces enhanced Fc-Fc interactions; either of the self-oligomerization inhibiting mutations K439E or S440K; G236R, G237A, G237Q, which suppress binding of C1q to the hetero-hexameric antibody complex; E333S, which enhances binding of C1q to the hetero-hexameric antibody complex. As controls, single antibodies were also mixed 1:1 with non-binding isotype control antibodies IgG1-b12 to enable direct comparison of the concentrations of individual components and mixtures composed thereof. Here, also unpurified supernatants from transiently transfected EXPI293 supernatants were used as source of IgG. A range of concentrations of purified antibodies (range 0.009-40.0 µg/mL final concentrations; 3.3-fold dilutions) was tested in an in vitro CDC assay on Raji cells with 20% NHS, essentially as described in Example 2. The percentage of cell lysis was calculated as (number of PI-positive cells/total number of cells)×100%. The data were analyzed using best-fit values of a non-linear dose-response fit using log-transformed concentrations in GraphPad PRISM and the area under the dose-response curves of three experimental replicates was calculated. CDC efficacy presented as relative areas under the curve (AUC) values represent values normalized per plate relative to minimal lysis (0% with IgG1-b12) and maximal lysis (100% for the mixture of IgG1-CD37-37-3-E430G+IgG1-11B8-E430G), that were subsequently averaged over the two independent experimental replicates. A positive control mixtures of IgG1-CD37-37-3-E430G and IgG1-11B8-E430G induced efficient CDC on Raji cells (FIG. 36A). The single agent activity of antibody variants of IgG1-11B8-E430G could strongly be suppressed by introduction of mutation K439E, which was not further affected by the additional introduction of C1q-binding inhibiting (G237A) or C1q-binding enhancing (E333S) mutations. CDC efficacy could also be strongly suppressed by introduction of mutation S440K, with or without C1q-binding inhibiting mutation G237A. Although introduction of mutations K439E-G236R in IgG1-CD37-37-3-E430G also abrogated single agent CDC efficacy, CDC efficacy could be restored by mixing IgG1-CD37-37-3-E430G-K439E-G236R with either IgG1-11B8-E430G-S440K or IgG1-11B8-E430G-S440K-G237A to approximately 72% and 62%, respectively, of the level induced by the positive control mixture. Likewise, introduction of mutations K439E-G237A, K439E-E333S (SEQ ID NO:82), S440K-G236R (SEQ ID NO: 104), S440K-G237A, or S440K-G237Q (SEQ ID NO: 107) in IgG1-CD37-37-3-E430G did not yield single agent activity, while mixtures of these antibodies with IgG1-11B8 antibody variants harboring a complementary self-oligomerization inhibiting mutation and either of the C1q-binding inhibiting (G237A) or enhancing (E333S) mutations partially restored CDC efficacy (ranging from approximately 43% to 94% of the control mixture potency). The maximal lysis at 40 μg/mL concentration induced by co-dependent mixtures of IgG1-CD37-37-3 and IgG1-11B8 antibody variants was strong, ranging from 76% to 93% of the control mixture potency (FIG. 36B).

In conclusion, while the single agent CDC activity of IgG1-C37-37-3 and IgG1-11B8 antibody variants harboring the E430G mutation could be abrogated by introduction of either of the K439E or S440K mutations and either of the C1q-binding modulating mutations G236R, G237A, G237Q, E333S, mixtures of such antibody variants restored CDC efficacy irrespective of which combination of self-oligomerization inhibiting mutation and C1q-binding inhibiting or enhancing mutations was introduced in either of the two antibodies.

Example 39: Selective Complement-Dependent Cytotoxicity of Patient CLL Cells by Co-Dependent Combinations of Anti-CD52 and Anti-CD20 Antibody Variants Harboring Mutations that Enhance Fc-Fc Interactions, Inhibit Self-Oligomerization and Modulate C1q-Binding In previous Examples, the CDC efficacy of antibody variant combinations was tested using in vitro cultured tumor cell lines. Here, the selective co-dependent induction of CDC was studied using tumor cells from chronic lymphatic leukemia (CLL) patients by mixing anti-CD20 IgG1-11B8 and anti-CD52 IgG1-CAMPATH-1H antibody variants that harbor Fc-Fc interaction enhancing mutation E430G, either of the self-oligomerization inhibiting mutations K439E or S440K and either of the C1q-binding modulating mutations G236R or E333S. As controls, single antibodies were also mixed 1:1 with non-binding isotype control antibodies IgG1-b12 to enable direct comparison of the concentrations of individual components and mixtures composed thereof. A range of concentrations of purified antibodies (range 0.003-10.0 μg/mL final concentrations; 3.3-fold dilutions) was tested in an in vitro CDC assay on tumor cells derived from three CLL patients with 20% NHS. Peripheral blood mononuclear cells (PBMC; Conversant-Bio) from three CLL patients were thawed at 37° C., washed in RPMI 1640 (Life technologies) supplemented with 10% donor bovine serum with iron (DBSI; Life Technologies, cat. no. 20371) and brought to a concentration of 3.33×10$^6$ PBMC/mL in RPMI+0.2% BSA. To each well of a 96-wells plate, 30 μL (corresponding to 100,000 cells/well) were added as well as 50 μL of a 2× concentration of the antibody dilution series. After 15 minutes of incubation at RT on a shaker, 20 μL non-human serum was added to each well and incubated for 45 minutes at 37° C. The cells were then centrifuged and washed with FACS buffer (PBS+0.1% BSA+0.02% sodium azide). Fifty μL of staining mix was added to each well and incubated for 30 minutes at 4° C. After washing the plates twice using FACS buffer, the percentage of viable cells was measured on a Fortessa flow cytometer (BD).

Target expression levels of CD20 and CD52 were determined by quantitative flow cytometric procedure using a QIFI kit (DAKO; cat. nr. K0078). CLL patient PBMC of three patients were seeded at 100,000 cells/well in a 96-wells round-bottom plate and centrifuged to pellet the cells. After discarding the supernatant, primary mouse anti-human-CD20 (IgG1-mm-IgG1-7D8-K409R) and -CD52 (Tebu Bio; cat. nr. MAB0944) antibodies or an isotype control antibody were added to each well and incubated for 30-45 minutes at 4° C. In separate wells, 50 μL of kit-provided set-up and calibration beads were added. After centrifuging the cells and discarding the supernatant, the cells were washed twice in FACS buffer. Then, cells were resuspended in 50 μL/well of secondary goat anti-mouse IgG-FITC conjugate (DAKO; cat. nr. F0479) and incubated for 30-45 minutes at 4° C. in the dark. The cells were washed twice and eventually resuspended in FACS buffer for analysis on a Fortessa flow cytometer. The antigen quantity was determined by calculating the antibody-binding capacity based on the calibration curve, according to the manufacturer's guidelines.

Figure 37B:
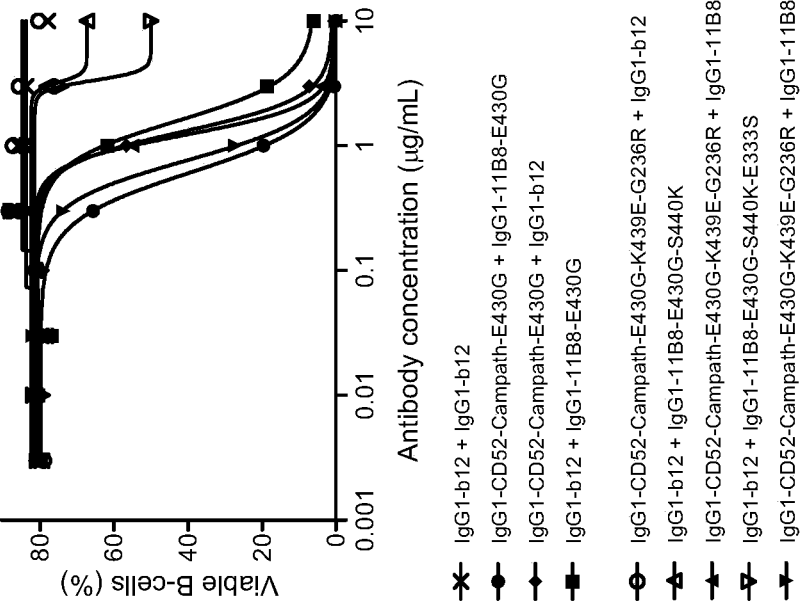
FIGS. 37A-37C show the selective co-dependent CDC activity of mixed antibody variants of anti-CD52 IgG1-CAMPATH-1H and anti-CD20 IgG1-11B8 by introduction of mutations that enhance Fc-Fc interactions, inhibit self-oligomerization and modulate C1q-binding. Patient CLL samples were incubated with antibody concentration series in the presence of 20% NHS. CDC efficacy is presented as the percentage of viable B cells upon incubation with the antibody variants. The results using CLL samples from patient 1 (FIG. 37A), 2 (FIG. 37B) and 3 (FIG. 37C) are shown.
Figure 37A:
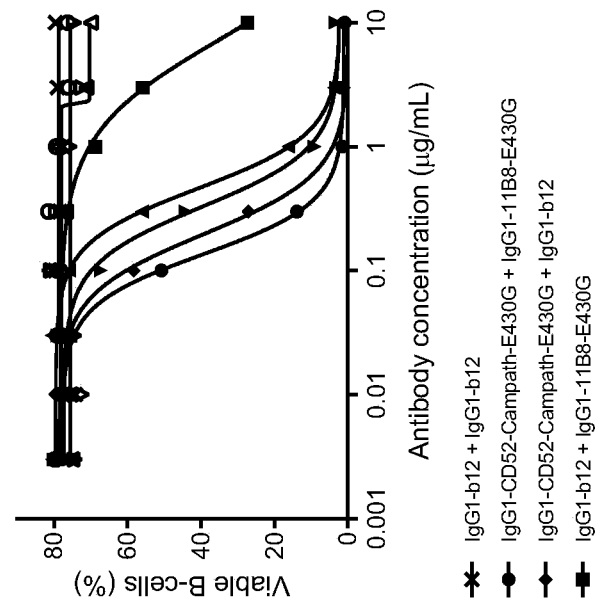
Figure 37C:
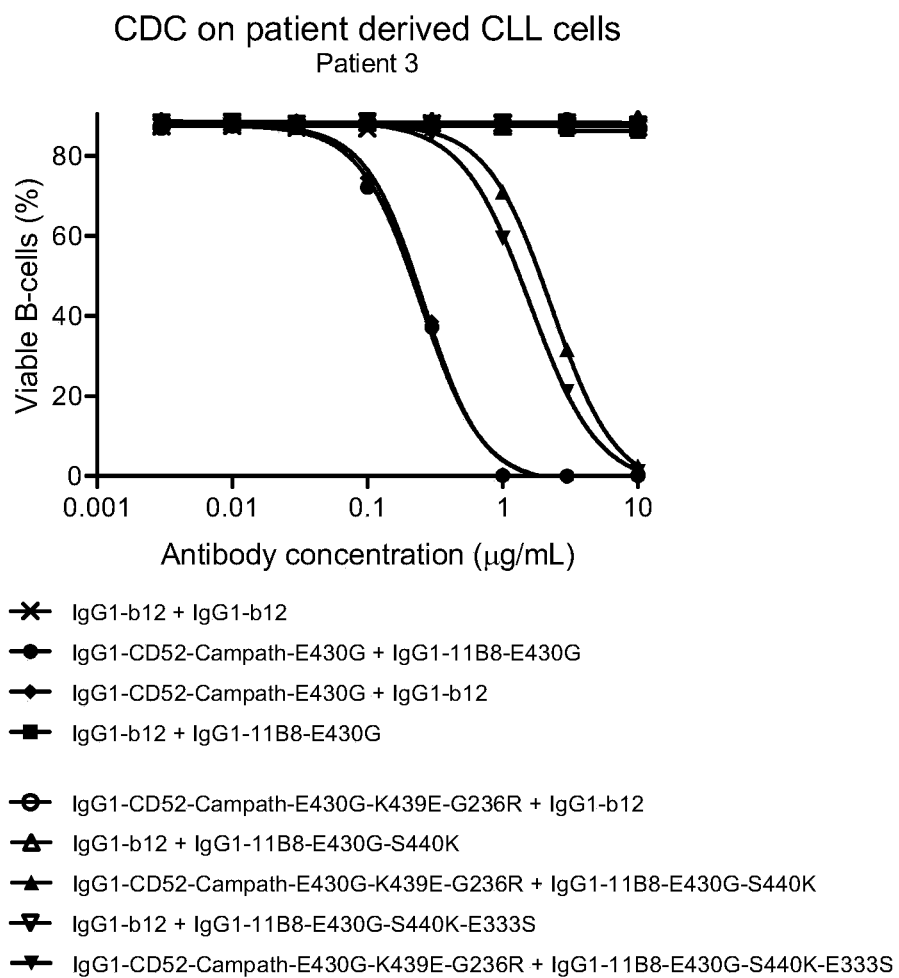

The strongest CDC efficacy in all three CLL patient samples was induced by a mixture of IgG1-CAMPATH-1H-E430G and IgG1-11B8-E430G (FIG. 37A-C). The single agent CDC activity of IgG1-CAMPATH-1H-E430G was close to (patient 1, 2) or comparable (patient 3) to the level induced by the mixture of IgG1-CAMPATH-1H-E430G+IgG1-11B8-E430G. The capacity to induce CDC by IgG1-11B8-E430G as a single agent varied per patient, ranging from no CDC activity (patient 3) and intermediate efficacy (patient 1) to CDC efficiency close to the level induced by single agent IgG1-CAMPATH-1H-E430G (patient 2). The single agent activity of IgG1-11B8 antibody variants correlated with the CD20 expression levels of the different samples (patient 1: 48E+03; patient 2: 172E+03; patient 3: 39E+03). Single agent activity was fully abrogated upon introduction of mutations K439E-G236R in IgG1-CAMPATH-1H-E430G and mutations S440K or S440K-E333S in IgG1-11B8-E430G. However, CDC efficacy could be restored by mixing IgG1-CAMPATH-1H-E430G-K439E-G236R with IgG1-11B8-E430G-S440K or IgG1-11B8-E430G-S440K-E333S. The extent of restoration of CDC efficacy varied per patient sample.

In conclusion, mixtures of anti-CD20 and anti-CD52 antibody variants harboring mutations E430G, K439E or S440K and G236R or E333S could induce CDC in patient CLL samples in a co-dependent fashion.

Example 40: Selective Depletion of T-Cell Populations within Peripheral Blood Mononuclear Cell Samples The generation of co-dependent antibody mixtures allows for the selective depletion of specific hematological subsets from whole blood samples, as was demonstrated in Example 20 for B-cells, while leaving T-cells untouched. Here, we tested whether mixtures of co-dependent antibody variants harboring an Fc-Fc interaction enhancing mutation, a self-oligomerization inhibiting mutation and C1q-binding modulating mutation could selectively deplete T cells from whole blood samples, while leaving the B cell fraction untouched.

Thirty μL samples of whole blood derived from four healthy human donors (UMC Utrecht), preserved with hirudin to prevent coagulation, were aliquoted in a 96-wells round-bottom plate (Greiner Bio-One; Cat #650101) and supplemented with 50 μL RPMI+0/2% BSA (Lonza; Cat #BE12-115F/U1). To each well, 20 μL was added of a mixture of two antibody variants (final concentration 10 µg/mL) of IgG1-CAMPATH-1H, IgG1-huCLB-T3/4 and IgG1-CD5-INSERM antibodies with the following mutations: E430G, which induces enhanced Fc-Fc interactions; either of the self-oligomerization inhibiting mutations K439E or S440K; and the C1q modulating mutations G236R, G237A or K326A. As controls, single antibodies were mixed 1:1 with variants of non-binding isotype control antibody IgG1-b12 harboring the E430G, K439E, S440K, G236R or G237A mutations to enable direct comparison of the concentrations of individual components and mixtures composed thereof. After an overnight incubation at 37° C. and 5% C02, the plates were centrifuged and the cells were washed once with 150 µL PBS (B. Braun; Cat #A220/12257874/1110). Next, the cells were resuspended in 80 uL Amine-reactive viability dye (Invitrogen; Cat #A10346A), 1:1000 diluted in PBS, and incubated in the dark for 30 minutes at 4° C. The cells were then centrifuged and the pellet was resuspended in 80 µL of a mix of fluorescently labeled antibodies directed against CD3 (eBioscience; Cat #48-0037), CD4 (eBioscience; Cat #47-0048), CD8 (BioLegend; Cat #301028), CD19 (BioLegend, Cat #302245), CD45 (BioLegend; Cat #368505), CD56 (BD; Cat #564849) and CD66b (BioLegend; Cat #305115), in addition to Fixable Viability Stain 510 (FVS510, BD; Cat #564406). The cells were incubated for 30 minutes at 4° C. in the dark and subsequently centrifuged before red blood cells were lysed using cold RBC lysis buffer. The cells were washed and taken up in FACS buffer (PBS+0.1% BSA+0.02% $NaN_3$) before being analyzed in 75 µL fixed-volume samples on a flow cytometer (BD Fortessa). The fraction of B cells, $CD4^+$ T cells and $CD8^+$ T cells was calculated using the following formula: Fraction recovered (target pop, %)=100%*(target cell count (sample)/target cell count (no Ab control))*(granulocyte count (no Ab control)/granulocyte count (sample). Here, we measure the relative recovery of targeted cells by comparing with the cell count in control samples incubated without lysis inducing antibodies, corrected for method induced inter-sample variation using the granulocyte population as an internal control, because it is not targeted by the lysis-inducing antibodies.

Figure 38A:
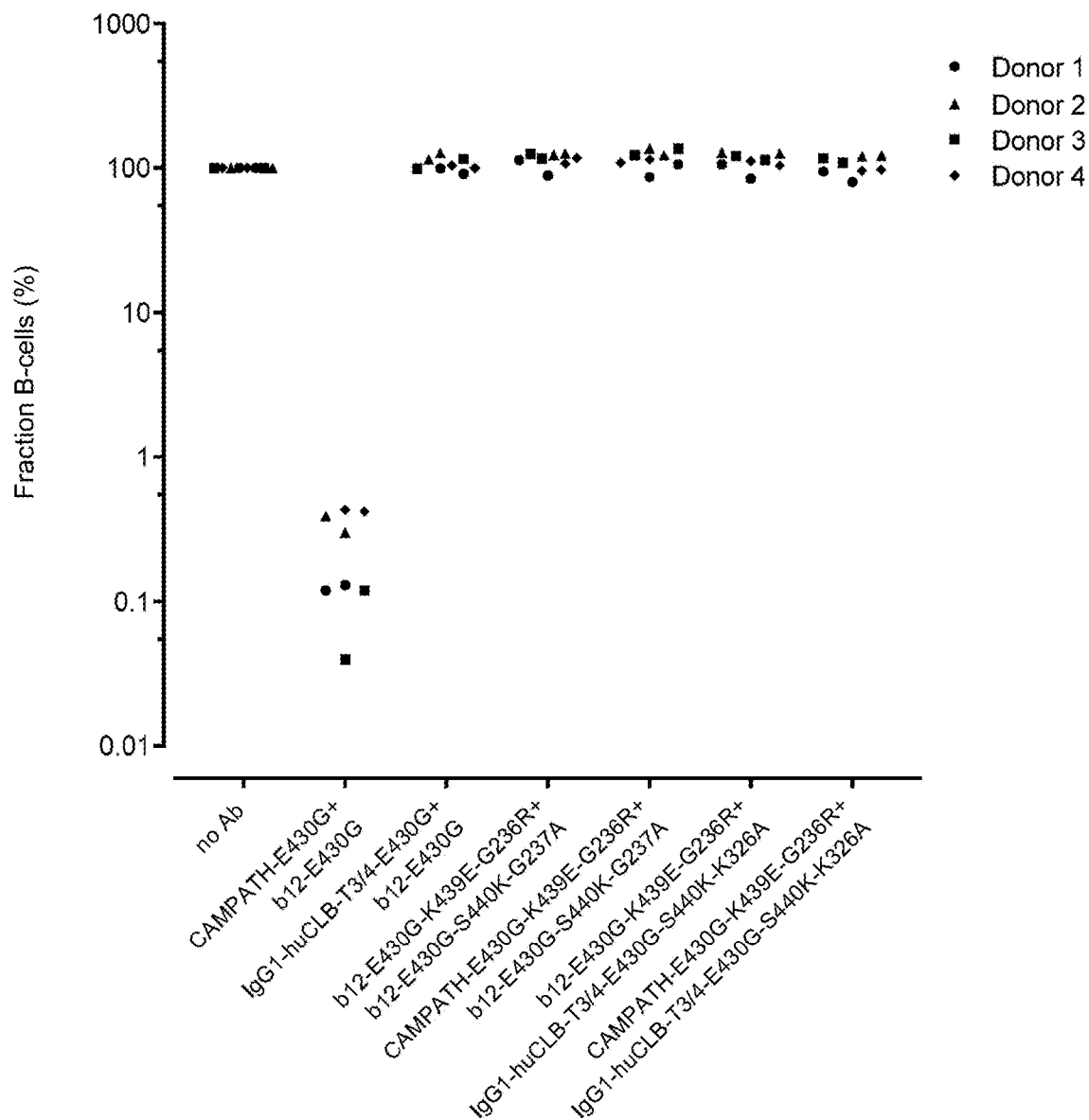
FIGS. 38A-38F show the fraction of B cells, $CD4^+$ T cells and $CD8^+$ T cells detected by flow cytometry after incubation of whole blood samples with mixtures of antibody variants of IgG1-CAMPATH-1H, IgG1-huCLB-T3/4 and IgG1-CD5-INSERM harboring mutations that enhance Fc-Fc interactions, inhibit self-oligomerization and modulate C1q-binding. Percentage of (FIG. 38A) B cells, (FIG. 38B) $CD4^+$ T cells and (FIG. 38C) $CD8^+$ T cells detected in whole blood samples of 4 donors after incubation with indicated IgG1-CAMPATH-1H, IgG1-huCLB-T3/4 and IgG1-b12 antibody variants. Percentage of (FIG. 38D) B cells, (FIG. 38E) $CD4^+$ T cells and (FIG. 38F) $CD8^+$ T cells detected in whole blood samples of 4 donors after incubation with indicated IgG1-CAMPATH-1H, IgG1-CD5-INSERM and IgG1-b12 antibody variants. Fractions were calculated as [100%×(cell count in sample/cell count in 'no Ab sample')× (Granulocyte count 'no Ab sample'/Granulocyte count in sample)].
Figure 38B:
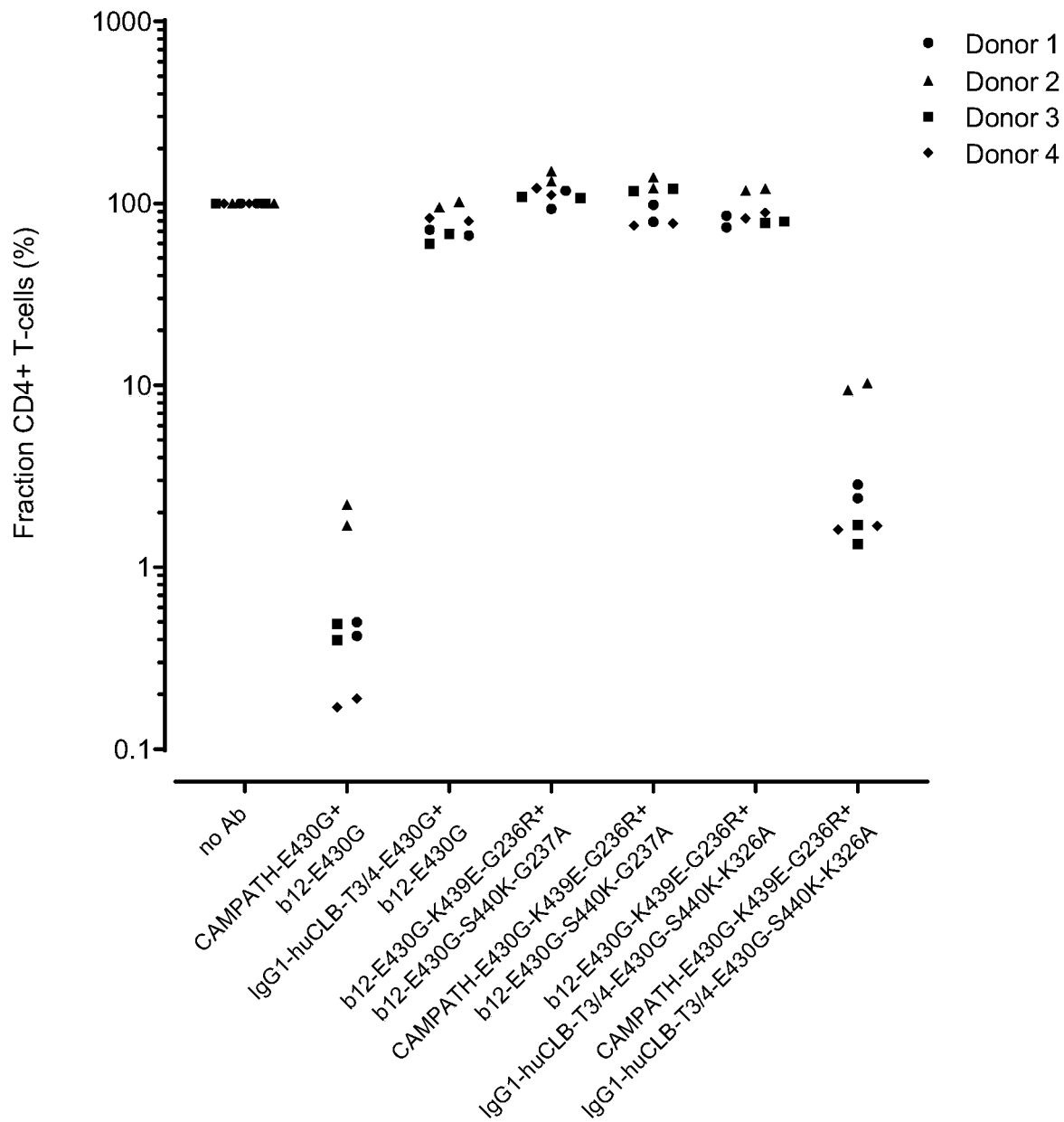
Figure 38C:
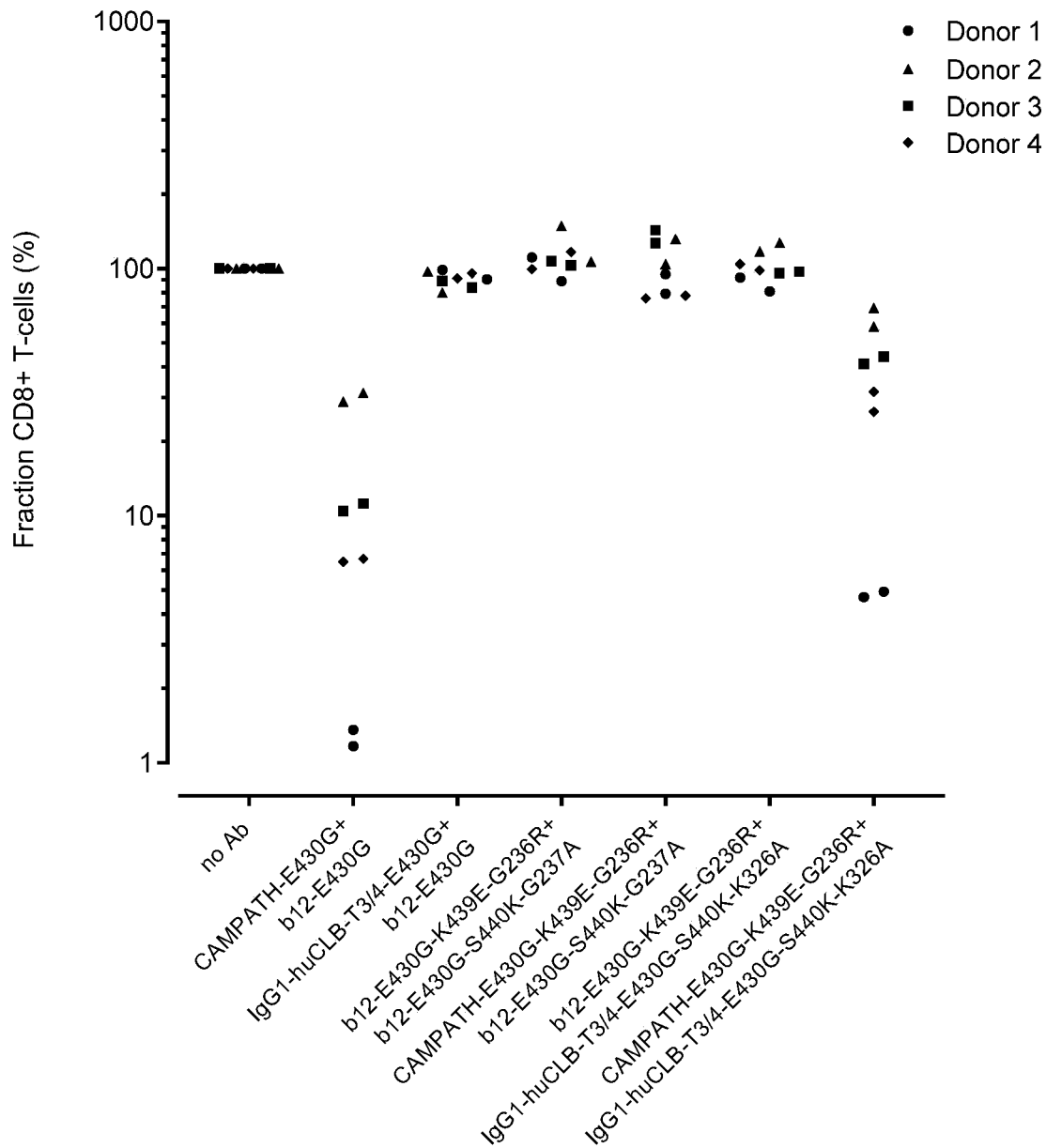
Figure 38D:
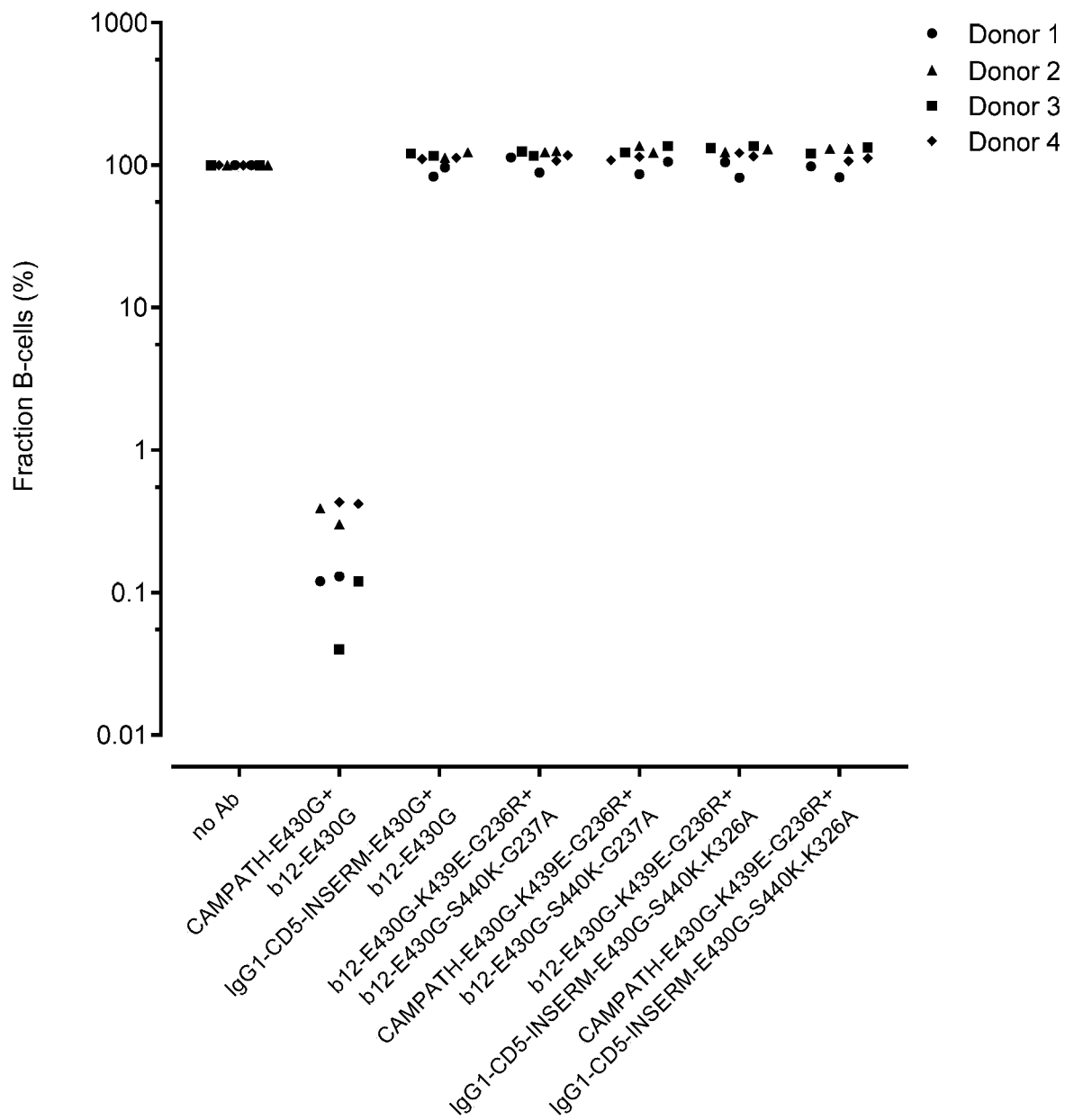
Figure 38E:
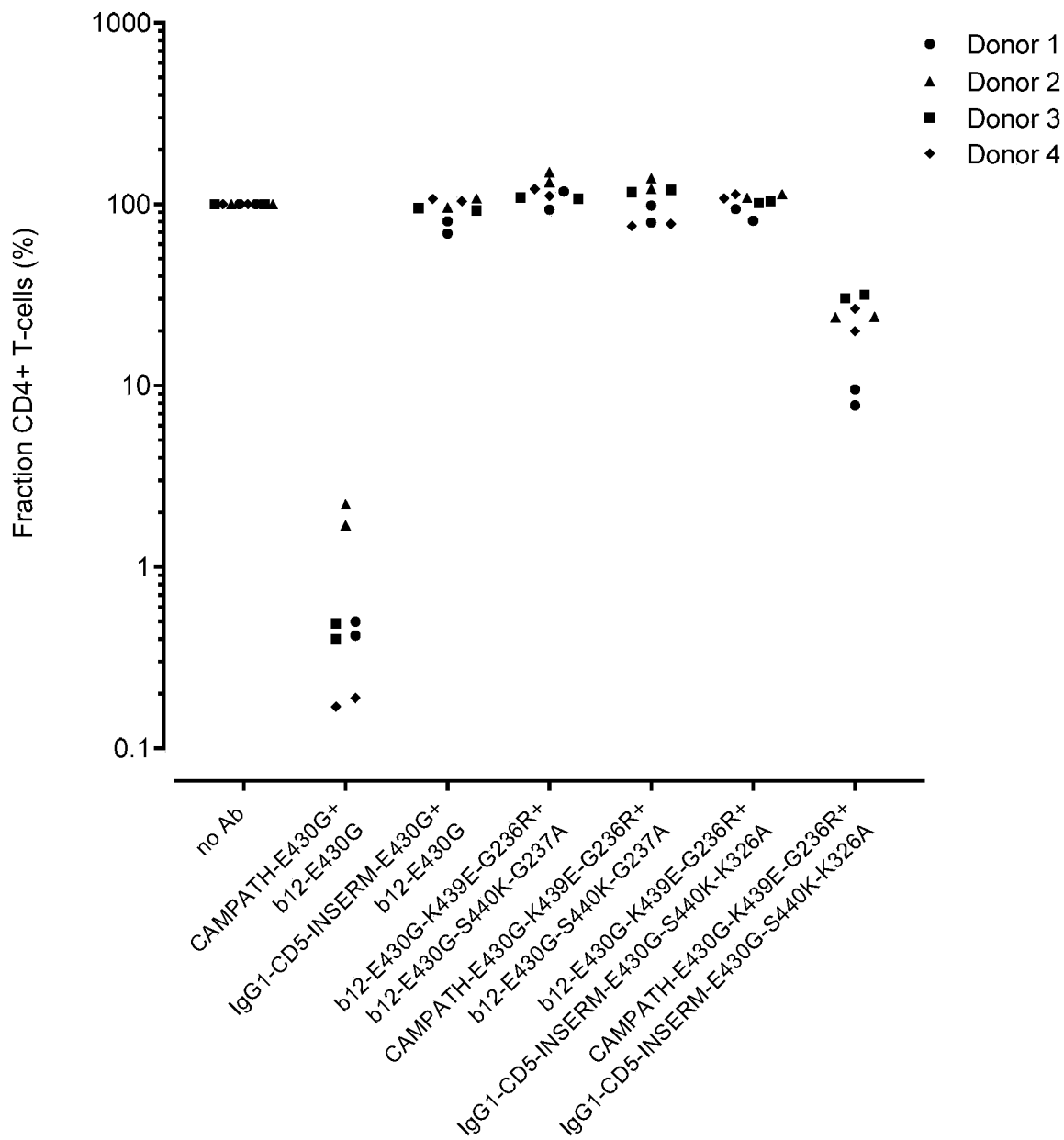
Figure 38F:
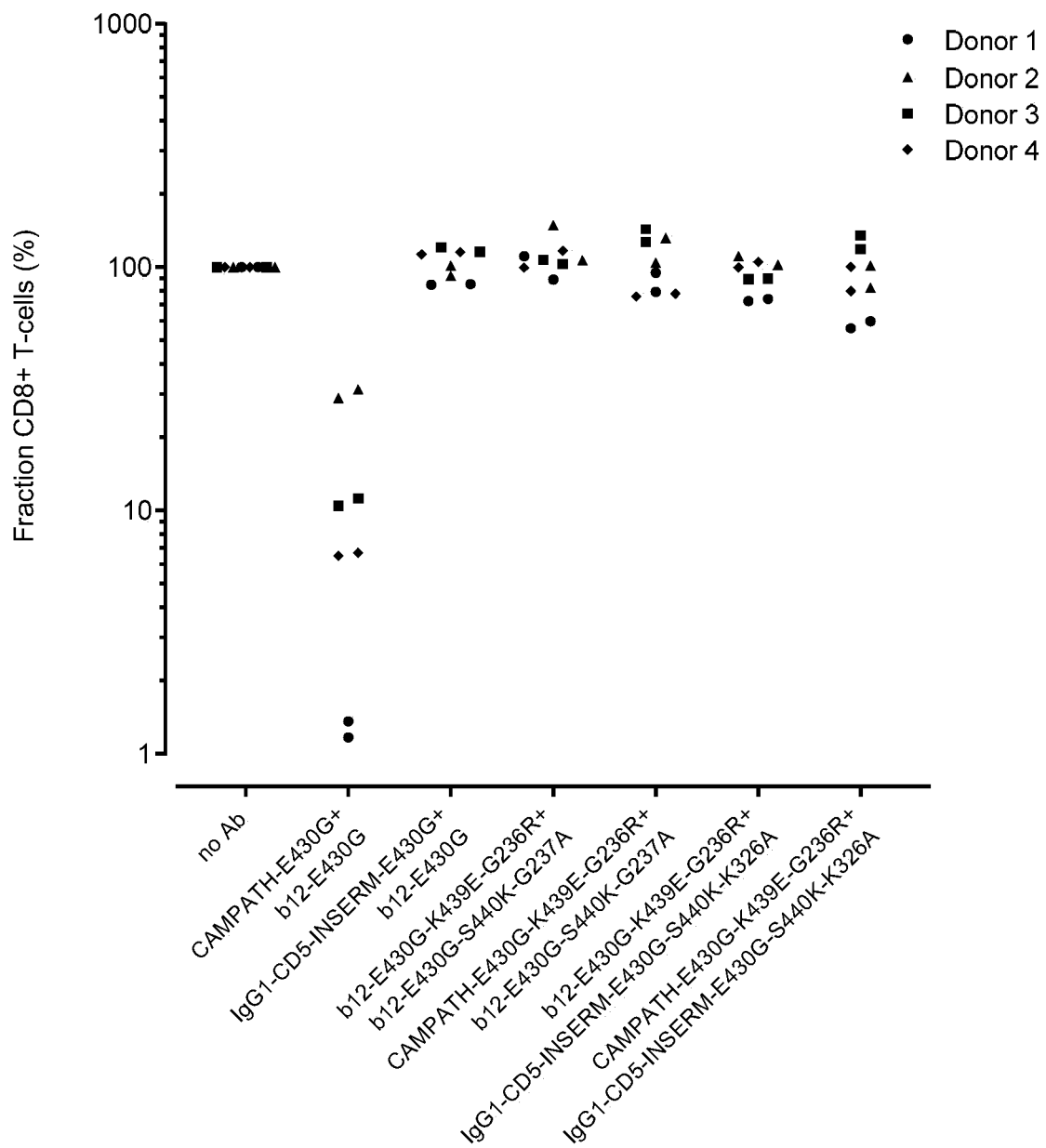

Variants of anti-CD52 antibody IgG1-CAMPATH-1H and anti-CD3 antibody IgG1-huCLB-T3/4 were used to selectively deplete T cells from whole blood samples without affecting B cells. When applied as a single agent, IgG1-CAMPATH-1H-E430G strongly depleted B cells, $CD4^+$ T cells and $CD8^+$ T cells while single agent IgG1-huCLB-T3/4-E430G partially depleted $CD4^+$ T cells (FIG. 38A, B, C). No depletion of lymphocytic subsets was observed by a mixture of non-target binding antibody variants IgG1-b12-E430G-K439E-G236R and IgG1-b12-E430G-S440K-G237A. Also, no depletion was observed when either of the latter antibody variants was mixed with complementary IgG1-CAMPATH-1H-E430G-K439E-G236R or IgG1-huCLB-T3/4-E430G-S440K-K326A. In contrast, a mixture of IgG1-CAMPATH-1H-E430G-K439E-G236R and IgG1-huCLB-T3/4-E430G-S440K-K326A strongly depleted $CD4^+$ T cells and to a lesser extent $CD8^+$ T cells in co-dependent manner, without affecting the B cell counted in these samples. In addition, variants of anti-CD52 antibody IgG1-CAMPATH-1H and anti-CD5 antibody IgG1-CD5-INSERM were used to selectively deplete T cells from whole blood samples without affecting B cells. Again, strong depletion of B cells, $CD4^+$ T cells and $CD8^+$ T cells was induced by single agent IgG1-CAMPATH-1H-E430G, while single agent IgG1-CD5-INSERM-E430G did not deplete any of the lymphocytic populations analyzed (FIG. 38D, E, F). No depletion of lymphocytic subsets was observed by a mixture of non-target binding antibody variants IgG1-b12-E430G-K439E-G236R and IgG1-b12-E430G-S440K-G237A. Also, no depletion was observed when either of the latter antibody variants was mixed with complementary IgG1-CAMPATH-1H-E430G-K439E-G236R or IgG1-CD5-INSERM-E430G-S440K-K326A. In contrast, a mixture of IgG1-CAMPATH-1H-E430G-K439E-G236R and IgG1-CD5-INSERM-E430G-S440K-K326A strongly and selectively depleted $CD4^+$ T cells, but not B cells, in co-dependent manner. The effects on $CD8^+$ T cells by the mixture of IgG1-CAMPATH-1H-E430G-K439E-K326A and IgG1-CD5-INSERM-E430G-S440K-G237A varied per donor.

In conclusion, mixtures of antibody variants of anti-CD52 IgG1-CAMPATH-1H, IgG1-huCLB-T3/4 and IgG1-CD5-INSERM harboring Fc-Fc interaction enhancing mutation E430G, self-oligomerization inhibiting mutations K439E or S440K and C1q-binding modulating mutations G236R or G237A could be applied to selectively and co-dependently deplete T cell populations from healthy donor whole blood samples while leaving the B cell population unharmed.

In combination with the results in Example 20, this argues that antibody combinations containing Fc-domains harboring the mutations disclosed in the present invention can be used to selectively deplete different hematological subsets beyond B-cells, CD8+ T-cells, or CD4+ T-cells, using target combinations of which co-expression is a selective hallmark of the targeted hematological subset.

Example 41: Co-Dependent Induction of Programmed Cell Death by Mixtures of Anti-DR4 and Anti-DR5 Antibody Variants Harboring Mutations that Enhance Fc-Fc Interactions, Inhibit Self-Oligomerization and Modulate C1q-Binding A viability assay was performed to study whether mixtures of anti-DR4 and anti-DR5 antibody variants harboring mutations that enhance Fc-Fc interactions, inhibit self-oligomerization and modulate C1q-binding can co-dependently induce programmed cell death (PCD) of BxPC-3 human pancreatic cancer cells and COLO 205 colon cancer cells.

Different mutations were introduced in anti-DR4 antibody IgG1-DR4-chCTB007 and anti-DR5 antibody IgG1-DR5-01: E430G, which induces enhanced Fc-Fc interactions; either of the self-oligomerization inhibiting mutations K439E or S440K; C1q binding modulating mutations G237T, K326W or E333S, which suppress (G237T) or enhance (K326W, E333S) binding of C1q. As controls, single antibodies were also mixed 1:1 with variants of non-binding isotype control antibodies IgG1-b12 harboring the E430G-K439E or E430G-S440K mutations to enable direct comparison of the concentrations of individual components and mixtures composed thereof. The viability assay was performed essentially as described in Example 14. In short, 90 µL of single cell suspensions (5,000 cells per well) were seeded in polystyrene 96-well flat-bottom plates (Greiner Bio-One, Cat nr 655182) and incubated overnight at 37° C. A serial dilution series of 20 µL antibody mixtures (range 0.0003 to 20 µg/mL final concentrations in 5-fold dilutions) and 10 µL of C1q (Quidel; final concentration 2.5 µg/mL) were added and incubated for 3 days at 37° C. As a negative and positive control on the induction of cell death, cells were incubated without antibody or with 5 µM staurosporine, respectively. The viability of the cultured cells was determined in a CellTiter-Glo luminescence cell viability assay as described in Example 14. Data were analyzed and plotted using non-linear regression (sigmoidal dose-response with variable slope) using GraphPad Prism software. The percentage viable cells was calculated using the following formula: % viable cells=[(luminescence antibody sample−luminescence staurosporine sample)/(luminescence no antibody sample−luminescence staurosporine sample)]* 100.

Figure 39A:
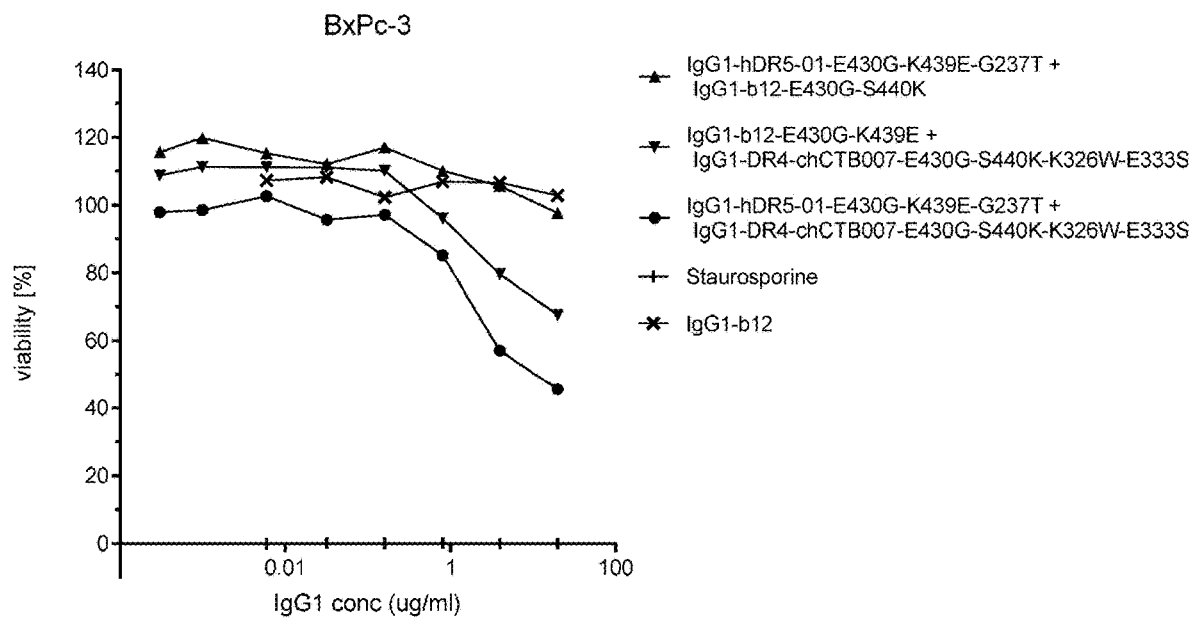
FIGS. 39A and 39B show cooperative activation of programmed cell death in cancer cells by anti-DR4 and anti-DR5 antibody variants harboring mutations that enhance Fc-Fc interactions, inhibit self-oligomerization and inhibit (G237T) or enhance (K326W-E333S) C1q-binding.
Figure 39B:
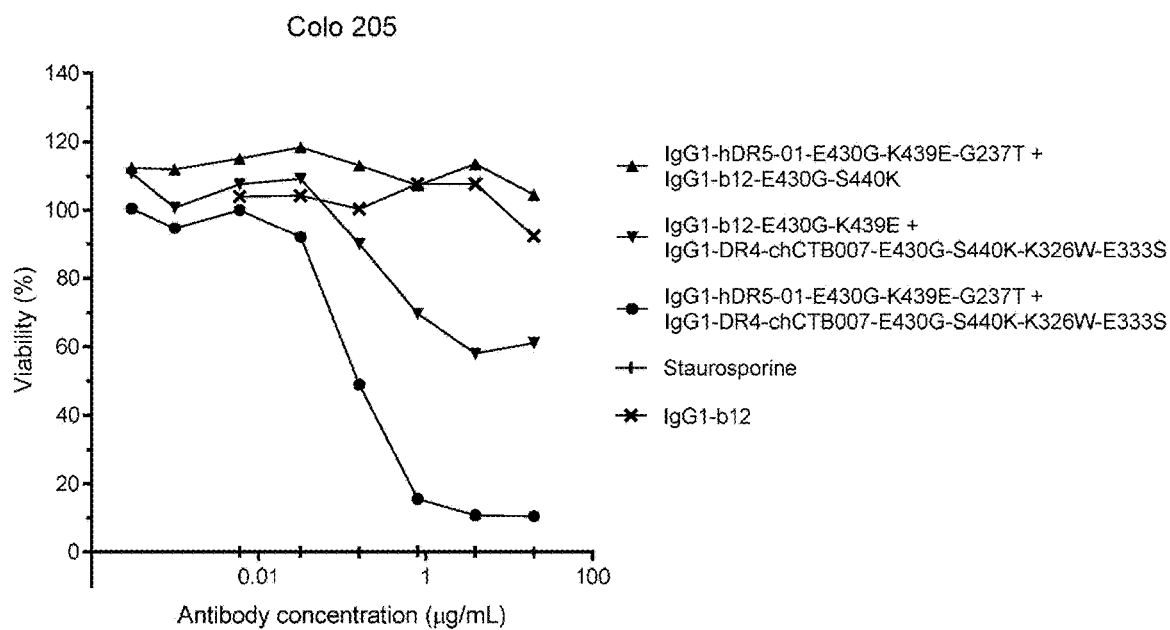

No programmed cell death was observed in BxPC-3 or COLO 205 cells by IgG1-DR5-01-E430G-K439E-G237T when applied as a single agent (FIG. 39A, B). IgG1-DR4-chCTB007-E430G-S440K-K326W-E333S did induce programmed cell death when applied as a single agent, as reflected by approximately 67% and 60% of viable cells left in the BxPC-3 and COLO 205 assays, respectively, at the highest concentrations used. The capacity of IgG1-DR4-chCTB007-E430G-S440K-K326W-E333S to induce programmed cell death could be enhanced by mixing it with IgG1-DR5-01-E430G-K439E-G237T, an effect that was observed using both cell lines.

Taken together, co-dependent activation of programmed cell death in BxPC-3 and COLO 205 cancer cells could be attained by mixtures of anti-DR4 and -DR5 antibody variants harboring mutations that enhance Fc-Fc interactions, inhibit self-oligomerization and inhibit (G237T) or enhance (K326W-E333S) C1q-binding.

The invention claimed is:

1. A method for treating a disease or disorder, the method comprising administering to a subject in need thereof a first antibody comprising a first Fc region of a human IgG and a first antigen-binding region capable of binding to a first antigen, and a second antibody comprising a second Fc region of a human IgG and a second antigen-binding region capable of binding to a second antigen, wherein the first Fc region comprises G236R, E345R, and K439E substitutions and the second Fc region comprises G237A, E345R, and S440K substitutions, and
wherein the amino acid positions correspond to human IgG1 according to Eu numbering system.

2. The method of claim 1, wherein the first and/or second antibody is human, humanized, or chimeric.

3. The method of claim 1, wherein the first and/or second antibody is a monoclonal antibody.

4. The method of claim 1, wherein the first and/or second antibody is a human IgG1, IgG2, IgG3 or IgG4 isotype.

5. The method of claim 1, wherein the first and second antigens are (a) both cell surface-exposed molecules and/or (b) co-located in cells or tissues that are target cells or target tissue for the disease or disorder to be treated.

6. The method of claim 1, wherein the first and second antigens are not identical.

7. The method of claim 1, which results in the depletion of a cell population expressing the first and second antigen.

8. The method of claim 7, wherein the cell population is a tumor cell.

9. The method of claim 8, wherein the cell population is a hematological tumor cell or a solid tumor cell.

10. The method of claim 7, wherein the cell population is a leukocyte, lymphocyte, B cell, T cell, regulatory T cell, NK cell, myeloid derived suppressor cell, or tumor associated macrophage cell population.

11. A composition comprising a first and a second antibody, wherein the first antibody comprises a first antigen-binding region capable of binding to a first antigen and a first Fc region of a human IgG, and the second antibody comprises a second antigen-binding region capable of binding to a second antigen and a second Fc region of a human IgG, wherein the first Fc region comprises G236R, E345R, and K439E substitutions and the second Fc region comprises G237A, E345R, and S440K substitutions, and
wherein the amino acid positions correspond to human IgG1 according to Eu numbering system.

12. The method of claim 1, wherein the antigen-binding region is capable of binding to an antigen selected from the group consisting of: DR4, DR5, CD20, CD37, CD52, HLA-DR, CD3, CD5, 4-1BB, and PD1.

13. The method of claim 1, wherein the antigen-binding region of the first antibody and second antibody comprises a VH region and VL region selected from the group consisting of:
(a) a VH region comprising a CDR1 sequence as set forth in SEQ ID NO:196, a CDR2 sequence as set forth in SEQ ID NO:196 and a CDR3 sequence as set forth SEQ ID NO:198, and a VL region comprising a CDR1 sequence as set forth in SEQ ID NO:200, a CDR2 sequence as set forth in: AAT and a CDR3 sequence as set forth SEQ ID NO:201;
(b) a VH region comprising a CDR1 sequence as set forth in SEQ ID NO:50, a CDR2 sequence as set forth in SEQ ID NO:51 and a CDR3 sequence as set forth SEQ ID NO:52, and a VL region comprising a CDR1 sequence as set forth in SEQ ID NO:54, a CDR2 sequence as set forth in: FAS and a CDR3 sequence as set forth SEQ ID NO:55;
(c) a VH region comprising a CDR1 sequence as set forth in SEQ ID NO:57, a CDR2 sequence as set forth in SEQ ID NO:58 and a CDR3 sequence as set forth SEQ ID NO:59, and a VL region comprising a CDR1 sequence as set forth in SEQ ID NO:61, a CDR2 sequence as set forth in: RTS and a CDR3 sequence as set forth SEQ ID NO:62;
(d) a VH region comprising a CDR1 sequence as set forth in SEQ ID NO:36, a CDR2 sequence as set forth in SEQ ID NO:37 and a CDR3 sequence as set forth SEQ ID NO:38, and a VL region comprising a CDR1 sequence as set forth in SEQ ID NO:40, a CDR2 sequence as set forth in: DAS and a CDR3 sequence as set forth SEQ ID NO:41;
(e) a VH region comprising a CDR1 sequence as set forth in SEQ ID NO:9, a CDR2 sequence as set forth in SEQ ID NO:10 and a CDR3 sequence as set forth SEQ ID NO:11, and a VL region comprising a CDR1 sequence as set forth in SEQ ID NO: 13, a CDR2 sequence as set forth in: DAS and a CDR3 sequence as set forth SEQ ID NO:14;
(f) a VH region comprising a CDR1 sequence as set forth in SEQ ID NO:43, a CDR2 sequence as set forth in SEQ ID NO:44 and a CDR3 sequence as set forth SEQ ID NO:45, and a VL region comprising a CDR1 sequence as set forth in SEQ ID NO:47, a CDR2 sequence as set forth in: VAT and a CDR3 sequence as set forth SEQ ID NO:48;

(g) a VH region comprising a CDR1 sequence as set forth in SEQ ID NO:2, a CDR2 sequence as set forth in SEQ ID NO:3 and a CDR3 sequence as set forth SEQ ID NO:4, and a VL region comprising a CDR1 sequence as set forth in SEQ ID NO:6, a CDR2 sequence as set forth in: NTN, and a CDR3 sequence as set forth SEQ ID NO:7;

(h) a VH region comprising a CDR1 sequence as set forth in SEQ ID NO:161, a CDR2 sequence as set forth in SEQ ID NO:162, and a CDR3 sequence as set forth SEQ ID NO:163, and a VL region comprising a CDR1 sequence as set forth in SEQ ID NO: 165, a CDR2 sequence as set forth in: LVS and a CDR3 sequence as set forth SEQ ID NO:166;

(i) Q a VH region comprising a CDR1 sequence as set forth in SEQ ID NO:168, a CDR2 sequence as set forth in SEQ ID NO:169 and a CDR3 sequence as set forth SEQ ID NO:170, and a VL region comprising a CDR1 sequence as set forth in SEQ ID NO: 172, a CDR2 sequence as set forth in SEQ ID NO:AAS and a CDR3 sequence as set forth SEQ ID NO:173;

(j) a VH region comprising a CDR1 sequence as set forth in SEQ ID NO:175, a CDR2 sequence as set forth in SEQ ID NO:176 and a CDR3 sequence as set forth SEQ ID NO:177, and a VL region comprising a CDR1 sequence as set forth in SEQ ID NO: 179, a CDR2 sequence as set forth in: DNN and a CDR3 sequence as set forth SEQ ID NO:180;

(k) a VH region comprising a CDR1 sequence as set forth in SEQ ID NO:182, a CDR2 sequence as set forth in SEQ ID NO:183 and a CDR3 sequence as set forth SEQ ID NO:184, and a VL region comprising a CDR1 sequence as set forth in SEQ ID NO: 186, a CDR2 sequence as set forth in SEQ ID NO:DTS and a CDR3 sequence as set forth SEQ ID NO:187; and (l) a VH region comprising a CDR1 sequence as set forth in SEQ ID NO:189, a CDR2 sequence as set forth in SEQ ID NO:190 and a CDR3 sequence as set forth SEQ ID NO:191, and a VL region comprising a CDR1 sequence as set forth in SEQ ID NO: 193, a CDR2 sequence as set forth in: ATS and a CDR3 sequence as set forth SEQ ID NO:194, wherein the first antibody and second antibody are not the same antibody.

14. The method according to claim 1, wherein the disease is selected from the group consisting of: cancer, autoimmune disease, inflammatory disease, and infectious disease.

15. The method according to claim 14, wherein the method comprises administering an additional therapeutic agent.

16. A method of depleting a cell population expressing a first antigen and a second antigen, which method comprises contacting said cell population with a first antibody and second antibody, wherein the first antibody and second antibody are as defined in claim 1.

17. A kit comprising a first container comprising a first antibody and a second container comprising a second antibody, wherein the first antibody and second antibody are as defined in claim 1.

* * * * *

UNITED STATES PATENT AND TRADEMARK OFFICE
CERTIFICATE OF CORRECTION

PATENT NO. : 12,338,289 B2
APPLICATION NO. : 17/051205
DATED : June 24, 2025
INVENTOR(S) : Rob De Jong et al.

It is certified that error appears in the above-identified patent and that said Letters Patent is hereby corrected as shown below:

In the Claims

At Column 412, Claim number 13(a), Line 31, delete "SEQ ID NO:196 and CDR3 sequence as set forth" and insert --SEQ ID NO:196 and CDR3 sequence as set forth in--

At Column 412, Claim number 13(a), Line 35, delete "set forth SEQ ID NO:201;" and insert --set forth in SEQ ID NO:201;--

At Column 412, Claim number 13(b), Line 38, delete "SEQ ID NO:51 and a CDR3 sequence as set forth SEQ" and insert --SEQ ID NO:51 and a CDR3 sequence as set forth in SEQ--

At Column 412, Claim number 13(b), Line 42, delete "set forth SEQ ID NO:55;" and insert --set forth in SEQ ID NO:55;--

At Column 412, Claim number 13(c), Line 45, delete "SEQ ID NO:58 and a CDR3 sequence as set forth SEQ" and insert --SEQ ID NO:58 and a CDR3 sequence as set forth in SEQ--

At Column 412, Claim number 13(c), Line 49, delete "set forth SEQ ID NO:62" and insert --set forth in SEQ ID NO:62--

At Column 412, Claim number 13(d), Line 52, delete "SEQ ID NO:37 and a CDR3 sequence as set forth SEQ" and insert --SEQ ID NO:37 and a CDR3 sequence as set forth in SEQ--

At Column 412, Claim number 13(d), Line 56, delete "set forth SEQ ID NO:41;" and insert --set forth in SEQ ID NO:41;--

At Column 412, Claim number 13(e), Line 59, delete "ID NO:10 and a CDR3 sequence as set forth SEQ ID" and insert --ID NO:10 and a CDR3 sequence as set forth in SEQ ID--

Signed and Sealed this
Fifth Day of August, 2025

Coke Morgan Stewart
*Acting Director of the United States Patent and Trademark Office*

CERTIFICATE OF CORRECTION (continued)
U.S. Pat. No. 12,338,289 B2

At Column 412, Claim number 13(e), Line 62, delete "forth in: DAS and a CDR3 sequence as set forth SEQ" and insert --forth in: DAS and a CDR3 sequence as set forth in SEQ--

At Column 412, Claim number 13(f), Line 66, delete "SEQ ID NO:44 and a CDR3 sequence as set forth SEQ" and insert --SEQ ID NO:44 and a CDR3 sequence as set forth in SEQ--

At Column 413, Claim number 13(f), Line 3, delete "set forth SEQ ID NO:48;" and insert --set forth in SEQ ID NO:48;--

At Column 413, Claim number 13(g), Line 6, delete "ID NO:3 and a CDR3 sequence as set forth SEQ ID" and insert --ID NO:3 and a CDR3 sequence as set forth in SEQ ID--

At Column 413, Claim number 13(g), Line 9, delete "forth in: NTN, and a CDR3 sequence as set forth SEQ" and insert --forth in: NTN, and a CDR3 sequence as set forth in SEQ--

At Column 413, Claim number 13(h), Line 13, delete "SEQ ID NO:162, and a CDR3 sequence as set forth" and insert --SEQ ID NO:162, and a CDR3 sequence as set forth in--

At Column 413, Claim number 13(h), Line 17, delete "set forth SEQ ID NO:166;" and insert --set forth in SEQ ID NO:166;--

At Column 413, Claim number 13(i), Line 18, delete "Q a VH region comprising a CDR1 sequence as set" and insert --a VH region comprising a CDR1 sequence as set--

At Column 413, Claim number 13(i), Line 20, delete "in SEQ ID NO:169 and a CDR3 sequence as set forth" and insert --in SEQ ID NO:169 and a CDR3 sequence as set forth in--

At Column 413, Claim number 13(i), Line 24, delete "sequence as set forth SEQ ID NO:173;" and insert --sequence as set forth in SEQ ID NO:173;--

At Column 413, Claim number 13(j), Line 27, delete "SEQ ID NO:176 and a CDR3 sequence as set forth" and insert --SEQ ID NO:176 and a CDR3 sequence as set forth in--

At Column 413, Claim number 13(j), Line 31, delete "set forth SEQ ID NO:180;" and insert --set forth in SEQ ID NO:180;--

At Column 414, Claim number 13(k), Line 3, delete "SEQ ID NO:183 and a CDR3 sequence as set forth" and insert --SEQ ID NO:183 and a CDR3 sequence as set forth in--

At Column 414, Claim number 13(k), Line 7, delete "sequence as set forth SEQ ID NO:187; and" and insert --sequence as set forth in SEQ ID NO:187; and--

At Column 414, Claim number 13(l), Line 10, delete "SEQ ID NO:190 and a CDR3 sequence as set forth" and insert --SEQ ID NO:190 and a CDR3 sequence as set forth in--

At Column 414, Claim number 13(l), Line 14, delete "set forth SEQ ID NO:194, wherein the first antibody" and insert --set forth in SEQ ID NO:194, wherein the first antibody--

```
                        SEQUENCE LISTING

<160> NUMBER OF SEQ ID NOS: 201

<210> SEQ ID NO 1
<211> LENGTH: 121
<212> TYPE: PRT
<213> ORGANISM: Artificial sequence
<220> FEATURE:
<223> OTHER INFORMATION: Humanized, VH region

<400> SEQUENCE: 1

Gln Val Gln Leu Gln Glu Ser Gly Pro Gly Leu Val Arg Pro Ser Gln
1               5                   10                  15

Thr Leu Ser Leu Thr Cys Thr Val Ser Gly Phe Thr Phe Thr Asp Phe
            20                  25                  30

Tyr Met Asn Trp Val Arg Gln Pro Gly Arg Gly Leu Glu Trp Ile
        35                  40                  45

Gly Phe Ile Arg Asp Lys Ala Lys Gly Tyr Thr Thr Glu Tyr Asn Pro
    50                  55                  60

Ser Val Lys Gly Arg Val Thr Met Leu Val Asp Thr Ser Lys Asn Gln
65                  70                  75                  80

Phe Ser Leu Arg Leu Ser Ser Val Thr Ala Ala Asp Thr Ala Val Tyr
                85                  90                  95

Tyr Cys Ala Arg Glu Gly His Thr Ala Ala Pro Phe Asp Tyr Trp Gly
            100                 105                 110

Gln Gly Ser Leu Val Thr Val Ser Ser
        115                 120

<210> SEQ ID NO 2
<211> LENGTH: 8
<212> TYPE: PRT
<213> ORGANISM: Artificial sequence
<220> FEATURE:
<223> OTHER INFORMATION: VH region CDR1

<400> SEQUENCE: 2

Gly Phe Thr Phe Thr Asp Phe Tyr
1               5

<210> SEQ ID NO 3
<211> LENGTH: 10
<212> TYPE: PRT
<213> ORGANISM: Artificial sequence
<220> FEATURE:
<223> OTHER INFORMATION: VH region CDR2

<400> SEQUENCE: 3

Ile Arg Asp Lys Ala Lys Gly Tyr Thr Thr
1               5                   10
```

```
<210> SEQ ID NO 4
<211> LENGTH: 12
<212> TYPE: PRT
<213> ORGANISM: Artificial sequence
<220> FEATURE:
<223> OTHER INFORMATION: VH region CDR2

<400> SEQUENCE: 4

Ala Arg Glu Gly His Thr Ala Ala Pro Phe Asp Tyr
1               5                   10

<210> SEQ ID NO 5
<211> LENGTH: 107
<212> TYPE: PRT
<213> ORGANISM: Artificial sequence
<220> FEATURE:
<223> OTHER INFORMATION: Humanized VL region

<400> SEQUENCE: 5

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Ile Asp Lys Tyr
            20                  25                  30

Leu Asn Trp Tyr Gln Gln Lys Pro Gly Lys Ala Pro Lys Leu Leu Ile
        35                  40                  45

Tyr Asn Thr Asn Asn Leu Gln Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Leu Gln His Ile Ser Arg Pro Arg
                85                  90                  95

Thr Phe Gly Gln Gly Thr Lys Val Glu Ile Lys
            100                 105

<210> SEQ ID NO 6
<211> LENGTH: 6
<212> TYPE: PRT
<213> ORGANISM: Artificial sequence
<220> FEATURE:
<223> OTHER INFORMATION: VL region CDR1

<400> SEQUENCE: 6

Gln Asn Ile Asp Lys Tyr
1               5

<210> SEQ ID NO 7
<211> LENGTH: 9
<212> TYPE: PRT
<213> ORGANISM: Artificial sequence
<220> FEATURE:
<223> OTHER INFORMATION: VL region CDR3

<400> SEQUENCE: 7

Leu Gln His Ile Ser Arg Pro Arg Thr
1               5

<210> SEQ ID NO 8
<211> LENGTH: 125
<212> TYPE: PRT
<213> ORGANISM: Artificial sequence
<220> FEATURE:
<223> OTHER INFORMATION: VH region

<400> SEQUENCE: 8
```

```
Glu Val Gln Leu Val Gln Ser Gly Gly Gly Leu Val His Pro Gly Gly
1               5                   10                  15

Ser Leu Arg Leu Ser Cys Thr Gly Ser Gly Phe Thr Phe Ser Tyr His
            20                  25                  30

Ala Met His Trp Val Arg Gln Ala Pro Gly Lys Gly Leu Glu Trp Val
        35                  40                  45

Ser Ile Ile Gly Thr Gly Gly Val Thr Tyr Tyr Ala Asp Ser Val Lys
50                  55                  60

Gly Arg Phe Thr Ile Ser Arg Asp Asn Val Lys Asn Ser Leu Tyr Leu
65                  70                  75                  80

Gln Met Asn Ser Leu Arg Ala Glu Asp Met Ala Val Tyr Tyr Cys Ala
                85                  90                  95

Arg Asp Tyr Tyr Gly Ala Gly Ser Phe Tyr Asp Gly Leu Tyr Gly Met
            100                 105                 110

Asp Val Trp Gly Gln Gly Thr Thr Val Thr Val Ser Ser
        115                 120                 125
```

```
<210> SEQ ID NO 9
<211> LENGTH: 8
<212> TYPE: PRT
<213> ORGANISM: Artificial sequence
<220> FEATURE:
<223> OTHER INFORMATION: VH region CDR1

<400> SEQUENCE: 9

Gly Phe Thr Phe Ser Tyr His Ala
1               5
```

```
<210> SEQ ID NO 10
<211> LENGTH: 7
<212> TYPE: PRT
<213> ORGANISM: Artificial sequence
<220> FEATURE:
<223> OTHER INFORMATION: VH region CDR2

<400> SEQUENCE: 10

Ile Gly Thr Gly Gly Val Thr
1               5
```

```
<210> SEQ ID NO 11
<211> LENGTH: 19
<212> TYPE: PRT
<213> ORGANISM: Artificial sequence
<220> FEATURE:
<223> OTHER INFORMATION: VH region CDR3

<400> SEQUENCE: 11

Ala Arg Asp Tyr Tyr Gly Ala Gly Ser Phe Tyr Asp Gly Leu Tyr Gly
1               5                   10                  15

Met Asp Val
```

```
<210> SEQ ID NO 12
<211> LENGTH: 107
<212> TYPE: PRT
<213> ORGANISM: Artificial sequence
<220> FEATURE:
<223> OTHER INFORMATION: VL region

<400> SEQUENCE: 12

Glu Ile Val Leu Thr Gln Ser Pro Ala Thr Leu Ser Leu Ser Pro Gly
1               5                   10                  15
```

-continued

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asp Trp Pro Leu
                85                  90                  95

Thr Phe Gly Gly Gly Thr Lys Val Glu Ile Lys
            100                 105

<210> SEQ ID NO 13
<211> LENGTH: 6
<212> TYPE: PRT
<213> ORGANISM: Artificial sequence
<220> FEATURE:
<223> OTHER INFORMATION: VL region CDR1

<400> SEQUENCE: 13

Gln Ser Val Ser Ser Tyr
1               5

<210> SEQ ID NO 14
<211> LENGTH: 9
<212> TYPE: PRT
<213> ORGANISM: Artificial sequence
<220> FEATURE:
<223> OTHER INFORMATION: VL region CDR3

<400> SEQUENCE: 14

Gln Gln Arg Ser Asp Trp Pro Leu Thr
1               5

<210> SEQ ID NO 15
<211> LENGTH: 127
<212> TYPE: PRT
<213> ORGANISM: Artificial sequence
<220> FEATURE:
<223> OTHER INFORMATION: VH region

<400> SEQUENCE: 15

Gln Val Gln Leu Val Gln Ser Gly Ala Glu Val Lys Lys Pro Gly Ala
1               5                   10                  15

Ser Val Lys Val Ser Cys Gln Ala Ser Gly Tyr Arg Phe Ser Asn Phe
                20                  25                  30

Val Ile His Trp Val Arg Gln Ala Pro Gly Gln Arg Phe Glu Trp Met
            35                  40                  45

Gly Trp Ile Asn Pro Tyr Asn Gly Asn Lys Glu Phe Ser Ala Lys Phe
        50                  55                  60

Gln Asp Arg Val Thr Phe Thr Ala Asp Thr Ser Ala Asn Thr Ala Tyr
65                  70                  75                  80

Met Glu Leu Arg Ser Leu Arg Ser Ala Asp Thr Ala Val Tyr Tyr Cys
                85                  90                  95

Ala Arg Val Gly Pro Tyr Ser Trp Asp Asp Ser Pro Gln Asp Asn Tyr
            100                 105                 110

Tyr Met Asp Val Trp Gly Lys Gly Thr Thr Val Ile Val Ser Ser
        115                 120                 125

```
<210> SEQ ID NO 16
<211> LENGTH: 8
<212> TYPE: PRT
<213> ORGANISM: Artificial sequence
<220> FEATURE:
<223> OTHER INFORMATION: VH region CDR1

<400> SEQUENCE: 16

Gly Tyr Arg Phe Ser Asn Phe Val
1               5

<210> SEQ ID NO 17
<211> LENGTH: 8
<212> TYPE: PRT
<213> ORGANISM: Artificial sequence
<220> FEATURE:
<223> OTHER INFORMATION: VH region CDR2

<400> SEQUENCE: 17

Ile Asn Pro Tyr Asn Gly Asn Lys
1               5

<210> SEQ ID NO 18
<211> LENGTH: 20
<212> TYPE: PRT
<213> ORGANISM: Artificial sequence
<220> FEATURE:
<223> OTHER INFORMATION: VH region CDR3

<400> SEQUENCE: 18

Ala Arg Val Gly Pro Tyr Ser Trp Asp Asp Ser Pro Gln Asp Asn Tyr
1               5                   10                  15

Tyr Met Asp Val
            20

<210> SEQ ID NO 19
<211> LENGTH: 108
<212> TYPE: PRT
<213> ORGANISM: Artificial sequence
<220> FEATURE:
<223> OTHER INFORMATION: VL region

<400> SEQUENCE: 19

Glu Ile Val Leu Thr Gln Ser Pro Gly Thr Leu Ser Leu Ser Pro Gly
1               5                   10                  15

Glu Arg Ala Thr Phe Ser Cys Arg Ser Ser His Ser Ile Arg Ser Arg
                20                  25                  30

Arg Val Ala Trp Tyr Gln His Lys Pro Gly Gln Ala Pro Arg Leu Val
            35                  40                  45

Ile His Gly Val Ser Asn Arg Ala Ser Gly Ile Ser Asp Arg Phe Ser
        50                  55                  60

Gly Ser Gly Ser Gly Thr Asp Phe Thr Leu Thr Ile Thr Arg Val Glu
65                  70                  75                  80

Pro Glu Asp Phe Ala Leu Tyr Tyr Cys Gln Val Tyr Gly Ala Ser Ser
                85                  90                  95

Tyr Thr Phe Gly Gln Gly Thr Lys Leu Glu Arg Lys
                100                 105

<210> SEQ ID NO 20
<211> LENGTH: 7
<212> TYPE: PRT
<213> ORGANISM: Artificial sequence
<220> FEATURE:
<223> OTHER INFORMATION: VL region CDR1
```

```
<400> SEQUENCE: 20

His Ser Ile Arg Ser Arg Arg
1               5

<210> SEQ ID NO 21
<211> LENGTH: 9
<212> TYPE: PRT
<213> ORGANISM: Artificial sequence
<220> FEATURE:
<223> OTHER INFORMATION: VL region CDR1

<400> SEQUENCE: 21

Gln Val Tyr Gly Ala Ser Ser Tyr Thr
1               5

<210> SEQ ID NO 22
<211> LENGTH: 330
<212> TYPE: PRT
<213> ORGANISM: Human

<400> SEQUENCE: 22

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
```

```
                275                 280                 285
Leu Tyr Ser Lys Leu Thr Val Asp Lys Ser Arg Trp Gln Gln Gly Asn
        290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330

<210> SEQ ID NO 23
<211> LENGTH: 330
<212> TYPE: PRT
<213> ORGANISM: Human

<400> SEQUENCE: 23

Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Ser Leu Gly Thr Gln Thr
65                  70                  75                  80
Tyr Ile Cys Asn Val Asn His Lys Pro Ser Asn Thr Lys Val Asp Lys
                85                  90                  95
Lys Val Glu Pro Lys Ser Cys Asp Lys Thr His Thr Cys Pro Pro Cys
            100                 105                 110
Pro Ala Pro Glu Leu Leu Gly Gly Pro Ser Val Phe Leu Phe Pro Pro
        115                 120                 125
Lys Pro Lys Asp Thr Leu Met Ile Ser Arg Thr Pro Glu Val Thr Cys
    130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
    210                 215                 220
Gln Pro Arg Glu Pro Gln Val Tyr Thr Leu Pro Pro Ser Arg Glu Glu
225                 230                 235                 240
Met Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
    290                 295                 300
Val Phe Ser Cys Ser Val Met His Glu Ala Leu His Asn His Tyr Thr
305                 310                 315                 320
```

Gln Lys Ser Leu Ser Leu Ser Pro Gly Lys
            325                 330

<210> SEQ ID NO 24
<211> LENGTH: 330
<212> TYPE: PRT
<213> ORGANISM: Human

<400> SEQUENCE: 24

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Pro Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 25
<211> LENGTH: 330
<212> TYPE: PRT
<213> ORGANISM: Human

<400> SEQUENCE: 25

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Pro Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Gly Leu His Asn His Tyr Thr
305                 310                 315                 320

Gln Lys Ser Leu Ser Leu Ser Pro Gly Lys
                325                 330
```

<210> SEQ ID NO 26
<211> LENGTH: 330
<212> TYPE: PRT
<213> ORGANISM: Artificial sequence
<220> FEATURE:
<223> OTHER INFORMATION: modified Fc region

<400> SEQUENCE: 26

```
Ala Ser Thr Lys Gly Pro Ser Val Phe Pro Leu Ala Pro Ser Ser Lys
1               5                   10                  15
```

```
Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Gly Ala Leu His Asn His Tyr Thr
305                 310                 315                 320

Gln Lys Ser Leu Ser Leu Ser Pro Gly Lys
                325                 330

<210> SEQ ID NO 27
<211> LENGTH: 330
<212> TYPE: PRT
<213> ORGANISM: Artificial sequence
<220> FEATURE:
<223> OTHER INFORMATION: modified Fc region

<400> SEQUENCE: 27

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45
```

```
Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Lys Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 28
<211> LENGTH: 330
<212> TYPE: PRT
<213> ORGANISM: Artificial sequence
<220> FEATURE:
<223> OTHER INFORMATION: modified Fc region

<400> SEQUENCE: 28

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80
```

Tyr Ile Cys Asn Val Asn His Lys Pro Ser Asn Thr Lys Val Asp Lys
                 85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Arg Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 29
<211> LENGTH: 330
<212> TYPE: PRT
<213> ORGANISM: Artificial sequence
<220> FEATURE:
<223> OTHER INFORMATION: modified Fc region

<400> SEQUENCE: 29

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Glu Ser Leu Ser Leu Ser Pro Gly Lys
                325                 330

<210> SEQ ID NO 30
<211> LENGTH: 330
<212> TYPE: PRT
<213> ORGANISM: Artificial sequence
<220> FEATURE:
<223> OTHER INFORMATION: modified Fc region

<400> SEQUENCE: 30

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

-continued

```
Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
        180                 185                 190

His Gln Asp Trp Leu Asn Gly Lys Glu Tyr Lys Cys Lys Val Ser Asn
    195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Lys Leu Ser Leu Ser Pro Gly Lys
                325                 330

<210> SEQ ID NO 31
<211> LENGTH: 326
<212> TYPE: PRT
<213> ORGANISM: Human

<400> SEQUENCE: 31

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190
```

```
Leu Asn Gly Lys Glu Tyr Lys Cys Lys Val Ser Asn Lys Gly Leu Pro
            195                 200                 205

Ala Pro Ile Glu Lys Thr Ile Ser Lys Thr Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 32
<211> LENGTH: 377
<212> TYPE: PRT
<213> ORGANISM: Human

<400> SEQUENCE: 32

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Glu Pro Lys Ser Cys Asp Thr Pro Pro Pro Cys Pro Arg Cys
    130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
    210                 215                 220

Gln Tyr Asn Ser Thr Phe Arg Val Val Ser Val Leu Thr Val Leu His
```

Gln Asp Trp Leu Asn Gly Lys Glu Tyr Lys Cys Lys Val Ser Asn Lys
225                 230                 235                 240

Ala Leu Pro Ala Pro Ile Glu Lys Thr Ile Ser Lys Thr Lys Gly Gln
            245                 250                 255

Pro Arg Glu Pro Gln Val Tyr Thr Leu Pro Pro Ser Arg Glu Glu Met
        260                 265                 270

Thr Lys Asn Gln Val Ser Leu Thr Cys Leu Val Lys Gly Phe Tyr Pro
    275                 280                 285

Ser Asp Ile Ala Val Glu Trp Glu Ser Ser Gly Gln Pro Glu Asn Asn
290                 295                 300

Tyr Asn Thr Thr Pro Pro Met Leu Asp Ser Asp Gly Ser Phe Phe Leu
305                 310                 315                 320

Tyr Ser Lys Leu Thr Val Asp Lys Ser Arg Trp Gln Gln Gly Asn Ile
            325                 330                 335

Phe Ser Cys Ser Val Met His Glu Ala Leu His Asn Arg Phe Thr Gln
        340                 345                 350

Lys Ser Leu Ser Leu Ser Pro Gly Lys
    355                 360                 365

Lys Ser Leu Ser Leu Ser Pro Gly Lys
370                 375

<210> SEQ ID NO 33
<211> LENGTH: 327
<212> TYPE: PRT
<213> ORGANISM: Human

<400> SEQUENCE: 33

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Met Thr Lys
225                 230                 235                 240

Asn Gln Val Ser Leu Thr Cys Leu Val Lys Gly Phe Tyr Pro Ser Asp
            245                 250                 255

Ile Ala Val Glu Trp Glu Ser Asn Gly Gln Pro Glu Asn Asn Tyr Lys
        260                 265                 270

Thr Thr Pro Pro Val Leu Asp Ser Asp Gly Ser Phe Phe Leu Tyr Ser
    275                 280                 285

Arg Leu Thr Val Asp Lys Ser Arg Trp Gln Gln Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 34
<211> LENGTH: 107
<212> TYPE: PRT
<213> ORGANISM: Human

<400> SEQUENCE: 34

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 35
<211> LENGTH: 122
<212> TYPE: PRT
<213> ORGANISM: Artificial sequence
<220> FEATURE:
<223> OTHER INFORMATION: VH region

<400> SEQUENCE: 35

Glu Val Gln Leu Val Glu Ser Gly Gly Gly Leu Val Gln Pro Asp Arg
1               5                   10                  15

Ser Leu Arg Leu Ser Cys Ala Ala Ser Gly Phe Thr Phe His Asp Tyr
            20                  25                  30

Ala Met His Trp Val Arg Gln Ala Pro Gly Lys Gly Leu Glu Trp Val
        35                  40                  45

Ser Thr Ile Ser Trp Asn Ser Gly Thr Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Ile Gln Tyr Gly Asn Tyr Tyr Tyr Gly Met Asp Val Trp

```
                  100                 105                 110
Gly Gln Gly Thr Thr Val Thr Val Ser Ser
        115                 120

<210> SEQ ID NO 36
<211> LENGTH: 8
<212> TYPE: PRT
<213> ORGANISM: Artificial sequence
<220> FEATURE:
<223> OTHER INFORMATION: VH region CDR1

<400> SEQUENCE: 36

Gly Phe Thr Phe His Asp Tyr Ala
1               5

<210> SEQ ID NO 37
<211> LENGTH: 8
<212> TYPE: PRT
<213> ORGANISM: Artificial sequence
<220> FEATURE:
<223> OTHER INFORMATION: VH region CDR2

<400> SEQUENCE: 37

Ile Ser Trp Asn Ser Gly Thr Ile
1               5

<210> SEQ ID NO 38
<211> LENGTH: 15
<212> TYPE: PRT
<213> ORGANISM: Artificial Sequence
<220> FEATURE:
<223> OTHER INFORMATION: VH region CDR3

<400> SEQUENCE: 38

Ala Lys Asp Ile Gln Tyr Gly Asn Tyr Tyr Gly Met Asp Val
1               5                   10                  15

<210> SEQ ID NO 39
<211> LENGTH: 107
<212> TYPE: PRT
<213> ORGANISM: Artificial sequence
<220> FEATURE:
<223> OTHER INFORMATION: VL region

<400> SEQUENCE: 39

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Ile
                85                  90                  95

Thr Phe Gly Gln Gly Thr Arg Leu Glu Ile Lys
            100                 105

<210> SEQ ID NO 40
<211> LENGTH: 6
<212> TYPE: PRT
```

<213> ORGANISM: Artificial sequence
<220> FEATURE:
<223> OTHER INFORMATION: VL region CDR1

<400> SEQUENCE: 40

Gln Ser Val Ser Ser Tyr
1               5

<210> SEQ ID NO 41
<211> LENGTH: 9
<212> TYPE: PRT
<213> ORGANISM: Artificial sequence
<220> FEATURE:
<223> OTHER INFORMATION: VL region CDR3

<400> SEQUENCE: 41

Gln Gln Arg Ser Asn Trp Pro Ile Thr
1               5

<210> SEQ ID NO 42
<211> LENGTH: 115
<212> TYPE: PRT
<213> ORGANISM: Artificial sequence
<220> FEATURE:
<223> OTHER INFORMATION: VH region

<400> SEQUENCE: 42

Gln Val Gln Val Lys Glu Ser Gly Pro Gly Leu Val Ala Pro Ser Gln
1               5                   10                  15

Ser Leu Ser Ile Thr Cys Thr Val Ser Gly Phe Ser Leu Thr Thr Ser
            20                  25                  30

Gly Val Ser Trp Val Arg Gln Pro Pro Gly Lys Gly Leu Glu Trp Leu
        35                  40                  45

Gly Val Ile Trp Gly Asp Gly Ser Thr Asn Tyr His Ser Ala Leu Lys
    50                  55                  60

Ser Arg Leu Ser Ile Lys Lys Asp His Ser Lys Ser Gln Val Phe Leu
65                  70                  75                  80

Lys Leu Asn Ser Leu Gln Thr Asp Asp Thr Ala Thr Tyr Tyr Cys Ala
                85                  90                  95

Lys Gly Gly Tyr Ser Leu Ala His Trp Gly Gln Gly Thr Leu Val Thr
            100                 105                 110

Val Ser Ala
        115

<210> SEQ ID NO 43
<211> LENGTH: 8
<212> TYPE: PRT
<213> ORGANISM: Artificial sequence
<220> FEATURE:
<223> OTHER INFORMATION: VH region CDR1

<400> SEQUENCE: 43

Gly Phe Ser Leu Thr Thr Ser Gly
1               5

<210> SEQ ID NO 44
<211> LENGTH: 7
<212> TYPE: PRT
<213> ORGANISM: Artificial sequence
<220> FEATURE:
<223> OTHER INFORMATION: VH region CDR2

<400> SEQUENCE: 44

```
Ile Trp Gly Asp Gly Ser Thr
1               5
```

<210> SEQ ID NO 45
<211> LENGTH: 9
<212> TYPE: PRT
<213> ORGANISM: Artificial sequence
<220> FEATURE:
<223> OTHER INFORMATION: VH region CDR3

<400> SEQUENCE: 45

```
Ala Lys Gly Gly Tyr Ser Leu Ala His
1               5
```

<210> SEQ ID NO 46
<211> LENGTH: 107
<212> TYPE: PRT
<213> ORGANISM: Artificial sequence
<220> FEATURE:
<223> OTHER INFORMATION: VL region

<400> SEQUENCE: 46

```
Asp Ile Gln Met Thr Gln Ser Pro Ala Ser Leu Ser Val Ser Val Gly
1               5                   10                  15

Glu Thr Val Thr Ile Thr Cys Arg Ala Ser Glu Asn Ile Arg Ser Asn
            20                  25                  30

Leu Ala Trp Tyr Gln Gln Lys Gln Gly Lys Ser Pro Gln Leu Leu Val
        35                  40                  45

Asn Val Ala Thr Asn Leu Ala Asp Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Phe Gly Thr Tyr Tyr Cys Gln His Tyr Trp Gly Thr Thr Trp
                85                  90                  95

Thr Phe Gly Gly Gly Thr Lys Leu Glu Ile Lys
            100                 105
```

<210> SEQ ID NO 47
<211> LENGTH: 6
<212> TYPE: PRT
<213> ORGANISM: Artificial sequence
<220> FEATURE:
<223> OTHER INFORMATION: VL region CDR1

<400> SEQUENCE: 47

```
Glu Asn Ile Arg Ser Asn
1               5
```

<210> SEQ ID NO 48
<211> LENGTH: 9
<212> TYPE: PRT
<213> ORGANISM: Artificial sequence
<220> FEATURE:
<223> OTHER INFORMATION: VL region CDR1

<400> SEQUENCE: 48

```
Gln His Tyr Trp Gly Thr Thr Trp Thr
1               5
```

<210> SEQ ID NO 49
<211> LENGTH: 118
<212> TYPE: PRT
<213> ORGANISM: Artificial sequence
<220> FEATURE:

<223> OTHER INFORMATION: Humanized VH region

<400> SEQUENCE: 49

Glu Val Gln Leu Gln Gln Ser Gly Ala Glu Val Val Lys Pro Gly Ala
1               5                   10                  15

Ser Val Lys Leu Ser Cys Lys Ala Ser Gly Phe Asn Ile Lys Asp Thr
            20                  25                  30

Phe Ile His Trp Val Lys Gln Ala Pro Gly Gln Gly Leu Glu Trp Ile
        35                  40                  45

Gly Arg Ile Asp Pro Ala Asn Thr Asn Thr Lys Tyr Asp Pro Lys Phe
    50                  55                  60

Gln Gly Lys Ala Thr Ile Thr Thr Asp Thr Ser Ser Asn Thr Ala Tyr
65                  70                  75                  80

Met Glu Leu Ser Ser Leu Arg Ser Glu Asp Thr Ala Val Tyr Tyr Cys
                85                  90                  95

Val Arg Gly Leu Tyr Thr Tyr Tyr Phe Asp Tyr Trp Gly Gln Gly Thr
            100                 105                 110

Leu Val Thr Val Ser Ser
            115

<210> SEQ ID NO 50
<211> LENGTH: 8
<212> TYPE: PRT
<213> ORGANISM: Artificial sequence
<220> FEATURE:
<223> OTHER INFORMATION: Humanized VH region CDR1

<400> SEQUENCE: 50

Gly Phe Asn Ile Lys Asp Thr Phe
1               5

<210> SEQ ID NO 51
<211> LENGTH: 8
<212> TYPE: PRT
<213> ORGANISM: Artificial sequence
<220> FEATURE:
<223> OTHER INFORMATION: Humanized VH region CDR2

<400> SEQUENCE: 51

Ile Asp Pro Ala Asn Thr Asn Thr
1               5

<210> SEQ ID NO 52
<211> LENGTH: 11
<212> TYPE: PRT
<213> ORGANISM: Artificial sequence
<220> FEATURE:
<223> OTHER INFORMATION: Humanized VH region CDR3

<400> SEQUENCE: 52

Val Arg Gly Leu Tyr Thr Tyr Tyr Phe Asp Tyr
1               5                   10

<210> SEQ ID NO 53
<211> LENGTH: 107
<212> TYPE: PRT
<213> ORGANISM: Artificial sequence
<220> FEATURE:
<223> OTHER INFORMATION: Humanized VL region

<400> SEQUENCE: 53

Glu Ile Val Met Thr Gln Ser Pro Ala Thr Leu Ser Val Ser Pro Gly
1               5                   10                  15

```
Glu Arg Ala Thr Leu Ser Cys Arg Ala Ser Gln Ser Ile Ser Asn Asn
            20                  25                  30

Leu His Trp Tyr Gln Gln Lys Pro Gly Gln Ala Pro Arg Leu Leu Ile
        35                  40                  45

Lys Phe Ala Ser Gln Ser Ile Thr Gly Ile Pro Ala Arg Phe Ser Gly
 50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln Gln Gly Asn Ser Trp Pro Tyr
                85                  90                  95

Thr Phe Gly Gln Gly Thr Lys Leu Glu Ile Lys
            100                 105
```

<210> SEQ ID NO 54
<211> LENGTH: 6
<212> TYPE: PRT
<213> ORGANISM: Artificial sequence
<220> FEATURE:
<223> OTHER INFORMATION: Humanized VL region CDR1

<400> SEQUENCE: 54

```
Gln Ser Ile Ser Asn Asn
 1               5
```

<210> SEQ ID NO 55
<211> LENGTH: 9
<212> TYPE: PRT
<213> ORGANISM: Artificial sequence
<220> FEATURE:
<223> OTHER INFORMATION: Humanized VL region CDR3

<400> SEQUENCE: 55

```
Gln Gln Gly Asn Ser Trp Pro Tyr Thr
 1               5
```

<210> SEQ ID NO 56
<211> LENGTH: 118
<212> TYPE: PRT
<213> ORGANISM: Artificial sequence
<220> FEATURE:
<223> OTHER INFORMATION: Humanized VH region

<400> SEQUENCE: 56

```
Gln Val Gln Leu Val Gln Ser Gly Ala Glu Val Lys Lys Pro Gly Ala
 1               5                  10                  15

Ser Val Lys Val Ser Cys Lys Ala Ser Gly Phe Asn Ile Lys Asp Thr
            20                  25                  30

His Met His Trp Val Arg Gln Ala Pro Gly Gln Arg Leu Glu Trp Ile
        35                  40                  45

Gly Arg Ile Asp Pro Ala Asn Gly Asn Thr Glu Tyr Asp Gln Lys Phe
 50                  55                  60

Gln Gly Arg Val Thr Ile Thr Val Asp Thr Ser Ala Ser Thr Ala Tyr
 65                  70                  75                  80

Met Glu Leu Ser Ser Leu Arg Ser Glu Asp Thr Ala Val Tyr Tyr Cys
                85                  90                  95

Ala Arg Trp Gly Thr Asn Val Tyr Phe Ala Tyr Trp Gly Gln Gly Thr
            100                 105                 110

Leu Val Thr Val Ser Ser
            115
```

```
<210> SEQ ID NO 57
<211> LENGTH: 8
<212> TYPE: PRT
<213> ORGANISM: Artificial sequence
<220> FEATURE:
<223> OTHER INFORMATION: Humanized VH region CDR1

<400> SEQUENCE: 57

Gly Phe Asn Ile Lys Asp Thr His
1               5

<210> SEQ ID NO 58
<211> LENGTH: 8
<212> TYPE: PRT
<213> ORGANISM: Artificial sequence
<220> FEATURE:
<223> OTHER INFORMATION: Humanized, VH region CDR2

<400> SEQUENCE: 58

Ile Asp Pro Ala Asn Gly Asn Thr
1               5

<210> SEQ ID NO 59
<211> LENGTH: 11
<212> TYPE: PRT
<213> ORGANISM: Artificial sequence
<220> FEATURE:
<223> OTHER INFORMATION: Humanized, VH region CDR3

<400> SEQUENCE: 59

Ala Arg Trp Gly Thr Asn Val Tyr Phe Ala Tyr
1               5                   10

<210> SEQ ID NO 60
<211> LENGTH: 106
<212> TYPE: PRT
<213> ORGANISM: Artificial sequence
<220> FEATURE:
<223> OTHER INFORMATION: Humanized, VL region

<400> SEQUENCE: 60

Asp Ile Gln Leu Thr Gln Ser Pro Ser Ser Leu Ser Ala Ser Val Gly
1               5                   10                  15

Asp Arg Val Thr Ile Thr Cys Ser Ala Ser Ser Ser Val Ser Tyr Met
                20                  25                  30

Tyr Trp Tyr Gln Gln Lys Pro Gly Lys Ala Pro Lys Pro Trp Ile Tyr
            35                  40                  45

Arg Thr Ser Asn Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Tyr His Ser Tyr Pro Pro Thr
                85                  90                  95

Phe Gly Gly Gly Thr Lys Val Glu Ile Lys
            100                 105

<210> SEQ ID NO 61
<211> LENGTH: 5
<212> TYPE: PRT
<213> ORGANISM: Artificial sequence
<220> FEATURE:
<223> OTHER INFORMATION: Humanized, VL region CDR1

<400> SEQUENCE: 61
```

```
Ser Ser Val Ser Tyr
1               5

<210> SEQ ID NO 62
<211> LENGTH: 9
<212> TYPE: PRT
<213> ORGANISM: Artificial sequence
<220> FEATURE:
<223> OTHER INFORMATION: Humanized, VL region CDR3

<400> SEQUENCE: 62

Gln Gln Tyr His Ser Tyr Pro Pro Thr
1               5

<210> SEQ ID NO 63
<211> LENGTH: 330
<212> TYPE: PRT
<213> ORGANISM: Artificial sequence
<220> FEATURE:
<223> OTHER INFORMATION: modified Fc region

<400> SEQUENCE: 63

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Lys Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
```

```
                    275                 280                 285
Leu Tyr Ser Lys Leu Thr Val Asp Lys Ser Arg Trp Gln Gln Gly Asn
            290                 295                 300

Val Phe Ser Cys Ser Val Met His Gly Ala Leu His Asn His Tyr Thr
305                 310                 315                 320

Gln Lys Ser Leu Ser Leu Ser Pro Gly Lys
                325                 330

<210> SEQ ID NO 64
<211> LENGTH: 330
<212> TYPE: PRT
<213> ORGANISM: Artificial sequence
<220> FEATURE:
<223> OTHER INFORMATION: modified Fc region

<400> SEQUENCE: 64

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Arg Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Ala Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
```

Gln Glu Ser Leu Ser Leu Ser Pro Gly Lys
            325                 330

<210> SEQ ID NO 65
<211> LENGTH: 330
<212> TYPE: PRT
<213> ORGANISM: Artificial sequence
<220> FEATURE:
<223> OTHER INFORMATION: modified Fc region

<400> SEQUENCE: 65

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Ala Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Ala Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Lys Leu Ser Leu Ser Pro Gly Lys
                325                 330

-continued

```
<210> SEQ ID NO 66
<211> LENGTH: 330
<212> TYPE: PRT
<213> ORGANISM: Artificial sequence
<220> FEATURE:
<223> OTHER INFORMATION: modified Fc region

<400> SEQUENCE: 66

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Arg Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Lys Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Glu Ser Leu Ser Leu Ser Pro Gly Lys
                325                 330

<210> SEQ ID NO 67
<211> LENGTH: 330
<212> TYPE: PRT
<213> ORGANISM: Artificial sequence
<220> FEATURE:
<223> OTHER INFORMATION: modified Fc region
```

<400> SEQUENCE: 67

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Ala Val Ser Asn
        195                 200                 205

Lys Ala Leu Pro Ala Pro Ile Glu Lys Thr Ile Ser Lys Ala Lys Gly
    210                 215                 220

Gln Pro Arg Lys Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Glu Ser Leu Ser Leu Ser Pro Gly Lys
                325                 330

<210> SEQ ID NO 68
<211> LENGTH: 330
<212> TYPE: PRT
<213> ORGANISM: Artificial sequence
<220> FEATURE:
<223> OTHER INFORMATION: modified Fc region

<400> SEQUENCE: 68

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Ser Lys Thr Ile Ser Lys Ala Lys Gly
210                 215                 220

Gln Pro Arg Lys Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Lys Leu Ser Leu Ser Pro Gly Lys
                325                 330

<210> SEQ ID NO 69
<211> LENGTH: 330
<212> TYPE: PRT
<213> ORGANISM: Artificial sequence
<220> FEATURE:
<223> OTHER INFORMATION: modified Fc region

<400> SEQUENCE: 69

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Arg Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Gln Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Glu Ser Leu Ser Leu Ser Pro Gly Lys
                325                 330

<210> SEQ ID NO 70
<211> LENGTH: 330
<212> TYPE: PRT
<213> ORGANISM: Artificial sequence
<220> FEATURE:
<223> OTHER INFORMATION: modified Fc region

<400> SEQUENCE: 70

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Leu Gly Thr Gln Thr
65                  70                  75                  80

```
Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Ala Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Gln Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Lys Leu Ser Leu Ser Pro Gly Lys
                325                 330

<210> SEQ ID NO 71
<211> LENGTH: 330
<212> TYPE: PRT
<213> ORGANISM: Artificial sequence
<220> FEATURE:
<223> OTHER INFORMATION: modified Fc region

<400> SEQUENCE: 71

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110
```

```
Pro Ala Pro Glu Leu Leu Arg Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
        180                 185                 190

His Gln Asp Trp Leu Asn Gly Lys Glu Tyr Lys Cys Lys Val Ser Asn
    195                 200                 205

Lys Ala Leu Pro Ala Pro Ile Glu Lys Thr Ile Ser Lys Ala Lys Gly
210                 215                 220

Gln Pro Arg Arg Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
        260                 265                 270

Asn Tyr Lys Thr Thr Pro Pro Val Leu Asp Ser Asp Gly Ser Phe Phe
    275                 280                 285

Leu Tyr Ser Lys Leu Thr Val Asp Lys Ser Arg Trp Gln Gln Gly Asn
290                 295                 300

Val Phe Ser Cys Ser Val Met His Gly Ala Leu His Asn His Tyr Thr
305                 310                 315                 320

Gln Glu Ser Leu Ser Leu Ser Pro Gly Lys
            325                 330

<210> SEQ ID NO 72
<211> LENGTH: 330
<212> TYPE: PRT
<213> ORGANISM: Artificial sequence
<220> FEATURE:
<223> OTHER INFORMATION: modified Fc region

<400> SEQUENCE: 72

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
            85                  90                  95

Arg Val Glu Pro Lys Ser Cys Asp Lys Thr His Thr Cys Pro Pro Cys
        100                 105                 110

Pro Ala Pro Glu Leu Leu Gly Gly Pro Ser Val Phe Leu Phe Pro Pro
    115                 120                 125

Lys Pro Lys Asp Thr Leu Met Ile Ser Arg Thr Pro Glu Val Thr Cys
130                 135                 140
```

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
        180                 185                 190

His Gln Asp Trp Leu Asn Gly Lys Glu Tyr Lys Cys Lys Val Ser Asn
    195                 200                 205

Lys Ala Leu Pro Ala Pro Ile Ser Lys Thr Ile Ser Lys Ala Lys Gly
210                 215                 220

Gln Pro Arg Arg Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Gly Ala Leu His Asn His Tyr Thr
305                 310                 315                 320

Gln Lys Lys Leu Ser Leu Ser Pro Gly Lys
            325                 330

<210> SEQ ID NO 73
<211> LENGTH: 330
<212> TYPE: PRT
<213> ORGANISM: Artificial sequence
<220> FEATURE:
<223> OTHER INFORMATION: modified Fc region

<400> SEQUENCE: 73

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
            85                  90                  95

Arg Val Glu Pro Lys Ser Cys Asp Lys Thr His Thr Cys Pro Pro Cys
        100                 105                 110

Pro Ala Pro Glu Leu Leu Arg Gly Pro Ser Val Phe Leu Phe Pro Pro
    115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

```
Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Arg Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Glu Ser Leu Ser Leu Ser Pro Gly Lys
                325                 330

<210> SEQ ID NO 74
<211> LENGTH: 330
<212> TYPE: PRT
<213> ORGANISM: Artificial sequence
<220> FEATURE:
<223> OTHER INFORMATION: modified Fc region

<400> SEQUENCE: 74

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Ala Val Ser Asn
        195                 200                 205
```

```
Lys Ala Leu Pro Ala Pro Ile Glu Lys Thr Ile Ser Lys Ala Lys Gly
    210                 215                 220

Gln Pro Arg Arg Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Glu Ser Leu Ser Leu Ser Pro Gly Lys
                325                 330

<210> SEQ ID NO 75
<211> LENGTH: 330
<212> TYPE: PRT
<213> ORGANISM: Artificial sequence
<220> FEATURE:
<223> OTHER INFORMATION: modified Fc region

<400> SEQUENCE: 75

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Arg Gly Pro Ser Val Phe Leu Phe Pro Pro
    115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
    195                 200                 205

Lys Ala Leu Pro Ala Pro Ile Glu Lys Thr Ile Ser Lys Ala Lys Gly
210                 215                 220

Gln Pro Arg Val Pro Gln Val Tyr Thr Leu Pro Pro Ser Arg Glu Glu
225                 230                 235                 240
```

Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
        260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Glu Ser Leu Ser Leu Ser Pro Gly Lys
            325                 330

<210> SEQ ID NO 76
<211> LENGTH: 330
<212> TYPE: PRT
<213> ORGANISM: Artificial sequence
<220> FEATURE:
<223> OTHER INFORMATION: modified Fc region

<400> SEQUENCE: 76

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Ala Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Val Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

```
Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Lys Leu Ser Leu Ser Pro Gly Lys
            325                 330

<210> SEQ ID NO 77
<211> LENGTH: 330
<212> TYPE: PRT
<213> ORGANISM: Artificial sequence
<220> FEATURE:
<223> OTHER INFORMATION: modified Fc region

<400> SEQUENCE: 77

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Arg Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Tyr Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300
```

```
Val Phe Ser Cys Ser Val Met His Glu Ala Leu His Asn His Tyr Thr
305                 310                 315                 320

Gln Glu Ser Leu Ser Leu Ser Pro Gly Lys
            325                 330

<210> SEQ ID NO 78
<211> LENGTH: 330
<212> TYPE: PRT
<213> ORGANISM: Artificial sequence
<220> FEATURE:
<223> OTHER INFORMATION: modified Fc region

<400> SEQUENCE: 78

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Ala Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Tyr Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Lys Leu Ser Leu Ser Pro Gly Lys
                325                 330
```

```
<210> SEQ ID NO 79
<211> LENGTH: 330
<212> TYPE: PRT
<213> ORGANISM: Artificial sequence
<220> FEATURE:
<223> OTHER INFORMATION: modified Fc region

<400> SEQUENCE: 79

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Gly Ala Leu His Asn His Tyr Thr
305                 310                 315                 320

Gln Lys Ser Leu Ser Leu Ser Pro Gly Lys
                325                 330

<210> SEQ ID NO 80
<211> LENGTH: 330
<212> TYPE: PRT
<213> ORGANISM: Artificial sequence
<220> FEATURE:
```

<223> OTHER INFORMATION: modified Fc region

<400> SEQUENCE: 80

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Gly Ala Leu His Asn His Tyr Thr
305                 310                 315                 320

Gln Glu Ser Leu Ser Leu Ser Pro Gly Lys
                325                 330
```

<210> SEQ ID NO 81
<211> LENGTH: 330
<212> TYPE: PRT
<213> ORGANISM: Artificial sequence
<220> FEATURE:
<223> OTHER INFORMATION: modified Fc region

<400> SEQUENCE: 81

```
Ala Ser Thr Lys Gly Pro Ser Val Phe Pro Leu Ala Pro Ser Ser Lys
1               5                   10                  15
```

```
Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                    85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
 130                 135                 140

Val Val Val Asp Val Ser His Lys Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
 290                 295                 300

Val Phe Ser Cys Ser Val Met His Gly Ala Leu His Asn His Tyr Thr
305                 310                 315                 320

Gln Glu Ser Leu Ser Leu Ser Pro Gly Lys
                325                 330
```

<210> SEQ ID NO 82
<211> LENGTH: 330
<212> TYPE: PRT
<213> ORGANISM: Artificial sequence
<220> FEATURE:
<223> OTHER INFORMATION: modified Fc region

<400> SEQUENCE: 82

```
Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45
```

Gly Val His Thr Phe Pro Ala Val Leu Gln Ser Ser Gly Leu Tyr Ser
            50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Ser Lys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Gly Ala Leu His Asn His Tyr Thr
305                 310                 315                 320

Gln Glu Ser Leu Ser Leu Ser Pro Gly Lys
                325                 330

<210> SEQ ID NO 83
<211> LENGTH: 330
<212> TYPE: PRT
<213> ORGANISM: Artificial sequence
<220> FEATURE:
<223> OTHER INFORMATION: modified Fc region

<400> SEQUENCE: 83

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Lys Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Gly Ala Leu His Asn His Tyr Thr
305                 310                 315                 320

Gln Glu Ser Leu Ser Leu Ser Pro Gly Lys
                325                 330

<210> SEQ ID NO 84
<211> LENGTH: 330
<212> TYPE: PRT
<213> ORGANISM: Artificial sequence
<220> FEATURE:
<223> OTHER INFORMATION: modified Fc region

<400> SEQUENCE: 84

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

```
Pro Ala Pro Glu Leu Leu Arg Gly Pro Ser Val Phe Leu Phe Pro Pro
            115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
    290                 295                 300

Val Phe Ser Cys Ser Val Met His Gly Ala Leu His Asn His Tyr Thr
305                 310                 315                 320

Gln Glu Ser Leu Ser Leu Ser Pro Gly Lys
                325                 330

<210> SEQ ID NO 85
<211> LENGTH: 330
<212> TYPE: PRT
<213> ORGANISM: Artificial sequence
<220> FEATURE:
<223> OTHER INFORMATION: modified Fc region

<400> SEQUENCE: 85

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Ala Pro Ser Val Phe Leu Phe Pro Pro
            115                 120                 125

Lys Pro Lys Asp Thr Leu Met Ile Ser Arg Thr Pro Glu Val Thr Cys
    130                 135                 140
```

```
Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Gly Ala Leu His Asn His Tyr Thr
305                 310                 315                 320

Gln Glu Ser Leu Ser Leu Ser Pro Gly Lys
                325                 330

<210> SEQ ID NO 86
<211> LENGTH: 330
<212> TYPE: PRT
<213> ORGANISM: Artificial sequence
<220> FEATURE:
<223> OTHER INFORMATION: modified Fc region

<400> SEQUENCE: 86

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Ala Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175
```

```
Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Ala Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Gly Ala Leu His Asn His Tyr Thr
305                 310                 315                 320

Gln Glu Ser Leu Ser Leu Ser Pro Gly Lys
                325                 330

<210> SEQ ID NO 87
<211> LENGTH: 330
<212> TYPE: PRT
<213> ORGANISM: Artificial sequence
<220> FEATURE:
<223> OTHER INFORMATION: modified Fc region

<400> SEQUENCE: 87

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gln Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205
```

```
Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Gly Ala Leu His Asn His Tyr Thr
305                 310                 315                 320

Gln Glu Ser Leu Ser Leu Ser Pro Gly Lys
            325                 330

<210> SEQ ID NO 88
<211> LENGTH: 330
<212> TYPE: PRT
<213> ORGANISM: Artificial sequence
<220> FEATURE:
<223> OTHER INFORMATION: modified Fc region

<400> SEQUENCE: 88

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Arg Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240
```

Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Gly Ala Leu His Asn His Tyr Thr
305                 310                 315                 320

Gln Glu Ser Leu Ser Leu Ser Pro Gly Lys
            325                 330

<210> SEQ ID NO 89
<211> LENGTH: 330
<212> TYPE: PRT
<213> ORGANISM: Artificial sequence
<220> FEATURE:
<223> OTHER INFORMATION: modified Fc region

<400> SEQUENCE: 89

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Thr Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

```
Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Gly Ala Leu His Asn His Tyr Thr
305                 310                 315                 320

Gln Glu Ser Leu Ser Leu Ser Pro Gly Lys
                325                 330

<210> SEQ ID NO 90
<211> LENGTH: 330
<212> TYPE: PRT
<213> ORGANISM: Artificial sequence
<220> FEATURE:
<223> OTHER INFORMATION: modified Fc region

<400> SEQUENCE: 90

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Ala Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300
```

Val Phe Ser Cys Ser Val Met His Gly Ala Leu His Asn His Tyr Thr
305                 310                 315                 320

Gln Glu Ser Leu Ser Leu Ser Pro Gly Lys
                325                 330

<210> SEQ ID NO 91
<211> LENGTH: 330
<212> TYPE: PRT
<213> ORGANISM: Artificial sequence
<220> FEATURE:
<223> OTHER INFORMATION: modified Fc region

<400> SEQUENCE: 91

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Glu Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Gly Ala Leu His Asn His Tyr Thr
305                 310                 315                 320

Gln Glu Ser Leu Ser Leu Ser Pro Gly Lys
                325                 330

```
<210> SEQ ID NO 92
<211> LENGTH: 330
<212> TYPE: PRT
<213> ORGANISM: Artificial sequence
<220> FEATURE:
<223> OTHER INFORMATION: modified Fc region

<400> SEQUENCE: 92

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Ala Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Gly Ala Leu His Asn His Tyr Thr
305                 310                 315                 320

Gln Glu Ser Leu Ser Leu Ser Pro Gly Lys
                325                 330

<210> SEQ ID NO 93
<211> LENGTH: 330
<212> TYPE: PRT
<213> ORGANISM: Artificial sequence
```

```
<220> FEATURE:
<223> OTHER INFORMATION: modified Fc region

<400> SEQUENCE: 93

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Gly Ala Leu His Asn His Tyr Thr
305                 310                 315                 320

Gln Glu Ser Leu Ser Leu Ser Pro Gly Lys
                325                 330

<210> SEQ ID NO 94
<211> LENGTH: 330
<212> TYPE: PRT
<213> ORGANISM: Artificial sequence
<220> FEATURE:
<223> OTHER INFORMATION: modified Fc region

<400> SEQUENCE: 94

Ala Ser Thr Lys Gly Pro Ser Val Phe Pro Leu Ala Pro Ser Ser Lys
```

```
             1               5                  10                 15
           Ser Thr Ser Gly Gly Thr Ala Ala Leu Gly Cys Leu Val Lys Asp Tyr
                           20                 25                 30

Phe Pro Glu Pro Val Thr Val Ser Trp Asn Ser Gly Ala Leu Thr Ser
                           35                 40                 45

Gly Val His Thr Phe Pro Ala Val Leu Gln Ser Ser Gly Leu Tyr Ser
                   50                 55                 60

Leu Ser Ser Val Val Thr Val Pro Ser Ser Leu Gly Thr Gln Thr
            65                 70                 75                 80

Tyr Ile Cys Asn Val Asn His Lys Pro Ser Asn Thr Lys Val Asp Lys
                           85                 90                 95

Arg Val Glu Pro Lys Ser Cys Asp Lys Thr His Thr Cys Pro Pro Cys
                          100                105                110

Pro Ala Pro Glu Phe Leu Gly Gly Pro Ser Val Phe Leu Phe Pro Pro
                          115                120                125

Lys Pro Lys Asp Thr Leu Met Ile Ser Arg Thr Pro Glu Val Thr Cys
            130                135                140

Val Val Val Asp Val Ser His Glu Asp Pro Glu Val Lys Phe Asn Trp
            145                150                155                160

Tyr Val Asp Gly Val Glu Val His Asn Ala Lys Thr Lys Pro Arg Glu
                          165                170                175

Glu Gln Tyr Asn Ser Thr Tyr Arg Val Val Ser Val Leu Thr Val Leu
                          180                185                190

His Gln Asp Trp Leu Asn Gly Lys Glu Tyr Lys Cys Lys Val Ser Asn
                          195                200                205

Lys Ala Leu Pro Ala Pro Ile Glu Lys Thr Ile Ser Lys Ala Lys Gly
            210                215                220

Gln Pro Arg Glu Pro Gln Val Tyr Thr Leu Pro Pro Ser Arg Glu Glu
            225                230                235                240

Met Thr Lys Asn Gln Val Ser Leu Thr Cys Leu Val Lys Gly Phe Tyr
                          245                250                255

Pro Ser Asp Ile Ala Val Glu Trp Glu Ser Asn Gly Gln Pro Glu Asn
                          260                265                270

Asn Tyr Lys Thr Thr Pro Pro Val Leu Asp Ser Asp Gly Ser Phe Phe
                          275                280                285

Leu Tyr Ser Lys Leu Thr Val Asp Lys Ser Arg Trp Gln Gln Gly Asn
                          290                295                300

Val Phe Ser Cys Ser Val Met His Gly Ala Leu His Asn His Tyr Thr
            305                310                315                320

Gln Glu Ser Leu Ser Leu Ser Pro Gly Lys
                          325                330

<210> SEQ ID NO 95
<211> LENGTH: 330
<212> TYPE: PRT
<213> ORGANISM: Artificial sequence
<220> FEATURE:
<223> OTHER INFORMATION: modified Fc region

<400> SEQUENCE: 95

Ala Ser Thr Lys Gly Pro Ser Val Phe Pro Leu Ala Pro Ser Ser Lys
            1               5                  10                 15

Ser Thr Ser Gly Gly Thr Ala Ala Leu Gly Cys Leu Val Lys Asp Tyr
                           20                 25                 30

Phe Pro Glu Pro Val Thr Val Ser Trp Asn Ser Gly Ala Leu Thr Ser
```

```
            35                  40                  45
Gly Val His Thr Phe Pro Ala Val Leu Gln Ser Ser Gly Leu Tyr Ser
         50                  55                  60
Leu Ser Ser Val Val Thr Val Pro Ser Ser Ser Leu Gly Thr Gln Thr
 65                  70                  75                  80
Tyr Ile Cys Asn Val Asn His Lys Pro Ser Asn Thr Lys Val Asp Lys
                 85                  90                  95
Arg Val Glu Pro Lys Ser Cys Asp Lys Thr His Thr Cys Pro Pro Cys
            100                 105                 110
Pro Ala Pro Glu Phe Glu Gly Gly Pro Ser Val Phe Leu Phe Pro Pro
        115                 120                 125
Lys Pro Lys Asp Thr Leu Met Ile Ser Arg Thr Pro Glu Val Thr Cys
    130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
    210                 215                 220
Gln Pro Arg Glu Pro Gln Val Tyr Thr Leu Pro Pro Ser Arg Glu Glu
225                 230                 235                 240
Met Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
    290                 295                 300
Val Phe Ser Cys Ser Val Met His Gly Ala Leu His Asn His Tyr Thr
305                 310                 315                 320
Gln Glu Ser Leu Ser Leu Ser Pro Gly Lys
                325                 330

<210> SEQ ID NO 96
<211> LENGTH: 330
<212> TYPE: PRT
<213> ORGANISM: Artificial sequence
<220> FEATURE:
<223> OTHER INFORMATION: modified Fc region

<400> SEQUENCE: 96

Ala Ser Thr Lys Gly Pro Ser Val Phe Pro Leu Ala Pro Ser Ser Lys
 1               5                  10                  15
Ser Thr Ser Gly Gly Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Ser Leu Gly Thr Gln Thr
```

```
                65                  70                  75                  80
Tyr Ile Cys Asn Val Asn His Lys Pro Ser Asn Thr Lys Val Asp Lys
                    85                  90                  95
Arg Val Glu Pro Lys Ser Cys Asp Lys Thr His Thr Cys Pro Pro Cys
                100                 105                 110
Pro Ala Pro Glu Leu Ala Gly Gly Pro Ser Val Phe Leu Phe Pro Pro
                115                 120                 125
Lys Pro Lys Asp Thr Leu Met Ile Ser Arg Thr Pro Glu Val Thr Cys
130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
                180                 185                 190
His Gln Asp Trp Leu Asn Gly Lys Glu Tyr Lys Cys Lys Val Ser Asn
                195                 200                 205
Lys Ala Leu Pro Ala Pro Ile Glu Lys Thr Ile Ser Lys Ala Lys Gly
                210                 215                 220
Gln Pro Arg Glu Pro Gln Val Tyr Thr Leu Pro Pro Ser Arg Glu Glu
225                 230                 235                 240
Met Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
                260                 265                 270
Asn Tyr Lys Thr Thr Pro Pro Val Leu Asp Ser Asp Gly Ser Phe Phe
                275                 280                 285
Leu Tyr Ser Lys Leu Thr Val Asp Lys Ser Arg Trp Gln Gln Gly Asn
                290                 295                 300
Val Phe Ser Cys Ser Val Met His Gly Ala Leu His Asn His Tyr Thr
305                 310                 315                 320
Gln Glu Ser Leu Ser Leu Ser Pro Gly Lys
                325                 330

<210> SEQ ID NO 97
<211> LENGTH: 330
<212> TYPE: PRT
<213> ORGANISM: Artificial sequence
<220> FEATURE:
<223> OTHER INFORMATION: modified Fc region

<400> SEQUENCE: 97

Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
                20                  25                  30
Phe Pro Glu Pro Val Thr Val Ser Trp Asn Ser Gly Ala Leu Thr Ser
                35                  40                  45
Gly Val His Thr Phe Pro Ala Val Leu Gln Ser Ser Gly Leu Tyr Ser
                50                  55                  60
Leu Ser Ser Val Val Thr Val Pro Ser Ser Leu Gly Thr Gln Thr
65                  70                  75                  80
Tyr Ile Cys Asn Val Asn His Lys Pro Ser Asn Thr Lys Val Asp Lys
                85                  90                  95
Arg Val Glu Pro Lys Ser Cys Asp Lys Thr His Thr Cys Pro Pro Cys
```

```
            100                 105                 110
Pro Ala Pro Glu Leu Glu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
                195                 200                 205

Lys Ala Leu Pro Ala Pro Ile Glu Lys Thr Ile Ser Lys Ala Lys Gly
                210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
                290                 295                 300

Val Phe Ser Cys Ser Val Met His Gly Ala Leu His Asn His Tyr Thr
305                 310                 315                 320

Gln Glu Ser Leu Ser Leu Ser Pro Gly Lys
                325                 330

<210> SEQ ID NO 98
<211> LENGTH: 330
<212> TYPE: PRT
<213> ORGANISM: Artificial sequence
<220> FEATURE:
<223> OTHER INFORMATION: modified Fc region

<400> SEQUENCE: 98

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
                100                 105                 110

Pro Ala Pro Glu Leu Gln Gly Gly Pro Ser Val Phe Leu Phe Pro Pro
            115                 120                 125

Lys Pro Lys Asp Thr Leu Met Ile Ser Arg Thr Pro Glu Val Thr Cys
```

```
                    130                 135                 140
Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                    180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Gly Ala Leu His Asn His Tyr Thr
305                 310                 315                 320

Gln Glu Ser Leu Ser Leu Ser Pro Gly Lys
                325                 330

<210> SEQ ID NO 99
<211> LENGTH: 330
<212> TYPE: PRT
<213> ORGANISM: Artificial sequence
<220> FEATURE:
<223> OTHER INFORMATION: modified Fc region

<400> SEQUENCE: 99

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
```

```
                 165                 170                 175
Glu Gln Tyr Gln Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Gly Ala Leu His Asn His Tyr Thr
305                 310                 315                 320

Gln Glu Ser Leu Ser Leu Ser Pro Gly Lys
                325                 330

<210> SEQ ID NO 100
<211> LENGTH: 330
<212> TYPE: PRT
<213> ORGANISM: Artificial sequence
<220> FEATURE:
<223> OTHER INFORMATION: modified Fc region

<400> SEQUENCE: 100

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
```

195                 200                 205
Lys Ala Leu Arg Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
        290                 295                 300

Val Phe Ser Cys Ser Val Met His Gly Ala Leu His Asn His Tyr Thr
305                 310                 315                 320

Gln Glu Ser Leu Ser Leu Ser Pro Gly Lys
                325                 330

<210> SEQ ID NO 101
<211> LENGTH: 330
<212> TYPE: PRT
<213> ORGANISM: Artificial sequence
<220> FEATURE:
<223> OTHER INFORMATION: modified Fc region

<400> SEQUENCE: 101

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu

```
                    225                 230                 235                 240
Met Thr Lys Asn Gln Val Ser Leu Thr Cys Leu Val Lys Gly Phe Tyr
                    245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Gly Ala Leu His Asn His Tyr Thr
305                 310                 315                 320

Gln Lys Lys Leu Ser Leu Ser Pro Gly Lys
                325                 330

<210> SEQ ID NO 102
<211> LENGTH: 330
<212> TYPE: PRT
<213> ORGANISM: Artificial sequence
<220> FEATURE:
<223> OTHER INFORMATION: modified Fc region

<400> SEQUENCE: 102

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Ala Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
```

```
            260                 265                 270
Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
        290                 295                 300

Val Phe Ser Cys Ser Val Met His Gly Ala Leu His Asn His Tyr Thr
305                 310                 315                 320

Gln Lys Lys Leu Ser Leu Ser Pro Gly Lys
            325                 330

<210> SEQ ID NO 103
<211> LENGTH: 330
<212> TYPE: PRT
<213> ORGANISM: Artificial sequence
<220> FEATURE:
<223> OTHER INFORMATION: modified Fc region

<400> SEQUENCE: 103

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Ser Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
```

```
                    290                 295                 300

Val Phe Ser Cys Ser Val Met His Gly Ala Leu His Asn His Tyr Thr
305                 310                 315                 320

Gln Lys Lys Leu Ser Leu Ser Pro Gly Lys
                325                 330

<210> SEQ ID NO 104
<211> LENGTH: 330
<212> TYPE: PRT
<213> ORGANISM: Artificial sequence
<220> FEATURE:
<223> OTHER INFORMATION: modified Fc region

<400> SEQUENCE: 104

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Arg Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
        290                 295                 300

Val Phe Ser Cys Ser Val Met His Gly Ala Leu His Asn His Tyr Thr
305                 310                 315                 320

Gln Lys Lys Leu Ser Leu Ser Pro Gly Lys
                325                 330
```

325                 330

<210> SEQ ID NO 105
<211> LENGTH: 330
<212> TYPE: PRT
<213> ORGANISM: Artificial sequence
<220> FEATURE:
<223> OTHER INFORMATION: modified Fc region

<400> SEQUENCE: 105

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Ala Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Gly Ala Leu His Asn His Tyr Thr
305                 310                 315                 320

Gln Lys Lys Leu Ser Leu Ser Pro Gly Lys
                325                 330

<210> SEQ ID NO 106
<211> LENGTH: 330
<212> TYPE: PRT

<213> ORGANISM: Artificial sequence
<220> FEATURE:
<223> OTHER INFORMATION: modified Fc region

<400> SEQUENCE: 106

```
Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Ser Leu Gly Thr Gln Thr
65                  70                  75                  80
Tyr Ile Cys Asn Val Asn His Lys Pro Ser Asn Thr Lys Val Asp Lys
                85                  90                  95
Arg Val Glu Pro Lys Ser Cys Asp Lys Thr His Thr Cys Pro Pro Cys
            100                 105                 110
Pro Ala Pro Glu Leu Leu Gly Ala Pro Ser Val Phe Leu Phe Pro Pro
        115                 120                 125
Lys Pro Lys Asp Thr Leu Met Ile Ser Arg Thr Pro Glu Val Thr Cys
    130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Ser Lys Thr Ile Ser Lys Ala Lys Gly
    210                 215                 220
Gln Pro Arg Glu Pro Gln Val Tyr Thr Leu Pro Pro Ser Arg Glu Glu
225                 230                 235                 240
Met Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
    290                 295                 300
Val Phe Ser Cys Ser Val Met His Gly Ala Leu His Asn His Tyr Thr
305                 310                 315                 320
Gln Lys Lys Leu Ser Leu Ser Pro Gly Lys
                325                 330
```

<210> SEQ ID NO 107
<211> LENGTH: 330
<212> TYPE: PRT
<213> ORGANISM: Artificial sequence
<220> FEATURE:
<223> OTHER INFORMATION: modified Fc region

<400> SEQUENCE: 107

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gln Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
        290                 295                 300

Val Phe Ser Cys Ser Val Met His Gly Ala Leu His Asn His Tyr Thr
305                 310                 315                 320

Gln Lys Lys Leu Ser Leu Ser Pro Gly Lys
                325                 330

<210> SEQ ID NO 108
<211> LENGTH: 330
<212> TYPE: PRT
<213> ORGANISM: Artificial sequence
<220> FEATURE:
<223> OTHER INFORMATION: modified Fc region

<400> SEQUENCE: 108

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

```
Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Arg Val Glu Pro Lys Ser Cys Asp Lys Thr His Thr Cys Pro Pro Cys
            100                 105                 110

Pro Ala Pro Glu Leu Leu Gly Arg Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Gly Ala Leu His Asn His Tyr Thr
305                 310                 315                 320

Gln Lys Lys Leu Ser Leu Ser Pro Gly Lys
                325                 330

<210> SEQ ID NO 109
<211> LENGTH: 330
<212> TYPE: PRT
<213> ORGANISM: Artificial sequence
<220> FEATURE:
<223> OTHER INFORMATION: modified Fc region

<400> SEQUENCE: 109

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
 50                  55                  60
```

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Glu Val Ser Asn
            195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Gly Ala Leu His Asn His Tyr Thr
305                 310                 315                 320

Gln Lys Lys Leu Ser Leu Ser Pro Gly Lys
                325                 330

<210> SEQ ID NO 110
<211> LENGTH: 330
<212> TYPE: PRT
<213> ORGANISM: Artificial sequence
<220> FEATURE:
<223> OTHER INFORMATION: modified Fc region

<400> SEQUENCE: 110

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
             100                 105                 110

Pro Ala Pro Glu Leu Leu Gly Gly Pro Ser Val Phe Leu Phe Pro Pro
             115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
             165                 170                 175

Glu Gln Tyr Asn Ser Thr Tyr Arg Val Val Ser Val Leu Thr Val Leu
             180                 185                 190

His Gln Asp Trp Leu Asn Gly Lys Glu Tyr Lys Cys Lys Val Ser Asn
             195                 200                 205

Ala Ala Leu Pro Ala Pro Ile Glu Lys Thr Ile Ser Lys Ala Lys Gly
             210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
             245                 250                 255

Pro Ser Asp Ile Ala Val Glu Trp Glu Ser Asn Gly Gln Pro Glu Asn
             260                 265                 270

Asn Tyr Lys Thr Thr Pro Pro Val Leu Asp Ser Asp Gly Ser Phe Phe
             275                 280                 285

Leu Tyr Ser Lys Leu Thr Val Asp Lys Ser Arg Trp Gln Gln Gly Asn
             290                 295                 300

Val Phe Ser Cys Ser Val Met His Gly Ala Leu His Asn His Tyr Thr
305                 310                 315                 320

Gln Lys Lys Leu Ser Leu Ser Pro Gly Lys
             325                 330

<210> SEQ ID NO 111
<211> LENGTH: 330
<212> TYPE: PRT
<213> ORGANISM: Artificial sequence
<220> FEATURE:
<223> OTHER INFORMATION: modified Fc region

<400> SEQUENCE: 111

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
             50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
             85                  90                  95

Arg Val Glu Pro Lys Ser Cys Asp Lys Thr His Thr Cys Pro Pro Cys
             100                 105                 110

Pro Ala Pro Glu Leu Leu Gly Gly Pro Ser Val Phe Leu Phe Pro Pro
             115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
        180                 185                 190

His Gln Asp Trp Leu Asn Gly Lys Glu Tyr Lys Cys Lys Val Ser Asn
    195                 200                 205

Ala Ala Leu Pro Ala Pro Ile Ala Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
        260                 265                 270

Asn Tyr Lys Thr Thr Pro Pro Val Leu Asp Ser Asp Gly Ser Phe Phe
    275                 280                 285

Leu Tyr Ser Lys Leu Thr Val Asp Lys Ser Arg Trp Gln Gln Gly Asn
290                 295                 300

Val Phe Ser Cys Ser Val Met His Gly Ala Leu His Asn His Tyr Thr
305                 310                 315                 320

Gln Lys Lys Leu Ser Leu Ser Pro Gly Lys
            325                 330

<210> SEQ ID NO 112
<211> LENGTH: 330
<212> TYPE: PRT
<213> ORGANISM: Artificial sequence
<220> FEATURE:
<223> OTHER INFORMATION: modified Fc region

<400> SEQUENCE: 112

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
            85                  90                  95

Arg Val Glu Pro Lys Ser Cys Asp Lys Thr His Thr Cys Pro Pro Cys
        100                 105                 110

Pro Ala Pro Glu Leu Leu Gly Gly Pro Ser Val Phe Leu Phe Pro Pro
    115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

```
Tyr Val Asp Gly Val Glu Val His Asn Ala Lys Thr Lys Pro Arg Glu
            165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
            195                 200                 205
Trp Ala Leu Pro Ala Pro Ile Glu Lys Thr Ile Ser Lys Ala Lys Gly
210                 215                 220
Gln Pro Arg Glu Pro Gln Val Tyr Thr Leu Pro Pro Ser Arg Glu Glu
225                 230                 235                 240
Met Thr Lys Asn Gln Val Ser Leu Thr Cys Leu Val Lys Gly Phe Tyr
            245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
            275                 280                 285
Leu Tyr Ser Lys Leu Thr Val Asp Lys Ser Arg Trp Gln Gln Gly Asn
            290                 295                 300
Val Phe Ser Cys Ser Val Met His Gly Ala Leu His Asn His Tyr Thr
305                 310                 315                 320
Gln Lys Lys Leu Ser Leu Ser Pro Gly Lys
            325                 330

<210> SEQ ID NO 113
<211> LENGTH: 330
<212> TYPE: PRT
<213> ORGANISM: Artificial sequence
<220> FEATURE:
<223> OTHER INFORMATION: modified Fc region

<400> SEQUENCE: 113

Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
            35                  40                  45
Gly Val His Thr Phe Pro Ala Val Leu Gln Ser Ser Gly Leu Tyr Ser
50                  55                  60
Leu Ser Ser Val Val Thr Val Pro Ser Ser Leu Gly Thr Gln Thr
65                  70                  75                  80
Tyr Ile Cys Asn Val Asn His Lys Pro Ser Asn Thr Lys Val Asp Lys
            85                  90                  95
Arg Val Glu Pro Lys Ser Cys Asp Lys Thr His Thr Cys Pro Pro Cys
            100                 105                 110
Pro Ala Pro Glu Leu Leu Gly Gly Pro Ser Val Phe Leu Phe Pro Pro
            115                 120                 125
Lys Pro Lys Asp Thr Leu Met Ile Ser Arg Thr Pro Glu Val Thr Cys
130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
            165                 170                 175
Glu Gln Tyr Asn Ser Thr Tyr Arg Val Val Ser Val Leu Thr Val Leu
            180                 185                 190
```

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Gly Ala Leu His Asn His Tyr Thr
305                 310                 315                 320

Gln Lys Lys Leu Ser Leu Ser Pro Gly Lys
                325                 330

<210> SEQ ID NO 114
<211> LENGTH: 330
<212> TYPE: PRT
<213> ORGANISM: Artificial sequence
<220> FEATURE:
<223> OTHER INFORMATION: modified Fc region

<400> SEQUENCE: 114

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Arg Ala Pro Ile Glu Lys Thr Ile Ser Lys Ala Lys Gly
    210                 215                 220

```
Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Gly Ala Leu His Asn His Tyr Thr
305                 310                 315                 320

Gln Lys Lys Leu Ser Leu Ser Pro Gly Lys
            325                 330

<210> SEQ ID NO 115
<211> LENGTH: 330
<212> TYPE: PRT
<213> ORGANISM: Artificial sequence
<220> FEATURE:
<223> OTHER INFORMATION: modified Fc region

<400> SEQUENCE: 115

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
            85                  90                  95

Arg Val Glu Pro Lys Ser Cys Asp Lys Thr His Thr Cys Pro Pro Cys
        100                 105                 110

Pro Ala Pro Glu Leu Leu Arg Gly Pro Ser Val Phe Leu Phe Pro Pro
    115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
        180                 185                 190

His Gln Asp Trp Leu Asn Gly Lys Glu Tyr Lys Cys Lys Val Ser Asn
    195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
            245                 250                 255
```

```
Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Asn Ala Leu His Asn His Tyr Thr
305                 310                 315                 320

Gln Glu Ser Leu Ser Leu Ser Pro Gly Lys
                325                 330

<210> SEQ ID NO 116
<211> LENGTH: 330
<212> TYPE: PRT
<213> ORGANISM: Artificial sequence
<220> FEATURE:
<223> OTHER INFORMATION: modified Fc region

<400> SEQUENCE: 116

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Ala Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285
```

Leu Tyr Ser Lys Leu Thr Val Asp Lys Ser Arg Trp Gln Gln Gly Asn
290                 295                 300

Val Phe Ser Cys Ser Val Met His Asn Ala Leu His Asn His Tyr Thr
305                 310                 315                 320

Gln Lys Lys Leu Ser Leu Ser Pro Gly Lys
                325                 330

<210> SEQ ID NO 117
<211> LENGTH: 330
<212> TYPE: PRT
<213> ORGANISM: Artificial sequence
<220> FEATURE:
<223> OTHER INFORMATION: modified Fc region

<400> SEQUENCE: 117

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Arg Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Thr Ala Leu His Asn His Tyr Thr
305                 310                 315                 320

Gln Glu Ser Leu Ser Leu Ser Pro Gly Lys
            325                 330

<210> SEQ ID NO 118
<211> LENGTH: 330
<212> TYPE: PRT
<213> ORGANISM: Artificial sequence
<220> FEATURE:
<223> OTHER INFORMATION: modified Fc region

<400> SEQUENCE: 118

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Ala Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Thr Ala Leu His Asn His Tyr Thr
305                 310                 315                 320

Gln Lys Lys Leu Ser Leu Ser Pro Gly Lys
                325                 330

<210> SEQ ID NO 119
<211> LENGTH: 330

```
<212> TYPE: PRT
<213> ORGANISM: Artificial sequence
<220> FEATURE:
<223> OTHER INFORMATION: modified Fc region

<400> SEQUENCE: 119

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Arg Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Val Ala Leu His Asn His Tyr Thr
305                 310                 315                 320

Gln Glu Ser Leu Ser Leu Ser Pro Gly Lys
                325                 330

<210> SEQ ID NO 120
<211> LENGTH: 330
<212> TYPE: PRT
<213> ORGANISM: Artificial sequence
<220> FEATURE:
<223> OTHER INFORMATION: modified Fc region

<400> SEQUENCE: 120
```

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Ala Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Val Ala Leu His Asn His Tyr Thr
305                 310                 315                 320

Gln Lys Lys Leu Ser Leu Ser Pro Gly Lys
                325                 330

<210> SEQ ID NO 121
<211> LENGTH: 330
<212> TYPE: PRT
<213> ORGANISM: Artificial sequence
<220> FEATURE:
<223> OTHER INFORMATION: modified Fc region

<400> SEQUENCE: 121

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
         50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                 85                  90                  95

Arg Val Glu Pro Lys Ser Cys Asp Lys Thr His Thr Cys Pro Pro Cys
            100                 105                 110

Pro Ala Pro Glu Leu Leu Arg Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Tyr Ala Leu His Asn His Tyr Thr
305                 310                 315                 320

Gln Glu Ser Leu Ser Leu Ser Pro Gly Lys
            325                 330

<210> SEQ ID NO 122
<211> LENGTH: 330
<212> TYPE: PRT
<213> ORGANISM: Artificial sequence
<220> FEATURE:
<223> OTHER INFORMATION: modified Fc region

<400> SEQUENCE: 122

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
         50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Ala Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Tyr Ala Leu His Asn His Tyr Thr
305                 310                 315                 320

Gln Lys Lys Leu Ser Leu Ser Pro Gly Lys
                325                 330

<210> SEQ ID NO 123
<211> LENGTH: 330
<212> TYPE: PRT
<213> ORGANISM: Artificial sequence
<220> FEATURE:
<223> OTHER INFORMATION: modified Fc region

<400> SEQUENCE: 123

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

```
Arg Val Glu Pro Lys Ser Cys Asp Lys Thr His Thr Cys Pro Pro Cys
            100                 105                 110

Pro Ala Pro Glu Leu Leu Arg Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
    290                 295                 300

Val Phe Ser Cys Ser Val Met His Gly Ala Leu His Asn His Tyr Thr
305                 310                 315                 320

Gln Lys Ser Leu Ser Leu Ser Pro Gly Lys
                325                 330

<210> SEQ ID NO 124
<211> LENGTH: 330
<212> TYPE: PRT
<213> ORGANISM: Artificial sequence
<220> FEATURE:
<223> OTHER INFORMATION: modified Fc region

<400> SEQUENCE: 124

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Ala Pro Ser Val Phe Leu Phe Pro Pro
            115                 120                 125
```

```
Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Gly Ala Leu His Asn His Tyr Thr
305                 310                 315                 320

Gln Lys Ser Leu Ser Leu Ser Pro Gly Lys
                325                 330

<210> SEQ ID NO 125
<211> LENGTH: 330
<212> TYPE: PRT
<213> ORGANISM: Artificial sequence
<220> FEATURE:
<223> OTHER INFORMATION: modified Fc region

<400> SEQUENCE: 125

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gln Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160
```

```
Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Gly Ala Leu His Asn His Tyr Thr
305                 310                 315                 320

Gln Lys Ser Leu Ser Leu Ser Pro Gly Lys
                325                 330

<210> SEQ ID NO 126
<211> LENGTH: 330
<212> TYPE: PRT
<213> ORGANISM: Artificial sequence
<220> FEATURE:
<223> OTHER INFORMATION: modified Fc region

<400> SEQUENCE: 126

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Arg Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190
```

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Gly Ala Leu His Asn His Tyr Thr
305                 310                 315                 320

Gln Lys Ser Leu Ser Leu Ser Pro Gly Lys
                325                 330

<210> SEQ ID NO 127
<211> LENGTH: 330
<212> TYPE: PRT
<213> ORGANISM: Artificial sequence
<220> FEATURE:
<223> OTHER INFORMATION: modified Fc region

<400> SEQUENCE: 127

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Thr Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

```
Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
        260                 265                 270

Asn Tyr Lys Thr Thr Pro Pro Val Leu Asp Ser Asp Gly Ser Phe Phe
    275                 280                 285

Leu Tyr Ser Lys Leu Thr Val Asp Lys Ser Arg Trp Gln Gln Gly Asn
290                 295                 300

Val Phe Ser Cys Ser Val Met His Gly Ala Leu His Asn His Tyr Thr
305                 310                 315                 320

Gln Lys Ser Leu Ser Leu Ser Pro Gly Lys
            325                 330

<210> SEQ ID NO 128
<211> LENGTH: 330
<212> TYPE: PRT
<213> ORGANISM: Artificial sequence
<220> FEATURE:
<223> OTHER INFORMATION: modified Fc region

<400> SEQUENCE: 128

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Arg Gly Pro Ser Val Phe Leu Phe Pro Pro
        115                 120                 125

Lys Pro Glu Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
            245                 250                 255
```

```
Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Arg
305                 310                 315                 320

Gln Glu Ser Leu Ser Leu Ser Pro Gly Lys
                325                 330

<210> SEQ ID NO 129
<211> LENGTH: 330
<212> TYPE: PRT
<213> ORGANISM: Artificial sequence
<220> FEATURE:
<223> OTHER INFORMATION: modified Fc region

<400> SEQUENCE: 129

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gln Pro Ser Val Phe Leu Phe Pro Pro
        115                 120                 125

Lys Pro Glu Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285
```

```
Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Arg
305                 310                 315                 320

Gln Glu Ser Leu Ser Leu Ser Pro Gly Lys
                325                 330

<210> SEQ ID NO 130
<211> LENGTH: 330
<212> TYPE: PRT
<213> ORGANISM: Artificial sequence
<220> FEATURE:
<223> OTHER INFORMATION: modified Fc region

<400> SEQUENCE: 130

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Glu Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Ser Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Arg
305                 310                 315                 320
```

Gln Lys Lys Leu Ser Leu Ser Pro Gly Lys
                325                 330

<210> SEQ ID NO 131
<211> LENGTH: 330
<212> TYPE: PRT
<213> ORGANISM: Artificial sequence
<220> FEATURE:
<223> OTHER INFORMATION: modified Fc region

<400> SEQUENCE: 131

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Ala Pro Ser Val Phe Leu Phe Pro Pro
        115                 120                 125

Lys Pro Glu Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Arg
305                 310                 315                 320

Gln Lys Lys Leu Ser Leu Ser Pro Gly Lys
                325                 330

<210> SEQ ID NO 132

```
<211> LENGTH: 330
<212> TYPE: PRT
<213> ORGANISM: Artificial sequence
<220> FEATURE:
<223> OTHER INFORMATION: modified Fc region

<400> SEQUENCE: 132

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Glu Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Gly Ala Leu His Asn His Tyr Thr
305                 310                 315                 320

Gln Lys Ser Leu Ser Leu Ser Pro Gly Lys
                325                 330

<210> SEQ ID NO 133
<211> LENGTH: 330
<212> TYPE: PRT
<213> ORGANISM: Artificial sequence
<220> FEATURE:
<223> OTHER INFORMATION: modified Fc region
```

<400> SEQUENCE: 133

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Arg Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Gly Ala Leu His Asn His Tyr Thr
305                 310                 315                 320

Gln Lys Ser Leu Ser Leu Ser Pro Gly Lys
                325                 330
```

<210> SEQ ID NO 134
<211> LENGTH: 326
<212> TYPE: PRT
<213> ORGANISM: Artificial sequence
<220> FEATURE:
<223> OTHER INFORMATION: modified Fc region

<400> SEQUENCE: 134

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
```

```
                    20                  25                  30
Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
            130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
            195                 200                 205

Ala Pro Ile Glu Lys Thr Ile Ser Lys Thr Lys Gly Gln Pro Arg Glu
            210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
            290                 295                 300

Ser Val Met His Gly Ala Leu His Asn His Tyr Thr Gln Lys Ser Leu
305                 310                 315                 320

Ser Leu Ser Pro Gly Lys
                325

<210> SEQ ID NO 135
<211> LENGTH: 326
<212> TYPE: PRT
<213> ORGANISM: Artificial sequence
<220> FEATURE:
<223> OTHER INFORMATION: modified Fc region

<400> SEQUENCE: 135

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
```

```
                    50                  55                  60
Leu Ser Ser Val Val Thr Val Pro Ser Ser Asn Phe Gly Thr Gln Thr
 65                  70                  75                  80

Tyr Thr Cys Asn Val Asp His Lys Pro Ser Asn Thr Lys Val Asp Lys
                 85                  90                  95

Thr Val Glu Arg Lys Cys Cys Val Glu Cys Pro Pro Cys Pro Ala Pro
                100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Gly Ala Leu His Asn His Tyr Thr Gln Glu Ser Leu
305                 310                 315                 320

Ser Leu Ser Pro Gly Lys
                325

<210> SEQ ID NO 136
<211> LENGTH: 326
<212> TYPE: PRT
<213> ORGANISM: Artificial sequence
<220> FEATURE:
<223> OTHER INFORMATION: modified Fc region

<400> SEQUENCE: 136

Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
 65                  70                  75                  80

Tyr Thr Cys Asn Val Asp His Lys Pro Ser Asn Thr Lys Val Asp Lys
```

```
                    85                  90                  95
Thr Val Glu Arg Lys Cys Cys Val Glu Cys Pro Pro Cys Pro Ala Pro
                100                 105                 110

Pro Val Ala Arg Pro Ser Val Phe Leu Phe Pro Pro Lys Pro Lys Asp
            115                 120                 125

Thr Leu Met Ile Ser Arg Thr Pro Glu Val Thr Cys Val Val Val Asp
        130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
290                 295                 300

Ser Val Met His Gly Ala Leu His Asn His Tyr Thr Gln Glu Ser Leu
305                 310                 315                 320

Ser Leu Ser Pro Gly Lys
                325

<210> SEQ ID NO 137
<211> LENGTH: 326
<212> TYPE: PRT
<213> ORGANISM: Artificial sequence
<220> FEATURE:
<223> OTHER INFORMATION: modified Fc region

<400> SEQUENCE: 137

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
```

```
                115                 120                 125
Thr Leu Met Ile Ser Arg Thr Pro Glu Val Thr Cys Val Val Asp
        130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
        180                 185                 190

Leu Asn Gly Lys Glu Tyr Lys Cys Lys Val Ser Asn Lys Gly Leu Pro
            195                 200                 205

Ala Pro Ile Glu Lys Thr Ile Ser Lys Thr Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Gly Ala Leu His Asn His Tyr Thr Gln Lys Lys Leu
305                 310                 315                 320

Ser Leu Ser Pro Gly Lys
                325

<210> SEQ ID NO 138
<211> LENGTH: 326
<212> TYPE: PRT
<213> ORGANISM: Artificial sequence
<220> FEATURE:
<223> OTHER INFORMATION: modified Fc region

<400> SEQUENCE: 138

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Asp
    130                 135                 140

Val Ser His Glu Asp Pro Glu Val Gln Phe Asn Trp Tyr Val Asp Gly
```

```
                145                 150                 155                 160
Val Glu Val His Asn Ala Lys Thr Lys Pro Arg Glu Glu Gln Phe Asn
                    165                 170                 175
Ser Thr Phe Arg Val Val Ser Val Leu Thr Val Val His Gln Asp Trp
                180                 185                 190
Leu Asn Gly Lys Glu Tyr Lys Cys Lys Val Ser Asn Lys Gly Leu Pro
                    195                 200                 205
Ala Pro Ile Ser Lys Thr Ile Ser Lys Thr Lys Gly Gln Pro Arg Glu
                210                 215                 220
Pro Gln Val Tyr Thr Leu Pro Pro Ser Arg Glu Glu Met Thr Lys Asn
225                 230                 235                 240
Gln Val Ser Leu Thr Cys Leu Val Lys Gly Phe Tyr Pro Ser Asp Ile
                    245                 250                 255
Ala Val Glu Trp Glu Ser Asn Gly Gln Pro Glu Asn Asn Tyr Lys Thr
                260                 265                 270
Thr Pro Pro Met Leu Asp Ser Asp Gly Ser Phe Phe Leu Tyr Ser Lys
                    275                 280                 285
Leu Thr Val Asp Lys Ser Arg Trp Gln Gln Gly Asn Val Phe Ser Cys
                290                 295                 300
Ser Val Met His Gly Ala Leu His Asn His Tyr Thr Gln Lys Lys Leu
305                 310                 315                 320
Ser Leu Ser Pro Gly Lys
                    325

<210> SEQ ID NO 139
<211> LENGTH: 377
<212> TYPE: PRT
<213> ORGANISM: Artificial sequence
<220> FEATURE:
<223> OTHER INFORMATION: modified Fc region

<400> SEQUENCE: 139

Ala Ser Thr Lys Gly Pro Ser Val Phe Pro Leu Ala Pro Cys Ser Arg
1               5                   10                  15
Ser Thr Ser Gly Gly Thr Ala Ala Leu Gly Cys Leu Val Lys Asp Tyr
                20                  25                  30
Phe Pro Glu Pro Val Thr Val Ser Trp Asn Ser Gly Ala Leu Thr Ser
                35                  40                  45
Gly Val His Thr Phe Pro Ala Val Leu Gln Ser Ser Gly Leu Tyr Ser
            50                  55                  60
Leu Ser Ser Val Val Thr Val Pro Ser Ser Ser Leu Gly Thr Gln Thr
65                  70                  75                  80
Tyr Thr Cys Asn Val Asn His Lys Pro Ser Asn Thr Lys Val Asp Lys
                    85                  90                  95
Arg Val Glu Leu Lys Thr Pro Leu Gly Asp Thr Thr His Thr Cys Pro
                100                 105                 110
Arg Cys Pro Glu Pro Lys Ser Cys Asp Thr Pro Pro Pro Cys Pro Arg
                115                 120                 125
Cys Pro Glu Pro Lys Ser Cys Asp Thr Pro Pro Pro Cys Pro Arg Cys
                130                 135                 140
Pro Glu Pro Lys Ser Cys Asp Thr Pro Pro Pro Cys Pro Arg Cys Pro
145                 150                 155                 160
Ala Pro Glu Leu Leu Gly Gly Pro Ser Val Phe Leu Phe Pro Pro Lys
                    165                 170                 175
Pro Lys Asp Thr Leu Met Ile Ser Arg Thr Pro Glu Val Thr Cys Val
```

```
                180                 185                 190
Val Val Asp Val Ser His Glu Asp Pro Glu Val Gln Phe Lys Trp Tyr
            195                 200                 205

Val Asp Gly Val Glu Val His Asn Ala Lys Thr Lys Pro Arg Glu Glu
            210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
            245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
            275                 280                 285

Thr Lys Asn Gln Val Ser Leu Thr Cys Leu Val Lys Gly Phe Tyr Pro
            290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
            325                 330                 335

Tyr Ser Lys Leu Thr Val Asp Lys Ser Arg Trp Gln Gln Gly Asn Ile
            340                 345                 350

Phe Ser Cys Ser Val Met His Gly Ala Leu His Asn Arg Phe Thr Gln
            355                 360                 365

Lys Ser Leu Ser Leu Ser Pro Gly Lys
            370                 375

<210> SEQ ID NO 140
<211> LENGTH: 377
<212> TYPE: PRT
<213> ORGANISM: Artificial sequence
<220> FEATURE:
<223> OTHER INFORMATION: modified Fc region

<400> SEQUENCE: 140

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Cys Pro Arg
            115                 120                 125

Cys Pro Glu Pro Lys Ser Cys Asp Thr Pro Pro Cys Pro Arg Cys
            130                 135                 140

Pro Glu Pro Lys Ser Cys Asp Thr Pro Pro Cys Pro Arg Cys Pro
145                 150                 155                 160

Ala Pro Glu Leu Leu Gly Gly Pro Ser Val Phe Leu Phe Pro Pro Lys
```

```
            165                 170                 175
Pro Lys Asp Thr Leu Met Ile Ser Arg Thr Pro Glu Val Thr Cys Val
        180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
        210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
        290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Gly Ala Leu His Asn Arg Phe Thr Gln
        355                 360                 365

Glu Ser Leu Ser Leu Ser Pro Gly Lys
        370                 375

<210> SEQ ID NO 141
<211> LENGTH: 377
<212> TYPE: PRT
<213> ORGANISM: Artificial sequence
<220> FEATURE:
<223> OTHER INFORMATION: modified Fc region

<400> SEQUENCE: 141

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Cys Pro Arg
        115                 120                 125

Cys Pro Glu Pro Lys Ser Cys Asp Thr Pro Pro Cys Pro Arg Cys
        130                 135                 140

Pro Glu Pro Lys Ser Cys Asp Thr Pro Pro Cys Pro Arg Cys Pro
```

```
                        145                 150                 155                 160
Ala Pro Glu Leu Leu Arg Gly Pro Ser Val Phe Leu Phe Pro Pro Lys
                165                 170                 175

Pro Lys Asp Thr Leu Met Ile Ser Arg Thr Pro Glu Val Thr Cys Val
                180                 185                 190

Val Val Asp Val Ser His Glu Asp Pro Glu Val Gln Phe Lys Trp Tyr
                195                 200                 205

Val Asp Gly Val Glu Val His Asn Ala Lys Thr Lys Pro Arg Glu Glu
        210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
                260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
        290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
                340                 345                 350

Phe Ser Cys Ser Val Met His Gly Ala Leu His Asn Arg Phe Thr Gln
                355                 360                 365

Glu Ser Leu Ser Leu Ser Pro Gly Lys
        370                 375

<210> SEQ ID NO 142
<211> LENGTH: 377
<212> TYPE: PRT
<213> ORGANISM: Artificial sequence
<220> FEATURE:
<223> OTHER INFORMATION: modified Fc region

<400> SEQUENCE: 142

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
                100                 105                 110

Arg Cys Pro Glu Pro Lys Ser Cys Asp Thr Pro Pro Pro Cys Pro Arg
            115                 120                 125

Cys Pro Glu Pro Lys Ser Cys Asp Thr Pro Pro Pro Cys Pro Arg Cys
```

```
            130                 135                 140
Pro Glu Pro Lys Ser Cys Asp Thr Pro Pro Cys Pro Arg Cys Pro
145                 150                 155                 160

Ala Pro Glu Leu Leu Gly Gly Pro Ser Val Phe Leu Phe Pro Lys
                165                 170                 175

Pro Lys Asp Thr Leu Met Ile Ser Arg Thr Pro Glu Val Thr Cys Val
                180                 185                 190

Val Val Asp Val Ser His Glu Asp Pro Glu Val Gln Phe Lys Trp Tyr
                195                 200                 205

Val Asp Gly Val Glu Val His Asn Ala Lys Thr Lys Pro Arg Glu Glu
                210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
                260                 265                 270

Pro Arg Glu Pro Gln Val Tyr Thr Leu Pro Pro Ser Arg Glu Glu Met
                275                 280                 285

Thr Lys Asn Gln Val Ser Leu Thr Cys Leu Val Lys Gly Phe Tyr Pro
                290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
                340                 345                 350

Phe Ser Cys Ser Val Met His Gly Ala Leu His Asn Arg Phe Thr Gln
                355                 360                 365

Lys Lys Leu Ser Leu Ser Pro Gly Lys
                370                 375

<210> SEQ ID NO 143
<211> LENGTH: 377
<212> TYPE: PRT
<213> ORGANISM: Artificial sequence
<220> FEATURE:
<223> OTHER INFORMATION: modified Fc region

<400> SEQUENCE: 143

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
                50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
                100                 105                 110

Arg Cys Pro Glu Pro Lys Ser Cys Asp Thr Pro Pro Pro Cys Pro Arg
```

```
            115                 120                 125
Cys Pro Glu Pro Lys Ser Cys Asp Thr Pro Pro Cys Pro Arg Cys
    130                 135                 140

Pro Glu Pro Lys Ser Cys Asp Thr Pro Pro Cys Pro Arg Cys Pro
145                 150                 155                 160

Ala Pro Glu Leu Leu Gly Gly Pro Ser Val Phe Leu Phe Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
    210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Ser Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Gly Ala Leu His Asn Arg Phe Thr Gln
        355                 360                 365

Lys Lys Leu Ser Leu Ser Pro Gly Lys
    370                 375

<210> SEQ ID NO 144
<211> LENGTH: 327
<212> TYPE: PRT
<213> ORGANISM: Artificial sequence
<220> FEATURE:
<223> OTHER INFORMATION: modified Fc region

<400> SEQUENCE: 144

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
```

```
                100             105             110
Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Gly Ala Leu His Asn His Tyr Thr Gln Lys Ser
305                 310                 315                 320

Leu Ser Leu Ser Leu Gly Lys
                325

<210> SEQ ID NO 145
<211> LENGTH: 327
<212> TYPE: PRT
<213> ORGANISM: Artificial sequence
<220> FEATURE:
<223> OTHER INFORMATION: modified Fc region

<400> SEQUENCE: 145

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
```

```
                130                 135                 140
Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Gly Leu
                195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
                275                 280                 285

Arg Leu Thr Val Asp Lys Ser Arg Trp Gln Glu Gly Asn Val Phe Ser
                290                 295                 300

Cys Ser Val Met His Gly Ala Leu His Asn His Tyr Thr Gln Glu Ser
305                 310                 315                 320

Leu Ser Leu Ser Leu Gly Lys
                325

<210> SEQ ID NO 146
<211> LENGTH: 327
<212> TYPE: PRT
<213> ORGANISM: Artificial sequence
<220> FEATURE:
<223> OTHER INFORMATION: modified Fc region

<400> SEQUENCE: 146

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
                50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
                100                 105                 110

Glu Phe Leu Arg Gly Pro Ser Val Phe Leu Phe Pro Pro Lys Pro Lys
                115                 120                 125

Asp Thr Leu Met Ile Ser Arg Thr Pro Glu Val Thr Cys Val Val Val
                130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
```

```
                    165                 170                 175
Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Gly Ala Leu His Asn His Tyr Thr Gln Glu Ser
305                 310                 315                 320

Leu Ser Leu Ser Leu Gly Lys
                325

<210> SEQ ID NO 147
<211> LENGTH: 327
<212> TYPE: PRT
<213> ORGANISM: Artificial sequence
<220> FEATURE:
<223> OTHER INFORMATION: modified Fc region

<400> SEQUENCE: 147

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
```

```
                195                 200                 205
Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Lys
305                 310                 315                 320

Leu Ser Leu Ser Leu Gly Lys
                325

<210> SEQ ID NO 148
<211> LENGTH: 327
<212> TYPE: PRT
<213> ORGANISM: Artificial sequence
<220> FEATURE:
<223> OTHER INFORMATION: modified Fc region

<400> SEQUENCE: 148

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Ser Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
```

```
                225                 230                 235                 240
Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
        290                 295                 300

Cys Ser Val Met His Gly Ala Leu His Asn His Tyr Thr Gln Lys Lys
305                 310                 315                 320

Leu Ser Leu Ser Leu Gly Lys
                325

<210> SEQ ID NO 149
<211> LENGTH: 298
<212> TYPE: PRT
<213> ORGANISM: Artificial sequence
<220> FEATURE:
<223> OTHER INFORMATION: modified Fc gamma receptor

<400> SEQUENCE: 149

Met Trp Phe Leu Thr Thr Leu Leu Leu Trp Val Pro Val Asp Gly Gln
1               5                   10                  15

Val Asp Thr Thr Lys Ala Val Ile Thr Leu Gln Pro Pro Trp Val Ser
            20                  25                  30

Val Phe Gln Glu Glu Thr Val Thr Leu His Cys Glu Val Leu His Leu
        35                  40                  45

Pro Gly Ser Ser Ser Thr Gln Trp Phe Leu Asn Gly Thr Ala Thr Gln
    50                  55                  60

Thr Ser Thr Pro Ser Tyr Arg Ile Thr Ser Ala Ser Val Asn Asp Ser
65                  70                  75                  80

Gly Glu Tyr Arg Cys Gln Arg Gly Leu Ser Gly Arg Ser Asp Pro Ile
                85                  90                  95

Gln Leu Glu Ile His Arg Gly Trp Leu Leu Leu Gln Val Ser Ser Arg
            100                 105                 110

Val Phe Thr Glu Gly Glu Pro Leu Ala Leu Arg Cys His Ala Trp Lys
        115                 120                 125

Asp Lys Leu Val Tyr Asn Val Leu Tyr Tyr Arg Asn Gly Lys Ala Phe
    130                 135                 140

Lys Phe Phe His Trp Asn Ser Asn Leu Thr Ile Leu Lys Thr Asn Ile
145                 150                 155                 160

Ser His Asn Gly Thr Tyr His Cys Ser Gly Met Gly Lys His Arg Tyr
                165                 170                 175

Thr Ser Ala Gly Ile Ser Val Thr Val Lys Glu Leu Phe Pro Ala Pro
            180                 185                 190

Val Leu Asn Ala Ser Val Thr Ser Pro Leu Leu Glu Gly Asn Leu Val
        195                 200                 205

Thr Leu Ser Cys Glu Thr Lys Leu Leu Leu Gln Arg Pro Gly Leu Gln
    210                 215                 220

Leu Tyr Phe Ser Phe Tyr Met Gly Ser Lys Thr Leu Arg Gly Arg Asn
225                 230                 235                 240

Thr Ser Ser Glu Tyr Gln Ile Leu Thr Ala Arg Arg Glu Asp Ser Gly
                245                 250                 255

Leu Tyr Trp Cys Glu Ala Ala Thr Glu Asp Gly Asn Val Leu Lys Arg
```

```
                    260                 265                 270
Ser Pro Glu Leu Glu Leu Gln Val Leu Gly Leu Gln Leu Pro Thr Pro
            275                 280                 285

Val Trp Phe His His His His His His
            290                 295

<210> SEQ ID NO 150
<211> LENGTH: 418
<212> TYPE: PRT
<213> ORGANISM: Artificial sequence
<220> FEATURE:
<223> OTHER INFORMATION: modified Fc gamma receptor

<400> SEQUENCE: 150

Met Glu Thr Gln Met Ser Gln Asn Val Cys Pro Arg Asn Leu Trp Leu
1               5                   10                  15

Leu Gln Pro Leu Thr Val Leu Leu Leu Leu Ala Ser Ala Asp Ser Gln
            20                  25                  30

Ala Ala Ala Pro Pro Lys Ala Val Leu Lys Leu Glu Pro Pro Trp Ile
        35                  40                  45

Asn Val Leu Gln Glu Asp Ser Val Thr Leu Thr Cys Gln Gly Ala Arg
50                  55                  60

Ser Pro Glu Ser Asp Ser Ile Gln Trp Phe His Asn Gly Asn Leu Ile
65                  70                  75                  80

Pro Thr His Thr Gln Pro Ser Tyr Arg Phe Lys Ala Asn Asn Asn Asp
            85                  90                  95

Ser Gly Glu Tyr Thr Cys Gln Thr Gly Gln Thr Ser Leu Ser Asp Pro
            100                 105                 110

Val His Leu Thr Val Leu Ser Glu Trp Leu Val Leu Gln Thr Pro His
        115                 120                 125

Leu Glu Phe Gln Glu Gly Glu Thr Ile Met Leu Arg Cys His Ser Trp
130                 135                 140

Lys Asp Lys Pro Leu Val Lys Val Thr Phe Phe Gln Asn Gly Lys Ser
145                 150                 155                 160

Gln Lys Phe Ser His Leu Asp Pro Thr Phe Ser Ile Pro Gln Ala Asn
            165                 170                 175

His Ser His Ser Gly Asp Tyr His Cys Thr Gly Asn Ile Gly Tyr Thr
        180                 185                 190

Leu Phe Ser Ser Lys Pro Val Thr Ile Thr Val Gln Val Pro Ser Met
        195                 200                 205

Gly Ser Ser Ser Pro Val Ala Pro Pro Lys Ala Val Leu Lys Leu Glu
    210                 215                 220

Pro Pro Trp Ile Asn Val Leu Gln Glu Asp Ser Val Thr Leu Thr Cys
225                 230                 235                 240

Gln Gly Ala Arg Ser Pro Glu Ser Asp Ser Ile Gln Trp Phe His Asn
            245                 250                 255

Gly Asn Leu Ile Pro Thr His Thr Gln Pro Ser Tyr Arg Phe Lys Ala
            260                 265                 270

Asn Asn Asn Asp Ser Gly Glu Tyr Thr Cys Gln Thr Gly Gln Thr Ser
            275                 280                 285

Leu Ser Asp Pro Val His Leu Thr Val Leu Ser Glu Trp Leu Val Leu
        290                 295                 300

Gln Thr Pro His Leu Glu Phe Gln Glu Gly Glu Thr Ile Met Leu Arg
305                 310                 315                 320

Cys His Ser Trp Lys Asp Lys Pro Leu Val Lys Val Thr Phe Phe Gln
```

```
                    325                 330                 335
Asn Gly Lys Ser Gln Lys Phe Ser His Leu Asp Pro Thr Phe Ser Ile
            340                 345                 350
Pro Gln Ala Asn His Ser His Ser Gly Asp Tyr His Cys Thr Gly Asn
                355                 360                 365
Ile Gly Tyr Thr Leu Phe Ser Ser Lys Pro Val Thr Ile Thr Val Gln
370                 375                 380
Val Pro Ser Met Gly Pro Gly Ser Ser His His His His
385                 390                 395                 400
Pro Gly Gly Gly Leu Asn Asp Ile Phe Glu Ala Gln Lys Ile Glu Trp
                405                 410                 415
His Glu

<210> SEQ ID NO 151
<211> LENGTH: 405
<212> TYPE: PRT
<213> ORGANISM: Artificial sequence
<220> FEATURE:
<223> OTHER INFORMATION: modified Fc gamma receptor

<400> SEQUENCE: 151

Met Val Leu Ser Leu Leu Tyr Leu Leu Thr Ala Leu Pro Gly Ile Leu
1               5                   10                  15
Ser Ala Ala Pro Pro Lys Ala Val Leu Lys Leu Glu Pro Pro Trp Ile
            20                  25                  30
Asn Val Leu Gln Glu Asp Ser Val Thr Leu Thr Cys Gln Gly Ala Arg
        35                  40                  45
Ser Pro Glu Ser Asp Ser Ile Gln Trp Phe His Asn Gly Asn Leu Ile
    50                  55                  60
Pro Thr His Thr Gln Pro Ser Tyr Arg Phe Lys Ala Asn Asn Asn Asp
65                  70                  75                  80
Ser Gly Glu Tyr Thr Cys Gln Thr Gly Gln Thr Ser Leu Ser Asp Pro
                85                  90                  95
Val His Leu Thr Val Leu Ser Glu Trp Leu Val Leu Gln Thr Pro His
            100                 105                 110
Leu Glu Phe Gln Glu Gly Glu Thr Ile Met Leu Arg Cys His Ser Trp
        115                 120                 125
Lys Asp Lys Pro Leu Val Lys Val Thr Phe Phe Gln Asn Gly Lys Ser
    130                 135                 140
Gln Lys Phe Ser Arg Leu Asp Pro Thr Phe Ser Ile Pro Gln Ala Asn
145                 150                 155                 160
His Ser His Ser Gly Asp Tyr His Cys Thr Gly Asn Ile Gly Tyr Thr
                165                 170                 175
Leu Phe Ser Ser Lys Pro Val Thr Ile Thr Val Gln Val Pro Ser Met
            180                 185                 190
Gly Ser Ser Ser Pro Ala Ala Pro Pro Lys Ala Val Leu Lys Leu Glu
        195                 200                 205
Pro Pro Trp Ile Asn Val Leu Gln Glu Asp Ser Val Thr Leu Thr Cys
    210                 215                 220
Gln Gly Ala Arg Ser Pro Glu Ser Asp Ser Ile Gln Trp Phe His Asn
225                 230                 235                 240
Gly Asn Leu Ile Pro Thr His Thr Gln Pro Ser Tyr Arg Phe Lys Ala
                245                 250                 255
Asn Asn Asn Asp Ser Gly Glu Tyr Thr Cys Gln Thr Gly Gln Thr Ser
            260                 265                 270
```

-continued

```
Leu Ser Asp Pro Val His Leu Thr Val Leu Ser Glu Trp Leu Val Leu
        275                 280                 285

Gln Thr Pro His Leu Glu Phe Gln Glu Gly Glu Thr Ile Met Leu Arg
        290                 295                 300

Cys His Ser Trp Lys Asp Lys Pro Leu Val Lys Val Thr Phe Phe Gln
305                 310                 315                 320

Asn Gly Lys Ser Gln Lys Phe Ser Arg Leu Asp Pro Thr Phe Ser Ile
                325                 330                 335

Pro Gln Ala Asn His Ser His Ser Gly Asp Tyr His Cys Thr Gly Asn
                340                 345                 350

Ile Gly Tyr Thr Leu Phe Ser Ser Lys Pro Val Thr Ile Thr Val Gln
            355                 360                 365

Val Pro Ser Met Gly Ser Ser Ser Pro Gly Ser Ser Ser His His His
        370                 375                 380

His His His Pro Gly Gly Gly Leu Asn Asp Ile Phe Glu Ala Gln Lys
385                 390                 395                 400

Ile Glu Trp His Glu
                405

<210> SEQ ID NO 152
<211> LENGTH: 405
<212> TYPE: PRT
<213> ORGANISM: Artificial sequence
<220> FEATURE:
<223> OTHER INFORMATION: modified Fc gamma receptor

<400> SEQUENCE: 152

Met Val Leu Ser Leu Leu Tyr Leu Leu Thr Ala Leu Pro Gly Ile Leu
1               5                   10                  15

Ser Ala Ala Pro Pro Lys Ala Val Leu Lys Leu Glu Pro Gln Trp Ile
            20                  25                  30

Asn Val Leu Gln Glu Asp Ser Val Thr Leu Thr Cys Arg Gly Thr His
        35                  40                  45

Ser Pro Glu Ser Asp Ser Ile Gln Trp Phe His Asn Gly Asn Leu Ile
    50                  55                  60

Pro Thr His Thr Gln Pro Ser Tyr Arg Phe Lys Ala Asn Asn Asn Asp
65                  70                  75                  80

Ser Gly Glu Tyr Thr Cys Gln Thr Gly Gln Thr Ser Leu Ser Asp Pro
                85                  90                  95

Val His Leu Thr Val Leu Ser Glu Trp Leu Val Leu Gln Thr Pro His
            100                 105                 110

Leu Glu Phe Gln Glu Gly Glu Thr Ile Val Leu Arg Cys His Ser Trp
        115                 120                 125

Lys Asp Lys Pro Leu Val Lys Val Thr Phe Phe Gln Asn Gly Lys Ser
    130                 135                 140

Lys Lys Phe Ser Arg Ser Asp Pro Asn Phe Ser Ile Pro Gln Ala Asn
145                 150                 155                 160

His Ser His Ser Gly Asp Tyr His Cys Thr Gly Asn Ile Gly Tyr Thr
                165                 170                 175

Leu Tyr Ser Ser Lys Pro Val Thr Ile Thr Val Gln Ala Pro Ser Ser
            180                 185                 190

Ser Pro Met Gly Pro Ala Ala Pro Lys Ala Val Leu Lys Leu Glu
        195                 200                 205

Pro Gln Trp Ile Asn Val Leu Gln Glu Asp Ser Val Thr Leu Thr Cys
    210                 215                 220
```

```
Arg Gly Thr His Ser Pro Glu Ser Asp Ser Ile Gln Trp Phe His Asn
225                 230                 235                 240

Gly Asn Leu Ile Pro Thr His Thr Gln Pro Ser Tyr Arg Phe Lys Ala
            245                 250                 255

Asn Asn Asn Asp Ser Gly Glu Tyr Thr Cys Gln Thr Gly Gln Thr Ser
        260                 265                 270

Leu Ser Asp Pro Val His Leu Thr Val Leu Ser Glu Trp Leu Val Leu
    275                 280                 285

Gln Thr Pro His Leu Glu Phe Gln Glu Gly Glu Thr Ile Val Leu Arg
290                 295                 300

Cys His Ser Trp Lys Asp Lys Pro Leu Val Lys Val Thr Phe Phe Gln
305                 310                 315                 320

Asn Gly Lys Ser Lys Lys Phe Ser Arg Ser Asp Pro Asn Phe Ser Ile
                325                 330                 335

Pro Gln Ala Asn His Ser His Ser Gly Asp Tyr His Cys Thr Gly Asn
            340                 345                 350

Ile Gly Tyr Thr Leu Tyr Ser Ser Lys Pro Val Thr Ile Thr Val Gln
        355                 360                 365

Ala Pro Ser Ser Pro Met Gly Pro Gly Ser Ser His His His His His
    370                 375                 380

His His His Pro Gly Gly Gly Leu Asn Asp Ile Phe Glu Ala Gln Lys
385                 390                 395                 400

Ile Glu Trp His Glu
                405

<210> SEQ ID NO 153
<211> LENGTH: 410
<212> TYPE: PRT
<213> ORGANISM: Artificial sequence
<220> FEATURE:
<223> OTHER INFORMATION: modified Fc gamma receptor

<400> SEQUENCE: 153

Met Val Leu Ser Leu Leu Tyr Leu Leu Thr Ala Leu Pro Gly Ile Ser
1               5                   10                  15

Thr Glu Asp Leu Pro Lys Ala Val Val Phe Leu Glu Pro Gln Trp Tyr
            20                  25                  30

Arg Val Leu Glu Lys Asp Ser Val Thr Leu Lys Cys Gln Gly Ala Tyr
        35                  40                  45

Ser Pro Glu Asp Asn Ser Thr Gln Trp Phe His Asn Glu Ser Leu Ile
    50                  55                  60

Ser Ser Gln Ala Ser Ser Tyr Phe Ile Asp Ala Ala Thr Val Asp Asp
65                  70                  75                  80

Ser Gly Glu Tyr Arg Cys Gln Thr Asn Leu Ser Thr Leu Ser Asp Pro
                85                  90                  95

Val Gln Leu Glu Val His Ile Gly Trp Leu Leu Leu Gln Ala Pro Arg
            100                 105                 110

Trp Val Phe Lys Glu Glu Asp Pro Ile His Leu Arg Cys His Ser Trp
        115                 120                 125

Lys Asn Thr Ala Leu His Lys Val Thr Tyr Leu Gln Asn Gly Lys Gly
    130                 135                 140

Arg Lys Tyr Phe His His Asn Ser Asp Phe Tyr Ile Pro Lys Ala Thr
145                 150                 155                 160

Leu Lys Asp Ser Gly Ser Tyr Phe Cys Arg Gly Leu Phe Gly Ser Lys
                165                 170                 175
```

```
Asn Val Ser Ser Glu Thr Val Asn Ile Thr Ile Thr Gln Gly Pro Ser
                180                 185                 190

Met Gly Ser Ser Ser Pro Ser Glu Asp Leu Pro Lys Ala Val Val Phe
            195                 200                 205

Leu Glu Pro Gln Trp Tyr Arg Val Leu Glu Lys Asp Ser Val Thr Leu
210                 215                 220

Lys Cys Gln Gly Ala Tyr Ser Pro Glu Asp Asn Ser Thr Gln Trp Phe
225                 230                 235                 240

His Asn Glu Ser Leu Ile Ser Ser Gln Ala Ser Ser Tyr Phe Ile Asp
                245                 250                 255

Ala Ala Thr Val Asp Asp Ser Gly Glu Tyr Arg Cys Gln Thr Asn Leu
            260                 265                 270

Ser Thr Leu Ser Asp Pro Val Gln Leu Glu Val His Ile Gly Trp Leu
        275                 280                 285

Leu Leu Gln Ala Pro Arg Trp Val Phe Lys Glu Glu Asp Pro Ile His
    290                 295                 300

Leu Arg Cys His Ser Trp Lys Asn Thr Ala Leu His Lys Val Thr Tyr
305                 310                 315                 320

Leu Gln Asn Gly Lys Gly Arg Lys Tyr Phe His His Asn Ser Asp Phe
                325                 330                 335

Tyr Ile Pro Lys Ala Thr Leu Lys Asp Ser Gly Ser Tyr Phe Cys Arg
            340                 345                 350

Gly Leu Phe Gly Ser Lys Asn Val Ser Ser Glu Thr Val Asn Ile Thr
        355                 360                 365

Ile Thr Gln Gly Pro Ser Met Gly Ser Ser Ser Pro Gly Pro Gly Ser
    370                 375                 380

Ser Ser His His His His His His Pro Gly Gly Gly Leu Asn Asp Ile
385                 390                 395                 400

Phe Glu Ala Gln Lys Ile Glu Trp His Glu
                405                 410

<210> SEQ ID NO 154
<211> LENGTH: 410
<212> TYPE: PRT
<213> ORGANISM: Artificial sequence
<220> FEATURE:
<223> OTHER INFORMATION: modified Fc gamma receptor

<400> SEQUENCE: 154

Met Val Leu Ser Leu Leu Tyr Leu Leu Thr Ala Leu Pro Gly Ile Ser
1               5                   10                  15

Thr Glu Asp Leu Pro Lys Ala Val Val Phe Leu Glu Pro Gln Trp Tyr
            20                  25                  30

Arg Val Leu Glu Lys Asp Ser Val Thr Leu Lys Cys Gln Gly Ala Tyr
        35                  40                  45

Ser Pro Glu Asp Asn Ser Thr Gln Trp Phe His Asn Glu Ser Leu Ile
    50                  55                  60

Ser Ser Gln Ala Ser Ser Tyr Phe Ile Asp Ala Ala Thr Val Asp Asp
65                  70                  75                  80

Ser Gly Glu Tyr Arg Cys Gln Thr Asn Leu Ser Thr Leu Ser Asp Pro
                85                  90                  95

Val Gln Leu Glu Val His Ile Gly Trp Leu Leu Leu Gln Ala Pro Arg
            100                 105                 110

Trp Val Phe Lys Glu Glu Asp Pro Ile His Leu Arg Cys His Ser Trp
        115                 120                 125
```

```
Lys Asn Thr Ala Leu His Lys Val Thr Tyr Leu Gln Asn Gly Lys Gly
            130                 135                 140

Arg Lys Tyr Phe His His Asn Ser Asp Phe Tyr Ile Pro Lys Ala Thr
145                 150                 155                 160

Leu Lys Asp Ser Gly Ser Tyr Phe Cys Arg Gly Leu Val Gly Ser Lys
                165                 170                 175

Asn Val Ser Ser Glu Thr Val Asn Ile Thr Ile Thr Gln Gly Pro Ser
            180                 185                 190

Met Gly Ser Ser Ser Pro Ser Glu Asp Leu Pro Lys Ala Val Val Phe
        195                 200                 205

Leu Glu Pro Gln Trp Tyr Arg Val Leu Glu Lys Asp Ser Val Thr Leu
210                 215                 220

Lys Cys Gln Gly Ala Tyr Ser Pro Glu Asp Asn Ser Thr Gln Trp Phe
225                 230                 235                 240

His Asn Glu Ser Leu Ile Ser Ser Gln Ala Ser Ser Tyr Phe Ile Asp
                245                 250                 255

Ala Ala Thr Val Asp Asp Ser Gly Glu Tyr Arg Cys Gln Thr Asn Leu
            260                 265                 270

Ser Thr Leu Ser Asp Pro Val Gln Leu Glu Val His Ile Gly Trp Leu
        275                 280                 285

Leu Leu Gln Ala Pro Arg Trp Val Phe Lys Glu Glu Asp Pro Ile His
290                 295                 300

Leu Arg Cys His Ser Trp Lys Asn Thr Ala Leu His Lys Val Thr Tyr
305                 310                 315                 320

Leu Gln Asn Gly Lys Gly Arg Lys Tyr Phe His His Asn Ser Asp Phe
                325                 330                 335

Tyr Ile Pro Lys Ala Thr Leu Lys Asp Ser Gly Ser Tyr Phe Cys Arg
            340                 345                 350

Gly Leu Val Gly Ser Lys Asn Val Ser Ser Glu Thr Val Asn Ile Thr
        355                 360                 365

Ile Thr Gln Gly Pro Ser Met Gly Ser Ser Ser Pro Gly Pro Gly Ser
370                 375                 380

Ser Ser His His His His His His Pro Gly Gly Leu Asn Asp Ile
385                 390                 395                 400

Phe Glu Ala Gln Lys Ile Glu Trp His Glu
                405                 410

<210> SEQ ID NO 155
<211> LENGTH: 280
<212> TYPE: PRT
<213> ORGANISM: Artificial sequence
<220> FEATURE:
<223> OTHER INFORMATION: modified Fc region

<400> SEQUENCE: 155

Ala Glu Ser His Leu Ser Leu Leu Tyr His Leu Thr Ala Val Ser Ser
1               5                   10                  15

Pro Ala Pro Gly Thr Pro Ala Phe Trp Val Ser Gly Trp Leu Gly Pro
            20                  25                  30

Gln Gln Tyr Leu Ser Tyr Asn Ser Leu Arg Gly Glu Ala Glu Pro Cys
        35                  40                  45

Gly Ala Trp Val Trp Glu Asn Gln Val Ser Trp Tyr Trp Glu Lys Glu
    50                  55                  60

Thr Thr Asp Leu Arg Ile Lys Glu Lys Leu Phe Leu Glu Ala Phe Lys
65                  70                  75                  80
```

```
Ala Leu Gly Gly Lys Gly Pro Tyr Thr Leu Gln Gly Leu Leu Gly Cys
            85                  90                  95

Glu Leu Gly Pro Asp Asn Thr Ser Val Pro Thr Ala Lys Phe Ala Leu
        100                 105                 110

Asn Gly Glu Glu Phe Met Asn Phe Asp Leu Lys Gln Gly Thr Trp Gly
    115                 120                 125

Gly Asp Trp Pro Glu Ala Leu Ala Ile Ser Gln Arg Trp Gln Gln Gln
130                 135                 140

Asp Lys Ala Ala Asn Lys Glu Leu Thr Phe Leu Leu Phe Ser Cys Pro
145                 150                 155                 160

His Arg Leu Arg Glu His Leu Glu Arg Gly Arg Gly Asn Leu Glu Trp
                165                 170                 175

Lys Glu Pro Pro Ser Met Arg Leu Lys Ala Arg Pro Ser Ser Pro Gly
            180                 185                 190

Phe Ser Val Leu Thr Cys Ser Ala Phe Ser Phe Tyr Pro Pro Glu Leu
        195                 200                 205

Gln Leu Arg Phe Leu Arg Asn Gly Leu Ala Ala Gly Thr Gly Gln Gly
    210                 215                 220

Asp Phe Gly Pro Asn Ser Asp Gly Ser Phe His Ala Ser Ser Ser Leu
225                 230                 235                 240

Thr Val Lys Ser Gly Asp Glu His His Tyr Cys Cys Ile Val Gln His
                245                 250                 255

Ala Gly Leu Ala Gln Pro Leu Arg Val Glu Leu Glu Ser Pro Ala Lys
            260                 265                 270

Ser Ser His His His His His His
            275                 280

<210> SEQ ID NO 156
<211> LENGTH: 99
<212> TYPE: PRT
<213> ORGANISM: Human

<400> SEQUENCE: 156

Ile Gln Arg Thr Pro Lys Ile Gln Val Tyr Ser Arg His Pro Ala Glu
1               5                   10                  15

Asn Gly Lys Ser Asn Phe Leu Asn Cys Tyr Val Ser Gly Phe His Pro
            20                  25                  30

Ser Asp Ile Glu Val Asp Leu Leu Lys Asn Gly Glu Arg Ile Glu Lys
        35                  40                  45

Val Glu His Ser Asp Leu Ser Phe Ser Lys Asp Trp Ser Phe Tyr Leu
    50                  55                  60

Leu Tyr Tyr Thr Glu Phe Thr Pro Thr Glu Lys Asp Glu Tyr Ala Cys
65                  70                  75                  80

Arg Val Asn His Val Thr Leu Ser Gln Pro Lys Ile Val Lys Trp Asp
                85                  90                  95

Arg Asp Met

<210> SEQ ID NO 157
<211> LENGTH: 330
<212> TYPE: PRT
<213> ORGANISM: Artificial sequence
<220> FEATURE:
<223> OTHER INFORMATION: modified Fc region

<400> SEQUENCE: 157

Ala Ser Thr Lys Gly Pro Ser Val Phe Pro Leu Ala Pro Ser Ser Lys
```

```
                1               5                   10                  15
Ser Thr Ser Gly Gly Thr Ala Ala Leu Gly Cys Leu Val Lys Asp Tyr
                    20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                        85                  90                  95

Arg Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
                115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
                195                 200                 205

Trp Ala Leu Pro Ala Pro Ile Ser Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
                290                 295                 300

Val Phe Ser Cys Ser Val Met His Gly Ala Leu His Asn His Tyr Thr
305                 310                 315                 320

Gln Lys Lys Leu Ser Leu Ser Pro Gly Lys
                325                 330

<210> SEQ ID NO 158
<211> LENGTH: 330
<212> TYPE: PRT
<213> ORGANISM: Artificial sequence
<220> FEATURE:
<223> OTHER INFORMATION: modified Fc region

<400> SEQUENCE: 158

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                    20                  25                  30

Phe Pro Glu Pro Val Thr Val Ser Trp Asn Ser Gly Ala Leu Thr Ser
```

```
                   35                  40                  45
Gly Val His Thr Phe Pro Ala Val Leu Gln Ser Ser Gly Leu Tyr Ser
 50                  55                  60

Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Arg Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
                115                 120                 125

Lys Pro Lys Asp Thr Leu Met Ile Ser Arg Thr Pro Glu Val Thr Cys
                130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
                195                 200                 205

Lys Ala Leu Pro Ala Pro Ile Glu Lys Thr Ile Ser Lys Ala Lys Gly
                210                 215                 220

Gln Pro Arg Arg Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
                290                 295                 300

Val Phe Ser Cys Ser Val Met His Gly Ala Leu His Asn His Tyr Thr
305                 310                 315                 320

Gln Lys Tyr Leu Ser Leu Ser Pro Gly Lys
                325                 330

<210> SEQ ID NO 159
<211> LENGTH: 653
<212> TYPE: PRT
<213> ORGANISM: Artificial sequence
<220> FEATURE:
<223> OTHER INFORMATION: Modified Her2

<400> SEQUENCE: 159

Met Glu Leu Ala Ala Leu Cys Arg Trp Gly Leu Leu Leu Ala Leu Leu
 1               5                  10                  15

Pro Pro Gly Ala Ala Ser Thr Gln Val Cys Thr Gly Thr Asp Met Lys
                20                  25                  30

Leu Arg Leu Pro Ala Ser Pro Glu Thr His Leu Asp Met Leu Arg His
                35                  40                  45

Leu Tyr Gln Gly Cys Gln Val Val Gln Gly Asn Leu Glu Leu Thr Tyr
 50                  55                  60

Leu Pro Thr Asn Ala Ser Leu Ser Phe Leu Gln Asp Ile Gln Glu Val
```

```
                65                  70                  75                  80
Gln Gly Tyr Val Leu Ile Ala His Asn Gln Val Arg Gln Val Pro Leu
                    85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
    210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
        275                 280                 285

Tyr Thr Phe Gly Ala Ser Cys Val Thr Ala Cys Pro Tyr Asn Tyr Leu
    290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
            340                 345                 350

Val Arg Ala Val Thr Ser Ala Asn Ile Gln Glu Phe Ala Gly Cys Lys
        355                 360                 365

Lys Ile Phe Gly Ser Leu Ala Phe Leu Pro Glu Ser Phe Asp Gly Asp
    370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Gln Val Ile Arg
            420                 425                 430

Gly Arg Ile Leu His Asn Gly Ala Tyr Ser Leu Thr Leu Gln Gly Leu
        435                 440                 445

Gly Ile Ser Trp Leu Gly Leu Arg Ser Leu Arg Glu Leu Gly Ser Gly
    450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
                485                 490                 495
```

```
Ala Asn Arg Pro Glu Asp Glu Cys Val Gly Glu Gly Leu Ala Cys His
            500                 505                 510

Gln Leu Cys Ala Arg Gly His Cys Trp Gly Pro Gly Pro Thr Gln Cys
        515                 520                 525

Val Asn Cys Ser Gln Phe Leu Arg Gly Gln Glu Cys Val Glu Glu Cys
    530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575

Phe Gly Pro Glu Ala Asp Gln Cys Val Ala Cys Ala His Tyr Lys Asp
                580                 585                 590

Pro Pro Phe Cys Val Ala Arg Cys Pro Ser Gly Val Lys Pro Asp Leu
                595                 600                 605

Ser Tyr Met Pro Ile Trp Lys Phe Pro Asp Glu Glu Gly Ala Cys Gln
            610                 615                 620

Pro Cys Pro Ile Asn Cys Thr His Ser Cys Val Asp Leu Asp Asp Lys
625                 630                 635                 640

Gly Cys Pro Ala Glu Gln Arg His His His His His His
                645                 650
```

<210> SEQ ID NO 160
<211> LENGTH: 113
<212> TYPE: PRT
<213> ORGANISM: Artificial sequence
<220> FEATURE:
<223> OTHER INFORMATION: humanized VH region

<400> SEQUENCE: 160

```
Glu Val His Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Gly Met Ser Trp Val Arg Gln Ala Pro Gly Lys Gly Leu Glu Leu Val
        35                  40                  45

Ala Met Met Lys Thr Lys Gly Gly Arg Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Ile Tyr Tyr Cys
                85                  90                  95

Ala Ser Asp Gly Tyr Tyr Trp Gly Gln Gly Thr Thr Val Thr Val Ser
            100                 105                 110

Ser
```

<210> SEQ ID NO 161
<211> LENGTH: 8
<212> TYPE: PRT
<213> ORGANISM: Artificial sequence
<220> FEATURE:
<223> OTHER INFORMATION: humanized VH region CDR1

<400> SEQUENCE: 161

```
Gly Phe Thr Phe Ser Arg Tyr Gly
1               5
```

<210> SEQ ID NO 162

```
<211> LENGTH: 8
<212> TYPE: PRT
<213> ORGANISM: Artificial sequence
<220> FEATURE:
<223> OTHER INFORMATION: humanized VH region CDR2

<400> SEQUENCE: 162

Met Lys Thr Lys Gly Gly Arg Thr
1               5

<210> SEQ ID NO 163
<211> LENGTH: 6
<212> TYPE: PRT
<213> ORGANISM: Artificial sequence
<220> FEATURE:
<223> OTHER INFORMATION: humanized VH region CDR3

<400> SEQUENCE: 163

Ala Ser Asp Gly Tyr Tyr
1               5

<210> SEQ ID NO 164
<211> LENGTH: 111
<212> TYPE: PRT
<213> ORGANISM: Artificial sequence
<220> FEATURE:
<223> OTHER INFORMATION: humanized VL region

<400> SEQUENCE: 164

Asp Val Val Met Thr Gln Thr Pro Leu Ser Leu Ser Val Thr Leu Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Asn Trp Leu Gln Gln Arg Pro Gly Gln Ser
        35                  40                  45

Pro Arg Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Ile Tyr Tyr Cys Trp Gln Gly
                85                  90                  95

Thr His Leu Trp Thr Phe Gly Gly Gly Thr Lys Val Glu Ile Lys
            100                 105                 110

<210> SEQ ID NO 165
<211> LENGTH: 11
<212> TYPE: PRT
<213> ORGANISM: Artificial sequence
<220> FEATURE:
<223> OTHER INFORMATION: humanized VL region CDR1

<400> SEQUENCE: 165

Gln Ser Leu Leu His Ser Asp Gly Lys Thr Tyr
1               5                   10

<210> SEQ ID NO 166
<211> LENGTH: 8
<212> TYPE: PRT
<213> ORGANISM: Artificial sequence
<220> FEATURE:
<223> OTHER INFORMATION: humanized VL region CDR3

<400> SEQUENCE: 166

Trp Gln Gly Thr His Leu Trp Thr
```

<210> SEQ ID NO 167
<211> LENGTH: 121
<212> TYPE: PRT
<213> ORGANISM: Artificial sequence
<220> FEATURE:
<223> OTHER INFORMATION: humanized VH region

<400> SEQUENCE: 167

Gln Val Gln Leu Gln Gln Ser Gly Ser Glu Leu Lys Lys Pro Gly Ala
1               5                   10                  15

Ser Val Lys Val Ser Cys Lys Ala Ser Gly Phe Thr Phe Thr Asn Tyr
            20                  25                  30

Gly Met Asn Trp Val Lys Gln Ala Pro Gly Gln Gly Leu Lys Trp Met
        35                  40                  45

Gly Trp Ile Asn Thr Tyr Thr Arg Glu Pro Thr Tyr Ala Asp Asp Phe
    50                  55                  60

Lys Gly Arg Phe Ala Phe Ser Leu Asp Thr Ser Val Ser Thr Ala Tyr
65                  70                  75                  80

Leu Gln Ile Ser Ser Leu Lys Ala Asp Asp Thr Ala Val Tyr Phe Cys
                85                  90                  95

Ala Arg Asp Ile Thr Ala Val Val Pro Thr Gly Phe Asp Tyr Trp Gly
            100                 105                 110

Gln Gly Ser Leu Val Thr Val Ser Ser
        115                 120

<210> SEQ ID NO 168
<211> LENGTH: 8
<212> TYPE: PRT
<213> ORGANISM: Artificial sequence
<220> FEATURE:
<223> OTHER INFORMATION: VH region CDR1

<400> SEQUENCE: 168

Gly Phe Thr Phe Thr Asn Tyr Gly
1               5

<210> SEQ ID NO 169
<211> LENGTH: 8
<212> TYPE: PRT
<213> ORGANISM: Artificial sequence
<220> FEATURE:
<223> OTHER INFORMATION: humanized VH region CDR2

<400> SEQUENCE: 169

Ile Asn Thr Tyr Thr Arg Glu Pro
1               5

<210> SEQ ID NO 170
<211> LENGTH: 14
<212> TYPE: PRT
<213> ORGANISM: Artificial sequence
<220> FEATURE:
<223> OTHER INFORMATION: humanized VH region CDR3

<400> SEQUENCE: 170

Ala Arg Asp Ile Thr Ala Val Val Pro Thr Gly Phe Asp Tyr
1               5                   10

<210> SEQ ID NO 171
<211> LENGTH: 107
<212> TYPE: PRT

<213> ORGANISM: Artificial sequence
<220> FEATURE:
<223> OTHER INFORMATION: humanized VL region

<400> SEQUENCE: 171

Asp Ile Gln Leu Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Asn
            20                  25                  30

Leu Ala Trp Tyr Arg Gln Lys Pro Gly Lys Ala Pro Lys Leu Leu Val
        35                  40                  45

Phe Ala Ala Ser Asn Leu Ala Asp Gly Val Pro Ser Arg Phe Ser Gly
50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys Gln His Phe Trp Thr Thr Pro Trp
                85                  90                  95

Ala Phe Gly Gly Gly Thr Lys Leu Gln Ile Lys
            100                 105

<210> SEQ ID NO 172
<211> LENGTH: 6
<212> TYPE: PRT
<213> ORGANISM: Artificial sequence
<220> FEATURE:
<223> OTHER INFORMATION: humanized VL region CDR1

<400> SEQUENCE: 172

Glu Asn Ile Tyr Ser Asn
1               5

<210> SEQ ID NO 173
<211> LENGTH: 9
<212> TYPE: PRT
<213> ORGANISM: Artificial sequence
<220> FEATURE:
<223> OTHER INFORMATION: humanized VL region CDR3

<400> SEQUENCE: 173

Gln His Phe Trp Thr Thr Pro Trp Ala
1               5

<210> SEQ ID NO 174
<211> LENGTH: 120
<212> TYPE: PRT
<213> ORGANISM: Artificial sequence
<220> FEATURE:
<223> OTHER INFORMATION: VH region

<400> SEQUENCE: 174

Gln Val Gln Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Val Gly Val Gly Trp Ile Arg Gln Pro Pro Gly Lys Ala Leu Glu
        35                  40                  45

Trp Leu Ala Leu Ile Asp Trp Asp Asp Lys Tyr Tyr Ser Thr Ser
50                  55                  60

Leu Lys Thr Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr

```
                        85                  90                  95
Cys Ala Arg Ser Pro Arg Tyr Arg Gly Ala Phe Asp Tyr Trp Gly Gln
                100                 105                 110

Gly Thr Leu Val Thr Val Ser Ser
        115                 120

<210> SEQ ID NO 175
<211> LENGTH: 10
<212> TYPE: PRT
<213> ORGANISM: Artificial sequence
<220> FEATURE:
<223> OTHER INFORMATION: VH region CDR1

<400> SEQUENCE: 175

Gly Phe Ser Leu Ser Thr Ser Gly Val Gly
1               5                   10

<210> SEQ ID NO 176
<211> LENGTH: 7
<212> TYPE: PRT
<213> ORGANISM: Artificial sequence
<220> FEATURE:
<223> OTHER INFORMATION: VH region CDR2

<400> SEQUENCE: 176

Ile Asp Trp Asp Asp Asp Lys
1               5

<210> SEQ ID NO 177
<211> LENGTH: 12
<212> TYPE: PRT
<213> ORGANISM: Artificial sequence
<220> FEATURE:
<223> OTHER INFORMATION: VH region CDR3

<400> SEQUENCE: 177

Ala Arg Ser Pro Arg Tyr Arg Gly Ala Phe Asp Tyr
1               5                   10

<210> SEQ ID NO 178
<211> LENGTH: 108
<212> TYPE: PRT
<213> ORGANISM: Artificial sequence
<220> FEATURE:
<223> OTHER INFORMATION: VL region

<400> SEQUENCE: 178

Asp Ile Val Leu Thr Gln Pro Pro Ser Val Ser Gly Ala Pro Gly Gln
1               5                   10                  15

Arg Val Thr Ile Ser Cys Ser Gly Ser Glu Ser Asn Ile Gly Asn Asn
            20                  25                  30

Tyr Val Gln Trp Tyr Gln Gln Leu Pro Gly Thr Ala Pro Lys Leu Leu
        35                  40                  45

Ile Tyr Asp Asn Asn Gln Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ser Glu Asp Glu Ala Asp Tyr Tyr Cys Gln Ser Tyr Asp Met Asn Val
                85                  90                  95

His Val Phe Gly Gly Gly Thr Lys Leu Thr Val Leu
            100                 105
```

```
<210> SEQ ID NO 179
<211> LENGTH: 8
<212> TYPE: PRT
<213> ORGANISM: Artificial sequence
<220> FEATURE:
<223> OTHER INFORMATION: VL region CDR1

<400> SEQUENCE: 179

Glu Ser Asn Ile Gly Asn Asn Tyr
1               5

<210> SEQ ID NO 180
<211> LENGTH: 9
<212> TYPE: PRT
<213> ORGANISM: Artificial sequence
<220> FEATURE:
<223> OTHER INFORMATION: VL region CDR3

<400> SEQUENCE: 180

Gln Ser Tyr Asp Met Asn Val His Val
1               5

<210> SEQ ID NO 181
<211> LENGTH: 119
<212> TYPE: PRT
<213> ORGANISM: Artificial sequence
<220> FEATURE:
<223> OTHER INFORMATION: humanized VH region

<400> SEQUENCE: 181

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Gly Met Phe Trp Val Arg Gln Ala Pro Gly Lys Gly Leu Glu Trp Val
        35                  40                  45

Ala Thr Ile Ser Arg Tyr Ser Arg Tyr Ile Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Arg Pro Leu Tyr Gly Ser Ser Pro Asp Tyr Trp Gly Gln Gly
            100                 105                 110

Thr Leu Val Thr Val Ser Ser
        115

<210> SEQ ID NO 182
<211> LENGTH: 8
<212> TYPE: PRT
<213> ORGANISM: Artificial sequence
<220> FEATURE:
<223> OTHER INFORMATION: humanized VH region CDR1

<400> SEQUENCE: 182

Gly Phe Thr Phe Ser Ser Tyr Gly
1               5

<210> SEQ ID NO 183
<211> LENGTH: 8
<212> TYPE: PRT
<213> ORGANISM: Artificial sequence
<220> FEATURE:
<223> OTHER INFORMATION: humanized VH region CDR2
```

<400> SEQUENCE: 183

Ile Ser Arg Tyr Ser Arg Tyr Ile
1               5

<210> SEQ ID NO 184
<211> LENGTH: 12
<212> TYPE: PRT
<213> ORGANISM: Artificial sequence
<220> FEATURE:
<223> OTHER INFORMATION: humanized VH region CDR3

<400> SEQUENCE: 184

Ala Arg Arg Pro Leu Tyr Gly Ser Ser Pro Asp Tyr
1               5                   10

<210> SEQ ID NO 185
<211> LENGTH: 106
<212> TYPE: PRT
<213> ORGANISM: Artificial sequence
<220> FEATURE:
<223> OTHER INFORMATION: humanized VL region

<400> SEQUENCE: 185

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Val Thr Tyr Val
            20                  25                  30

His Trp Tyr Gln Gln Lys Pro Gly Gln Ala Pro Arg Leu Leu Ile Tyr
        35                  40                  45

Asp Thr Ser Lys Leu Ala Ser Gly Ile Pro Ala Arg Phe Ser Gly Ser
    50                  55                  60

Gly Ser Gly Thr Asp Phe Thr Leu Thr Ile Ser Leu Glu Pro Glu
65                  70                  75                  80

Asp Phe Ala Val Tyr Tyr Cys Phe Gln Gly Ser Gly Tyr Pro Leu Thr
                85                  90                  95

Phe Gly Ser Gly Thr Lys Leu Glu Met Arg
            100                 105

<210> SEQ ID NO 186
<211> LENGTH: 5
<212> TYPE: PRT
<213> ORGANISM: Artificial sequence
<220> FEATURE:
<223> OTHER INFORMATION: humanized VL region CDR1

<400> SEQUENCE: 186

Ser Ser Val Thr Tyr
1               5

<210> SEQ ID NO 187
<211> LENGTH: 9
<212> TYPE: PRT
<213> ORGANISM: Artificial sequence
<220> FEATURE:
<223> OTHER INFORMATION: humanized VL region CDR3

<400> SEQUENCE: 187

Phe Gln Gly Ser Gly Tyr Pro Leu Thr
1               5

<210> SEQ ID NO 188
<211> LENGTH: 118

<212> TYPE: PRT
<213> ORGANISM: Artificial sequence
<220> FEATURE:
<223> OTHER INFORMATION: VH region

<400> SEQUENCE: 188

Glu Val Gln Leu Gln Glu Ser Gly Pro Gly Leu Val Lys Pro Ser Gln
1               5                   10                  15

Thr Leu Ser Leu Thr Cys Ser Val Thr Gly Tyr Ser Ile Thr Ser Gly
            20                  25                  30

Tyr Tyr Trp His Trp Ile Arg Gln Phe Pro Gly Asn Lys Leu Glu Trp
        35                  40                  45

Met Gly Tyr Ile Ser Tyr Ser Gly Phe Thr Asn Tyr Lys Thr Ser Leu
    50                  55                  60

Ile Asn Arg Ile Ser Ile Thr His Asp Thr Ser Glu Asn Gln Phe Phe
65                  70                  75                  80

Leu Asn Leu Asn Ser Val Thr Thr Glu Asp Thr Ala Thr Tyr Tyr Cys
                85                  90                  95

Ala Gly Asp Arg Thr Gly Ser Trp Phe Ala Tyr Trp Gly Gln Gly Thr
            100                 105                 110

Leu Val Thr Val Ser Ser
            115

<210> SEQ ID NO 189
<211> LENGTH: 9
<212> TYPE: PRT
<213> ORGANISM: Artificial sequence
<220> FEATURE:
<223> OTHER INFORMATION: VH region CDR1

<400> SEQUENCE: 189

Gly Tyr Ser Ile Thr Ser Gly Tyr Tyr
1               5

<210> SEQ ID NO 190
<211> LENGTH: 7
<212> TYPE: PRT
<213> ORGANISM: Artificial sequence
<220> FEATURE:
<223> OTHER INFORMATION: VH region CDR2

<400> SEQUENCE: 190

Ile Ser Tyr Ser Gly Phe Thr
1               5

<210> SEQ ID NO 191
<211> LENGTH: 11
<212> TYPE: PRT
<213> ORGANISM: Artificial sequence
<220> FEATURE:
<223> OTHER INFORMATION: VH region CDR3

<400> SEQUENCE: 191

Ala Gly Asp Arg Thr Gly Ser Trp Phe Ala Tyr
1               5                   10

<210> SEQ ID NO 192
<211> LENGTH: 107
<212> TYPE: PRT
<213> ORGANISM: Artificial sequence
<220> FEATURE:
<223> OTHER INFORMATION: VL region

<400> SEQUENCE: 192

```
Asp Ile Gln Val Thr Gln Ser Pro Ser Ser Leu Ser Ala Ser Leu Gly
1               5                   10                  15

Glu Arg Ile Ser Leu Thr Cys Arg Thr Ser Gln Asp Ile Ser Asn Tyr
            20                  25                  30

Leu Asn Trp Phe Gln Lys Pro Asp Gly Thr Phe Lys Arg Leu Ile
        35                  40                  45

Tyr Ala Thr Ser Ser Leu Asp Ser Gly Val Pro Lys Arg Phe Ser Gly
    50                  55                  60

Ser Gly Ser Gly Ser Asp Tyr Ser Leu Thr Ile Ser Ser Leu Glu Ser
65                  70                  75                  80

Glu Asp Phe Ala Asp Tyr Tyr Cys Leu Gln Tyr Ala Ser Tyr Pro Phe
                85                  90                  95

Thr Phe Gly Ser Gly Thr Lys Leu Glu Ile Lys
            100                 105

<210> SEQ ID NO 193
<211> LENGTH: 6
<212> TYPE: PRT
<213> ORGANISM: Artificial sequence
<220> FEATURE:
<223> OTHER INFORMATION: VL region CDR1

<400> SEQUENCE: 193

Gln Asp Ile Ser Asn Tyr
1               5

<210> SEQ ID NO 194
<211> LENGTH: 9
<212> TYPE: PRT
<213> ORGANISM: Artificial sequence
<220> FEATURE:
<223> OTHER INFORMATION: VL region CDR3

<400> SEQUENCE: 194

Leu Gln Tyr Ala Ser Tyr Pro Phe Thr
1               5

<210> SEQ ID NO 195
<211> LENGTH: 119
<212> TYPE: PRT
<213> ORGANISM: Artificial sequence
<220> FEATURE:
<223> OTHER INFORMATION: humanized VH region

<400> SEQUENCE: 195

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Met His Trp Val Lys Gln Arg Pro Glu Gln Gly Leu Glu Trp Ile
        35                  40                  45

Gly Arg Ile Asp Pro Ala Asn Gly Asn Thr Lys Tyr Asp Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Tyr Tyr Tyr Val Ser Asn Ala Trp Phe Thr Tyr Trp Gly Gln Gly
            100                 105                 110
```

Thr Leu Val Thr Val Ser Ala
        115

<210> SEQ ID NO 196
<211> LENGTH: 8
<212> TYPE: PRT
<213> ORGANISM: Artificial sequence
<220> FEATURE:
<223> OTHER INFORMATION: humanized VH region CDR1

<400> SEQUENCE: 196

Gly Phe Asn Ile Lys Asp Thr Tyr
1               5

<210> SEQ ID NO 197
<211> LENGTH: 8
<212> TYPE: PRT
<213> ORGANISM: Artificial sequence
<220> FEATURE:
<223> OTHER INFORMATION: humanized VH region CDR2

<400> SEQUENCE: 197

Ile Asp Pro Ala Asn Gly Asn Thr
1               5

<210> SEQ ID NO 198
<211> LENGTH: 12
<212> TYPE: PRT
<213> ORGANISM: Artificial sequence
<220> FEATURE:
<223> OTHER INFORMATION: VH region CDR3

<400> SEQUENCE: 198

Ala Tyr Tyr Tyr Val Ser Asn Ala Trp Phe Thr Tyr
1               5                   10

<210> SEQ ID NO 199
<211> LENGTH: 106
<212> TYPE: PRT
<213> ORGANISM: Artificial sequence
<220> FEATURE:
<223> OTHER INFORMATION: humanized VL region

<400> SEQUENCE: 199

Asp Ile Gln Met Thr Gln Ser Pro Ala Ser Leu Ser Val Ser Val Gly
1               5                   10                  15

Glu Thr Val Thr Ile Thr Cys Arg Ala Ser Glu Asn Ile Tyr Ser Asn
            20                  25                  30

Leu Glu Trp Tyr Gln Gln Lys Gln Gly Lys Ser Pro Gln Leu Leu Val
        35                  40                  45

Tyr Ala Ala Thr Asn Leu Ala Asp Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Phe Gly Ser Tyr Tyr Cys Gln His Phe Trp Gly Thr Trp Thr
                85                  90                  95

Phe Gly Gly Gly Thr Lys Leu Glu Ile Lys
            100                 105

<210> SEQ ID NO 200
<211> LENGTH: 6
<212> TYPE: PRT
<213> ORGANISM: Artificial sequence
<220> FEATURE:

-continued

```
<223> OTHER INFORMATION: humanized VL region CDR1

<400> SEQUENCE: 200

Glu Asn Ile Tyr Ser Asn
1               5

<210> SEQ ID NO 201
<211> LENGTH: 8
<212> TYPE: PRT
<213> ORGANISM: Artificial sequence
<220> FEATURE:
<223> OTHER INFORMATION: humanized VL region CDR3

<400> SEQUENCE: 201

Gln His Phe Trp Gly Thr Trp Thr
1               5
```